US012715881B2

(12) United States Patent
Nittoli et al.

(10) Patent No.: US 12,715,881 B2
(45) Date of Patent: Aug. 25, 2026

(54) RIFAMYCIN ANALOGS AND ANTIBODY-DRUG CONJUGATES THEREOF

(71) Applicant: Regeneron Pharmaceuticals, Inc., Tarrytown, NY (US)

(72) Inventors: Thomas Nittoli, Orangeburg, NY (US); Seungyong Sean Choi, Bristol, PA (US); Mrinmoy Saha, Bristol, PA (US)

(73) Assignee: Regeneron Pharmaceuticals, Inc.

( * ) Notice: Subject to any disclaimer, the term of this patent is extended or adjusted under 35 U.S.C. 154(b) by 625 days.

(21) Appl. No.: 18/090,138

(22) Filed: Dec. 28, 2022

(65) Prior Publication Data

US 2023/0285581 A1 Sep. 14, 2023

Related U.S. Application Data

(63) Continuation of application No. 16/722,958, filed on Dec. 20, 2019, now Pat. No. 11,666,658.

(60) Provisional application No. 62/844,860, filed on May 8, 2019, provisional application No. 62/783,506, filed on Dec. 21, 2018.

(51) Int. Cl.

*C07D 498/18* (2006.01)
*A61K 47/68* (2017.01)

(52) U.S. Cl.

CPC ........ *C07D 498/18* (2013.01); *A61K 47/6803* (2017.08)

(58) Field of Classification Search

None

See application file for complete search history.

(56) References Cited

U.S. PATENT DOCUMENTS 11,666,658 B2 6/2023 Nittoli et al.
2024/0189319 A1* 6/2024 Nittoli .................... A61K 38/14

FOREIGN PATENT DOCUMENTS

| | | | |
|---|---|---|---|
| JP | S59231092 | A | 12/1984 |
| JP | S6345282 | A | 2/1988 |
| JP | H01175938 | A | 7/1989 |
| JP | H01207293 | A | 8/1989 |
| WO | 2016/090038 | A1 | 6/2016 |
| WO | 2017/152083 | A1 | 9/2017 |
| WO | 2019/217591 | A1 | 11/2019 |
| WO | 2020132483 | A1 | 6/2020 |

OTHER PUBLICATIONS

Dayan. Expert Review of Vaccines, 2016, vol. 15, No. 11, 1373-92 (Year: 2016).*

Argudin. Toxins, 2010, 2, 1761-1773 (Year: 2010).*

Domoto. JP 01-175938, published Jul. 1, 19892, machine translation thereof (Year: 1989).*

Bickel Hans et al.; "New derivatives of rifomycin antibiotics", Antimicrobial Agents and Chemotherapy, American Society for Microbiology, US, vol. 6, Jan. 1, 1966 (Jan. 1, 1966), pp. 352-358, XP009519333, ISSN: 0066-4804.

Kump Wilhelm et al.; "Zur Kenntnis von Rifamycin-S. Reaktionen des chinoiden Nucleus. Modifikationen von Antibiotica, 9. Mitteilung [1]", Helvetica Chimica Acta, Verlag Helvetica Chimica Acta, vol. 56, No. 7 Nov. 7, 1973 (Nov. 7, 1973), pp. 2348-2377, XP009519300, ISSN: 0018-019X, Doi: 10.1002/HLCA.19730560720.

International Preliminary Report on Patentability dated Jun. 16, 2021, from corresponding International application No. PCT/US2019/067914.

Communication (Written Opinion) issued by the International Searching Authority in International Application No. PCT/US19/67914 dated Jun. 25, 2020, 5 pages total.

International Search Reported and Written Opinion issued by the International Searching Authority in International Application No. PCT/US2022/021922 dated Jun. 9, 2022; 15 pages.

* cited by examiner

*Primary Examiner* — Noble E Jarrell

(74) *Attorney, Agent, or Firm* — Troutman Pepper Locke LLP

(57) ABSTRACT

The disclosure relates to rifamycin analog compounds, intermediates and precursors thereof, and pharmaceutical compositions capable of inhibiting bacterial growth (e.g., *S. aureus* growth) and treating bacterial infections (e.g., *S. aureus* infections). The disclosure further relates to antibody-drug conjugates of rifamycin analog compounds and antibodies, for example, antibodies specific for infectious disease-related targets such as membrane glycoprotein receptor (MSR1), wall teichoic acids (WTA) or Protein A, and methods of use thereof to inhibit bacterial growth and treat bacterial infections.

15 Claims, 7 Drawing Sheets

Specification includes a Sequence Listing.

RIFAMYCIN ANALOGS AND ANTIBODY-DRUG CONJUGATES THEREOF

CROSS-REFERENCE TO RELATED APPLICATIONS

This application claims priority to U.S. Utility application Ser. No. 16/722,958, filed on Dec. 20, 2019, now issued as U.S. Pat. No. 11,666,658, issued on Jun. 6, 2023, which claims priority to U.S. Provisional Applications Ser. No. 62/783,506, filed on Dec. 21, 2018, and 62/844,860, filed on May 8, 2019, the contents of which are incorporated herein by reference in their entirety.

FIELD OF DISCLOSURE

The present disclosure relates to rifamycin analog compounds and pharmaceutical compositions capable of inhibiting bacterial growth and treating bacterial infections, as well as antibody-drug conjugates of rifamycin analog compounds and antibodies, for example, antibodies specific for infectious disease-related targets, and methods of use thereof.

SEQUENCE LISTING

The instant application contains a Sequence Listing which has been submitted electronically in XML file format and is hereby incorporated by reference in its entirety. Said XML copy, created on May 9, 2023, is named 250298_000441_SL.xml and is 868,157 bytes in size.

BACKGROUND OF THE DISCLOSURE

*Staphylococcus aureus* (*S. aureus*) is a Gram-positive, round-shaped bacterium that is a member of the Firmicutes, and it is a usual member of the microbiota of the body, frequently found in the upper respiratory tract and on the skin. It is often positive for catalase and nitrate reduction and is a facultative anaerobe that can grow without the need for oxygen. Although *S. aureus* usually acts as a commensal of the human microbiota, it can also become an opportunistic pathogen, being a common cause of skin infections including abscesses, respiratory infections such as sinusitis, and food poisoning. Pathogenic strains often promote infections by producing virulence factors such as potent protein toxins, and the expression of a cell-surface protein that binds and inactivates antibodies.

An estimated 20% to 30% of the human population are long-term carriers of *S. aureus*, which can be found as part of the normal skin flora, in the nostrils, and as a normal inhabitant of the lower reproductive tract of women. *S. aureus* can cause a range of illnesses, from minor skin infections, such as pimples, impetigo, boils, cellulitis, folliculitis, carbuncles, scalded skin syndrome, and abscesses, to life-threatening diseases such as pneumonia, meningitis, osteomyelitis, endocarditis, toxic shock syndrome, bacteremia, and sepsis. It is still one of the five most common causes of hospital-acquired infections and is often the cause of wound infections following surgery. Each year, around 500,000 patients in hospitals of the United States contract a staphylococcal infection, chiefly by *S. aureus*. Up to 50,000 deaths each year in the USA are linked with *S. aureus* infections. Schlecht L M et al, 2015, *Microbiology,* 161, 1, 168-181. Despite much research and development, no vaccine for *S. aureus* has been approved at present.

Initially, the treatment of choice for *S. aureus* infection was penicillin. Antibiotic resistance in *S. aureus* was uncommon when penicillin was first introduced in 1943. By 1950, 40% of hospital *S. aureus* isolates were penicillin-resistant; by 1960, this had risen to 80%. Chambers H F, 2001, *Emerging Infectious Diseases,* 7, 2, 178-82. Today, *S. aureus* has become resistant to many commonly used antibiotics.

The emergence of antibiotic-resistant strains of *S. aureus* such as methicillin-resistant *S. aureus* (MRSA) is a worldwide problem in clinical medicine. MRSA strains are most often found associated with institutions such as hospitals, but are becoming increasingly prevalent in community-acquired infections. MRSA is one of a number of greatly feared strains of *S. aureus* which have become resistant to most β-lactam antibiotics. MRSA infections in both the hospital and community setting are commonly treated with non-β-lactam antibiotics, such as clindamycin (a lincosamine) and co-trimoxazole (also commonly known as trimethoprim/sulfamethoxazole). Resistance to these antibiotics has also led to the use of new, broad-spectrum anti-Gram-positive antibiotics, such as linezolid, because of its availability as an oral drug. First-line treatment for serious invasive infections due to MRSA is currently glycopeptide antibiotics (vancomycin and teicoplanin). A number of problems with these antibiotics occur, such as the need for intravenous administration (no oral preparation is available), toxicity, and the need to monitor drug levels regularly by blood tests. Also, glycopeptide antibiotics do not penetrate very well into infected tissues (this is a particular concern with infections of the brain and meninges and in endocarditis). Thus, there exists a strong unmet need for novel antibiotic treatments for *S. aureus* in general, and in addressing intracellular *S. aureus* infections in particular.

Rifamycins, a subclass of the ansamycin antibiotic family, are a group of antibiotics that are synthesized either naturally by the bacterium *Amycolatopsis rifamycinica* or artificially. Rifamycins are particularly effective against mycobacteria, and are therefore used to treat tuberculosis, leprosy, and *Mycobacterium avium* complex (MAC) infections. The rifamycin group includes the "classic" rifamycin drugs as well as the rifamycin analogs rifampicin (or rifampin), rifabutin, rifapentine, rifalazil and rifaximin. Rifamycin SV, sold under the trade name Aemcolo, is FDA-approved for treatment of travelers' diarrhea in some circumstances.

Rifamycin class antibiotics inhibit bacterial RNA polymerase (RNAP) and have potent activity against *S. aureus*. Monotherapy with this class of antibiotics, however, can lead to selection of a resistant population during treatment. Therefore, rifamycin antibiotics can be used in combination with first line antibiotics to improve outcomes, commonly in infections involving prostheses or foreign devices.

Macrophage scavenger receptor 1 (MSR1) is a single-pass, trimeric type II transmembrane glycoprotein pattern recognition receptor that mediates uptake of a series of negatively charged/polyanionic ligands, including modified low density lipoproteins (LDL) (Krieger, M. 1994. *Annu. Rev. Biochem.* 63:601-637; Platt, N. and S. Gordon. 2001. *J Clin Invest.* 108(5):649-654) and advanced glycation end products of bovine serum albumin (AGE-BSA) (Smedsrod et al. 1997. *Biochem J.* 322(Pt 2):567-573.) MSR1 receptors have been implicated in many macrophage-associated physiological and pathological processes including atherosclerosis, Alzheimer's disease, and host defense.

MSR1 expression was originally considered to be macrophage-specific. However, it has recently been demonstrated to be present on different classes of dendritic cells (Herber et al. 2010. *Nat. Med.* 16(8): 880-886). In addition, MSR1 appears to be expressed in endothelial cells and smooth muscle cells. It is internalized via coated pits at the cell surface and releases its ligand at acidic pH before being recycled back to the cell surface from the trans-Golgi apparatus (Doi et al. 1994. *Journal of Biological Chemistry; Mori, T.* 1994. Lab Invest.). It promotes conversion of monocyte-derived macrophages into foam cells, which is a critical step for atherosclerosis progression.

*S. aureus* is a facultative intracellular bacterium that can survive phagocytosis by macrophages and other cells types (Horn et al. 2018. Int. J. Med. Microbiol. 308(6): 607-624; Jubrail et al. 2016. Cell Microbiol. 18(1): 80-96; Mitchell et al. 2016. Microbiol. Spectr. 4(3)). Intravital imaging has demonstrated that macrophages can serve as a reservoir wherein *S. aureus* replicates and then seeds other organs during infection (Surewaard et al. 2016. J. Exp. Med. 213(7): 1141-51). Most antibiotics do not penetrate cells, including macrophages, very well, indicating that the intracellular *S. aureus* reservoir can evade treatment with standard of care antibiotics (Lehar et al. 2015. Nature. 527 (7578): 323-8). However, liposomal formulation of vancomycin increased penetration of the antibiotic into macrophages and reduced *S. aureus* organ burden more effectively than standard of care vancomycin (Surewaard et al. 2016. J. Exp. Med. 213(7): 1141-51). Together, these data indicate that delivering an antibiotic to macrophages may be an effective method to eliminate the intracellular *S. aureus* reservoir.

Teichoic acids are phosphate-rich molecules found on many glycan-binding proteins within the cell wall of most Gram-positive bacteria including *S. aureus*. Teichoic acids, as well as many other glycoproteins, form a thick layer of multiple peptidoglycan sheaths around the bacteria that not only stabilize the cell membrane but also provide many sites for other molecules to be attached to. Wall teichoic acids ("WTA") is one type of teichoic acids, which are covalently attached to peptidoglycan and extend through and beyond the cell wall. WTA can account for as much as 60% of the total cell wall mass in glycan-binding proteins. As a result, it presents a highly expressed cell surface antigen for Gram-positive bacteria including *S. aureus.*

*S. aureus* also expresses a number of surface determinant antigens, including the *S. aureus* Protein A (SpA) and polysaccharide poly-N-aceytlglucosamine (PNAG), iron-regulated surface determinant proteins IsdA, IsdB, IsdC, IsdE and IsdH, the clumping factor proteins ClfA and ClfB, capsular polysaccharide type (CP) 5 and CP8, the serine-aspartic acid repeat proteins SdrC, SdrD, and SdrE, fibronectin binding proteins A and B (FnBpA, FnBpB), Cna (collagen binding protein), and SasG (*S. aureus* surface protein G). These surface antigens play a role in colonization of host tissue, evasion of the host immune response, and bacterial fitness.

The development of ADCs comprising rifamycin analogs would thus allow for target-specific delivery of rifamycin analogs inside macrophage cells, or tethering of the rifamycin analogs onto the surface of the bacteria. Furthermore, such ADCs may provide improved activity against e.g., resistant bacterial targets, improved bioavailability, and improved therapeutic window. Therefore, there is a continuing need for effective treatments of antibiotic-resistant bacteria using antibody-drug conjugates of rifamycin analogs.

Thus, there exists a strong unmet need for developing effective analogs of rifamycin in order to combat the growing problem of antibiotic-resistant bacteria, including antibiotic-resistant *S. aureus* strains. MSR1 antibodies may provide a means for specific targeting of therapeutic molecules such as analogs of rifamycin to minimize unwanted side effects arising from systemic administration of such compounds as well as assist with these compounds' internalization into macrophage cells. Alternatively, conjugation to antibodies targeting a cell surface antigen (e.g., WTA, Protein A) may improve the therapeutic effects of the rifamycin analogs.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE DISCLOSURE

As discussed herein, there is a strong need to develop effective treatments for bacterial infections in general and *S. aureus* infections in particular. The present disclosure addresses these and other needs by providing new rifamycin analog compounds, intermediates and precursors thereof, antibody-drug conjugates, pharmaceutical compositions, and methods of treatment based on such compounds and pharmaceutical compositions.

Various non-limiting aspects and embodiments are described below.

In one aspect, the present disclosure provides a rifamycin analog compound, intermediate or precursor thereof having a structure of formula (A):

(A)

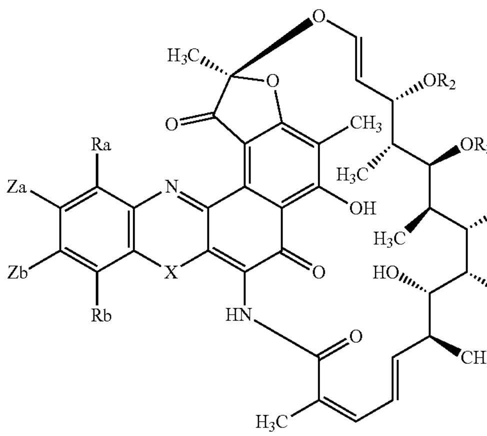

or a pharmaceutically acceptable salt thereof, wherein:

X is selected from —O— and —NR*—;

Za and Zb are independently selected from a hydrogen, —Cl, —Br, —$OR_1$ and —$R_N$; with the proviso that at least one of Za or Zb is not a hydrogen; wherein:

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

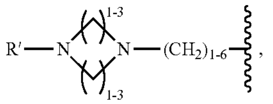

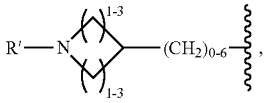

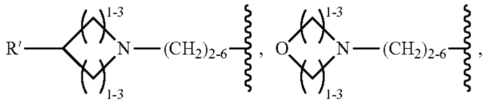

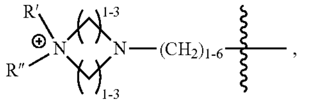

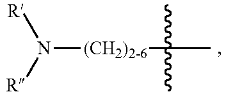

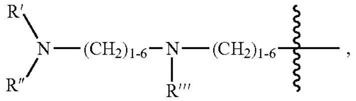

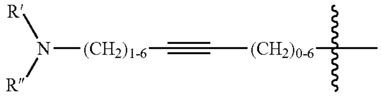

and

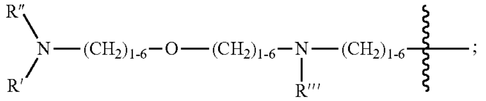

wherein the ~~~ symbol represents the point of attachment; and R', R" and R''' are selected from a hydrogen, a $C_1$-$C_6$ aliphatic hydrocarbon, and a protecting group selected from Fluorenylmethyloxycarbonyl (FMOC) and tert-Butyloxycarbonyl (BOC), or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one aspect, the present disclosure provides a rifamycin analog compound having a structure of formula (I):

(I)

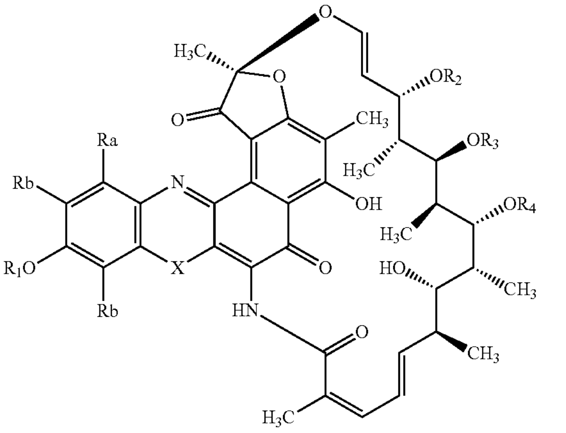

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

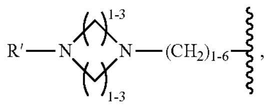

-continued

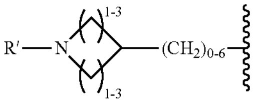

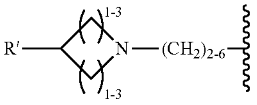

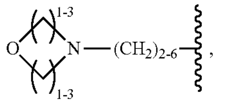

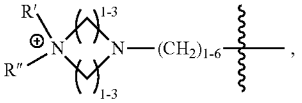

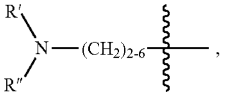

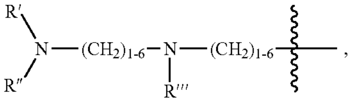

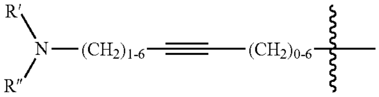

and

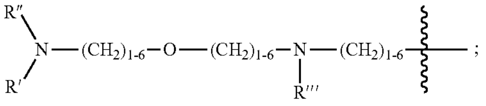

wherein the ∿∿∿ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —N(R*)$_2$, —N(R*)$_3^+$, —(C═O)—R*, —CHO, —$CO_2$H, —$CO_2$R*, —SR*, —$SO_2$R*, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2$H, —$CO_2$R* and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one aspect, the present disclosure provides a rifamycin analog compound having a structure of formula (I'):

(I')

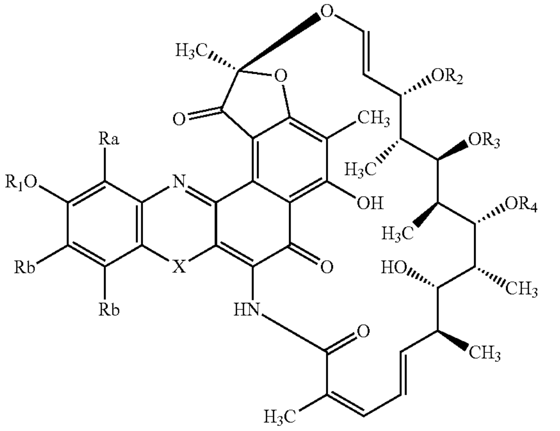

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —N(R*)$_2$, —N(R*)$_3^+$, —N(R*)—OH, —O—N(R*)$_2$, —N(R*)—O—R*, —CN, —NC, —(C═O)—R*, —CHO, —$CO_2$H, —$CO_2$R*, —(C═O)—S—R*, —O—(C═O)—H, —O—(C═O)—R*, —S—(C═O)—R*, —(C═O)—$NH_2$, —(C═O)—N(R*)$_2$, —(C═O)—$NHNH_2$, —O—(C═O)—$NHNH_2$, —(C═S)—$NH_2$, —(C═S)—N(R*)$_2$, —N(R*)—CHO, —N(R*)—(C═O)—R*, —SCN, —NCS, —NSO, —SSR*, —$SO_2$R*, —$SO_2$—N(R*)$_2$, —S(═O)—OR*, —S(═O)—R*, —Si(R*)$_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

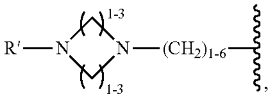

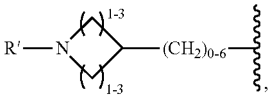

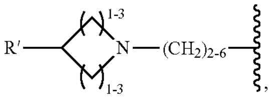

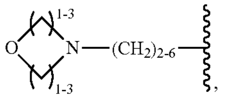

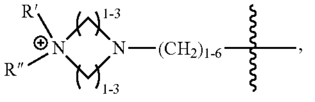

-continued

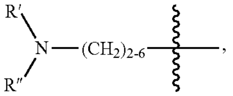,

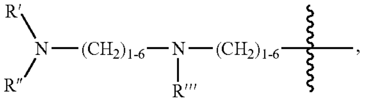,

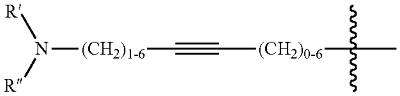 and

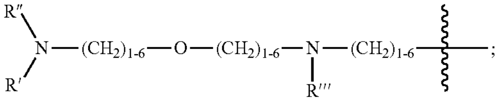;

wherein the symbol represents the point of attachment; and R', R'' and R''' are selected from a hydrogen, a $C_1$-$C_6$ aliphatic hydrocarbon, and a protecting group selected from $F_{MOC}$ and $B_{OC}$, or wherein R' and R'' together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In an embodiment of a compound of the formulas (A), (I), or (I'), X is —O—, $R_1$ is an aliphatic $C_1$-$C_3$ hydrocarbon, $R_2$ is a methyl group, $R_3$ is Ac (—(C═O)—$CH_3$), $R_4$ is a hydrogen, and $R_a$ is a hydrogen.

In an embodiment of a compound of the formulas (A), (I), or (I'), X is —O—, $R_1$ is a benzyl group, $R_2$ is a methyl group, $R_3$ is Ac (—(C═O)—$CH_3$), $R_4$ is a hydrogen; $R_a$ is a hydrogen and $R_b$ is hydrogen.

In an embodiment of a compound of the formulas (A), (I), or (I'), X is —O—, $R_1$ is an aliphatic $C_1$-$C_8$ hydrocarbon comprising 1-8 heteroatoms selected from O and N, $R_2$ is a methyl group, $R_3$ is Ac (—(C═O)—$CH_3$), $R_4$ is a hydrogen; $R_a$ is a hydrogen and $R_b$ is hydrogen.

In an embodiment of a compound of the formulas (A), (I), or (I'), X is —O—; $R_1$ is an aliphatic $C_1$-$C_8$ hydrocarbon substituted with one or more of —$NH_2$, —NHR*, —$N(R^*)_2$; R* is hydrogen or an aliphatic $C_1$-$C_3$ hydrocarbon; $R_2$ is a methyl group; $R_3$ is Ac (—(C═O)—$CH_3$); $R_4$ is a hydrogen; $R_a$ is a hydrogen and $R_b$ is hydrogen.

In an embodiment of a compound of the formulas (A), (I), or (I'), X is —$NCH_3$—, $R_1$ is —OH, $R_2$ is a methyl group, $R_3$ is Ac (—(C═O)—$CH_3$), $R_4$ is a hydrogen, $R_a$ is a hydrogen and $R_b$ is hydrogen.

In one embodiment, the rifamycin analog compounds of the disclosure have the structure of formula (II):

(II)

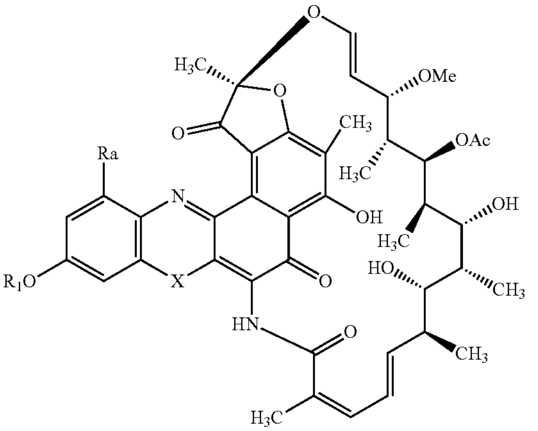

or a pharmaceutically acceptable salt thereof wherein:

X is selected from —O— and —NR*—;

$R_a$ is selected from hydrogen, —Cl, and —OR*;

$R_1$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with a proviso that $R_1$ is not an n-butyl group;

$R_N$ is selected from:

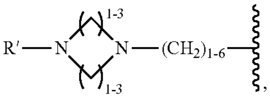,

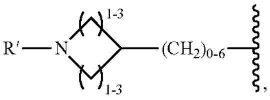,

-continued

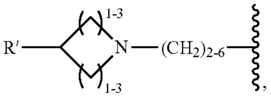,
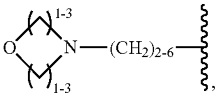,

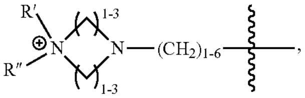,

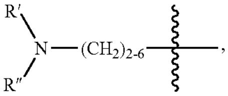,

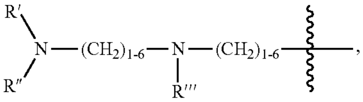,

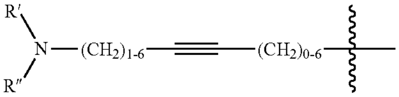 and

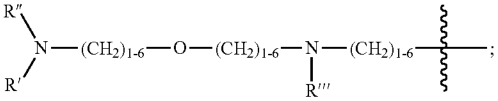;

wherein the ~~~ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (II'):

(II')

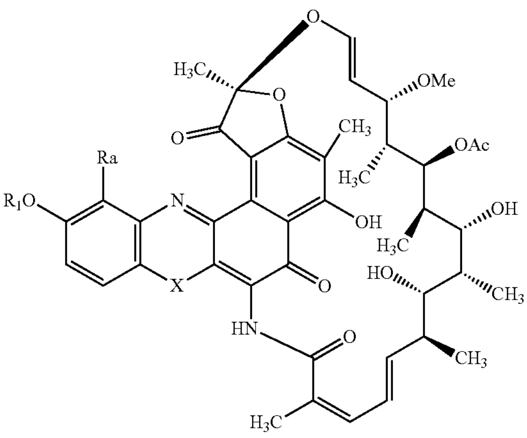

or a pharmaceutically acceptable salt thereof wherein:

X is selected from —O— and —NR*—;

$R_a$ is selected from hydrogen and —OR*;

$R_1$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—N$(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with a proviso that $R_1$ is not an n-butyl group;

$R_N$ is selected from:

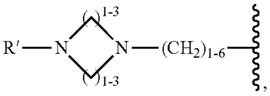,

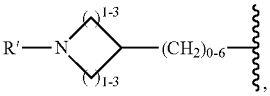,

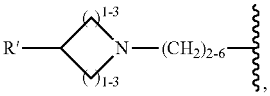,
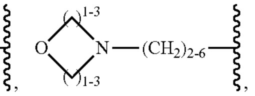,

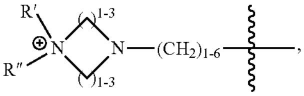,

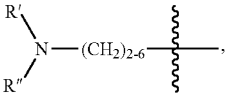,

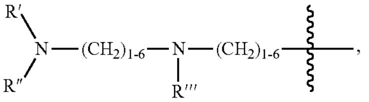,

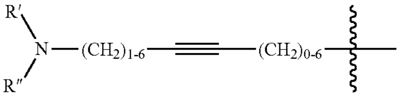 and

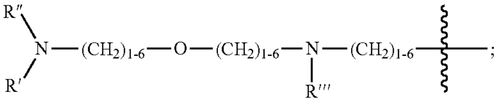;

wherein the ~~~ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (III):

(III)

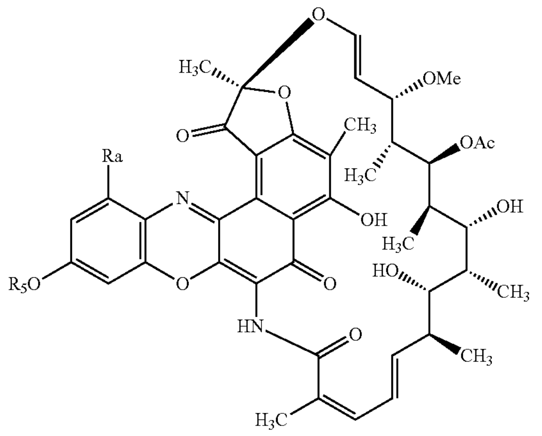

or a pharmaceutically acceptable salt thereof wherein:

$R_a$ is selected from hydrogen and —OR*;

$R_5$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —$N(R^*)$—(C═O)—R*, —(C═O)—R*, —CHO, —$CO_2H$, —$CO_2R^*$ and combinations thereof, with a proviso that $R_5$ is not an n-butyl group;

R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, and $R_N$ is selected from:

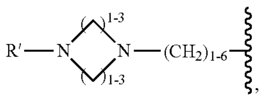,
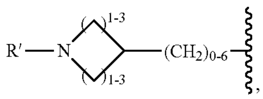,
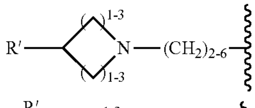,
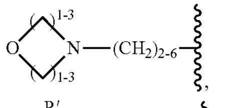,
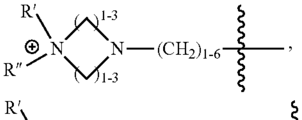,
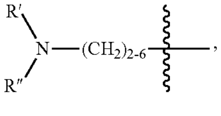,
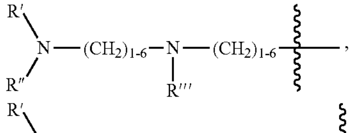,
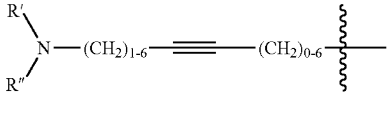 and -continued

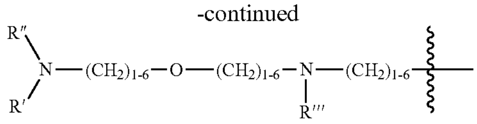;

wherein the symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure.

In one embodiment, the rifamycin analog compounds of the disclosure have the structure of formula (III'):

(III')

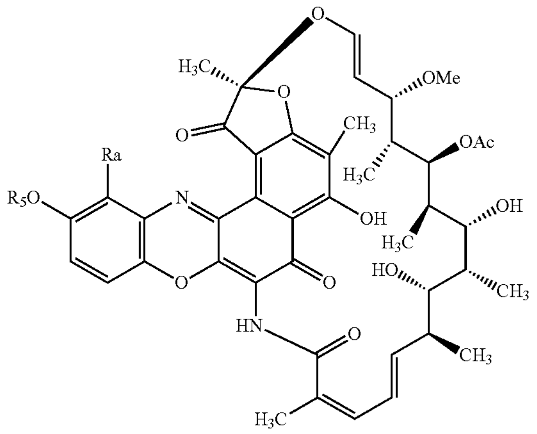

or a pharmaceutically acceptable salt thereof wherein:

$R_a$ is selected from hydrogen and —OR*;

$R_5$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —$N(R^*)$—(C═O)—R*, —(C═O)—R*, —CHO, —$CO_2H$, —$CO_2R^*$ and combinations thereof, with a proviso that $R_5$ is not an n-butyl group;

R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, and $R_N$ is selected from:

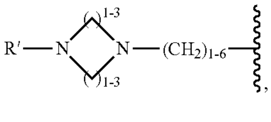,

-continued

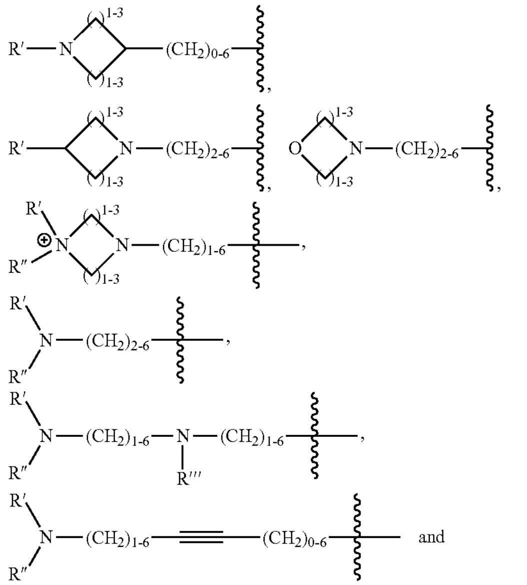

and

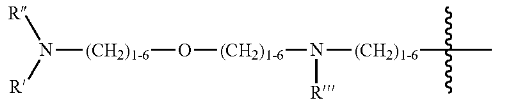

wherein the ~~~ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure.

In one embodiment, the rifamycin analog compounds of the disclosure have the structure of formula (IV):

(IV)

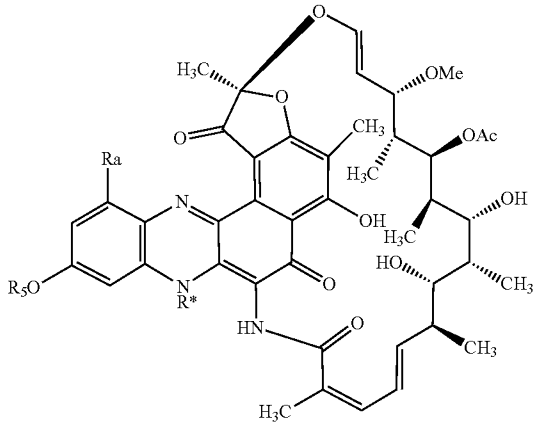

or a pharmaceutically acceptable salt thereof wherein:

$R_a$ is selected from hydrogen and —OR*;

$R_5$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof;

$R_N$ is selected from:

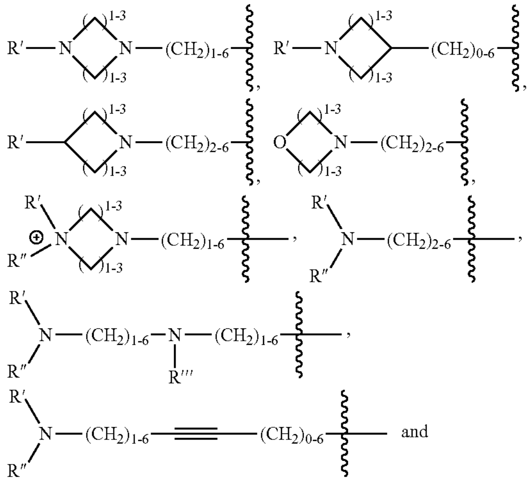

and

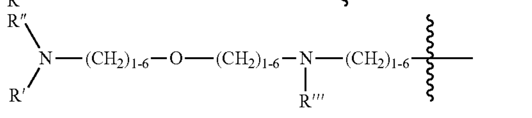

wherein the ~~~ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (IV'):

(IV')

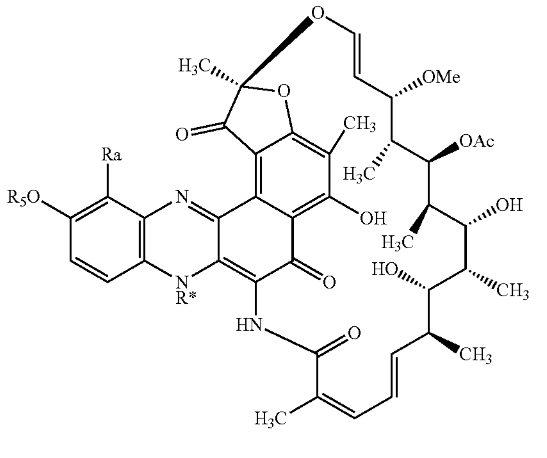

or a pharmaceutically acceptable salt thereof wherein:

$R_a$ is selected from hydrogen and —OR*;

$R_5$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof;

$R_N$ is selected from:

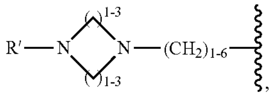
,

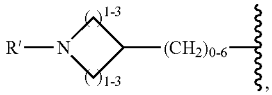
,

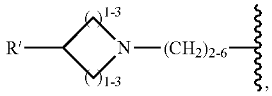
,
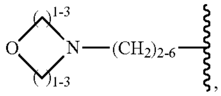
,

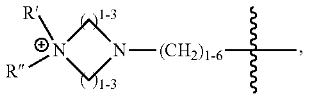

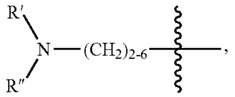

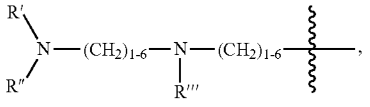

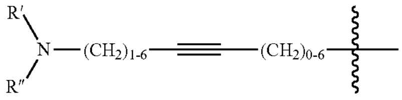
and

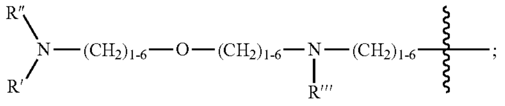

wherein the ~~~ symbol represents the point of attachment; and R', R" and R''' are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (V):

(V)

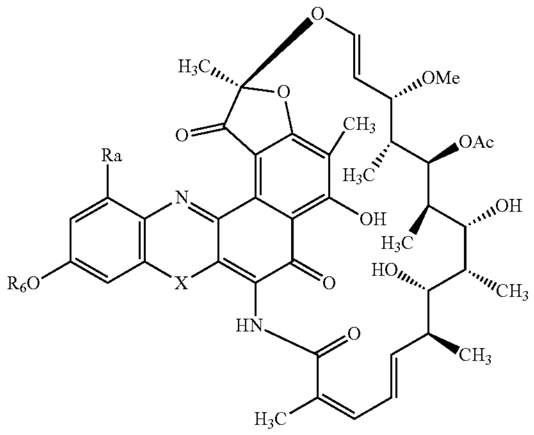

or a pharmaceutically acceptable salt thereof wherein:

X is selected from —O— and —NR*—;

$R_a$ is selected from hydrogen and —OR*;

$R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_6$ is optionally substituted with one or more of —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof, with a proviso that $R_6$ is not an n-butyl group;

$R_N$ is selected from:

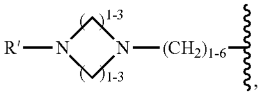
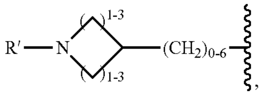
,

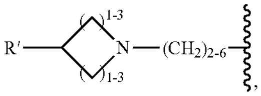
,
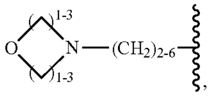
,

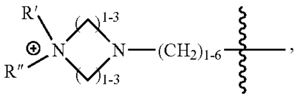
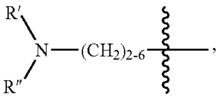

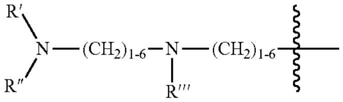

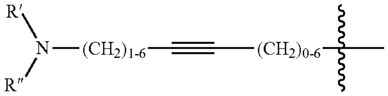
and

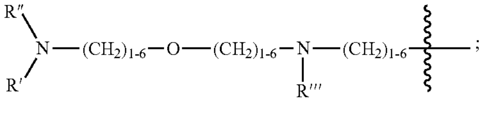

wherein the ~~~ symbol represents the point of attachment; and R', R" and R''' are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (V'):

(V')

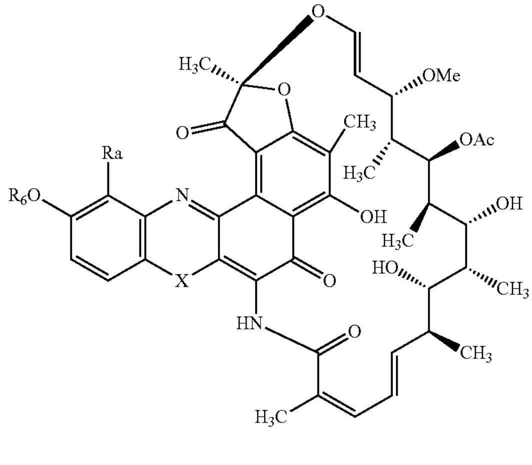

or a pharmaceutically acceptable salt thereof wherein:

X is selected from —O— and —NR*—;

$R_a$ is selected from hydrogen and —OR*;

$R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, each of which further comprises 0-8 heteroatoms selected from halogen, O, N, and S, and wherein $R_6$ is optionally substituted with one or more of —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof, with a proviso that $R_6$ is not an n-butyl group;

$R_N$ is selected from:

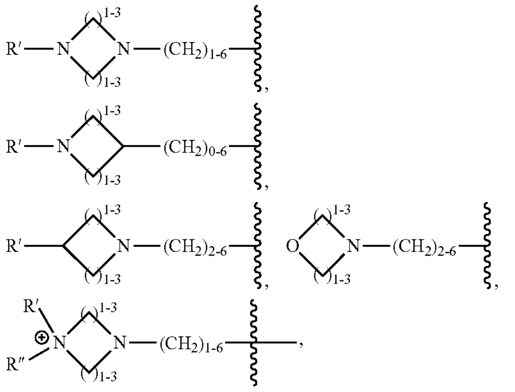

-continued

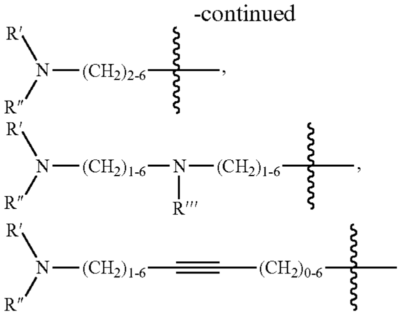

and

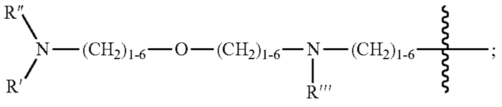

wherein the ~~~~ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a rifamycin analog compound, intermediate or precursor thereof having a structure of formula (B):

(B)

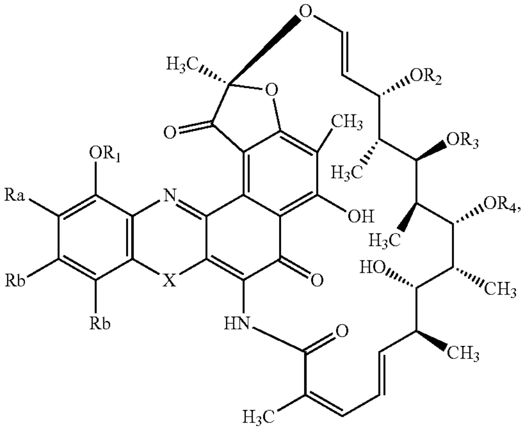

or a pharmaceutically acceptable salt thereof, wherein:

X is selected from —O— and —NR*—;

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—N(R*)$_2$, —N(R*)—O—R*, —CN, —NC, —(C═O)—R*, —CHO, —CO$_2$H, —CO$_2$R*, —(C═O)—S—R*, —O—(C═O)—H, —O—(C═O)—R*, —S—(C═O)—R*, —(C═O)—NH$_2$, —(C═O)—N(R*)$_2$, —(C═O)—NHNH$_2$, —O—(C═O)—NHNH$_2$, —(C═S)—NH$_2$, —(C═S)—N(R*)$_2$, —N(R*)—CHO, —N(R*)—(C═O)—R*, —SCN, —NCS, —NSO, —SSR*, —SO$_2$R*, —SO$_2$—N(R*)$_2$, —S(═O)—OR*, —S(═O)—R*, —Si(R*)$_3$, —CF$_3$, —O—CF$_3$ and combinations thereof, with the provisos that $R_1$ is not an n-butyl group, and when X is —O— and Ra is hydrogen, $R_1$ is not hydrogen;

$R_N$ is selected from:

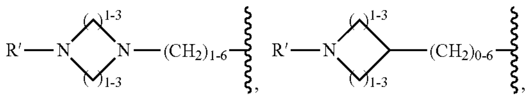
,
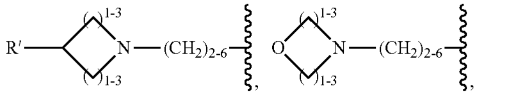
,
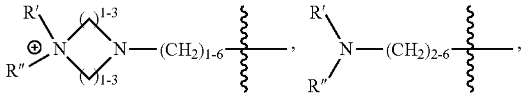
,
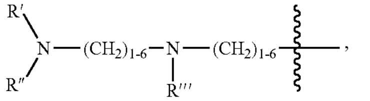
,
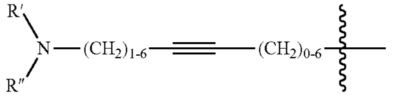
and
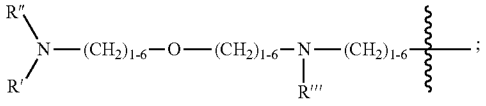
;

wherein the ∿∿ symbol represents the point of attachment; and R', R" and R'" are selected from a hydrogen, a $C_1$-$C_6$ aliphatic hydrocarbon, and a protecting group selected from Fluorenylmethyloxycarbonyl (FMOC) and tert-Butyloxycarbonyl (BOC), or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, —NH$_2$, —NHR*, —N(R*)$_2$, —N(R*)$_3^+$, —(C═O)—R*, —CHO, —CO$_2$H, —CO$_2$R*, —SR*, —SO$_2$R*, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —CO$_2$H, —CO$_2$R* and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a rifamycin analog compound having a structure of formula (B-1):

(B-1)

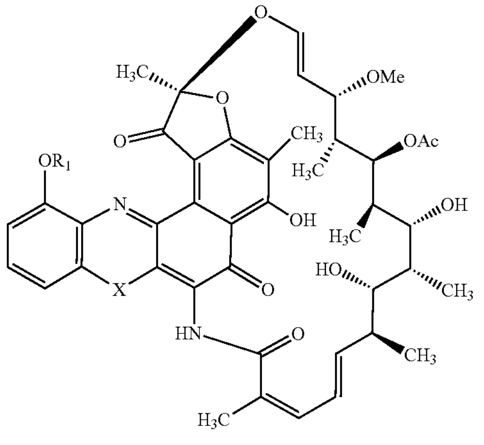

or a pharmaceutically acceptable salt thereof wherein:

X is selected from —O— and —NR*—;

$R_1$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —NO$_2$, —NO$_3$, —O—NO, —N$_3$, —NH$_2$, —NHR*, —N(R*)$_2$, —N(R*)$_3^+$, —N(R*)—OH, —O—N(R*)$_2$, —N(R*)—O—R*, —CN, —NC, —(C═O)—R*, —CHO, —CO$_2$H, —CO$_2$R*, —(C═O)—S—R*, —O—(C═O)—H, —O—(C═O)—R*, —S—(C═O)—R*, —(C═O)—NH$_2$, —(C═O)—N(R*)$_2$, —(C═O)—NHNH$_2$, —O—(C═O)—NHNH$_2$, —(C═S)—NH$_2$, —(C═S)—N(R*)$_2$, —N(R*)—CHO, —N(R*)—(C═O)—R*, —SCN, —NCS, —NSO, —SSR*, —SO$_2$R*, —SO$_2$—N(R*)$_2$, —S(═O)—OR*, —S(═O)—R*, —Si(R*)$_3$, —CF$_3$, —O—CF$_3$ and combinations thereof, with a proviso that $R_1$ is not an n-butyl group;

$R_N$ is selected from:

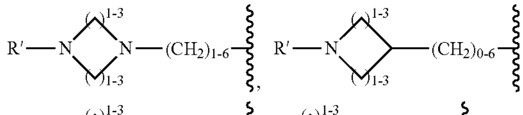
,
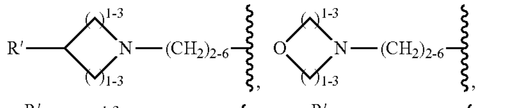
,
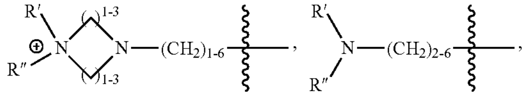
,

-continued

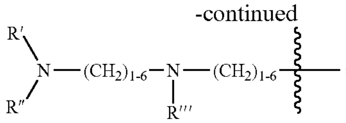

,

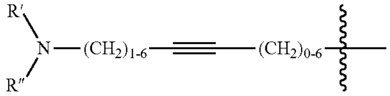

and

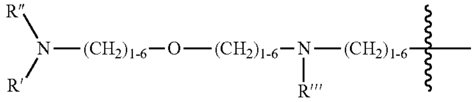

;

wherein the ~~~ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a rifamycin analog compound having a structure of formula (B-2):

(B-2)

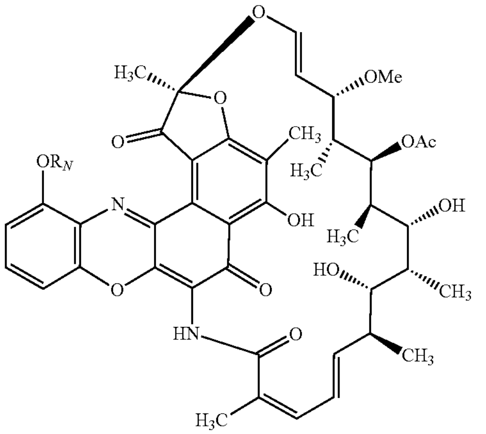

or a pharmaceutically acceptable salt thereof wherein:

$R_N$ is selected from:

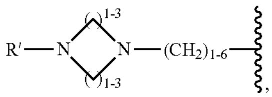

,

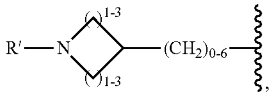

,

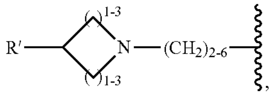

,

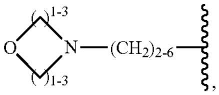

,

-continued

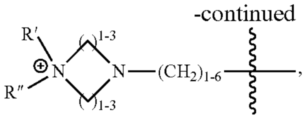

,

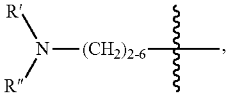

,

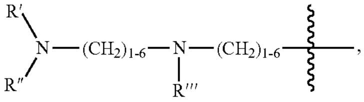

,

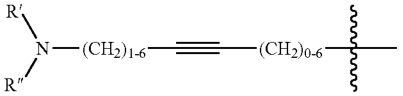

and

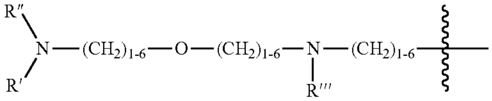

wherein the ~~~ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure.

In another aspect, the present disclosure provides a rifamycin analog compound having a structure of formula (B-2):

(B-2)

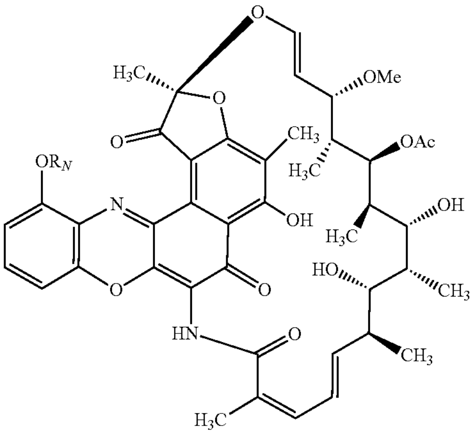

or a pharmaceutically acceptable salt thereof wherein:

$R_N$ is

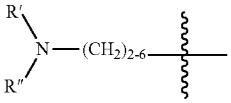

wherein the ~~~ symbol represents the point of attachment; and R' and R" are selected from a hydrogen and a $C_1$-$C_6$ aliphatic hydrocarbon.

In one embodiment, a rifamycin analog compound has a structure according to the following formula:

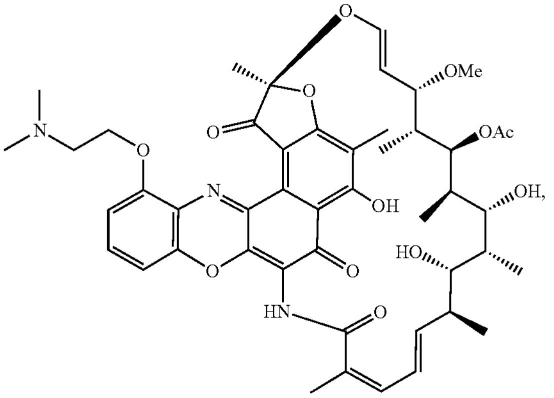 [SMILES: CO[C@H]1/C=C/O[C@@]2(C)Oc3c(C)c(O)c4c(=O)c(c5oc6cccc(OCCN(C)C)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

or a pharmaceutically acceptable salt thereof.

In an embodiment of any of the preceding formulas is provided a compound wherein $R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-3 heteroatoms selected from O and N, and wherein $R_1$ is optionally substituted with one or more of —F, —Cl, —Br, —I, —OH, $C_{1-3}$ alkoxide, $—NH_2$, —NHR*, $—N(R^*)_2$, $—N(R^*)_3^+$, —N(R*)—OH, $—O—N(R^*)_2$, —N(R*)—O—R*, —N(R*)—(C═O)—R*, —(C═O)—R*, —CHO, $—CO_2H$, $—CO_2R^*$, —O—(C═O)—H, —O—(C═O)—R*, $—(C═O)—NH_2$, $—(C═O)—N(R^*)_2$, $—Si(R^*)_3$, $—CF_3$, $—O—CF_3$ and combinations thereof, with the provisos that $R_1$ is not an n-butyl group, and when X is —O—, $R_1$ is not hydrogen.

In an embodiment of any of the preceding formulas is provided a compound wherein $R_1$ is a combination of an aliphatic $C_1$-$C_{20}$ hydrocarbon and an aromatic $C_1$-$C_{20}$ hydrocarbon.

In an embodiment of any of the preceding formulas is provided a compound wherein $R_1$ is a combination of an aliphatic $C_1$-$C_{20}$ hydrocarbon and a heteroaromatic $C_1$-$C_{20}$ hydrocarbon.

In an embodiment of any of the preceding formulas is provided a compound wherein $R_1$ is selected from:

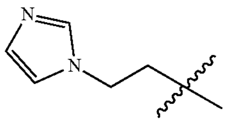
,
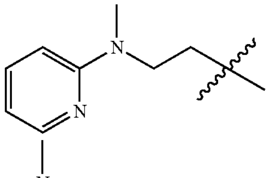
, and
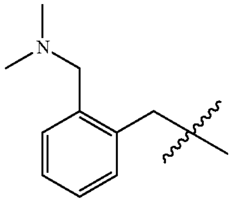
.

In an embodiment of any of the preceding formulas is provided a compound wherein $R_1$ is an aliphatic $C_1$-$C_{20}$ hydrocarbon substituted with one or more of $—NH_2$, —NHR*, $—N(R^*)_2$, or —N(R*)—(C═O)—R*.

In an embodiment of any of the preceding formulas is provided a compound wherein $R_1$ is an aliphatic $C_1$-$C_{20}$ hydrocarbon substituted with $—NH—(C═O)—CH_3$ or $—N(CH_3)—(C═O)—CH_3$.

In an embodiment of any of the preceding formulas is provided a compound wherein $R_a$ is hydrogen.

In an embodiment of any of the preceding formulas is provided a compound wherein $R_a$ is —OH.

In an embodiment of any of the preceding formulas is provided a compound wherein $R_a$ is —Cl.

In an embodiment of any of the preceding formulas is provided a compound wherein $R_a$ is —OR*, and R* is selected from an aliphatic $C_1$-$C_{20}$ hydrocarbon, an aromatic $C_1$-$C_{20}$ hydrocarbon, and combinations thereof.

In an embodiment of any of the preceding formulas is provided a compound wherein $R_N$ is selected from:

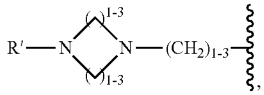
,
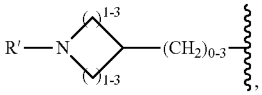
,
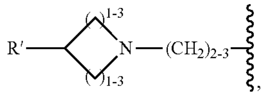
,
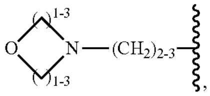
,
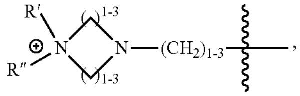
,
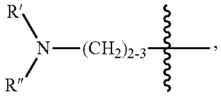
,
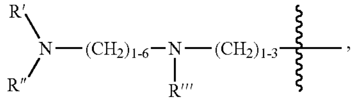
,
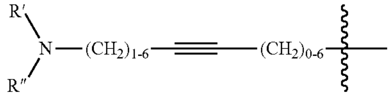
and
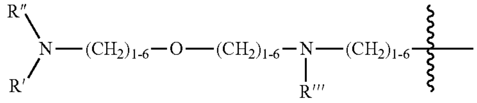
;

wherein the ∿∿ symbol represents the point of attachment; and R', R" and R"' are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure.

In an embodiment of any of the preceding formulas is provided a compound wherein $R_N$ is selected from:

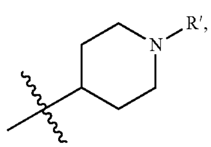
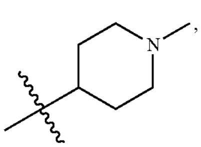
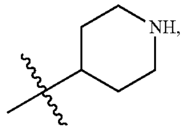
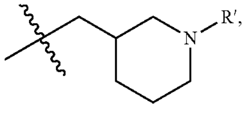

-continued

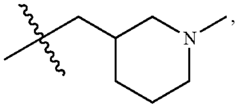 , 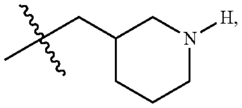

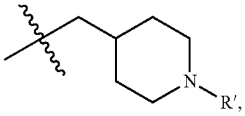 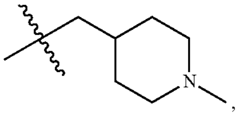

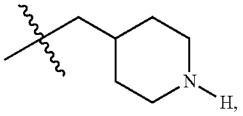

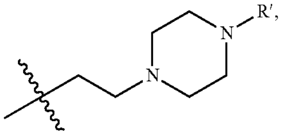

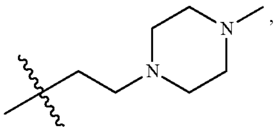

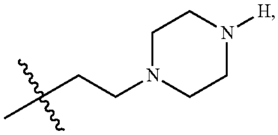 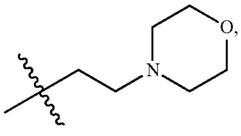

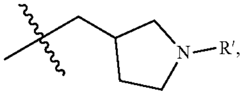 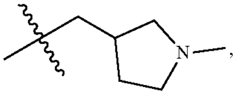

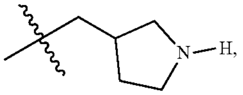 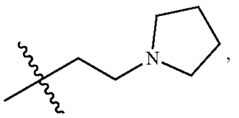

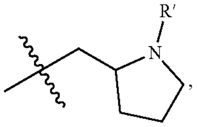 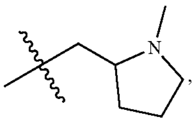

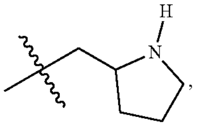 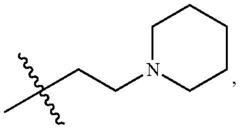

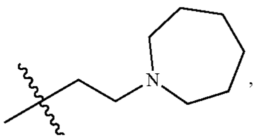 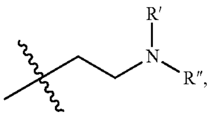

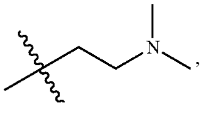 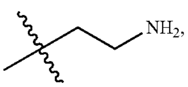

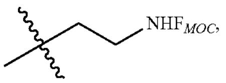 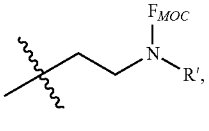

-continued

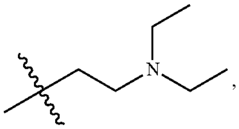 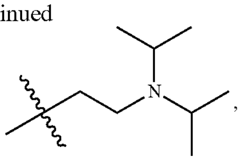

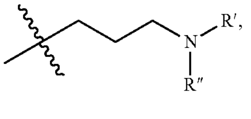 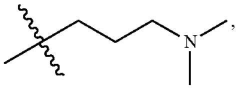

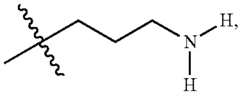 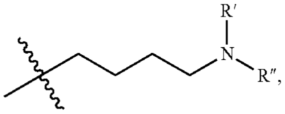

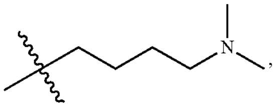

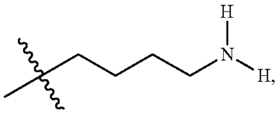

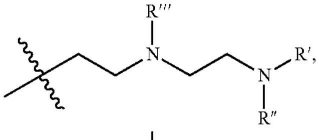

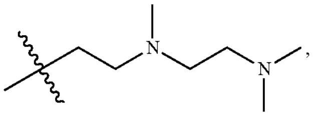

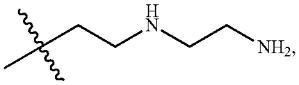

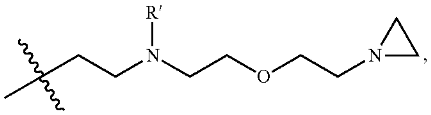

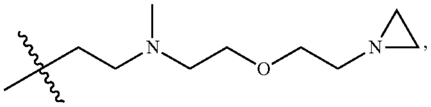

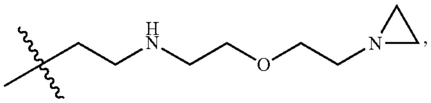

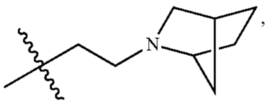 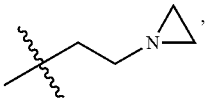 , and

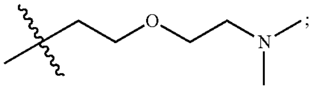

wherein R' is hydrogen, aliphatic hydrocarbon or a protecting group, and wherein the ~~~~ symbol represents the point of attachment.

In an embodiment of a compound of any of the preceding formulas is provided a compound wherein R* is independently at each occurrence selected from hydrogen, an aliphatic $C_1$-$C_6$ hydrocarbon, an aromatic $C_4$-$C_6$ hydrocarbon, and combinations thereof, which optionally comprise 1-3 heteroatoms selected from O, N and combinations thereof.

In one embodiment, a rifamycin analog compound of the disclosure has a structure selected from the group consisting of:
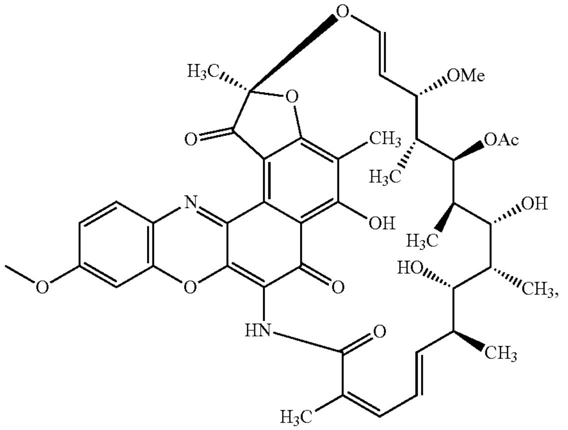
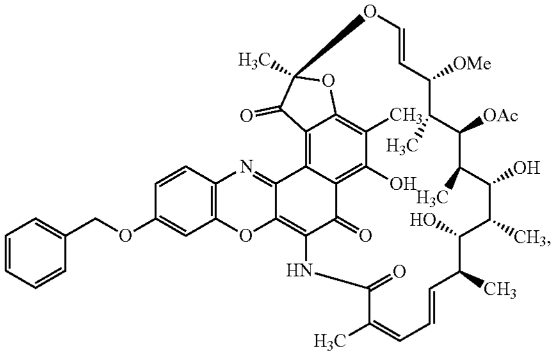
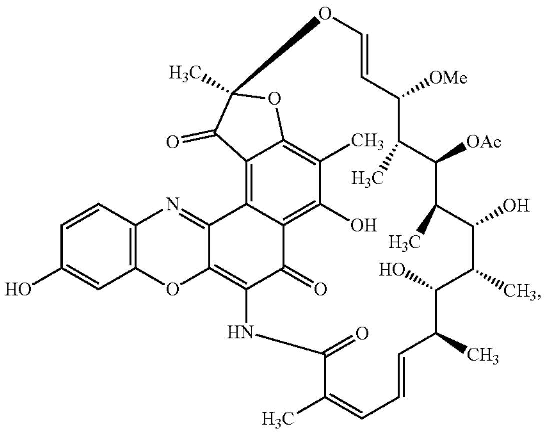
-continued
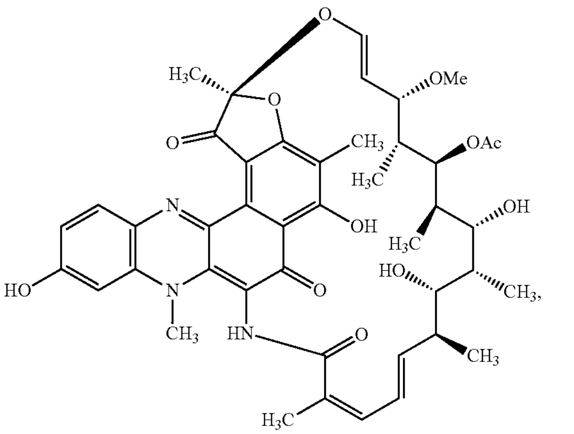
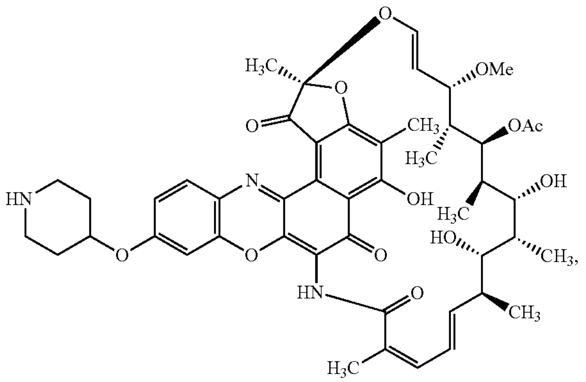
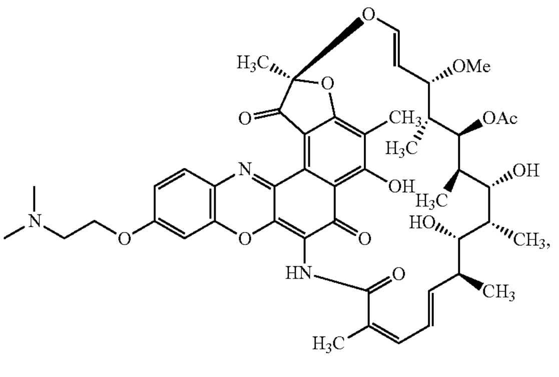
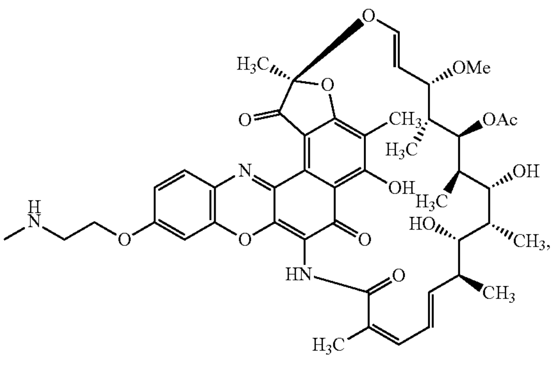

-continued
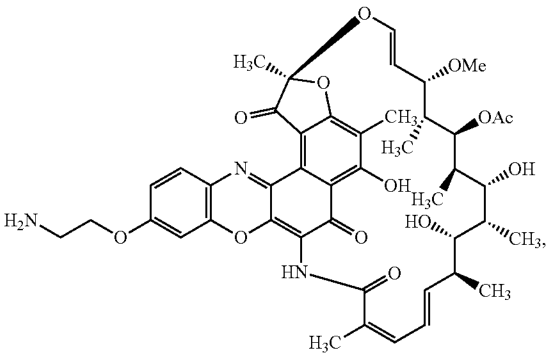
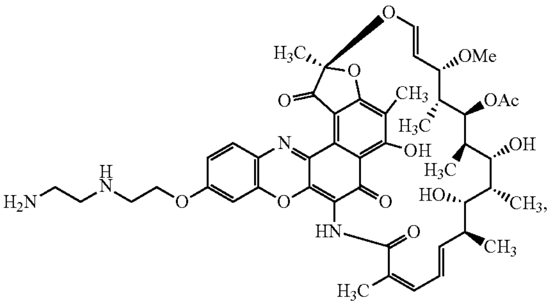
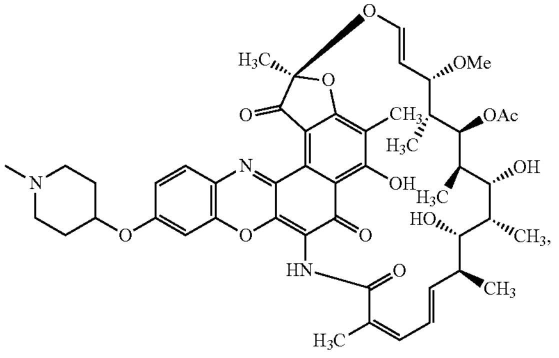
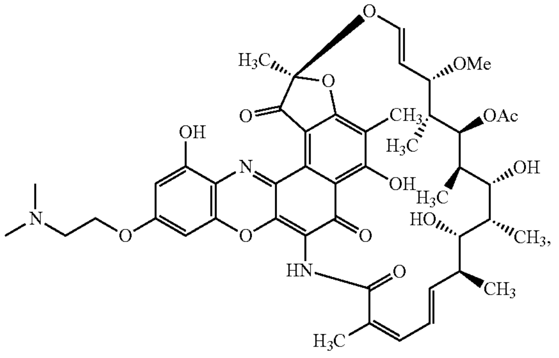
-continued
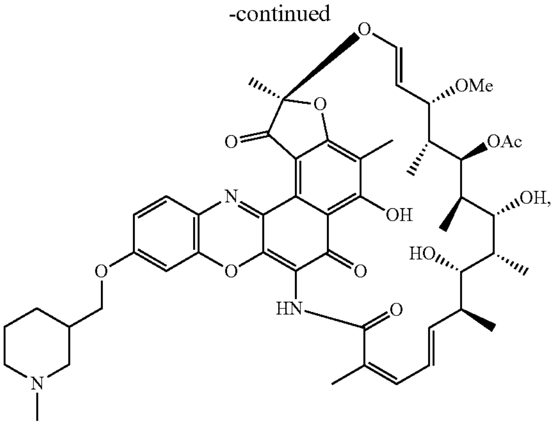
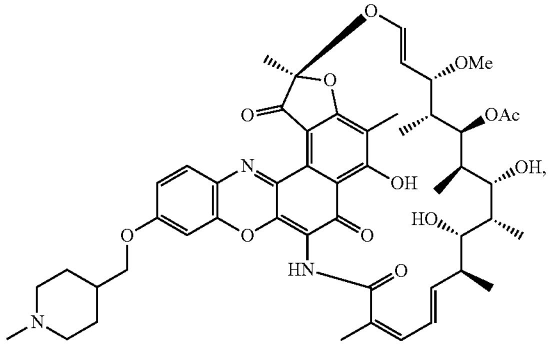
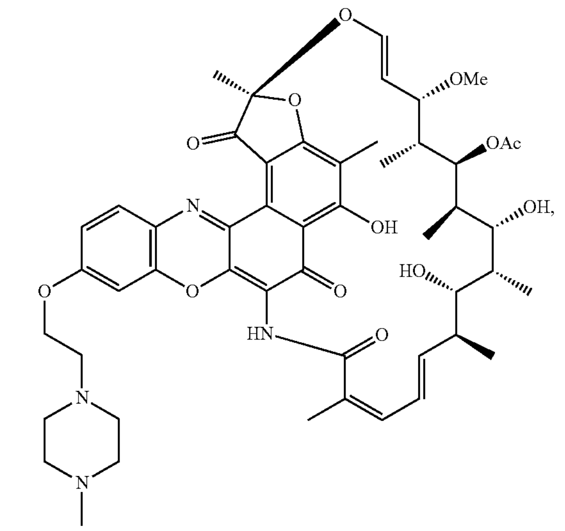

-continued
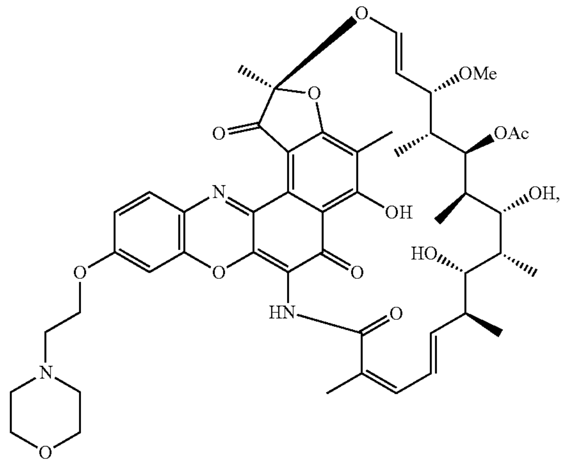
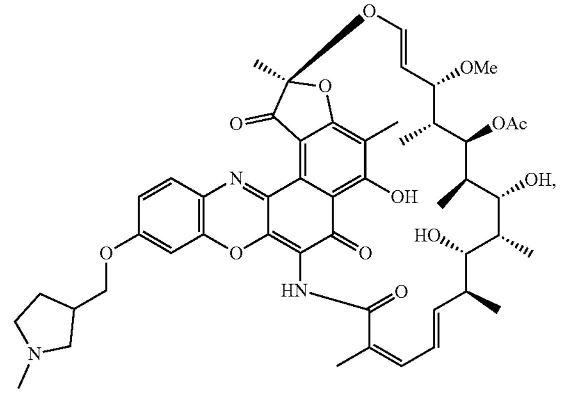
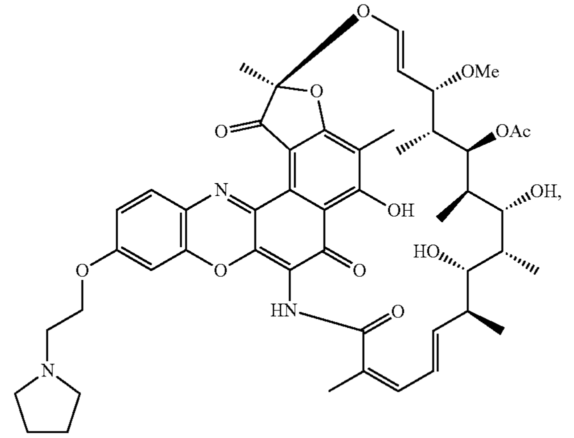
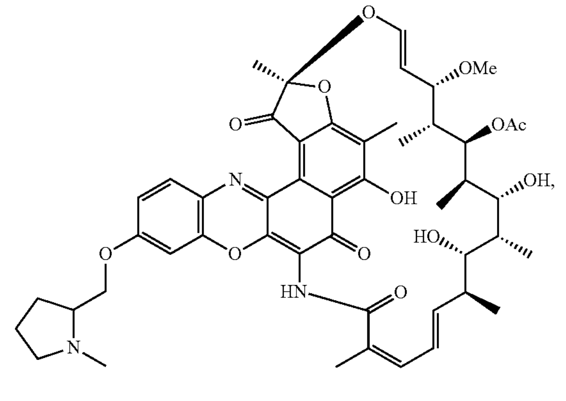
-continued
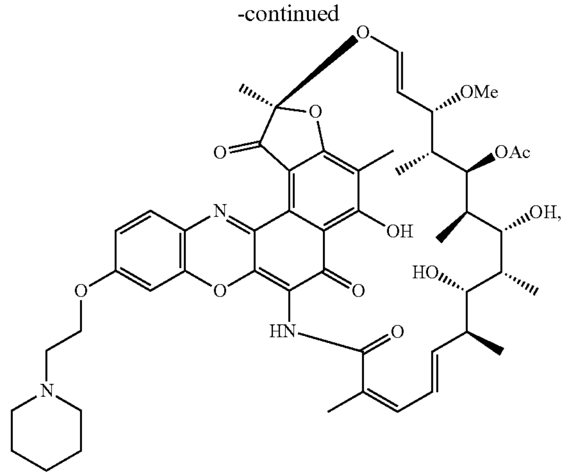
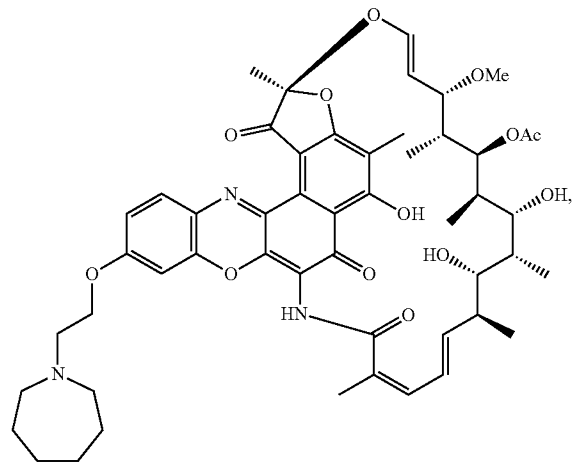
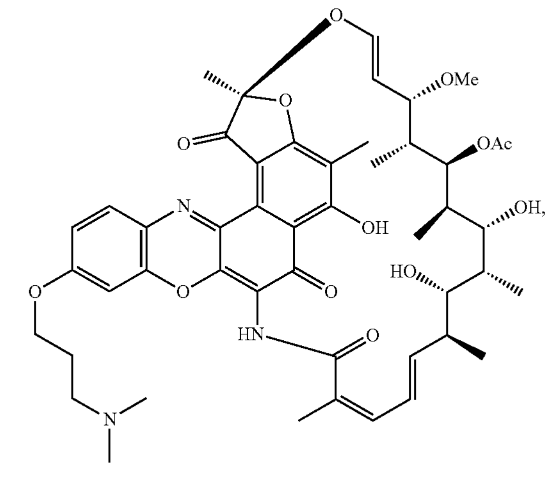

-continued
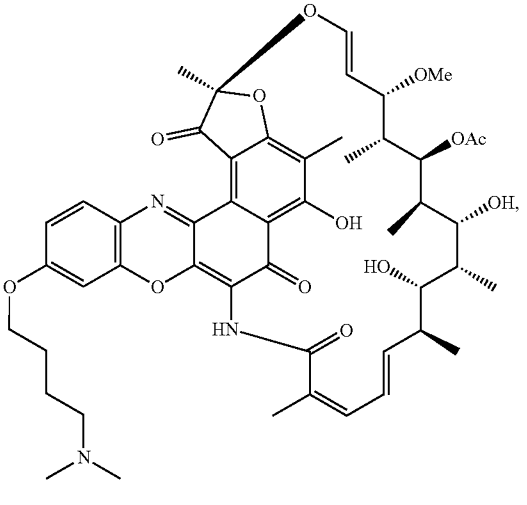
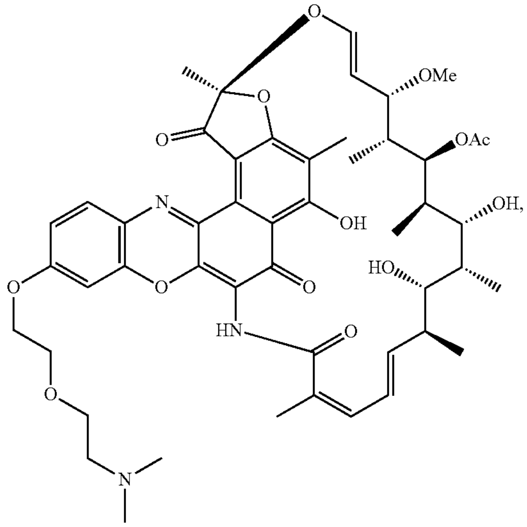
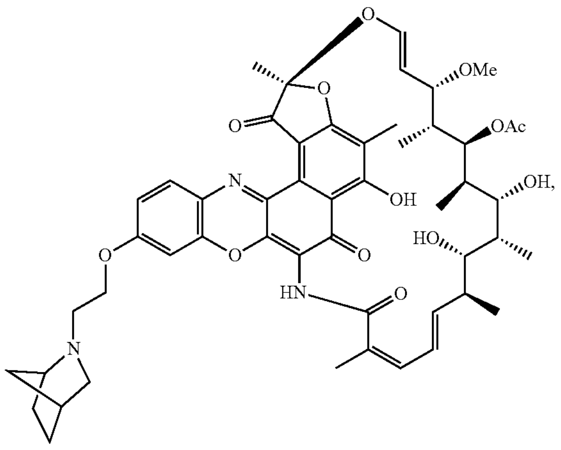
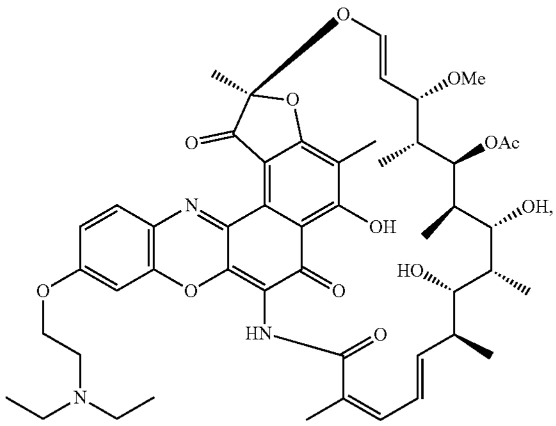
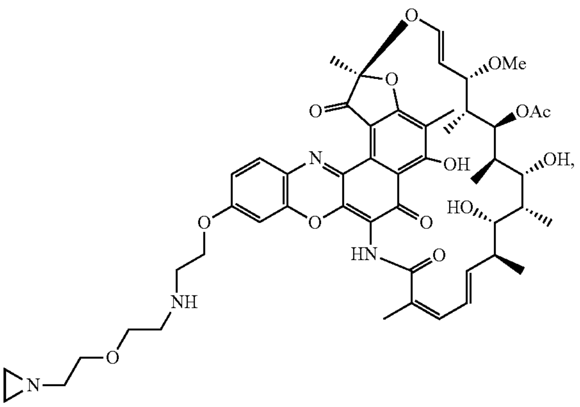
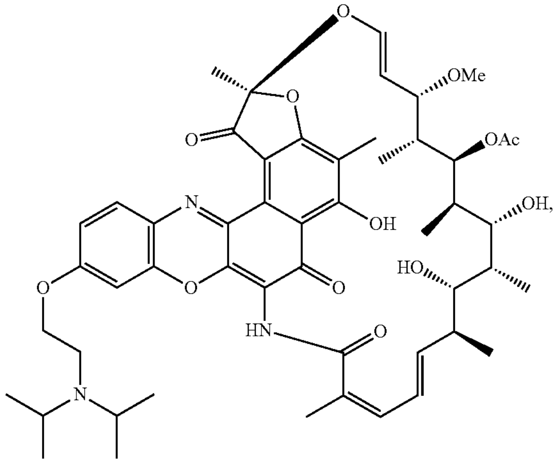

-continued
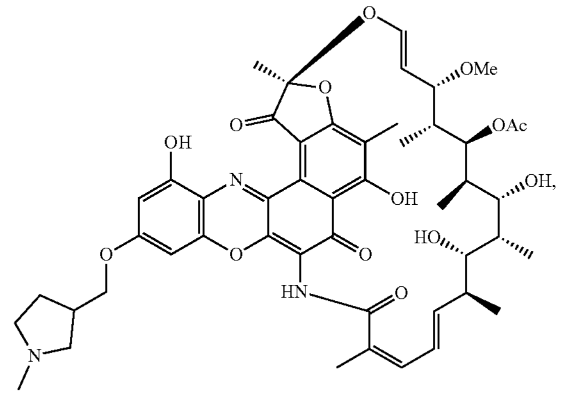
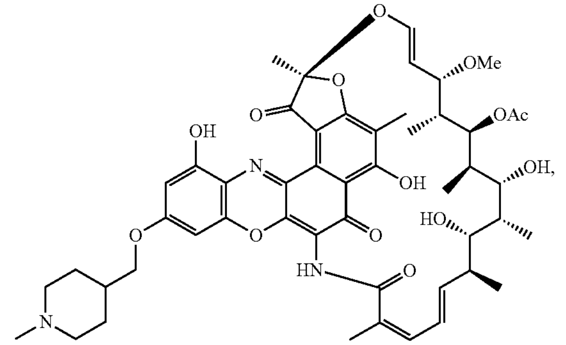
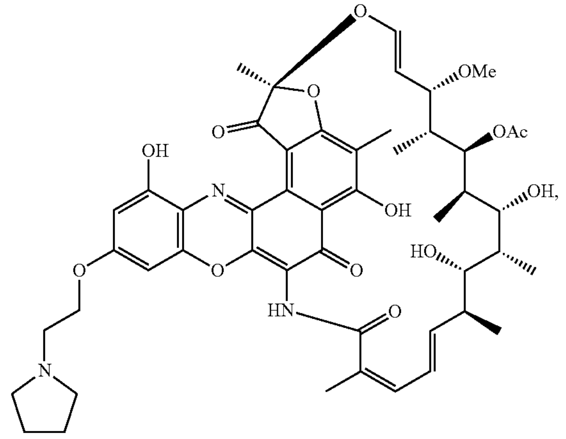
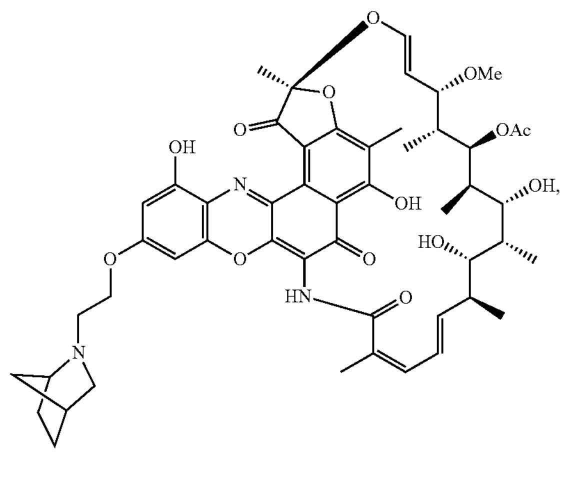
-continued
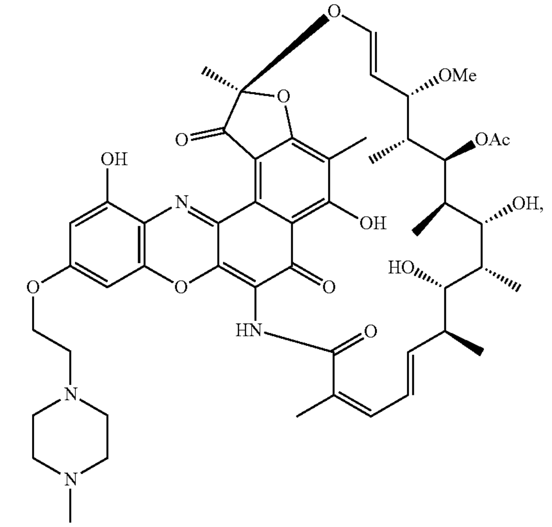
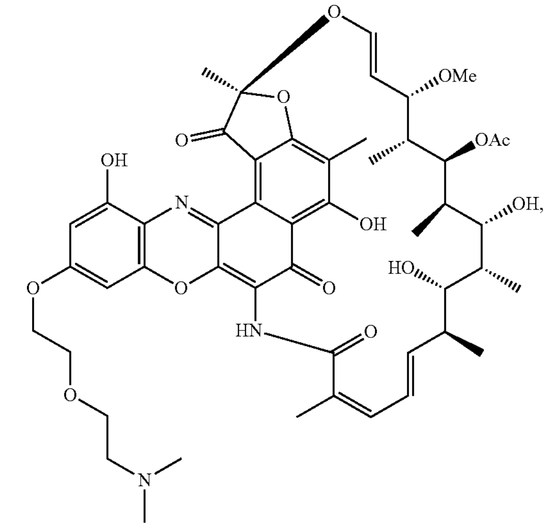
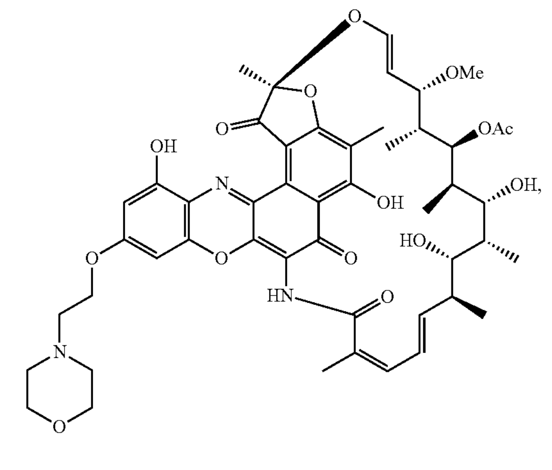

-continued
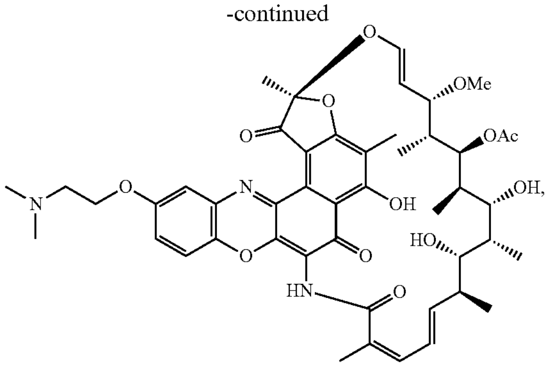
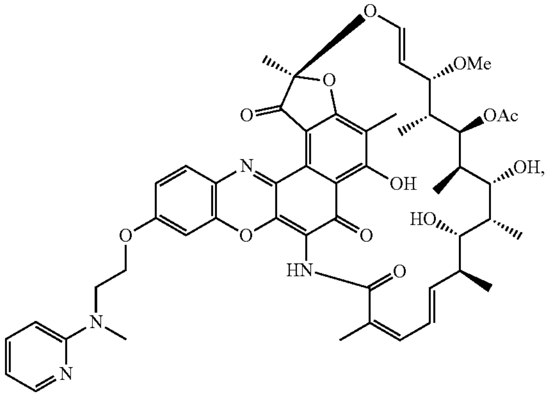
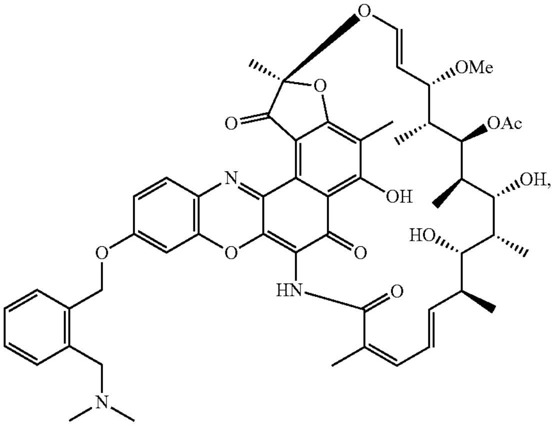
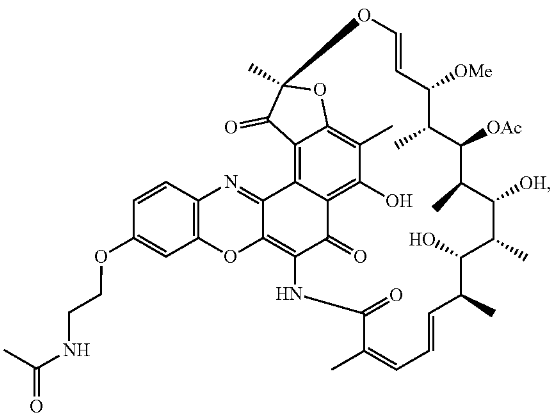
-continued
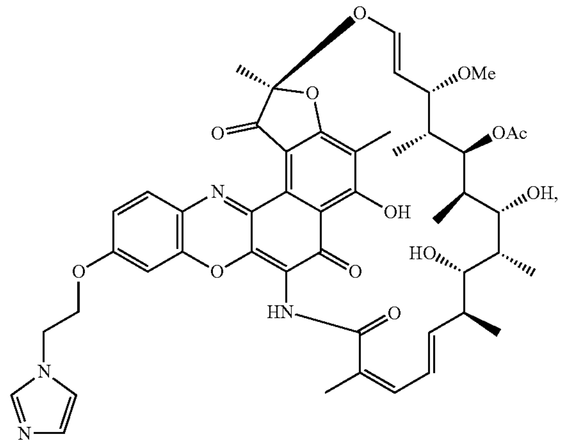
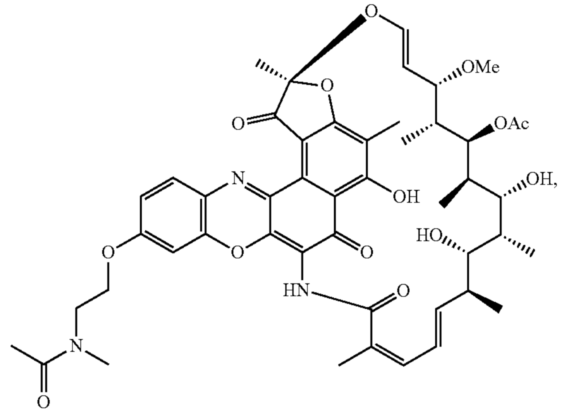
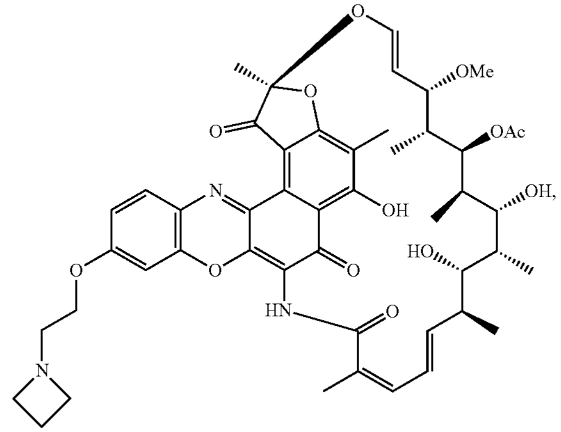
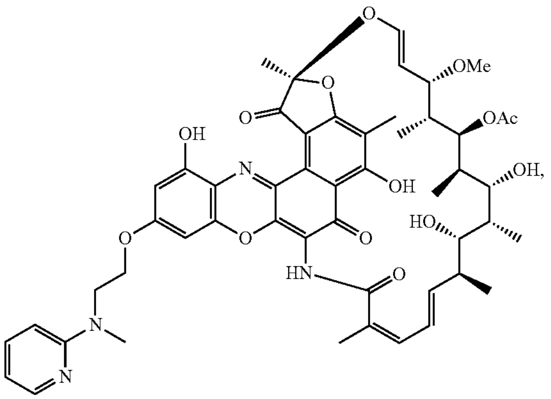

-continued
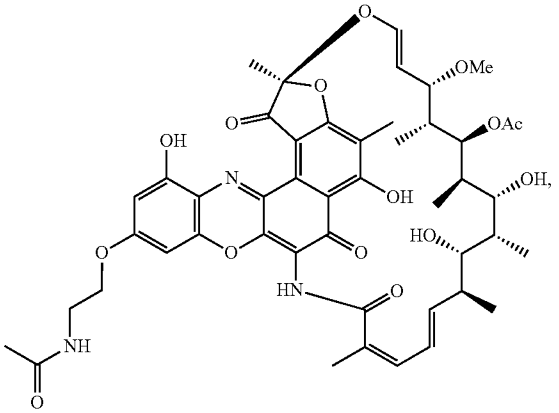
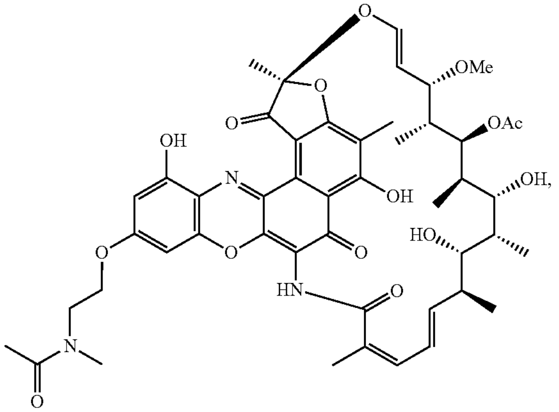
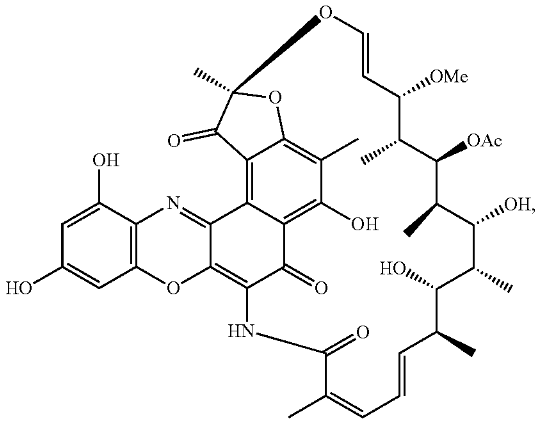
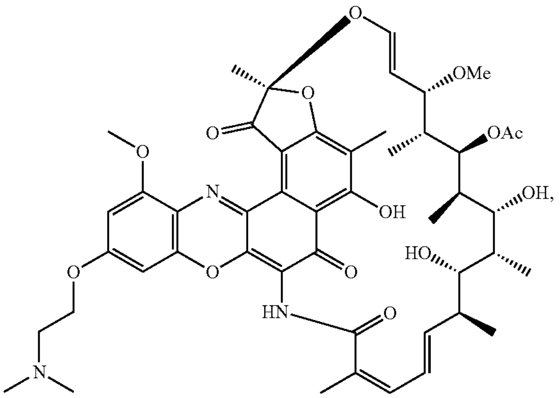
-continued
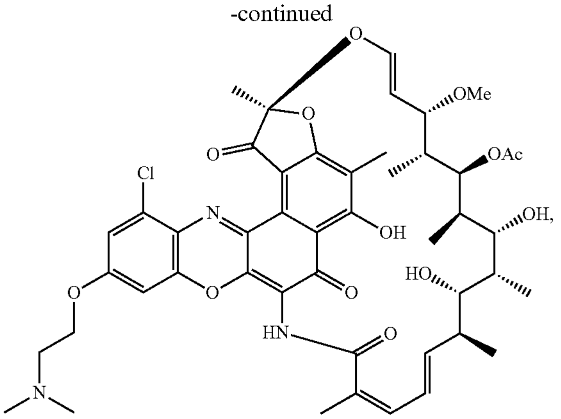
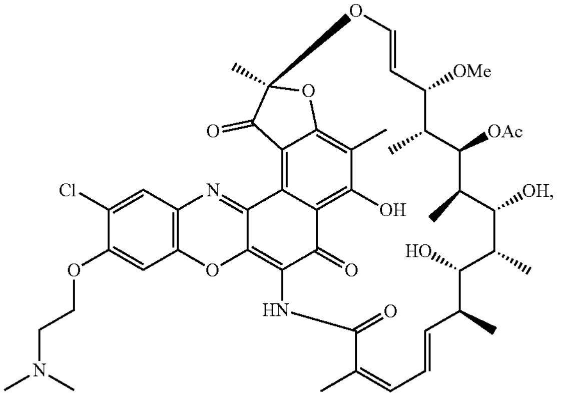
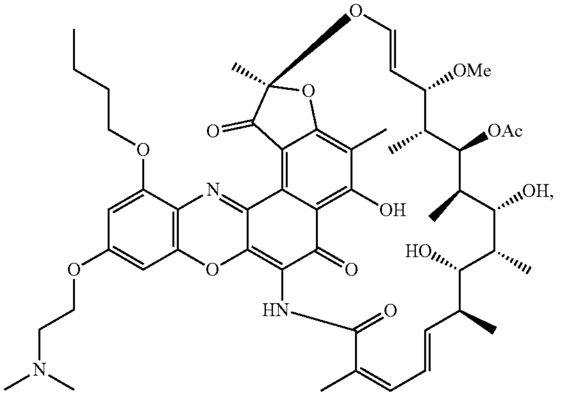
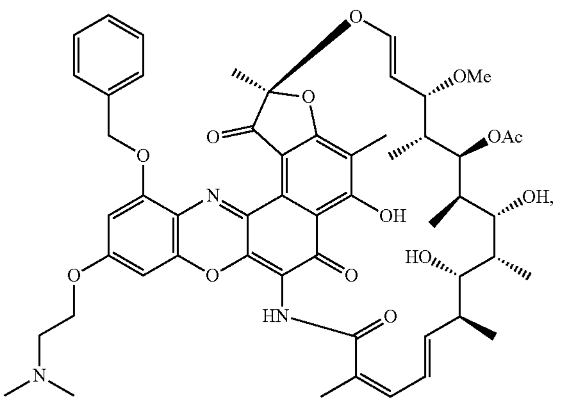

-continued
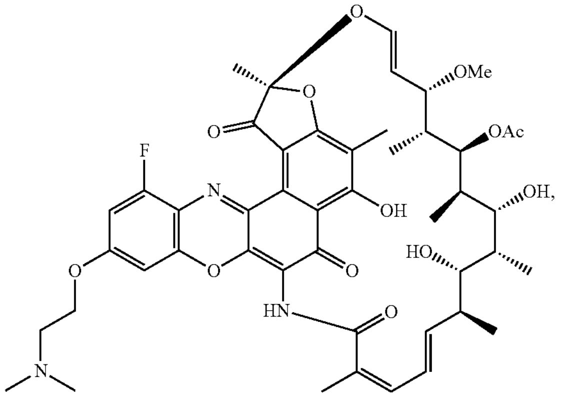
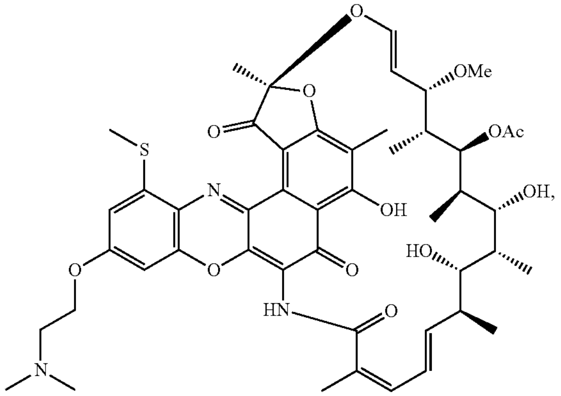
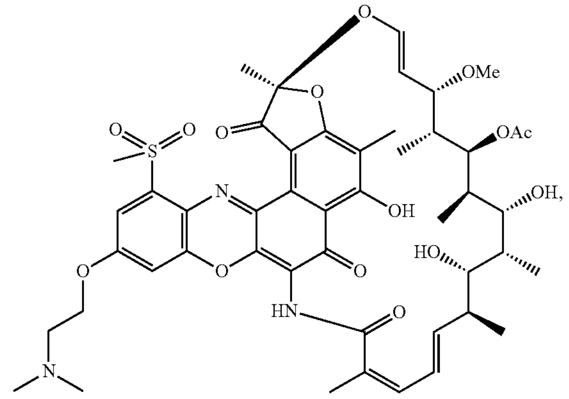
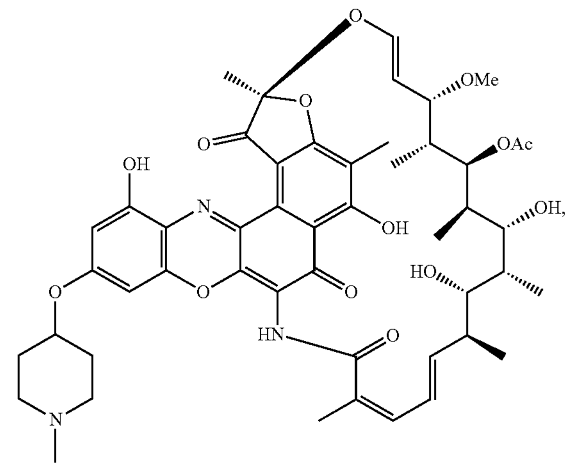
-continued
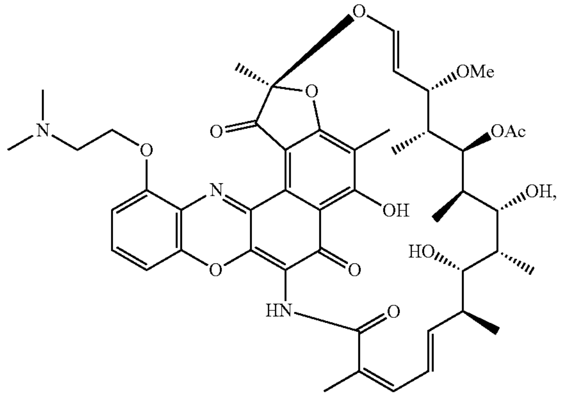
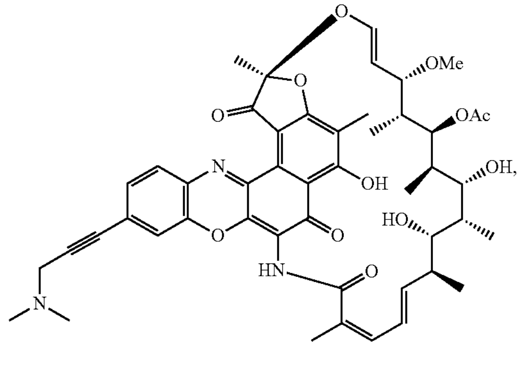
and
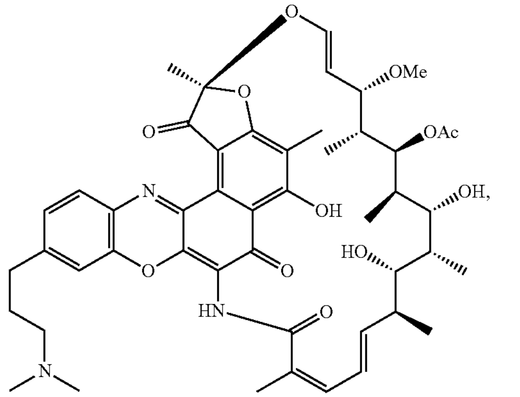
or a pharmaceutically acceptable salt thereof.
In one embodiment, a rifamycin analog compound of the disclosure has a structure selected from the group consisting of

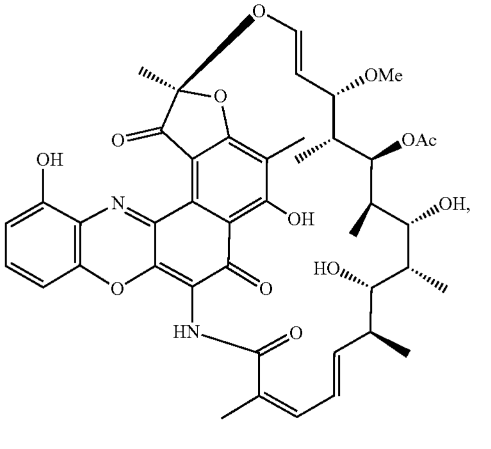

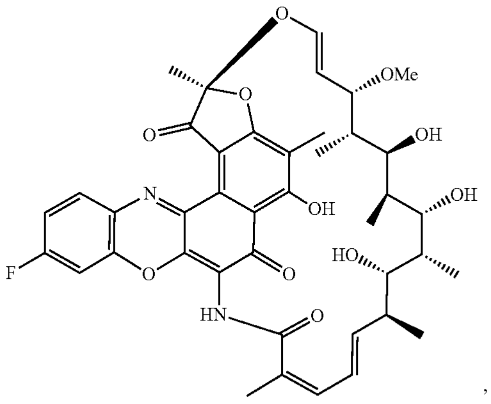

, and

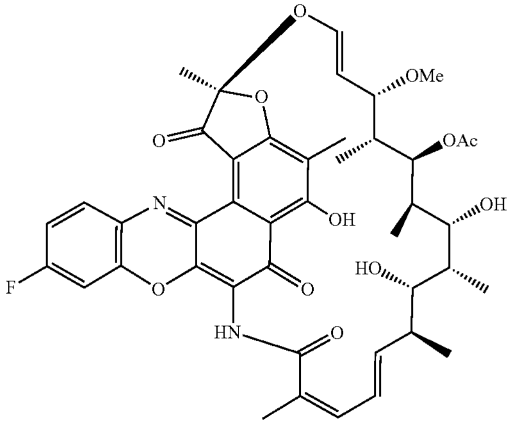

or a pharmaceutically acceptable salt thereof.

In one aspect, the present disclosure provides a method of manufacturing a rifamycin analog compound having the structure of formula (V):

(V)

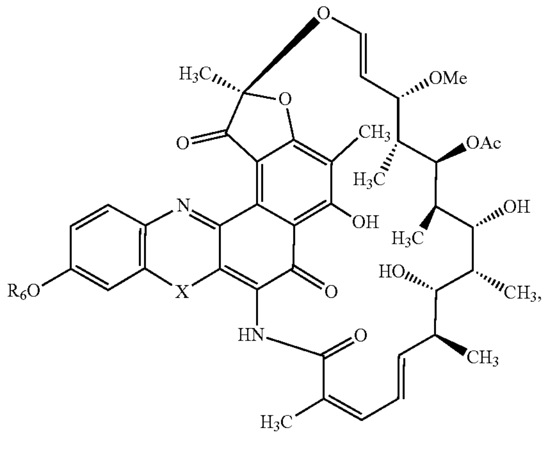

wherein X is selected from —O— and NR*—;

$R_6$ is selected from a $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, $R_N$ is selected from:

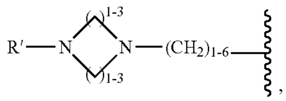
,
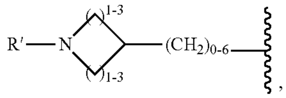
,
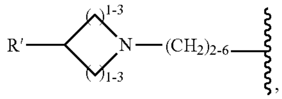
,
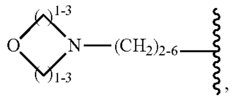
,
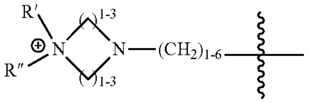
,
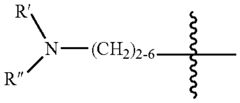
,
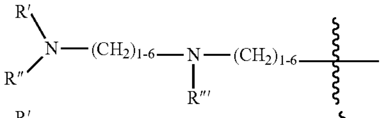
,
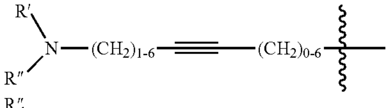
and
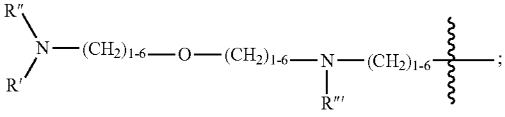
;

wherein the ~~~ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R"

together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising the steps of:

(a) contacting Rifamycin S having the structure:

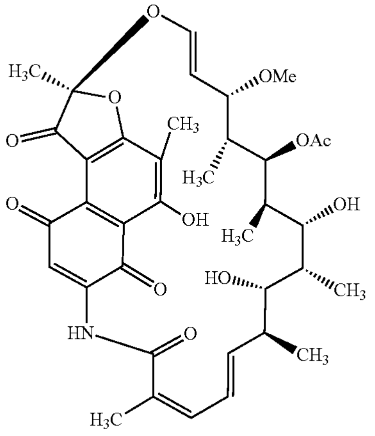 [SMILES: CO[C@H]1/C=C/O[C@@]2(C)Oc3c(C)c(O)c4c(c3C2=O)C(=O)C=C(NC(=O)/C(C)=C\C=C\[C@H](C)[C@H](O)[C@@H](C)[C@@H](O)[C@@H](C)[C@H](OC(C)=O)[C@@H]1C)C4=O]

with a compound having the structure of formula (VI):

(VI)

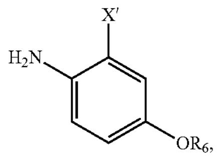

wherein X' is selected from —OH and —NHR*, and (b) treating the product of step (a) with an oxidizing agent.

In one aspect, the present disclosure provides a method of manufacturing a rifamycin analog compound having the structure of formula (V'):

(V')

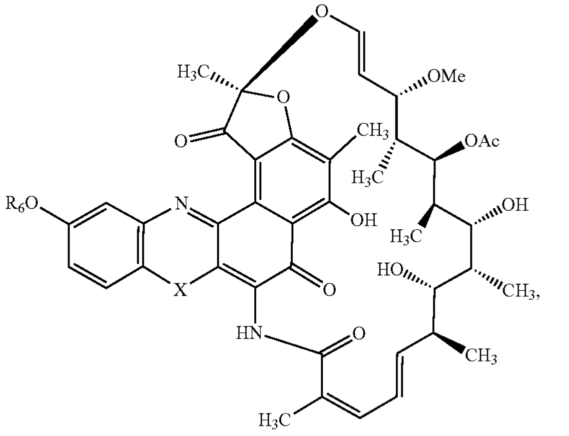

wherein X is selected from —O— and NR*—;

$R_6$ is selected from a $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, $R_N$ is selected from:

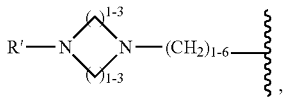,

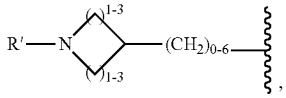,

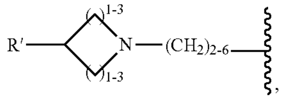, 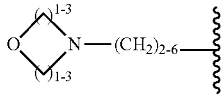,

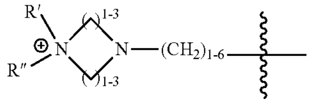,

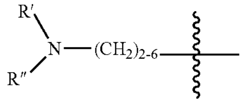,

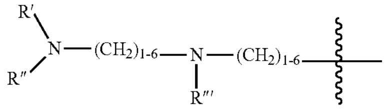,

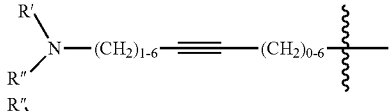 and

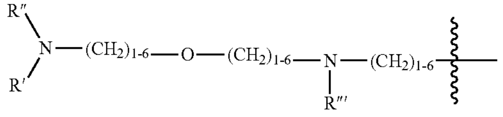

wherein the ~~~ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R"

together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising the steps of:

(a) contacting Rifamycin S having the structure:

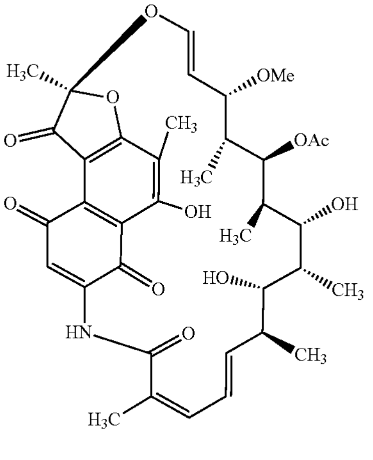 [SMILES: CO[C@H]1/C=C/O[C@@]2(C)Oc3c(C)c(O)c4c(c3C2=O)C(=O)C=C(NC(=O)/C(C)=C\C=C\[C@H](C)[C@H](O)[C@@H](C)[C@@H](O)[C@@H](C)[C@H](OC(C)=O)[C@@H]1C)C4=O]

with a compound having the structure of formula (VI'):

(VI')

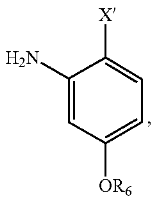

wherein X' is selected from —OH and —NHR*, and (b) treating the product of step (a) with an oxidizing agent.

In one aspect, the present disclosure provides a method of manufacturing a compound having the structure:

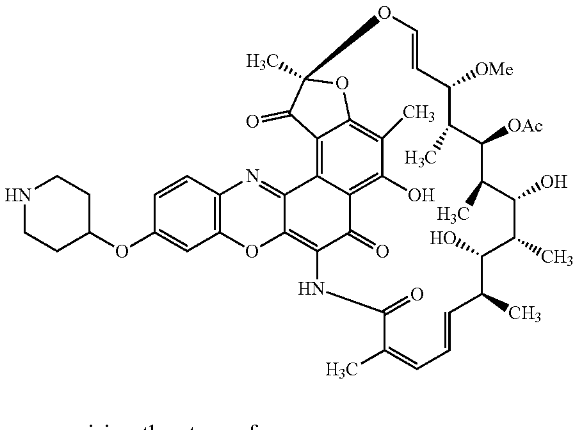

comprising the steps of:

(a) contacting Rifamycin S with a compound having the structure of formula (VII):

(VII)

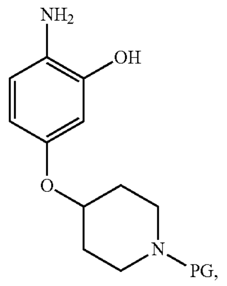

wherein PG is a protecting group;

(b) treating the product of step (a) with an oxidizing agent, and (c) removing the protecting group PG.

In one embodiment, the compound of formula (VII) is prepared by removing protecting group PG' from a compound of formula (VIII):

(VIII)

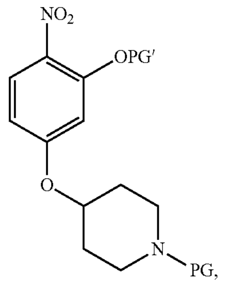

wherein protecting groups PG and PG' may be the same or different from each other.

In one embodiment, the compound of formula (VIII) is prepared by contacting a compound of formula (IX):

(IX)

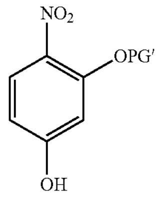

with a compound of formula (X):

(X)

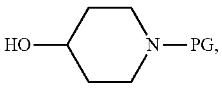

wherein protecting groups PG and PG' may be the same or different from each other.

In one aspect, the present disclosure provides a method of manufacturing a compound having the structure of formula (XI):

(XI)

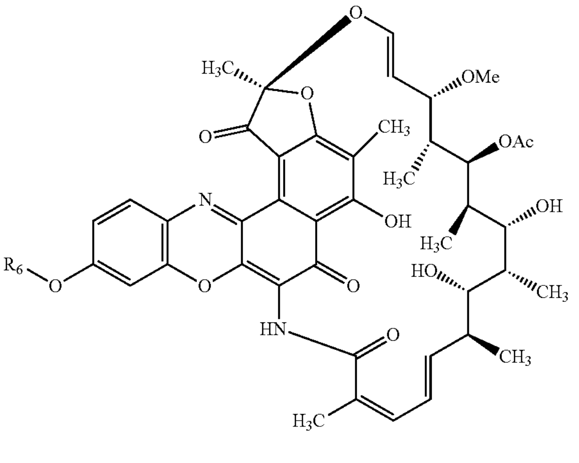

wherein $R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof and wherein $R_6$ is optionally substituted with one or more of —F—Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof;

$R_N$ is selected from:

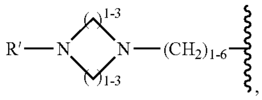 , 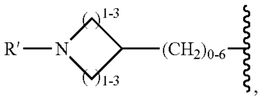 ,

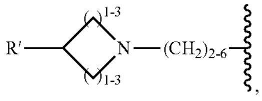 , 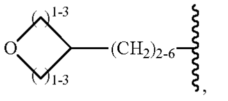 ,

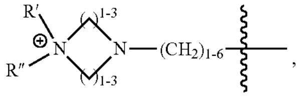 , 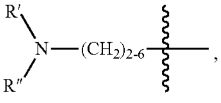 ,

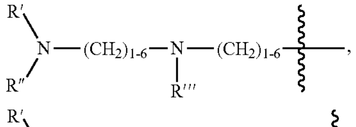 ,

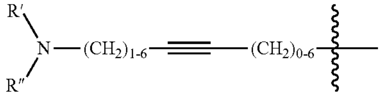 and

-continued

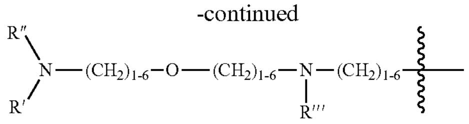

wherein the ~~~ symbol represents the point of attachment; and R', R" and R''' are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII)

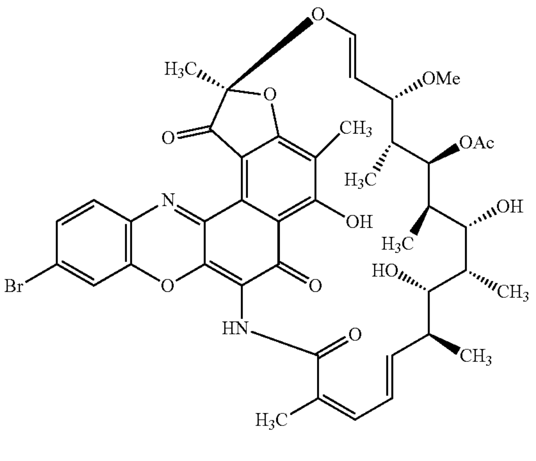

with an alcohol having the structure $R_6$—OH.

In one aspect, the present disclosure provides a method of manufacturing a compound having the structure of formula (XIII):

(XIII)

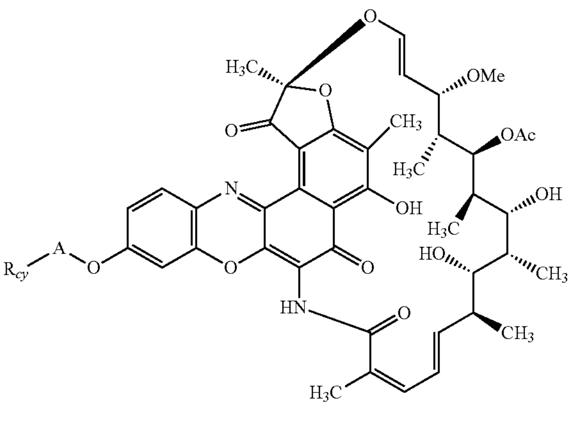

wherein A is selected from a bond (A is absent) or an aliphatic $C_1$-$C_{20}$ hydrocarbon;

$R_{cy}$ is a $C_3$-$C_{14}$ cycloaliphatic hydrocarbon which further comprises 0-8 heteroatoms selected from halogen, O, N, and S and combinations thereof and wherein $R_{cy}$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII)

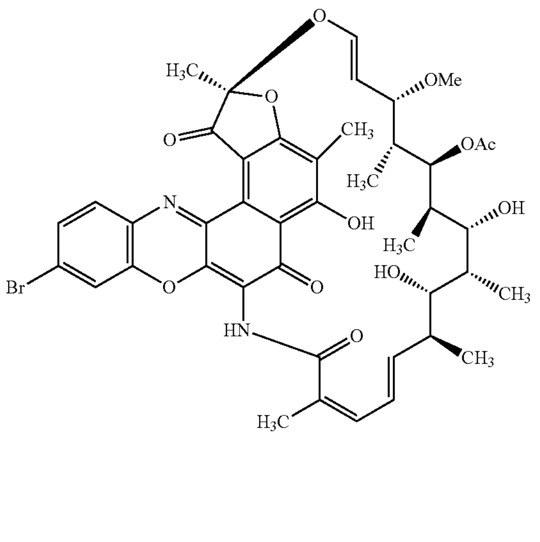

with an alcohol having the structure $R_{cy}$-A-OH.

In one aspect, the present disclosure provides a method of manufacturing a compound having the structure of formula (XIII'):

(XIII')

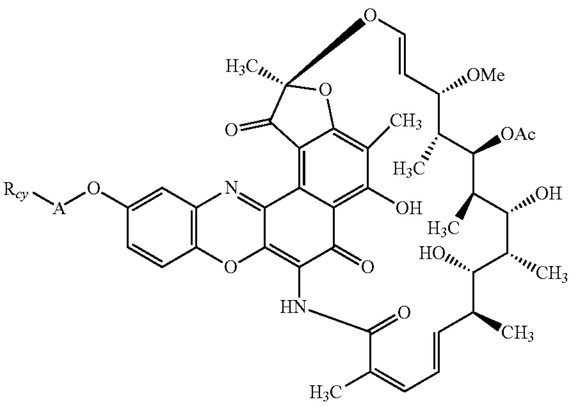

wherein A is selected from a bond (A is absent) or an aliphatic $C_1$-$C_{20}$ hydrocarbon; $R_{cy}$ is a $C_3$-$C_{14}$ cycloaliphatic hydrocarbon which further comprises 0-8 heteroatoms selected from halogen, O, N, and S and combinations thereof and wherein Rey is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII)
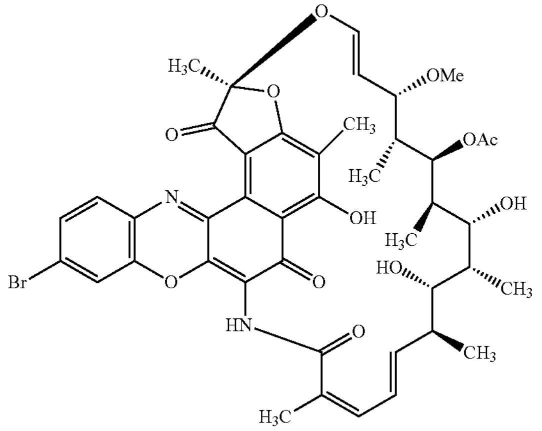
with an alcohol having the structure $R_{cy}$-A-OH.
In one aspect, the present disclosure provides a method of manufacturing a compound having the structure of formula (XIV):
(XIV)
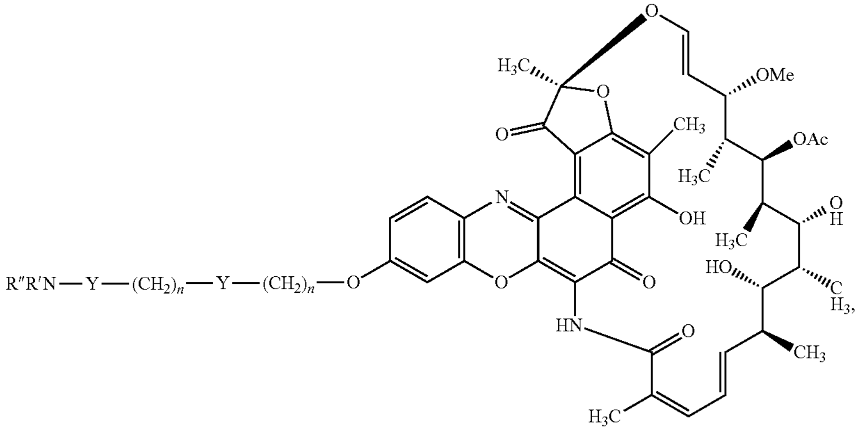

wherein Y is at each occurrence selected from —O— and —NR'R"—; n is independently at each occurrence an integer from 1-6, and R', R", and R''' are each independently selected from a hydrogen, an aliphatic $C_1$-$C_{20}$ hydrocarbon; said method comprising contacting a compound having the structure of formula (XII):

(XII)

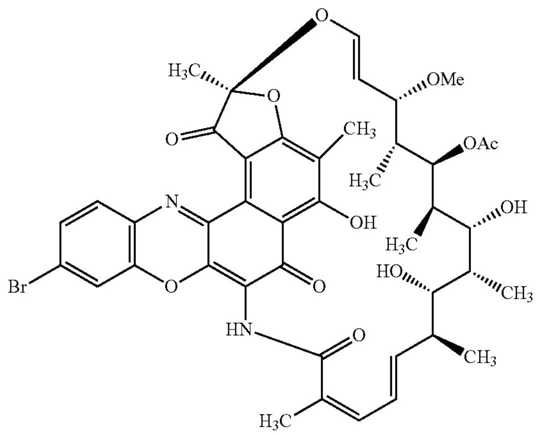

with an alcohol having the structure R"R'N—Y—$(CH_2)_n$—Y—$(CH_2)_n$—OH.

In one aspect, the present disclosure provides a method of manufacturing a compound having the structure of formula (XIV'):

(XII')

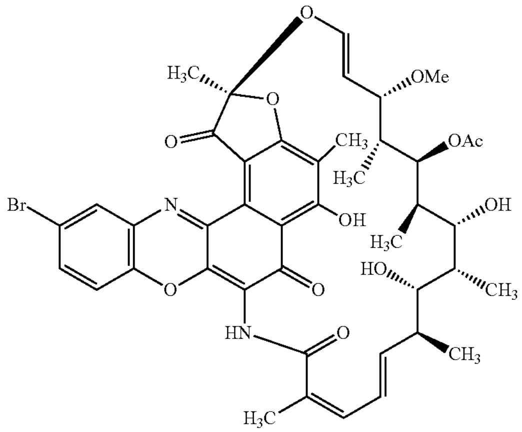

with an alcohol having the structure R"R'N—Y—$(CH_2)_n$—Y—$(CH_2)_n$—OH.

In one embodiment, the compound of formula (XII) is prepared by contacting Rifamycin S with 2-amino-5-bromophenol, and treating the product with an oxidizing agent.

In one embodiment, the compound of formula (XII') is prepared by contacting Rifamycin S with 2-amino-4-bromophenol, and treating the product with an oxidizing agent.

In one aspect, the present disclosure provides a pharmaceutical composition comprising any one or more of compounds as described above, or a pharmaceutically acceptable salt thereof, and a pharmaceutically acceptable carrier.

(XIV')

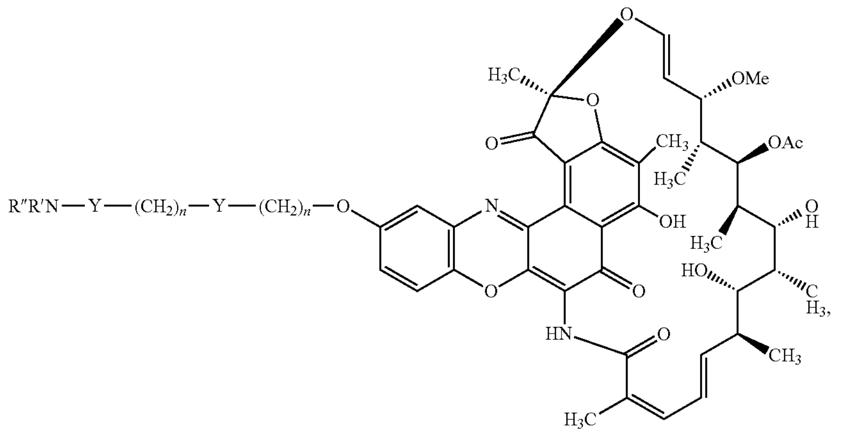

wherein Y is at each occurrence selected from —O— and —NR'R"—; n is independently at each occurrence an integer from 1 to 6, and R', R", and R''' are each independently selected from a hydrogen and an aliphatic $C_1$-$C_{20}$ hydrocarbon; said method comprising contacting a compound having the structure of formula (XII'):

In another aspect, the present disclosure provides a pharmaceutical dosage form comprising any one or more of compounds as described above, or a pharmaceutically acceptable salt thereof, or a pharmaceutical composition as described above.

In another aspect, the present disclosure provides a method of preventing or inhibiting growth of a bacterium comprising administering an effective amount of a rifamycin analog compound having a structure according to any one of formula (A), (B), (I), (I'), (II), (II'), (III), (III'), (IV), (IV'), (V), (V') as provided herein.

In one embodiment, the bacterium is a Gram-positive bacterium.

In one embodiment, the bacterium is a penicillin-resistant bacterium.

In one embodiment, the bacterium is *Staphylococcus aureus.*

In one embodiment, the bacterium is methicillin-resistant *Staphylococcus aureus* (MRSA).

In one embodiment, the bacterium is vancomycin-resistant *Staphylococcus aureus* (VRSA).

In one embodiment, the bacterium is methicillin-susceptible *Staphylococcus aureus* (MSSA).

In yet another aspect, the present disclosure provides a method of treating a bacterial infection in a subject in need of such treatment comprising administering to the subject an effective amount of a rifamycin analog compound having a structure according to any one of formula (A), (B), (I), (I'), (II), (II'), (III), (III'), (IV), (IV'), (V), (V') as provided herein.

In one embodiment, the bacterial infection is a Gram-positive bacterial infection.

In one embodiment, the bacterial infection is a penicillin-resistant bacterial infection.

In one embodiment, the bacterial infection is a *Staphylococcus aureus* infection.

In one embodiment, the bacterial infection is a methicillin-resistant *Staphylococcus aureus* (MRSA) infection.

In one embodiment, the bacterial infection is a vancomycin-resistant *Staphylococcus aureus* (VRSA) infection.

In one embodiment, wherein the bacterial infection is a methicillin-susceptible *Staphylococcus aureus* (MS SA) infection.

In one embodiment, the bacterial infection is an intracellular bacterial infection.

In one embodiment, the subject is human.

In one embodiment, the method further comprises administering a second therapeutic agent.

In one embodiment, the second therapeutic agent is a second antibiotic.

In one embodiment, the second antibiotic is effective against *Staphylococcus aureus.*

In one embodiment, the second antibiotic is selected from an aminoglycoside, a beta-lactam, a macrolide, a cyclic peptide, a tetracycline, a fluoroquinoline, a fluoroquinolone, and an oxazolidinone.

In one embodiment, the second antibiotic is selected from clindamycin, novobiocin, retapamulin, daptomycin, sitafloxacin, teicoplanin, triclosan, napthyridone, radezolid, doxorubicin, ampicillin, vancomycin, imipenem, doripenem, gemcitabine, dalbavancin, and azithromycin.

In one embodiment, the compound is administered to the subject orally, topically, intranasally, intravenously, intramuscularly, or subcutaneously.

In another aspect, provided herein are antibody-drug conjugates comprising antibodies, or antigen-binding fragments of antibodies, and further comprising a rifamycin analog. In some embodiments of the antibody-drug conjugates of the present invention, the antibodies, or antigen-binding fragments of antibodies, bind to an infectious disease-related target. Infectious disease-related targets useful for the present disclosure include, but are not limited to, Macrophage scavenger receptor 1 (MSR1), wall teichoic acids (WTA), *S. aureus* antigens such as Protein A, IsdA, IsdB, IsdC, IsdE, IsdH, ClfA, ClfB, CP5, CP8, SdrC, SdrD, SdrE, FnBpA, FnBpB, Cna, polysaccharide poly-N-aceytl-glucosamine (PNAG), and SasG.

In some embodiments, the antibodies, or antigen-binding fragments of antibodies bind to MSR1. In some embodiments, the antibodies, or antigen-binding fragments of antibodies bind to WTA. In some embodiments, the antibodies, or antigen-binding fragments of antibodies bind to Protein A.

In another aspect, provided herein are antibody-drug conjugates comprising antibodies, or antigen-binding fragments of antibodies, that bind the membrane glycoprotein receptor known as MSR1, and further comprising a rifamycin analog. The antibodies are useful, inter alia, for targeting cells that express MSR1, such as macrophage cells.

In another aspect, provided herein are antibody-drug conjugates comprising antibodies, or antigen-binding fragments of antibodies, that bind wall teichoic acids (WTA), and further comprising a rifamycin analog.

In another aspect, provided herein are antibody-drug conjugates comprising antibodies, or antigen-binding fragments of antibodies, that bind Protein A, and further comprising a rifamycin analog.

In another aspect, provided herein is a pharmaceutical composition comprising an antibody-drug conjugate comprising a recombinant human antibody or fragment thereof, further comprising a rifamycin analog, and a pharmaceutically acceptable carrier. In some embodiments, the recombinant human antibody or fragment thereof specifically binds an infectious disease-related target. In some embodiments, the recombinant human antibody or fragment thereof specifically binds MSR1, WTA or Protein A. In a related aspect, embodiments relate to a composition which is a combination of an antibody-drug conjugate comprising antibody described herein and further comprising a rifamycin analog, and a second therapeutic agent. In one embodiment, the second therapeutic agent is any agent that is advantageously combined with an antibody-drug conjugate comprising an antibody described herein. In one embodiment, the second therapeutic agent is an antibody-drug conjugate comprising an antibody described herein conjugated to a second drug or a therapeutic agent. Exemplary combination therapies, co-formulations, and ADCs involving the antibodies are disclosed elsewhere herein.

Also provided herein are reactive linker-payloads comprising rifamycin analogs, for example, the compounds having a structure according to any embodiment of formulas (A), (B), (I), (I'), (II), (II'), (III), (III'), (IV), (IV'), (V), (V'), (B-1), (B-2) as provided herein, useful for making the antibody-drug conjugates comprising an antibody. Further provided herein are modified antibodies and modified antigen-binding fragments useful for making the antibody-drug conjugates comprising rifamycin analogs. In some embodiments, the antibody or antigen-binding fragment thereof specifically binds an infectious disease-related target. In some embodiments, the antibody or antigen-binding fragment thereof specifically binds MSR1, WTA or Protein A.

Also provided herein are methods of preventing or inhibiting growth of a bacterium comprising administration of an effective amount of an antibody-drug conjugate (ADC) comprising an antibody or antigen-binding fragment thereof and a rifamycin analog. In some embodiments, the antibody or antigen-binding fragment thereof specifically binds an infectious disease-related target. In some embodiments, the antibody or antigen-binding fragment thereof specifically binds MSR1, WTA or Protein A.

Also provided herein are therapeutic methods comprising administration of an effective amount of an ADC comprising an antibody or antigen-binding fragment thereof and a rifamycin analog, to a subject in need thereof. The therapeutic methods comprise administering a therapeutically effective amount of a pharmaceutical composition comprising an ADC comprising an antibody or antigen-binding fragment thereof and a rifamycin analog to the subject. The disorder treated is any disease or condition which is improved, ameliorated, inhibited or prevented by targeting the infectious disease-related target and/or by the administration of an antibiotic agent. In some embodiments, the disease or condition is a proliferative disease, a metabolic disease, inflammation, a neurodegenerative disease, or disease, disorder, or condition associated with glucocorticoid receptor signaling. In some of such embodiments, the side effects associated with administration of the unconjugated rifamycin analog are reduced. Provided herein is the use of an antibody, an antigen-binding portion thereof, or an ADC comprising an antibody or antigen-binding fragment thereof, described herein, for the treatment of any disease disorder or condition described herein. In some embodiments, the antibody or antigen-binding fragment thereof specifically binds an infectious disease-related target. In some embodiments, the antibody or antigen-binding fragment thereof specifically binds MSR1, WTA or Protein A.

Also provided herein are therapeutic methods for treating, attenuating, or ameliorating a disease or disorder or condition associated with Staphylococcal infection, for example, a *S. aureus* infection and/or for ameliorating at least one symptom associated with such disease, disorder or condition, comprising administration of a rifamycin analog or an ADC comprising an antibody or antigen-binding fragment thereof and a rifamycin analog, to a subject in need thereof. Such disease, disorder or condition may be cellulitis, bacteremia, dermonecrosis, eyelid infection, eye infection, neonatal conjunctivitis, osteomyelitis, impetigo, boils, scalded skin syndrome, food poisoning, pneumonia, surgical infection, urinary tract infection, burn infection, meningitis, endocarditis, septicemia, toxic shock syndrome, or septic arthritis. In some embodiments, the subject has a prosthetic joint and the rifamycin analogs or ADCs comprising an antibody or antigen-binding fragment thereof and a rifamycin analog disclosed herein are used for treating and/or preventing *S. aureus* infection of the tissue surrounding the prosthetic joint. In some embodiments, the subject has a catheter and the rifamycin analogs or ADCs comprising an antibody or antigen-binding fragment thereof and a rifamycin analog disclosed herein are used for treating and/or preventing *S. aureus* infection of the catheter and/or the tissue surrounding the catheter. In some embodiments, the subject has a foreign body implanted, and the rifamycin analogs or ADCs comprising an antibody or antigen-binding fragment thereof and a rifamycin analog disclosed herein are used for treating and/or preventing *S. aureus* infection of the foreign body and/or the tissue surrounding the foreign body. In some embodiments, the subject has mastitis, and the antibodies disclosed herein are useful for treating mastitis. The therapeutic methods comprise administering a therapeutically effective amount of a pharmaceutical composition comprising a rifamycin analog or an ADC comprising an antibody or antigen-binding fragment thereof and a rifamycin analog, to a subject in need thereof. In some embodiments, the antibody or antigen-binding fragment thereof specifically binds an infectious disease-related target. In some embodiments, the antibody or antigen-binding fragment thereof specifically binds MSR1, WTA or Protein A.

In another aspect, the present disclosure provides an antibody-drug conjugate comprising an antibody, or an antigen-binding fragment thereof, conjugated to the rifamycin analog compound of any of the embodiments of the disclosure via a linker or through a linker-spacer.

In various embodiments, the antibody, or the antigen-binding fragment thereof, binds macrophage scavenger receptor 1 (MSR1). In various embodiments, the antibody, or the antigen-binding fragment thereof, binds wall teichoic acids (WTA). In various embodiments, the antibody, or the antigen-binding fragment thereof, binds *S. aureus* Protein A.

In one embodiment, the antibody, or the antigen-binding fragment thereof, may comprise: (a) the complementarity determining regions (CDRs) of a heavy chain variable region (HCVR) comprising an amino acid sequence as set forth in Table 9; and (b) the CDRs of a light chain variable region (LCVR) comprising an amino acid sequence as set forth in Table 9.

In one embodiment, the anti-MSR1 antibody, or the antigen-binding fragment thereof, may comprise:

(i) a HCDR1 domain comprising an amino acid sequence selected from the group consisting of SEQ ID NOs: 4, 36, 52, 92, and 284;

(ii) a HCDR2 domain comprising an amino acid sequence selected from the group consisting of SEQ ID NOs: 6, 38, 54, 94, and 286;

(iii) a HCDR3 domain comprising an amino acid sequence selected from the group consisting of SEQ ID NOs: 8, 40, 56, 96, and 288;

(iv) a LCDR1 domain comprising an amino acid sequence selected from the group consisting of SEQ ID NOs: 12, 44, 60, 100, and 292;

(v) a LCDR2 domain comprising an amino acid sequence selected from the group consisting of SEQ ID NOs: 14, 46, 62, 102, and 294; and (vi) a LCDR3 domain comprising an amino acid sequence selected from the group consisting of SEQ ID NOs: 16, 48, 64, 104, and 296.

In one embodiment, the anti-WTA antibody, or the antigen-binding fragment thereof, may comprise: (a) the complementarity determining regions (CDRs) of a heavy chain variable region (HCVR) comprising an amino acid sequence as set forth in Table 2A; and (b) the CDRs of a light chain variable region (LCVR) comprising an amino acid sequence as set forth in Table 2A.

In one embodiment, the anti-WTA antibody, or the antigen-binding fragment thereof, may comprise:

(i) a HCDR1 domain comprising an amino acid sequence selected from the group consisting of SEQ ID NOs: 470, 476, 482, and 488;

(ii) a HCDR2 domain comprising an amino acid sequence selected from the group consisting of SEQ ID NOs: 471, 477, 483, and 489;

(iii) a HCDR3 domain comprising an amino acid sequence selected from the group consisting of SEQ ID NOs: 472, 478, 484, and 490;

(iv) a LCDR1 domain comprising an amino acid sequence selected from the group consisting of SEQ ID NOs: 467, 473, 479, and 485;

(v) a LCDR2 domain comprising an amino acid sequence selected from the group consisting of SEQ ID NOs: 468, 474, 480, and 486; and (vi) a LCDR3 domain comprising an amino acid sequence selected from the group consisting of SEQ ID NOs: 469, 475, 481, and 487.

In one embodiment, the anti-WTA antibody, or the antigen-binding fragment thereof, may comprise: (a) the complementarity determining regions (CDRs) of a heavy chain variable region (HCVR) comprising an amino acid sequence as set forth in Table 2B; and (b) the CDRs of a light chain variable region (LCVR) comprising an amino acid sequence as set forth in Table 2B.

In one embodiment, the anti-WTA antibody, or the antigen-binding fragment thereof, may comprise:

(i) a HCDR1 domain comprising an amino acid sequence selected from the group consisting of SEQ ID NOs: 502, 508, 514, 520, 526, 532, 538, 544, 550, 556, 562, 568, and 574;

(ii) a HCDR2 domain comprising an amino acid sequence selected from the group consisting of SEQ ID NOs: 503, 509, 515, 521, 527, 533, 539, 545, 551, 557, 563, 569, and 575;

(iii) a HCDR3 domain comprising an amino acid sequence selected from the group consisting of SEQ ID NOs: 504, 510, 516, 522, 528, 534, 540, 546, 552, 558, 564, 570, 576, and 584;

(iv) a LCDR1 domain comprising an amino acid sequence selected from the group consisting of SEQ ID NOs: 499, 505, 511, 517, 523, 529, 535, 541, 547, 553, 559, 565, and 571;

(v) a LCDR2 domain comprising an amino acid sequence selected from the group consisting of SEQ ID NOs: 500, 506, 512, 518, 524, 530, 536, 542, 548, 554, 560, 566, and 572; and (vi) a LCDR3 domain comprising an amino acid sequence selected from the group consisting of SEQ ID NOs: 501, 507, 513, 519, 525, 531, 537, 543, 549, 555, 561, 567, and 573.

In some embodiments, the anti-WTA antibody, or the antigen-binding fragment thereof, comprises a V205C mutation (EU numbering) in the light chain.

In one embodiment, the anti-Protein A antibody, or the antigen-binding fragment thereof, may comprise: (a) the complementarity determining regions (CDRs) of a heavy chain variable region (HCVR) comprising an amino acid sequence as set forth in Table 3A; and (b) the CDRs of a light chain variable region (LCVR) comprising an amino acid sequence as set forth in Table 3A.

In one embodiment, the anti-Protein A antibody, or the antigen-binding fragment thereof, may comprise:

(i) a HCDR1 domain comprising an amino acid sequence selected from the group consisting of SEQ ID NOs: 632, 652, and 672;

(ii) a HCDR2 domain comprising an amino acid sequence selected from the group consisting of SEQ ID NOs: 634, 654, and 674;

(iii) a HCDR3 domain comprising an amino acid sequence selected from the group consisting of SEQ ID NOs: 636, 656, and 676;

(iv) a LCDR1 domain comprising an amino acid sequence selected from the group consisting of SEQ ID NOs: 640, 660, and 680;

(v) a LCDR2 domain comprising an amino acid sequence selected from the group consisting of SEQ ID NOs: 642 and 662; and (vi) a LCDR3 domain comprising an amino acid sequence selected from the group consisting of SEQ ID NOs: 644, 664, and 683.

In some embodiments, the anti-Protein A antibody, or the antigen-binding fragment thereof, comprises a H435R and a Y436F mutation (EU numbering) in the heavy chain Fc.

In various embodiments, the antibody, or antigen-binding fragment thereof, comprises a C103S mutation in the light chain.

The various embodiments, the antibody, or the antigen-binding fragment thereof, is conjugated to a compound of the present disclosure at position 103 of the light chain.

In one embodiment, the linker or linker spacer is selected from

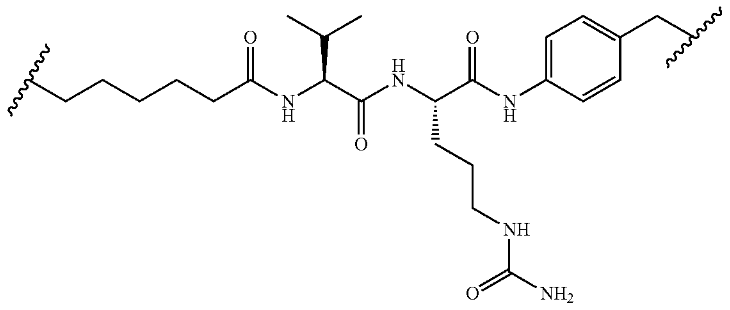

,

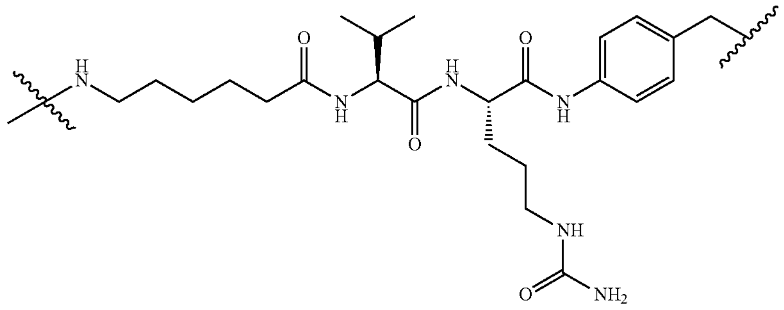

,

-continued

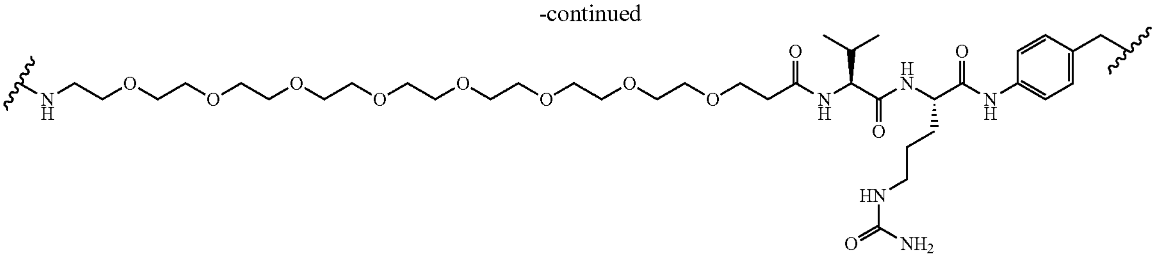

,

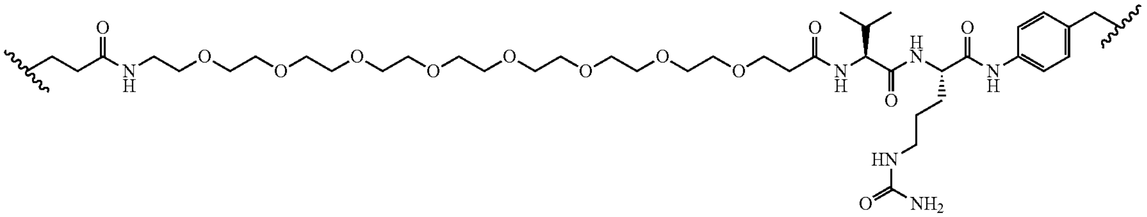

,

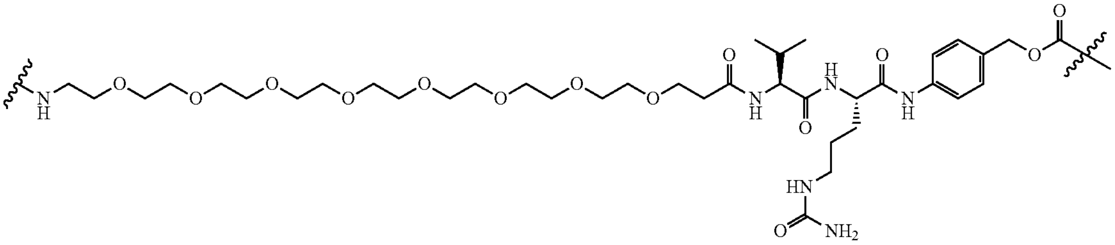

, and

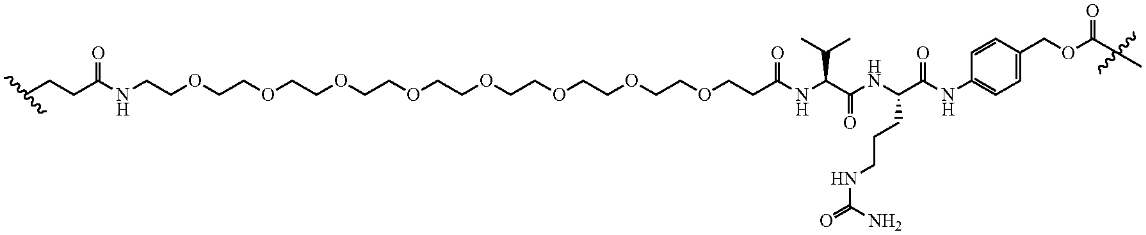

.

In another aspect, the present disclosure provides an antibody-drug conjugate having the structure according to Formula (XVIII):

$$BA\text{—}[RG\text{—}SP\text{—}AA\text{—}B\text{—}PA]_n, \qquad (XVIII)$$

wherein

- BA is an antibody, or an antigen-binding fragment thereof,
- RG is a reactive group selected from a maleimide, an N-hydroxy succinimide, or a succinimide;
- SP is absent or a spacer group residue selected from the group consisting of $C_{1-6}$ alkyl, —NH—, —C(O)—, —$CH_2$—$CH_2$—C(O)—NH—, —$(CH)_u$—C(O)—NH—, (—$CH_2$—$CH_2$—O$)_e$, —NH—$CH_2$—$CH_2$—(—O—$CH_2$—$CH_2)_e$—C(O)—, —C(O)—$(CH_2)_u$—C(O)—, —C(O)—NH—$(CH_2)_v$—, —$(CH)_u$—C(O)—NH—$(CH_2$—$CH_2$—O$)_e$—$(CH)_u$—C(O)—NH—, —$(CH)_2$—C(O)—NH—$(CH_2$—$CH_2$—O$)_8$—$(CH)_2$—C(O)—NH—, and combinations thereof, wherein independently at each occurrence subscript e is an integer from 0 to 20, subscript u is an integer from 1 to 8, and subscript v is an integer from 1 to 8;
- AA is a linker selected from valine-citrulline; citrulline-valine; valine-alanine; alanine-valine; valine-glycine, or glycine-valine;
- B is absent or

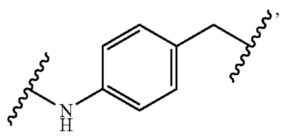 [SMILES: *Cc1ccc(N*)cc1]

, wherein the

indicates the atom through which the B is bonded to the adjacent groups in the formula;

- n is an integer from 1 to 30, and
- PA is a rifamycin analog according to any of the embodiments of the disclosure.

In one embodiment,
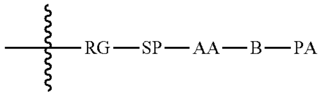
is
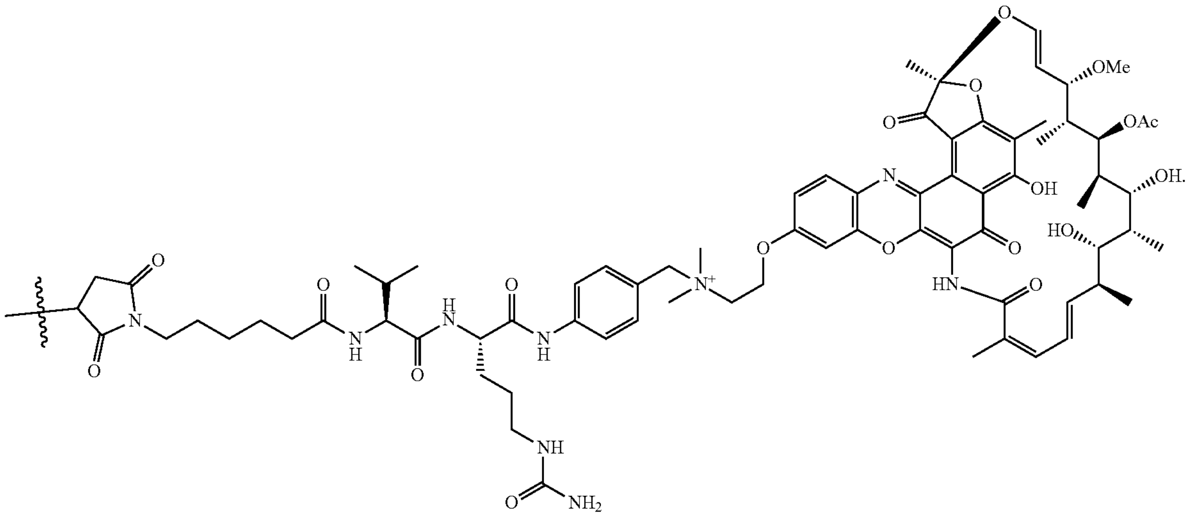
In one embodiment,
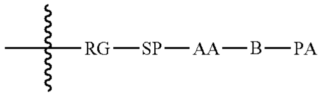
is
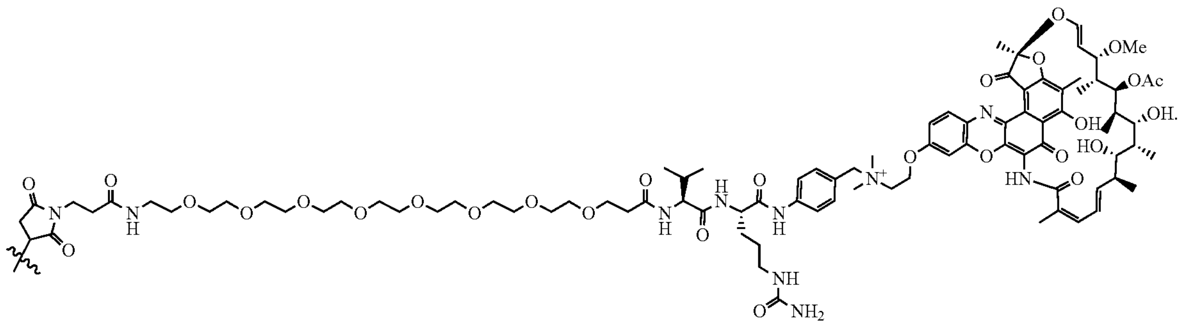
In one embodiment,
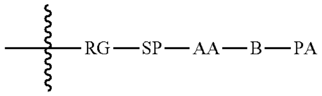
is -continued

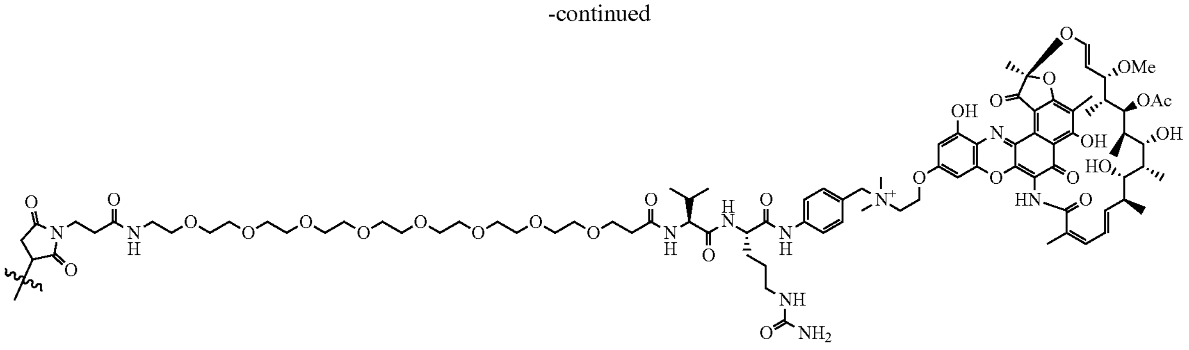

wherein the

is the bond to the antibody or the antigen-binding fragment thereof. In one aspect, the present disclosure provides an antibody-drug conjugate having the structure according to Formula (XIX):

$$BA-[RG-SP^1-(PEG)_m-SP^2-AA-B-PA]_n, \qquad (XIX)$$

wherein

BA is an antibody, or an antigen-binding fragment thereof;

RG is selected from a maleimide, a N-hydroxy succinimide, or a succinimide;

$SP^1$ and $SP^2$ are independently absent or a spacer group selected from the group consisting of $C_{1-6}$ alkyl, —NH—, —C(O)—, —$CH_2$—$CH_2$—C(O)—NH—

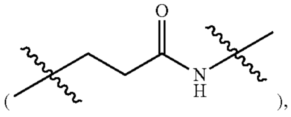 [SMILES: *CCC(=O)N*]

—$(CH)_u$—C(O)—NH—, (—$CH_2$—$CH_2$—O$)_e$, —NH—$CH_2$—$CH_2$—(—O—$CH_2$—$CH_2)_e$—C(O)—, —C(O)—$(CH_2)_u$—C(O)—, —C(O)—NH—$(CH_2)_v$—, and combinations thereof, wherein subscript e is an integer from 0 to 4, subscript u is an integer from 1 to 8, and subscript v is an integer from 1 to 8;

AA is a linker selected from valine-citrulline; citrulline-valine; valine-alanine; alanine-valine; valine-glycine, or glycine-valine;

PEG is a polyethylene glycol chain comprising between 1 and 30 polyethylene glycol residues;

B is absent or

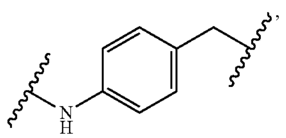 [SMILES: *Cc1ccc(N*)cc1]

wherein the

indicates the atom through which the B is bonded to the adjacent groups in the formula;

n is an integer from 1 to 30;

m is an integer from 0 to 20, and PA is a rifamycin analog according to any of the embodiments of the disclosure.

In one embodiment,

$$-RG-SP^1-(PEG)_m-SP^2-AA-B-PA$$ is

-continued

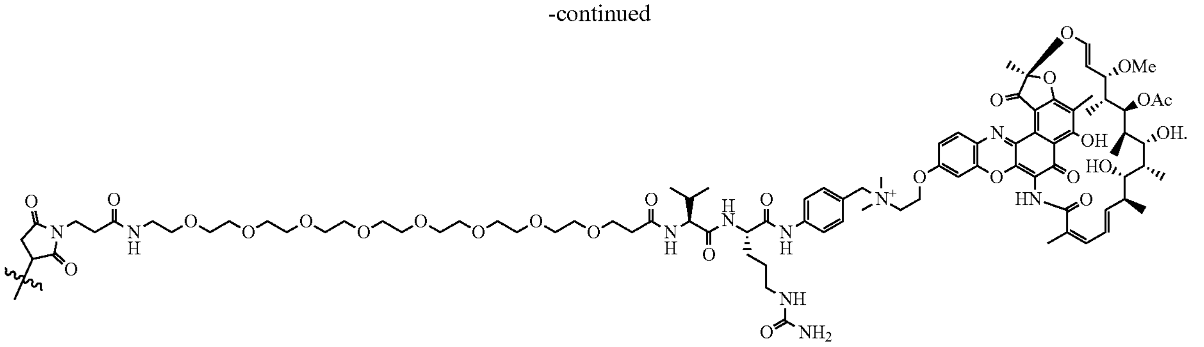

In one aspect, the present disclosure provides an antibody-drug conjugate comprising an antibody, or an antigen-binding fragment thereof, conjugated via a linker or through a linker-spacer to a rifamycin analog payload having the structure of Formula (XX):

(XX)

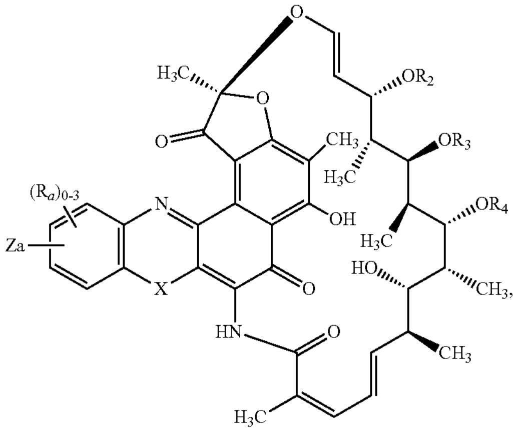

wherein:

X is selected from —O—, —S—, and —NR*—;

Za is selected from —$OR_1$ and —$R_N$;

$R_1$ is selected from a bond; an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F; —Cl; —Br; —I; —OH, —OR*; —NO; —$NO_2$; —$NO_3$; —O—NO; —$N_3$; —$NH_2$; —NHR*; —$N(R^*)_2$; —$N(R^*)_3^+$; —N(R*)—OH; —O—$N(R^*)_2$; —N(R*)—O—R*; —CN; —NC; —(C═O)—R*; —CHO; —$CO_2H$; —$CO_2R^*$; —(C═O)—S—R*; —O—(C═O)—H; —O—(C═O)—R*; —S—(C═O)—R*; —(C═O)—$NH_2$; —(C═O)—$N(R^*)_2$; —(C═O)—$NHNH_2$; —O—(C═O)—$NHNH_2$; —(C═S)—$NH_2$; —(C═S)—$N(R^*)_2$; —N(R*)—CHO; —N(R*)—(C═O)—R*; —SCN; —NCS; —NSO; —SSR*; —$SO_2R^*$; —$SO_2$—$N(R^*)_2$; —S(═O)—OR*; —S(═O)—R*; —$Si(R^*)_3$; —$CF_3$; —O—$CF_3$ and combinations thereof;

$R_N$ is selected from:

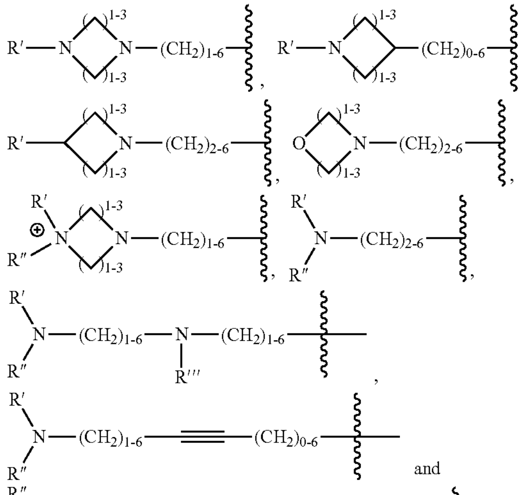

and

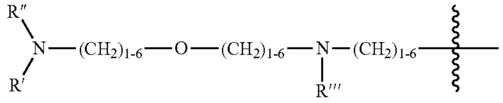

wherein the ~~~ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure;

$R_2$, $R_3$, and $R_4$ are independently selected from hydrogen, a straight chained, branched or cyclic aliphatic $C_1$-$C_{20}$ hydrocarbon, or —(C═O)—R*, each of which further comprises 0-8 heteroatoms selected from halogen, O, N, and S;

$R_a$ is independently at each occurrence selected from hydrogen, —F, —Cl, —Br, —I, —OH, OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, and wherein the group Za is bonded to the linker.

It is to be understood that the group $R_1$ is either a bond (i.e., $R_1$ is absent), or a divalent group, i.e. $R_1$ capable of bonding to the —O— of the rifamycin analog as well as to the linker.

In one embodiment, —$OR_1$ is —O— (i.e., $R_1$ is absent),

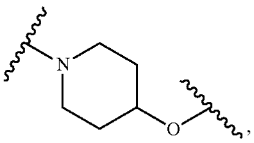,
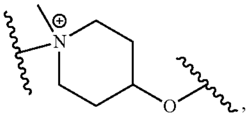,
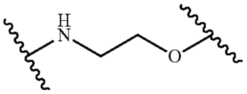,
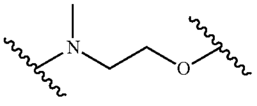,
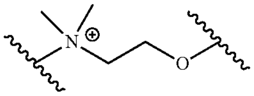, or
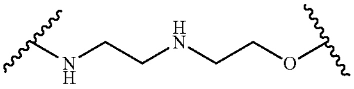.

In one embodiment, X is —O—, and —$OR_1$ comprises a tertiary amine. In some of such embodiments, —$OR_1$ is

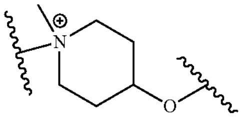 or
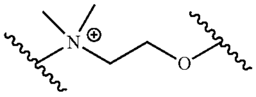.

In some embodiments, antibody-drug conjugates comprising linker-rifamycin analog payloads comprise ammonium salts having one or more counterions. Any pharmaceutically acceptable counterion may be suitable. For example, in an embodiment of the disclosure a suitable counterion may be an anion selected from $F^-$, $Cl^-$, $Br^-$, $I^-$, $OH^-$, $^-BF_4$, $CF_3SO_3^-$, monobasic sulfate, dibasic sulfate, monobasic phosphate, dibasic phosphate, or tribasic phosphate, $NO_3^-$, $PF_6^-$, $NO_2^-$, carboxylate, $C_eF_fSO_3^-$, (where in e=2-10 and f=2e+1), acetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, glycollyalarsanilate, hexanoate, hydrabamine, hydroxynaphthoate, isthionate, lactate, lactobionate, malate, maleate, mandelate, mesylate, methylbromide, methylnitrate, mucate, napsylate, octanoate, oleate, pamoate, pantothenate, polygalacturonate, propionate, salicylate, stearate, subacetate, succinate, tartrate, teoclate, tosylate, or triethiiodide.

In some embodiments, $R_a$ is absent. In some embodiments, $R_a$ is —OH and is present at one occurrence.

In one aspect, the present disclosure provides an antibody, or an antigen-binding fragment thereof, conjugated via a linker or through a linker-spacer to a rifamycin analog having the structure of Formula (XXI):

(XXI)

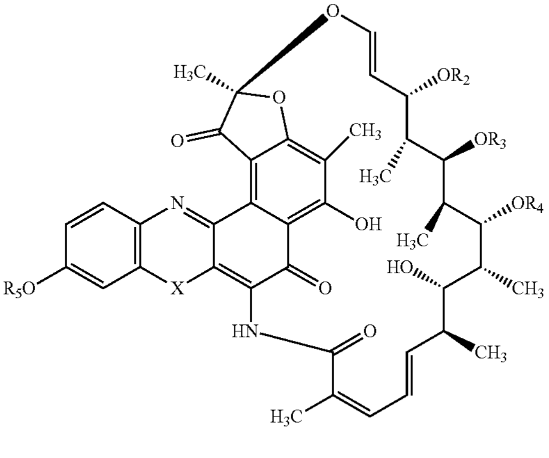, wherein:

X is selected from —O—, —S—, and —NR*—;

$R_5$ is selected from a bond; an aliphatic $C_1$-$C_{20}$ hydrocarbon which further comprises 0-8 heteroatoms selected from halogen, O, N, and S;

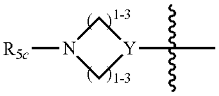; or
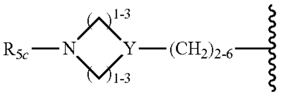;

wherein Y is C or N;

$R_2$, $R_3$, and $R_4$ are independently selected from a hydrogen, a straight chained, branched or cyclic aliphatic $C_1$-$C_{20}$ hydrocarbon, or —(C═O)—R*, each of which further comprises 0-8 heteroatoms selected from halogen, O, N, and S, and $R_{5c}$ is a bond or an aliphatic $C_1$-$C_8$ hydrocarbon, wherein the group $R_5$ is bonded to the linker.

It is to be understood that the group $R_5$ is either a bond (i.e., $R_5$ is absent), or a divalent group, i.e. $R_5$ capable of bonding to the —O— of rifamycin as well as to the linker.

In one embodiment, —$OR_5$ is —O— (i.e., $R_5$ is absent),

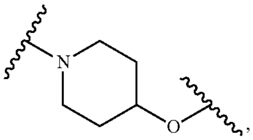,
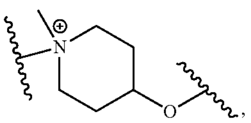,
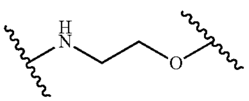,
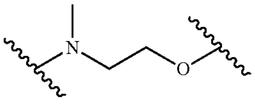,
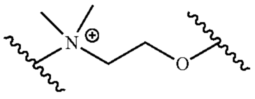, or

-continued

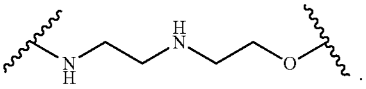

In one embodiment, X is O, and —$OR_5$ comprises a tertiary amine. In some of such embodiments, —$OR_5$ is

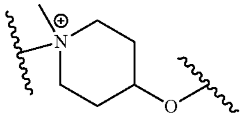

or

-continued

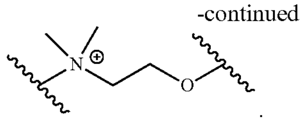

In one embodiment of any of the above, $R_2$ is methyl, ethyl, propyl or isopropyl; $R_3$ is $CH_3$—(C═O)— (acetyl) group, $CH_3CH_2$—(C═O)—, $CH_3CH_2CH_2$—(C═O)—, or $(CH_3)_2CH$—(C═O)—, and $R_4$ is hydrogen.

In one embodiment of any of the above, $R_2$ is methyl, $R_3$ is acetyl, and $R_4$ is hydrogen.

In one embodiment of any of the above, the compound is selected from the group consisting of:

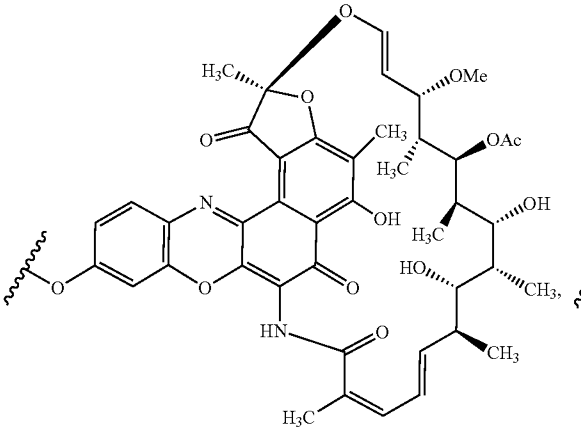

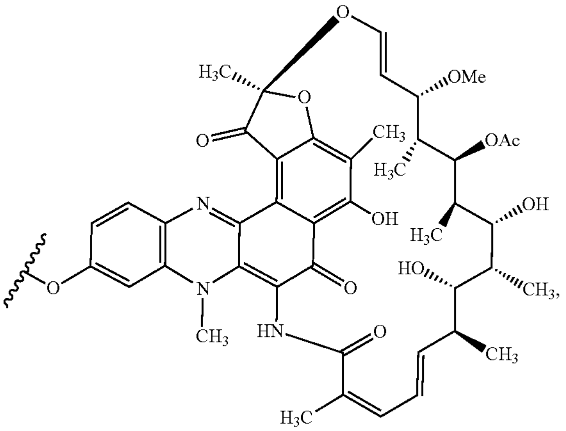

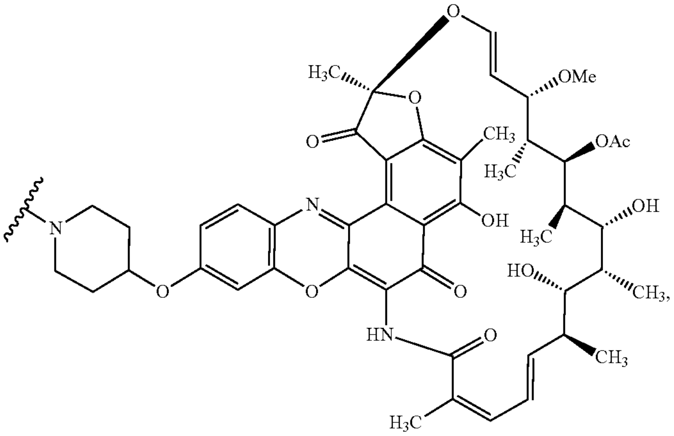

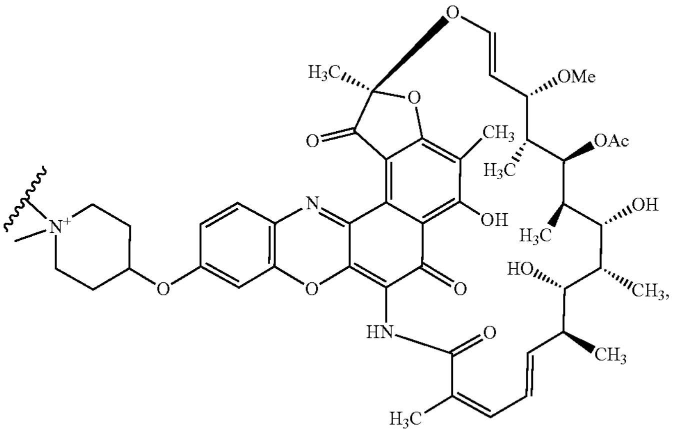

-continued
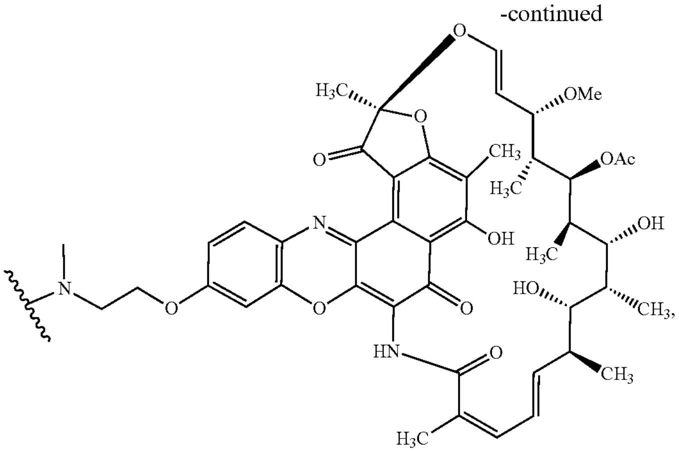
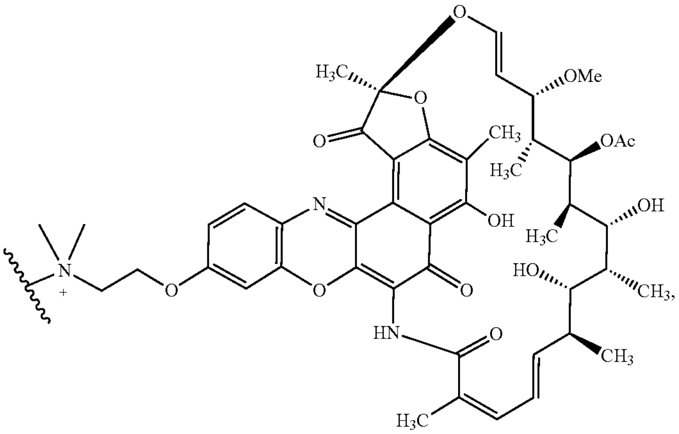
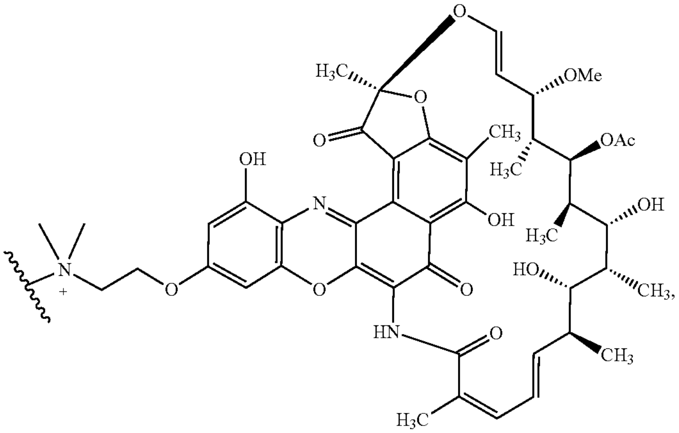
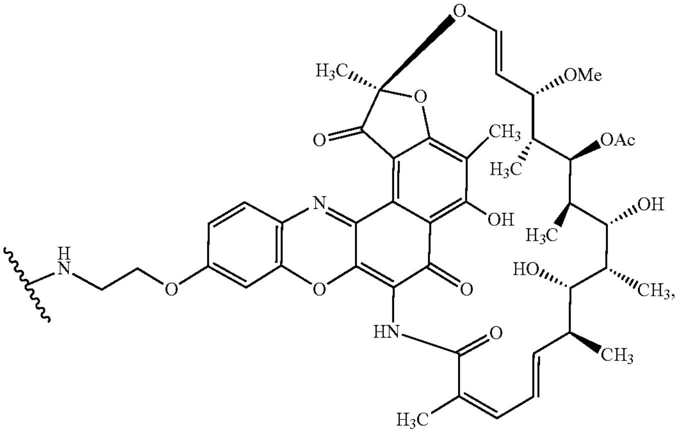

-continued
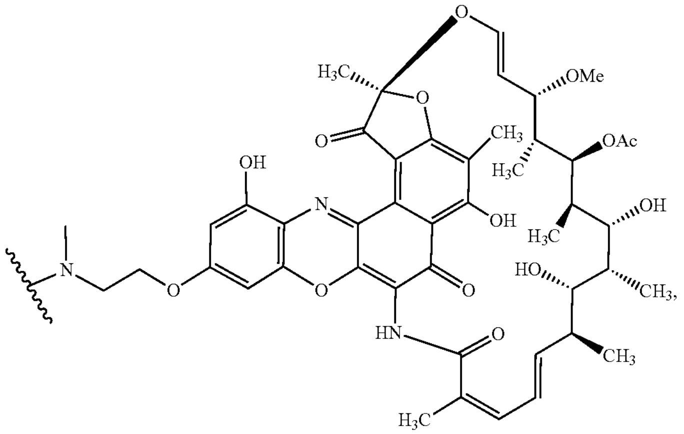
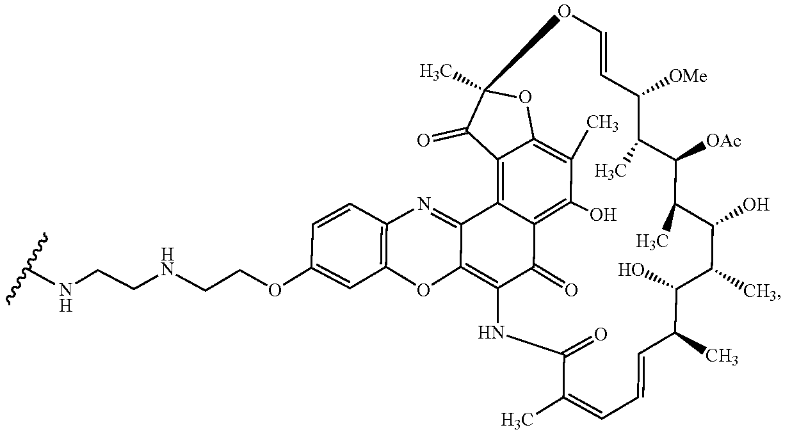
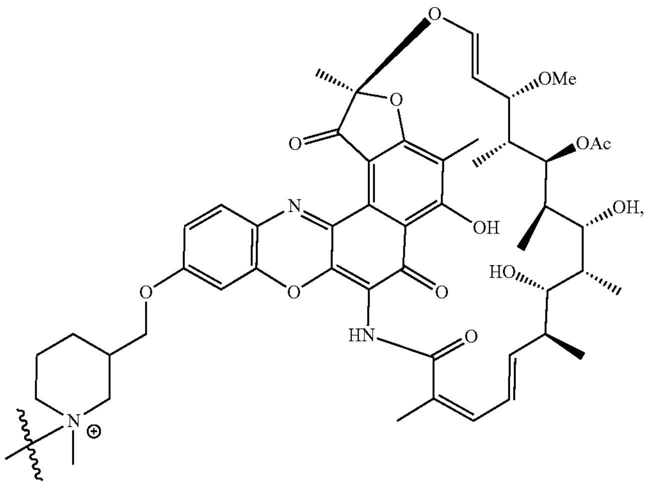

-continued
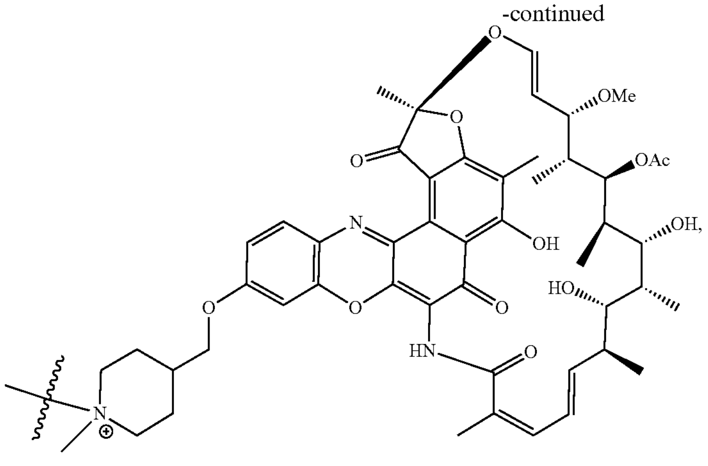
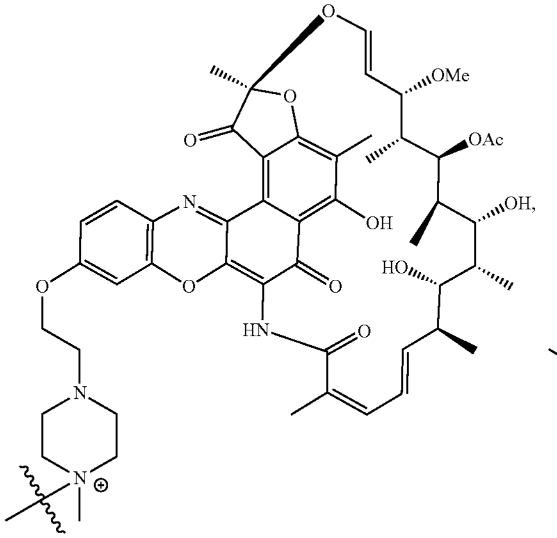
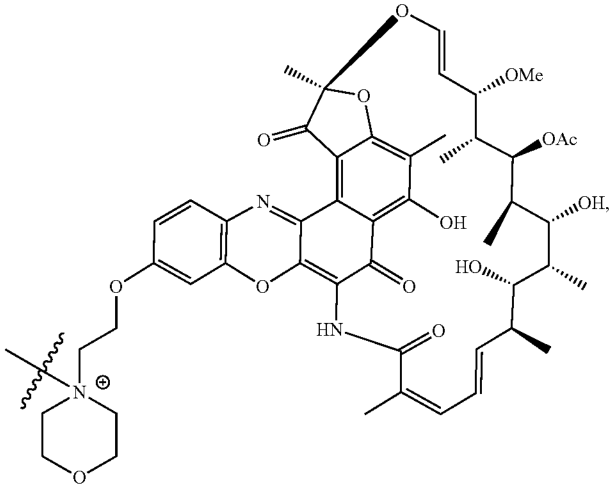
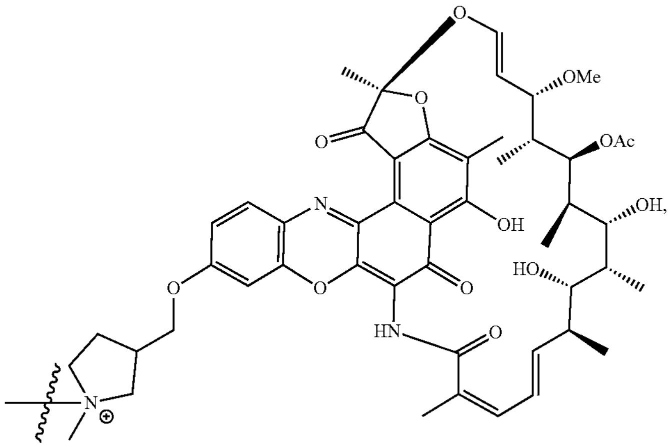

-continued
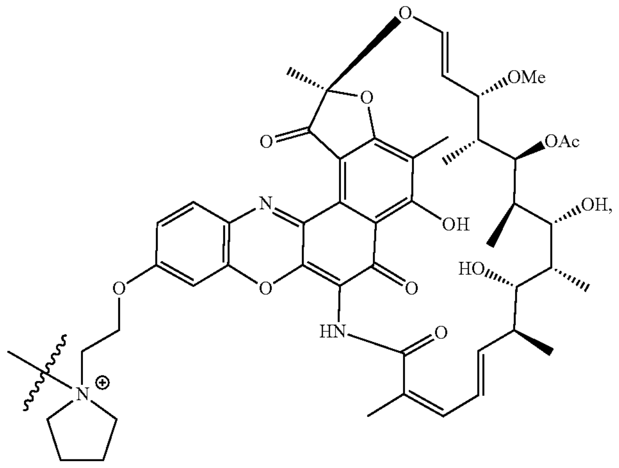
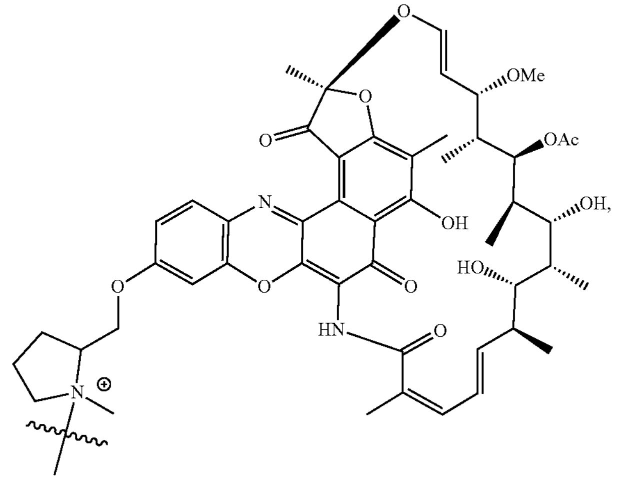
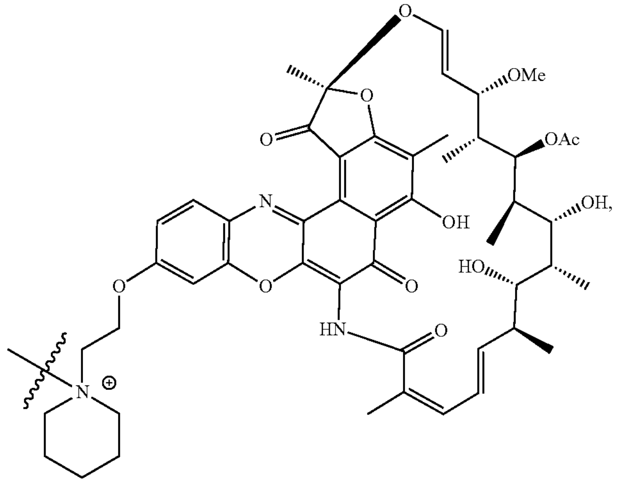

-continued
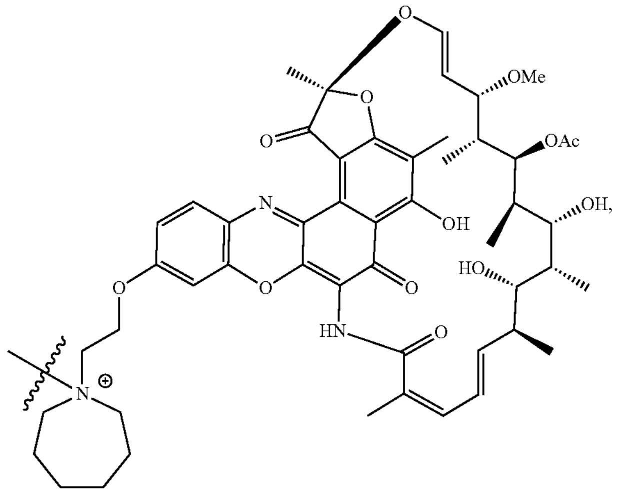
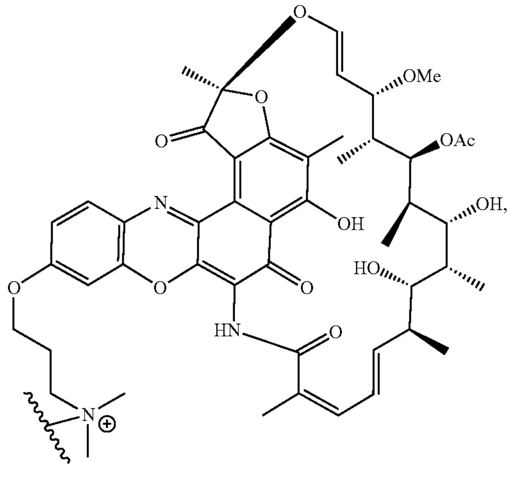
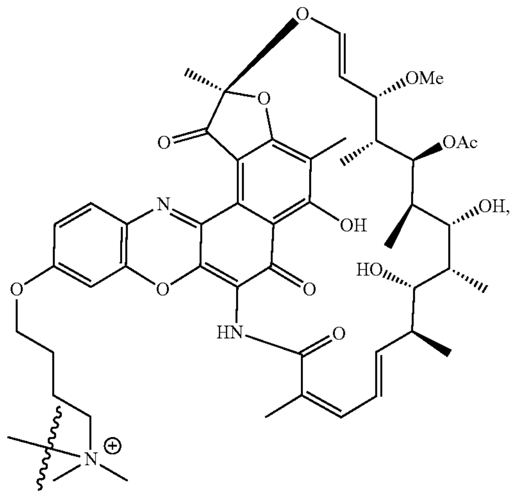
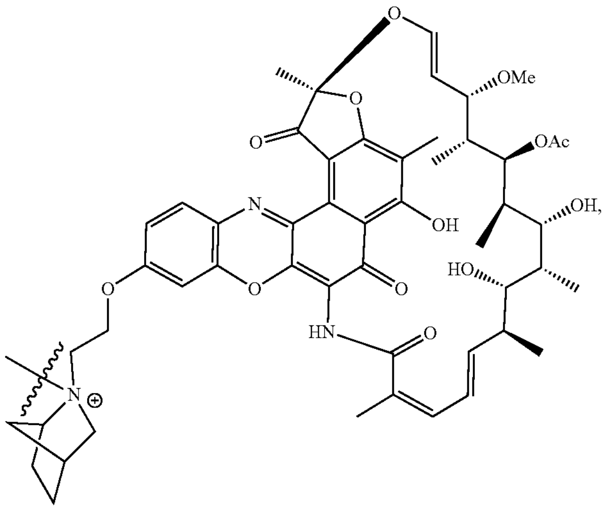
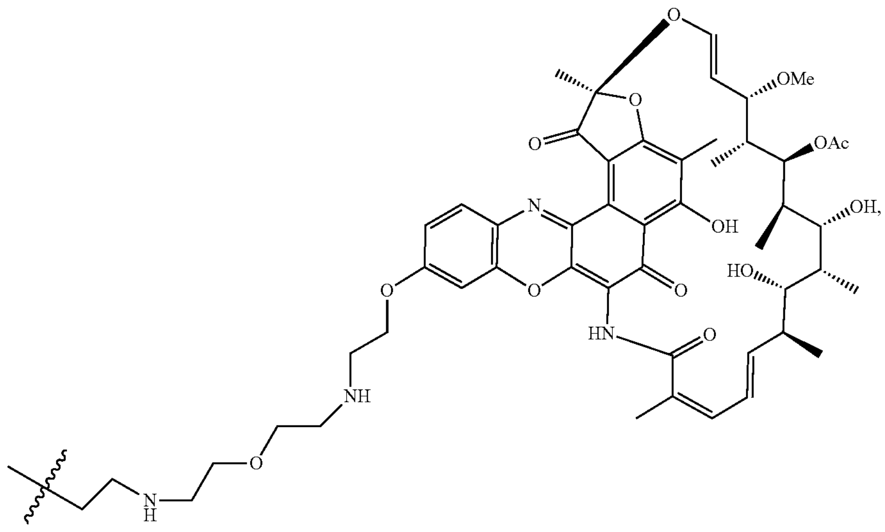

-continued
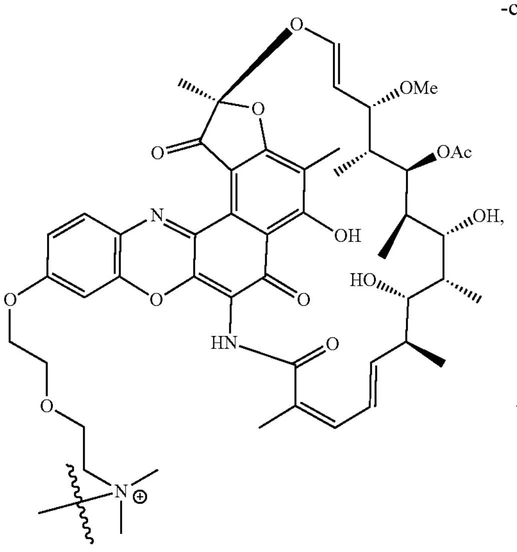
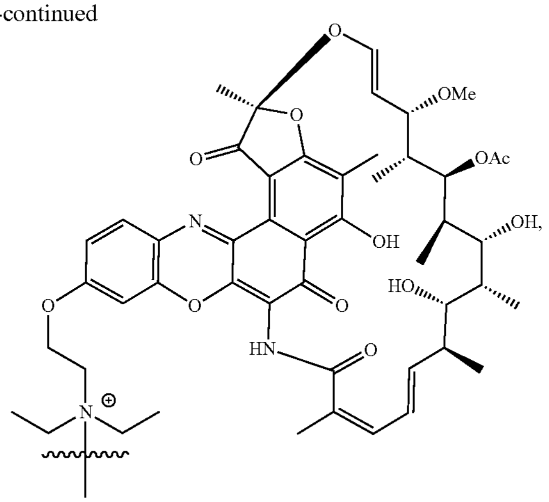
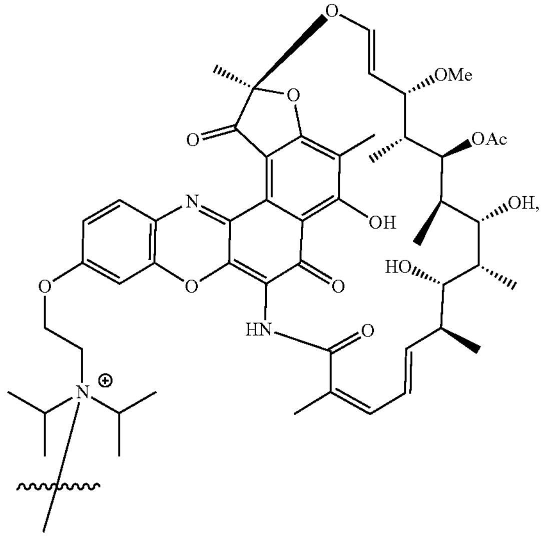
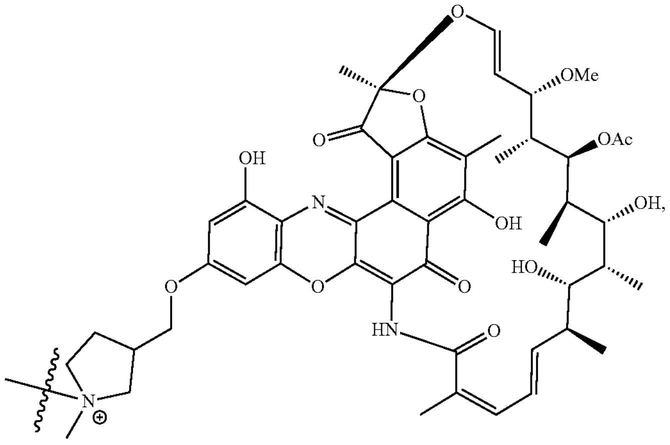

-continued
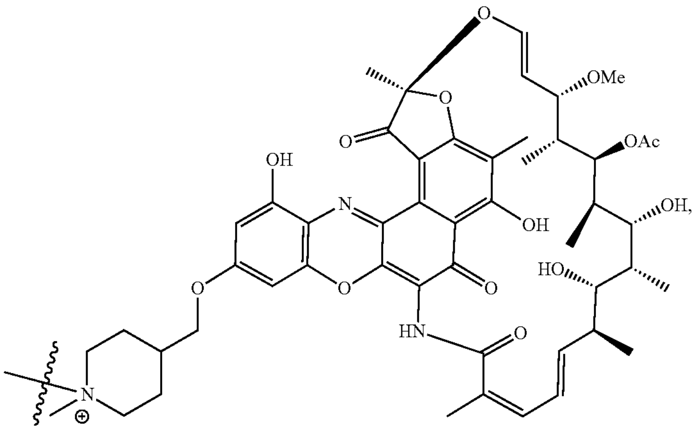
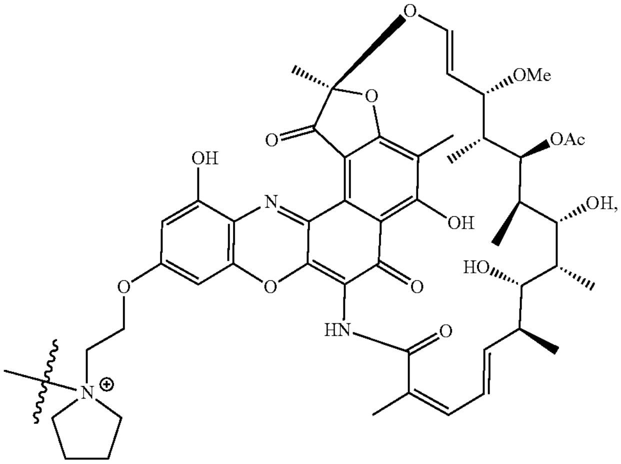
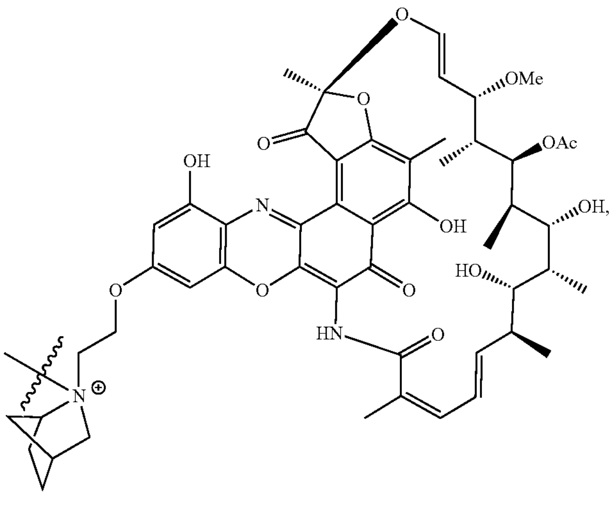
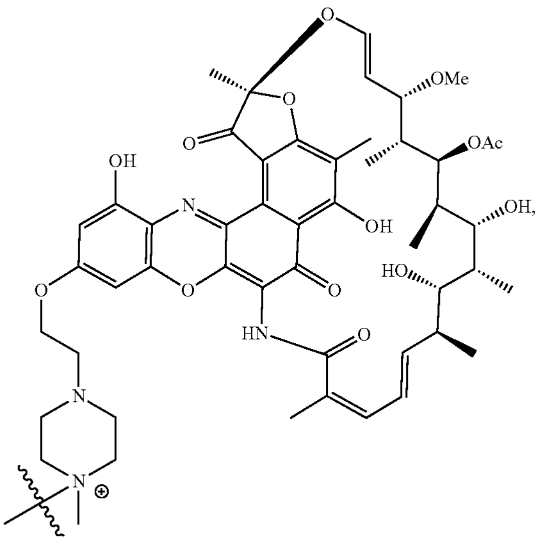

-continued
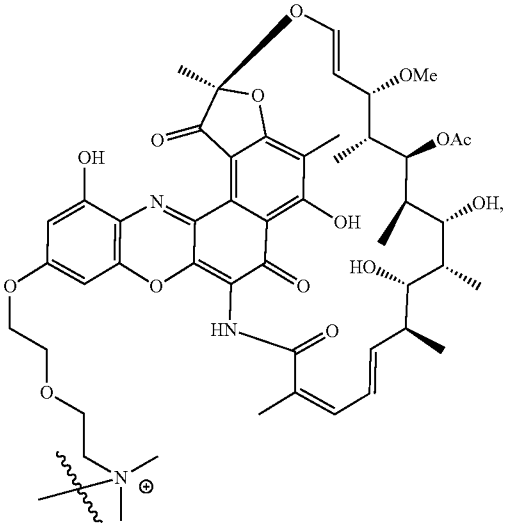
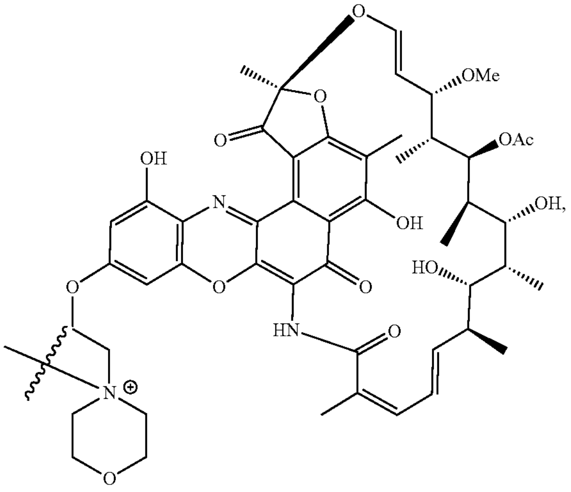
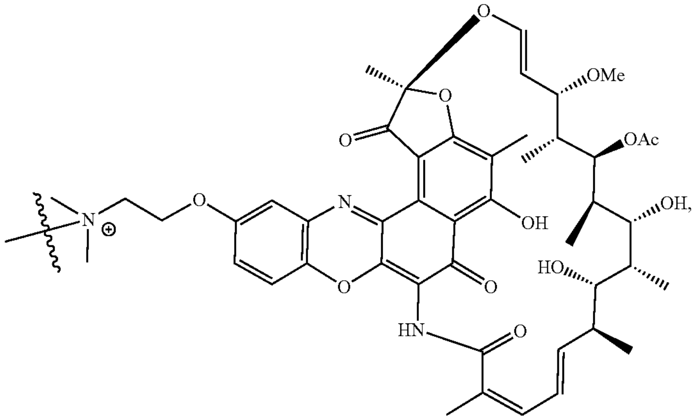
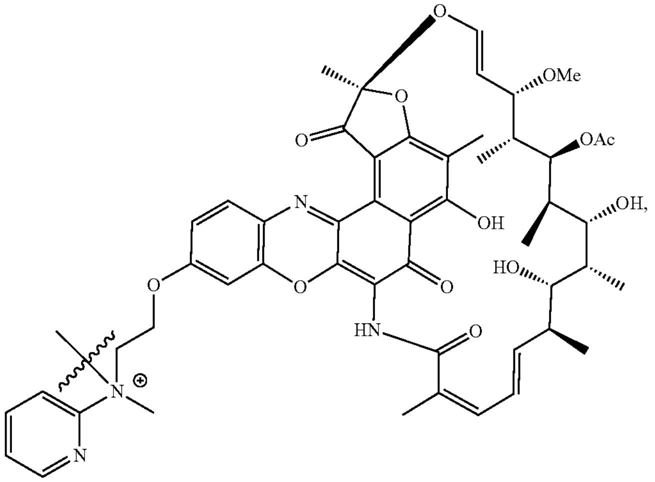

-continued
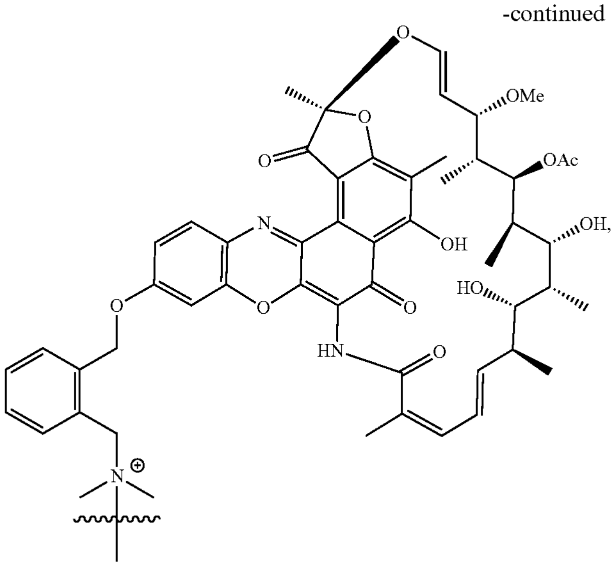
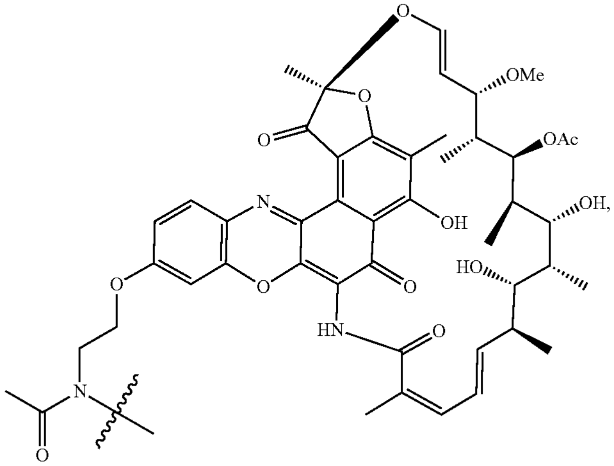
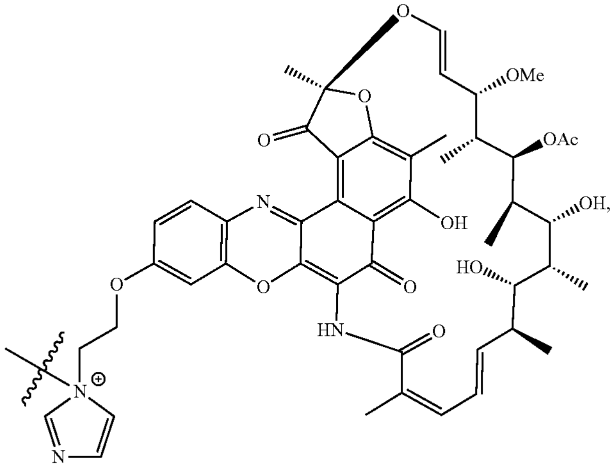

-continued
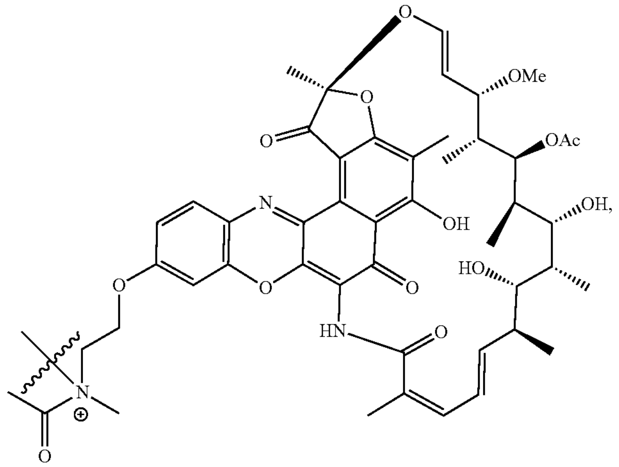
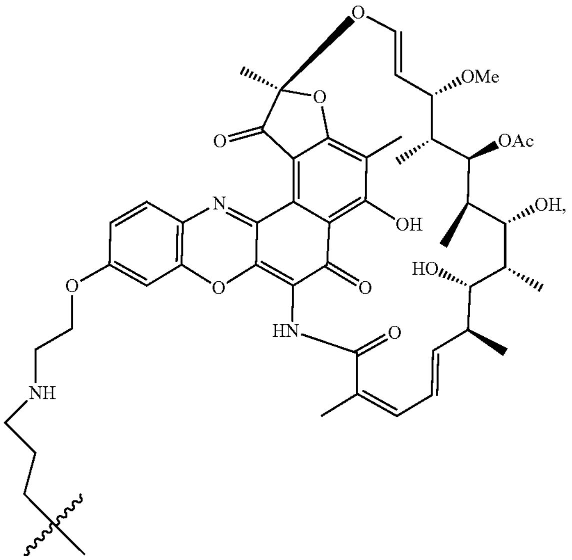
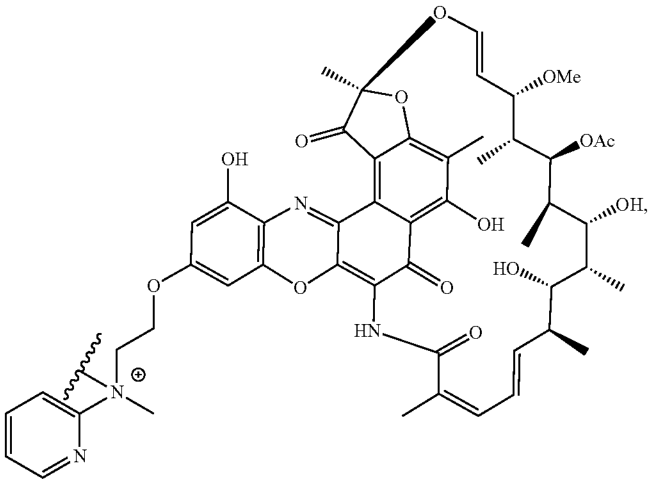

-continued
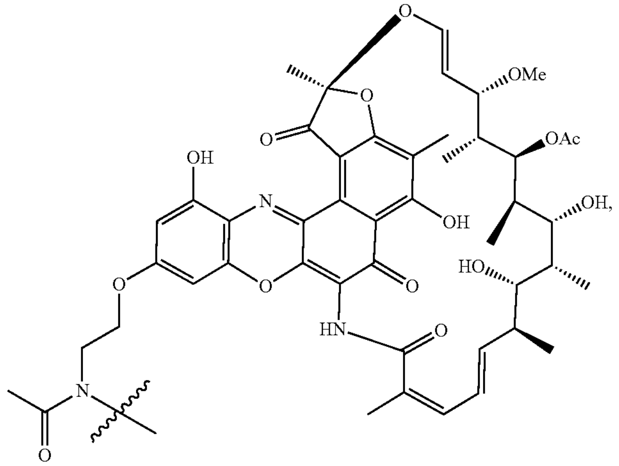
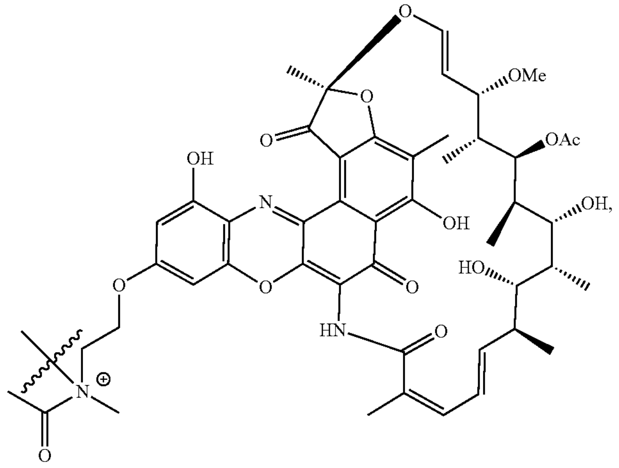
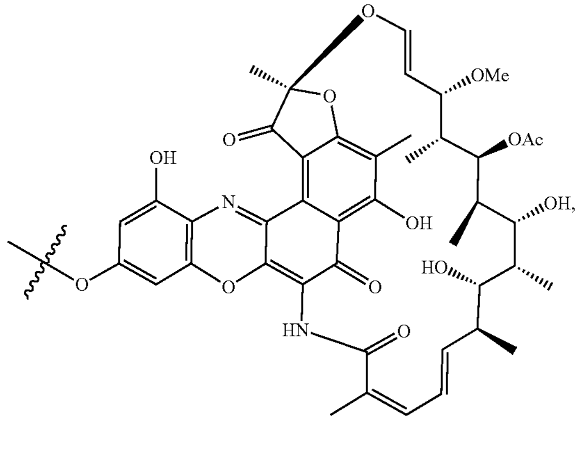

-continued
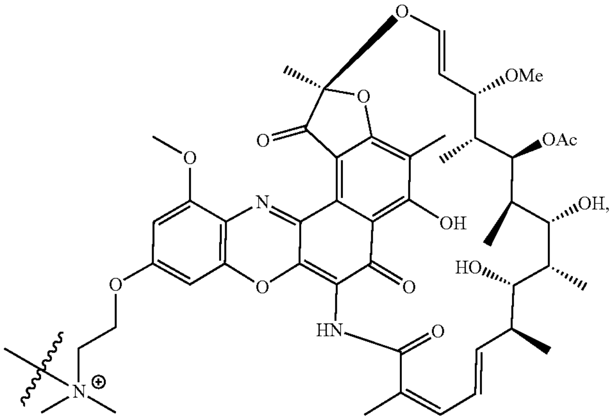
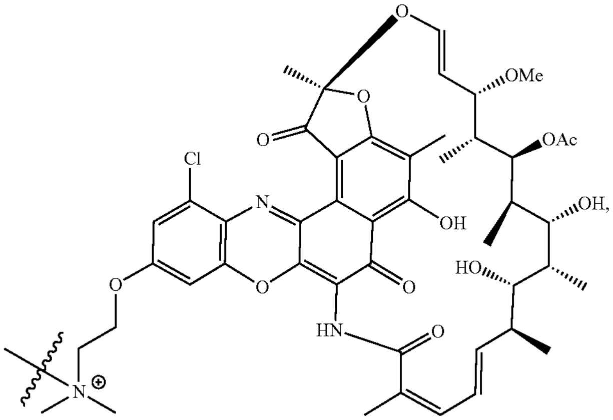
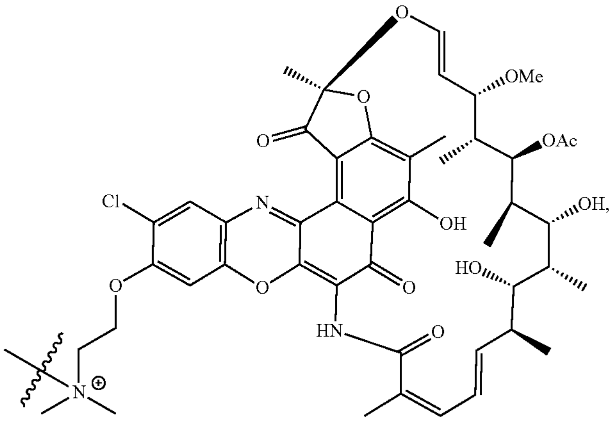
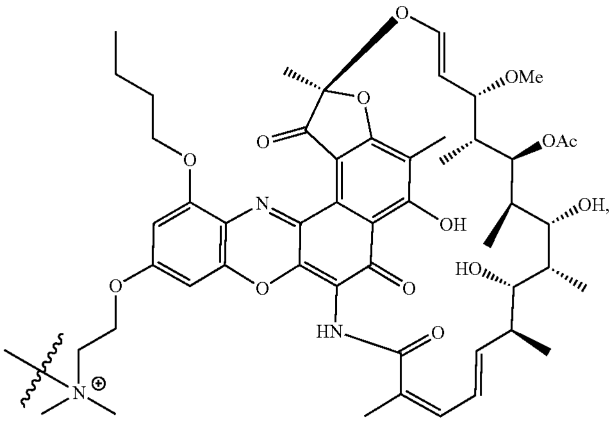

-continued
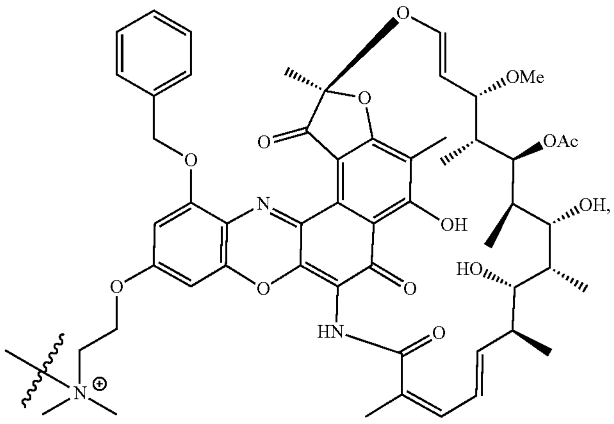
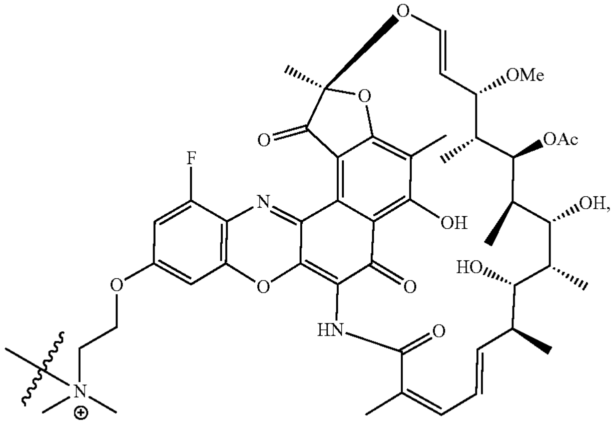
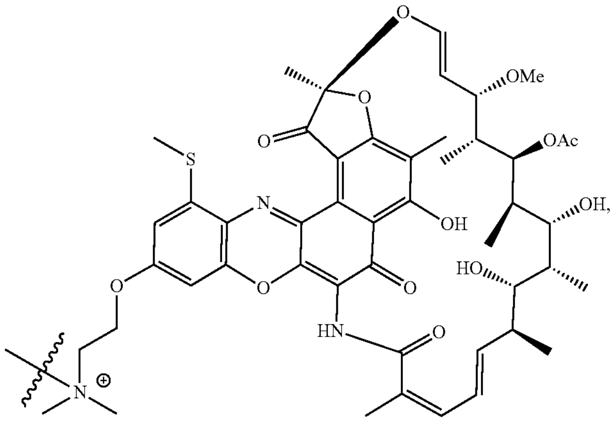
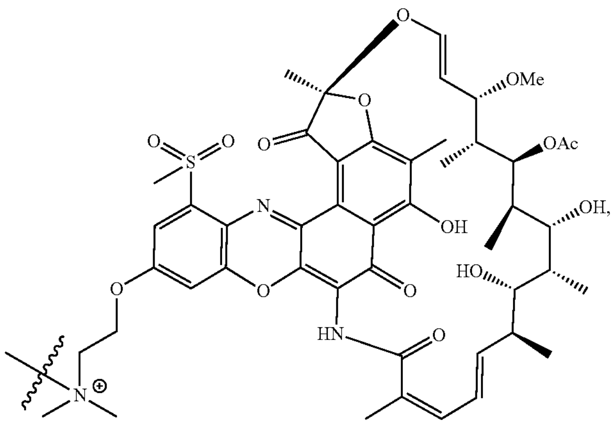

-continued
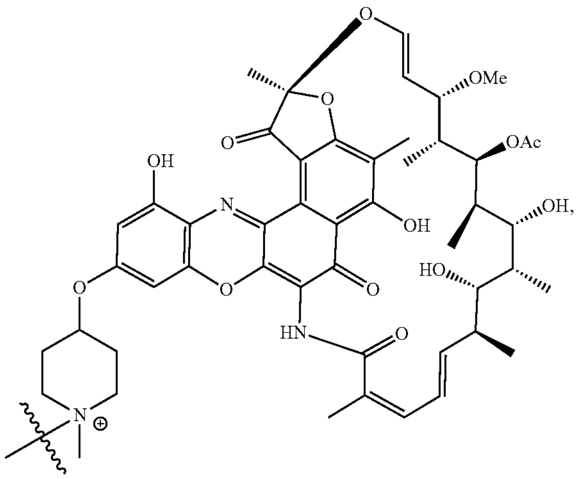
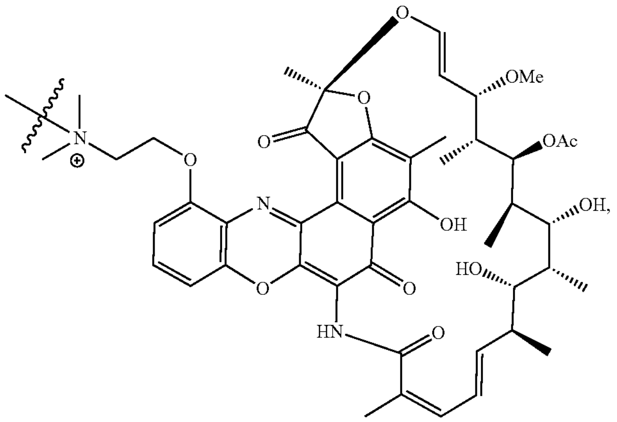
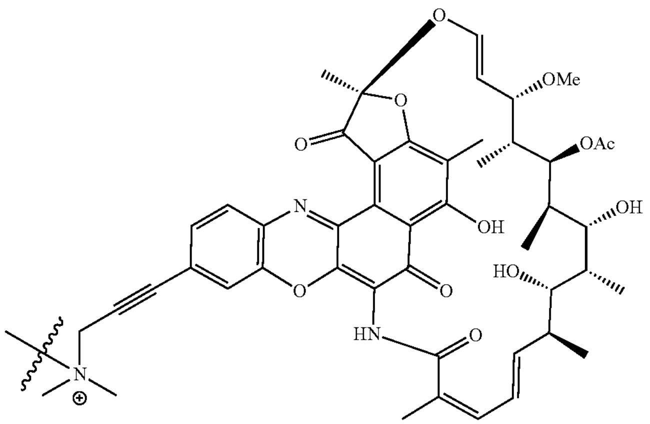
, and

-continued
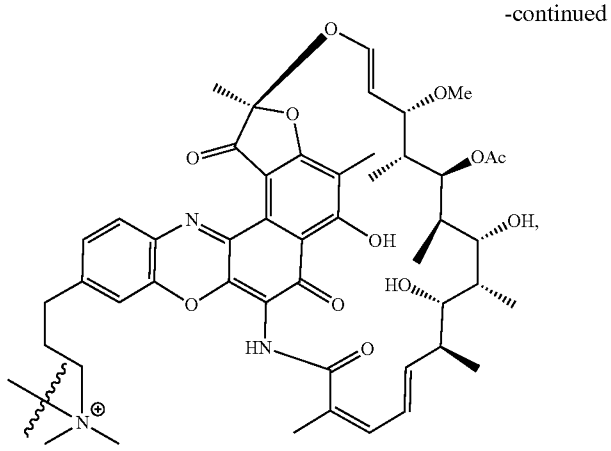
wherein the
is the bond to the linker.
In one aspect, the present disclosure provides an antibody-drug conjugate having the structure of Formula (XXII):
(XXII)
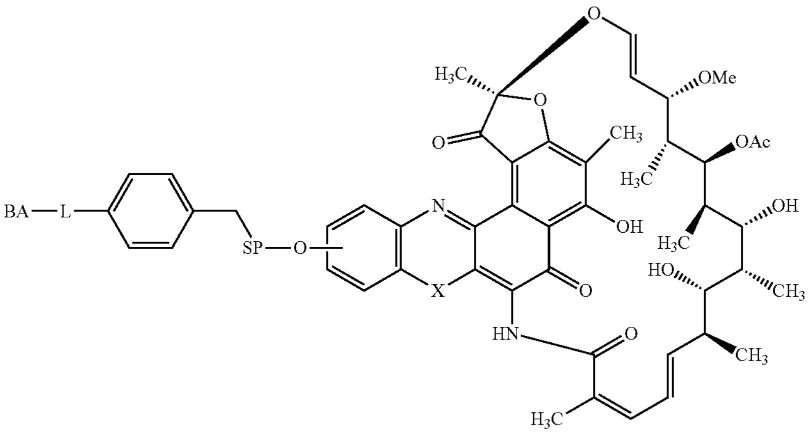

wherein:

BA is an antibody, or an antigen-binding fragment thereof;

L is a linker;

SP is a spacer group selected from

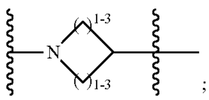
;
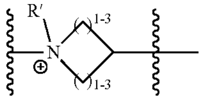
;
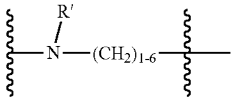
;
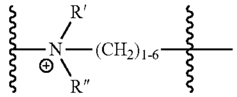
;
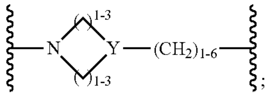
;
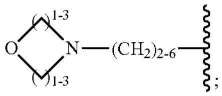
;
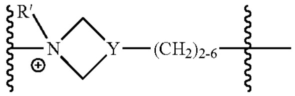
;
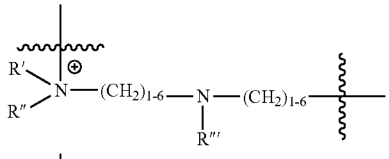
, and
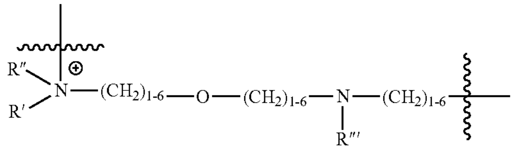

wherein the ∿ symbol represents the point of attachment; and R', R" and R"' are selected from a hydrogen, a $C_1$-$C_6$ aliphatic hydrocarbon, and a protecting group selected from Fluorenylmethyloxycarbonyl (FMOC) and tert-Butyloxycarbonyl (BOC), or wherein R' and R" together form an aliphatic monocyclic, an aliphatic bicyclic, or an aliphatic polycyclic structure;

Y is C or N;

R' and R" are independently at each occurrence selected from a hydrogen and a $C_{1-6}$ alkyl, and X is selected from —O—, —S—, and —NR*.

In one embodiment, the antibody is an anti-MSR1 antibody, or the antigen-binding fragment thereof, comprises: (a) the complementarity determining regions (CDRs) of a heavy chain variable region (HCVR) comprising an amino acid sequence as set forth in Table 9; and (b) the CDRs of a light chain variable region (LCVR) comprising an amino acid sequence as set forth in Table 9.

In one embodiment, the anti-MSR1 antibody, or the antigen-binding fragment thereof, comprises:

(i) a HCDR1 domain comprising an amino acid sequence selected from the group consisting of SEQ ID NOs: 4, 36, 52, 92, and 284;

(ii) a HCDR2 domain comprising an amino acid sequence selected from the group consisting of SEQ ID NOs: 6, 38, 54, 94, and 286;

(iii) a HCDR3 domain comprising an amino acid sequence selected from the group consisting of SEQ ID NOs: 8, 40, 56, 96, and 288;

(iv) a LCDR1 domain comprising an amino acid sequence selected from the group consisting of SEQ ID NOs: 12, 44, 60, 100, and 292;

(v) a LCDR2 domain comprising an amino acid sequence selected from the group consisting of SEQ ID NOs: 14, 46, 62, 102, and 294; and (vi) a LCDR3 domain comprising an amino acid sequence selected from the group consisting of SEQ ID NOs: 16, 48, 64, 104, and 296.

In one embodiment, the anti-MSR1 antibody, or the antigen-binding fragment thereof, comprises (i) a HCDR1 domain comprising an amino acid sequence of SEQ ID NO: 52;

(ii) a HCDR2 domain comprising an amino acid sequence of SEQ ID NO: 54;

(iii) a HCDR3 domain comprising an amino acid sequence of SEQ ID NO: 56;

(iv) a LCDR1 domain comprising an amino acid sequence of SEQ ID NO: 60;

(v) a LCDR2 domain comprising an amino acid sequence of SEQ ID NO: 62; and (vi) a LCDR3 domain comprising an amino acid sequence of SEQ ID NO: 64.

In one embodiment, the anti-MSR1 antibody, or the antigen-binding fragment thereof, comprises a N297Q mutation.

In one embodiment, the anti-WTA antibody, or the antigen-binding fragment thereof, may comprise: (a) the complementarity determining regions (CDRs) of a heavy chain variable region (HCVR) comprising an amino acid sequence as set forth in Table 2A; and (b) the CDRs of a light chain variable region (LCVR) comprising an amino acid sequence as set forth in Table 2A.

In one embodiment, the anti-WTA antibody, or the antigen-binding fragment thereof, may comprise:

(i) a HCDR1 domain comprising an amino acid sequence selected from the group consisting of SEQ ID NOs: 470, 476, 482, and 488;

(ii) a HCDR2 domain comprising an amino acid sequence selected from the group consisting of SEQ ID NOs: 471, 477, 483, and 489;

(iii) a HCDR3 domain comprising an amino acid sequence selected from the group consisting of SEQ ID NOs: 472, 478, 484, and 490;

(iv) a LCDR1 domain comprising an amino acid sequence selected from the group consisting of SEQ ID NOs: 467, 473, 479, and 485;

(v) a LCDR2 domain comprising an amino acid sequence selected from the group consisting of SEQ ID NOs: 468, 474, 480, and 486; and (vi) a LCDR3 domain comprising an amino acid sequence selected from the group consisting of SEQ ID NOs: 469, 475, 481, and 487.

In one embodiment, the anti-WTA antibody, or the antigen-binding fragment thereof, may comprise: (a) the complementarity determining regions (CDRs) of a heavy chain variable region (HCVR) comprising an amino acid sequence as set forth in Table 2B; and (b) the CDRs of a light chain variable region (LCVR) comprising an amino acid sequence as set forth in Table 2B.

In one embodiment, the anti-WTA antibody, or the antigen-binding fragment thereof, may comprise:

(i) a HCDR1 domain comprising an amino acid sequence selected from the group consisting of SEQ ID NOs: 502, 508, 514, 520, 526, 532, 538, 544, 550, 556, 562, 568, and 574;

(ii) a HCDR2 domain comprising an amino acid sequence selected from the group consisting of SEQ ID NOs: 503, 509, 515, 521, 527, 533, 539, 545, 551, 557, 563, 569, and 575;

(iii) a HCDR3 domain comprising an amino acid sequence selected from the group consisting of SEQ ID NOs: 504, 510, 516, 522, 528, 534, 540, 546, 552, 558, 564, 570, 576, and 584;

(iv) a LCDR1 domain comprising an amino acid sequence selected from the group consisting of SEQ ID NOs: 499, 505, 511, 517, 523, 529, 535, 541, 547, 553, 559, 565, and 571;

(v) a LCDR2 domain comprising an amino acid sequence selected from the group consisting of SEQ ID NOs: 500, 506, 512, 518, 524, 530, 536, 542, 548, 554, 560, 566, and 572; and (vi) a LCDR3 domain comprising an amino acid sequence selected from the group consisting of SEQ ID NOs: 501, 507, 513, 519, 525, 531, 537, 543, 549, 555, 561, 567, and 573.

In some embodiments, the anti-WTA antibody, or the antigen-binding fragment thereof, comprises a V205C mutation (EU numbering) in the light chain.

In one embodiment, the anti-WTA antibody, or the antigen-binding fragment thereof, is derived from antibody 4497 described in US Patent Application Publication 20140356375 (which is incorporated herein by reference in its entirety). In one embodiment, the anti-WTA antibody is derived from antibody 4497 and further comprises a V205C mutation in the light chain.

In one embodiment, the anti-WTA antibody, or the antigen-binding fragment thereof, comprises the HCDR1-HCDR2-HCDR3-LCDR1-LCDR2-LCDR3 of SEQ ID Nos: 568-569-570-565-566-567.

In some embodiments, the anti-WTA antibody or antigen binding fragment thereof comprises three heavy chain complementarity determining regions (HCDR1, HCDR2, and HCDR3) within a heavy chain variable region (HCVR) amino acid sequence of SEQ ID NOs: 586; and three light chain complementarity determining regions (LCDR1, LCDR2, and LCDR3) within a light chain variable region (LCVR) amino acid sequence of SEQ ID NO: 585.

In some embodiments, the anti-WTA antibody or antigen binding fragment thereof comprises an HCVR amino acid sequence of SEQ ID NOs: 586, and an LCVR amino acid sequence of SEQ ID NO: 585.

In some embodiments, the anti-WTA antibody comprises a heavy chain amino acid sequence of SEQ ID NOs: 602 and a light chain amino acid sequence of SEQ ID NO: 587 or SEQ ID NO: 589. In some embodiments, the anti-WTA antibody, or the antigen-binding fragment thereof comprises a V205C mutation in the light chain.

In one embodiment, the anti-Protein A antibody, or the antigen-binding fragment thereof, may comprise: (a) the complementarity determining regions (CDRs) of a heavy chain variable region (HCVR) comprising an amino acid sequence as set forth in Table 3A; and (b) the CDRs of a light chain variable region (LCVR) comprising an amino acid sequence as set forth in Table 3A.

In one embodiment, the anti-Protein A antibody, or the antigen-binding fragment thereof, may comprise:

(i) a HCDR1 domain comprising an amino acid sequence selected from the group consisting of SEQ ID NOs: 632, 652, and 672;

(ii) a HCDR2 domain comprising an amino acid sequence selected from the group consisting of SEQ ID NOs: 634, 654, and 674;

(iii) a HCDR3 domain comprising an amino acid sequence selected from the group consisting of SEQ ID NOs: 636, 656, and 676;

(iv) a LCDR1 domain comprising an amino acid sequence selected from the group consisting of SEQ ID NOs: 640, 660, and 680;

(v) a LCDR2 domain comprising an amino acid sequence selected from the group consisting of SEQ ID NOs: 642 and 662; and (vi) a LCDR3 domain comprising an amino acid sequence selected from the group consisting of SEQ ID NOs: 644, 664, and 683.

In some embodiments, the anti-Protein A antibody, or the antigen-binding fragment thereof, comprises a H435R and a Y436F mutation (EU numbering) in the heavy chain Fc.

In one embodiment, the anti-Protein A antibody or antigen binding fragment thereof comprises three heavy chain complementarity determining regions (HCDR1, HCDR2, and HCDR3) within a heavy chain variable region (HCVR) amino acid sequence of SEQ ID NOs: 630; and three light chain complementarity determining regions (LCDR1, LCDR2, and LCDR3) within a light chain variable region (LCVR) amino acid sequence of SEQ ID NO: 638. In one embodiment, the anti-Protein A antibody or antigen binding fragment thereof comprises a set of six CDRs (HCDR1-HCDR2-HCDR3-LCDR1-LCDR2-LCDR3) comprising SEQ ID NOs: 632-634-636-640-642-644.

In one embodiment, the anti-Protein A antibody or antigen binding fragment thereof comprises an HCVR amino acid sequence of SEQ ID NOs: 630; and an LCVR amino acid sequence of SEQ ID NO: 638.

In one embodiment, the anti-Protein A antibody comprises a heavy chain amino acid sequence of SEQ ID NOs: 666 and a light chain amino acid sequence of SEQ ID NO: 668. In one embodiments, the anti-Protein A antibody, further comprises a H435R and a Y436F mutation (EU numbering) in the heavy chain Fc. In one embodiment, anti-Protein A antibody further comprises a C103S mutation in the light chain. In one embodiment, the anti-Protein A antibody, or antigen-binding fragment thereof, is conjugated to a compound of the present disclosure at light chain position 103.

In various embodiments, the antibody, or antigen-binding fragment thereof, comprises a C103S mutation in the light chain.

The various embodiments, the antibody, or the antigen-binding fragment thereof, is conjugated to a compound of the present disclosure at position 103 of the light chain.

In one embodiment, L is a linker having the formula

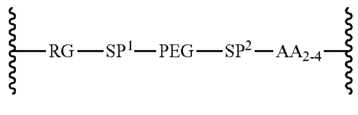
,

Wherein

RG is selected from a maleimide, a N-hydroxy succinimide, or a succinimide;

$SP^1$ and $SP^2$ are independently absent or a spacer group selected from the group consisting of

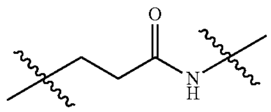
;

$C_{1-6}$ alkyl, —NH—, —C(O)—, —$CH_2$—$CH_2$—C(O)—NH—, —$(CH)_u$—C(O)—NH—, (—$CH_2$—$CH_2$—$O)_e$, —NH—$CH_2$—$CH_2$—(—O—$CH_2$—$CH_2)_e$—C(O)—, —C(O)—$(CH_2)_u$—C(O)—, —C(O)—NH—$(CH_2)_v$—, and combinations thereof, wherein subscript e is an integer from 0 to 4, subscript u is an integer from 1 to 8, and subscript v is an integer from 1 to 8;

$AA_{2-4}$ is a peptide unit comprising from 2 to 4 amino acids, and

PEG is a polyethylene glycol chain comprising between 1 and 30 polyethylene glycol residues.

In one embodiment, $AA_{2-4}$ is a dipeptide selected from valine-citrulline; citrulline-valine; valine-alanine; alanine-valine; valine-glycine, glycine-valine, or alanine-glycine, alanine-alanine.

In one embodiment, $AA_{2-4}$ is valine-citrulline.

In one embodiment, SP is

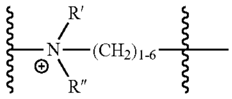

and R' and R" are each a $C_{1-6}$ alkyl.

In one embodiment, SP is

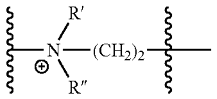

and R' and R" are each methyl.

In one embodiment, $SP^1$ and $SP^2$ are each

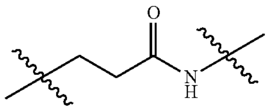
.

In one embodiment, PEG comprises 8 polyethylene glycol units.

In one embodiment, BA is an antibody, or an antigen-binding fragment thereof, L is a linker having the formula

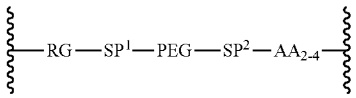
, wherein

RG is selected from a maleimide or a succinimide;

$SP^1$ and $SP^2$ are each

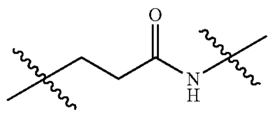
;

$AA_{2-4}$ is valine-citrulline;

PEG is a polyethylene glycol chain comprising 8 polyethylene glycol residues

SP is

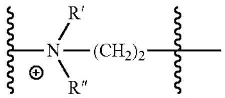

and R' and R" are each methyl, and

X is —O—.

In one embodiment, the antibody-drug conjugate has a structure:

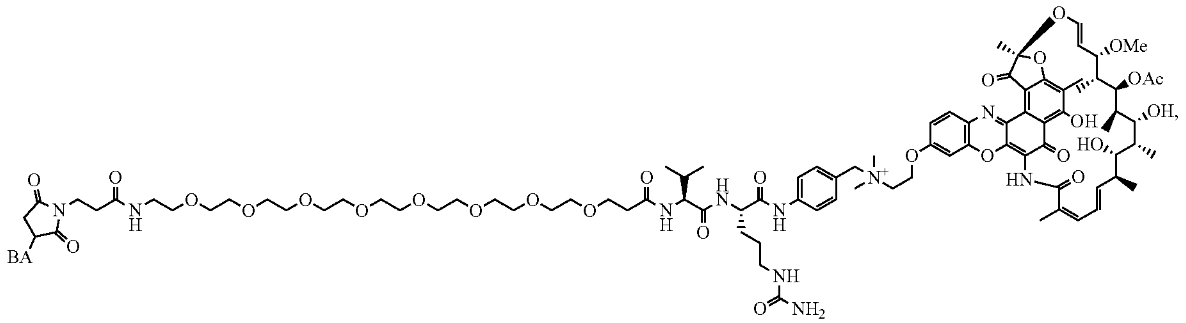

wherein BA is an antibody, or an antigen-binding fragment thereof.

In another aspect, the present disclosure provides an isolated antibody or antigen binding fragment thereof, wherein the antibody or antigen binding fragment thereof is conjugated, directly or through a linker or a linker-spacer, to a payload having the structure selected from the group consisting of:

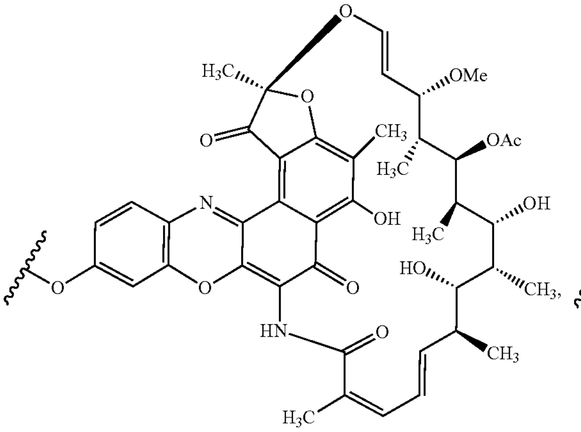

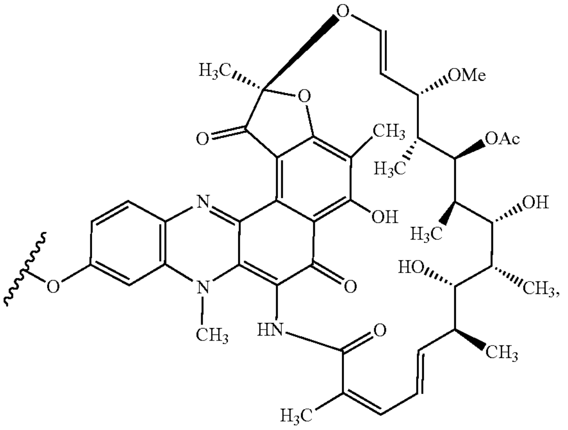

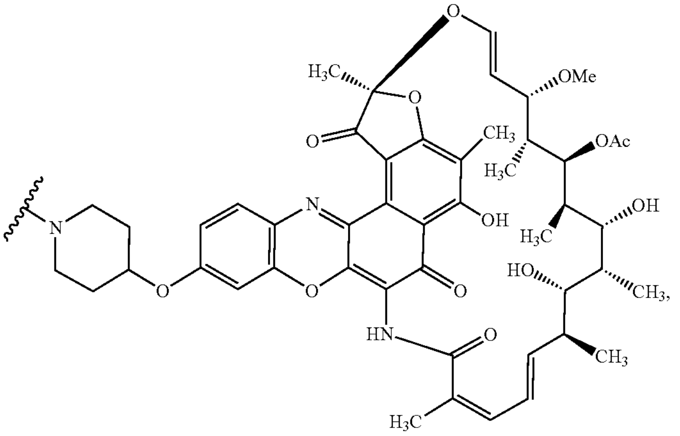

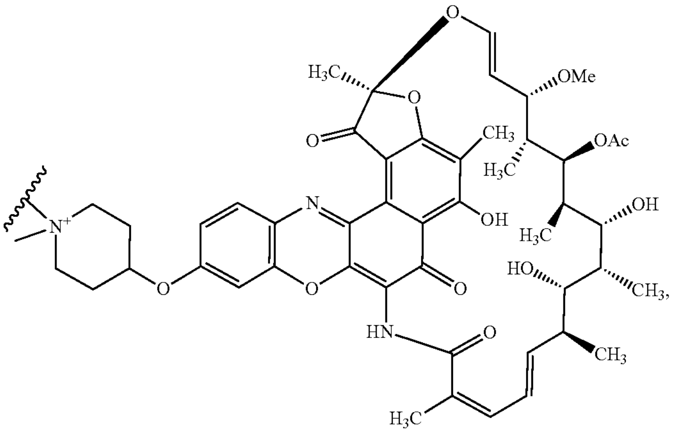

-continued
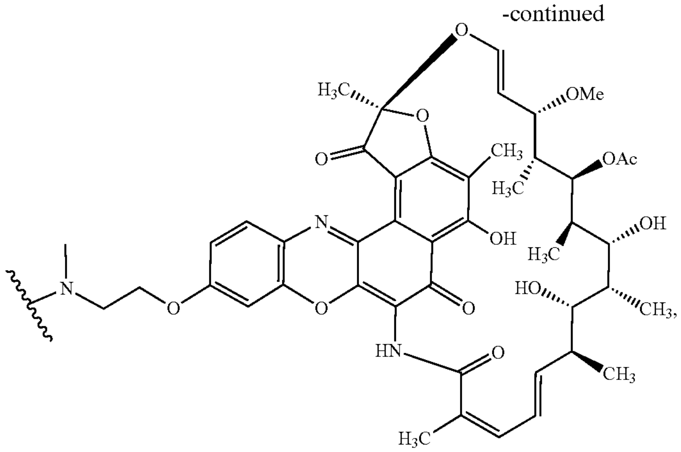
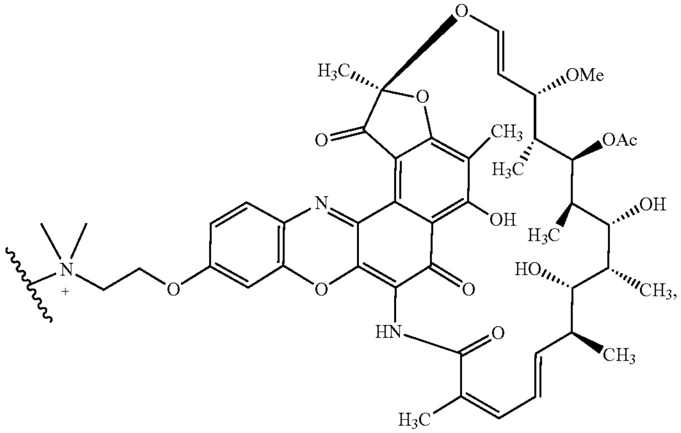
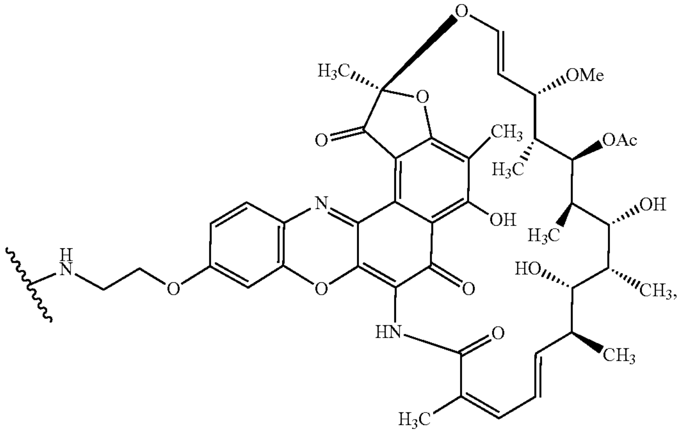
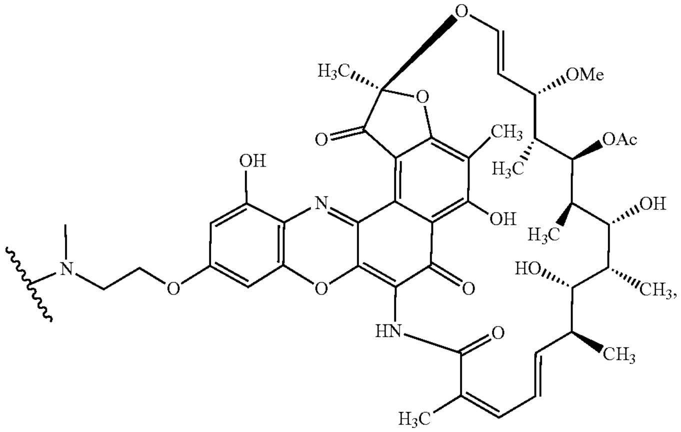

-continued
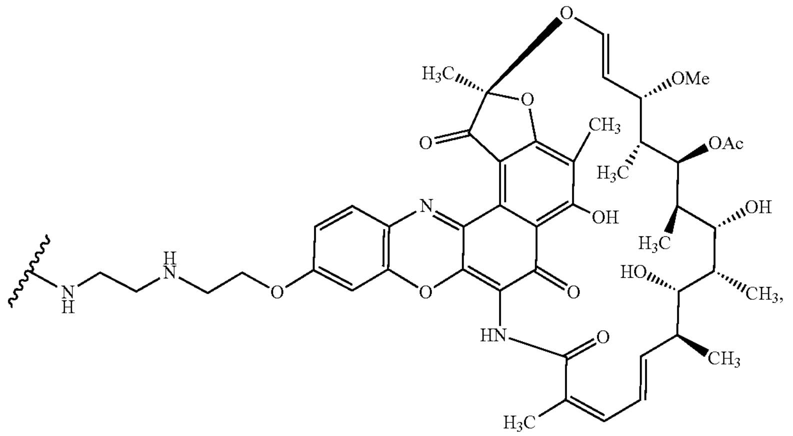
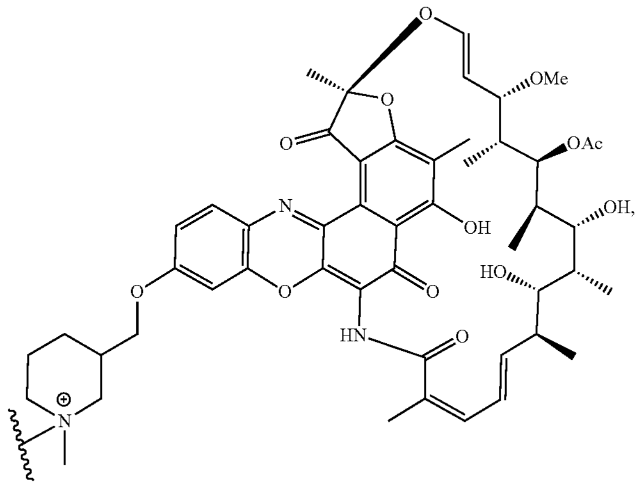
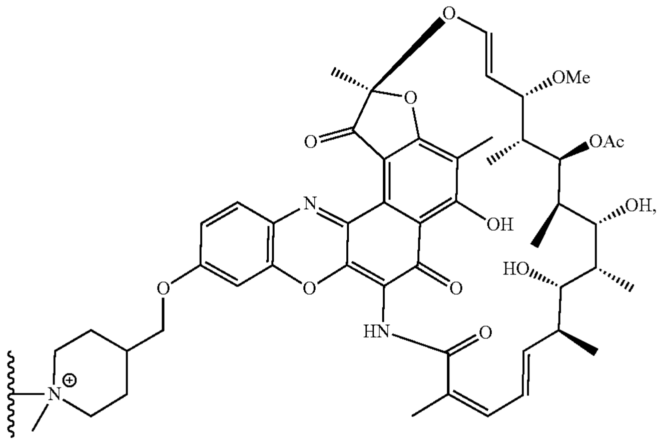

-continued
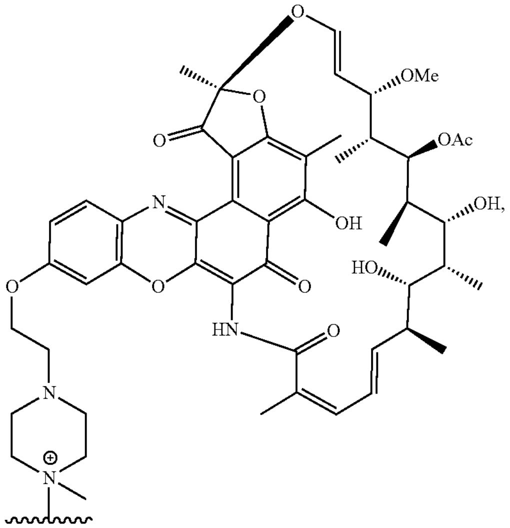
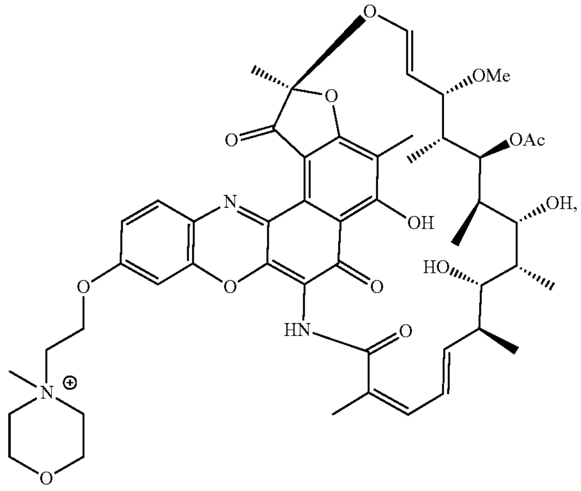
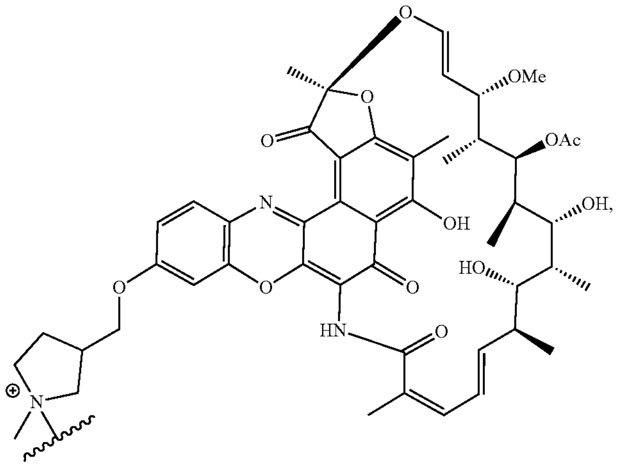
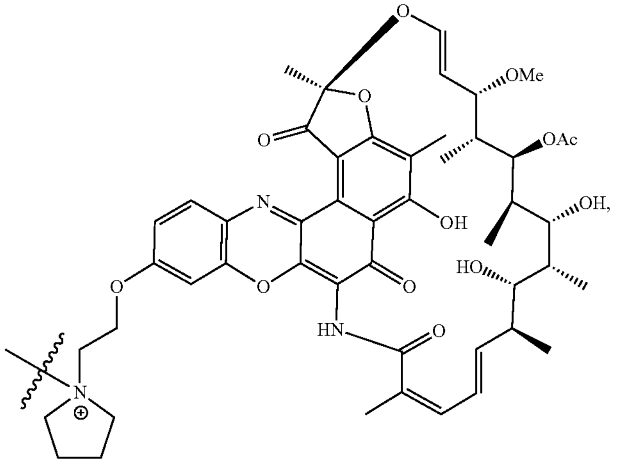

-continued
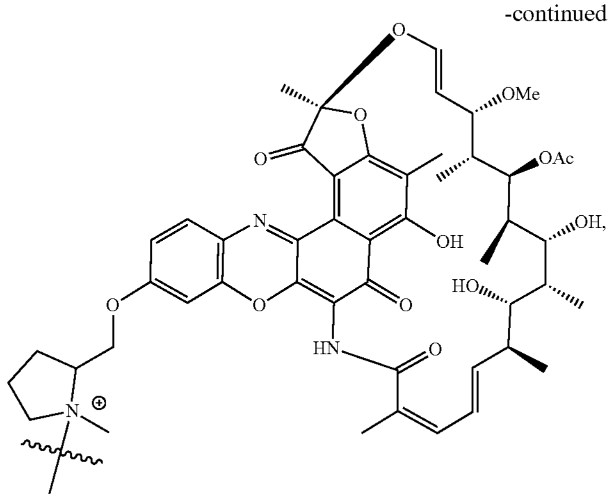
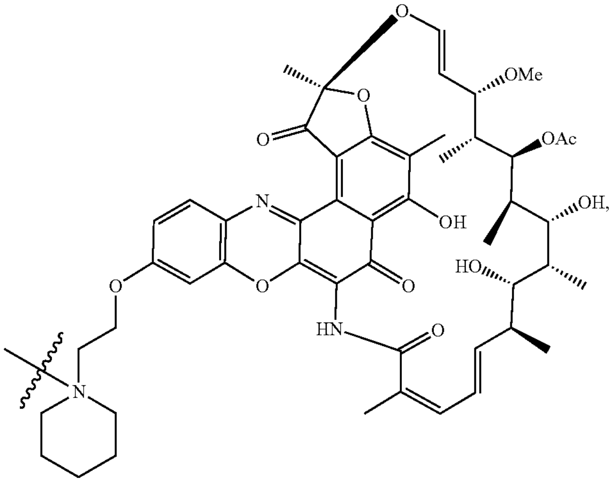
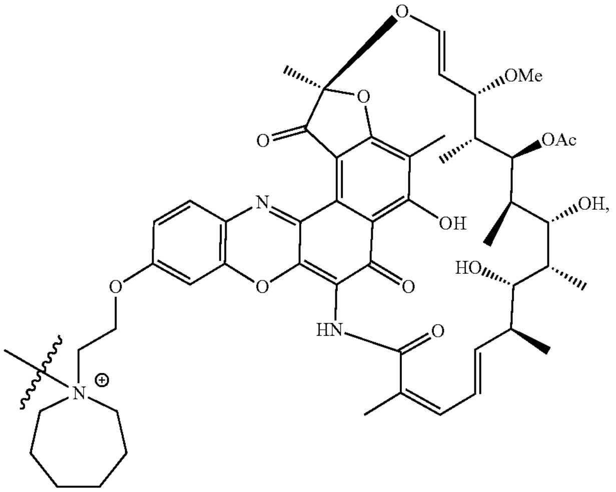
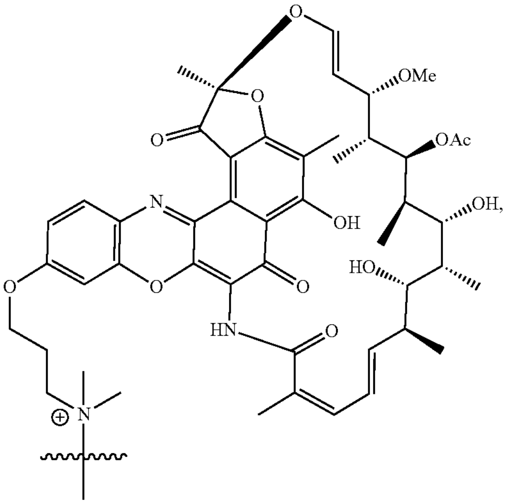

-continued
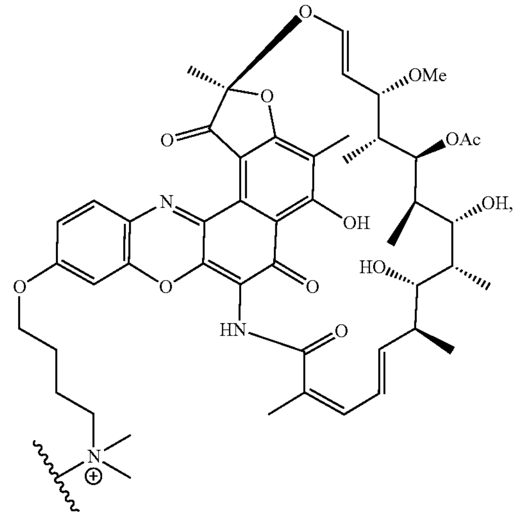
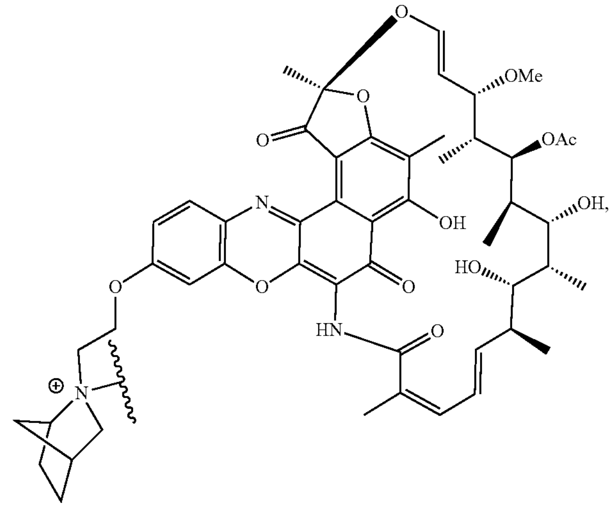
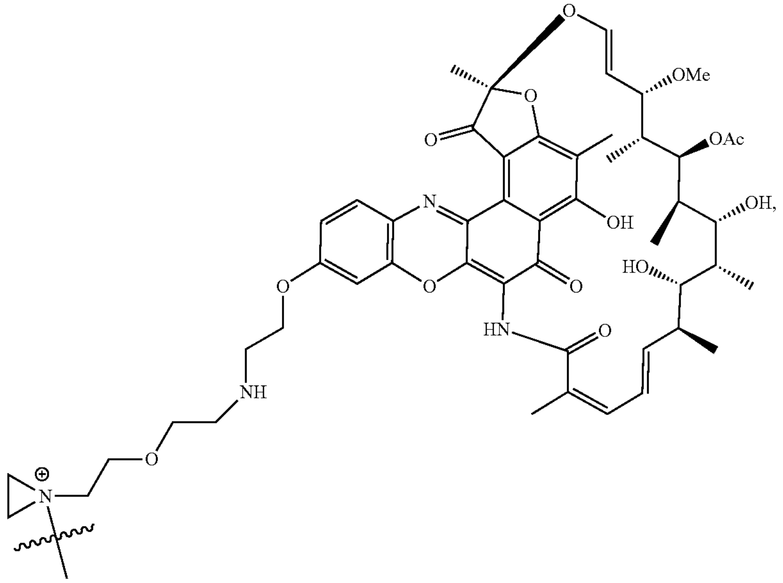
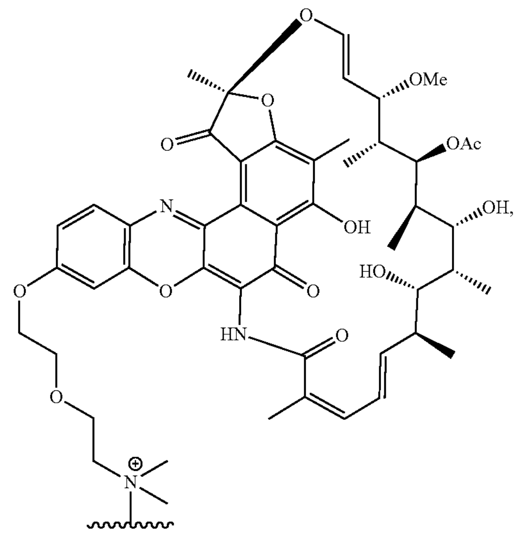
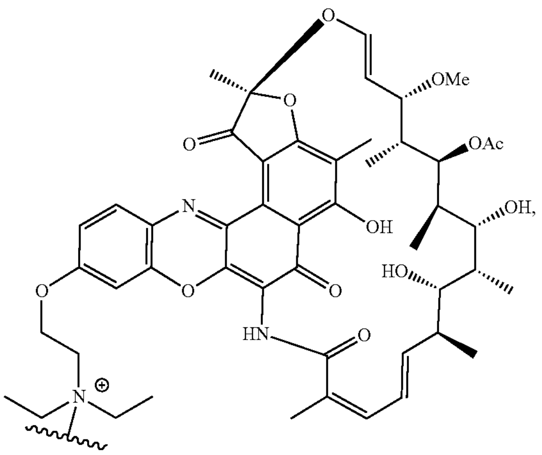

-continued
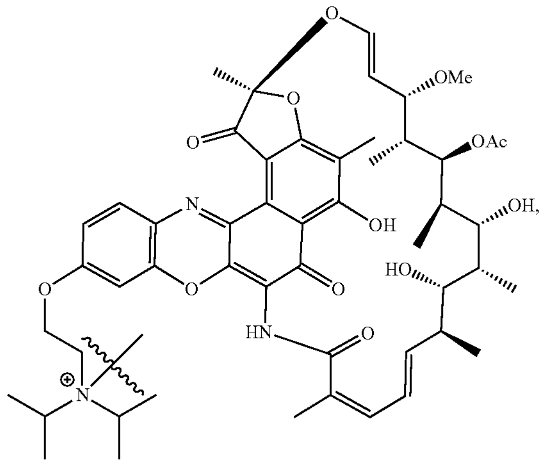
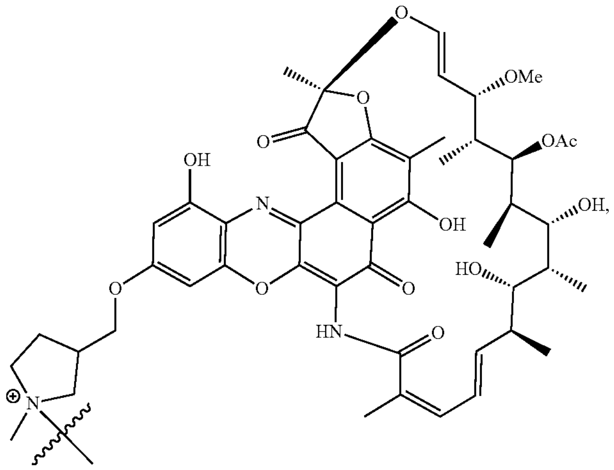
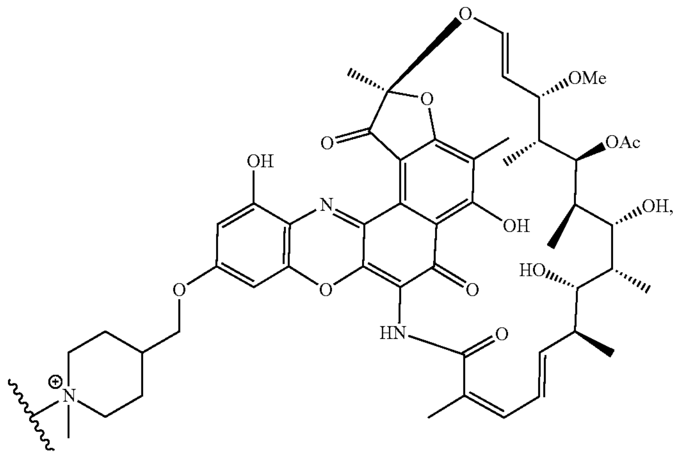
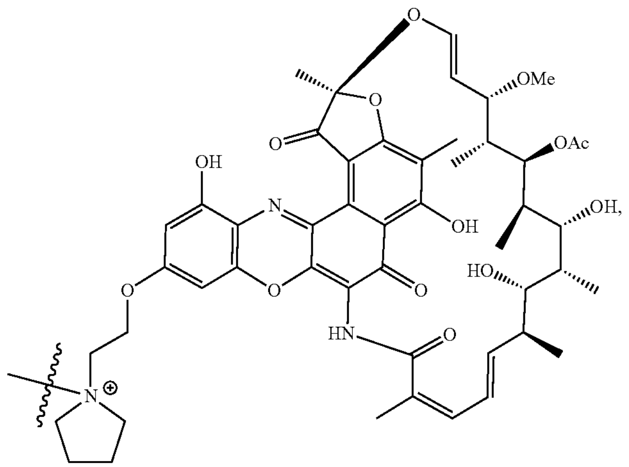

-continued
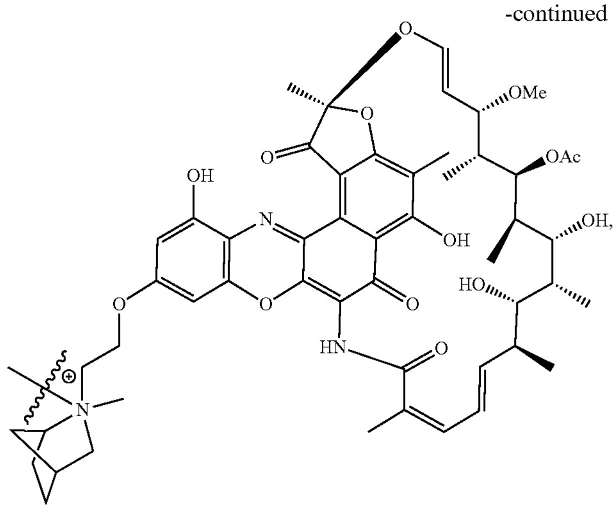
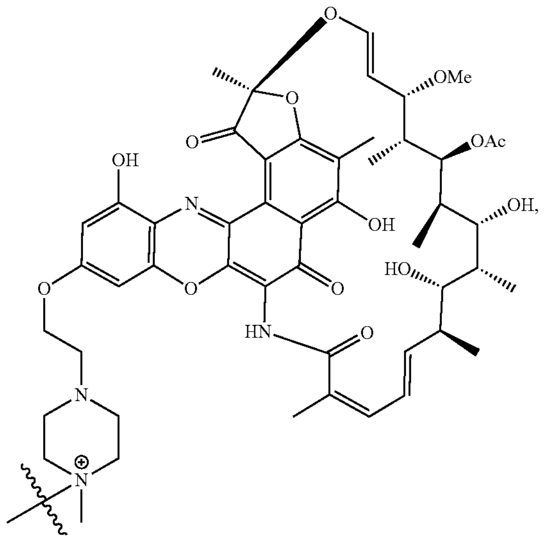
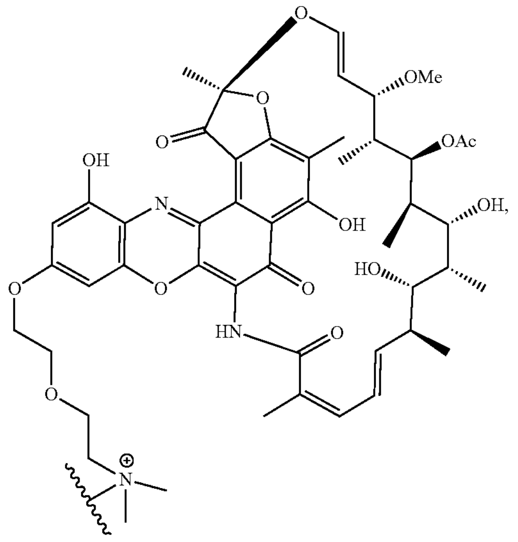
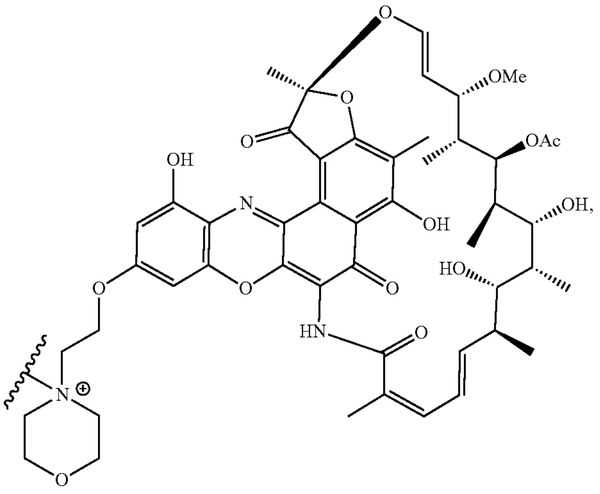
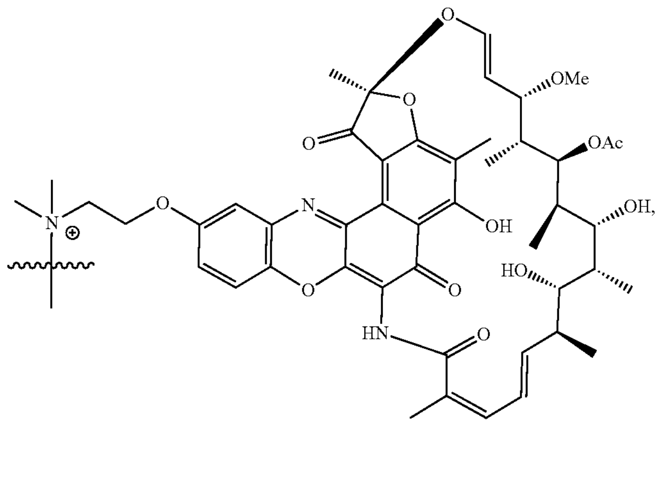

-continued
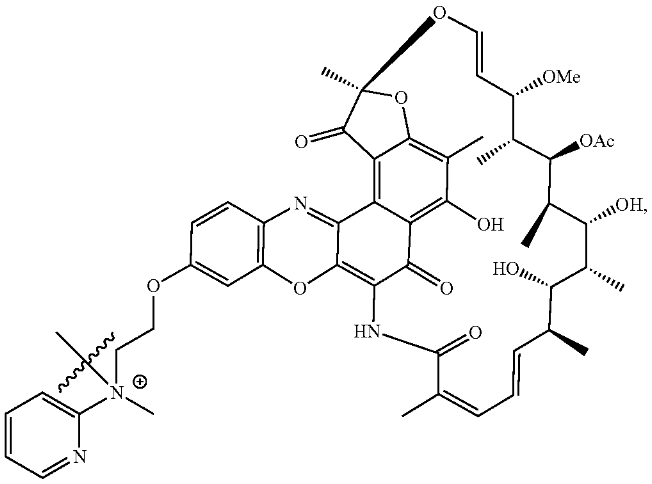
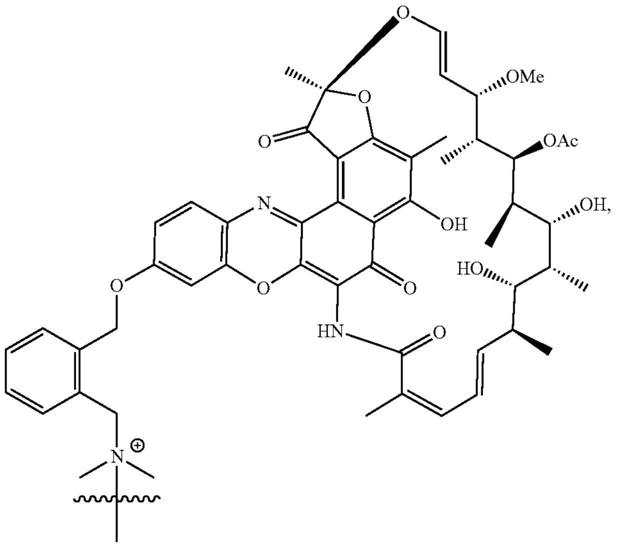
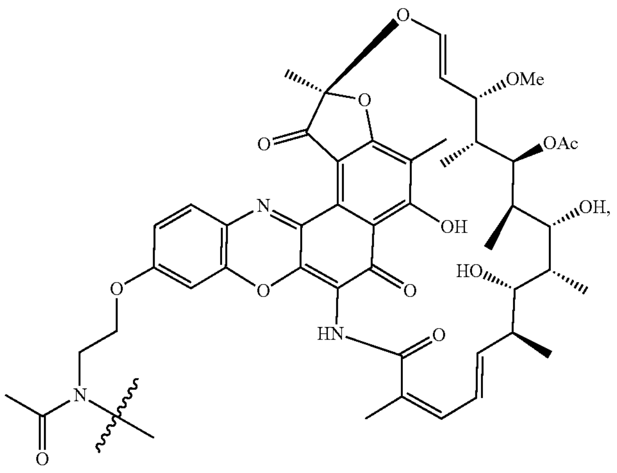

-continued
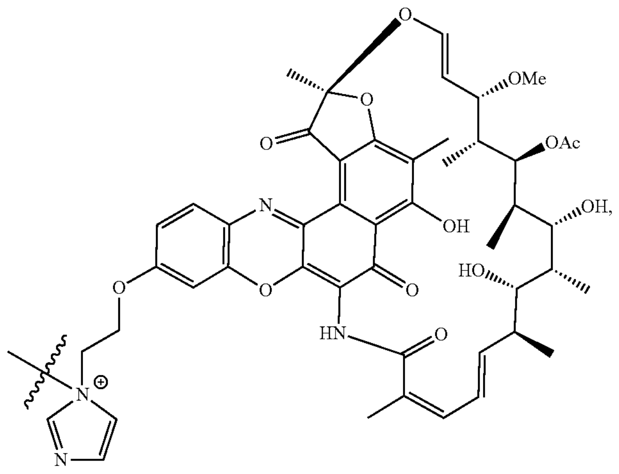
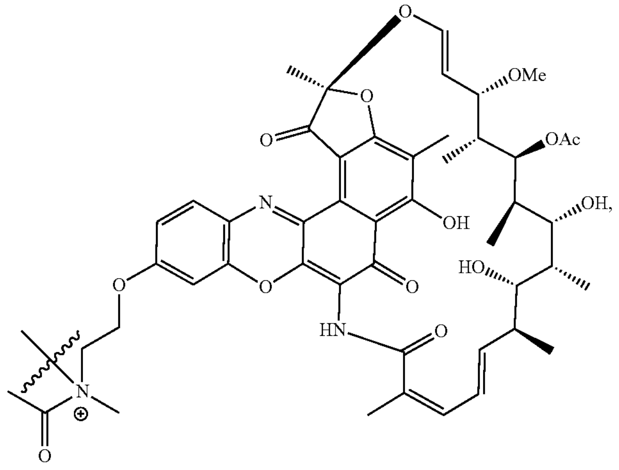
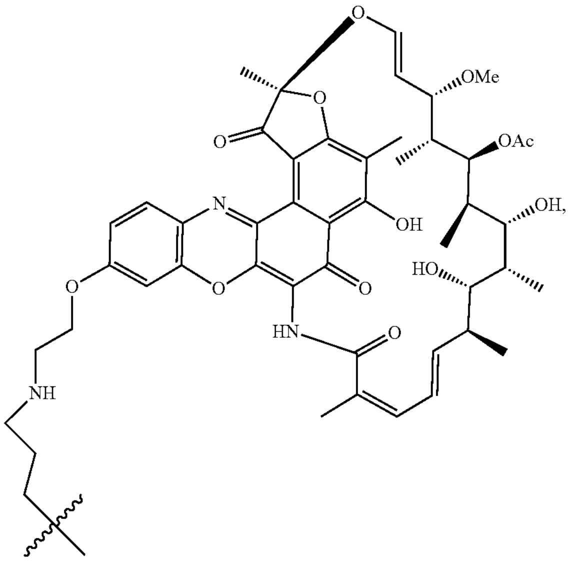

-continued
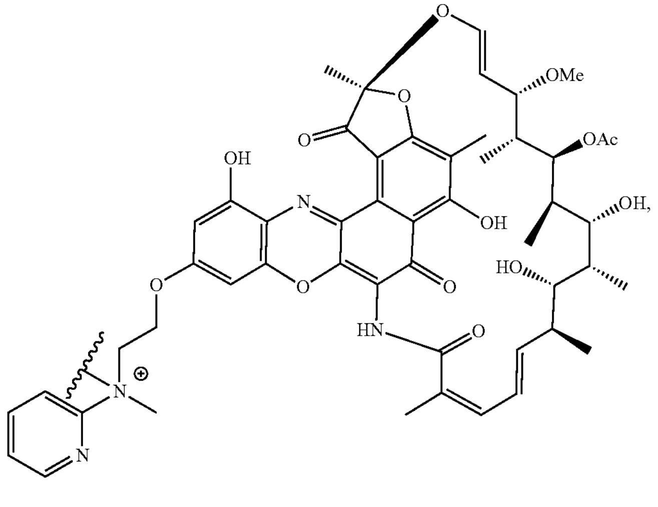
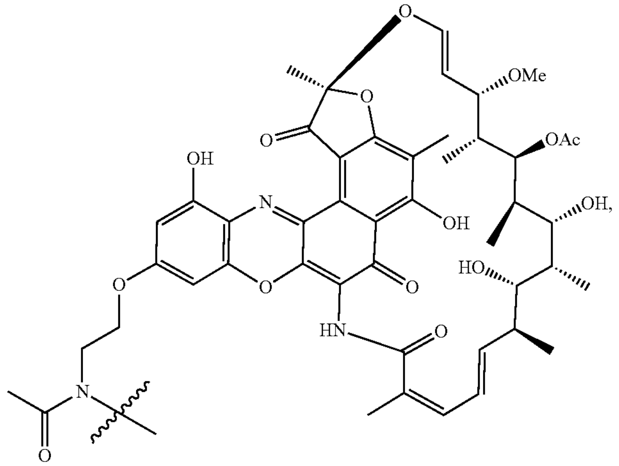
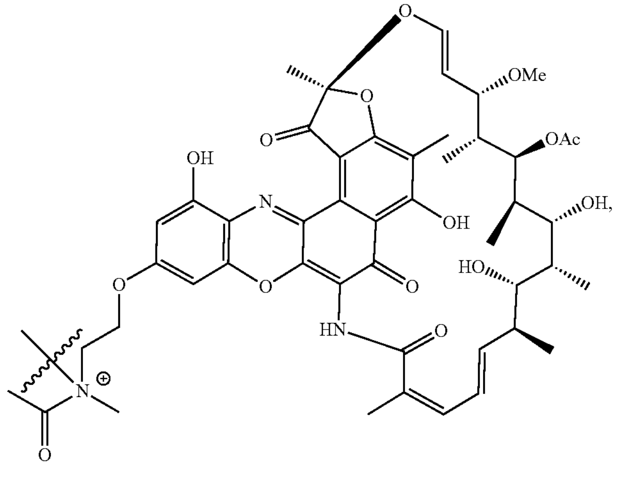

-continued
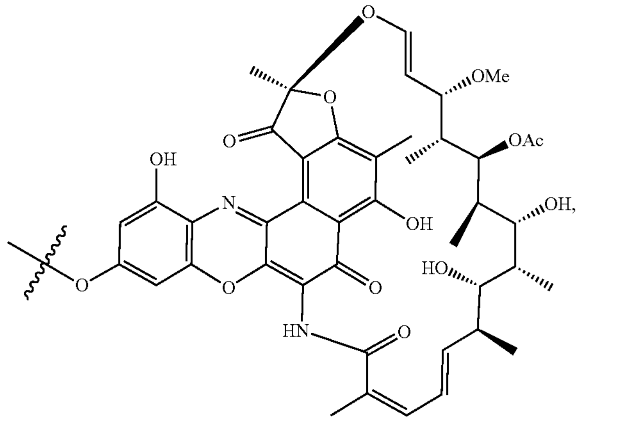
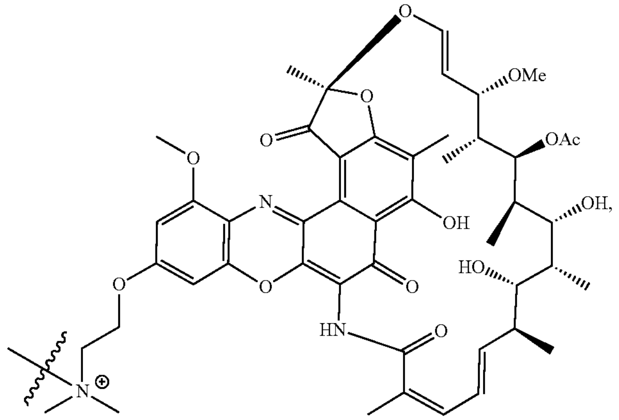
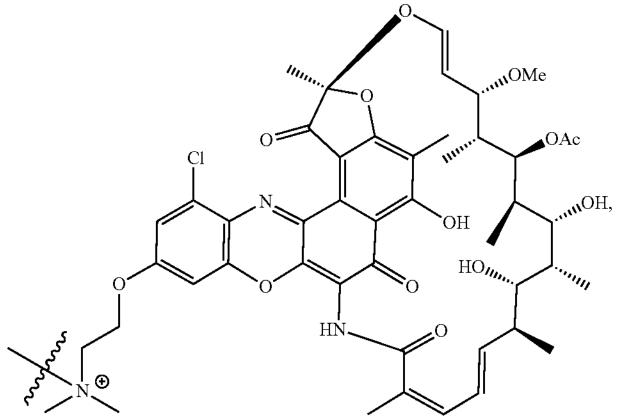
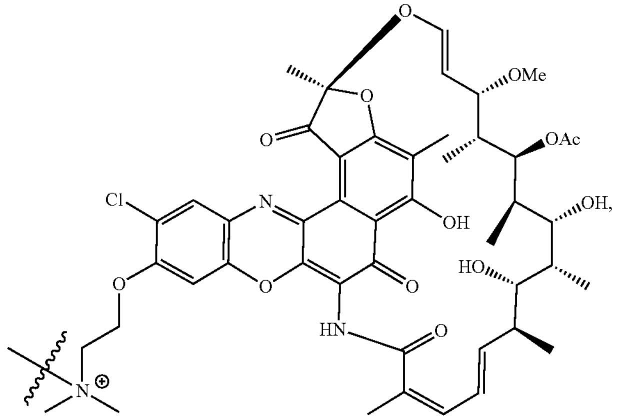

-continued
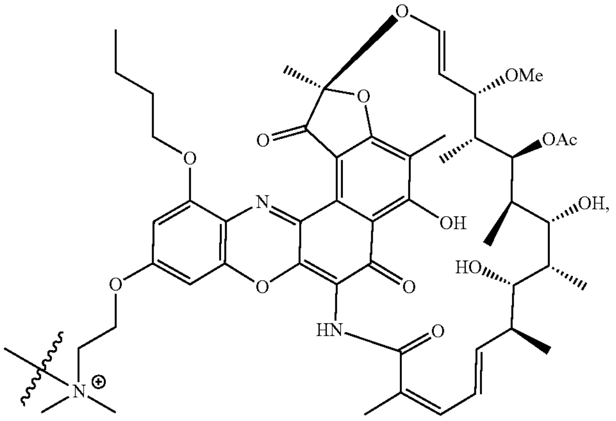
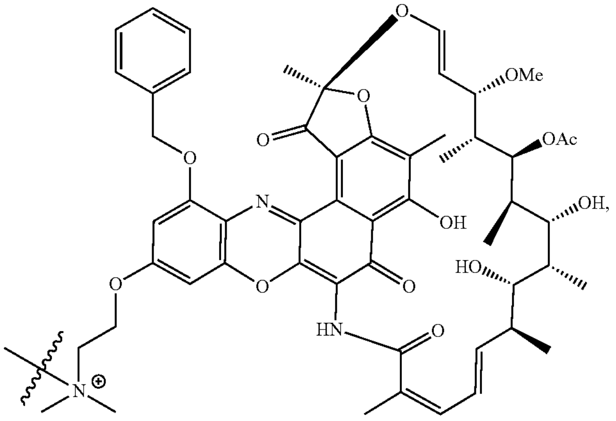
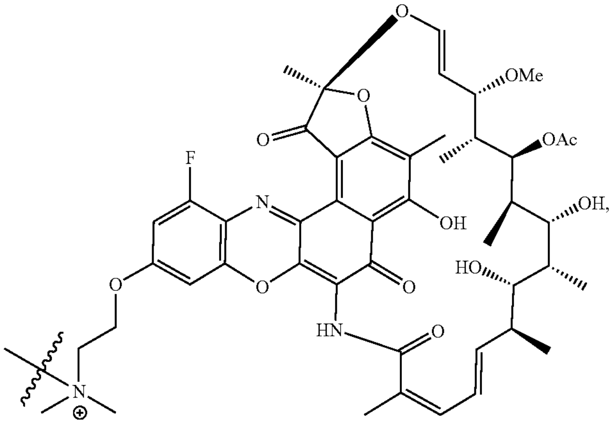
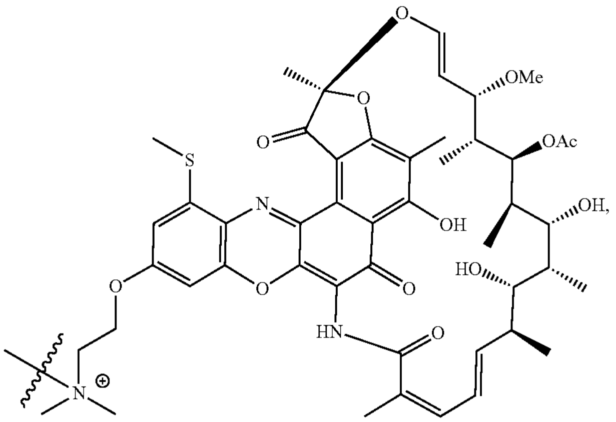

-continued
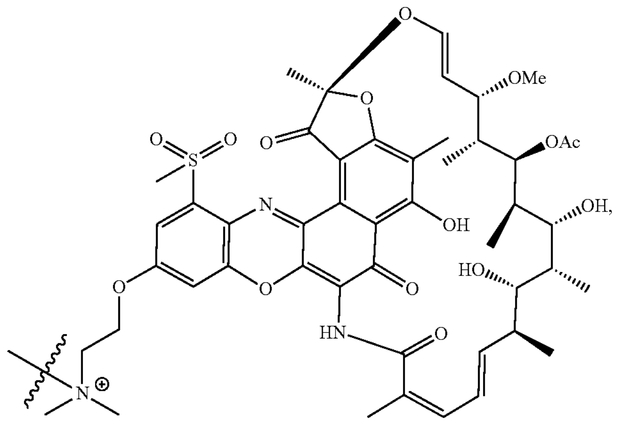
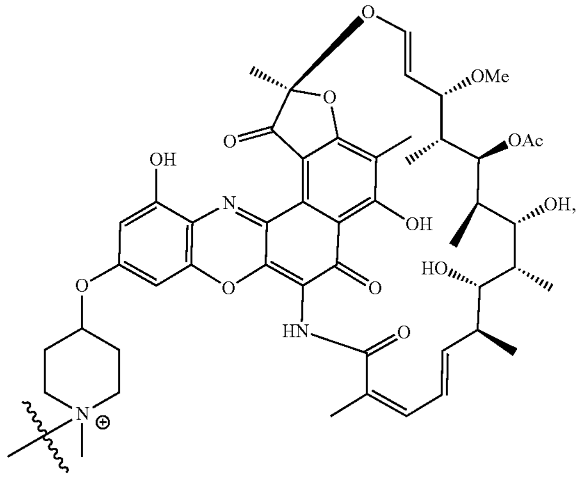
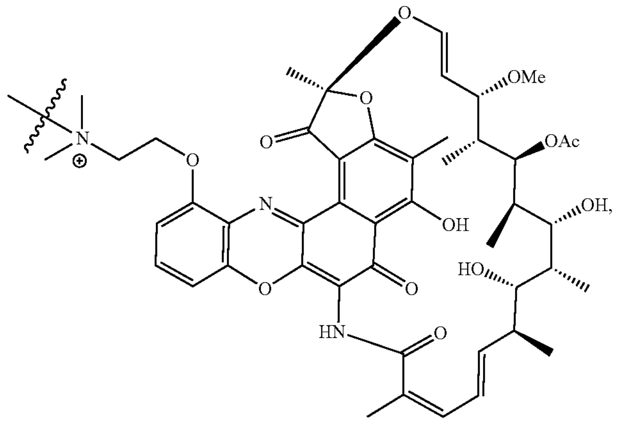

-continued
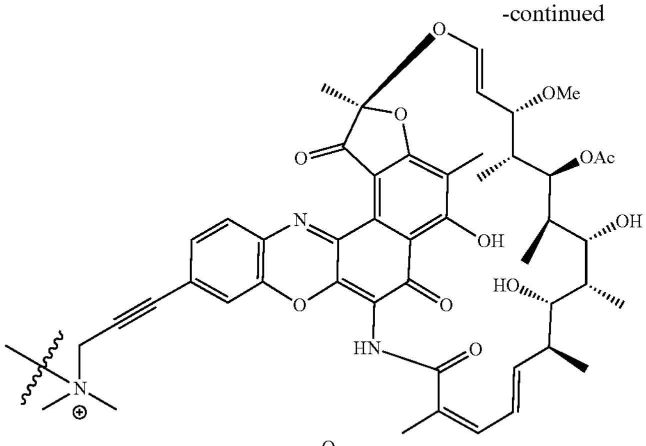
, and
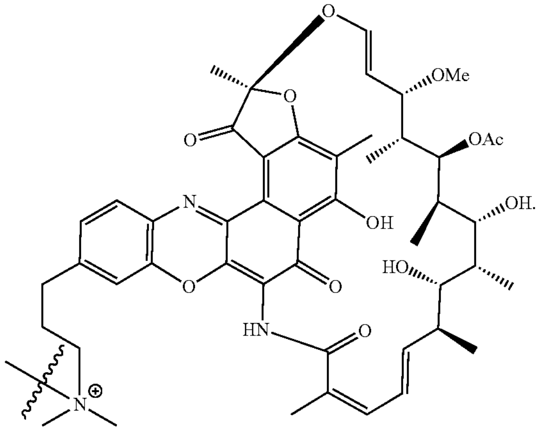
In one embodiment, the payload has the structure selected from:
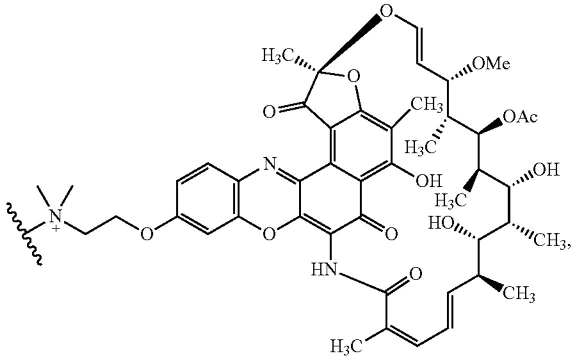
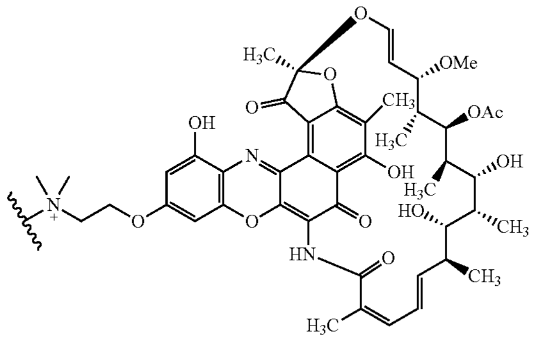
and
-continued
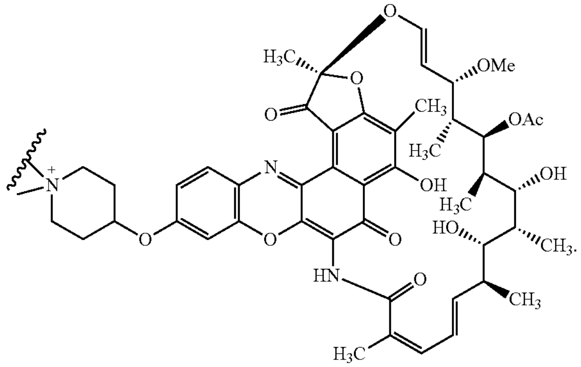
In one embodiment the payload is conjugated through a linker, the linker having the structure:
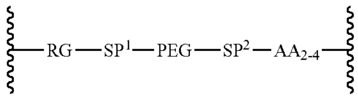
,
wherein
RG is selected from a maleimide or a succinimide;
$SP^1$ and $SP^2$ are independently absent or a spacer group selected from the group consisting of

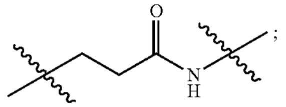

$C_{1-6}$ alkyl, —NH—, —C(O)—, —$CH_2$—$CH_2$—C(O)—NH—, —$(CH)_u$—C(O)—NH—, (—$CH_2$—$CH_2$—$O)_e$, —NH—$CH_2$—$CH_2$—(—O—$CH_2$—$CH_2)_e$—C(O)—, —C(O)—$(CH_2)_u$—C(O)—, —C(O)—NH—$(CH_2)_v$—, and combinations thereof, wherein subscript e is an integer from 0 to 4, subscript u is an integer from 1 to 8, and subscript v is an integer from 1 to 8;

$AA_{2-4}$ is a peptide unit comprising from 2 to 4 amino acids, and

PEG is a polyethylene glycol chain comprising between 1 and 30 polyethylene glycol residues.

In one embodiment, $AA_{2-4}$ is a dipeptide selected from valine-citrulline; citrulline-valine; valine-alanine; alanine-valine; valine-glycine, or glycine-valine.

In one embodiment, $AA_{2-4}$ is valine-citrulline.

In one embodiment, SP is

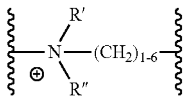

and R' and R" are each a $C_{1-6}$ alkyl.

In one embodiment, SP is

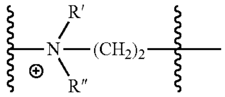

and R' and R" are each methyl.

In one embodiment, $SP^1$ and $SP^2$ are each

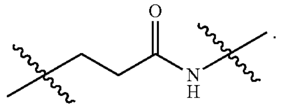

In one embodiment, PEG comprises 8 polyethylene glycol units.

In one embodiment, the payload is conjugated through a linker having the structure:

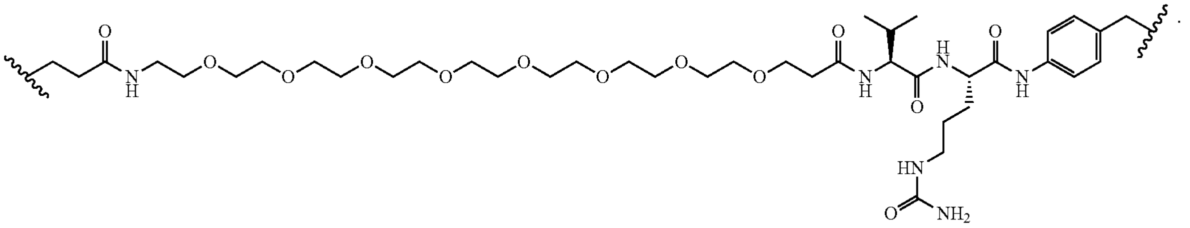 [SMILES: *CCC(=O)NCCOCCOCCOCCOCCOCCOCCOCCOCCC(=O)N[C@H](C(=O)N[C@@H](CCCNC(N)=O)C(=O)Nc1ccc(C*)cc1)C(C)C]

In one embodiment, the payload is conjugated through a linker, the linker-payload having the structure:

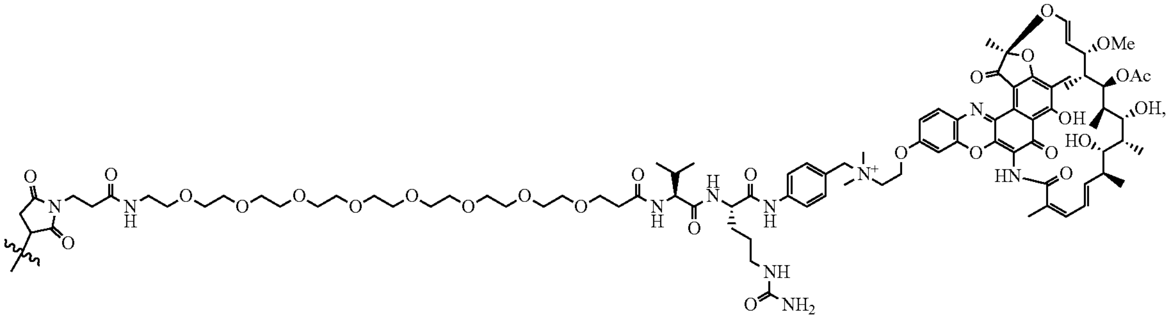 [SMILES: *C1CC(=O)N(CCC(=O)NCCOCCOCCOCCOCCOCCOCCOCCOCCC(=O)N[C@H](C(=O)N[C@@H](CCCNC(N)=O)C(=O)Nc2ccc(C[N+](C)(C)CCOc3ccc4nc5c6c7c8c(C)c(O)c6c(=O)c(c-5oc4c3)NC(=O)/C(C)=C\C=C\[C@H](C)[C@H](O)[C@@H](C)[C@@H](O)[C@@H](C)[C@H](OC(C)=O)[C@H](C)[C@@H](OC)/C=C/O[C@@](C)(O8)C7=O)cc2)C(C)C)C1=O]

wherein the

is the bond to the antibody or the antigen-binding fragment thereof.

In one embodiment, the payload is conjugated through a linker, the linker-payload having the structure:

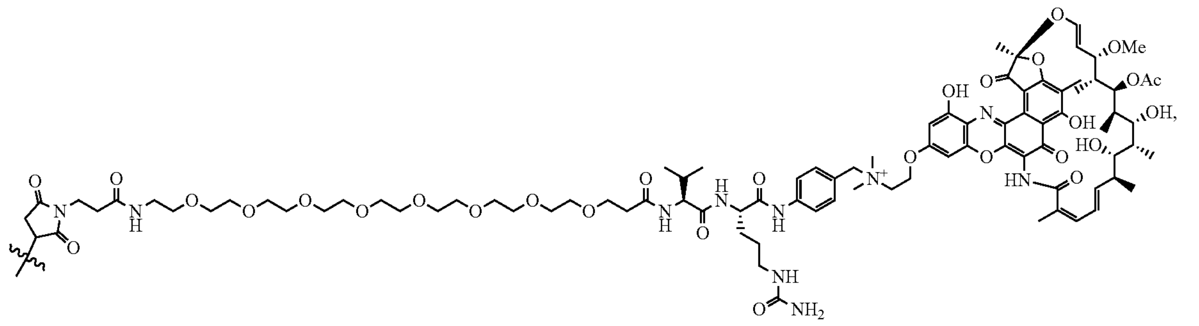 [SMILES: *C1CC(=O)N(CCC(=O)NCCOCCOCCOCCOCCOCCOCCOCCOCCC(=O)N[C@H](C(=O)N[C@@H](CCCNC(N)=O)C(=O)Nc2ccc(C[N+](C)(C)CCOc3cc(O)c4nc5c6c7c8c(C)c(O)c6c(=O)c(c-5oc4c3)NC(=O)/C(C)=C\C=C\[C@H](C)[C@H](O)[C@@H](C)[C@@H](O)[C@@H](C)[C@H](OC(C)=O)[C@H](C)[C@@H](OC)/C=C/O[C@@](C)(O8)C7=O)cc2)C(C)C)C1=O]

wherein the

is the bond to the antibody or the antigen-binding fragment thereof.

In one embodiment, the antibody, or the antigen-binding fragment thereof, that binds macrophage scavenger receptor 1 (MSR1) comprises: (a) the complementarity determining regions (CDRs) of a heavy chain variable region (HCVR) comprising an amino acid sequence as set forth in Table 9; and (b) the CDRs of a light chain variable region (LCVR) comprising an amino acid sequence as set forth in Table 9.

In one embodiment, the anti-MSR1 antibody, or the antigen-binding fragment thereof, comprises:

(i) a HCDR1 domain comprising an amino acid sequence selected from the group consisting of SEQ ID NOs: 4, 36, 52, 92, and 284;
(ii) a HCDR2 domain comprising an amino acid sequence selected from the group consisting of SEQ ID NOs: 6, 38, 54, 94, and 286;
(iii) a HCDR3 domain comprising an amino acid sequence selected from the group consisting of SEQ ID NOs: 8, 40, 56, 96, and 288;
(iv) a LCDR1 domain comprising an amino acid sequence selected from the group consisting of SEQ ID NOs: 12, 44, 60, 100, and 292;
(v) a LCDR2 domain comprising an amino acid sequence selected from the group consisting of SEQ ID NOs: 14, 46, 62, 102, and 294; and
(vi) a LCDR3 domain comprising an amino acid sequence selected from the group consisting of SEQ ID NOs: 16, 48, 64, 104, and 296.

In one embodiment, the anti-MSR1 antibody, or the antigen-binding fragment thereof, comprises (i) a HCDR1 domain comprising an amino acid sequence of SEQ ID NO: 52;
(ii) a HCDR2 domain comprising an amino acid sequence of SEQ ID NO: 54;
(iii) a HCDR3 domain comprising an amino acid sequence of SEQ ID NO: 56;
(iv) a LCDR1 domain comprising an amino acid sequence of SEQ ID NO: 60;
(v) a LCDR2 domain comprising an amino acid sequence of SEQ ID NO: 62; and
(vi) a LCDR3 domain comprising an amino acid sequence of SEQ ID NO: 64.

In one embodiment, the anti-MSR1 antibody, or the antigen-binding fragment thereof, comprises a N297Q mutation.

In one embodiment, the anti-WTA antibody, or the antigen-binding fragment thereof, may comprise: (a) the complementarity determining regions (CDRs) of a heavy chain variable region (HCVR) comprising an amino acid sequence as set forth in Table 2A; and (b) the CDRs of a light chain variable region (LCVR) comprising an amino acid sequence as set forth in Table 2A.

In one embodiment, the anti-WTA antibody, or the antigen-binding fragment thereof, may comprise:

(i) a HCDR1 domain comprising an amino acid sequence selected from the group consisting of SEQ ID NOs: 470, 476, 482, and 488;
(ii) a HCDR2 domain comprising an amino acid sequence selected from the group consisting of SEQ ID NOs: 471, 477, 483, and 489;
(iii) a HCDR3 domain comprising an amino acid sequence selected from the group consisting of SEQ ID NOs: 472, 478, 484, and 490;
(iv) a LCDR1 domain comprising an amino acid sequence selected from the group consisting of SEQ ID NOs: 467, 473, 479, and 485;
(v) a LCDR2 domain comprising an amino acid sequence selected from the group consisting of SEQ ID NOs: 468, 474, 480, and 486; and
(vi) a LCDR3 domain comprising an amino acid sequence selected from the group consisting of SEQ ID NOs: 469, 475, 481, and 487.

In one embodiment, the anti-WTA antibody, or the antigen-binding fragment thereof, may comprise: (a) the complementarity determining regions (CDRs) of a heavy chain variable region (HCVR) comprising an amino acid sequence as set forth in Table 2B; and (b) the CDRs of a light chain variable region (LCVR) comprising an amino acid sequence as set forth in Table 2B.

In one embodiment, the anti-WTA antibody, or the antigen-binding fragment thereof, may comprise:

(i) a HCDR1 domain comprising an amino acid sequence selected from the group consisting of SEQ ID NOs: 502, 508, 514, 520, 526, 532, 538, 544, 550, 556, 562, 568, and 574;

(ii) a HCDR2 domain comprising an amino acid sequence selected from the group consisting of SEQ ID NOs: 503, 509, 515, 521, 527, 533, 539, 545, 551, 557, 563, 569, and 575;

(iii) a HCDR3 domain comprising an amino acid sequence selected from the group consisting of SEQ ID NOs: 504, 510, 516, 522, 528, 534, 540, 546, 552, 558, 564, 570, 576, and 584;

(iv) a LCDR1 domain comprising an amino acid sequence selected from the group consisting of SEQ ID NOs: 499, 505, 511, 517, 523, 529, 535, 541, 547, 553, 559, 565, and 571;

(v) a LCDR2 domain comprising an amino acid sequence selected from the group consisting of SEQ ID NOs: 500, 506, 512, 518, 524, 530, 536, 542, 548, 554, 560, 566, and 572; and (vi) a LCDR3 domain comprising an amino acid sequence selected from the group consisting of SEQ ID NOs: 501, 507, 513, 519, 525, 531, 537, 543, 549, 555, 561, 567, and 573.

In some embodiments, the anti-WTA antibody, or the antigen-binding fragment thereof, comprises a V205C mutation (EU numbering) in the light chain.

In one embodiment, the anti-WTA antibody, or the antigen-binding fragment thereof, is derived from antibody 4497 described in US Patent Application Publication 20140356375 (which is incorporated herein by reference in its entirety). In one embodiment, the anti-WTA antibody is derived from antibody 4497 and further comprises a V205C mutation in the light chain.

In one embodiment, the anti-WTA antibody, or the antigen-binding fragment thereof, comprises the HCDR1-HCDR2-HCDR3-LCDR1-LCDR2-LCDR3 of SEQ ID Nos: 568-569-570-565-566-567.

In some embodiments, the anti-WTA antibody or antigen binding fragment thereof comprises three heavy chain complementarity determining regions (HCDR1, HCDR2, and HCDR3) within a heavy chain variable region (HCVR) amino acid sequence of SEQ ID NOs: 586; and three light chain complementarity determining regions (LCDR1, LCDR2, and LCDR3) within a light chain variable region (LCVR) amino acid sequence of SEQ ID NO: 585.

In some embodiments, the anti-WTA antibody or antigen binding fragment thereof comprises an HCVR amino acid sequence of SEQ ID NOs: 586, and an LCVR amino acid sequence of SEQ ID NO: 585.

In some embodiments, the anti-WTA antibody comprises a heavy chain amino acid sequence of SEQ ID NOs: 602 and a light chain amino acid sequence of SEQ ID NO: 587 or SEQ ID NO: 589. In some embodiments, the anti-WTA antibody, or the antigen-binding fragment thereof comprises a V205C mutation in the light chain.

In one embodiment, the anti-Protein A antibody, or the antigen-binding fragment thereof, may comprise: (a) the complementarity determining regions (CDRs) of a heavy chain variable region (HCVR) comprising an amino acid sequence as set forth in Table 3A; and (b) the CDRs of a light chain variable region (LCVR) comprising an amino acid sequence as set forth in Table 3A.

In one embodiment, the anti-Protein A antibody, or the antigen-binding fragment thereof, may comprise:

(i) a HCDR1 domain comprising an amino acid sequence selected from the group consisting of SEQ ID NOs: 632, 652, and 672;

(ii) a HCDR2 domain comprising an amino acid sequence selected from the group consisting of SEQ ID NOs: 634, 654, and 674;

(iii) a HCDR3 domain comprising an amino acid sequence selected from the group consisting of SEQ ID NOs: 636, 656, and 676;

(iv) a LCDR1 domain comprising an amino acid sequence selected from the group consisting of SEQ ID NOs: 640, 660, and 680;

(v) a LCDR2 domain comprising an amino acid sequence selected from the group consisting of SEQ ID NOs: 642 and 662; and (vi) a LCDR3 domain comprising an amino acid sequence selected from the group consisting of SEQ ID NOs: 644, 664, and 683.

In some embodiments, the anti-Protein A antibody, or the antigen-binding fragment thereof, comprises a H435R and a Y436F mutation (EU numbering) in the heavy chain Fc.

In some embodiments, the anti-Protein A antibody, or the antigen-binding fragment thereof, comprises a H435R and a Y436F mutation (EU numbering) in the heavy chain Fc.

In one embodiment, the anti-Protein A antibody or antigen binding fragment thereof comprises three heavy chain complementarity determining regions (HCDR1, HCDR2, and HCDR3) within a heavy chain variable region (HCVR) amino acid sequence of SEQ ID NOs: 630; and three light chain complementarity determining regions (LCDR1, LCDR2, and LCDR3) within a light chain variable region (LCVR) amino acid sequence of SEQ ID NO: 638. In one embodiment, the anti-Protein A antibody or antigen binding fragment thereof comprises a set of six CDRs (HCDR1-HCDR2-HCDR3-LCDR1-LCDR2-LCDR3) comprising SEQ ID NOs: 632-634-636-640-642-644.

In one embodiment, the anti-Protein A antibody or antigen binding fragment thereof comprises an HCVR amino acid sequence of SEQ ID NOs: 630; and an LCVR amino acid sequence of SEQ ID NO: 638.

In one embodiment, the anti-Protein A antibody comprises a heavy chain amino acid sequence of SEQ ID NOs: 666 and a light chain amino acid sequence of SEQ ID NO: 668. In one embodiments, the anti-Protein A antibody, further comprises a H435R and a Y436F mutation (EU numbering) in the heavy chain Fc. In one embodiment, anti-Protein A antibody further comprises a C103S mutation in the light chain. In one embodiment, the anti-Protein A antibody, or antigen-binding fragment thereof, is conjugated to a compound of the present disclosure at light chain position 103.

In various embodiments, the antibody, or antigen-binding fragment thereof, comprises a C103S mutation in the light chain.

The various embodiments, the antibody, or the antigen-binding fragment thereof, is conjugated to a compound of the present disclosure at position 103 of the light chain.

In one aspect, the present disclosure provides a method of preventing or inhibiting growth of a bacterium comprising administering an effective amount of an antibody-drug conjugate as described herein.

In one embodiment, the bacterium is a Gram-positive bacterium.

In one embodiment, the bacterium is a penicillin-resistant bacterium.

In one embodiment, the bacterium is *Staphylococcus aureus*.

In one embodiment, the bacterium is selected from methicillin-resistant *Staphylococcus aureus* (MRSA), vancomycin-resistant *Staphylococcus aureus* (VRSA), and methicillin-susceptible *Staphylococcus aureus* (MSSA).

In one aspect, the present disclosure provides a method of treating a bacterial infection in a subject in need of such treatment comprising administering to the subject an effective amount of an antibody-drug conjugate as described herein.

In one embodiment, the bacterial infection is a Gram-positive bacterial infection.

In one embodiment, the bacterial infection is a penicillin-resistant bacterial infection.

In one embodiment, the bacterial infection is a *Staphylococcus aureus* infection.

In one embodiment, the bacterial infection is selected from a methicillin-resistant *Staphylococcus aureus* (MRSA) infection, a vancomycin-resistant *Staphylococcus aureus* (VRSA) infection, and a methicillin-susceptible *Staphylococcus aureus* (MSSA) infection.

In one embodiment, the bacterial infection is an intracellular bacterial infection.

In one embodiment, the subject is human.

In one embodiment, the method further comprises administering a second therapeutic agent.

In one embodiment, the second therapeutic agent is a second antibiotic.

In one embodiment, the second antibiotic is effective against *Staphylococcus aureus.*

In one embodiment, the second antibiotic is selected from an aminoglycoside, a beta-lactam, a macrolide, a cyclic peptide, a tetracycline, a fluoroquinoline, a fluoroquinolone, and an oxazolidinone.

In one embodiment, the second antibiotic is selected from clindamycin, novobiocin, retapamulin, daptomycin, sitafloxacin, teicoplanin, triclosan, napthyridone, radezolid, doxorubicin, ampicillin, vancomycin, imipenem, doripenem, gemcitabine, dalbavancin, and azithromycin.

In one embodiment, the antibody-drug conjugate is administered to the subject orally, topically, intranasally, intravenously, intramuscularly, or subcutaneously.

In yet another aspect, the present disclosure provides a method of preventing or treating cellulitis, bacteremia, dermonecrosis, eyelid infection, eye infection, neonatal conjunctivitis, osteomyelitis, impetigo, boils, scalded skin syndrome, food poisoning, pneumonia, surgical infection, urinary tract infection, burn infection, meningitis, endocarditis, septicemia, toxic shock syndrome, septic arthritis, mastitis, infection associated with a prosthetic joint, infection associated with a catheter, or infection associated with an implant, in a subject comprising administering to the subject an effective treatment amount of the compounds, the antibody-drug conjugates, or the pharmaceutical compositions as described herein.

These and other aspects of the present disclosure will become apparent to those skilled in the art after a reading of the following detailed description of the disclosure, including the appended claims.

DETAILED DESCRIPTION

Figure 1:
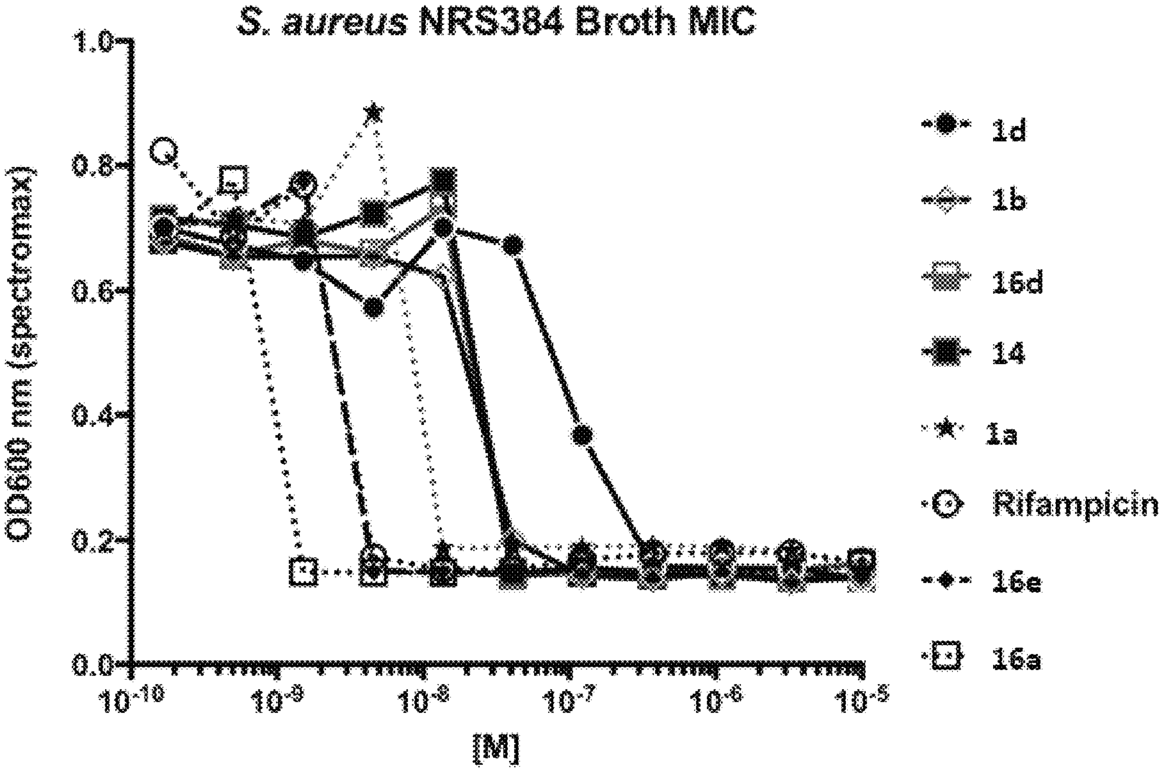
FIG. 1 is a plot of the results of the *S. aureus* growth inhibition assay conducted with rifamycin analogs according to the disclosure.

Detailed embodiments of the present disclosure are disclosed herein; however, it is to be understood that the disclosed embodiments are merely illustrative of the disclosure that may be embodied in various forms. In addition, each of the examples given in connection with the various embodiments of the disclosure is intended to be illustrative, and not restrictive. Therefore, specific structural and functional details disclosed herein are not to be interpreted as limiting, but merely as a representative basis for teaching one skilled in the art to variously employ the present disclosure.

Definitions

Unless defined otherwise, all technical and scientific terms used herein have the same meaning as commonly understood by one of ordinary skill in the art to which this disclosure belongs.

As used in this specification and the appended claims, the singular forms “a”, “an”, and “the” include plural references unless the context clearly dictates otherwise. Thus, for example, a reference to “a method” includes one or more methods, and/or steps of the type described herein and/or which will become apparent to those persons skilled in the art upon reading this disclosure.

The terms “treat” or “treatment” of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof, or (3) relieving the disease, i.e., causing regression of the state, disorder or condition or at least one of its clinical or sub-clinical symptoms. The benefit to a subject to be treated is either statistically significant or at least perceptible to the patient or to the physician.

A “subject” or “patient” or “individual” or “animal”, as used herein, refers to humans, veterinary animals (e.g., cats, dogs, cows, horses, sheep, pigs, etc.) and experimental animal models of diseases (e.g., mice, rats). In one embodiment, the subject is a human.

As used herein the term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions of the disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The phrase "therapeutically effective amount," as used herein, refers to an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

Ranges can be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, or method steps, even if the other such compounds, material, particles, or method steps have the same function as what is named.

Compounds of the present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference. The chemistry of protecting groups can be found, for example, in Wuts and Greene, *Greene's Protective Groups in Organic Synthesis,* 4th Ed., John Wiley & Sons: New York, 2006.

The term "hydrocarbon" is used herein to encompass hydrocarbon radicals (otherwise referred to as "groups") that comprise carbon and hydrogen and also encompasses derivatives thereof where in one or more carbons has been replaced by any heteroatom, such as oxygen, nitrogen, sulfur and phosphorus. The hydrocarbon of the instant disclosure is optionally substituted by oxygen, nitrogen, sulfur and phosphorus containing groups or by halogens without limitation. The term hydrocarbon encompasses straight chain, branched, cyclic or multicyclic aliphatic groups as well as aromatic and heteroaromatic groups as discussed in more detail below.

The term "optionally substituted" has the same meaning as wherein the substituted element "further comprises 0-n" of the optional element, where n is an integer, generally from 0-20, or from 0-10, or from 1-3. For example, when an aliphatic hydrocarbon optionally comprises one or more heteroatoms, this would have the same meaning as wherein the aliphatic hydrocarbon further comprises from 0-20 heteroatoms.

The term "aliphatic" or "aliphatic group", as used herein, mean a straight-chained (i.e., unbranched), branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule, and combinations thereof. In some embodiments, aliphatic groups comprise a combination (a hybrid) of a straight-chained and a cyclic aliphatic hydrocarbon. In some embodiments, aliphatic groups comprise a combination of a straight-chained and a cyclic aliphatic hydrocarbon. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-6 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and combinations/hybrids thereof such as (cycloalkyl)alkyl, (cycloalkenyl)alkyl or (cycloalkyl)alkenyl. Simple aliphatic hydrocarbons include methyl, ethyl, propyl, butyl, t-butyl, n-butyl, pentyl, and so on.

The terms "aliphatic cyclic," "cyclic aliphatic," "carbocyclic," "alicyclic" or "cycloaliphatic," as used herein, refer to saturated or partially unsaturated cyclic aliphatic monocyclic, bicyclic, or polycyclic ring structures, as described herein, having from 3 to 14 members, wherein the aliphatic ring system is optionally substituted as defined above and described herein. Cycloaliphatic groups include, without limitation, cy cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The aliphatic cyclic structures also include aliphatic rings that are fused to one or more aromatic or nonaromatic rings, such as decahydronaphthyl or tetrahydronaphthyl, where in the radical or point of attachment is on the aliphatic ring. In some embodiments, aliphatic cyclic group is bicyclic. In some embodiments, a 'carbocyclic group is tricyclic. In some embodiments, an aliphatic cyclic group is polycyclic. In some embodiments, the aliphatic polycyclic group is a spirocyclic structure that presents a twisted structure of two or more rings (a ring system), in which 2 or 3 rings are linked together by one common atom. In another embodiment, the aliphatic polycyclic group is a fused bicyclic structure wherein two rings share two adjacent atoms, that is, the rings share one covalent bond, i.e. the so-called bridgehead atoms are directly connected (e.g.

α-thujene and decalin). In some embodiments the aliphatic polycyclic structure is a bridged bicyclic structure where, e.g., two rings share three or more atoms, separating the two bridgehead atoms by a bridge containing at least one atom. For example, norbornane, also known as bicyclo[2.2.1] heptane, can be thought of as a pair of cyclopentane rings each sharing three of their five carbon atoms. In some embodiments, "aliphatic cyclic" (or "carbocycle" or "cycloalkyl") refers to a monocyclic $C_3$-$C_8$ hydrocarbon, or a $C_6$-$C_{12}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10 carbon atoms, or about 1 to 6 carbon atoms. In some embodiments, a cycloalkyl ring has from about 3-10 carbon atoms in their ring structure wherein such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., halogen, oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

As used herein, "aromatic" refers to a monocyclic or polycyclic, aromatic or heteroaromatic ring which may have from 5 to 20 ring atoms, and optionally may have from 1 to 20 heteroatom substituents. In some embodiments, the aromatic groups may optionally have from 1 to 10 heteroatom substituents. In some embodiments, the aromatic groups may optionally have from 1 to 5 heteroatom substituents. In some embodiments, the aromatic groups are monocyclic or polycyclic aromatic rings, such as cyclopentadienyl, phenyl, naphthyl or anthracenyl. In some embodiments, aromatic groups are monocyclic or polycyclic aromatic rings having from 5 to 10 ring atoms. In some embodiments, aromatic groups are monocyclic aromatic rings containing from 5 to 6 carbon atoms, such as phenyl and cyclopentadienyl. In one particular embodiment, an aromatic group is a phenyl group.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyi and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaromatic hydrocarbon", "heteroaryl" and "heteroar-," used alone of as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaromatic hydrocarbon or heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, wherein the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic, tricyclic, tetracyclic, and/or otherwise polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, tricyclic, tetracyclic, and/or otherwise polycyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "unsaturated," as used herein, means that a moiety has one or more units of unsaturation. The term "halogen" means F, Cl, Br, or I; the term "halide" refers to a halogen radical or substituent, namely —F, —Cl, —Br, or —I. As used herein, "haloalkyl" refers to alkyl, as defined above, wherein the alkyl includes at least one substituent selected from a halogen, for example, fluorine (F), chlorine (Cl), bromine (Br), or iodine (I). Examples of haloalkyl include, but are not limited to, $—CF_3$, $—CH_2CF_3$, $—CCl_2F$, and $—CCl_3$.

The term "protecting group" as used in herein refers to groups introduced into a molecule by chemical modification of a functional group such as an amino or alcohol, in order to obtain chemoselectivity in a subsequent chemical reaction. In one non-limiting embodiment, protecting groups may include 1-chloroethyl carbonyl (ACE), acetoyl, benzyl (Bn), benzyloxy carbonyl (CBz), formyl, methyl carbonyl, trifluoroacetyl, t-butoxy carbonyl (Boc), and fluorenylmethyloxycarbonyl (Fmoc). In another non-limiting embodiment, protecting groups include arbobenzyloxy (Cbz), p-Methoxybenzyl carbonyl (Moz or MeOZ), tert-Butyloxycarbonyl (BOC), 9-Fluorenylmethyloxycarbonyl (Fmoc), Acetyl (Ac), Benzoyl (Bz), Benzyl (Bn), p-Methoxybenzyl (PMB), 3,4-Dimethoxybenzyl (DMPM), p-Methoxyphenyl (PMP) group, Tosyl (Ts), Troc (trichloroethyl chloroformate), Sulfonamides such as Nosyl and Nps. In a further non-limiting embodiment, protecting groups include 3-Methoxyethoxymethyl ether (MEM), Dimethoxytrityl, [bis-(4-methoxyphenyl)phenylmethyl] (DMT), Methoxymethyl ether (MOM), Methoxytrityl [(4-methoxyphenyl)diphenylmethyl] (MMT), Methylthiomethyl ether, Pivaloyl (Piv), Tetrahydropyranyl (THP), Tetrahydrofuran (THF), Trityl (triphenylmethyl, Tr), Silyl ether (TMS), tert-butyldimethylsilyl (TBDMS), tri-iso-propylsilyloxymethyl (TOM), and triisopropylsilyl (TIPS) ethers), TBDMS and TOM; Methyl ethers and ethoxyethyl ethers (EE).

As used herein, the term "O-amino acid" or "HO-amino acid" designates an amino acid wherein the native amino group at the N-terminus of an amino acid or an amino acid sequence has been replaced with an oxygen or hydroxyl group, respectively. For example, "O-XXXX" or "HO-XXXX" is intended to designate an amino acid sequence (XXXX) wherein the native amino group at the N-terminus has been replaced with an oxygen or hydroxyl group, respectively (e.g.,

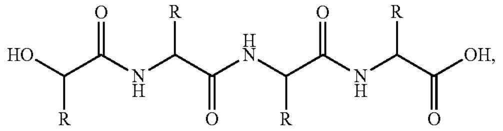

wherein each R is an amino acid side chain). Similarly, the terms "O-amino acid residue" or "HO-amino acid residue" refers to the chemical moiety within a compound that remains after a chemical reaction. For example, "O-amino acid residue" or "HO-amino acid residue" refers to the product of an amide coupling or peptide coupling of an O-amino acid or a HO-amino acid to a suitable coupling partner; wherein, for example, a water molecule is expelled after the amide or peptide coupling of the O-amino acid or a HO-amino acid, resulting in the product having the O-amino acid residue or a HO-amino acid residue incorporated therein.

Designation of an amino acid or amino acid residue without specifying its stereochemistry is intended to encompass the L form of the amino acid, the D form of the amino acid, or a racemic mixture thereof.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure.

Unless otherwise stated, all tautomeric forms of the compounds of the disclosure are within the scope of the disclosure.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}C$- or $^{13}C$- or $^{14}C$-enriched carbon, or the replacement of an oxygen by a $^{17}O$- or $^{18}O$-enriched oxygen, or the replacement of a nitrogen by a $^{15}N$-enriched nitrogen are within the scope of this disclosure.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Unless otherwise stated, all crystalline forms of the compounds of the disclosure and salts thereof are also within the scope of the disclosure. The compounds of the disclosure may be isolated in various amorphous and crystalline polymorphic forms, including without limitation amorphous and crystalline polymorphic forms which are anhydrous, hydrated, non-solvated, or solvated. Example hydrates include hemihydrates, monohydrates, dihydrates, and the like. In some embodiments, the compounds of the disclosure are anhydrous and non-solvated. By "anhydrous" is meant that the crystalline form of the compound contains essentially no bound water in the crystal lattice structure, i.e., the compound does not form a crystalline hydrate.

As used herein, "crystalline form" is meant to refer to a certain lattice configuration of a crystalline substance. Different crystalline forms (polymorphic forms) of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-ray powder diffraction (PXRD). Other characterization methods such as differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

In some embodiments, the compounds of the disclosure are substantially isolated. By "substantially isolated" is meant that a particular compound is at least partially isolated from impurities. For example, in some embodiments a compound of the disclosure comprises less than about 50%, less than about 40%, less than about 30%, less than about 20%, less than about 15%, less than about 10%, less than about 5%, less than about 2.5%, less than about 1%, or less than about 0.5% of impurities. Impurities generally include anything that is not the substantially isolated compound including, for example, other crystalline forms and other substances.

As used herein, the term "antibiotic" (abx or Abx) includes any molecule that specifically inhibits the growth of or kills micro-organisms, such as bacteria, but is non-lethal to the host at the concentration and dosing interval administered. In a specific aspect, an antibiotic is non-toxic to the host at the administered concentration and dosing intervals. Antibiotics effective against bacteria can be broadly classified as either bactericidal (i.e., directly kills) or bacteriostatic (i.e., prevents division). Anti-bactericidal antibiotics can be further subclassified as narrow-spectrum or broad-spectrum. A broad-spectrum antibiotic is one effective against a broad range of bacteria including both Gram-positive and Gram-negative bacteria, in contrast to a narrow-spectrum antibiotic, which is effective against a smaller range or specific families of bacteria. Examples of antibiotics include: aminoglycosides, e.g., amikacin, gentamicin, kanamycin, neomycin, netilmicin, streptomycin, tobramycin, paromycin, ansamycins, e.g., geldanamycin, herbimycin, carbacephems, e.g., loracarbef, carbapenems, e.g., ertapenum, doripenem, imipenem/cilastatin, meropenem, cephalosporins (first generation), e.g., cefadroxil, cefazolin, cefalotin, cefalexin, cephalosporins (second generation), e.g., ceflaclor, cefamandole, cefoxitin, cefprozil, cefuroxime, cephalosporins (third generation), e.g., cefixime, cefdinir, cefditoren, cefoperazone, cefotaxime, cefpodoxime, ceftazidime, ceftibuten, ceftizoxime, ceftriaxone, cephalosporins (fourth generation), e.g., cefepime, cephalosporins (fifth generation), e.g., ceftobiprole, glycopeptides, e.g., teicoplanin, vancomycin, macrolides, e.g., axithromycin, clarithromycin, dirithromycine, erythromycin, roxithromycin, troleandomycin, telithromycin, spectinomycin, monobactams, e.g., axtreonam, penicilins, e.g., amoxicillin, ampicillin, axlocillin, carbenicillin, cloxacillin, dicloxacillin, flucloxacillin, mezlocillin, meticillin, nafcilin, oxacillin, penicillin, peperacillin, ticarcillin, antibiotic polypeptides, e.g., bacitracin, colistin, polymyxin B, quinolones, e.g., ciprofloxacin, enoxacin, gatifloxacin, levofloxacin, lemefloxacin, moxifloxacin, norfloxacin, orfloxacin, trovafloxacin, sulfonamides, e.g., mafenide, prontosil, sulfacetamide, sulfamethizole, sulfanilamide, sulfasalazine, sulfisoxazole, trimethoprim, trimethoprim-sulfamethoxazole (TMP-SMX), tetracyclines, e.g., demeclocycline, doxycycline, minocycline, oxytetracycline, tetracycline and others such as arspenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin or timidazole.

The term "methicillin-resistant *Staphylococcus aureus*" (MRSA), alternatively known as multidrug resistant *Staphylococcus aureus* or oxacillin-resistant *Staphylococcus aureus* (ORSA), refers to any strain of *Staphylococcus aureus* that is resistant to beta-lactam antibiotics, which include the penicillins (e.g., methicillin, dicloxacillin, nafcillin, oxacillin, etc.) and the cephalosporins. "Methicillin sensitive *Staphylococcus aureus*" (MSSA) refers to any strain of *Staphylococcus aureus* that is sensitive to beta-lactam antibiotics.

The term "minimum inhibitory concentration" ("MIC") refers to the lowest concentration of an antimicrobial that will inhibit the visible growth of a microorganism after overnight incubation. Assay for determining MIC are known. One method is as described in the Examples below.

Drug-to-antibody ratio (DAR) is the average number of drugs conjugated to the antibody or antigen-binding fragment, which has an important effect on the efficacy, potency and pharmacokinetics of the ADC. In various embodiments, the DAR is from 1, 2, 3, 4, 5, 6, 7, or 8 drug molecules per antibody. In some embodiments, the DAR is from 1 to 8. In some embodiments, the DAR is from 1 to 6. In certain embodiments, the DAR is from 2 to 4. In some cases, the DAR is from 2 to 3. In certain cases, the DAR is from 0.5 to 3.5. In some embodiments, the DAR is about 1, or about 1.5, or about 2, or about 2.5, or about 3, or about 3.5.

The expressions "MSR1," "hMSR1" and the like, as used herein, refer to the human single-pass, trimeric type II transmembrane glycoprotein pattern recognition receptor comprising (i) the amino acid sequence as set forth in NCBI accession No. NP_002436.1, (ii) the amino acid sequence as set forth in NCBI accession No. NP_619729.1, and/or (iii) the amino acid sequence as set forth in NCBI accession No. NP_619730.1, which represent the various types and isoforms of class A macrophage scavenger receptors. The expression "MSR1" includes both monomeric and multimeric MSR1 molecules. As used herein, the expression "monomeric human MSR1" means a MSR1 protein or portion thereof that does not contain or possess any multimerizing domains and that exists under normal conditions as a single MSR1 molecule without a direct physical connection to another MSR1 molecule. An exemplary monomeric MSR1 molecule is the molecule referred to herein as "His-hMSR1" comprising the amino acid sequence of SEQ ID NO: 393 (see, e.g., Example 25, herein).

All references to proteins, polypeptides and protein fragments herein are intended to refer to the human version of the respective protein, polypeptide or protein fragment unless explicitly specified as being from a non-human species. Thus, the expression "MSR1" means human MSR1 unless specified as being from a non-human species, e.g., "mouse MSR1," "monkey MSR1," etc.

As used herein, the expression "cell surface-expressed MSR1" means one or more MSR1 protein(s), or the extracellular domain thereof, that is/are expressed on the surface of a cell in vitro or in vivo, such that at least a portion of a MSR1 protein is exposed to the extracellular side of the cell membrane and is accessible to an antigen-binding portion of an antibody. A "cell surface-expressed MSR1" can comprise or consist of a MSR1 protein expressed on the surface of a cell which normally expresses MSR1 protein. Alternatively, "cell surface-expressed MSR1" can comprise or consist of MSR1 protein expressed on the surface of a cell that normally does not express human MSR1 on its surface but has been artificially engineered to express MSR1 on its surface.

As used herein, the expression "anti-MSR1 antibody" includes monovalent antibodies with a single specificity, as well as bispecific antibodies comprising a first arm that binds MSR1 and a second arm that binds a second (target) antigen, wherein the anti-MSR1 arm comprises any of the HCVR/LCVR or CDR sequences as set forth in Table 9 herein. The expression "anti-MSR1 antibody" also includes antibody-drug conjugates (ADCs) comprising an anti-MSR1 antibody or antigen-binding portion thereof conjugated to a drug or a therapeutic agent. The expression "anti-MSR1 antibody" also includes antibody-radionuclide conjugates (ARCs) comprising an anti-MSR1 antibody or antigen-binding portion thereof conjugated to a radionuclide.

The term "wall teichoic acid" (WTA) refers to anionic glycopolymers that are covalently attached to peptidoglycan via phosphodiester linkage to the $C_6$ hydroxyl of the N-acetyl muramic acid sugars. While the precise chemical structure can vary among organisms, in some embodiments, WTA is a ribitol teichoic acid with repeating units of 1,5-phosphodiester linkages of D-ribitol and D-alanyl ester on position 2 and glycosyl substituents on position 4. The glycosyl groups may be N-acetylglucosaminyl α (alpha) or β (beta) as present in *S. aureus*. The hydroxyls on the alditol/sugar alcohol phosphate repeats may be substituted with cationic D-alanine esters and monosaccharides, such as N-acetylglucosamine. The hydroxyl substituents may include D-alanyl and alpha (α) or beta (β) GlcNHAc. In one specific embodiment, WTA comprises a compound of the formula:

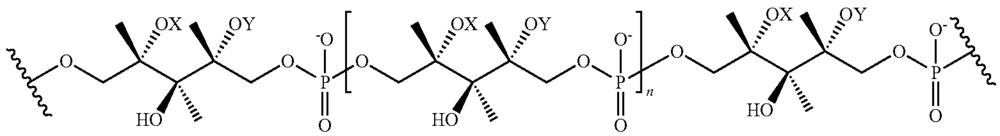

where the wavy lines indicate repeating linkage units or the attachment sites of Polyalditol-P or the peptidoglycan, where X is D-alanyl or —H; and Y is α (alpha)-GlcNHAc or β (beta)-GlcNHAc.

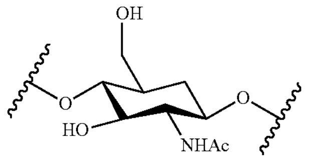

GlcNHAc

As used herein, the term "anti-WTA antibody" refers to any antibody that binds wall teichoic acid (WTA) whether WTA alpha or WTA beta. The terms "anti-wall teichoic acid alpha antibody" or "anti-WTA alpha antibody" or "anti-αWTA" or "anti-αGlcNac WTA antibody" are used interchangeably to refer to an antibody that specifically binds WTA alpha. Similarly, the terms "anti-wall teichoic acid beta antibody" or "anti-WTA beta antibody" or "anti-βWTA" or "anti-βGlcNac WTA antibody" are used interchangeably to refer to an antibody that specifically binds WTA beta. The expression "anti-WTA antibody" includes monovalent antibodies with a single specificity, as well as bispecific antibodies comprising a first arm that binds WTA (whether WTA alpha or WTA beta) and a second arm that binds a second (target) antigen, wherein the anti-WTA arm comprises any of the HCVR/LCVR or CDR sequences as set forth in Tables 2A and 2B herein. The expression "anti-WTA antibody" also includes antibody-drug conjugates (ADCs) comprising an anti-WTA antibody or antigen-binding portion thereof conjugated to a drug or a therapeutic agent.

The term "antibody", as used herein, means any antigen-binding molecule or molecular complex comprising at least one complementarity determining region (CDR) that specifically binds to or interacts with a particular antigen (e.g., MSR1, WTA, or Protein A). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$CH_2$; (x) $V_L$-$CH_3$; (xi) $V_L$-$C_H1$-$CH_2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

The antibodies of the present disclosure may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the disclosure in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments, the antibodies disclosed herein are human antibodies. The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies disclosed herein may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. Embodiments disclosed herein encompass antibodies having one or more mutations in the hinge, $C_H2$ or $C_H3$ region which may be desirable, for example, in production, to improve the yield of the desired antibody form.

The antibodies disclosed herein may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. Embodiments include antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within embodiments disclosed herein.

Embodiments also include antibodies comprising variants of any of the HCVR, LCVR, and/or CDR amino acid sequences disclosed herein having one or more conservative substitutions. For example, embodiments include anti-MSR1 antibodies comprising HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 9 herein. As another example, embodiments include anti-WTA antibodies comprising HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Tables 2A or 2B herein. As yet another example, embodiments include anti-Protein A antibodies comprising HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 3A herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide comprising the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutant thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

As used herein, "O-$PEG_n$" refers to a monovalent moiety attached via the terminal oxygen atom, where n is from 1 to 100. For example, when n is 1, then O-PEGn is $—O—CH_2CH_2OH$; when n is two, then O-PEGn is $—O—CH_2CH_2O—CH_2CH_2OH$; and when n is three, then O-PEGn is $—O—CH_2CH_2O—CH_2CH_2O—CH_2CH_2OH$.

As used herein, "binding agent" refers to any molecule, e.g., protein or antibody, capable of binding with specificity to a given binding partner, e.g., antigen.

As used herein, "linker" refers to a divalent, trivalent, or multivalent moiety that covalently links the binding agent to one or more compounds described herein, for instance payload compounds and a hydrophilic group, as described herein.

As used herein, "reactive group," or RG, refers to a moiety comprising a portion in its structure that is capable of reacting and forming a covalent bond with another chemical moiety, e.g. reacting with an antibody at its cysteine or lysine residues. Illustrative reactive groups for the present disclosure include, but are not limited to, those that comprise maleimides, succinimides, N-hydroxy succinimides (NHS), terminal primary amines, haloacetyl groups, isothiocyanates, thiols, alcohols, ketones, aldehydes, acids, esters, hydrozides, and anilines. RG also include moieties having the following structure:

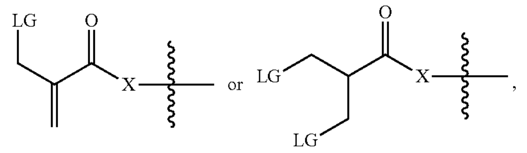

wherein X is —O— or —NH— and LG is a leaving group, e.g., Br.

As used herein, "amide synthesis conditions" refers to reaction conditions suitable to effect the formation of an amide, e.g., by the reaction of a carboxylic acid, activated carboxylic acid, or acyl halide with an amine. In some examples, amide synthesis conditions refer to reaction conditions suitable to effect the formation of an amide bond between a carboxylic acid and an amine. In some of these examples, the carboxylic acid is first converted to an activated carboxylic acid before the activated carboxylic acid reacts with an amine to form an amide. Suitable conditions to effect the formation of an amide include, but are not limited to, those utilizing reagents to effect the reaction between a carboxylic acid and an amine, including, but not limited to, dicyclohexylcarbodiimide (DCC), diisopropylcarbodiimide (DIC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-azabenzotriazol-1-yloxy) tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[Bis(dimethylamino)methylene]-1H-1,2,3-triazolo[4,5-b] pyridinium 3-oxid hexafluorophosphate (HATU), N-ethoxycarbonyl-2-ethoxy-1,2-dihydroquinoline (EEDQ), N-ethyl-N'-(3-dimethylaminopropyl)carbodiimide (EDC), 2-chloro-1,3-dimethylimidazolidinium hexafluorophosphate (CIP), 2-chloro-4,6-dimethoxy-1,3,5-triazine (CDMT), (1-Cyano-2-ethoxy-2-oxoethylidenaminooxy)dimethylamino-morpholino-carbenium hexafluorophosphate (COMU), and carbonyldiimidazole (CDI).

In some examples, a carboxylic acid is first converted to an activated carboxylic ester before treating the activated carboxylic ester with an amine to form an amide bond. In certain embodiments, the carboxylic acid is treated with a reagent. The reagent activates the carboxylic acid by deprotonating the carboxylic acid and then forming a product complex with the deprotonated carboxylic acid as a result of nucleophilic attack by the deprotonated carboxylic acid onto the protonated reagent. The activated carboxylic esters for certain carboxylic acids are subsequently more susceptible to nucleophilic attack by an amine than the carboxylic acid is before it is activated. This results in amide bond formation. As such, the carboxylic acid is described as activated. Exemplary reagents include DCC and DIC.

As used herein, "taurine" refers to the reagent

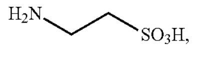

or the group

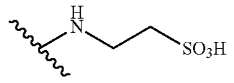 [SMILES: *NCCS(=O)(=O)O]

wherein

indicates the atom through which the taurine is bonded to the adjacent groups in the formula.

Compounds of the Disclosure

In accordance with the foregoing objective and others, the present disclosure provides rifamycin analog compounds, precursors and intermediates thereof, pharmaceutical compositions, and methods for inhibiting bacterial growth and/or treating a bacterial infection in a subject in need of such treatment.

In one aspect, the present disclosure provides a rifamycin analog compound or precursor thereof having a structure of formula (A):

(A)

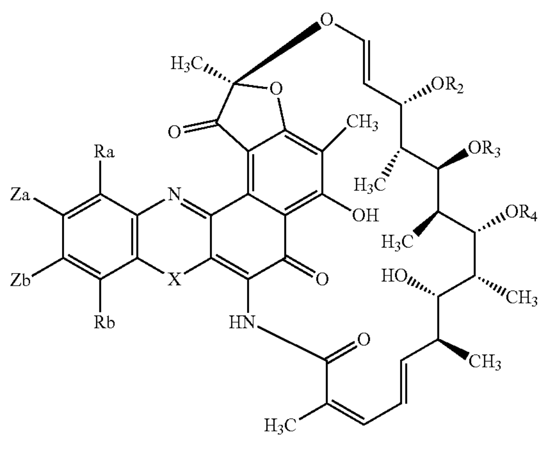

or a pharmaceutically acceptable salt thereof, wherein:

X is selected from —O— and —NR*—;

Za and Zb are independently selected from a hydrogen, —Cl, —Br, —$OR_1$ and —$R_N$; with the proviso that at least one of Za or Zb is not a hydrogen; wherein:

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and $R_a$ is hydrogen, $R_1$ is not hydrogen;

$R_N$ is selected from:

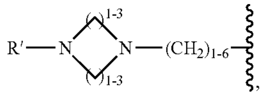

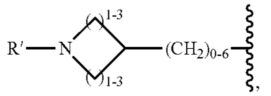

-continued

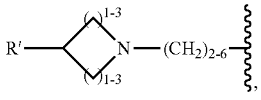, 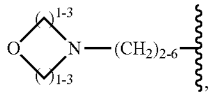,

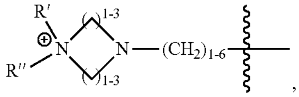,

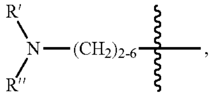,

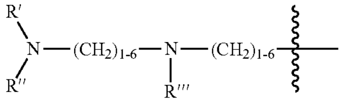,

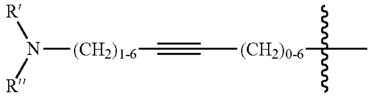 and

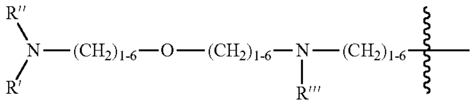

wherein the symbol represents the point of attachment; and R', R" and R'" are selected from a hydrogen, a $C_1$-$C_6$ aliphatic hydrocarbon, and a protecting group, for example, $F_{MOC}$ and $B_{OC}$, or wherein R' and R" together form an aliphatic cyclic structure, such as an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, $—NH_2$, —NHR*, $—N(R^*)_2$, $—N(R^*)_3$, —(C═O)—R*, —CHO, $—CO_2H$, $—CO_2R^*$, —SR*, $—SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, $—CO_2H$, $—CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one aspect, the present disclosure provides a rifamycin analog compound having a structure of formula (I):

(I)

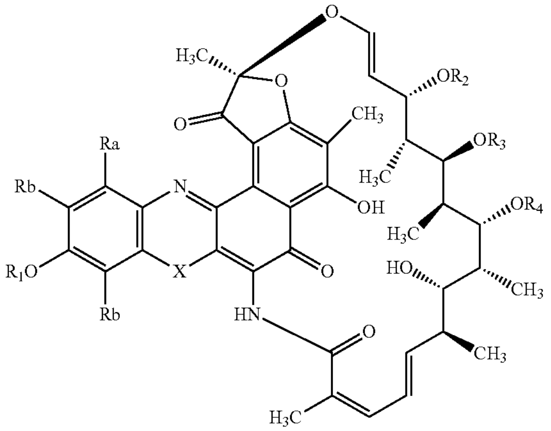

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, $—NO_2$, $—NO_3$, —O—NO, $—N_3$, $—NH_2$, —NHR*, $—N(R^*)_2$, $—N(R^*)_3^+$, —N(R*)—OH, $—O—N(R^*)_2$, —N(R*)—O—R*, —CN, —NC, —(C═O)—R*, —CHO, $—CO_2H$, $—CO_2R^*$, —(C═O)—S—R*, —O—(C═O)—H, —O—(C═O)—R*, —S—(C═O)—R*, $—(C═O)—NH_2$, $—(C═O)—N(R^*)_2$, $—(C═O)—NHNH_2$, $—O—(C═O)—NHNH_2$, $—(C═S)—NH_2$, $—(C═S)—N(R^*)_2$, —N(R*)—CHO, —N(R*)—(C═O)—R*, —SCN, —NCS, —NSO, —SSR*, $—SO_2R^*$, $—SO_2—N(R^*)_2$, —S(═O)—OR*, —S(═O)—R*, $—Si(R^*)_3$, $—CF_3$, $—O—CF_3$ and combinations thereof, with the provisos that $R_1$ is not an n-butyl group, and when X is —O— and $R_a$ is hydrogen, $R_1$ is not hydrogen;

$R_N$ is selected from:

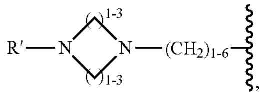,

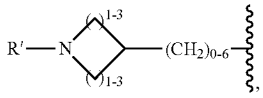,

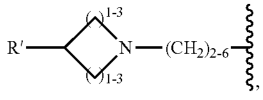, 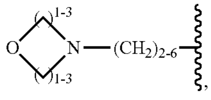,

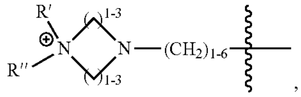,

-continued

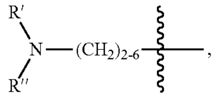

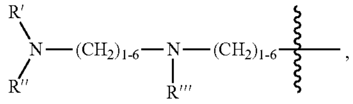

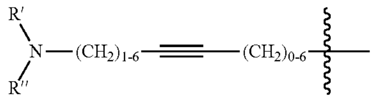

and

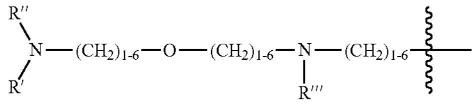

wherein the symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —$N(R^*)_2$, —$N(R^*)_3$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one aspect, the present disclosure provides a rifamycin analog compound having a structure of formula (I'):

(I')

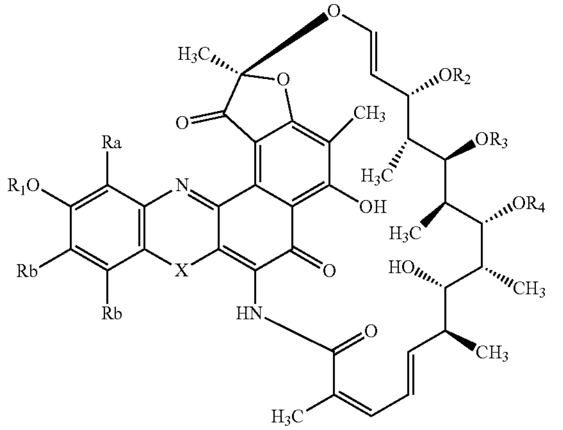

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

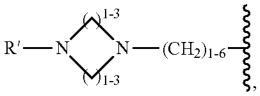

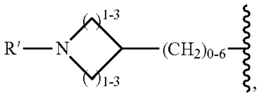

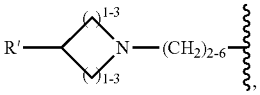

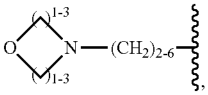

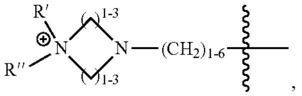

-continued

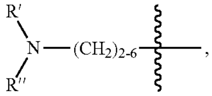
,
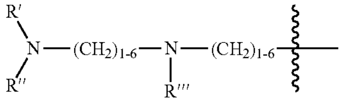
,
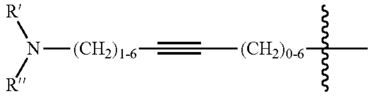
and
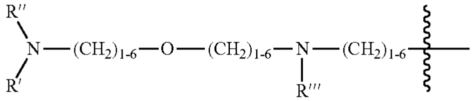

wherein the ~ symbol represents the point of attachment; and R', R'' and R''' are selected from a hydrogen, a $C_1$-$C_6$ aliphatic hydrocarbon, and a protecting group including $F_{MOC}$ and $B_{OC}$, or wherein R' and R'' together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —N(R*)$_2$, —N(R*)$_3$, —(C═O)—R*, —CHO, —$CO_2$H, —$CO_2$R*, —SR*, —$SO_2$R*, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2$H, —$CO_2$R* and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof. In an embodiment of a compound of the formulas (A), (I) or (I'), X is —O—, $R_1$ is an aliphatic $C_1$-$C_3$ hydrocarbon, $R_2$ is a methyl group, $R_3$ is Ac (—(C═O)—$CH_3$), $R_4$ is a hydrogen, and $R_a$ is a hydrogen.

In an embodiment of a compound of the formulas (A), (I) or (I'), X is —O—, $R_1$ is a benzyl group, $R_2$ is a methyl group, $R_3$ is Ac (—(C═O)—$CH_3$), $R_4$ is a hydrogen; $R_a$ is a hydrogen and $R_b$ is hydrogen.

In an embodiment of a compound of the formulas (A), (I) or (I'), X is —O—, $R_1$ is an aliphatic $C_1$-$C_8$ hydrocarbon comprising 1-8 heteroatoms selected from 0 and N, $R_2$ is a methyl group, $R_3$ is Ac (—(C═O)—$CH_3$), $R_4$ is a hydrogen; $R_a$ is a hydrogen and $R_b$ is hydrogen.

In an embodiment of a compound of the formulas (A), (I) or (I'), X is —O—; $R_1$ is an aliphatic $C_1$-$C_8$ hydrocarbon substituted with one or more of —$NH_2$, —NHR*, —N(R*)$_2$; R* is H or an aliphatic $C_1$-$C_3$ hydrocarbon; $R_2$ is a methyl group; $R_3$ is Ac (—(C═O)—$CH_3$); $R_4$ is a hydrogen; $R_a$ is a hydrogen and $R_b$ is hydrogen.

In an embodiment of a compound of the formulas (A), (I) or (I'), X is —$NCH_3$—, $R_1$ is —OH, $R_2$ is a methyl group, $R_3$ is Ac (—(C═O)—$CH_3$), $R_4$ is a hydrogen, $R_a$ is a hydrogen and $R_b$ is hydrogen.

In one embodiment, the rifamycin analog compounds of the disclosure have the structure of formula (II):

(II)

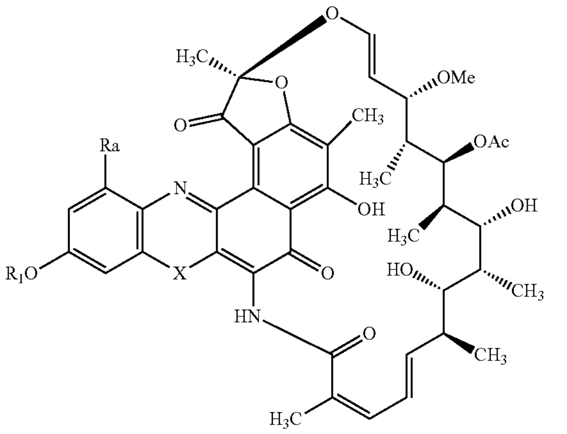

or a pharmaceutically acceptable salt thereof wherein:

X is selected from —O— and —NR*—;

$R_a$ is selected from hydrogen, —Cl, and —OR*;

$R_1$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —N(R*)$_2$, —N(R*)$_3^+$, —N(R*)—OH, —O—N(R*)$_2$, —N(R*)—O—R*, —CN, —NC, —(C═O)—R*, —CHO, —$CO_2$H, —$CO_2$R*, —(C═O)—S—R*, —O—(C═O)—H, —O—(C═O)—R*, —S—(C═O)—R*, —(C═O)—$NH_2$, —(C═O)—N(R*)$_2$, —(C═O)—$NHNH_2$, —O—(C═O)—$NHNH_2$, —(C═S)—$NH_2$, —(C═S)—N(R*)$_2$, —N(R*)—CHO, —N(R*)—(C═O)—R*, —SCN, —NCS, —NSO, —SSR*, —$SO_2$R*, —$SO_2$—N(R*)$_2$, —S(═O)—OR*, —S(═O)—R*, —Si(R*)$_3$, —$CF_3$, —O—$CF_3$ and combinations thereof, with a proviso that $R_1$ is not an n-butyl group;

$R_N$ is selected from:

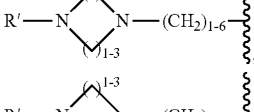
,
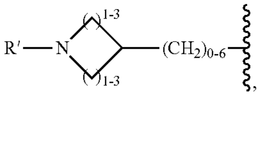
,

-continued

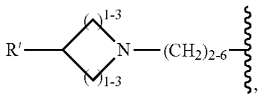, 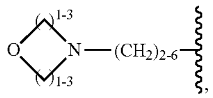,

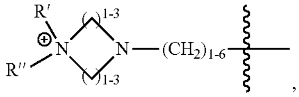,

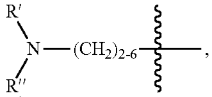,

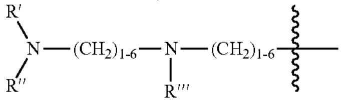,

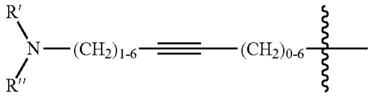 and

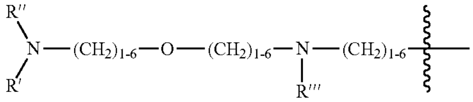

wherein the ~~~ symbol represents the point of attachment; and R', R'' and R''' are selected from a hydrogen, a $C_1$-$C_6$ aliphatic hydrocarbon, and a protecting group including $F_{MOC}$ and $B_{OC}$, or wherein R' and R'' together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (II'):

(II')

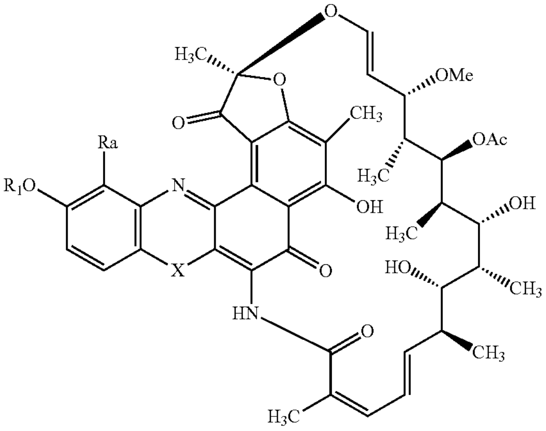

or a pharmaceutically acceptable salt thereof wherein:

X is selected from —O— and —NR*—;

$R_a$ is selected from hydrogen and —OR*;

$R_1$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—N$(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with a proviso that $R_1$ is not an n-butyl group;

$R_N$ is selected from:

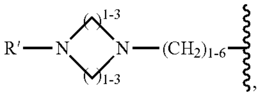,

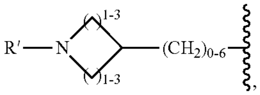,

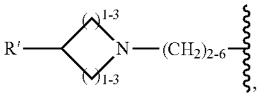, 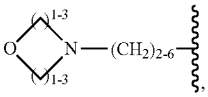,

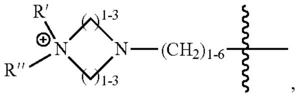,

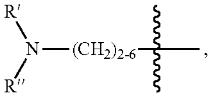,

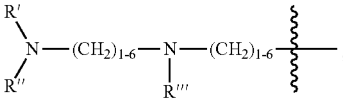,

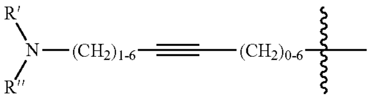 and

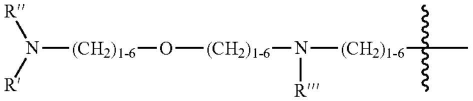

wherein the ~~~ symbol represents the point of attachment; and R', R'' and R''' are selected from a hydrogen, a $C_1$-$C_6$ aliphatic hydrocarbon, and a protecting group including $F_{MOC}$ and $B_{OC}$, or wherein R' and R'' together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (III):

(III)

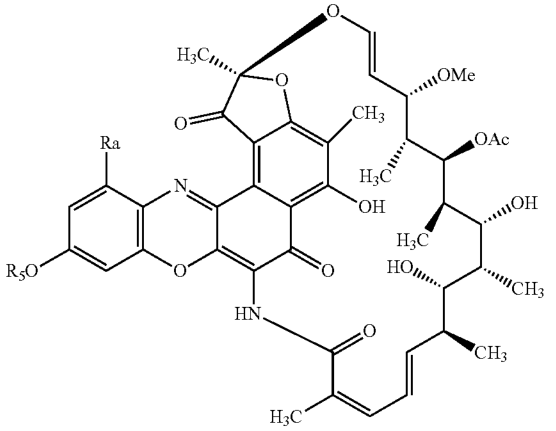

or a pharmaceutically acceptable salt thereof wherein:

$R_a$ is selected from hydrogen and —OR*;

$R_5$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof, with a proviso that $R_5$ is not an n-butyl group;

R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, and $R_N$ is selected from:

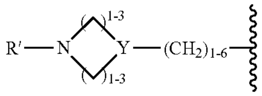

,

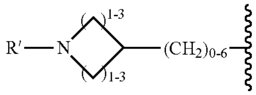

,

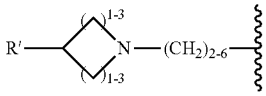

,

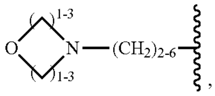

,

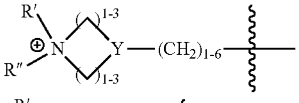

,

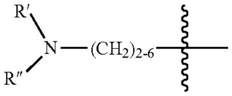

,

-continued

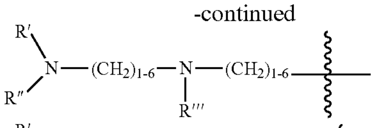

,

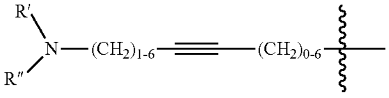

and

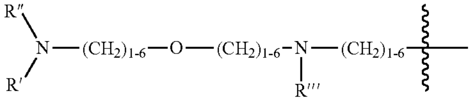

wherein the ~~~ symbol represents the point of attachment; and R', R'' and R''' are selected from a hydrogen, a $C_1$-$C_6$ aliphatic hydrocarbon, and a protecting group including $F_{MOC}$ and $B_{OC}$, or wherein R' and R'' together form an aliphatic monocyclic, an aliphatic bicyclic, or an aliphatic polycyclic structure.

In one embodiment, the rifamycin analog compounds of the disclosure have the structure of formula (III'):

(III')

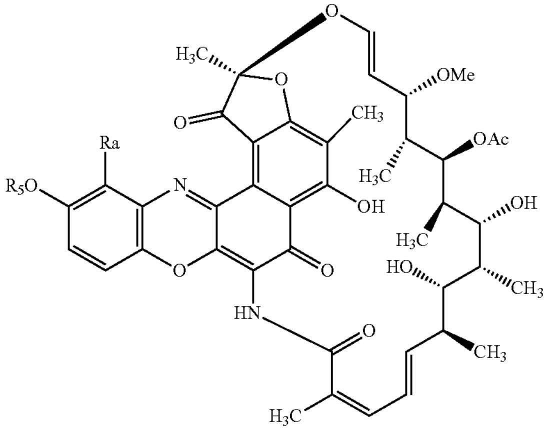

or a pharmaceutically acceptable salt thereof wherein:

$R_a$ is selected from hydrogen and —OR*;

$R_5$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof, with a proviso that $R_5$ is not an n-butyl group;

R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, and $R_N$ is selected from:

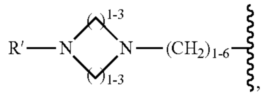,

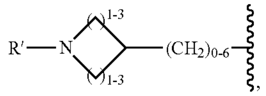,

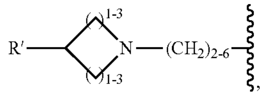, 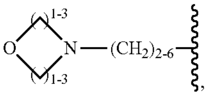,

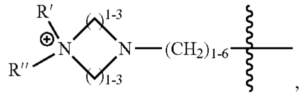,

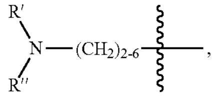,

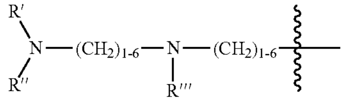,

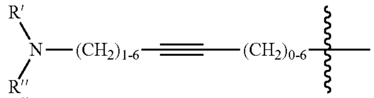 and

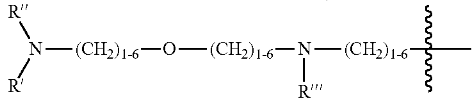

wherein the ~~~ symbol represents the point of attachment; and R', R'' and R''' are selected from a hydrogen, a $C_1$-$C_6$ aliphatic hydrocarbon, and a protecting group including $F_{MOC}$ and $B_{OC}$, or wherein R' and R'' together form an aliphatic monocyclic, an aliphatic bicyclic, or an aliphatic polycyclic structure.

In one embodiment, the rifamycin analog compounds of the disclosure have the structure of formula (IV):

(IV)

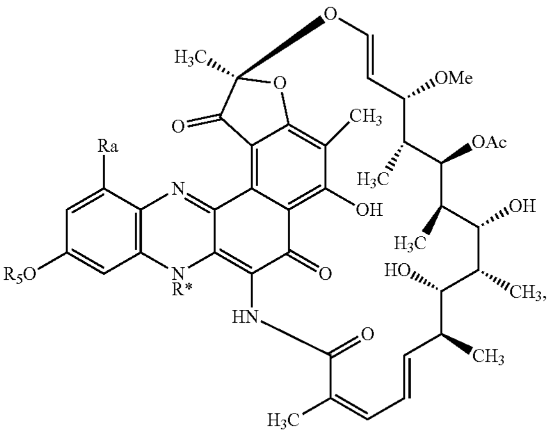

or a pharmaceutically acceptable salt thereof wherein:

$R_a$ is selected from hydrogen and —OR*;

$R_5$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof;

$R_N$ is selected from:

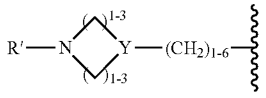,

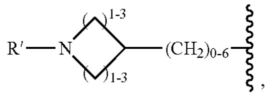,

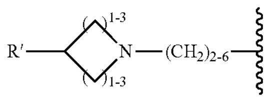, 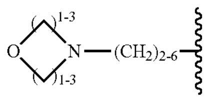,

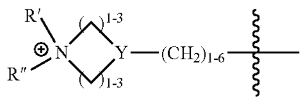,

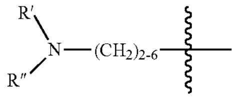,

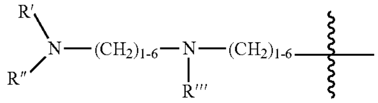,

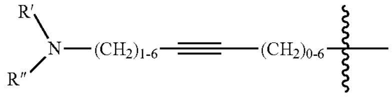 and

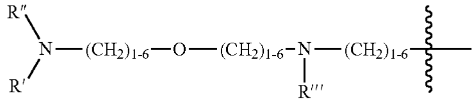

wherein the ~~~ symbol represents the point of attachment; and R', R'' and R''' are selected from a hydrogen, a $C_1$-$C_6$ aliphatic hydrocarbon, and a protecting group including $F_{MOC}$ and $B_{OC}$, or wherein R' and R'' together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (IV'):

(IV')

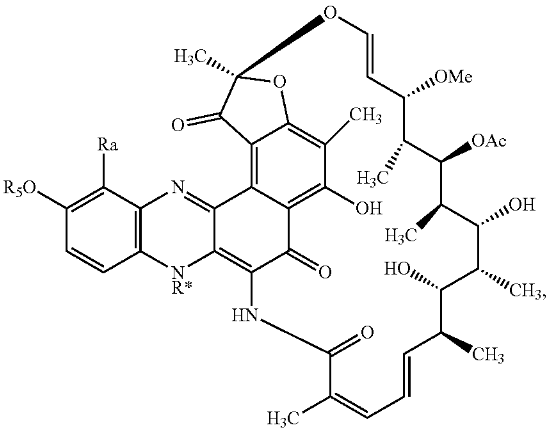

or a pharmaceutically acceptable salt thereof wherein:

$R_a$ is selected from hydrogen and —OR*;

$R_5$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof;

$R_N$ is selected from:

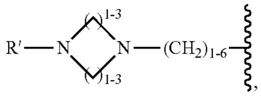,

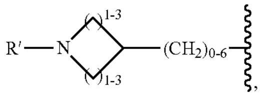,

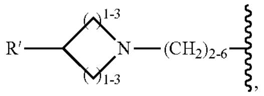, 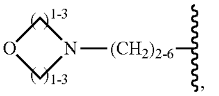,

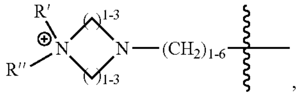,

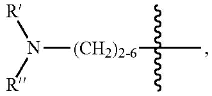,

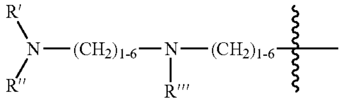,

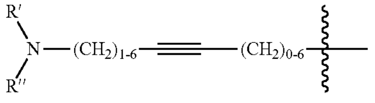 and

-continued

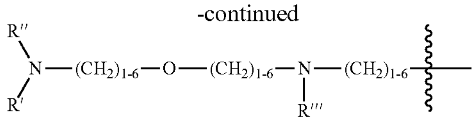

wherein the ~~~~ symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (V):

(V)

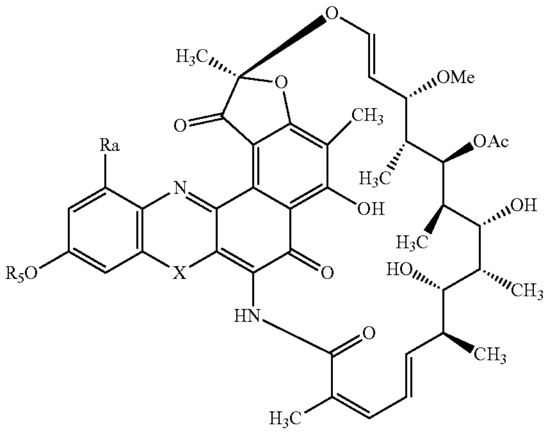

or a pharmaceutically acceptable salt thereof wherein:

X is selected from —O— and —NR*—;

$R_a$ is selected from hydrogen and —OR*;

$R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_6$ is optionally substituted with one or more of —OH, —OR*, —$NH_2$, —NHR*, —$N(R^*)_2$, —$N(R^*)_3^+$, —(C═O)—R*, —CHO, —$CO_2H$, —$CO_2R^*$ and combinations thereof, with a proviso that $R_6$ is not an n-butyl group;

$R_N$ is selected from:

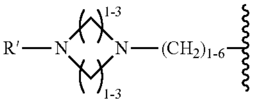,

-continued

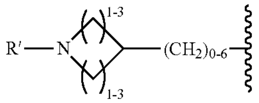

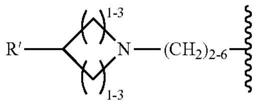, 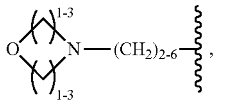,

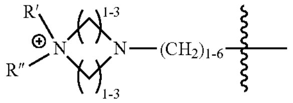,

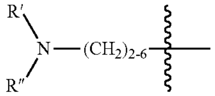,

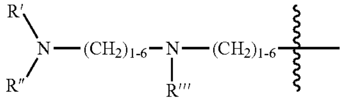,

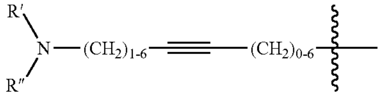 and

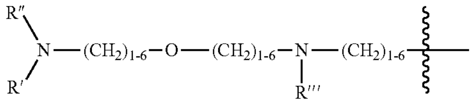

wherein the ∿∿∿ symbol represents the point of attachment; and R', R" and R"' are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (V'):

(V')

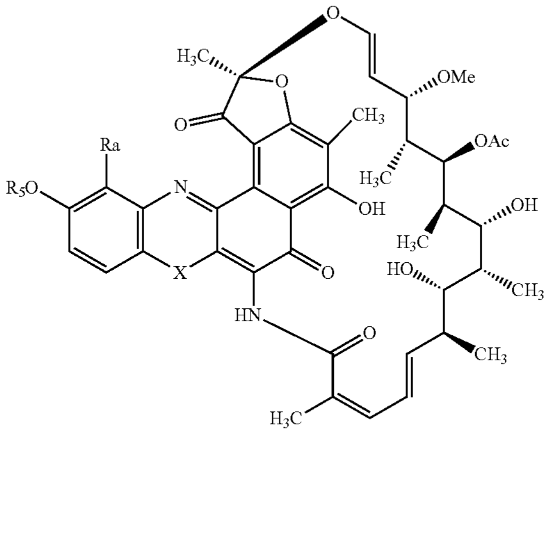

or a pharmaceutically acceptable salt thereof wherein:

X is selected from —O— and —NR*—;

$R_a$ is selected from hydrogen and —OR*;

$R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, each of which further comprises 0-8 heteroatoms selected from halogen, O, N, and S, and wherein $R_6$ is optionally substituted with one or more of —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof, with a proviso that $R_6$ is not an n-butyl group;

$R_N$ is selected from:

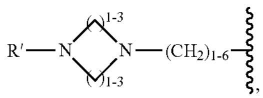,

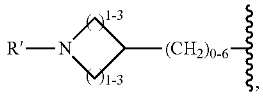,

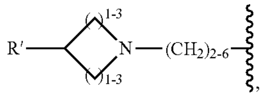 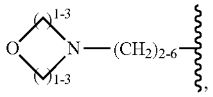,

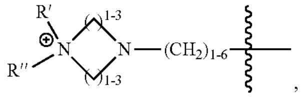,

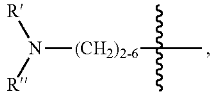,

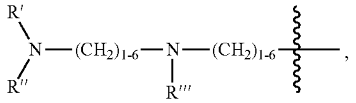,

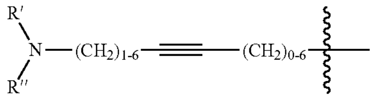 and

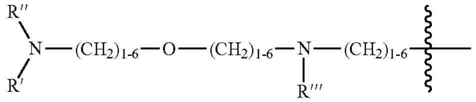

wherein the ∿∿∿ symbol represents the point of attachment; and R', R" and R"' are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a rifamycin analog compound, intermediate or precursor thereof having a structure of formula (B):

(B)

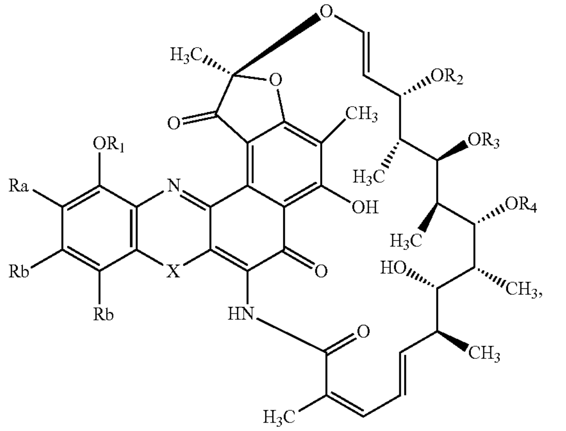

or a pharmaceutically acceptable salt thereof, wherein:

X is selected from —O— and —NR*—;

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

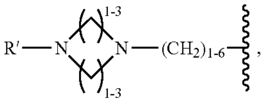
,

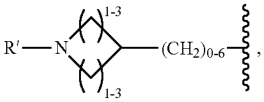
,

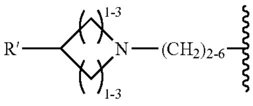
,
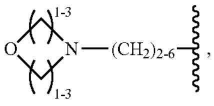
,

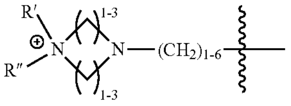
,

-continued

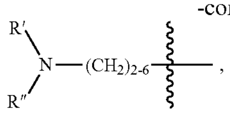
,

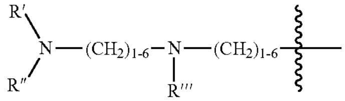
,

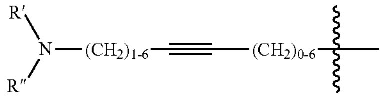
and

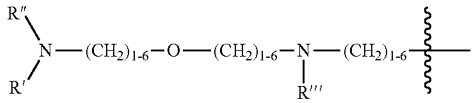
;

wherein the ~~~ symbol represents the point of attachment; and R', R" and R'" are selected from a hydrogen, a $C_1$-$C_6$ aliphatic hydrocarbon, and a protecting group selected from Fluorenylmethyloxycarbonyl (FMOC) and tert-Butyloxycarbonyl (BOC), or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, —$NH_2$, —NHR*, —$N(R^*)_2$, —$N(R^*)_3$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a rifamycin analog compound having a structure of formula (B-1):

(B-1)

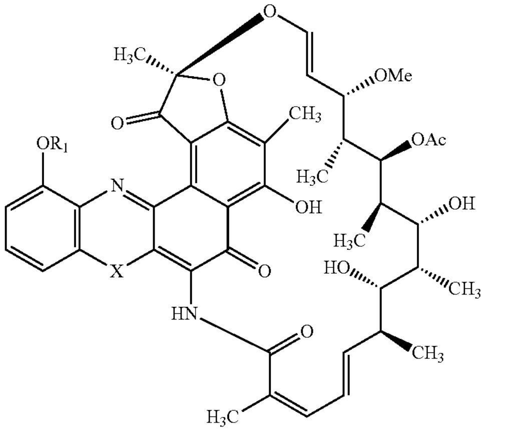

or a pharmaceutically acceptable salt thereof wherein:

X is selected from —O— and —NR*—;

$R_1$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with a proviso that $R_1$ is not an n-butyl group;

$R_N$ is selected from:

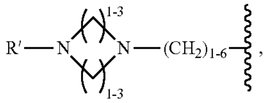,

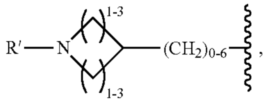,

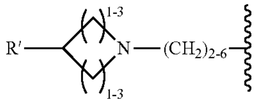, 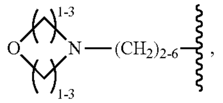,

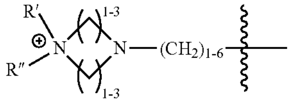,

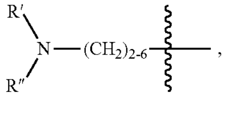,

-continued

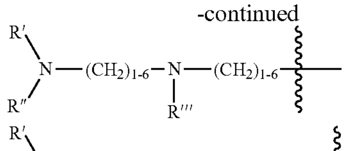,

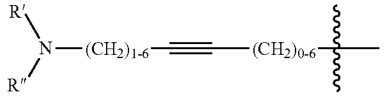 and

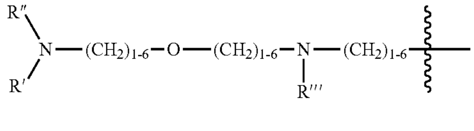;

wherein the ~~~ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a rifamycin analog compound having a structure of formula (B-2):

(B-2)

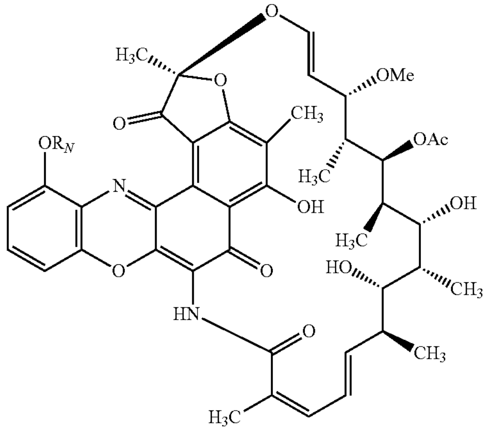

or a pharmaceutically acceptable salt thereof wherein:

$R_N$ is selected from:

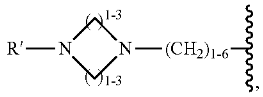,

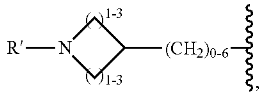,

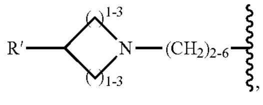, 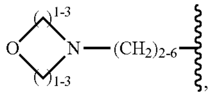,

-continued

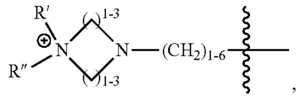

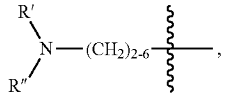

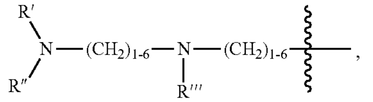

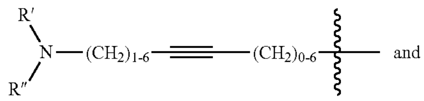 and

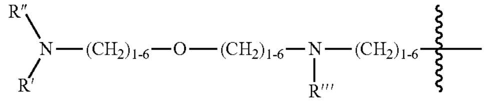

wherein the ~~~ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure.

In another aspect, the present disclosure provides a rifamycin analog compound having a structure of formula (B-2):

(B-2)

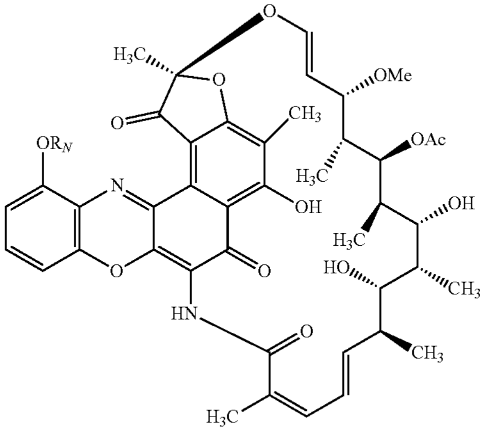

or a pharmaceutically acceptable salt thereof wherein:

$R_N$ is

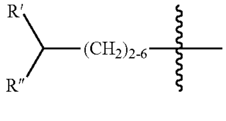

wherein the ~~~ symbol represents the point of attachment; and R' and R" are selected from a hydrogen and a $C_1$-$C_6$ aliphatic hydrocarbon.

In one embodiment, a rifamycin analog compound has a structure according to the following formula:

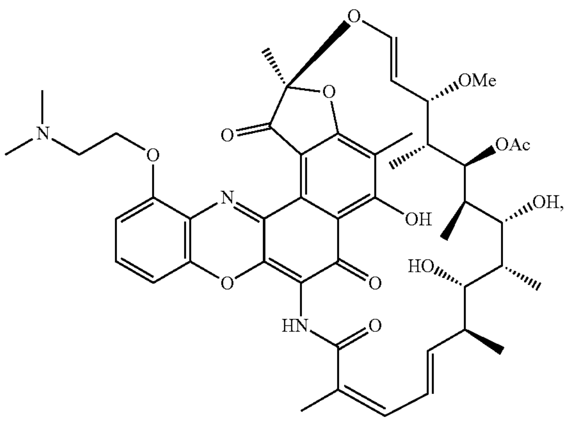 [SMILES: CO[C@H]1/C=C/O[C@@]2(C)Oc3c(C)c(O)c4c(=O)c(c5oc6cccc(OCCN(C)C)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

or a pharmaceutically acceptable salt thereof.

In an embodiment of any of the preceeding formulas is provided a compound wherein $R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-3 heteroatoms selected from O and N, and wherein $R_1$ is optionally substituted with one or more of —F, —Cl, —Br, —I, —OH, $C_{1-3}$ alkoxide, —$NH_2$, —NHR*, —$N(R^*)_2$, —$N(R^*)_3^+$, —N(R*)—OH, —O—$N(R^*)_2$, —N(R*)—O—R*, —N(R*)—(C═O)—R*, —(C═O)—R*, —CHO, —$CO_2H$, —$CO_2R^*$, —O—(C═O)—H, —O—(C═O)—R*, —(C═O)—$NH_2$, —(C═O)—$N(R^*)_2$, —$Si(R^*)_3$, —$CF_3$, —O—$CF_3$ and combinations thereof, with the provisos that $R_1$ is not an n-butyl group, and when X is —O— and $R_a$ is hydrogen, $R_1$ is not hydrogen.

In an embodiment of any of the preceeding formulas is provided a compound wherein $R_1$ is a combination of an aliphatic $C_1$-$C_{20}$ hydrocarbon and an aromatic $C_1$-$C_{20}$ hydrocarbon.

In an embodiment of any of the preceeding formulas is provided a compound wherein $R_1$ is a combination of an aliphatic $C_1$-$C_{20}$ hydrocarbon and a heteroaromatic $C_1$-$C_{20}$ hydrocarbon.

an embodiment of any of the preceeding formulas is provided a compound wherein $R_1$ is selected from:

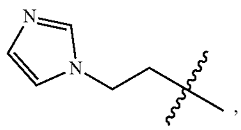

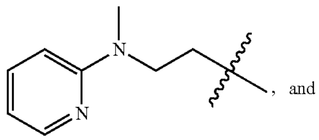 and

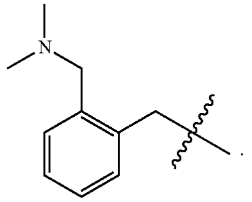

In an embodiment of any of the preceeding formulas is provided a compound wherein $R_1$ is an aliphatic $C_1$-$C_{20}$ hydrocarbon substituted with one or more of —$NH_2$, —NHR*, —$N(R^*)_2$, or —N(R*)—(C═O)—R*.

In an embodiment of any of the preceeding formulas is provided a compound wherein $R_1$ is an aliphatic $C_1$-$C_{20}$ hydrocarbon substituted with —NH—(C═O)—$CH_3$ or —$N(CH_3)$—(C═O)—$CH_3$.

In an embodiment of any of the preceeding formulas is provided a compound wherein $R_a$ is hydrogen.

In an embodiment of any of the preceeding formulas is provided a compound wherein $R_a$ is —OH.

In an embodiment of any of the preceeding formulas is provided a compound wherein $R_a$ is —Cl.

In an embodiment of any of the preceeding formulas is provided a compound wherein $R_a$ is —OR*, and R* is selected from an aliphatic $C_1$-$C_{20}$ hydrocarbon, an aromatic $C_1$-$C_{20}$ hydrocarbon, and combinations thereof.

In an embodiment of any of the preceeding formulas is provided a compound wherein $R_N$ is selected from:

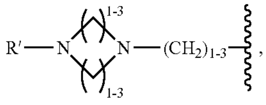

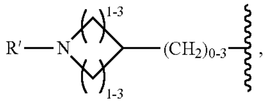

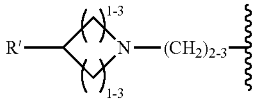

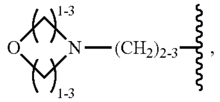

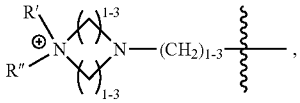

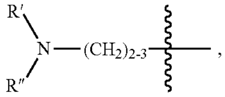

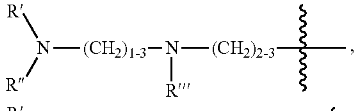

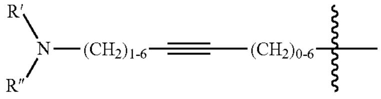

and

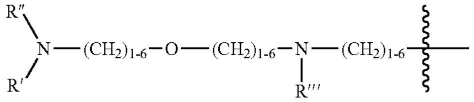

wherein the ~~~ symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure.

In an embodiment of any of the preceeding formulas is provided a compound wherein $R_N$ is selected from:

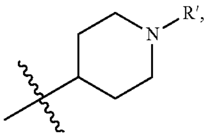

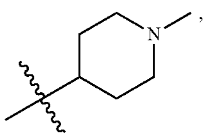

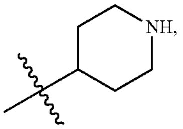

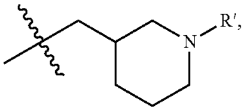

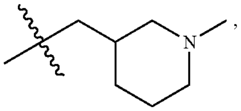

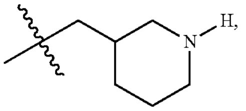

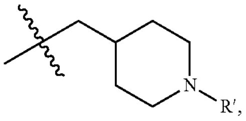

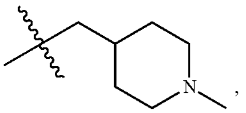

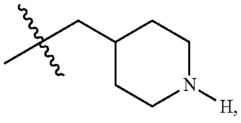

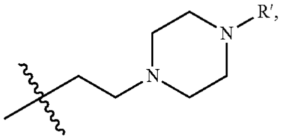

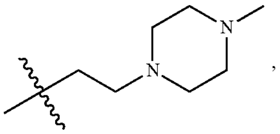

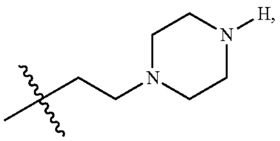

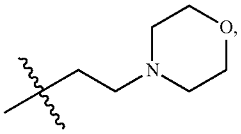

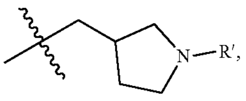

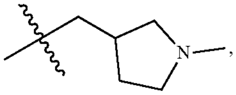

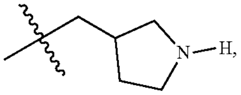

-continued

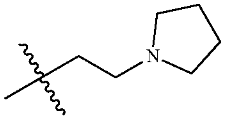 , 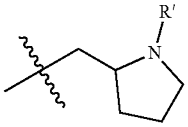 ,

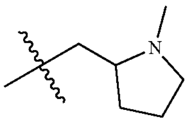 , 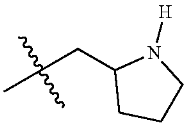 ,

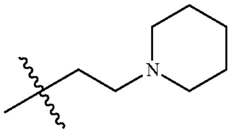 , 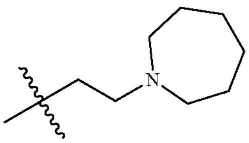 ,

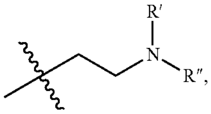 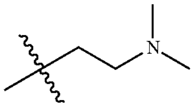 ,

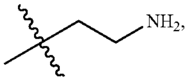 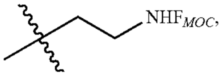

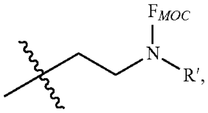 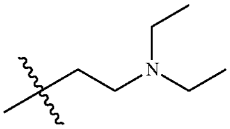 ,

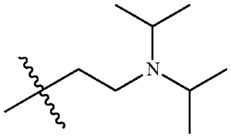 , 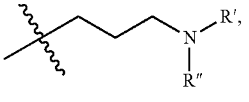

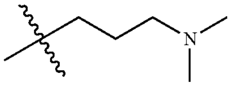 , 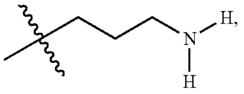

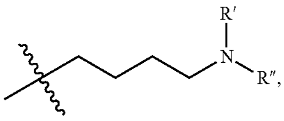

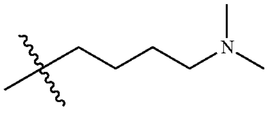 ,

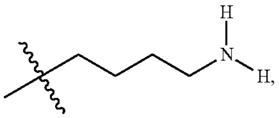

-continued

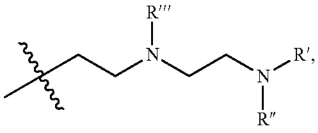

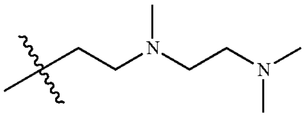 ,

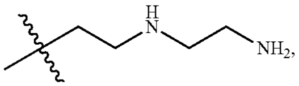

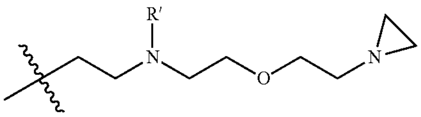 ,

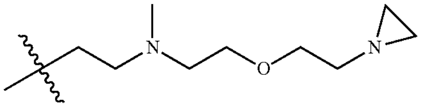 ,

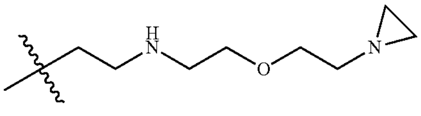 ,

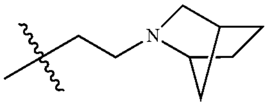 ,

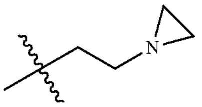 , and

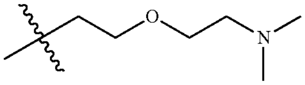 ;

wherein R' is hydrogen, aliphatic hydrocarbon or a protecting group, and wherein the ~~~ symbol represents the point of attachment;

In an embodiment of any of the preceeding formulas is provided a compound wherein R* is independently at each occurrence selected from hydrogen, an aliphatic $C_1$-$C_6$ hydrocarbon, an aromatic $C_6$-$C_7$ hydrocarbon, and combinations thereof, which further comprise 0-3 heteroatoms selected from O and N, and combinations thereof; an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O and N and combinations thereof.

Some exemplary non-limiting embodiments of the rifamycin analog compounds according to the disclosure are shown in Table 1 below:

TABLE 1
| Select rifamycin analogs according to the disclosure | |
|---|---|
| Rifamycin Analog Compound Structure | Compound Number |
| 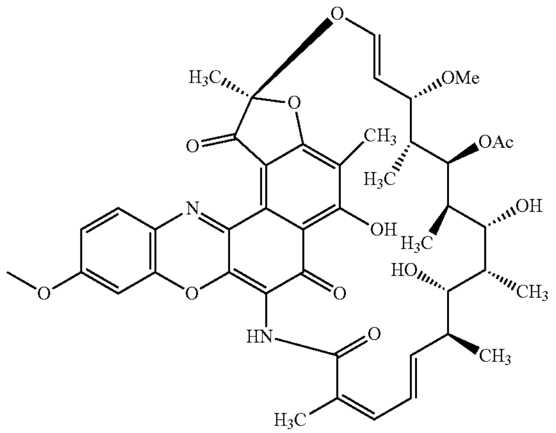 [SMILES: COc1ccc2nc3c4c5c6c(C)c(O)c4c(=O)c(c-3oc2c1)NC(=O)/C(C)=C\C=C\[C@H](C)[C@H](O)[C@@H](C)[C@@H](O)[C@@H](C)[C@H](OC(C)=O)[C@H](C)[C@@H](OC)/C=C/O[C@@](C)(O6)C5=O] | 1a |
| 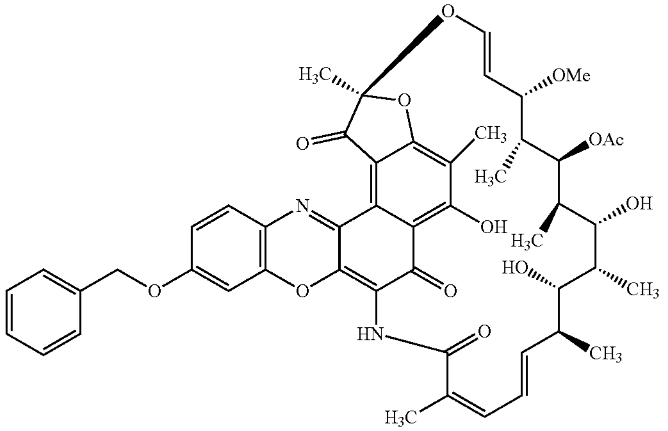 [SMILES: CO[C@H]1/C=C/O[C@@]2(C)Oc3c(C)c(O)c4c(=O)c(c5oc6cc(OCc7ccccc7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 1b |
| 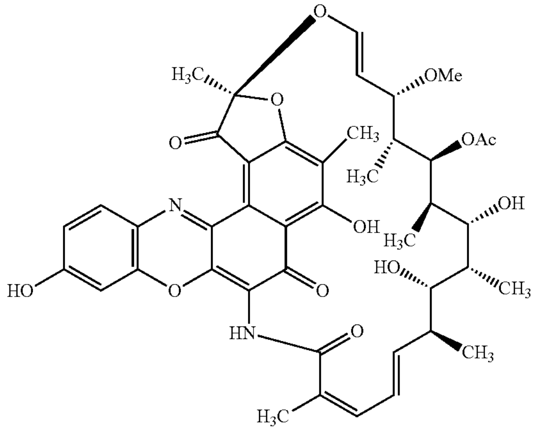 [SMILES: CO[C@H]1/C=C/O[C@@]2(C)Oc3c(C)c(O)c4c(=O)c(c5oc6cc(O)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 1c |

TABLE 1-continued
| Select rifamycin analogs according to the disclosure | |
|---|---|
| Rifamycin Analog Compound Structure | Compound Number |
| 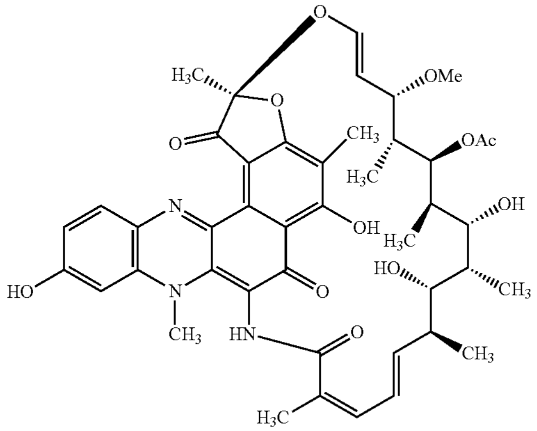 [SMILES: CO[C@H]1/C=C/O[C@@]2(C)Oc3c(C)c(O)c4c(=O)c(c5n(C)c6cc(O)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 1d |
| 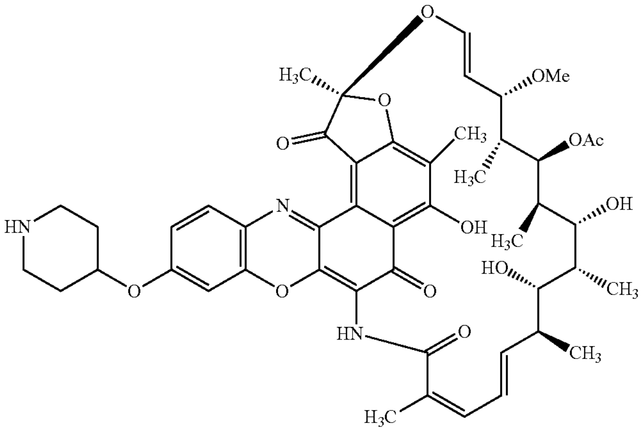 [SMILES: CO[C@H]1/C=C/O[C@@]2(C)Oc3c(C)c(O)c4c(=O)c(c5oc6cc(OC7CCNCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 14 |
| 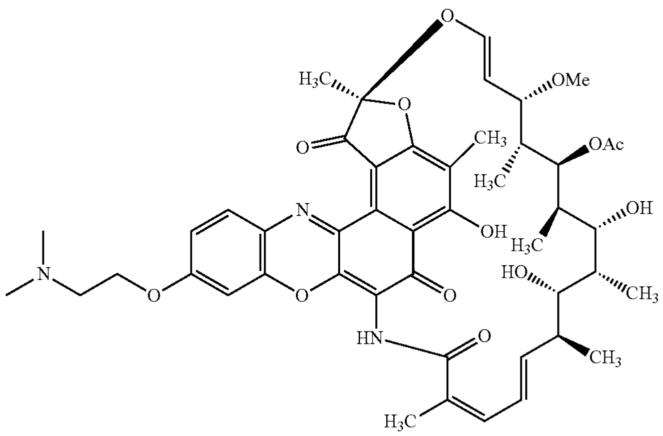 [SMILES: CO[C@H]1/C=C/O[C@@]2(C)Oc3c(C)c(O)c4c(=O)c(c5oc6cc(OCCN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16a |

TABLE 1-continued
| Select rifamycin analogs according to the disclosure | |
|---|---|
| Rifamycin Analog Compound Structure | Compound Number |
| 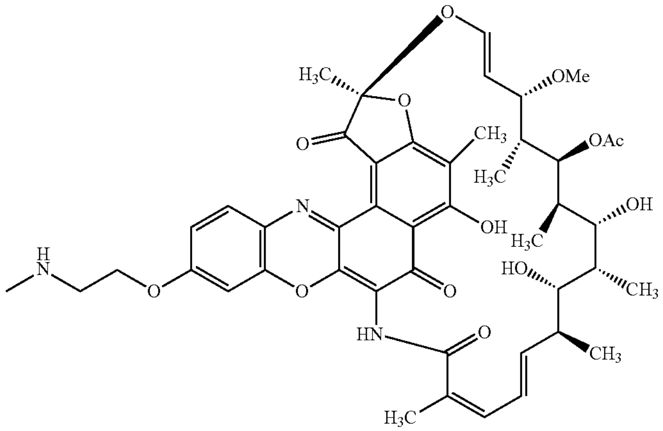 [SMILES: CNCCOc1ccc2nc3c4c5c6c(C)c(O)c4c(=O)c(c-3oc2c1)NC(=O)/C(C)=C\C=C\[C@H](C)[C@H](O)[C@@H](C)[C@@H](O)[C@@H](C)[C@H](OC(C)=O)[C@H](C)[C@@H](OC)/C=C/O[C@@](C)(O6)C5=O] | 16d |
| 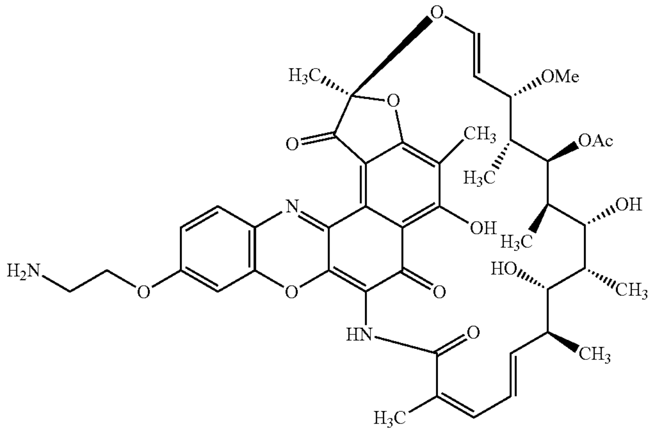 [SMILES: CO[C@H]1/C=C/O[C@@]2(C)Oc3c(C)c(O)c4c(=O)c(c5oc6cc(OCCN)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16e |
| 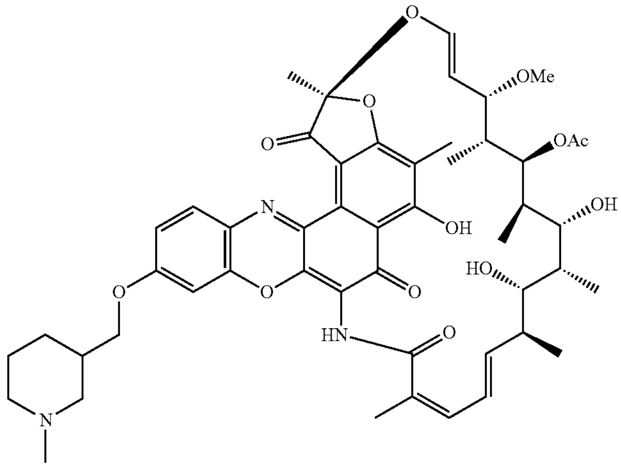 [SMILES: CO[C@H]1/C=C/O[C@@]2(C)Oc3c(C)c(O)c4c(=O)c(c5oc6cc(OCC7CCCN(C)C7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16f |

TABLE 1-continued
| Select rifamycin analogs according to the disclosure | |
|---|---|
| Rifamycin Analog Compound Structure | Compound Number |
| 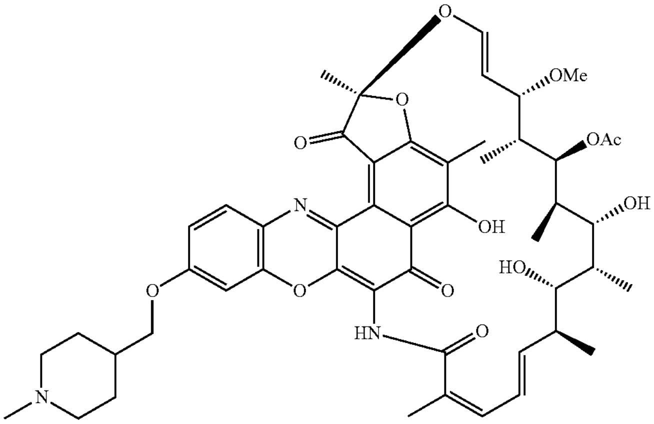 [SMILES: CO[C@H]1/C=C/O[C@@]2(C)Oc3c(C)c(O)c4c(=O)c(c5oc6cc(OCC7CCN(C)CC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16g |
| 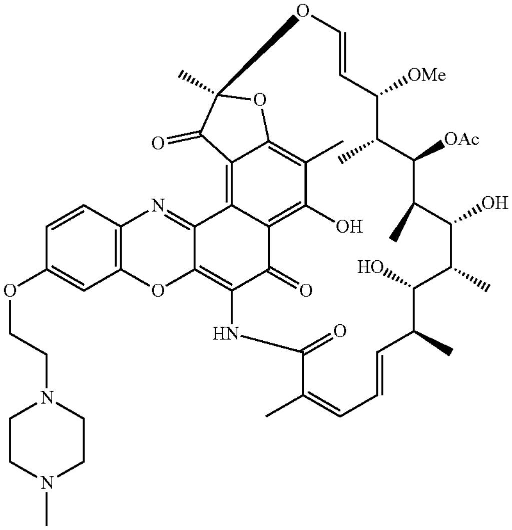 [SMILES: CO[C@H]1/C=C/O[C@@]2(C)Oc3c(C)c(O)c4c(=O)c(c5oc6cc(OCCN7CCN(C)CC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16h |
| 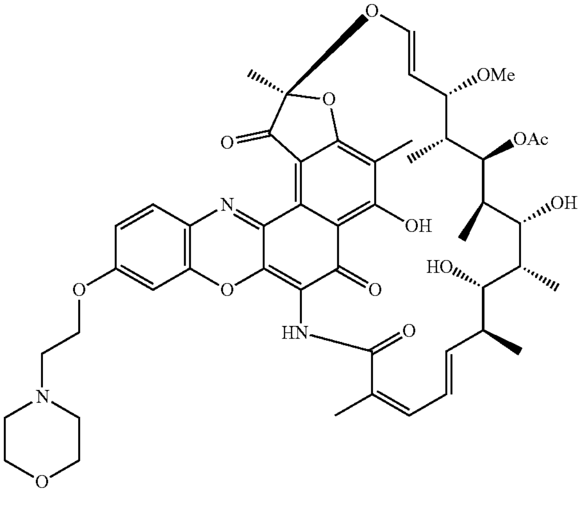 [SMILES: CO[C@H]1/C=C/O[C@@]2(C)Oc3c(C)c(O)c4c(=O)c(c5oc6cc(OCCN7CCOCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16i |

TABLE 1-continued
| Select rifamycin analogs according to the disclosure | |
|---|---|
| Rifamycin Analog Compound Structure | Compound Number |
| 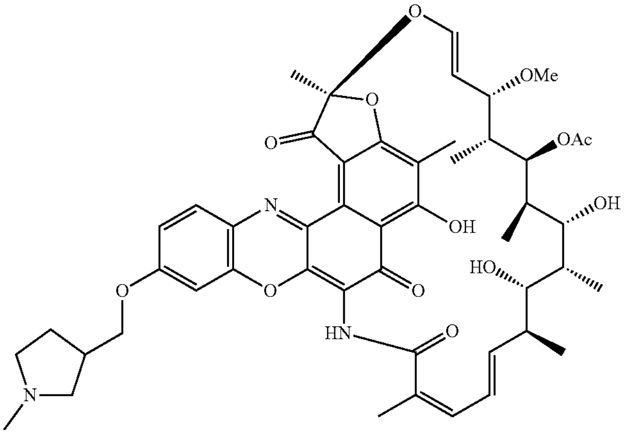 [SMILES: CO[C@H]1/C=C/O[C@@]2(C)Oc3c(C)c(O)c4c(=O)c(c5oc6cc(OCC7CCN(C)C7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16j |
| 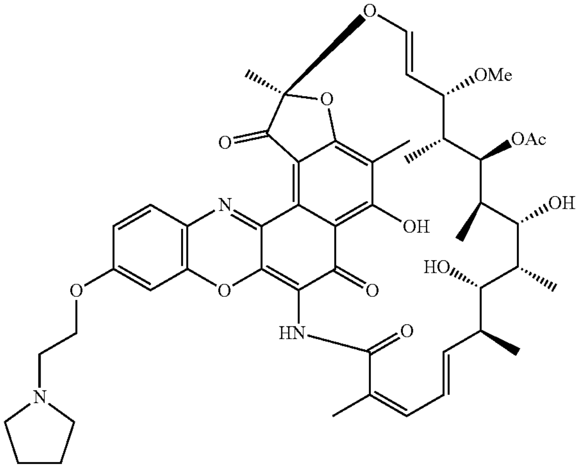 [SMILES: CO[C@H]1/C=C/O[C@@]2(C)Oc3c(C)c(O)c4c(=O)c(c5oc6cc(OCCN7CCCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16k |
| 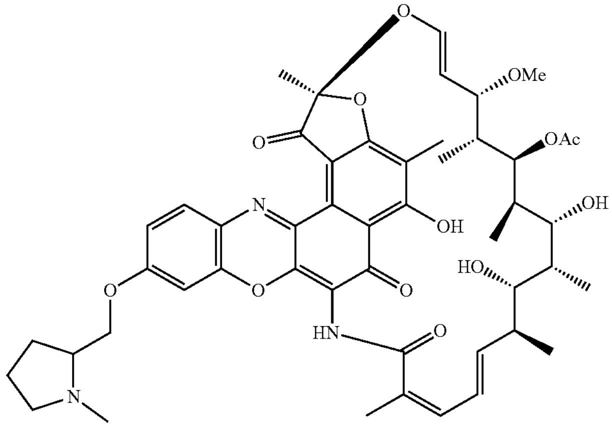 [SMILES: CO[C@H]1/C=C/O[C@@]2(C)Oc3c(C)c(O)c4c(=O)c(c5oc6cc(OCC7CCCN7C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16l |

TABLE 1-continued
| Select rifamycin analogs according to the disclosure | |
|---|---|
| Rifamycin Analog Compound Structure | Compound Number |
| 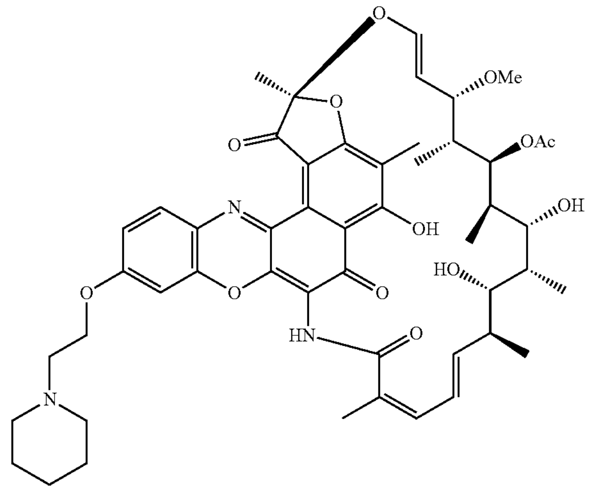 [SMILES: CO[C@H]1/C=C/O[C@@]2(C)Oc3c(C)c(O)c4c(=O)c(c5oc6cc(OCCN7CCCCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16m |
| 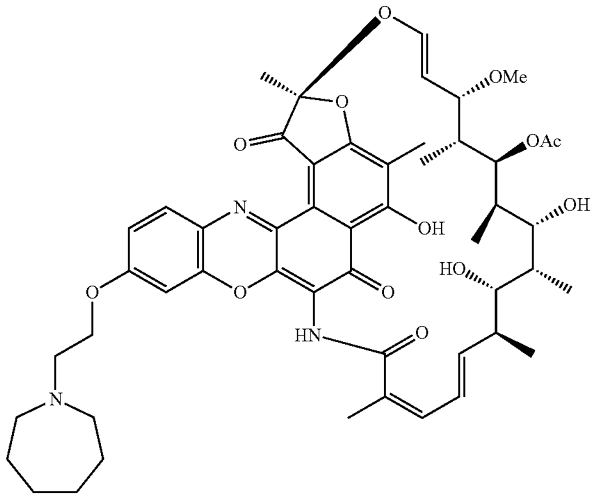 [SMILES: CO[C@H]1/C=C/O[C@@]2(C)Oc3c(C)c(O)c4c(=O)c(c5oc6cc(OCCN7CCCCCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16n |
| 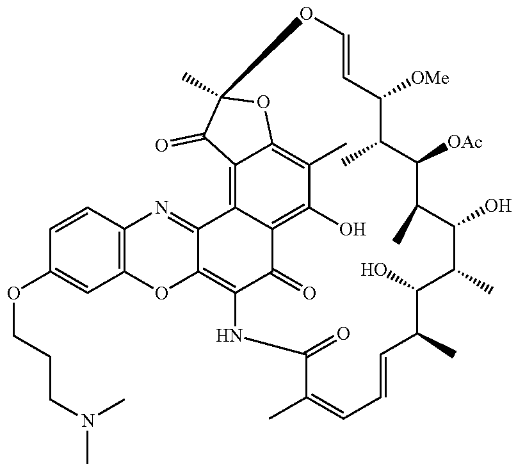 [SMILES: CO[C@H]1/C=C/O[C@@]2(C)Oc3c(C)c(O)c4c(=O)c(c5oc6cc(OCCCN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16o |

TABLE 1-continued
Select rifamycin analogs according to the disclosure
| Rifamycin Analog Compound Structure | Compound Number |
|---|---|
| 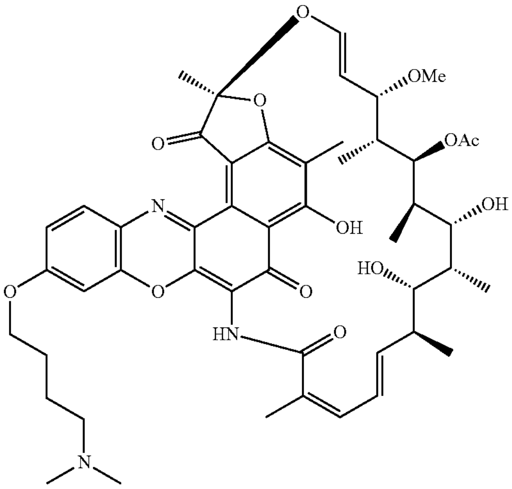 [SMILES: CO[C@H]1/C=C/O[C@@]2(C)Oc3c(C)c(O)c4c(=O)c(c5oc6cc(OCCCCN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16p |
| 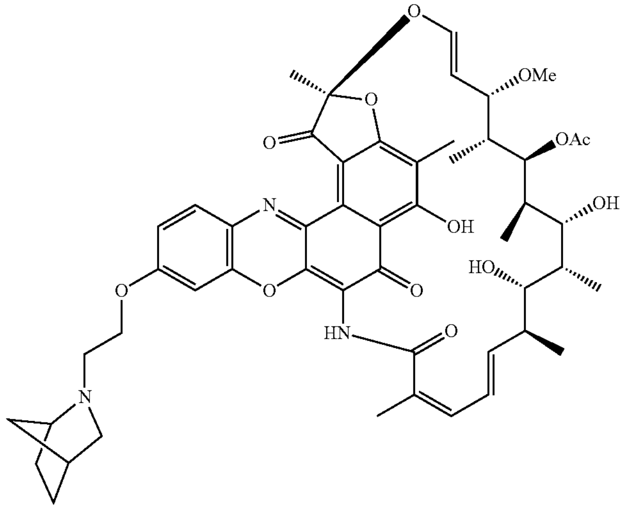 [SMILES: CO[C@H]1/C=C/O[C@@]2(C)Oc3c(C)c(O)c4c(=O)c(c5oc6cc(OCCN7CC8CCC7C8)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16q |
| 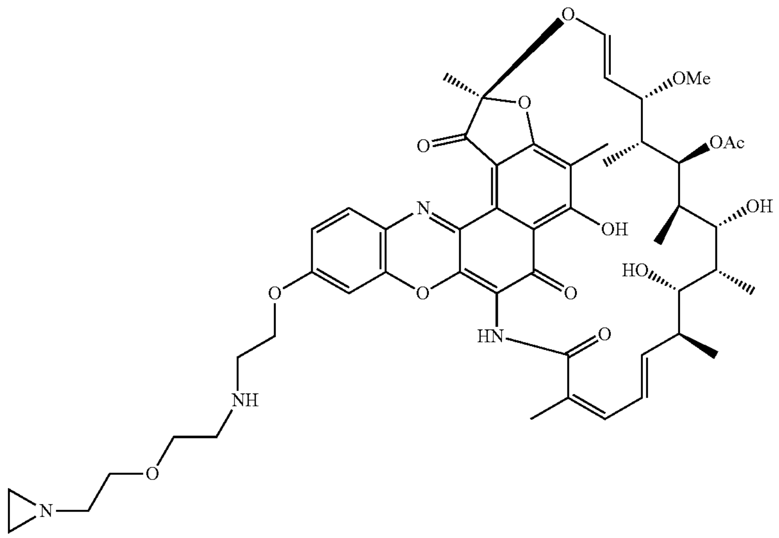 [SMILES: CO[C@H]1/C=C/O[C@@]2(C)Oc3c(C)c(O)c4c(=O)c(c5oc6cc(OCCNCCOCCN7CC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16r |

TABLE 1-continued
| Select rifamycin analogs according to the disclosure | |
|---|---|
| Rifamycin Analog Compound Structure | Compound Number |
| 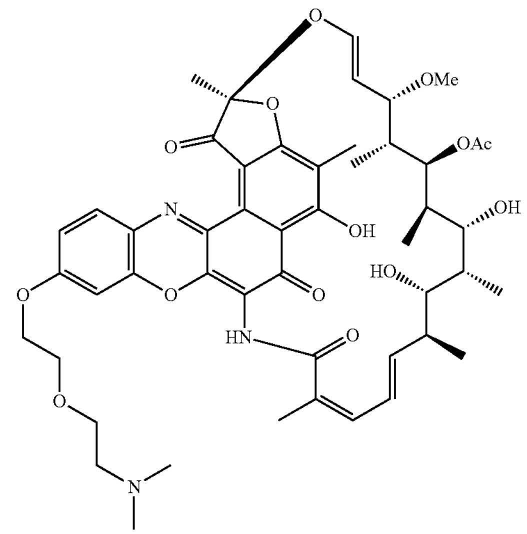 [SMILES: CO[C@H]1/C=C/O[C@@]2(C)Oc3c(C)c(O)c4c(=O)c(c5oc6cc(OCCOCCN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16s |
| 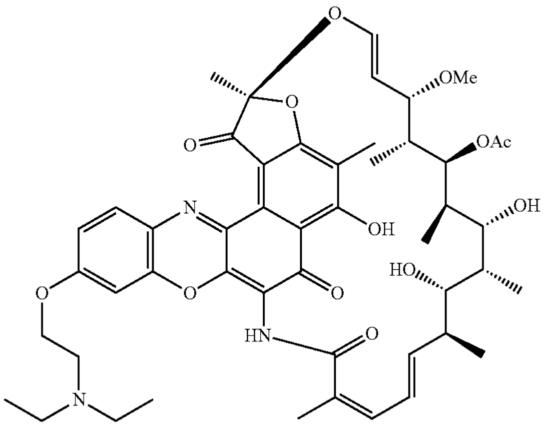 [SMILES: CCN(CC)CCOc1ccc2nc3c4c5c6c(C)c(O)c4c(=O)c(c-3oc2c1)NC(=O)/C(C)=C\C=C\[C@H](C)[C@H](O)[C@@H](C)[C@@H](O)[C@@H](C)[C@H](OC(C)=O)[C@H](C)[C@@H](OC)/C=C/O[C@@](C)(O6)C5=O] | 16t |
| 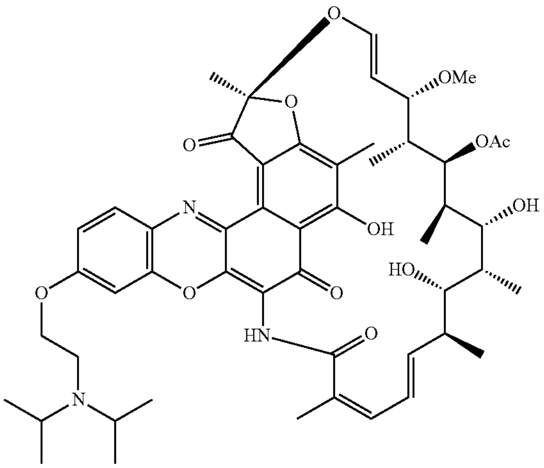 [SMILES: CO[C@H]1/C=C/O[C@@]2(C)Oc3c(C)c(O)c4c(=O)c(c5oc6cc(OCCN(C(C)C)C(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16u |

TABLE 1-continued
| Select rifamycin analogs according to the disclosure | |
|---|---|
| Rifamycin Analog Compound Structure | Compound Number |
| 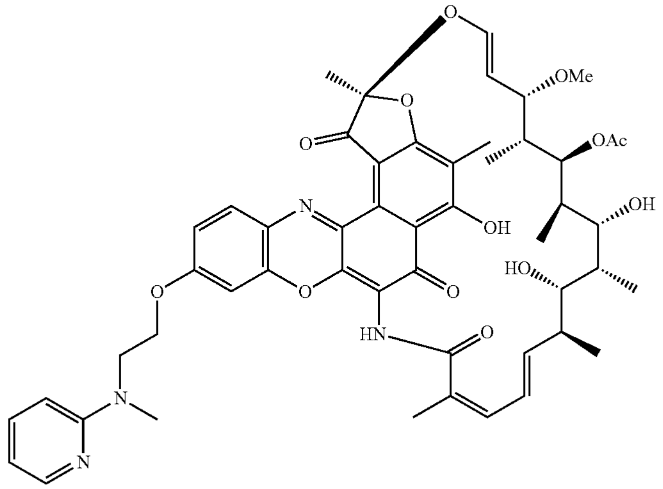 [SMILES: CO[C@H]1/C=C/O[C@@]2(C)Oc3c(C)c(O)c4c(=O)c(c5oc6cc(OCCN(C)c7ccccn7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16v |
| 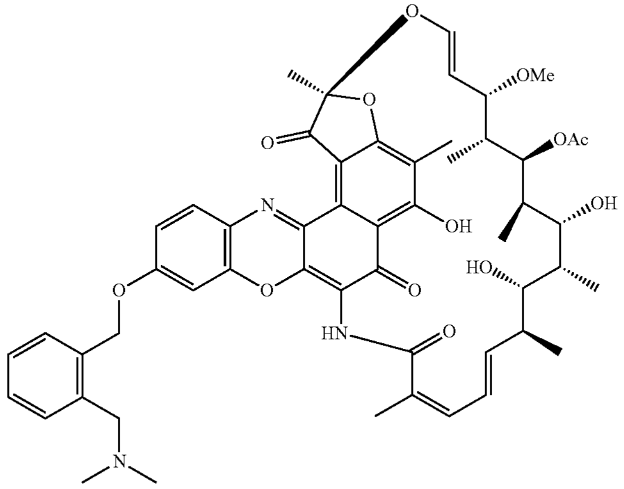 [SMILES: CO[C@H]1/C=C/O[C@@]2(C)Oc3c(C)c(O)c4c(=O)c(c5oc6cc(OCc7ccccc7CN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16w |
| 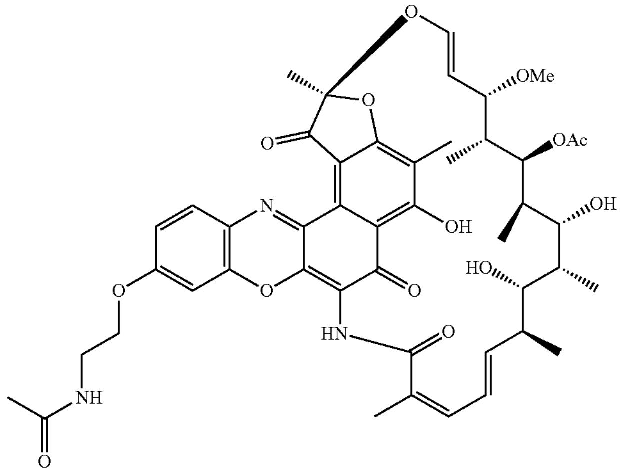 [SMILES: CO[C@H]1/C=C/O[C@@]2(C)Oc3c(C)c(O)c4c(=O)c(c5oc6cc(OCCNC(C)=O)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16x |

TABLE 1-continued
| Select rifamycin analogs according to the disclosure | |
|---|---|
| Rifamycin Analog Compound Structure | Compound Number |
| 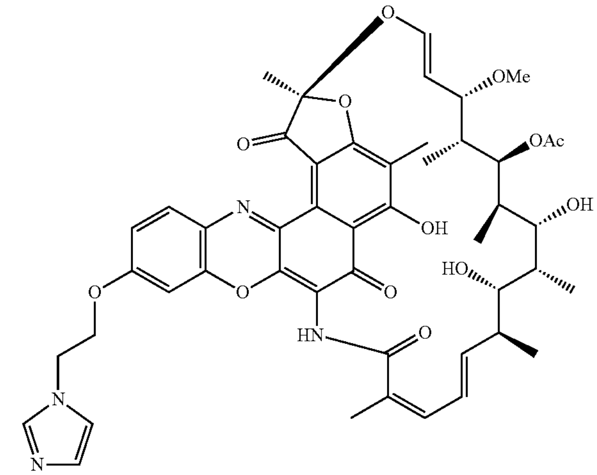 [SMILES: CO[C@H]1/C=C/O[C@@]2(C)Oc3c(C)c(O)c4c(=O)c(c5oc6cc(OCCn7ccnc7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16y |
| 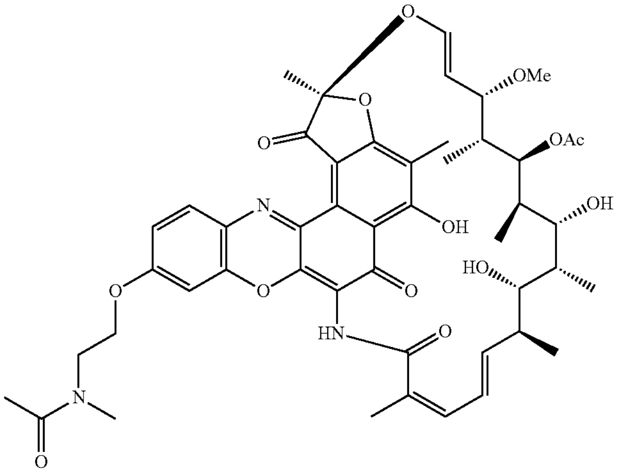 [SMILES: CO[C@H]1/C=C/O[C@@]2(C)Oc3c(C)c(O)c4c(=O)c(c5oc6cc(OCCN(C)C(C)=O)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16z |
| 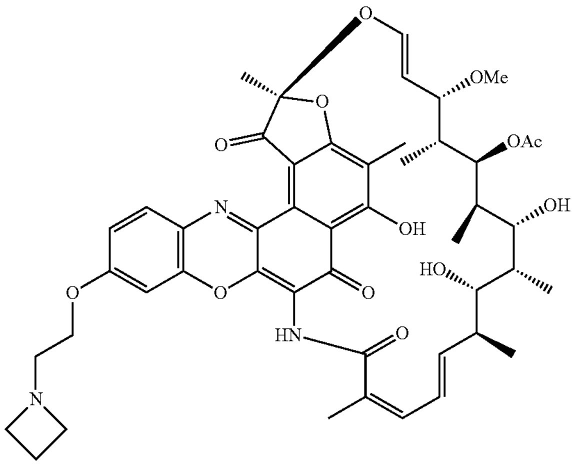 [SMILES: CO[C@H]1/C=C/O[C@@]2(C)Oc3c(C)c(O)c4c(=O)c(c5oc6cc(OCCN7CCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16z-1 |

TABLE 1-continued
| Select rifamycin analogs according to the disclosure | |
|---|---|
| Rifamycin Analog Compound Structure | Compound Number |
| 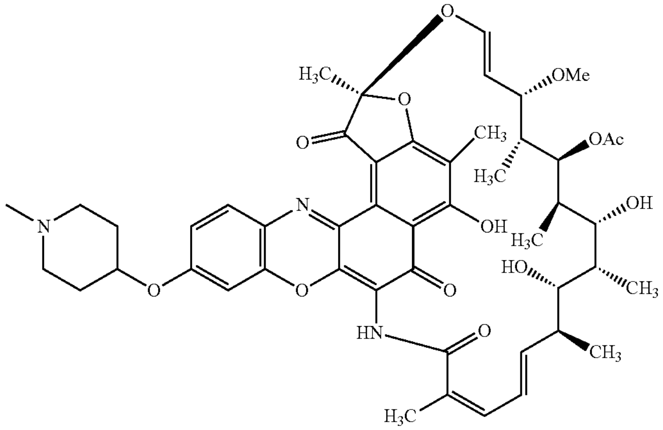 [SMILES: CO[C@H]1/C=C/O[C@@]2(C)Oc3c(C)c(O)c4c(=O)c(c5oc6cc(OC7CCN(C)CC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 17 |
| 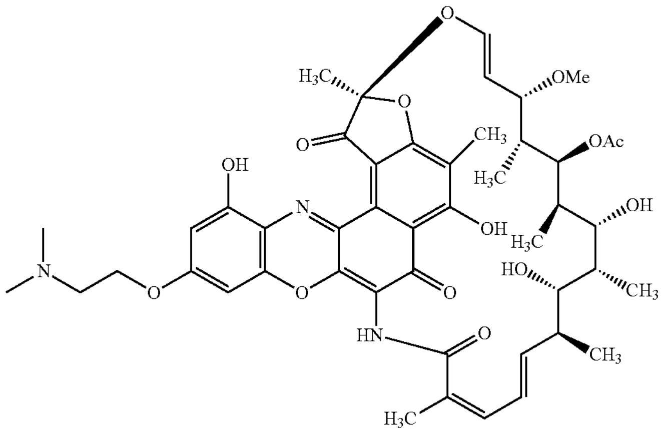 [SMILES: CO[C@H]1/C=C/O[C@@]2(C)Oc3c(C)c(O)c4c(=O)c(c5oc6cc(OCCN(C)C)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29 |
| 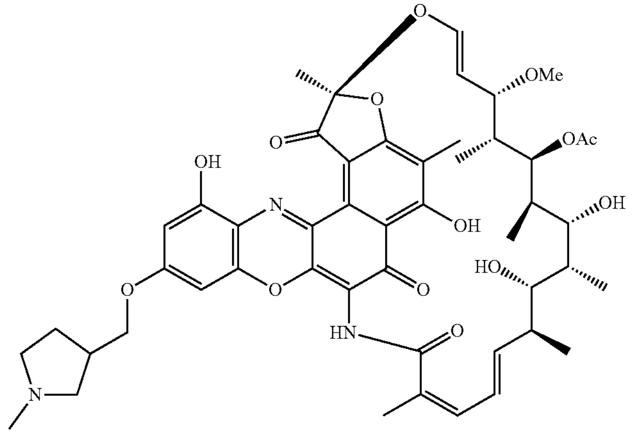 [SMILES: CO[C@H]1/C=C/O[C@@]2(C)Oc3c(C)c(O)c4c(=O)c(c5oc6cc(OCC7CCN(C)C7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29a |

TABLE 1-continued
| Select rifamycin analogs according to the disclosure | |
|---|---|
| Rifamycin Analog Compound Structure | Compound Number |
| 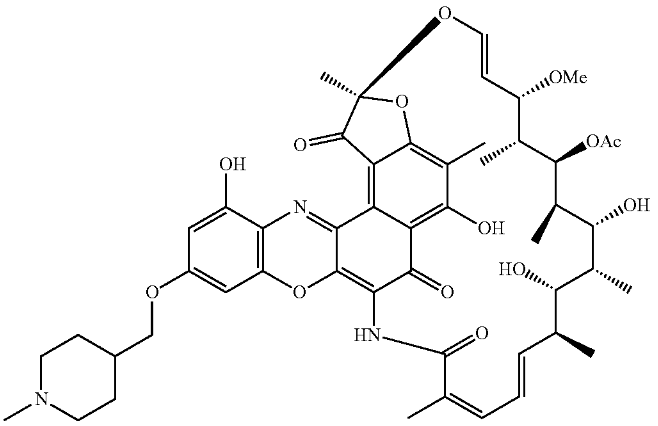 [SMILES: CO[C@H]1/C=C/O[C@@]2(C)Oc3c(C)c(O)c4c(=O)c(c5oc6cc(OCC7CCN(C)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29b |
| 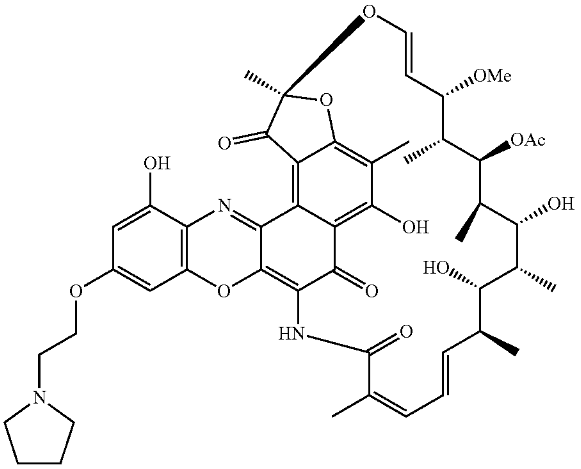 [SMILES: CO[C@H]1/C=C/O[C@@]2(C)Oc3c(C)c(O)c4c(=O)c(c5oc6cc(OCCN7CCCC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29c |
| 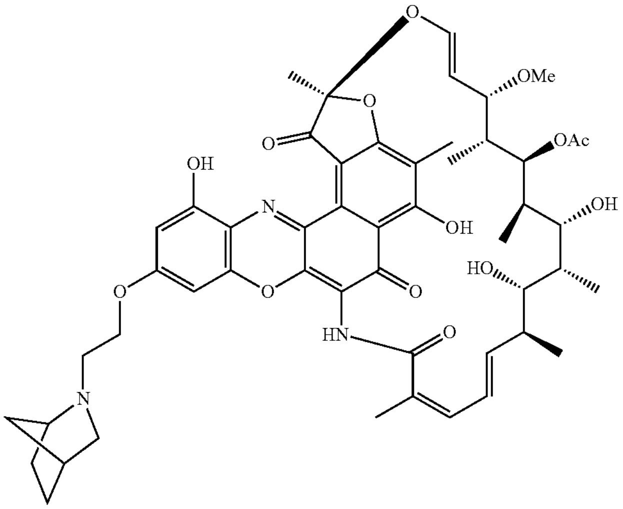 [SMILES: CO[C@H]1/C=C/O[C@@]2(C)Oc3c(C)c(O)c4c(=O)c(c5oc6cc(OCCN7CC8CCC7C8)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29d |

TABLE 1-continued
| Select rifamycin analogs according to the disclosure | |
|---|---|
| Rifamycin Analog Compound Structure | Compound Number |
| 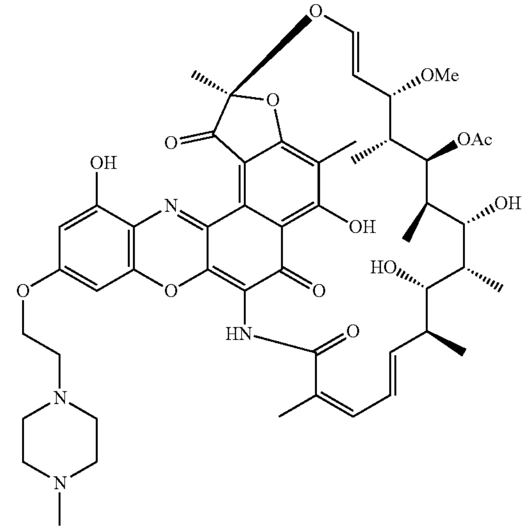 [SMILES: CO[C@H]1/C=C/O[C@@]2(C)Oc3c(C)c(O)c4c(=O)c(c5oc6cc(OCCN7CCN(C)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29e |
| 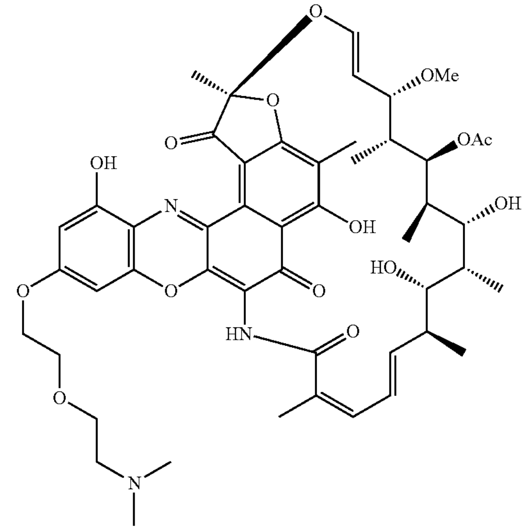 [SMILES: CO[C@H]1/C=C/O[C@@]2(C)Oc3c(C)c(O)c4c(=O)c(c5oc6cc(OCCOCCN(C)C)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29f |
| 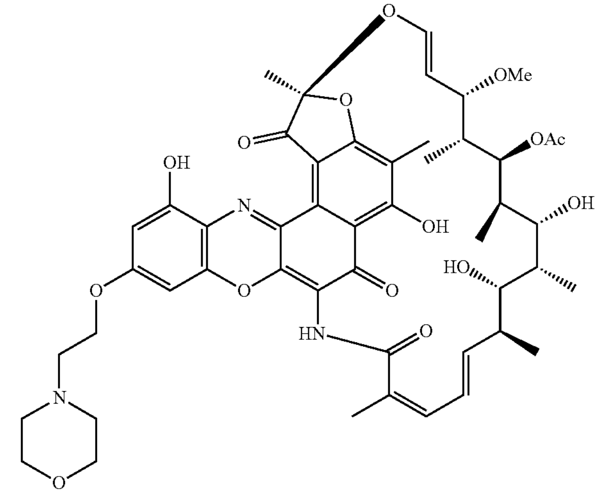 [SMILES: CO[C@H]1/C=C/O[C@@]2(C)Oc3c(C)c(O)c4c(=O)c(c5oc6cc(OCCN7CCOCC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29g |

TABLE 1-continued
| Rifamycin Analog Compound Structure | Compound Number |
| --- | --- |
| 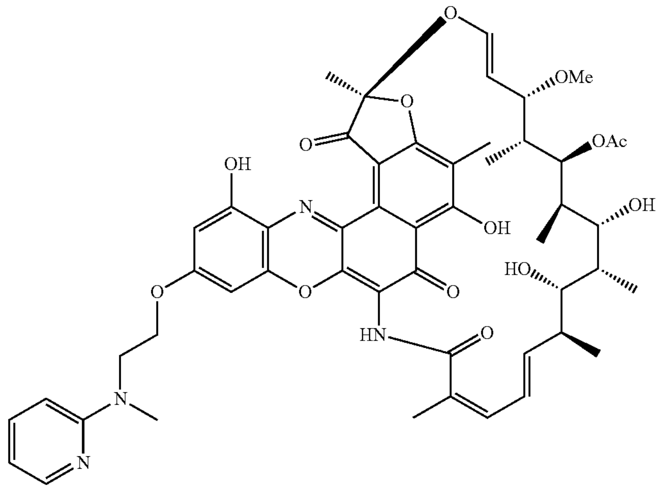 [SMILES: CO[C@H]1/C=C/O[C@@]2(C)Oc3c(C)c(O)c4c(=O)c(c5oc6cc(OCCN(C)c7ccccn7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29h |
| 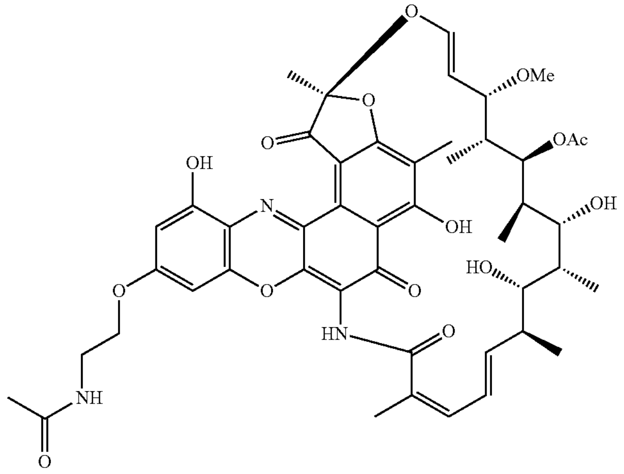 [SMILES: CO[C@H]1/C=C/O[C@@]2(C)Oc3c(C)c(O)c4c(=O)c(c5oc6cc(OCCNC(C)=O)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29i |
| 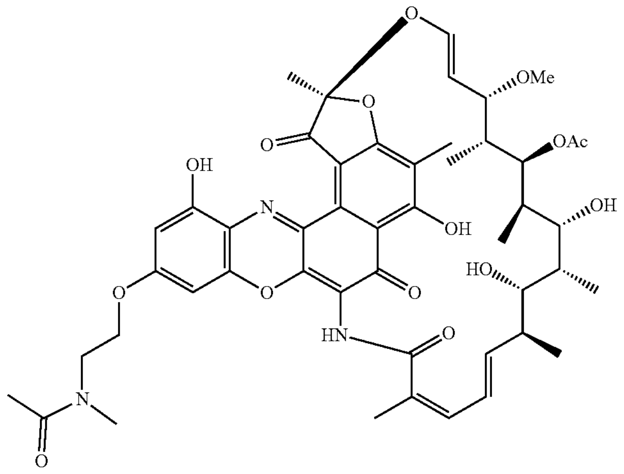 [SMILES: CO[C@H]1/C=C/O[C@@]2(C)Oc3c(C)c(O)c4c(=O)c(c5oc6cc(OCCN(C)C(C)=O)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29j |
Select rifamycin analogs according to the disclosure TABLE 1-continued
| Select rifamycin analogs according to the disclosure | |
|---|---|
| Rifamycin Analog Compound Structure | Compound Number |
| 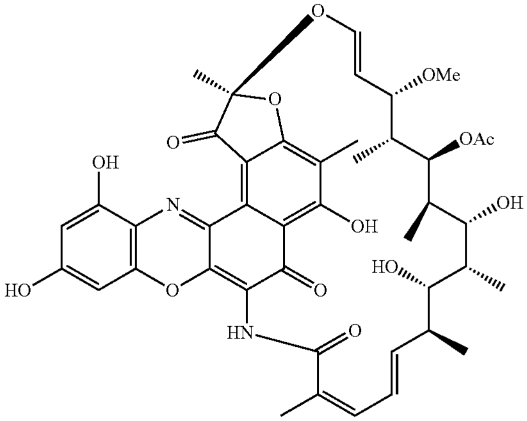 [SMILES: CO[C@H]1/C=C/O[C@@]2(C)Oc3c(C)c(O)c4c(=O)c(c5oc6cc(O)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29k |
| 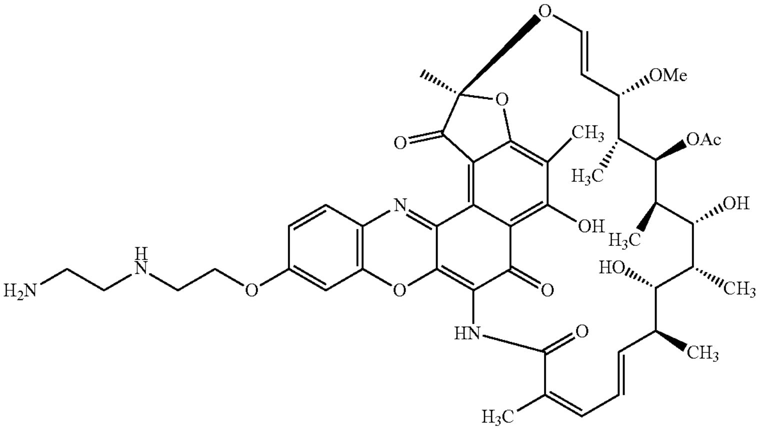 [SMILES: CO[C@H]1/C=C/O[C@@]2(C)Oc3c(C)c(O)c4c(=O)c(c5oc6cc(OCCNCCN)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 35 |
| 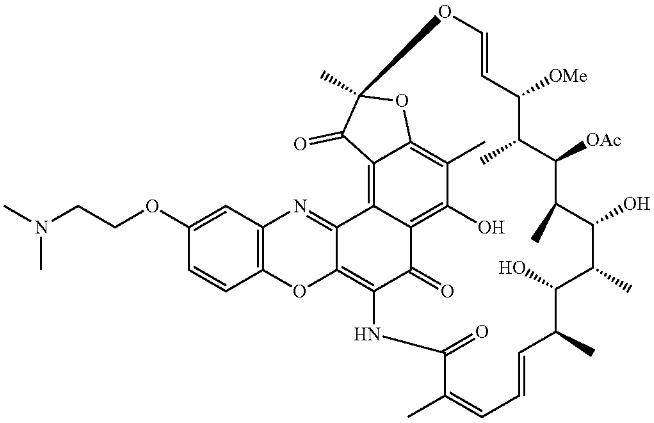 [SMILES: CO[C@H]1/C=C/O[C@@]2(C)Oc3c(C)c(O)c4c(=O)c(c5oc6ccc(OCCN(C)C)cc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 38 |

TABLE 1-continued
| Select rifamycin analogs according to the disclosure | |
|---|---|
| Rifamycin Analog Compound Structure | Compound Number |
| 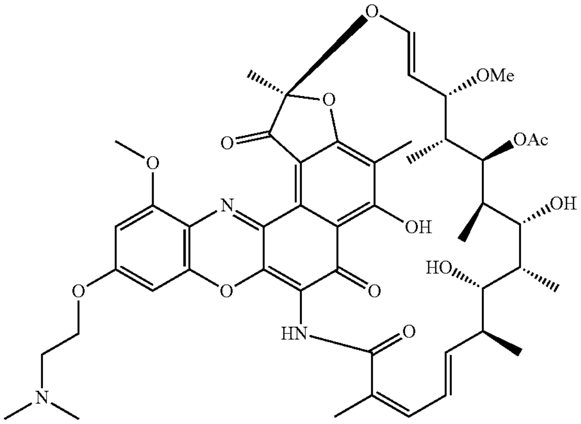 | 43 |
| 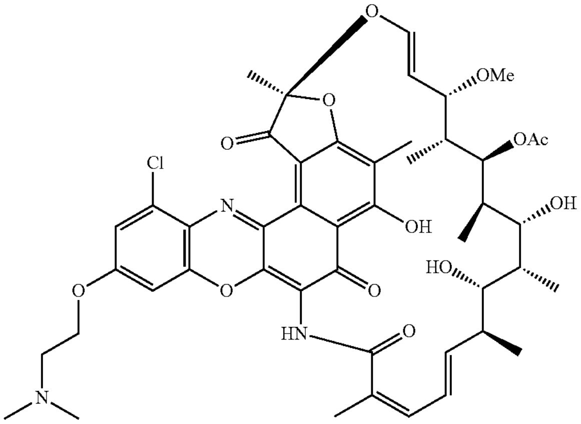 | 45 |
| 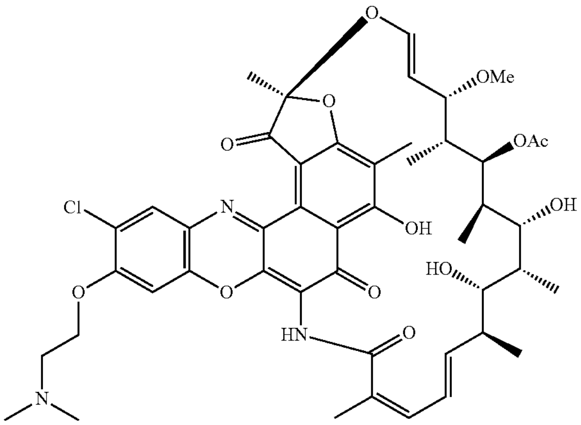 [SMILES: CO[C@H]1/C=C/O[C@@]2(C)Oc3c(C)c(O)c4c(=O)c(c5oc6cc(OCCN(C)C)c(Cl)cc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 48 |

TABLE 1-continued
| Select rifamycin analogs according to the disclosure | |
|---|---|
| Rifamycin Analog Compound Structure | Compound Number |
| 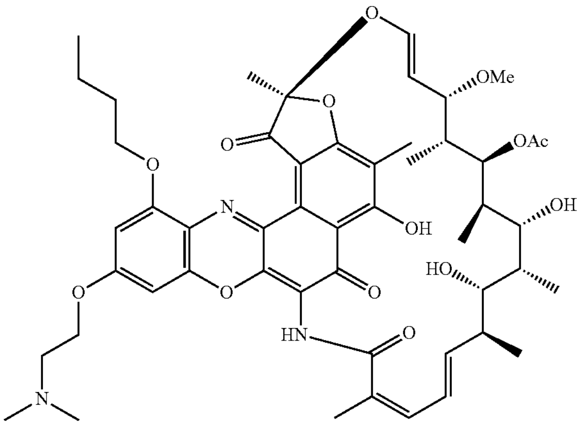 [SMILES: CCCCOc1cc(OCCN(C)C)cc2oc3c4c(=O)c5c(O)c(C)c6c(c5c-3nc12)C(=O)[C@@](C)(O/C=C/[C@H](OC)[C@@H](C)[C@@H](OC(C)=O)[C@H](C)[C@H](O)[C@H](C)[C@@H](O)[C@@H](C)/C=C/C=C(/C)C(=O)N4)O6] | 50 |
| 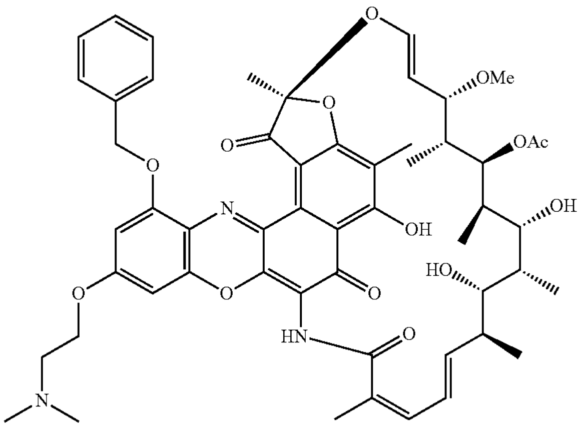 [SMILES: CO[C@H]1/C=C/O[C@@]2(C)Oc3c(C)c(O)c4c(=O)c(c5oc6cc(OCCN(C)C)cc(OCc7ccccc7)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 52 |
| 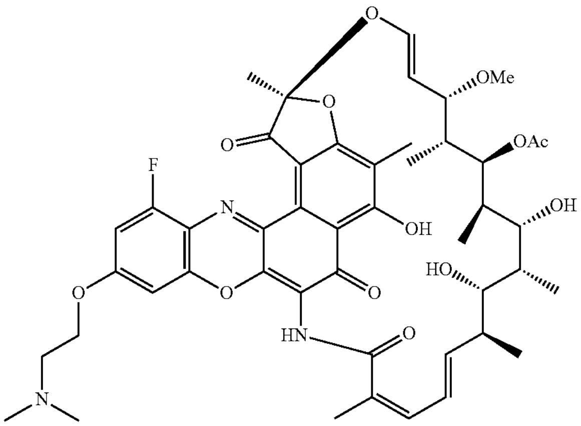 | 55 |

TABLE 1-continued
| Select rifamycin analogs according to the disclosure | |
|---|---|
| Rifamycin Analog Compound Structure | Compound Number |
| 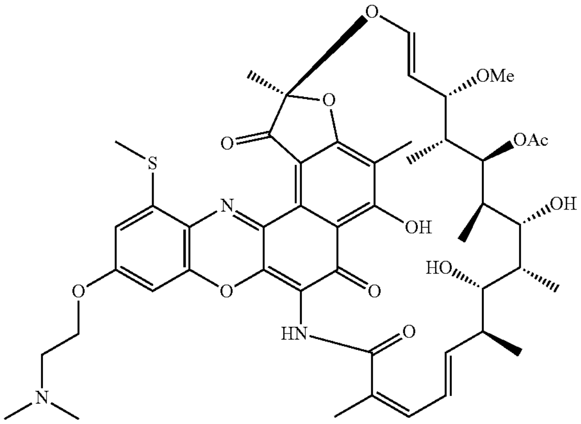 [SMILES: CO[C@H]1/C=C/O[C@@]2(C)Oc3c(C)c(O)c4c(=O)c(c5oc6cc(OCCN(C)C)cc(SC)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 60 |
| 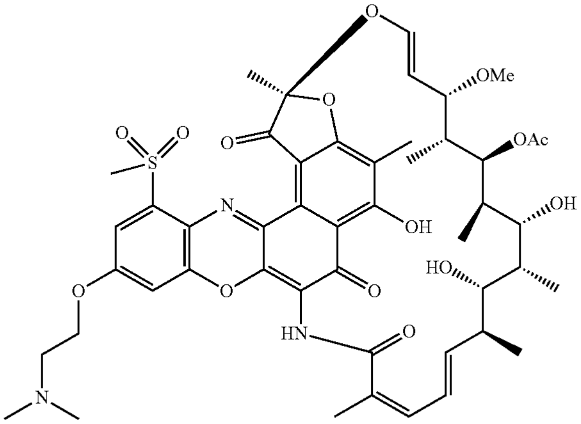 [SMILES: CO[C@H]1/C=C/O[C@@]2(C)Oc3c(C)c(O)c4c(=O)c(c5oc6cc(OCCN(C)C)cc(S(C)(=O)=O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 61 |
| 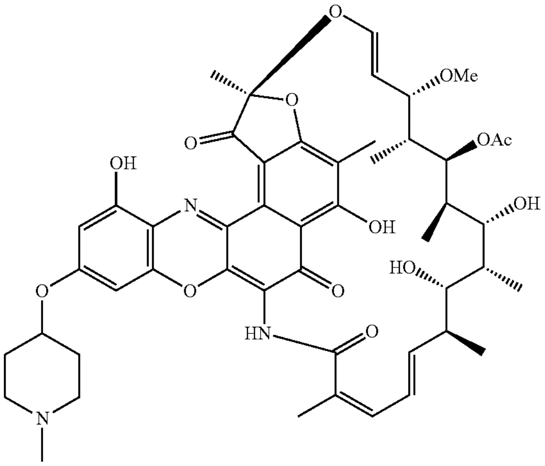 [SMILES: CO[C@H]1/C=C/O[C@@]2(C)Oc3c(C)c(O)c4c(=O)c(c5oc6cc(OC7CCN(C)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 68 |

TABLE 1-continued
| Select rifamycin analogs according to the disclosure | |
|---|---|
| Rifamycin Analog Compound Structure | Compound Number |
| 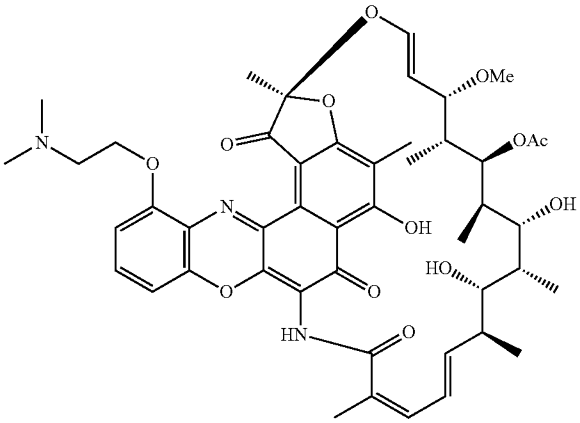 [SMILES: CO[C@H]1/C=C/O[C@@]2(C)Oc3c(C)c(O)c4c(=O)c(c5oc6cccc(OCCN(C)C)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 71 |
| 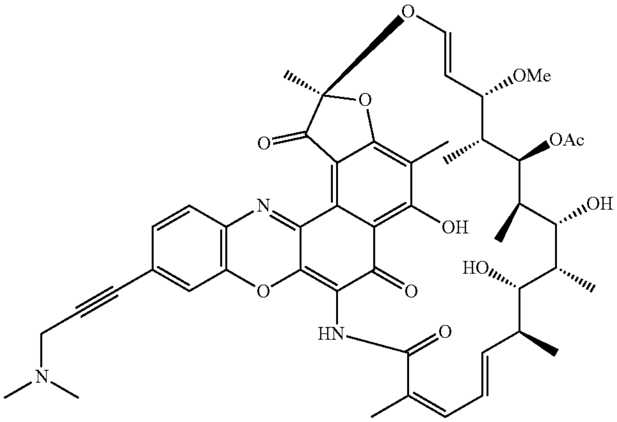 [SMILES: CO[C@H]1/C=C/O[C@@]2(C)Oc3c(C)c(O)c4c(=O)c(c5oc6cc(C#CCN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 72 |
| 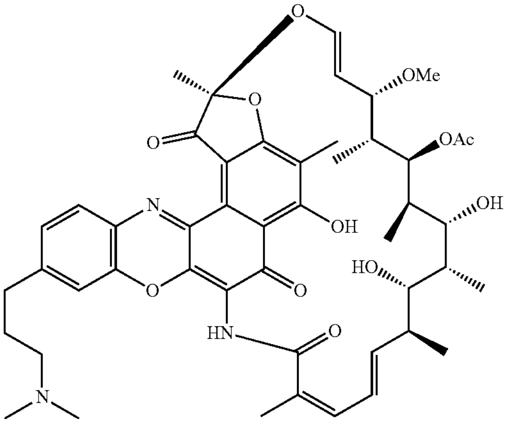 [SMILES: CO[C@H]1/C=C/O[C@@]2(C)Oc3c(C)c(O)c4c(=O)c(c5oc6cc(CCCN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 75 |

In one embodiment, a rifamycin analog compound of the disclosure has a structure selected from the group consisting of:

(P1)

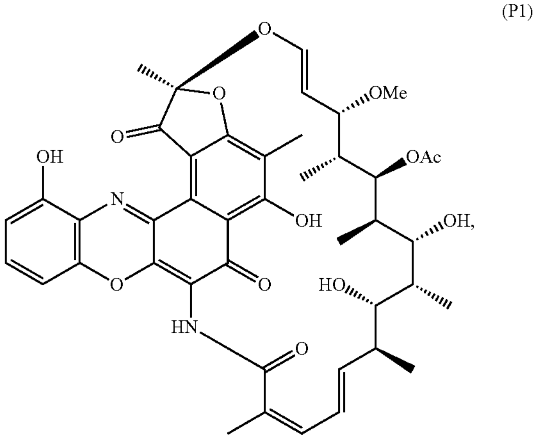

(P2)

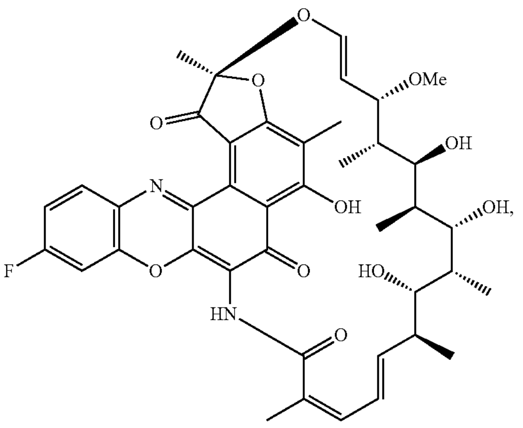

(P3)

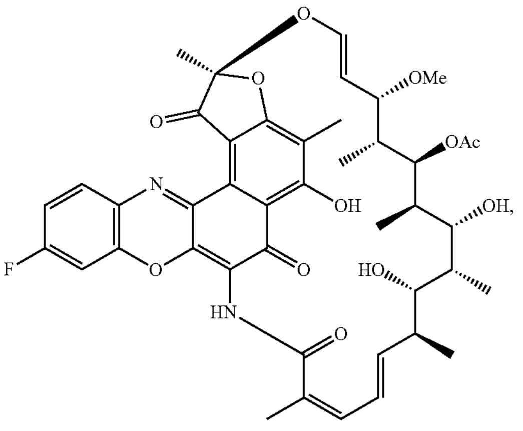

or a pharmaceutically acceptable salt thereof.

In one aspect, the compounds of the disclosure have the structure of Formula (IA):

(IA)

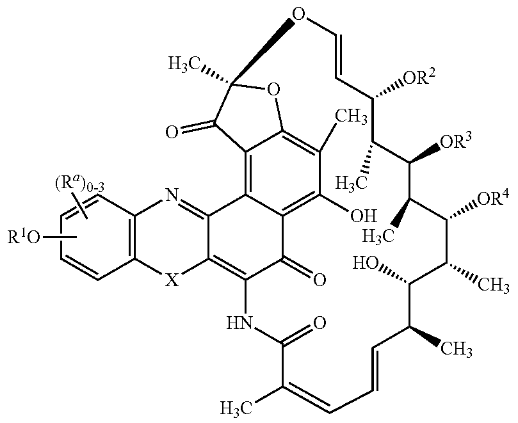

wherein:

X is selected from —O—, —S—, and —NR*—;

$R_1$ is selected from hydrogen, an aliphatic $C_1$-$C_{20}$ hydrocarbon, an aromatic $C_5$-$C_{20}$ hydrocarbon, a heteroaromatic $C_1$-$C_{20}$ hydrocarbon, an aryl $C_6$-$C_{20}$ hydrocarbon, a heteroaryl $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, $—NO_2$, $—NO_3$, —O—NO, $—N_3$, $—NH_2$, —NHR*, $—N(R^*)_2$, $—N(R^*)_3^+$, —N(R*)—OH, $—O—N(R^*)_2$, —N(R*)—O—R*, —CN, —NC, —(C═O)—R*, —CHO, $—CO_2H$, $—CO_2R^*$, —(C═O)—S—R*, —O—(C═O)—H, —O—(C═O)—R*, —S—(C═O)—R*, $—(C═O)—NH_2$, $—(C═O)—N(R^*)_2$, $—(C═O)—NHNH_2$, $—O—(C═O)—NHNH_2$, $—(C═S)—NH_2$, $—(C═S)—N(R^*)_2$, —N(R*)—CHO, —N(R*)—(C═O)—R*, —SCN, —NCS, —NSO, —SSR*, $—SO_2R^*$, $—SO_2—N(R^*)_2$, —S(═O)—OR*, —S(═O)—R*, $—Si(R^*)_3$, $—CF_3$, $—O—CF_3$ and combinations thereof;

$R_2$, $R_3$, and $R_4$ are independently selected from hydrogen, a straight chained, branched or cyclic aliphatic $C_1$-$C_{20}$ hydrocarbon, or —(C═O)—R*, each of which further comprises 0-8 heteroatoms selected from halogen, O, N, and S;

$R_a$ is independently at each occurrence selected from hydrogen, —F, —Cl, —Br, —I, —OH, OR*, $—NH_2$, —NHR*, $—N(R^*)_2$, $—N(R^*)_3^+$, —(C═O)—R*, —CHO, $—CO_2H$, $—CO_2R^*$, —SR*, $SO_2R^*$, and an aliphatic $C_1$-$C_{20}$ hydrocarbon, which further comprises 0-8 heteroatoms selected from halogen, O, N, and S, and wherein $R_a$ and $R_b$ are optionally substituted with one or more of —F, —Cl, —Br, —I, —OH, —OR*;

R* is independently at each occurrence selected from hydrogen, an aliphatic $C_1$-$C_{20}$ hydrocarbon, an aromatic $C_5$-$C_{20}$ hydrocarbon, a heteroaromatic $C_1$-$C_{20}$ hydrocarbon, an aryl $C_6$-$C_{20}$ hydrocarbon, a heteroaryl $C_1$-$C_{20}$ hydrocarbon, and combinations thereof, which further comprises 0-8 heteroatoms selected from halogen, O, N, and S and combinations thereof.

In one embodiment, X is —O—, $R_1$ is an aliphatic $C_1$-$C_3$ hydrocarbon, $R_2$ is a methyl group, $R_3$ is Ac ($—(C═O)—CH_3$), $R_4$ is a hydrogen, and $R_a$ is a hydrogen.

In one embodiment, X is —O—, $R_1$ is a benzyl group, $R_2$ is a methyl group, $R_3$ is Ac (—(C═O)—$CH_3$), $R_4$ is a hydrogen, and $R_a$ is a hydrogen.

In one embodiment, X is —O—, $R_1$ is an aliphatic $C_1$-$C_8$ hydrocarbon comprising 1-8 heteroatoms selected from halogen, O, N, and S, $R_2$ is a methyl group, $R_3$ is Ac (—(C═O)—$CH_3$), $R_4$ is a hydrogen, and $R_a$ is a hydrogen.

In one embodiment, X is —O—, $R_1$ is an aliphatic $C_1$-$C_8$ hydrocarbon substituted with one or more of —$NH_2$, —NHR*, —$N(R^*)_2$, $R_2$ is a methyl group, $R_3$ is Ac (—(C═O)—$CH_3$), $R_4$ is a hydrogen, and $R_a$ is a hydrogen.

In one embodiment, X is —$NCH_3$—, $R_1$ is —OH, $R_2$ is a methyl group, $R_3$ is Ac (—(C═O)—$CH_3$), $R_4$ is a hydrogen, and $R_a$ is a hydrogen.

The present disclosure also includes salts of the compounds described herein. As used herein, "salts" refers to derivatives of the disclosed compounds wherein the parent compound is modified by converting an existing acid or base moiety to its salt form. Examples of salts include, but are not limited to, mineral acid (such as HCl, HBr, $H_2SO_4$) or organic acid (such as acetic acid, benzoic acid, trifluoroacetic acid salts of basic residues such as amines; alkali (such as Li, Na, K, Mg, Ca) or organic (such as trialkylammonium) salts of acidic residues such as carboxylic acids; and the like. The salts of the present application can be synthesized from the parent compound which contains a basic or acidic moiety conventional chemical methods. Generally, such salts can be prepared by reacting the free acid or base forms of these compounds with a stoichiometric amount of the appropriate base or acid in water or in an organic solvent, or in a mixture of the two. In some embodiments, non-aqueous media like ether, ethyl acetate, ethanol, isopropanol, or acetonitrile (ACN) may be used.

The present application also includes pharmaceutically acceptable salts of the compounds described herein. The "pharmaceutically acceptable salts" include a subset of the "salts" described above which are conventional non-toxic salts of the parent compound formed, for example, from non-toxic inorganic or organic acids. Lists of suitable salts are found in Remington's Pharmaceutical Sciences, 17th ed., Mack Publishing Company, Easton, Pa., 1985, p. 1418 and Berge, S M et al, *Journal of Pharmaceutical Science,* 1977, 66, 1, 1-19. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene Protective Groups in Organic Synthesis,* 4th Ed., John Wiley & Sons: New York, 2006. In one non-limiting embodiment, protecting groups may include 1-chloroethyl carbonyl (ACE), acetoyl, benzyl (Bn), benzyloxy carbonyl (CBz), formyl, methyl carbonyl, trifluoroacetyl, t-butoxy carbonyl (Boc), and fluorenylmethyloxycarbonyl (Fmoc).

Rifamycin analog compounds depicted herein include all isomeric (e.g., enantiomeric, diastereomeric, and geometric (or conformational)) forms of the compound; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure. All tautomeric forms of the compounds presented herein are also within the scope of the disclosure.

Rifamycin analog compounds described herein also include all compounds that differ only in the presence of one or more isotopically enriched atoms. For example, compounds having the present structures except for the replacement of hydrogen by deuterium or tritium, or the replacement of a carbon by a $^{11}C$- or $^{13}C$- or $^{14}C$-enriched carbon, or the replacement of an oxygen by a $^{17}O$- or $^{18}O$-enriched oxygen, or the replacement of a nitrogen by a $^{15}N$-enriched nitrogen are within the scope of this disclosure.

Crystalline forms of the compounds of the disclosure and salts thereof are also within the scope of the disclosure. The compounds of the disclosure may be isolated in various amorphous and crystalline polymorphic forms, including without limitation amorphous and crystalline polymorphic forms which are anhydrous, hydrated, non-solvated, or solvated. Example hydrates include hemihydrates, monohydrates, dihydrates, and the like. In some embodiments, the compounds of the disclosure are anhydrous and non-solvated. By "anhydrous" is meant that the crystalline form of the compound contains essentially no bound water in the crystal lattice structure, i.e., the compound does not form a crystalline hydrate.

Methods of Manufacturing

In one aspect, the present disclosure provides a method of manufacturing a rifamycin analog compound having the structure of formula (V):

(V)

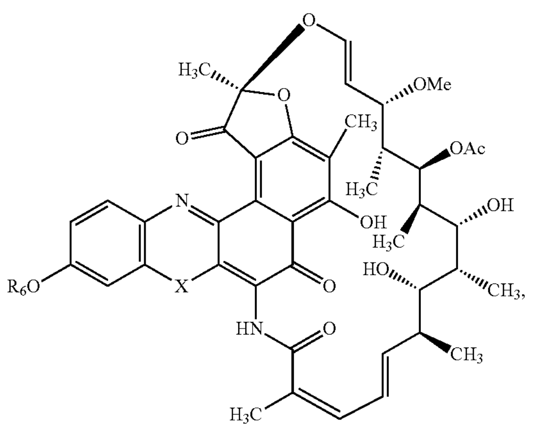

wherein X is selected from —O— and NR*—;

$R_6$ is selected from a $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, $R_N$ is selected from:

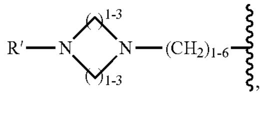
,

-continued

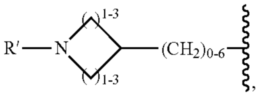,

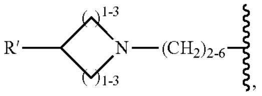, 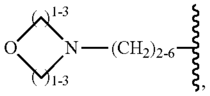,

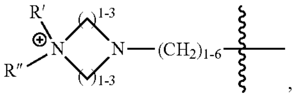,

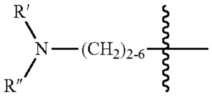,

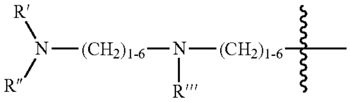,

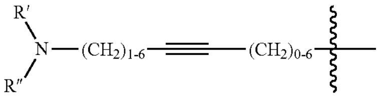 and

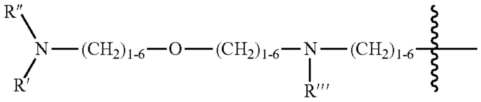

wherein the ∼∼∼ symbol represents the point of attachment; and R', R'' and R''' are selected from a hydrogen, a $C_1$-$C_6$ aliphatic hydrocarbon, and a protecting group including $F_{MOC}$ and $B_{OC}$, or wherein R' and R'' together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising the steps of:

(a) contacting Rifamycin S having the structure:

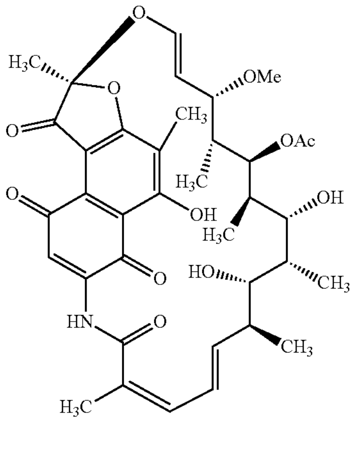 [SMILES: CO[C@H]1/C=C/O[C@@]2(C)Oc3c(C)c(O)c4c(c3C2=O)C(=O)C=C(NC(=O)/C(C)=C\C=C\[C@H](C)[C@H](O)[C@@H](C)[C@@H](O)[C@@H](C)[C@H](OC(C)=O)[C@@H]1C)C4=O]

with a compound having the structure of formula (VI):

(VI)

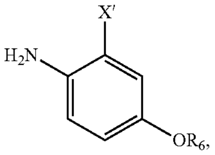

wherein X' is selected from —OH and —NHR*, and (b) treating the product of step (a) with an oxidizing agent.

In one aspect, the present disclosure provides a method of manufacturing a rifamycin analog compound having the structure of formula (V'):

(V')

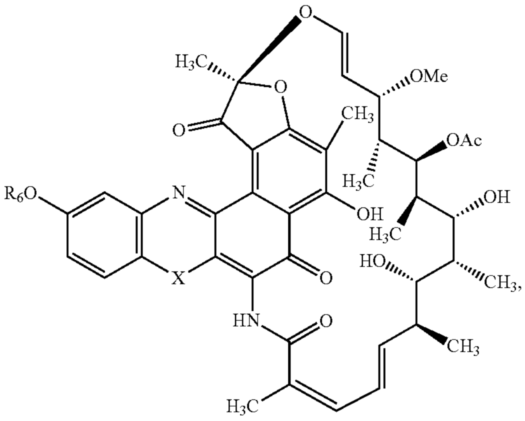

wherein X is selected from —O— and NR*—;

$R_6$ is selected from a $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, $R_N$ is selected from:

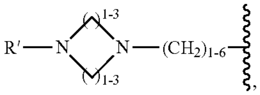,

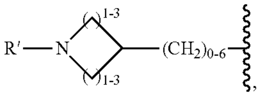,

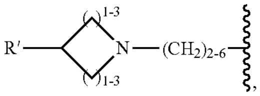, 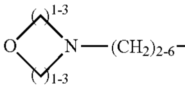,

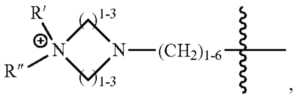,

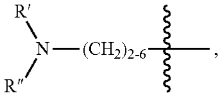,

-continued

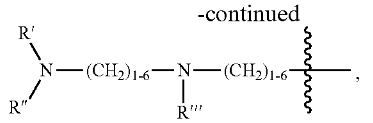

,

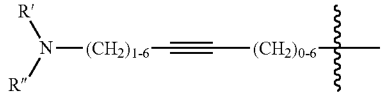

and

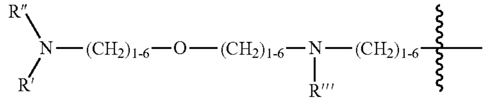

wherein the ~~~ symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising the steps of:

(a) contacting Rifamycin S having the structure:

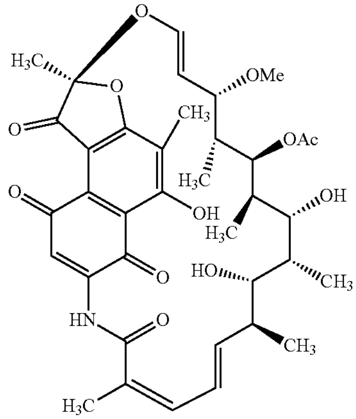 [SMILES: CO[C@H]1/C=C/O[C@@]2(C)Oc3c(C)c(O)c4c(c3C2=O)C(=O)C=C(NC(=O)/C(C)=C\C=C\[C@H](C)[C@H](O)[C@@H](C)[C@@H](O)[C@@H](C)[C@H](OC(C)=O)[C@@H]1C)C4=O]

with a compound having the structure of formula (VI'):

(VI')

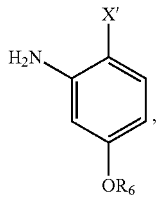

wherein X' is selected from —OH and —NHR*, and (b) treating the product of step (a) with an oxidizing agent.

In one aspect, the present disclosure provides a method of manufacturing a compound having the structure:

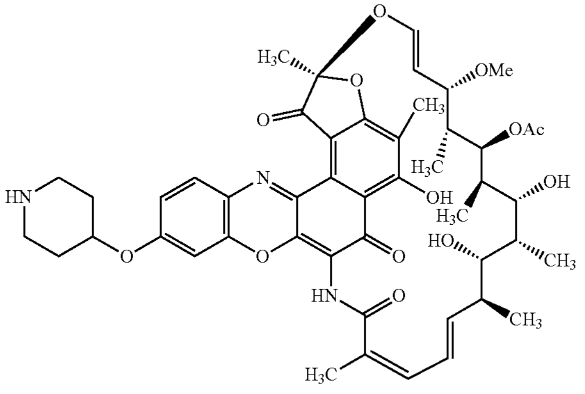 [SMILES: CO[C@H]1/C=C/O[C@@]2(C)Oc3c(C)c(O)c4c(=O)c(c5oc6cc(OC7CCNCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

comprising the steps of:

(a) contacting Rifamycin S with a compound having the structure of formula (VII):

(VII)

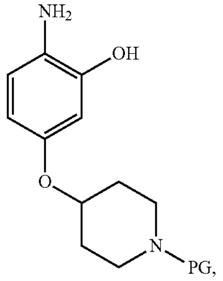

wherein PG is a protecting group;

(b) treating the product of step (a) with an oxidizing agent, and (c) removing the protecting group PG.

In one embodiment, the compound of formula (VII) is prepared by removing protecting group PG' from a compound of formula (VIII):

(VIII)

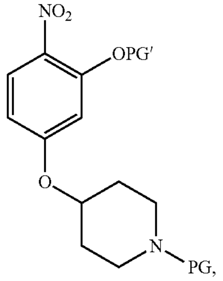

wherein protecting groups PG and PG' may be the same or different from each other.

In one embodiment, the compound of formula (VIII) is prepared by contacting a compound of formula (IX):

(IX)

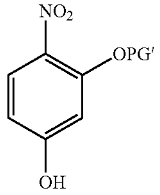

with a compound of formula (X):

(X)

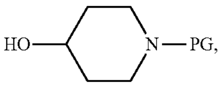

wherein protecting groups PG and PG' may be the same or different from each other.

In one aspect, the present disclosure provides a method of manufacturing a compound having the structure of formula (XI):

(XI)

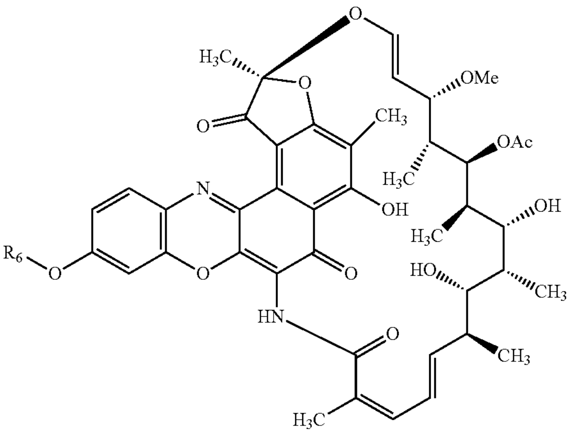

wherein $R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof and wherein $R_6$ is optionally substituted with one or more of —F—Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof;

$R_N$ is selected from:

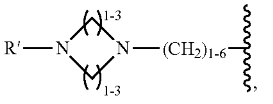

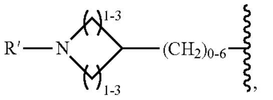

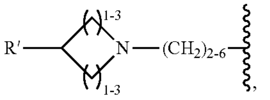 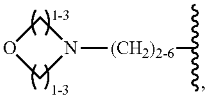

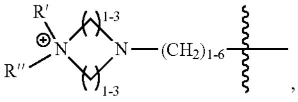

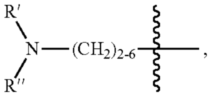

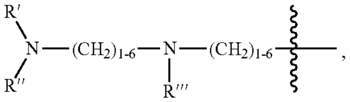

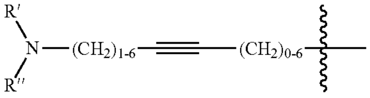 and

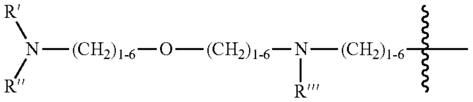

wherein the  symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII)

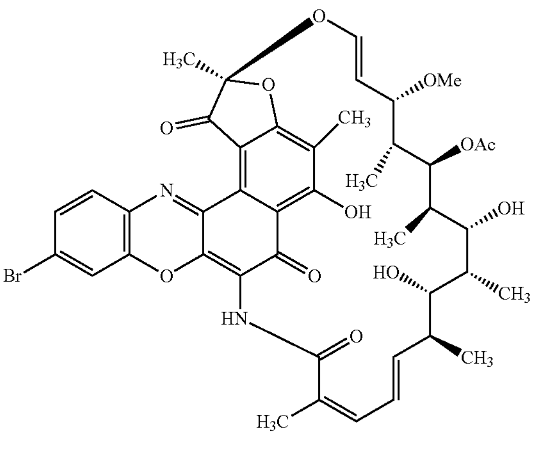

with an alcohol having the structure $R_6$—OH.

In one aspect, the present disclosure provides a method of manufacturing a compound having the structure of formula (XI'):

(XI')

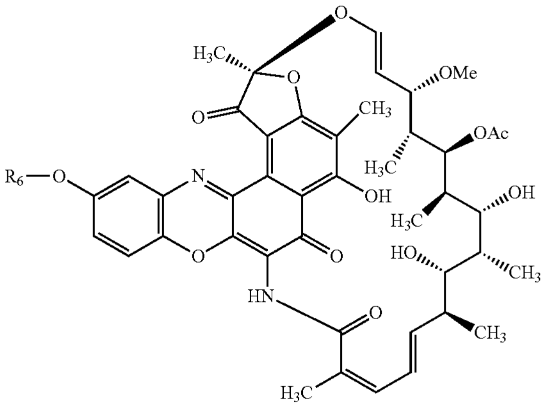

wherein $R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof and wherein $R_6$ is optionally substituted with one or more of —F; —Cl; —Br; —I; —OH, —OR*; —NO; —$NO_2$; —$NO_3$; —O—NO; —$N_3$; —$NH_2$; —NHR*; —N(R*)$_2$; —N(R*)$_3^+$; —N(R*)—OH; —O—N(R*)$_2$; —N(R*)—O—R*; —CN; —NC; —(C═O)—R*; —CHO; —$CO_2$H; —$CO_2$R*; —(C═O)—S—R*; —O—(C═O)—H; —O—(C═O)—R*; —S—(C═O)—R*; —(C═O)—$NH_2$; —(C═O)—N(R*)$_2$; —(C═O)—$NHNH_2$; —O—(C═O)—$NHNH_2$; —(C═S)—$NH_2$; —(C═S)—N(R*)$_2$; —N(R*)—CHO; —N(R*)—(C═O)—R*; —SCN; —NCS; —NSO; —SSR*; —$SO_2$R*; —$SO_2$—N(R*)$_2$; —S(═O)—OR*; —S(═O)—R*; —Si(R*)$_3$; —$CF_3$; —O—$CF_3$ and combinations thereof, $R_N$ is selected from:

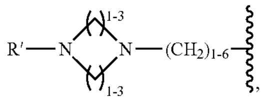
,
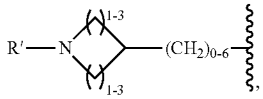
,
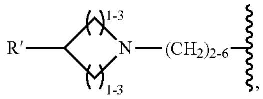
,
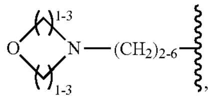
,
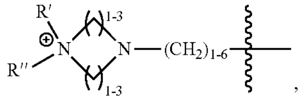
,
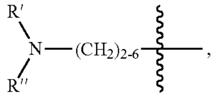
,
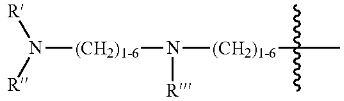
,
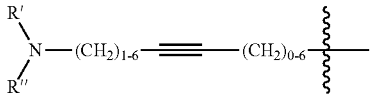
and
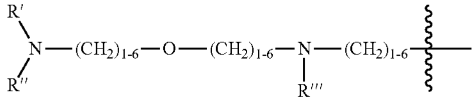

wherein the ∿∿∿ symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII')

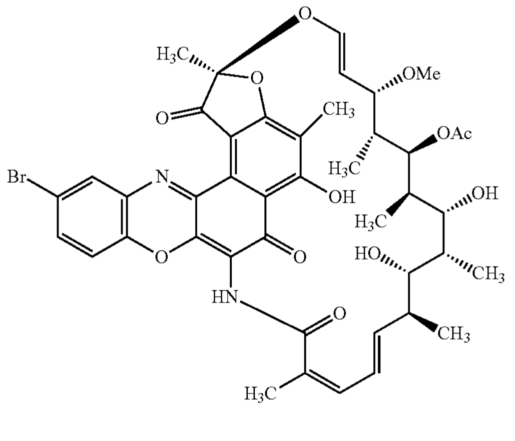

with an alcohol having the structure $R_6$—OH.

In one aspect, the present disclosure provides a method of manufacturing a compound having the structure of formula (XIII):

(XIII)

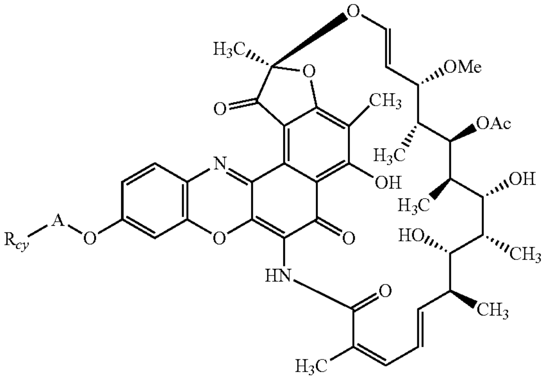

wherein A is selected from a bond (A is absent) or an aliphatic $C_1$-$C_{20}$ hydrocarbon;

$R_{cy}$ is a $C_3$-$C_{14}$ cycloaliphatic hydrocarbon which further comprises 0-8 heteroatoms selected from halogen, O, N, and S and combinations thereof and wherein $R_{cy}$ is optionally substituted with one or more of —F, —Cl, —Br, —I, —OH, —OR*, —NO, —$NO_2$, —$NO_3$, —O—NO, —$N_3$, —$NH_2$, —NHR*, —N(R*)$_2$, —N(R*)$_3^+$, —N(R*)—OH, —O—N(R*)$_2$, —N(R*)—O—R*, —CN, —NC, —(C═O)—R*, —CHO, —$CO_2$H, —$CO_2$R*, —(C═O)—S—R*, —O—(C═O)—H, —O—(C═O)—R*, —S—(C═O)—R*, —(C═O)—$NH_2$, —(C═O)—N(R*)$_2$, —(C═O)—$NHNH_2$, —O—(C═O)—$NHNH_2$, —(C═S)—$NH_2$, —(C═S)—N(R*)$_2$, —N(R*)—CHO, —N(R*)—(C═O)—R*, —SCN, —NCS, —NSO, —SSR*, —$SO_2$R*, —$SO_2$—N(R*)$_2$, —S(═O)—OR*, —S(═O)—R*, —Si(R*)$_3$, —$CF_3$, —O—$CF_3$ and combinations thereof; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII)

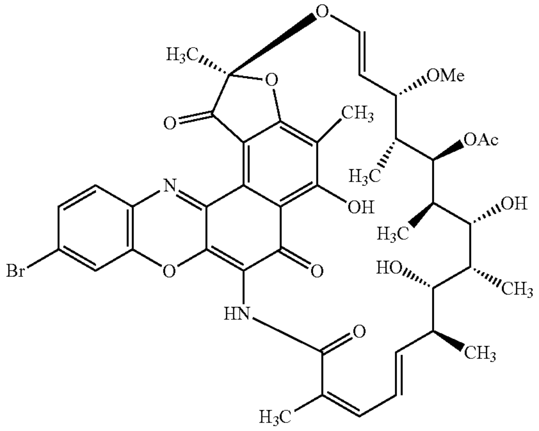

with an alcohol having the structure $R_{cy}$-A-OH.

In one aspect, the present disclosure provides a method of manufacturing a compound having the structure of formula (XIII'):

(XIII')

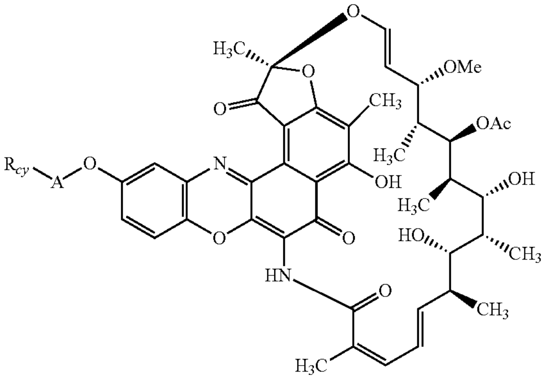

wherein A is selected from a bond (A is absent) or an aliphatic $C_1$-$C_{20}$ hydrocarbon;

$R_{cy}$ is a $C_3$-$C_{14}$ cycloaliphatic hydrocarbon which further comprises 0-8 heteroatoms selected from halogen, O, N, and S and combinations thereof and wherein $R_{cy}$ is optionally substituted with one or more of —F, —Cl, —Br, —I, —OH, —OR*, —NO, —$NO_2$, —$NO_3$, —O—NO, —$N_3$, —$NH_2$, —NHR*, —N(R*)$_2$, —N(R*)$_3^+$, —N(R*)—OH, —O—N(R*)$_2$, —N(R*)—O—R*, —CN, —NC, —(C═O)—R*, —CHO, —$CO_2$H, —$CO_2$R*, —(C═O)—S—R*, —O—(C═O)—H, —O—(C═O)—R*, —S—(C═O)—R*, —(C═O)—$NH_2$, —(C═O)—N(R*)$_2$, —(C═O)—$NHNH_2$, —O—(C═O)—$NHNH_2$, —(C═S)—$NH_2$, —(C═S)—N(R*)$_2$, —N(R*)—CHO, —N(R*)—(C═O)—R*, —SCN, —NCS, —NSO, —SSR*, —$SO_2$R*, —$SO_2$—N(R*)$_2$, —S(═O)—OR*, —S(═O)—R*, —Si(R*)$_3$, —$CF_3$, —O—$CF_3$ and combinations thereof; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII)

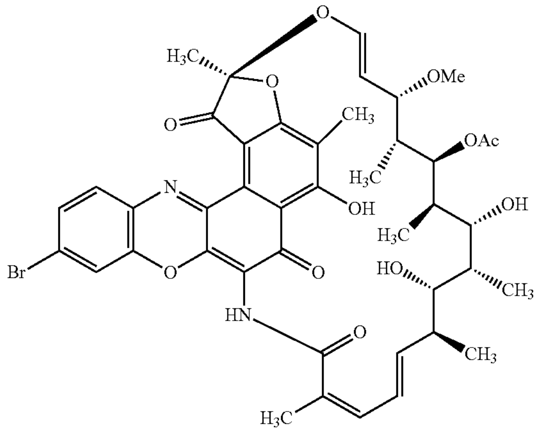

with an alcohol having the structure $R_{cy}$-A-OH.

In one aspect, the present disclosure provides a method of manufacturing a compound having the structure of formula (XIV:

(XIV)

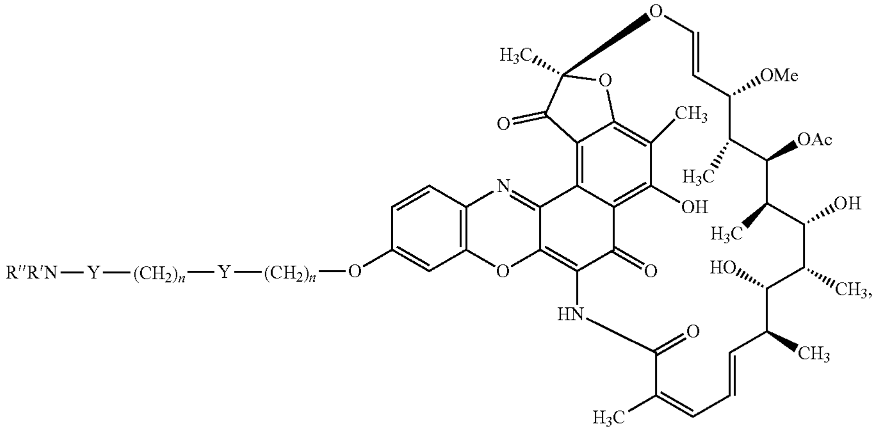

wherein Y is at each occurrence selected from —O— and —NR'R"—; n is independently at each occurrence an integer from 1-6, and R', R", and R'" are each independently selected from a hydrogen, an aliphatic $C_1$-$C_{20}$ hydrocarbon; said method comprising contacting a compound having the structure of formula (XII):

(XII)

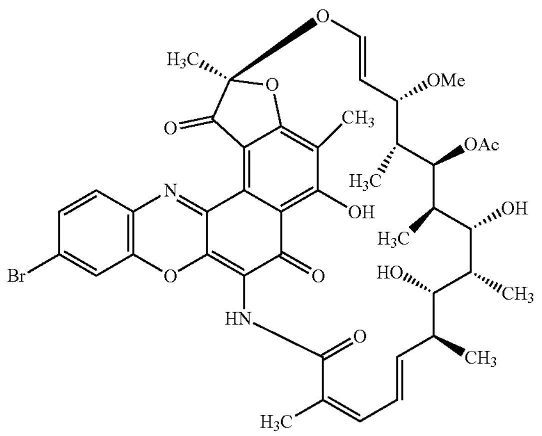

with an alcohol having the structure R"R'N—Y—$(CH_2)_n$—Y—$(CH_2)_n$—OH.

In one aspect, the present disclosure provides a method of manufacturing a compound having the structure of formula (XIV'):

(XIV')

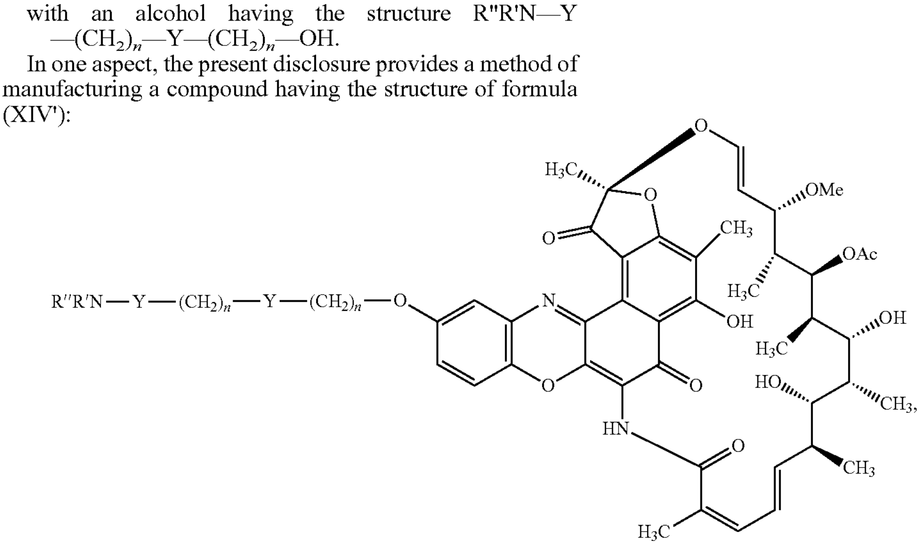

wherein Y is at each occurrence selected from —O— and —NR'R"—; n is independently at each occurrence an integer from 1 to 6, and R', R", and R'" are each independently selected from a hydrogen and an aliphatic $C_1$-$C_{20}$ hydrocarbon; said method comprising contacting a compound having the structure of formula (XII'):

(XII')

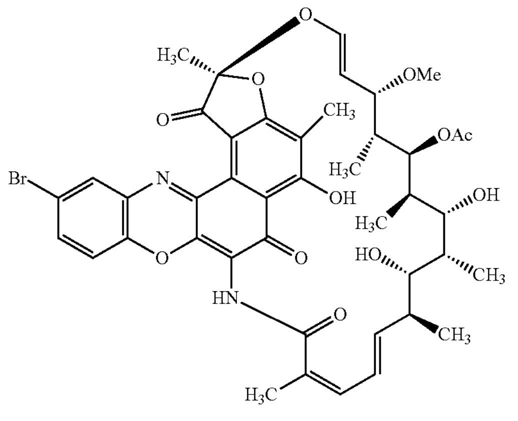

with an alcohol having the structure R"R'N—Y—$(CH_2)_n$—Y—$(CH_2)_n$—OH.

In one embodiment, the compound of formula (XII) is prepared by contacting Rifamycin S with 2-amino-5-bromophenol, and treating the product with an oxidizing agent.

In one embodiment, the compound of formula (XII') is prepared by contacting Rifamycin S with 2-amino-4-bromophenol, and treating the product with an oxidizing agent.

Pharmaceutical Compositions and Dosage Forms

The present disclosure also provides pharmaceutical compositions comprising the compounds described herein. When employed as pharmaceuticals, the compounds of the disclosure can be administered in the form of pharmaceutical compositions which is a combination of the compounds of the disclosure and a pharmaceutically acceptable carrier. These compositions can be prepared in a manner well known in the pharmaceutical art, and can be administered by a variety of routes. Such pharmaceutical compositions can be administered systemically. The term "systemic" as used herein includes parenteral, topical, transdermal, oral, by inhalation/pulmonary, rectal, nasal, buccal, and sublingual administration. The term "parenteral" as used herein includes subcutaneous, intradermal, intravenous, intramuscular, intracranial, and intraperitoneal administration. In some embodiments, the compounds are administered orally, topically, intranasally, intravenously, intramuscularly, or subcutaneously in therapeutically effective amounts to treat bacterial infections (e.g., *S. aureus* infections).

Pharmaceutical compositions containing the compounds of the disclosure can be prepared in combination with one or more pharmaceutically acceptable carriers. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In some embodiments, the pharmaceutical composition of the disclosure is in liquid form. Liquid forms include, by way of non-limiting example, emulsions, solutions, suspensions, syrups, slurries, dispersions, colloids and the like. In some embodiments, a pharmaceutical composition described herein is in liquid, semi-solid or solid (e.g., powder) form. In specific embodiments, a pharmaceutical composition described herein is in semi-solid form, e.g., a gel, a gel matrix, a cream, a paste, or the like. In some embodiments, semi-solid forms comprise a liquid vehicle. In some embodiments, the pharmaceutical composition of the disclosure is a solid dosage form, such a tablet, a granule, a sachet, or a powder. Also provided are pharmaceutical compositions comprising a compound of the disclosure or a pharmaceutically acceptable salt thereof in the form of a dissolving tablet, a dissolving wafer, a capsule, or a gel capsule. In certain embodiments, solid dosage forms described herein comprise a solid vehicle (e.g., as used in a tablet), and/or a gaseous vehicle (e.g., as used in DPI).

In some embodiments, a composition is in a unit dose formulation for oral, intranasal, intravenous, or other administration to a patient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, a composition or unit dosage form described herein is administered as an emulsion, a solution, a suspension, a syrup, a slurry, a dispersion, a colloid, a dissolving tablet, a dissolving wafer, a capsule, a gel capsule, a semi-solid, a solid forma gel, a gel matrix, a cream, a paste, a tablet, a granule, a sachet, a powder, or the like. In certain aspects, about 0.000001 mg to about 2000 mg, about 0.00001 mg to about 1000 mg, or about 0.0001 mg to about 750 mg, about 0.001 mg to about 500 mg, about 0.01 mg to about 250 mg, about 0.1 mg to about 100 mg, about 0.5 mg to about 75 mg, about 1 mg to about 50 mg, about 2 mg to about 40 mg, about 5 mg to about 20 mg, or about 7.5 mg to about 15 mg of compound of formula (I), or a compound having a structure according to any embodiment of formulas (A), (B), (I), (I'), (II), (II'), (III), (III'), (IV), (IV'), (V), (V') as provided herein, per day or per dose is administered to an individual.

In some embodiments, the compound of the disclosure is present in a composition or a unit dose of a composition described herein in an amount of from about 0.01 mg to about 10 mg (e.g., about 0.1-10 mg, about 0.25-5 mg, about 0.25-2.5 mg, about 1-2 mg or about 2-3 mg, about 0.5 mg to about 2 mg, about 1 to about 2 mg, about 1 mg, or about 2 mg). In some embodiments, the amount of compound administered daily or in a unit dose is between about 0.5 mg and about 3 mg, between about 0.5 mg and about 4 mg, or between about 0.35 mg and about 4 mg. In other embodiments, the amount of the compound present in a unit dose or administered daily is between about 1 and about 3 mg, or between about 1 and about 2 mg, or between about 2 and about 3 mg.

In certain aspects, about 0.05 mg to about 50 mg, about 0.25 mg to about 20 mg, about 0.25 mg to about 15 mg, about 0.25 mg to about 10 mg, or about 0.25 mg to about 5 mg (e.g., about 0.1 to about 5 mg, about 0.25 to about 2.5 mg, about 0.3 mg to about 2 mg, about 0.5 mg to about 1 mg, about 0.7 mg to about 1.5 mg, about 0.375 mg, about 0.75 mg, about 1 mg, about 1.25 mg, about 1.5 mg or about 2 mg) of the compound per day or per dose is administered to a patient.

In some embodiments, the compound is present in a unit dose in an amount of between about 5 mg and about 500 mg. In some embodiments, the amount of the compound administered daily or in a unit dose is between about 5 mg and about 300 mg. In other embodiments, the amount of the compound present in a unit dose or administered daily is between about 5 and about 250 mg, or between about 5 and about 200 mg, between about 5 mg and about 150 mg, between about 5 mg and about 100 mg, or between about 5 and about 50 mg.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid pre-formulation composition containing a homogeneous mixture of the compound of Formula I. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.000001 to about 2000 mg of the active ingredient of the present application.

The tablets or pills containing the compound of Formula I can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present application can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9. It will be understood that use of certain of the foregoing excipients, carriers, or stabilizers will result in the formation of pharmaceutical salts.

The therapeutic dosage of the compounds of the disclosure can vary according to, for example, the particular use for which the treatment is made, the manner of administration of the compound, the health and condition of the patient, and the judgment of the prescribing physician. The proportion or concentration of the compounds of the disclosure in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The present application also includes pharmaceutical kits useful, for example, in the treatment of bacterial infections (e.g., *S. aureus* infections), which include one or more containers containing a pharmaceutical composition comprising a therapeutically effective amount of the compounds of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Delivery devices are important not only for delivering the compounds of the disclosure, but also for providing an appropriate environment for storage. This would include protection from microbial contamination and chemical degradation. The device and formulation should be compatible so as to avoid potential leaching or adsorption. The delivery device (or its packaging) can be optionally provided with a label and/or with instructions for use indicating that the composition should be used intranasally.

Methods of Use

In another aspect, the present disclosure provides a method of preventing or inhibiting growth of a bacterium comprising administering an effective amount of a compound having the structure of formula (A):

(A)

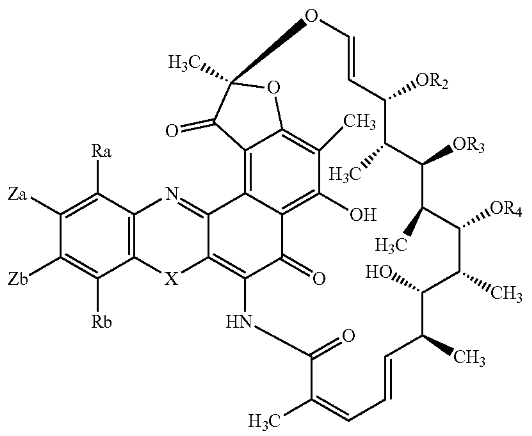

or a pharmaceutically acceptable salt thereof, wherein:

X is selected from —O—, —S— and —NR*—;

Za and Zb are independently selected from a hydrogen, —Cl, —Br, —$OR_1$ and —$R_N$; with the proviso that at least one of Za or Zb is not a hydrogen; wherein:

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—N$(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and $R_a$ is hydrogen, $R_1$ is not hydrogen;

$R_N$ is selected from:

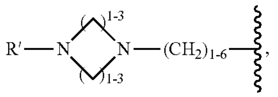
,

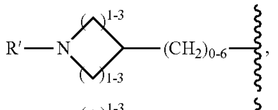
,

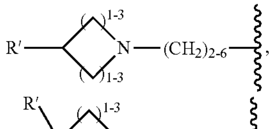
,
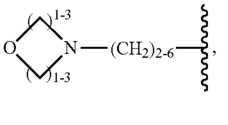
,

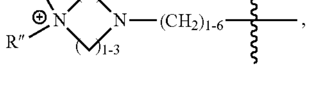
,

-continued

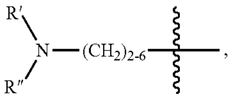
,

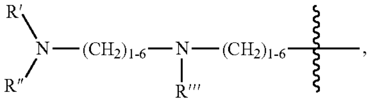
,

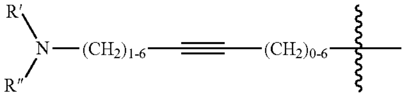
and

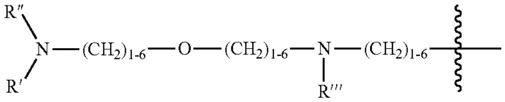

wherein the ~~~~ symbol represents the point of attachment; and R', R" and R'" are selected from a hydrogen, a $C_1$-$C_6$ aliphatic hydrocarbon, and a protecting group, for example, $F_{MOC}$ and $B_{OC}$, or wherein R' and R" together form an aliphatic cyclic structure, such as an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, —$NH_2$, —NHR*, —$N(R^*)_2$, —$N(R^*)_3$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of preventing or inhibiting growth of a bacterium comprising administering an effective amount of a compound having the structure of formula (I):

(I)

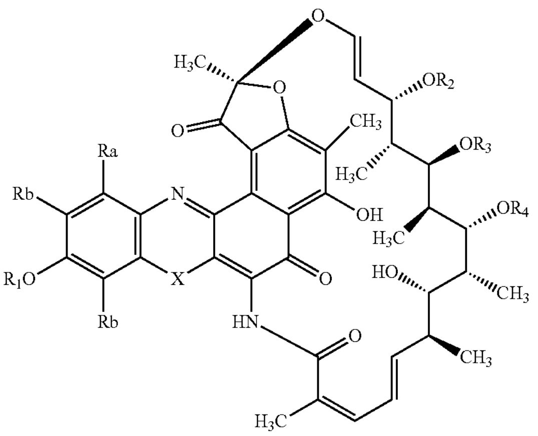

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—N$(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and $R_a$ is hydrogen, $R_1$ is not hydrogen;

$R_N$ is selected from:

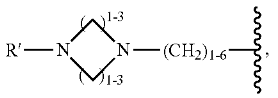
,
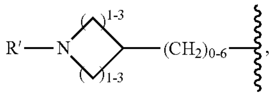
,
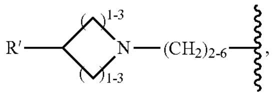
,
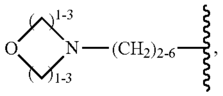
,
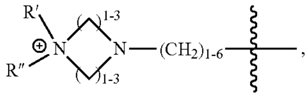
,
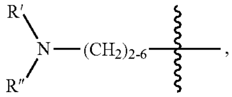
, -continued

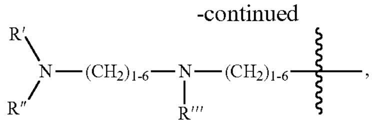
,

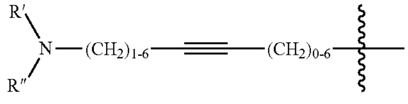
and

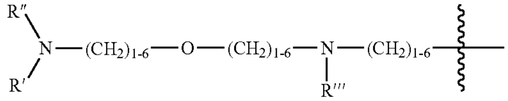

wherein the ~ symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —$N(R^*)_2$, —$N(R^*)_3$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of preventing or inhibiting growth of a bacterium comprising administering an effective amount of a compound having the structure of formula (I'):

(I')

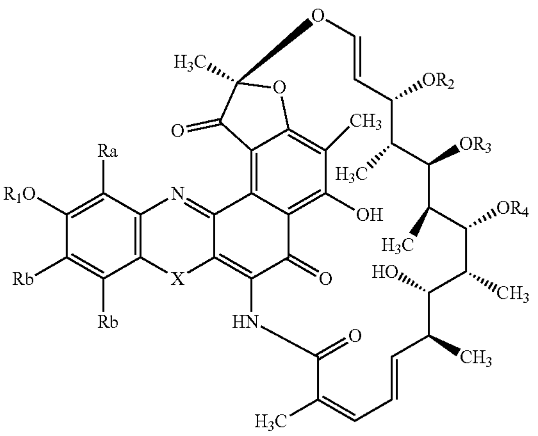

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —N(R*)$_2$, —N(R*)$_3$$^+$, —N(R*)—OH, —O—N(R*)$_2$, —N(R*)—O—R*, —CN, —NC, —(C═O)—R*, —CHO, —$CO_2$H, —$CO_2$R*, —(C═O)—S—R*, —O—(C═O)—H, —O—(C═O)—R*, —S—(C═O)—R*, —(C═O)—$NH_2$, —(C═O)—N(R*)$_2$, —(C═O)—$NHNH_2$, —O—(C═O)—$NHNH_2$, —(C═S)—$NH_2$, —(C═S)—N(R*)$_2$, —N(R*)—CHO, —N(R*)—(C═O)—R*, —SCN, —NCS, —NSO, —SSR*, —$SO_2$R*, —$SO_2$—N(R*)$_2$, —S(═O)—OR*, —S(═O)—R*, —Si(R*)$_3$, —$CF_3$, —O—$CF_3$ and combinations thereof, with the provisos that $R_1$ is not an n-butyl group, and when X is —O— and $R_a$ is hydrogen, $R_1$ is not hydrogen;

$R_N$ is selected from:

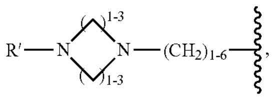

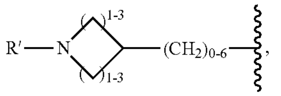

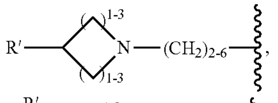

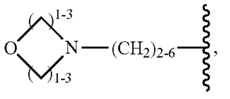

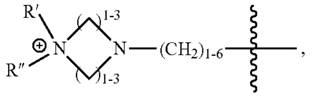

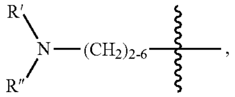

-continued

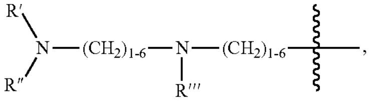

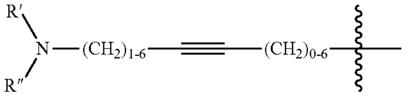

and

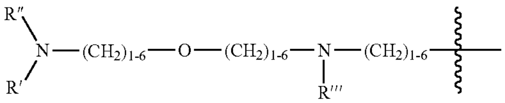

wherein the symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —N(R*)$_2$, —N(R*)$_3$, —(C═O)—R*, —CHO, —$CO_2$H, —$CO_2$R*, —SR*, —$SO_2$R*, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2$H, —$CO_2$R* and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of preventing or inhibiting growth of a bacterium comprising administering an effective amount of a compound having the structure of formula (B):

(B)

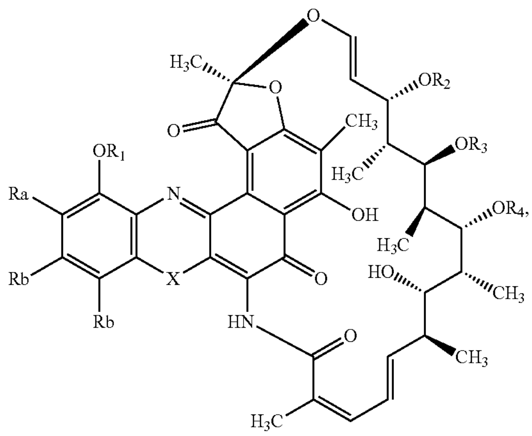

or a pharmaceutically acceptable salt thereof, wherein:

X is selected from —O— and —NR*—;

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —SO2R*, —SO2-$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and $R_a$ is hydrogen, $R_1$ is not hydrogen;

$R_N$ is selected from:

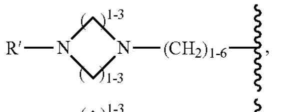

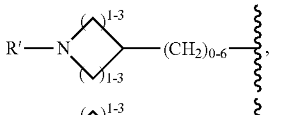

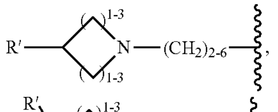

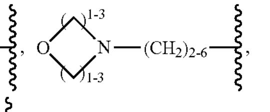

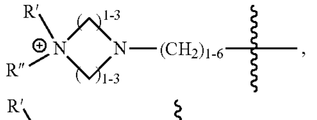

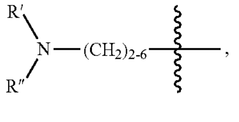

-continued

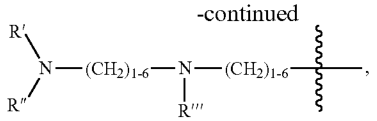

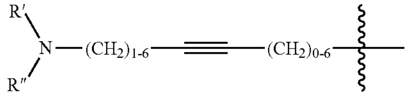

and

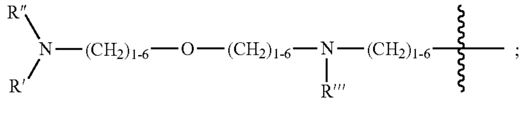

wherein the ～ symbol represents the point of attachment; and R', R" and R"' are selected from a hydrogen, a $C_1$-$C_6$ aliphatic hydrocarbon, and a protecting group selected from Fluorenylmethyloxycarbonyl ($F_{MOC}$) and tert-Butyloxycarbonyl ($B_{OC}$), or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, —$NH_2$, —NHR*, —$N(R^*)_2$, —$N(R^*)_3$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of preventing or inhibiting growth of a bacterium comprising administering an effective amount of a rifamycin analog compound having a structure according to any one of formulas (IA), (II), (II'), (III), (III'), (IV), (IV'), (V), (V'), (B-1), and (B-2) as provided herein. In one embodiment, the bacterium is a Gram-positive bacterium.

In one embodiment, the bacterium is a penicillin-resistant bacterium.

In one embodiment, the bacterium is *Staphylococcus aureus.*

In one embodiment, the bacterium is a resistant *Staphylococcus aureus* strain selected from MRSA and VRSA.

In one embodiment, the bacterium is methicillin-resistant *Staphylococcus aureus* (MRSA).

In one embodiment, the bacterium is vancomycin-resistant *Staphylococcus aureus* (VRSA).

In one embodiment, the bacterium is methicillin-susceptible *Staphylococcus aureus* (MSSA).

In yet another aspect, the present disclosure provides a method of treating a bacterial infection in a subject in need of such treatment, comprising administering to the subject an effective amount of a compound having the structure of formula (A):

(A)

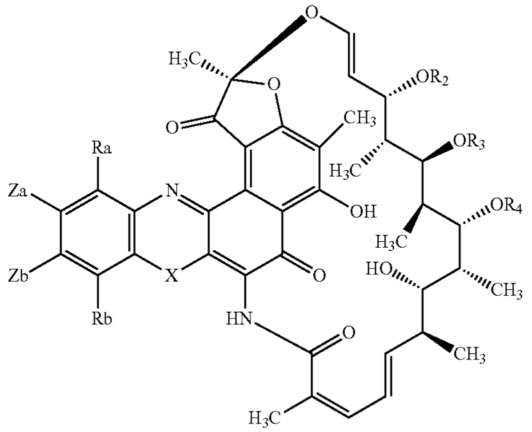

or a pharmaceutically acceptable salt thereof, wherein:

X is selected from —O—, —S— and —NR*—;

Za and Zb are independently selected from a hydrogen, —Cl, —Br, —$OR_1$ and —$R_N$; with the proviso that at least one of Za or Zb is not a hydrogen; wherein:

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—N$(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and $R_a$ is hydrogen, $R_1$ is not hydrogen;

$R_N$ is selected from:

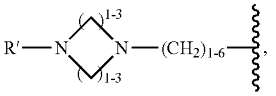

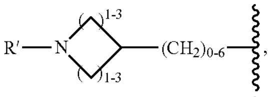

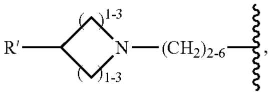

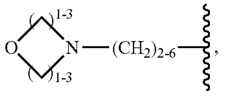

-continued

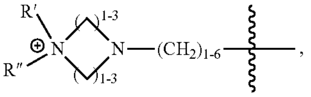

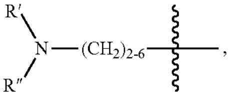

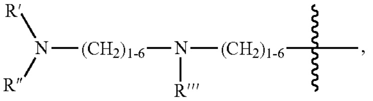

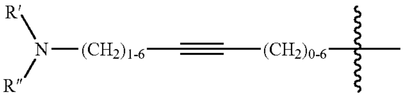

and

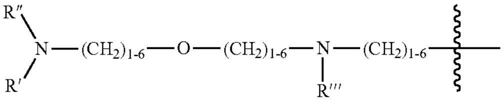

wherein the ⌇ symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, —$NH_2$, —NHR*, —$N(R^*)_2$, —$N(R^*)_3$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of treating a bacterial infection in a subject in need of such treatment, comprising administering an effective amount of a compound having the structure of formula (I):

(I)

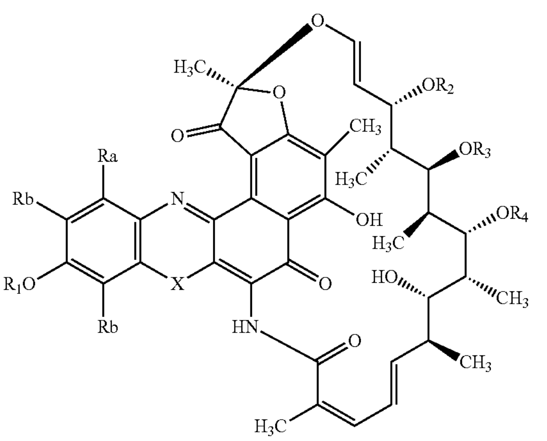

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—N$(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and $R_a$ is hydrogen, $R_1$ is not hydrogen;

$R_N$ is selected from:

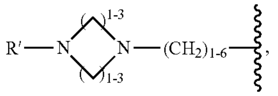
,

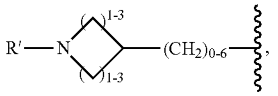
,

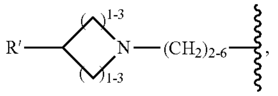
,
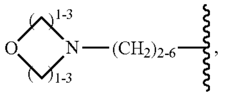
,

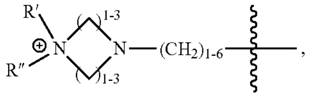
,

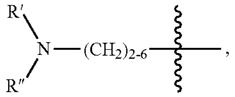
,

-continued

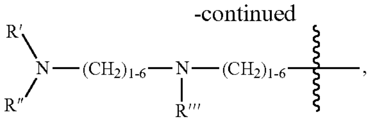
,

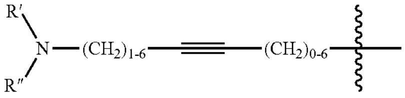
and

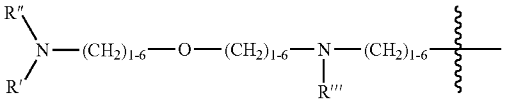

wherein the symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —$N(R^*)_2$, —$N(R^*)_3$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of treating a bacterial infection in a subject in need of such treatment, comprising administering an effective amount of a compound having the structure of formula (I'):

(I')

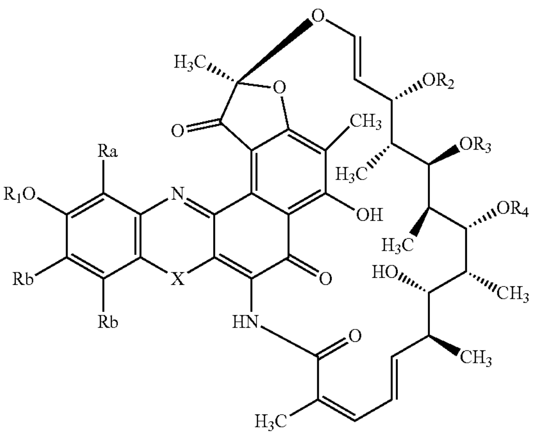

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—N$(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and $R_a$ is hydrogen, $R_1$ is not hydrogen;

$R_N$ is selected from:

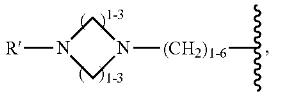
,
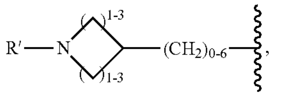
,
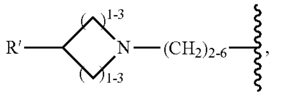
,
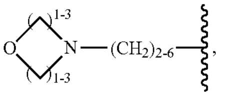
,
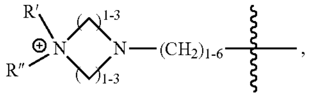
,
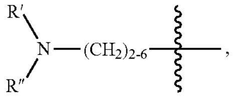
, -continued

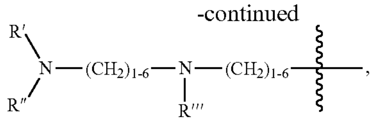
,

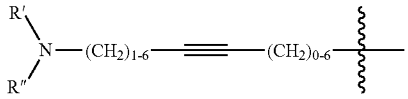
and

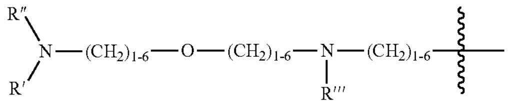

wherein the  symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In yet another aspect, the present disclosure provides a method of treating a bacterial infection in a subject in need of such treatment, comprising administering to the subject an effective amount of a compound having the structure of formula (B):

(B)

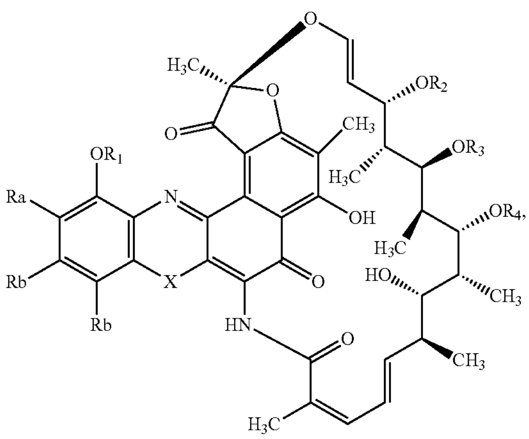

or a pharmaceutically acceptable salt thereof, wherein:

X is selected from —O— and —NR*—;

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —N(R*)$_2$, —N(R*)$_3^+$, —N(R*)—OH, —O—N(R*)$_2$, —N(R*)—O—R*, —CN, —NC, —(C═O)—R*, —CHO, —$CO_2$H, —$CO_2$R*, —(C═O)—S—R*, —O—(C═O)—H, —O—(C═O)—R*, —S—(C═O)—R*, —(C═O)—$NH_2$, —(C═O)—N(R*)$_2$, —(C═O)—$NHNH_2$, —O—(C═O)—$NHNH_2$, —(C═S)—$NH_2$, —(C═S)—N(R*)$_2$, —N(R*)—CHO, —N(R*)—(C═O)—R*, —SCN, —NCS, —NSO, —SSR*, —$SO_2$R*, —$SO_2$—N(R*)$_2$, —S(═O)—OR*, —S(═O)—R*, —Si(R*)$_3$, —$CF_3$, —O—$CF_3$ and combinations thereof, with the provisos that $R_1$ is not an n-butyl group, and when X is —O— and $R_a$ is hydrogen, $R_1$ is not hydrogen;

$R_N$ is selected from:

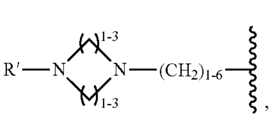
,
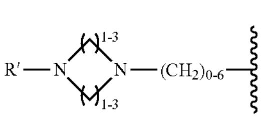
,
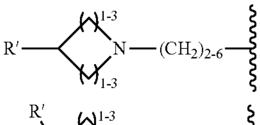
,
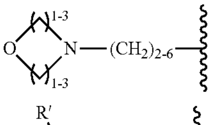
,
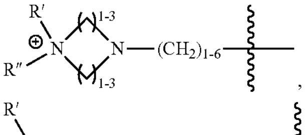
,
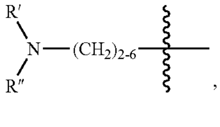
,
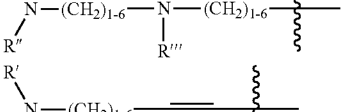
,
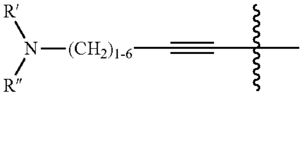
and -continued

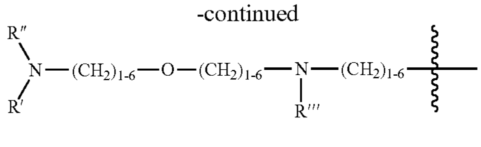
;

wherein the ~~~ symbol represents the point of attachment; and R', R" and R'" are selected from a hydrogen, a $C_1$-$C_6$ aliphatic hydrocarbon, and a protecting group selected from Fluorenylmethyloxycarbonyl (FMOC) and tert-Butyloxycarbonyl (BOC), or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, —$NH_2$, —NHR*, —N(R*)$_2$, —N(R*)$_3$, —(C═O)—R*, —CHO, —$CO_2$H, —$CO_2$R*, —SR*, —$SO_2$R*, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2$H, —$CO_2$R* and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of treating a bacterial infection in a subject in need of such treatment, comprising administering an effective amount of a rifamycin analog compound having a structure according to any one of formulas (IA) (II), (II'), (III), (III'), (IV), (IV'), (V), (V'), (B-1), and (B-2) as provided herein. In one embodiment, the bacterial infection is a Gram-positive bacterial infection.

In one embodiment, the bacterial infection is a penicillin-resistant bacterial infection.

In one embodiment, the bacterial infection is a *Staphylococcus aureus* infection.

In one embodiment, the bacterial infection is an intracellular bacterial infection.

In one embodiment, the subject is human.

In one embodiment, the method further comprises administering a second therapeutic agent.

In one embodiment, the second therapeutic agent is a second antibiotic.

In one embodiment, the second antibiotic is effective against *Staphylococcus aureus.*

In one embodiment, the second antibiotic is selected from an aminoglycoside, a beta-lactam, a macrolide, a cyclic peptide, a tetracycline, a fluoroquinoline, a fluoroquinolone, and an oxazolidinone.

In one embodiment, the second antibiotic is selected from clindamycin, novobiocin, retapamulin, daptomycin, sitafloxacin, teicoplanin, triclosan, napthyridone, radezolid, doxorubicin, ampicillin, vancomycin, imipenem, doripenem, gemcitabine, dalbavancin, and azithromycin.

In one embodiment, the compound is administered to the subject orally, topically, intranasally, intravenously, intramuscularly, or subcutaneously.

In another aspect, the present disclosure provides a method of preventing or inhibiting growth of a bacterium comprising administering an effective amount of a compound having the structure of formula (I):

(I)

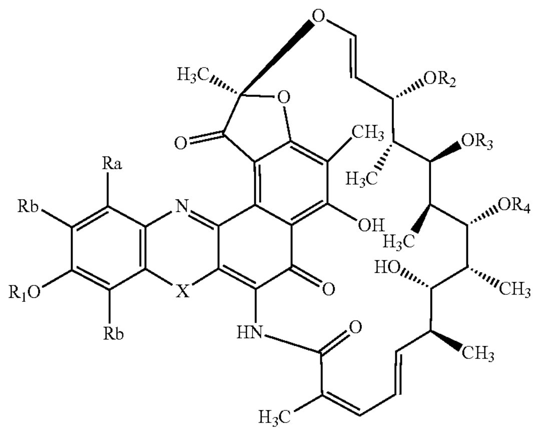

wherein:

X is selected from —O—, —S—, and —NR*—;

$R_1$ is selected from a hydrogen; an aliphatic $C_1$-$C_{20}$ hydrocarbon; an aromatic $C_5$-$C_{20}$ hydrocarbon; a heteroaromatic $C_1$-$C_{20}$ hydrocarbon; a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F; —Cl; —Br; —I; —OH; —OR*; —NO; —$NO_2$; —$NO_3$; —O—NO; —$N_3$; —$NH_2$; —NHR*; —$N(R^*)_2$; —$N(R^*)_3^+$; —N(R*)—OH; —O—$N(R^*)_2$; —N(R*)—O—R*; —CN; —NC; —(C═O)—R*; —CHO; —$CO_2H$; —$CO_2R^*$; —(C═O)—S—R*; —O—(C═O)—H; —O—(C═O)—R*; —S—(C═O)—R*; —(C═O)—$NH_2$; —(C═O)—$N(R^*)_2$; —(C═O)—$NHNH_2$; —O—(C═O)—$NHNH_2$; —(C═S)—$NH_2$; —(C═S)—N$(R^*)_2$; —N(R*)—CHO; —N(R*)—(C═O)—R*; —SCN; —NCS; —NSO; —SSR*; —$SO_2R^*$; —$SO_2$—$N(R^*)_2$; —S(═O)—OR*; —S(═O)—R*; —$Si(R^*)_3$; —$CF_3$; —O—$CF_3$ and combinations thereof, with a proviso that $R_1$ is not an n-butyl group; wherein when X is —O— and $R_a$ is hydrogen, $R_1$ is not hydrogen;

$R_2$, $R_3$, and $R_4$ are independently selected from hydrogen, a straight chained, branched or cyclic aliphatic $C_1$-$C_{20}$ hydrocarbon, or —(C═O)—R*, each of which further comprises 0-8 heteroatoms selected from halogen, O, N, and S;

$R_a$ is selected from hydrogen, F; —Cl; —Br; —I; —OH; OR*; —$NH_2$; —NHR*; —$N(R^*)_2$; —$N(R^*)_3^+$; —(C═O)—R*; —CHO; —$CO_2H$; —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F; —Cl; —Br; —I; —OH; —OR*;

$R_b$ is a hydrogen atom at each occurrence, and

R* is independently at each occurrence selected from hydrogen; an aliphatic $C_1$-$C_{20}$ hydrocarbon; an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, or a pharmaceutically acceptable salt thereof.

In yet another aspect, the present disclosure provides a method of treating a bacterial infection in a subject in need of such treatment, comprising administering to the subject an effective amount of a compound having the structure of Formula (I'):

(I')

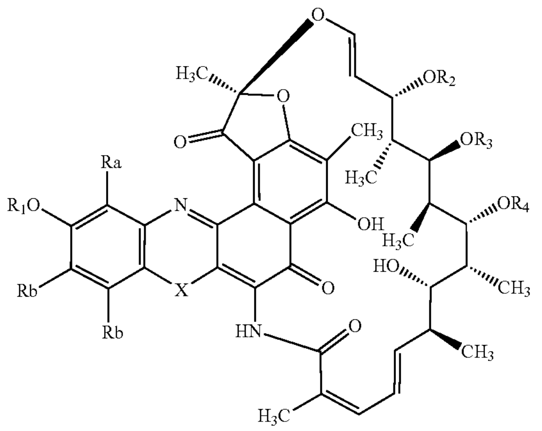

wherein:

X is selected from —O—, —S—, and —NR*—;

$R_1$ is selected from a hydrogen; an aliphatic $C_1$-$C_{20}$ hydrocarbon; an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F; —$C_1$; —Br; —I; —OH, —OR*; —NO; —$NO_2$; —$NO_3$; —O—NO; —$N_3$; —$NH_2$; —NHR*; —$N(R^*)_2$; —$N(R^*)_3^+$; —N(R*)—OH; —O—$N(R^*)_2$; —N(R*)—O—R*; —CN; —NC; —(C═O)—R*; —CHO; —$CO_2H$; —$CO_2R^*$; —(C═O)—S—R*; —O—(C═O)—H; —O—(C═O)—R*; —S—(C═O)—R*; —(C═O)—$NH_2$; —(C═O)—$N(R^*)_2$; —(C═O)—$NHNH_2$; —O—(C═O)—$NHNH_2$; —(C═S)—$NH_2$; —(C═S)—N$(R^*)_2$; —N(R*)—CHO; —N(R*)—(C═O)—R*; —SCN; —NCS; —NSO; —SSR*; —$SO_2R^*$; —$SO_2$—$N(R^*)_2$; —S(═O)—OR*; —S(═O)—R*; —$Si(R^*)_3$; —$CF_3$; —O—$CF_3$ and combinations thereof, with a proviso that $R_1$ is not an n-butyl group;

wherein when X is —O— and $R_a$ is hydrogen, $R_1$ is not hydrogen;

$R_2$, $R_3$, and $R_4$ are independently selected from hydrogen, a straight chained, branched or cyclic aliphatic $C_1$-$C_{20}$ hydrocarbon, or —(C═O)—R*, each of which further comprises 0-8 heteroatoms selected from halogen, O, N, and S;

$R_a$ is selected from hydrogen, F; —Cl; —Br; —I; —OH; OR*; —$NH_2$; —NHR*; —N$(R^*)_2$; —N$(R^*)_3^+$; —(C═O)—R*; —CHO; —$CO_2$H; —$CO_2$R*, —SR*, —$SO_2$R*, and an aliphatic $C_1$-$C_{20}$ hydrocarbon, which further comprises 0-8 heteroatoms selected from halogen, O, N, and S, and wherein $R_a$ is optionally substituted with one or more of —F; —Cl; —Br; —I; —OH, —OR*;

$R_b$ is a hydrogen atom at each occurrence, and

R* is independently at each occurrence selected from hydrogen; an aliphatic $C_1$-$C_{20}$ hydrocarbon; an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, or a pharmaceutically acceptable salt thereof.

In one aspect, the present disclosure provides a method of preventing or inhibiting growth of a bacterium comprising administering an effective amount of a rifamycin analog compound of the present disclosure, or a pharmaceutical composition comprising a rifamycin analog compound of the present disclosure, or a pharmaceutical dosage form comprising a rifamycin analog compound of the present disclosure.

In another aspect, the present disclosure provides a method of treating a bacterial infection in a subject in need of such treatment comprising administering to said subject an effective amount of a rifamycin analog compound of the present disclosure, or a pharmaceutical composition comprising a rifamycin analog compound of the present disclosure, or a pharmaceutical dosage form comprising a rifamycin analog compound of the present disclosure.

In one embodiment, the compound, the composition, or the dosage form is administered to the subject orally, topically, intranasally, intravenously, intramuscularly, or subcutaneously.

Anti-MSR1 Antibodies Suitable for ADCs

The antibody-drug conjugates described herein may comprise anti-MSR1 antibodies which are full-length (for example, an IgG1 or IgG4 antibody), or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

Embodiments of antibody-drug conjugates described herein may comprise anti-MSR1 antibodies listed in Tables 9 and 10. Table 9 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-MSR1 antibodies. Table 10 sets forth the nucleic acid sequence identifiers of the HCVRs, LCVRs, HCDR1, HCDR2 HCDR3, LCDR1, LCDR2 and LCDR3 of the exemplary anti-MSR1 antibodies.

Suitable antibodies or antigen-binding fragments thereof for the antibody-drug conjugates described herein include those that specifically bind MSR1 and comprise an HCVR comprising an amino acid sequence selected from any of the HCVR amino acid sequences listed in Table 9, or a substantially similar sequence thereof having at least 90%, at least 95%, at least 98% or at least 99% sequence identity thereto.

Further suitable antibodies or antigen-binding fragments thereof that specifically bind MSR1 comprise an LCVR comprising an amino acid sequence selected from any of the LCVR amino acid sequences listed in Table 9, or a substantially similar sequence thereof having at least 90%, at least 95%, at least 98% or at least 99% sequence identity thereto.

Further suitable antibodies or antigen-binding fragments thereof that specifically bind MSR1 comprise an HCVR and an LCVR amino acid sequence pair (HCVR/LCVR) comprising any of the HCVR amino acid sequences listed in Table 9 paired with any of the LCVR amino acid sequences listed in Table 9. Certain embodiments relate to antibody-drug conjugates comprising antibodies, or antigen-binding fragments thereof, comprising an HCVR/LCVR amino acid sequence pair contained within any of the exemplary anti-MSR1 antibodies listed in Table 9. In some embodiments, the HCVR/LCVR amino acid sequence pair is selected from the group consisting of: 2/10, 23/42, 50/58; 90/98, and 282/290.

Suitable antibodies or antigen-binding fragments thereof for the antibody-drug conjugates described herein include those that specifically bind MSR1 and comprise a heavy chain CDR1 (HCDR1) comprising an amino acid sequence selected from any of the HCDR1 amino acid sequences listed in Table 9 or a substantially similar sequence thereof having at least 90%, at least 95%, at least 98% or at least 99% sequence identity.

Further suitable antibodies or antigen-binding fragments thereof that specifically bind MSR1 comprise a heavy chain CDR2 (HCDR2) comprising an amino acid sequence selected from any of the HCDR2 amino acid sequences listed in Table 9 or a substantially similar sequence thereof having at least 90%, at least 95%, at least 98% or at least 99% sequence identity.

Further suitable antibodies or antigen-binding fragments thereof that specifically bind MSR1 comprise a heavy chain CDR3 (HCDR3) comprising an amino acid sequence selected from any of the HCDR3 amino acid sequences listed in Table 9 or a substantially similar sequence thereof having at least 90%, at least 95%, at least 98% or at least 99% sequence identity.

Suitable antibodies or antigen-binding fragments thereof for the antibody-drug conjugates described herein include those that specifically bind MSR1 and comprise a light chain CDR1 (LCDR1) comprising an amino acid sequence selected from any of the LCDR1 amino acid sequences listed in Table 9 or a substantially similar sequence thereof having at least 90%, at least 95%, at least 98% or at least 99% sequence identity.

Further suitable antibodies or antigen-binding fragments thereof that specifically bind MSR1 comprise a light chain CDR2 (LCDR2) comprising an amino acid sequence selected from any of the LCDR2 amino acid sequences listed in Table 9 or a substantially similar sequence thereof having at least 90%, at least 95%, at least 98% or at least 99% sequence identity.

Further suitable antibodies or antigen-binding fragments thereof that specifically bind MSR1 comprise a light chain CDR3 (LCDR3) comprising an amino acid sequence selected from any of the LCDR3 amino acid sequences listed in Table 9 or a substantially similar sequence thereof having at least 90%, at least 95%, at least 98% or at least 99% sequence identity.

Further suitable antibodies or antigen-binding fragments thereof that specifically bind MSR1 comprise an HCDR3 and an LCDR3 amino acid sequence pair (HCDR3/LCDR3) comprising any of the HCDR3 amino acid sequences listed in Table 9 paired with any of the LCDR3 amino acid sequences listed in Table 9. Certain embodiments relate to antibodies, or antigen-binding fragments thereof, comprising an HCDR3/LCDR3 amino acid sequence pair contained within any of the exemplary anti-MSR1 antibodies listed in Table 9. In some embodiments, the HCDR3/LCDR3 amino acid sequence pair is selected from the group consisting of: 8/16, 40/48, 56/64; 96/104, and 288/296.

Suitable antibodies or antigen-binding fragments thereof for the antibody-drug conjugates described herein include those that specifically bind MSR1 and comprise a set of six CDRs (i.e., HCDR1-HCDR2-HCDR3-LCDR1-LCDR2-LCDR3) contained within any of the exemplary anti-MSR1 antibodies listed in Table 9. In certain embodiments, the HCDR1-HCDR2-HCDR3-LCDR1-LCDR2-LCDR3 amino acid sequences set is selected from the group consisting of: 4-6-8-12-14-16; 36-38-40-44-46-48; 52-54-56-60-62-64; 92-94-96-100-102-104, and 284-286-288-292-294-296.

In a related embodiment, suitable antibodies, or antigen-binding fragments thereof that specifically bind MSR1 comprise a set of six CDRs (i.e., HCDR1-HCDR2-HCDR3-LCDR1-LCDR2-LCDR3) contained within an HCVR/LCVR amino acid sequence pair as defined by any of the exemplary anti-MSR1 antibodies listed in Table 9. For example, the present disclosure includes suitable antibodies or antigen-binding fragments thereof that specifically bind MSR1 and comprise the HCDR1-HCDR2-HCDR3-LCDR1-LCDR2-LCDR3 amino acid sequences set contained within an HCVR/LCVR amino acid sequence pair selected from the group consisting of: 2/10, 23/42, 50/58, 90/98, and 282/290. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Also provided herein are nucleic acid molecules encoding anti-MSR1 antibodies or portions thereof for the preparation of antibody-drug conjugates described herein. For example, provided herein are nucleic acid molecules encoding any of the HCVR amino acid sequences listed in Table 9; in certain embodiments the nucleic acid molecule may comprise a polynucleotide sequence selected from any of the HCVR nucleic acid sequences listed in Table 10, or a substantially similar sequence thereof having at least 90%, at least 95%, at least 98% or at least 99% sequence identity thereto.

Also provided herein are nucleic acid molecules encoding any of the LCVR amino acid sequences listed in Table 9; in certain embodiments the nucleic acid molecule may comprise a polynucleotide sequence selected from any of the LCVR nucleic acid sequences listed in Table 10, or a substantially similar sequence thereof having at least 90%, at least 95%, at least 98% or at least 99% sequence identity thereto.

Also provided herein are nucleic acid molecules encoding any of the HCDR1 amino acid sequences listed in Table 9; in certain embodiments the nucleic acid molecule may comprise a polynucleotide sequence selected from any of the HCDR1 nucleic acid sequences listed in Table 10, or a substantially similar sequence thereof having at least 90%, at least 95%, at least 98% or at least 99% sequence identity thereto.

Also provided herein are nucleic acid molecules encoding any of the HCDR2 amino acid sequences listed in Table 9; in certain embodiments the nucleic acid molecule may comprise a polynucleotide sequence selected from any of the HCDR2 nucleic acid sequences listed in Table 10, or a substantially similar sequence thereof having at least 90%, at least 95%, at least 98% or at least 99% sequence identity thereto.

Also provided herein are nucleic acid molecules encoding any of the HCDR3 amino acid sequences listed in Table 9; in certain embodiments the nucleic acid molecule may comprise a polynucleotide sequence selected from any of the HCDR3 nucleic acid sequences listed in Table 10, or a substantially similar sequence thereof having at least 90%, at least 95%, at least 98% or at least 99% sequence identity thereto.

Also provided herein are nucleic acid molecules encoding any of the LCDR1 amino acid sequences listed in Table 9; in certain embodiments the nucleic acid molecule may comprise a polynucleotide sequence selected from any of the LCDR1 nucleic acid sequences listed in Table 10, or a substantially similar sequence thereof having at least 90%, at least 95%, at least 98% or at least 99% sequence identity thereto.

Also provided herein are nucleic acid molecules encoding any of the LCDR2 amino acid sequences listed in Table 9; in certain embodiments the nucleic acid molecule may comprise a polynucleotide sequence selected from any of the LCDR2 nucleic acid sequences listed in Table 10, or a substantially similar sequence thereof having at least 90%, at least 95%, at least 98% or at least 99% sequence identity thereto.

Also provided herein are nucleic acid molecules encoding any of the LCDR3 amino acid sequences listed in Table 9; in certain embodiments the nucleic acid molecule may comprise a polynucleotide sequence selected from any of the LCDR3 nucleic acid sequences listed in Table 10, or a substantially similar sequence thereof having at least 90%, at least 95%, at least 98% or at least 99% sequence identity thereto.

Also provided herein are nucleic acid molecules encoding an HCVR, wherein the HCVR may comprise a set of three CDRs (i.e., HCDR1-HCDR2-HCDR3), wherein the HCDR1-HCDR2-HCDR3 amino acid sequence set is as defined by any of the exemplary anti-MSR1 antibodies listed in Table 9.

Also provided herein are nucleic acid molecules encoding an LCVR, wherein the LCVR may comprise a set of three CDRs (i.e., LCDR1-LCDR2-LCDR3), wherein the LCDR1-LCDR2-LCDR3 amino acid sequence set is as defined by any of the exemplary anti-MSR1 antibodies listed in Table 9.

Also provided herein are nucleic acid molecules encoding both an HCVR and an LCVR, wherein the HCVR may comprise an amino acid sequence of any of the HCVR amino acid sequences listed in Table 9, and wherein the LCVR may comprise an amino acid sequence of any of the LCVR amino acid sequences listed in Table 9. In certain embodiments, the nucleic acid molecule may comprise a polynucleotide sequence selected from any of the HCVR nucleic acid sequences listed in Table 10, or a substantially similar sequence thereof having at least 90%, at least 95%, at least 98% or at least 99% sequence identity thereto, and a polynucleotide sequence selected from any of the LCVR nucleic acid sequences listed in Table 10, or a substantially similar sequence thereof having at least 90%, at least 95%, at least 98% or at least 99% sequence identity thereto. In certain embodiments according to this aspect of the disclosure, the nucleic acid molecule encodes an HCVR and LCVR, wherein the HCVR and LCVR are both derived from the same anti-MSR1 antibody listed in Table 9.

Also provided herein are recombinant expression vectors capable of expressing a polypeptide comprising a heavy or light chain variable region of an anti-MSR1 antibody for the preparation of antibody-drug conjugates described herein. For example, embodiments include recombinant expression vectors comprising any of the nucleic acid molecules mentioned above, i.e., nucleic acid molecules encoding any of the HCVR, LCVR, and/or CDR sequences as set forth in Table 9. Also included within the scope of the present disclosure are host cells into which such vectors have been introduced, as well as methods of producing the antibodies or portions thereof for the preparation of antibody-drug conjugates described herein by culturing the host cells under conditions permitting production of the antibodies or antibody fragments, and recovering the antibodies and antibody fragments so produced.

Suitable anti-MSR1 antibodies for the antibody-drug conjugates described herein include those that have a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

According to certain embodiments, antibody-drug conjugates according to the disclosure comprise anti-MSR1 antibodies comprising an Fc domain comprising one or more mutations which enhance or diminish antibody binding to the FcRn receptor, e.g., at acidic pH as compared to neutral pH. For example, provided herein are antibody-drug conjugates comprising anti-MSR1 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification may comprise a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, embodiments include antibody-drug conjugates comprising anti-MSR1 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present disclosure.

Biological Characteristics of the Anti-MSR1 Antibodies

Embodiments include antibody-drug conjugates comprising rifamycin analogs and antibodies and antigen-binding fragments thereof that bind human MSR1 with high affinity. For example, the present disclosure includes antibody-drug conjugates comprising anti-MSR1 antibodies that bind human MSR1 extracellular domain expressed with an N-terminal nonahistidine tag (SEQ ID NO: 688) (e.g., His9-hMSR1) with a $K_D$ of less than about 10 nM as measured by surface plasmon resonance at 25° C. or 37° C., e.g., using an assay format as defined in Example 25 herein, or a substantially similar assay. According to certain embodiments, antibody-drug conjugates comprising anti-MSR1 antibodies are provided that bind human MSR1 at 37° C. with a $K_D$ of less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM, as measured by surface plasmon resonance, e.g., using an assay format as defined in Example 25 herein, or a substantially similar assay. In some embodiments, the antibody-drug conjugates comprise anti-MSR1 antibodies disclosed herein which bind human MSR1 at 25° C. with a $K_D$ of less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, or less than about 20 pM, as measured by surface plasmon resonance, e.g., using an assay format as defined in Example 25 herein, or a substantially similar assay.

Embodiments also include antibody-drug conjugates comprising antibodies and antigen-binding fragments thereof that bind monkey MSR1 with high affinity. For example, disclosed herein are antibody-drug conjugates comprising anti-MSR1 antibodies that bind monkey MSR1 extracellular domain expressed with an N-terminal myc-myc-hexahistidine tag ("hexahistidine" disclosed as SEQ ID NO: 689) (e.g., HMM-mfMSR1) with a $K_D$ of less than about 20 nM as measured by surface plasmon resonance at 25° C. or 37° C., e.g., using an assay format as defined in Example 25 herein, or a substantially similar assay. According to certain embodiments, antibody-drug conjugates comprising anti-MSR1 antibodies are provided that bind monkey MSR1 at 37° C. with a $K_D$ of less than about 20 nM, less than about 18 pM, less than about 15 nM, less than about 12 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM, as measured by surface plasmon resonance, e.g., using an assay format as defined in Example 25 herein, or a substantially similar assay. In some embodiments, antibody-drug conjugates comprising the anti-MSR1 antibodies disclosed herein bind monkey MSR1 at 25° C. with a $K_D$ of less than about 12 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, or less than about 20 pM, as measured by surface plasmon resonance, e.g., using an assay format as defined in Example 25 herein, or a substantially similar assay.

The present disclosure also includes antibody-drug conjugates comprising antibodies and antigen-binding fragments thereof that bind human MSR1 extracellular domain expressed with an N-terminal nonahistidine tag (SEQ ID NO: 688) (e.g., His9-hMSR1) with a dissociative half-life (t1/2) of greater than about 5 minutes as measured by surface plasmon resonance at 25° C. or 37° C., e.g., using an assay format as defined in Example 25 herein, or a substantially similar assay. According to certain embodiments, antibody-drug conjugates comprising anti-MSR1 antibodies are provided that bind human MSR1 at 37° C. with a t %2 of greater than about 4 minutes, greater than about 5 minutes, greater than about 6 minutes, greater than about 8 minutes, greater than about 10 minutes, greater than about 12 minutes, greater than about 14 minutes, greater than about 16 minutes, greater than about 18 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 120 minutes, greater than about 150 minutes, greater than about 180 minutes, greater than about 210 minutes, greater than about 240 minutes, or longer, as measured by surface plasmon resonance, e.g., using an assay format as defined in Example 25 herein, or a substantially similar assay.

Embodiments also include antibody-drug conjugates comprising antibodies and antigen-binding fragments thereof that can bind monkey MSR1 extracellular domain expressed with an N-terminal myc-myc-hexahistidine tag ("hexahistidine" disclosed as SEQ ID NO: 689) (e.g. HMM-mfMSR1) with high affinity. For example, the present disclosure includes antibody-drug conjugates comprising anti-MSR1 antibodies that bind HMM-mfMSR1 with a $K_D$ of less than about 20 nM as measured by surface plasmon resonance at 25° C. or 37° C., e.g., using an assay format as defined in Example 25 herein, or a substantially similar assay. According to certain embodiments, antibody-drug conjugates comprising anti-MSR1 antibodies are provided that bind HMM-mfMSR1 at 37° C. with a $K_D$ of less than about 20 nM, less than about 15 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 800 pM, less than about 700 pM, less than about 600 pM, less than about 500 pM, less than about 400 pM, less than about 300 pM, less than about 200 pM, less than about 150 pM, less than about 100 pM, less than about 90 pM, less than about 80 pM, less than about 70 pM, less than about 60 pM, or less than about 50 pM, as measured by surface plasmon resonance, e.g., using an assay format as defined in Example 25 herein, or a substantially similar assay. In some embodiments, the anti-MSR1 antibodies disclosed herein bind HMM-mfMSR1 at 25° C. with a $K_D$ of less than about 12 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 800 pM, less than about 700 pM, less than about 600 pM, less than about 500 pM, less than about 400 pM, less than about 300 pM, less than about 200 pM, less than about 150 pM, less than about 100 pM, less than about 90 pM, less than about 80 pM, less than about 70 pM, less than about 60 pM, or less than about 50 pM, as measured by surface plasmon resonance, e.g., using an assay format as defined in Example 25 herein, or a substantially similar assay.

Embodiments also include antibody-drug conjugates comprising antibodies and antigen-binding fragments thereof that bind monkey MSR1 extracellular domain expressed with an N-terminal myc-myc-hexahistidine tag ("hexahistidine" disclosed as SEQ ID NO: 689) (e.g. HMM-mfMSR1) with a dissociative half-life (t½) of greater than about 55 minutes as measured by surface plasmon resonance at 25° C. or 37° C., e.g., using an assay format as defined in Example 25 herein, or a substantially similar assay. According to certain embodiments, antibody-drug conjugates comprising anti-MSR1 antibodies are provided that bind dimeric human MSR1 at 37° C. with a t½ of greater than about 1 minute, greater than about 2 minutes, greater than about 3 minutes, greater than about 4 minutes, greater than about 5 minutes, greater than about 6 minutes, greater than about 8 minutes, greater than about 10 minutes, greater than about 12 minutes, greater than about 14 minutes, greater than about 16 minutes, greater than about 18 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 120 minutes, greater than about 150 minutes, greater than about 180 minutes, greater than about 210 minutes, or longer, as measured by surface plasmon resonance, e.g., using an assay format as defined in Example 25 herein, or a substantially similar assay.

Embodiments also include antibody-drug conjugates comprising antibodies and antigen-binding fragments thereof that bind engineered cell-surface expressed hMSR1 with binding ratios of engineered hMSR1-expressing cells to non-expressing cells of at least about 2-fold, at least about 3-fold, at least about 4-fold, at least about 5-fold, at least about 6-fold, at least about 7-fold, at least about 8-fold, at least about 9-fold, at least about 10-fold, at least about 12-fold, at least about 15-fold, at least about 20-fold, at least about 25-fold, at least about 30-fold, at least about 35-fold, at least about 40-fold, at least about 45-fold, at least about 50-fold, or greater, as measured by antibody binding assay, e.g., using an assay format as defined in Example 27 herein, or a substantially similar assay. In some embodiments, provided herein are antibody-drug conjugates comprising antibodies that bind cells with endogenously-expressed hMSR1 with binding ratios of endogenous hMSR1-expressing cells to non-expressing cells of at least about 2-fold, at least about 3-fold, at least about 4-fold, at least about 5-fold, at least about 6-fold, at least about 7-fold, at least about 8-fold, at least about 9-fold, at least about 10-fold, or greater at least about 12-fold, at least about 15-fold, at least about 20-fold, at least about 25-fold, at least about 30-fold, at least about 35-fold, at least about 40-fold, at least about 45-fold, at least about 50-fold, or greater, as measured by antibody binding assay, e.g., using an assay format as defined in Example 27 herein, or a substantially similar assay. In some embodiments, antibody-drug conjugates comprise an MSR1 antibody or antigen binding fragment disclosed herein which binds engineered cell-surface expressed mouse MSR1 with binding ratios of engineered mouse MSR1-expressing cells to non-expressing cells of at least about 2-fold, at least about 3-fold, at least about 4-fold, at least about 5-fold, at least about 6-fold, at least about 7-fold, at least about 8-fold, at least about 9-fold, at least about 10-fold, at least about 12-fold, at least about 15-fold, at least about 20-fold, at least about 25-fold, at least about 30-fold, at least about 35-fold, at least about 40-fold, at least about 45-fold, at least about 50-fold, or greater, as measured by antibody binding assay, e.g., using an assay format as defined in Example 27 herein, or a substantially similar assay.

The antibody-drug conjugates comprise antibodies disclosed herein which may possess one or more of the aforementioned biological characteristics, or any combination thereof. The foregoing list of biological characteristics of the antibodies disclosed herein is not intended to be exhaustive. Other biological characteristics of the antibodies disclosed herein will be evident to a person of ordinary skill in the art from a review of the present disclosure including the working Examples herein.

Anti-WTA Antibodies Suitable for ADCs

According to certain embodiments, antibody-drug conjugates of the present disclosure may comprise an anti-WTA antibody or an antigen-binding fragment thereof. Such anti-WTA antibodies or antigen-binding fragments thereof bind to wall teichoic acids (WTAs) which are expressed on a number of Gram-positive bacteria including *Staphylococcus aureus*. Anti-WTA antibodies may be selected and produced by the methods taught in, for example, U.S. Pat. No. 8,283,294; Meijer P J et al (2006) J Mol Biol. 358(3):764-72; Lantto J, et al (2011) J Virol. 85(4):1820-33; and WO2016090038, each of which is incorporated herein by reference in its entirety for all purposes.

The chemical structures of WTAs vary among organisms. In *S. aureus*, WTA is covalently linked to the 6-OH of N-acetyl muramic acid (MurNAc) via a disaccharide composed of N-acetylglycosamine (GlcNAc)-1-P and N-acetylmannoseamine (ManNAc), which is followed by about two or three units of glycerol-phosphates. The actual WTA polymer is then composed of about 11-40 ribitol-phosphate (Rbo-P) repeating units. The step-wise synthesis of WTA is first initiated by the enzyme called TagO, and *S. aureus* strains lacking the TagO gene (by deletion of the gene) do not make any WTA. The repeating units can be further tailored with D-alanine (D-Ala) at C2-OH and/or with N-acetylglucosamine (GlcNAc) at the C4-OH position via α-(alpha) or β-(beta) glycosidic linkages. Depending of the *S. aureus* strain, or the growth phase of the bacteria the glycosidic linkages could be α-, β-, or a mixture of the two anomers. These GlcNAc sugar modifications are tailored by two specific *S. aureus*-derived glycosyltransferases (Gtfs): TarM Gtf mediates α-glycosidic linkages, whereas TarS Gtfs mediates β-(beta)glycosidic linkages.

The anti-WTA antibody suitable for ADCs of the present disclosure can be an anti-WTAα or anti-WTAβ antibody. The anti-WTA antibody may be cloned from B cells from *S. aureus* infected patients. In one embodiment, the anti-WTA antibody are human monoclonal antibodies. The ADCs of the present disclosure encompass chimeric antibodies and humanized antibodies comprising the CDRs of the anti-WTA antibodies described herein.

The antibody-drug conjugates of the present disclosure can comprise any one of the anti-WTA antibodies described herein, or antigen-binding fragments thereof. In some embodiments, the anti-WTA antibodies or antigen-binding fragments thereof bind to *Staphylococcus aureus*.

In some embodiments, antibody-drug conjugates of the present disclosure comprise an anti-WTAα monoclonal antibody, or an antigen-binding fragment thereof. As a non-limiting example, the anti-WTAα antibody, or the antigen-binding fragment thereof, comprises: (a) the complementarity determining regions (CDRs) of a heavy chain variable region (HCVR) comprising an amino acid sequence as set forth in Table 2A; and (b) the CDRs of a light chain variable region (LCVR) comprising an amino acid sequence as set forth in Table 2A.

TABLE 2A

CDR sequences of exemplary anti-WTAα antibodies

| Anti-WTAα antibody | LCDR1 SEQ ID NO | LCDR2 SEQ ID NO | LCDR3 SEQ ID NO | HCDR1 SEQ ID NO | HCDR2 SEQ ID NO | HCDR3 SEQ ID NO |
|---|---|---|---|---|---|---|
| A1 | 467 | 468 | 469 | 470 | 471 | 472 |
| A2 | 473 | 474 | 475 | 476 | 477 | 478 |
| A3 | 479 | 480 | 481 | 482 | 483 | 484 |
| A4 | 485 | 486 | 487 | 488 | 489 | 490 |

In one embodiment, the anti-WT. Aa antibody, or an antigen-binding fragment thereof, comprises:

(i) a HCDR1 domain comprising an amino acid sequence selected from the group consisting of SEQ ID NOs: 470, 476, 482, and 488;

(ii) a HCDR2 domain comprising an amino acid sequence selected from the group consisting of SEQ ID NOs: 471, 477, 483, and 489;

(iii) a HCDR3 domain comprising an amino acid sequence selected from the group consisting of SEQ ID NOs: 472, 478, 484, and 490;

(iv) a LCDR1 domain comprising an amino acid sequence selected from the group consisting of SEQ ID NOs: 467, 473, 479, and 485;

(v) a LCDR2 domain comprising an amino acid sequence selected from the group consisting of SEQ ID NOs: 468, 474, 480, and 486; and (vi) a LCDR3 domain comprising an amino acid sequence selected from the group consisting of SEQ ID NOs: 469, 475, 481, and 487.

In some embodiments, the anti-WTAα antibody, or the antigen-binding fragment thereof, comprises a heavy chain variable region (HCVR), comprising an amino acid sequence selected from SEQ ID NO: 492, SEQ ID NO: 494, SEQ ID NO: 496, and SEQ ID NO: 498, or a substantially similar sequence thereof having at least 90%, at least 95%, at least 98% or at least 99% sequence identity thereto. The antibodies may further comprise a light chain variable region (LCVR), comprising an amino acid sequence selected from SEQ ID NO: 491, SEQ ID NO: 493, SEQ ID NO: 495, and SEQ ID NO: 497, or a substantially similar sequence thereof having at least 90%, at least 95%, at least 98% or at least 99% sequence identity thereto.

In one embodiment, the anti-WTAα antibody, or the antigen-binding fragment thereof, comprises a LCVR having the amino acid sequence of SEQ ID NO: 491, or a substantially similar sequence thereof having at least 90%, at least 95%, at least 98% or at least 99% sequence identity thereto; and a HCVR having the amino acid sequence of SEQ ID NO: 492, or a substantially similar sequence thereof having at least 90%, at least 95%, at least 98% or at least 99% sequence identity thereto.

In another embodiment, the anti-WTAα antibody, or the antigen-binding fragment thereof, comprises a LCVR having the amino acid sequence of SEQ ID NO: 493, or a substantially similar sequence thereof having at least 90%, at least 95%, at least 98% or at least 99% sequence identity thereto; and a HCVR having the amino acid sequence of SEQ ID NO: 494, or a substantially similar sequence thereof having at least 90%, at least 95%, at least 98% or at least 99% sequence identity thereto.

In another embodiment, the anti-WTAα antibody, or the antigen-binding fragment thereof, comprises a LCVR having the amino acid sequence of SEQ ID NO: 495, or a substantially similar sequence thereof having at least 90%, at least 95%, at least 98% or at least 99% sequence identity thereto; and a HCVR having the amino acid sequence of SEQ ID NO: 496, or a substantially similar sequence thereof having at least 90%, at least 95%, at least 98% or at least 99% sequence identity thereto.

In another embodiment, the anti-WTAα antibody, or the antigen-binding fragment thereof, comprises a LCVR having the amino acid sequence of SEQ ID NO: 497, or a substantially similar sequence thereof having at least 90%, at least 95%, at least 98% or at least 99% sequence identity thereto; and a HCVR having the amino acid sequence of SEQ ID NO: 498, or a substantially similar sequence thereof having at least 90%, at least 95%, at least 98% or at least 99% sequence identity thereto.

In some embodiments, antibody-drug conjugates of the present disclosure comprise an anti-WTAβ monoclonal antibody, or an antigen-binding fragment thereof. Exemplary anti-WTAβ antibodies of the present invention are listed in Table 2B herein. Table 2B sets forth the amino acid sequence identifiers of the heavy chain complementarity determining regions (HCDR1, HCDR2 and HCDR3), and light chain complementarity determining regions (LCDR1, LCDR2 and LCDR3) of the exemplary anti-W TAP antibodies.

TABLE 2B

CDR sequences of exemplary anti-WTAβ antibodies

| Anti-WTAβ antibody | LCDR1 | LCDR2 | LCDR3 | HCDR1 | HCDR2 | HCDR3 |
|---|---|---|---|---|---|---|
| B1 | 499 | 500 | 501 | 502 | 503 | 504 |
| B2 | 505 | 506 | 507 | 508 | 509 | 510 |
| B3 | 511 | 512 | 513 | 514 | 515 | 516 |
| B4 | 517 | 518 | 519 | 520 | 521 | 522 |
| B5 | 523 | 524 | 525 | 526 | 527 | 528 |
| B6 | 529 | 530 | 531 | 532 | 533 | 534 |
| B7 | 535 | 536 | 537 | 538 | 539 | 540 |
| B8 | 541 | 542 | 543 | 544 | 545 | 546 |
| B9 | 547 | 548 | 549 | 550 | 551 | 552 |
| B10 | 553 | 554 | 555 | 556 | 557 | 558 |
| B11 | 559 | 560 | 561 | 562 | 563 | 564 |
| B12 | 565 | 566 | 567 | 568 | 569 | 570 |
| B13 | 571 | 572 | 573 | 574 | 575 | 576 |
| B12 variant | 565 | 566 | 567 | 568 | 569 | 584 |

In one embodiment, the anti-WTA antibody, or an antigen-binding fragment thereof, comprises:

(i) a HCDR1 domain comprising an amino acid sequence selected from the group consisting of SEQ ID NOs: 502, 508, 514, 520, 526, 532, 538, 544, 550, 556, 562, 568, and 574;

(ii) a HCDR2 domain comprising an amino acid sequence selected from the group consisting of SEQ ID NOs: 503, 509, 515, 521, 527, 533, 539, 545, 551, 557, 563, 569, and 575;

(iii) a HCDR3 domain comprising an amino acid sequence selected from the group consisting of SEQ ID NOs: 504, 510, 516, 522, 528, 534, 540, 546, 552, 558, 564, 570, 576, and 584;

(iv) a LCDR1 domain comprising an amino acid sequence selected from the group consisting of SEQ ID NOs: 499, 505, 511, 517, 523, 529, 535, 541, 547, 553, 559, 565, and 571;

(v) a LCDR2 domain comprising an amino acid sequence selected from the group consisting of SEQ ID NOs: 500, 506, 512, 518, 524, 530, 536, 542, 548, 554, 560, 566, and 572; and (vi) a LCDR3 domain comprising an amino acid sequence selected from the group consisting of SEQ ID NOs: 501, 507, 513, 519, 525, 531, 537, 543, 549, 555, 561, 567, and 573.

The present invention also provides anti-WTAβ antibodies, or antigen-binding fragments thereof, comprising a heavy chain CDR1 (HCDR1) comprising an amino acid sequence selected from any of the HCDR1 amino acid sequences listed in Table 2B or a substantially similar sequence thereof having at least 90%, at least 95%, at least 98% or at least 99% sequence identity.

The present invention also provides anti-WTAβ antibodies, or antigen-binding fragments thereof, comprising a heavy chain CDR2 (HCDR2) comprising an amino acid sequence selected from any of the HCDR2 amino acid sequences listed in Table 2B or a substantially similar sequence thereof having at least 90%, at least 95%, at least 98% or at least 99% sequence identity.

The present invention also provides anti-WTAβ antibodies, or antigen-binding fragments thereof, comprising a heavy chain CDR3 (HCDR3) comprising an amino acid sequence selected from any of the HCDR3 amino acid sequences listed in Table 2B or a substantially similar sequence thereof having at least 90%, at least 95%, at least 98% or at least 99% sequence identity.

The present invention also provides anti-WTAβ antibodies, or antigen-binding fragments thereof, comprising a light chain CDR1 (LCDR1) comprising an amino acid sequence selected from any of the LCDR1 amino acid sequences listed in Table 2B or a substantially similar sequence thereof having at least 90%, at least 95%, at least 98% or at least 99% sequence identity.

The present invention also provides anti-WTAβ antibodies, or antigen-binding fragments thereof, comprising a light chain CDR2 (LCDR2) comprising an amino acid sequence selected from any of the LCDR2 amino acid sequences listed in Table 2B or a substantially similar sequence thereof having at least 90%, at least 95%, at least 98% or at least 99% sequence identity.

The present invention also provides anti-WTAβ antibodies, or antigen-binding fragments thereof, comprising a light chain CDR3 (LCDR3) comprising an amino acid sequence selected from any of the LCDR3 amino acid sequences listed in Table 2B or a substantially similar sequence thereof having at least 90%, at least 95%, at least 98% or at least 99% sequence identity.

The present invention also provides anti-WTAβ antibodies, or antigen-binding fragments thereof, comprising a set of six CDRs (i.e., HCDR1-HCDR2-HCDR3-LCDR1-LCDR2-LCDR3) contained within any of the exemplary anti-WTAβ antibodies listed in Table 2B. In certain embodiments, the HCDR1-HCDR2-HCDR3-LCDR1-LCDR2-LCDR3 amino acid sequences set is selected from the group consisting of SEQ ID NOs: 502-503-504-499-500-501, 508-509-510-505-506-507, 514-515-516-511-512-513, 520-521-522-517-518-519, 526-527-528-523-524-525, 532-533-534-529-530-531, 538-539-540-535-536-537, 544-545-546-541-542-543, 550-551-552-547-548-549, 556-557-558-553-554-555, 562-563-564-559-560-561, 568-569-570-565-566-567, 574-575-576-571-572-573, and 568-569-584-565-566-567.

In one embodiment, the anti-WTAβ antibody, or the antigen-binding fragment thereof, is derived from antibody 4497 described in US Patent Application Publication 20140356375 (which is incorporated herein by reference in its entirety). In some embodiments, the anti-WTAβ antibody, or the antigen-binding fragment thereof derived from antibody 4497 further comprises a V205C mutation in the light chain.

In one embodiment, the anti-WTAβ antibody, or the antigen-binding fragment thereof, comprises the HCDR1-HCDR2-HCDR3-LCDR1-LCDR2-LCDR3 of SEQ ID Nos: 568-569-570-565-566-567.

In some embodiments, the anti-WTAβ antibody or antigen binding fragment thereof comprises three heavy chain complementarity determining regions (HCDR1, HCDR2, and HCDR3) within a heavy chain variable region (HCVR) amino acid sequence of SEQ ID NOs: 586; and three light chain complementarity determining regions (LCDR1, LCDR2, and LCDR3) within a light chain variable region (LCVR) amino acid sequence of SEQ ID NO: 585.

In some embodiments, the anti-WTAβ antibody or antigen binding fragment thereof comprises an HCVR amino acid sequence of SEQ ID NOs: 586, and an LCVR amino acid sequence of SEQ ID NO: 585.

In some embodiments, the anti-WTAβ antibody comprises a heavy chain amino acid sequence of SEQ ID NOs: 602 and a light chain amino acid sequence of SEQ ID NO: 587 or SEQ ID NO: 589. In some embodiments, the anti-WTAβ antibody, or the antigen-binding fragment thereof comprises a V205C mutation in the light chain.

In some embodiments, the anti-WTAβ antibody, or the antigen-binding fragment thereof, comprises a heavy chain variable region (HCVR), comprising an amino acid sequence corresponding to Kabat positions 1-113 of a full-length heavy chain sequence selected from SEQ ID Nos: 580, 621-628, and 591-594, or a substantially similar sequence thereof having at least 90%, at least 95%, at least 98% or at least 99% sequence identity thereto. The antibodies may further comprise a light chain variable region (LCVR), comprising an amino acid sequence corresponding to Kabat positions 1-107 of a full-length light chain sequence selected from SEQ ID Nos: 579, 610-620, and 587, or a substantially similar sequence thereof having at least 90%, at least 95%, at least 98% or at least 99% sequence identity thereto. Reference of Kabat positions of the full-length heavy chain and full-length light chain can be found, for example, in FIGS. 15A-1, 15A-2, and 15A-3, and FIGS. 15B-1, 15-B 2, 15-B 3, 15-B 4, 15-B 5, and 15-B 6 of US Patent Application Publication No. 20180021450, which is incorporated herein by reference in its entirety for all purposes.

In one embodiment, the anti-WTAβ antibody, or the antigen-binding fragment thereof, comprises a LCVR comprising the amino acid sequence of SEQ ID NO: 577, or a substantially similar sequence thereof having at least 90%, at least 95%, at least 98% or at least 99% sequence identity thereto; and a HCVR comprising the amino acid sequence of SEQ ID NO: 578 wherein X is Q or E and X1 is M, I or V, or a substantially similar sequence thereof having at least 90%, at least 95%, at least 98% or at least 99% sequence identity thereto.

In one embodiment, the anti-WTAβ antibody, or the antigen-binding fragment thereof, comprises a light chain comprising the amino acid sequence of SEQ ID NO: 579, or a substantially similar sequence thereof having at least 90%, at least 95%, at least 98% or at least 99% sequence identity thereto; and a heavy chain comprising the amino acid sequence of SEQ ID NO: 580, or a substantially similar sequence thereof having at least 90%, at least 95%, at least 98% or at least 99% sequence identity thereto.

In a specific embodiment, the anti-WTAβ antibody, or the antigen-binding fragment thereof, comprises a LCVR comprising the amino acid sequence of SEQ ID NO: 577, and a HCVR comprising the amino acid sequence of SEQ ID NO: 578. In a yet more specific embodiment, the anti-WTAβ antibody, or the antigen-binding fragment thereof, comprises a light chain comprising the amino acid sequence of SEQ ID NO: 579, and a heavy chain comprising the amino acid sequence of SEQ ID NO: 580.

In some embodiments, anti-WTAβ antibodies, or the antigen-binding fragments thereof, suitable for ADCs of the present disclosure may contain one or more engineered cysteine in the antibody light chain and/or heavy chain.

In some embodiments, the light chain of the anti-WTAβ antibody, or the antigen-binding fragment thereof, contains an engineered cysteine. In one embodiment, the anti-WTAβ antibody, or the antigen-binding fragment thereof, comprises a light chain comprising the amino acid sequence of SEQ ID NO: 581; and a heavy chain comprising the amino acid sequence of SEQ ID NO: 582 wherein X is M, I or V. In one embodiment, the anti-WTAβ antibody, or the antigen-binding fragment thereof, comprises a light chain comprising the amino acid sequence of SEQ ID NO: 581; and a heavy chain comprising the amino acid sequence of SEQ ID NO: 580.

In some embodiments, the heavy chain of the anti-WTAβ antibody, or the antigen-binding fragment thereof, contains an engineered cysteine. In one embodiment, the anti-WTAβ antibody, or the antigen-binding fragment thereof, comprises a light chain comprising the amino acid sequence of SEQ ID NO: 579; and a heavy chain comprising the amino acid sequence of SEQ ID NO: 583 wherein X is M, I or V.

In some embodiments, both the light chain and the heavy chain of the anti-WTAβ antibody, or the antigen-binding fragment thereof, contain an engineered cysteine. In one embodiment, the anti-WTAβ antibody, or the antigen-binding fragment thereof, comprises a light chain containing an engineered cysteine and comprising the sequence of SEQ ID NO: 581; a heavy chain containing an engineered cysteine and comprising the amino acid sequence of SEQ ID NO: 583 wherein X is M, I or V.

In some embodiments, the anti-WTAβ antibody, or the antigen-binding fragment thereof, comprises a LCVR having the amino acid sequence of SEQ ID NO: 585, or a substantially similar sequence thereof having at least 90%, at least 95%, at least 98% or at least 99% sequence identity thereto; and a HCVR having the amino acid sequence of SEQ ID NO: 608, or a substantially similar sequence thereof having at least 90%, at least 95%, at least 98% or at least 99% sequence identity thereto. In one embodiment, the anti-WTAβ antibody, or the antigen-binding fragment thereof, comprises a LCVR having the amino acid sequence of SEQ ID NO: 585, and a HCVR having the amino acid sequence of SEQ ID NO: 608.

In one embodiment, the anti-WTAβ antibody, or the antigen-binding fragment thereof, comprises a light chain having the amino acid sequence of SEQ ID NO: 587; and a heavy chain having the amino acid sequence of SEQ ID NO: 590. In one embodiment, the anti-WTAβ antibody, or the antigen-binding fragment thereof, comprises a light chain having the amino acid sequence of SEQ ID NO: 589; and a heavy chain having the amino acid sequence of SEQ ID NO: 609. In one embodiment, the anti-WTAβ antibody, or the antigen-binding fragment thereof, comprises a light chain having the amino acid sequence of SEQ ID NO: 589; and a heavy chain having the amino acid sequence of SEQ ID NO: 590.

In some embodiments, the anti-WTAβ antibody comprises a LCVR having the amino acid sequence of SEQ ID NO:585 and a HCVR having the amino acid sequence of SEQ ID NO: 586 or SEQ ID NO: 608.

In some embodiments, the anti-WTAβ antibody comprises a LCVR having the amino acid sequence of SEQ ID NO: 577 and a HCVR having the amino acid sequence of SEQ ID NO: 578.

In some embodiments of the ADCs of the present disclosure, the anti-WTA antibody binds to the same epitope as any one of the anti-WTA antibodies disclosed herein.

Anti-WTA antibodies or antigen-binding fragments thereof suitable for ADCs of the present invention can be altered at one or more residues, for example to improve the pK, stability, expression, manufacturability, while maintaining substantially about the same or improved binding affinity to the antigen as compared to the wild type, unmodified antibody. Variants of the present anti-WTA antibodies having conservative amino acid substitutions are encompassed by the invention.

In some embodiments, ADCs of the present disclosure may comprise an anti-WTA antigen-binding fragment lacking a Fe region. In some embodiments, the antigen-binding fragment is a F(ab) or F(ab')2. In some embodiments, the antigen-binding fragment further comprises a heavy chain constant region and/or a light chain constant region, wherein the heavy chain constant region and/or the light chain constant region comprise one or more amino acids that are substituted with cysteine residues. In some embodiments, the antigen-binding fragment comprises a heavy chain constant region comprising amino acid substitution A118C and/or S400C, and/or a light chain constant region comprising amino acid substitution V205C, wherein the numbering system is according to EU numbering.

In certain embodiments, it may be desirable to create cysteine engineered anti-WTA antibodies, e.g., "thioMAbs," in which one or more residues of an antibody are substituted with cysteine residues. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. In particular embodiments, the substituted residues occur at accessible sites of the antibody. By substituting those residues with cysteine, reactive thiol groups are thereby positioned at accessible sites of the antibody and may be used to conjugate the antibody to other moieties, such as antibiotic moieties (e.g., rifamycin analogs) or linker-antibiotic moieties (e.g., linker-rifamycin analog payload), to create an antibody-drug conjugate, as described further herein. In certain embodiments, any one or more of the following residues may be substituted with cysteine, including V205 (Kabat numbering) of the light chain; A118 (EU numbering) of the heavy chain; and 5400 (EU numbering) of the heavy chain Fc region. Nonlimiting exemplary cysteine engineered heavy chain A118C (SEQ ID NO: 605) and light chain V205C (SEQ ID NO: 607) mutants of an anti-WTA antibody are shown. Cysteine engineered anti-WTA antibodies may be generated as described, for example, in Junutula, et al., 2008b Nature Biotech., 26(8):925-932; U.S. Pat. No. 7,521,541; US-2011/0301334; Lehar et al, *Nature* 2015 527, 323-328, each of which are incorporated herein by reference in its entirety.

The engineered cysteine thiols may react with linker reagents or the linker-drug intermediates of the present invention which have thiol-reactive, electrophilic groups such as maleimide or alpha-halo amides to form ADCs with cysteine engineered antibodies (THIOMAB™ or thioMabs) and the antibiotic moieties (e.g., rifamycin analogs). The location of the antibiotic moiety can thus be designed, controlled, and known. The antibiotic loading can be controlled since the engineered cysteine thiol groups typically react with thiol-reactive linker reagents or linker-antibiotic intermediates in high yield. Engineering an anti-WTA antibody to introduce a cysteine amino acid by substitution at a single site on the heavy or light chain gives two new cysteines on the symmetrical tetramer antibody. An antibiotic loading near 2 can be achieved and near homogeneity of the ADC.

Anti-Protein A Antibodies Suitable for ADCs

According to certain embodiments, antibody-drug conjugates of the present disclosure may comprise an anti-Protein A antibody, or an antigen-binding fragment thereof.

Protein A is a 42-kDa protein that exists in both secreted and membrane-associated forms, possesses two distinct Ig-binding activities: each domain can bind Fcγ, the constant region of IgG involved in effector functions, and Fab, the Ig fragment responsible for antigen recognition. Protein A is covalently anchored in the staphylococcal cell wall through its carboxyl terminal end. The protein is comprised of five repeated domains (E, D, A, B, C) linked to the cell surface by region Xr, and each domain can bind with high affinity to the Fc region of immunoglobulin G and to the Fab region of immunoglobulin of the VH3 subclass. The interaction with IgG Fc hinders effector function. In addition, antibodies bound to Protein A through the Fc region cannot stimulate complement fixation by the classical pathway.

Non-limiting examples of anti-Protein A antibodies suitable for ADCs of the present disclosure are listed in Tables 3A and 3B herein. Table 3A sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-Protein A antibody from which the antibodies of the present disclosure may be derived. Table 3B sets forth the nucleic acid sequence identifiers of the HCVRs, LCVRs, HCDR1, HCDR2 HCDR3, LCDR1, LCDR2 and LCDR3 of the exemplary anti-Protein A antibodies.

In some embodiments, anti-Protein A antibodies suitable for ADCs of the present disclosure have attenuated Fc binding. Such antibodies have HCVR amino acid sequences and LCVR amino acid sequences as shown in Table 3A, and also can comprise an IgG1 heavy chain amino acid sequence of SEQ ID NO: 648. This IgG1 sequence comprises H435R and Y436F mutations in the hIgG1 Fc (EU index numbering; equivalent to H318R and Y319F of SEQ ID NO: 648), which is noted as "*/*" or "*" herein.

TABLE 3A

Amino Acid Sequence Identifiers for Exemplary Anti-Protein A Antibodies

| Antibody | SEQ ID NOs: | | | | | | | |
|---|---|---|---|---|---|---|---|---|
| Designation | HCVR | HCDR1 | HCDR2 | HCDR3 | LCVR | LCDR1 | LCDR2 | LCDR3 |
| H1xH15140P*/* | 630 | 632 | 634 | 636 | 638 | 640 | 642 | 644 |
| H1xH15135P*/* | 650 | 652 | 654 | 656 | 658 | 660 | 662 | 664 |
| H1xH15120P*/* | 670 | 672 | 674 | 676 | 678 | 680 | 662 | 683 |

TABLE 3B

Nucleic Acid Sequence Identifiers for Exemplary Anti-Protein A Antibodies

| Antibody | SEQ ID NOs: | | | | | | | |
|---|---|---|---|---|---|---|---|---|
| Designation | HCVR | HCDR1 | HCDR2 | HCDR3 | LCVR | LCDR1 | LCDR2 | LCDR3 |
| H1xH15140P*/* | 629 | 631 | 633 | 635 | 637 | 639 | 641 | 643 |
| H1xH15135P*/* | 649 | 651 | 653 | 655 | 657 | 659 | 661 | 663 |
| H1xH15120P*/* | 669 | 671 | 673 | 675 | 677 | 679 | 681 | 682 |

In one embodiment, the anti-Protein A antibody, or an antigen-binding fragment thereof, comprises:

(i) a HCDR1 domain comprising an amino acid sequence selected from the group consisting of SEQ ID NOs: 632, 652, and 672;

(ii) a HCDR2 domain comprising an amino acid sequence selected from the group consisting of SEQ ID NOs: 634, 654, and 674;

(iii) a HCDR3 domain comprising an amino acid sequence selected from the group consisting of SEQ ID NOs: 636, 656, and 676;

(iv) a LCDR1 domain comprising an amino acid sequence selected from the group consisting of SEQ ID NOs: 640, 660, and 680;

(v) a LCDR2 domain comprising an amino acid sequence selected from the group consisting of SEQ ID NOs: 642 and 662; and (vi) a LCDR3 domain comprising an amino acid sequence selected from the group consisting of SEQ ID NOs: 644, 664, and 683.

In some embodiments, antibody-drug conjugates of the present disclosure comprise an antibody or antigen-binding fragment thereof that specifically bind Protein A, comprising an HCVR comprising an amino acid sequence selected from the group consisting of SEQ ID NOs: 630, 650, and 670, or a substantially similar sequence thereof having at least 90%, at least 95%, at least 98% or at least 99% sequence identity thereto.

In some embodiments, antibody-drug conjugates of the present disclosure comprise an antibody or antigen-binding fragment thereof that specifically bind Protein A, comprising an LCVR comprising an amino acid sequence selected from the group consisting of SEQ ID NOs: 638, 658, and 678, or a substantially similar sequence thereof having at least 90%, at least 95%, at least 98% or at least 99% sequence identity thereto.

In some embodiments, antibody-drug conjugates of the present disclosure comprise an antibody or antigen-binding fragment thereof that specifically bind Protein A, comprising an HCVR and an LCVR amino acid sequence pair (HCVR/LCVR) comprising an anti-Protein A HCVR amino acid sequence listed in Table 3A and an anti-Protein A LCVR amino acid sequence listed in Table 3A. According to certain embodiments, antibody-drug conjugates of the present disclosure comprise an antibody or antigen-binding fragment thereof that specifically bind Protein A, comprising an HCVR/LCVR amino acid sequence pair contained within the exemplary anti-Protein A antibody listed in Table 3A. In certain embodiments, the HCVR/LCVR amino acid sequence pair is selected from the group consisting of SEQ ID NOs: 630/638, 650/658, and 670/678.

In some embodiments, antibody-drug conjugates of the present disclosure comprise an antibody or antigen-binding fragment thereof that specifically bind Protein A, comprising a set of six CDRs (i.e., HCDR1-HCDR2-HCDR3-LCDR1-LCDR2-LCDR3) contained within any of the exemplary anti-Protein A antibodies listed in Table 3A. In certain embodiments, the HCDR1-HCDR2-HCDR3-LCDR1-LCDR2-LCDR3 amino acid sequences set comprises SEQ ID NOs: 632-634-636-640-642-644, 652-654-656-660-662-664, or 672-674-676-680-662-683.

In a related embodiment, antibody-drug conjugates of the present disclosure comprise an antibody or antigen-binding fragment thereof that specifically bind Protein A, comprising a set of six CDRs (i.e., HCDR1-HCDR2-HCDR3-LCDR1-LCDR2-LCDR3) contained within an HCVR/LCVR amino acid sequence pair as defined by the exemplary anti-Protein A antibodies listed in Table 3A. For example, the present invention includes antibodies or antigen-binding fragments thereof that specifically bind Protein A, comprising the HCDR1-HCDR2-HCDR3-LCDR1-LCDR2-LCDR3 amino acid sequences set contained within an HCVR/LCVR amino acid sequence pair selected from the group consisting of: SEQ ID NOs: 630/638, 650/658, and 670/678.

In some embodiments, the anti-Protein A antibody, or an antigen-binding fragment thereof, comprises a heavy chain amino acid sequence of SEQ ID NO: 666, or a substantially similar sequence thereof having at least 90%, at least 95%, at least 98% or at least 99% sequence identity thereof. In some aspects, the anti-Protein A antibody, or an antigen-binding fragment thereof, comprises a light chain amino acid sequence of SEQ ID NO: 668, or a substantially similar sequence thereof having at least 90%, at least 95%, at least 98% or at least 99% sequence identity thereof.

In some embodiments, the anti-Protein A antibody, or an antigen-binding fragment thereof, comprises a heavy chain amino acid sequence of SEQ ID NO: 685, or a substantially similar sequence thereof having at least 90%, at least 95%, at least 98% or at least 99% sequence identity thereof. In some embodiments, the anti-Protein A antibody, or an antigen-binding fragment thereof, comprises a light chain amino acid sequence of SEQ ID NO: 687, or a substantially similar sequence thereof having at least 90%, at least 95%, at least 98% or at least 99% sequence identity thereof.

In one embodiment, the anti-Protein A antibody or antigen binding fragment thereof comprises three heavy chain complementarity determining regions (HCDR1, HCDR2, and HCDR3) within a heavy chain variable region (HCVR) amino acid sequence of SEQ ID NOs: 630; and three light chain complementarity determining regions (LCDR1, LCDR2, and LCDR3) within a light chain variable region (LCVR) amino acid sequence of SEQ ID NO: 638. In one embodiment, the anti-Protein A antibody or antigen binding fragment thereof comprises a set of six CDRs (HCDR1-HCDR2-HCDR3-LCDR1-LCDR2-LCDR3) comprising SEQ ID NOs: 632-634-636-640-642-644.

In one embodiment, the anti-Protein A antibody or antigen binding fragment thereof comprises an HCVR amino acid sequence of SEQ ID NOs: 630; and an LCVR amino acid sequence of SEQ ID NO: 638.

In one embodiment, the anti-Protein A antibody comprises a heavy chain amino acid sequence of SEQ ID NOs: 666 and a light chain amino acid sequence of SEQ ID NO: 668. In one embodiment, anti-Protein A antibody comprises a light chain mutation at position 103 (C103S). In one embodiment, the anti-Protein A antibody, or antigen-binding fragment thereof, is conjugated to a compound of the present disclosure at light chain position 103.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272

(1989). Public databases are also available for identifying CDR sequences within an antibody.

Nucleic acid molecules encoding anti-Protein A antibodies or portions thereof suitable for ADCs of the present disclosure are also provided. For example, the anti-Protein A HCVR amino acid sequences and anti-Protein A LCVR amino acid sequences listed in Table 3A may be encoded by the nucleic acid molecules listed in Table 3B. In certain embodiments, the nucleic acid molecule comprises a polynucleotide sequence selected from the anti-Protein A HCVR nucleic acid sequences and anti-Protein A LCVR nucleic acid sequences listed in Table 3B, or a substantially similar sequence thereof having at least 90%, at least 95%, at least 98% or at least 99% sequence identity thereto.

For example, the anti-Protein A CDR amino acid sequences listed in Table 3A may be encoded by the nucleic acid molecules listed in Table 3B. In certain embodiments, the nucleic acid molecule comprises a polynucleotide sequence selected from any of the anti-Protein A CDR nucleic acid sequences listed in Table 3B, or a substantially similar sequence thereof having at least 90%, at least 95%, at least 98% or at least 99% sequence identity thereto.

In some embodiments, a nucleic acid molecule encoding anti-Protein A antibody or an antigen-binding fragment thereof may comprise a nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by the exemplary anti-Protein A antibodies listed in Table 3A.

A nucleic acid molecule encoding anti-Protein A antibody or an antigen-binding fragment thereof may comprise a nucleic acid molecule encoding an LCVR, wherein the LCVR comprises a set of three CDRs (i.e., LCDR1-LCDR2-LCDR3), wherein the LCDR1-LCDR2-LCDR3 amino acid sequence set is as defined by the exemplary anti-Protein A antibodies listed in Table 3A.

Also provided are recombinant expression vectors capable of expressing a polypeptide comprising a heavy or light chain variable region of an anti-Protein A antibody. For example, the present disclosure includes recombinant expression vectors comprising any of the nucleic acid molecules mentioned above, i.e., nucleic acid molecules encoding any of the HCVR, LCVR, and/or CDR sequences as set forth in Table 3A. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

Anti-Protein A antibodies suitable for ADCs of the present disclosure may have a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277: 26733). In other applications, modification of galactosylation can be made in order to modify complement dependent cytotoxicity (CDC).

The monoclonal antibodies and antigen-binding fragments thereof that specifically bind a Protein A as provided herein may have attenuated Fc binding to Protein A (and/or SpsQ or other homologous protein). In the present disclosure this is noted as "*/*" or "**", and refers to antibodies, or antigen-binding fragments thereof, comprising H435R and Y436F mutations in the hIgG1 Fc according to EU index numbering. The H435R and Y436F mutations are equivalent to H318R and Y319F of SEQ ID NO: 648, an hIgG1 heavy chain. While the */* mutation position refers to H435R and Y436F according to EU numbering, the */* mutation can be found at different positions in the actual heavy chain for a given antibody (or antigen-binding fragment thereof) depending on the variable domain sequence lengths.

In addition to the */* variants described above, certain additional Fc variants are contemplated herein. According to certain embodiments, speciated antibodies to Protein A will be modified in the Fc region of the antibody to attenuate binding by Protein A or homologous protein appropriate for the respective animal species.

According to certain embodiments, antibodies to Protein A suitable for ADCs of the present disclosure comprise an Fc domain comprising one or more mutations which enhance or diminish antibody binding to the FcRn receptor, e.g., at acidic pH as compared to neutral pH. For example, the present invention includes antibodies to Protein A comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, antibodies to Protein A comprise an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present disclosure.

The antibodies to Protein A suitable for ADCs of the present disclosure may comprise a modified Fc domain having altered effector function, for example, increased or reduced effector function. As used herein, a "modified Fc domain having altered effector function" means any Fc portion of an immunoglobulin that has been modified, mutated, truncated, etc., relative to a wild-type, naturally occurring Fc domain such that a molecule comprising the modified Fc exhibits an increase or reduction in the severity or extent of at least one effect selected from the group consisting of cell killing (e.g., ADCC and/or CDC), complement activation, phagocytosis and opsonization, relative to a comparator molecule comprising the wild-type, naturally occurring version of the Fc portion. In certain embodiments, a "modified Fc domain having altered effector function" is an Fc domain with reduced or attenuated binding to an Fc receptor (e.g., FcγR). Exemplary modified Fc domains are described in US 2006/0024298, incorporated by reference herein in its entirety. In some embodiments, the modification is G236A.

In certain embodiments, the modified Fc domain is a variant IgG1 Fc or a variant IgG4 Fc comprising a substitution in the hinge region. For example, a modified Fc for use in the context of the present invention may comprise a variant IgG1 Fc wherein at least one amino acid of the IgG1 Fc hinge region is replaced with the corresponding amino acid from the IgG2 Fc hinge region. Alternatively, a modified Fc for use in the context of the present invention may comprise a variant IgG4 Fc wherein at least one amino acid of the IgG4 Fc hinge region is replaced with the corresponding amino acid from the IgG2 Fc hinge region. Non-limiting, exemplary modified Fc regions that can be used in the context of the present invention are set forth in US Patent Application Publication No. 2014/0243504, the disclosure of which is hereby incorporated by reference in its entirety, as well as any functionally equivalent variants of the modified Fc regions set forth therein.

Other modified Fc domains and Fc modifications that can be used in the context of the present invention include any of the modifications as set forth in US 2014/0171623; U.S. Pat. No. 8,697,396; US 2014/0134162; WO 2014/043361, the disclosures of which are hereby incorporated by reference in their entireties. Methods of constructing antibodies or other antigen-binding fusion proteins comprising a modified Fc domain as described herein are known in the art.

Antibody-Drug Conjugates (ADCs)

Provided herein are antibody-drug conjugates (ADCs) comprising an antibody or antigen-binding fragment thereof conjugated to a drug or a therapeutic agent. In some embodiments, the therapeutic agent may be a rifamycin analog. Also provided herein are reactive linker-payloads for example, the compounds having a structure according to any embodiment of formulas (A), (B), (I), (I'), (II), (II'), (III), (III'), (IV), (IV'), (V), (V') as provided herein, useful for making the ADCs. Further provided herein are modified antibodies and modified antigen-binding fragments useful for making the ADCs.

In some embodiments, the antibodies, or antigen-binding fragments of antibodies, suitable for making ADCs of the present disclosure, bind to an infectious disease-related target. In some embodiments, the antibodies, or antigen-binding fragments of antibodies bind to MSR1. In some embodiments, the antibodies, or antigen-binding fragments of antibodies bind to WTA. In some embodiments, the antibodies, or antigen-binding fragments of antibodies bind to Protein A.

The ADCs generally have the Formula (XV): BA-[L-PA]$_n$. In the formula, BA is a binding agent, for instance, an antibody, or an antigen-binding fragment thereof. L is a linker, described in detail below. PA is a payload, for instance a rifamycin analog, as described in detail herein. In the formula, n is an integer from 1 to 30, for instance from 1 to 4, e.g., 2 or 4. Each L-PA is covalently bonded to a functional group of PA. In particular embodiments, each L-PA is covalently bonded to a lysine side chain, a cysteine side chain, a glutamine side chain, or an amino terminus of BA.

In some embodiments, L-PA is covalently bonded to a side chain of the binding agent BA, for instance, an antibody, or an antigen-binding fragment thereof, via a reactive group, or RG. Following conjugation to the binding agent, the reactive group becomes part of the linker L of the ADC having the formula (XV): BA-[L-PA]n. Illustrative reactive groups RG useful for the present disclosure include, but are not limited to, those that comprise maleimides, succinimides, N-hydroxy succinimides (NHS), terminal primary amines, haloacetyl groups, isothiocyanates, thiols, alcohols, ketones, aldehydes, acids, esters, hydrozides, and anilines. RG also include moieties having the following structure:

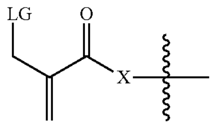

or

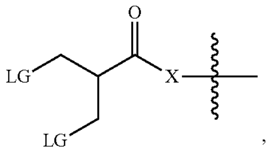

, wherein X is —O— or —NH— and LG is a leaving group, e.g., Br.

In some embodiments, the reactive linker is

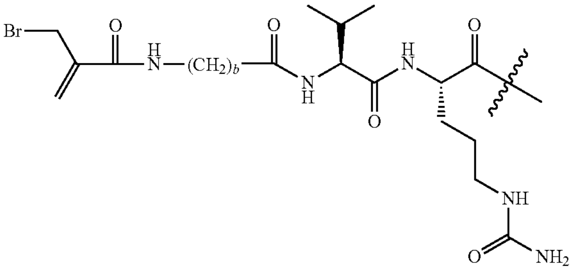

wherein b is an integer from 2 to 8.

In some embodiments, the reactive linker is

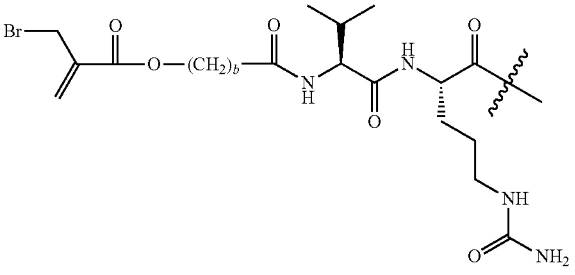

wherein b is an integer from 2 to 8.

In some embodiments, the reactive linker is

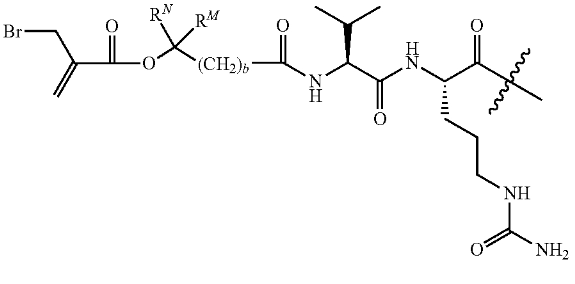

wherein b is an integer from 2 to 8, $R^N$ is a hydrogen atom or an alkyl group, and $R^M$ is an alkyl group.

In some embodiments, the reactive linker is

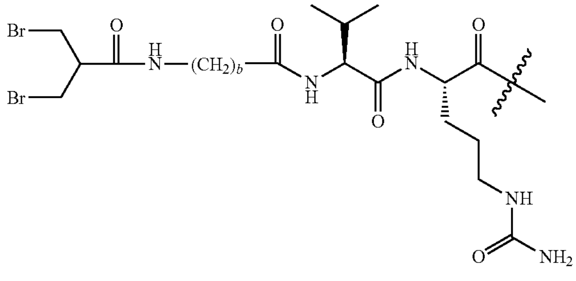

wherein b is an integer from 2 to 8.

In some embodiments, the reactive linker is

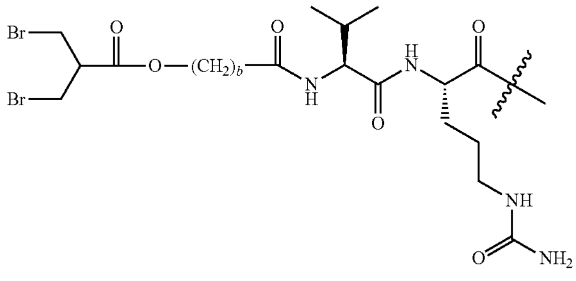

wherein b is an integer from 2 to 8.

In some embodiments, the reactive linker is

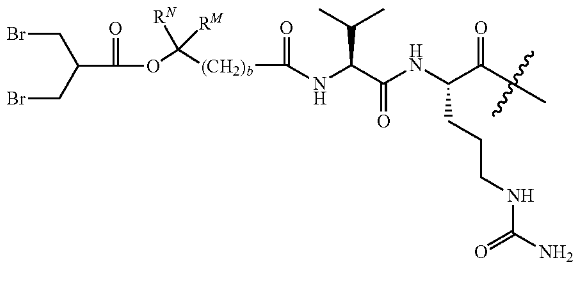

wherein b is an integer from 2 to 8, $R^N$ is a hydrogen atom or an alkyl group, and $R^M$ is an alkyl group.

Techniques and linkers for conjugating to residues of an antibody or antigen binding fragment are known in the art. Exemplary amino acid attachments that can be used in the context of this aspect, e.g., lysine (see, e.g., U.S. Pat. No. 5,208,020; US 2010/0129314; Hollander et al., *Bioconjugate Chem.,* 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA,* 2008, 105:12451-12456), formyl glycine (see, e.g., Carrico et al., *Nat. Chem. Biol.,* 2007, 3:321-322; Agarwal et al., *Proc. Natl. Acad. Sci., USA,* 2013, 110:46-51, and Rabuka et al., *Nat. Protocols,* 2012, 10:1052-1067), non-natural amino acids (see, e.g., WO 2013/068874, and WO 2012/166559), and acidic amino acids (see, e.g., WO 2012/05982). Lysine conjugation can also proceed through NHS (N-hydroxy succinimide). Linkers can also be conjugated to cysteine residues, including cysteine residues of a cleaved interchain disulfide bond, by forming a carbon bridge between thiols (see, e.g., U.S. Pat. Nos. 9,951,141, and 9,950,076). Linkers can also be conjugated to an antigen-binding protein via attachment to carbohydrates (see, e.g., US 2008/0305497, WO 2014/065661, and Ryan et al., *Food & Agriculture Immunol.,* 2001, 13:127-130) and disulfide linkers (see, e.g., WO 2013/085925, WO 2010/010324, WO 2011/018611, and Shaunak et al., *Nat. Chem. Biol.,* 2006, 2:312-313). Site specific conjugation techniques can also be employed to direct conjugation to particular residues of the antibody or antigen binding protein (see, e.g., Schumacher et al. *J Clin Immunol* (2016) 36(Suppl 1): 100). Site specific conjugation techniques, include, but are not limited to glutamine conjugation via transglutaminase (see e.g., Schibli, *Angew Chemie* Inter Ed. 2010, 49, 9995).

Linkers can be conjugated to one or more glutamine residues via transglutaminase-based chemo-enzymatic conjugation (see, e.g., Dennler et al., *Bioconjugate Chem.* 2014, 25, 569-578, and WO 2017/147542). For example, in the presence of transglutaminase, one or more glutamine residues of an antibody can be coupled to a primary amine compound. Briefly, in some embodiments, an antibody having a glutamine residue (e.g., a Gln295 residue) is treated with a primary amine compound, described in more detail below, in the presence of the enzyme transglutaminase. Primary amine compounds include payloads or linker-payloads, which directly provide antibody drug conjugates via transglutaminase-mediated coupling. Primary amine compounds also include linkers and spacers that are functionalized with reactive groups that can be subsequently reacted with further compounds towards the synthesis of antibody drug conjugates. Antibodies comprising glutamine residues can be isolated from natural sources or engineered to comprise one or more glutamine residues. Techniques for engineering glutamine residues into an antibody polypeptide chain (glutaminyl-modified antibodies or antigen binding molecules) are within the skill of the practitioners in the art. In certain embodiments, the antibody is aglycosylated.

In certain embodiments, the antibody or a glutaminyl-modified antibody or antigen binding molecule may comprise at least one glutamine residue in at least one polypeptide chain sequence. In certain embodiments, the antibody or a glutaminyl-modified antibody or antigen binding molecule may comprise two heavy chain polypeptides, each with one Gln295 residue. In further embodiments, the antibody or a glutaminyl-modified antibody or antigen binding molecule may comprise one or more glutamine residues at a site other than a heavy chain 295. In some embodiments, an antibody can be prepared by site-directed mutagenesis to insert a glutamine residue at a site without resulting in disabled antibody function or binding. For example, included herein are antibodies bearing Asn297Gln (N297Q) mutation(s) as described herein. In some embodiments, an antibody having a Gln295 residue and/or an N297Q mutation contains one or more additional naturally occurring glutamine residues in their variable regions, which can be accessible to transglutaminase and therefore capable of conjugation to a linker or a linker-payload. An exemplary naturally occurring glutamine residue can be found, e.g., at Q55 of the light chain. In such instances, the antibody conjugated via transglutaminase can have a higher than expected DAR value (e.g., a DAR higher than 4). Any such antibodies can be isolated from natural or artificial sources.

In various embodiments, the antibodies, or antigen-binding fragments thereof, suitable for ADCs of the present disclosure, may comprise one or more site-specific cysteine mutations for conjugation. In one embodiment, the antibody, or antigen-binding fragment thereof, comprises a light chain mutation at position 103 (Cys103Ser or C103S). In one embodiment, the antibody, or antigen-binding fragment thereof, is conjugated to a compound of the present disclosure at light chain position 103.

As a non-limiting example, the anti-Protein A antibody, or antigen-binding fragment thereof, may comprise one or more site-specific cysteine mutations for conjugation. In one embodiment, the anti-Protein A antibody, or antigen-binding fragment thereof, comprises a light chain mutation at position 103 (C103S). In one embodiment, the anti-Protein A antibody, or antigen-binding fragment thereof, is conjugated to a compound of the present disclosure at light chain position 103.

The primary amine compound useful for the transglutaminase mediated coupling of an antibody (or antigen binding compound) comprising a glutamine can be any primary amine compound deemed useful by the practitioner of ordinary skill. Generally, the primary amine compound has the formula $H_2N—R$, wherein R can be any group compatible with the antibody and reaction conditions. In certain embodiments, R is alkyl, substituted alkyl, heteroalkyl, or substituted heteroalkyl.

In some embodiments, the primary amine compound may comprise a reactive group or protected reactive group. Useful reactive groups include azides, alkynes, cycloalkynes, thiols, alcohols, ketones, aldehydes, acids, esters, hydrozides, analines, and amines. In certain embodiments, the reactive group is selected from the group consisting of azide, alkyne, sulfhydryl, cycloalkyne, aldehyde, and carboxyl.

In certain embodiments, the primary amine compound is according to the formula $H_2N$-LL-X, wherein LL is a divalent spacer and X is a reactive group or protected reactive group. In particular embodiments, LL is a divalent polyethylene glycol (PEG) group. In certain embodiments, X is selected from the group consisting of —SH, $—N_3$, alkyne, aldehyde, and tetrazole. In particular embodiments, X is $—N_3$.

In certain embodiments, the primary amine compound is according to one of the following formulas:

$H_2N—(CH_2)_n—X$; $H_2N—(CH_2CH_2O)_n—(CH_2)_p—X$;

-continued $H_2N—(CH_2)_n—N(H)C(O)—(CH_2)_m—X$;

$H_2N—(CH_2CH_2O)_n—N(H)C(O)—(CH_2CH_2O)_m—(CH_2)_p—X$;

$H_2N—(CH_2)_n—C(O)N(H)—(CH_2)_m—X$;

$H_2N—(CH_2CH_2O)_n—C(O)N(H)—(CH_2CH_2O)_m—(CH_2)_p—X$;

$H_2N—(CH_2)_n—N(H)C(O)—(CH_2CH_2O)_m—(CH_2)_p—X$;

$H_2N—(CH_2CH_2O)_n—N(H)C(O)—(CH_2)_m—X$;

$H_2N—(CH_2)_n—C(O)N(H)—(CH_2CH_2O)_m—(CH_2)_p—X$; and $H_2N—(CH_2CH_2O)_n—C(O)N(H)—(CH_2)_m—X$;

wherein n is an integer selected from 1 to 12;

m is an integer selected from 0 to 12;

p is an integer selected from 0 to 2;

and X is selected from the group consisting of —SH, $—N_3$, —C≡CH, —C(O)H, tetrazole, and any of

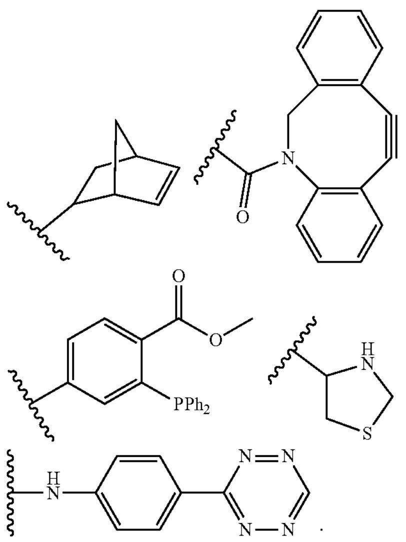

In the above, any of the alkyl or alkylene (i.e., $—CH_2—$) groups can optionally be substituted, for example with $C_{1-8}$alkyl, methylformyl, or $—SO_3H$. In certain embodiments, the alkyl groups are unsubstituted.

In certain embodiments, the primary amine compound is selected from the group consisting of:

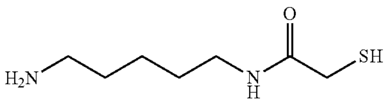

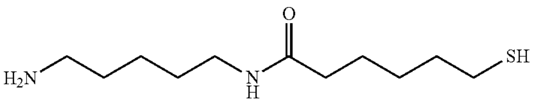

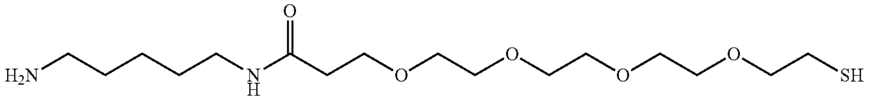

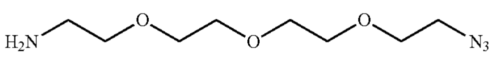

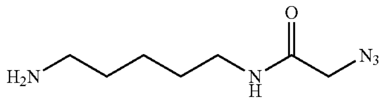

and

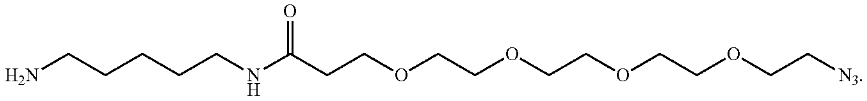

In particular embodiments, the primary amine compound is

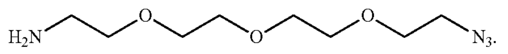

Accordingly, provided herein are modified antibodies, and antigen-binding fragments thereof, linked to one or more primary amine compounds. In particular embodiments, provided herein are modified antibodies, and antigen-binding fragments thereof, according to the formula:

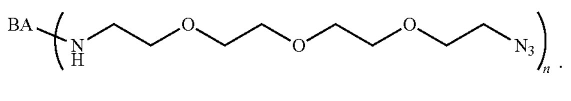

In the formula, BA is an antibody, or an antigen binding fragment thereof. The variable n is an integer from 1 to 30.

In certain embodiments, n is from 1 to the number of glutamine residues in BA. In certain embodiments, n is from 1 to 4. In certain embodiments, n is 1, 2, 3, or 4. In some embodiments, n is 2. In some embodiments, n is 4. The modified antibodies, and antigen-binding fragments thereof, are useful, for example, for linking to one or more L-PA molecules to form an ADC.

In certain embodiments, BA may comprise two or four glutamine residues. In certain embodiments, BA may comprise a Q295 residue. In certain embodiments, BA may comprise an N297Q mutation. In certain embodiments, BA may comprise Q295 and N297Q. In such embodiments, because BA can be dimeric, BA has four glutamine residues for conjugation to L-PA moieties.

In the Formula (XV) BA-[L-PA]$_n$, PA can be any payload deemed useful. In certain embodiments, PA is a rifamycin analog according to the disclosure.

In some embodiments of Formula (XV), L is $-L^1-L^2-(L^3)_{0-1}-$ and $L^2$ may comprise

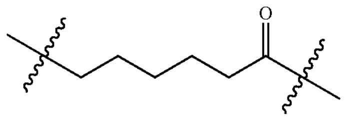 , 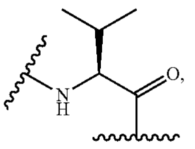 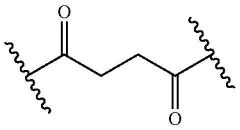 ,

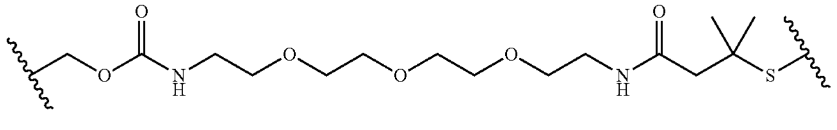 , 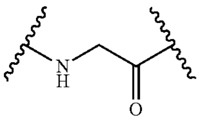 ,

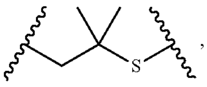 , 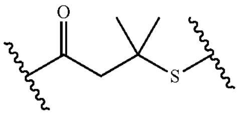 , 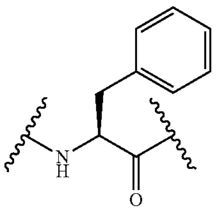 , 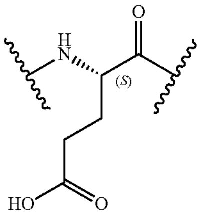 ,

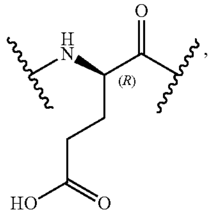 , 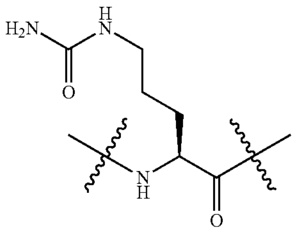 , 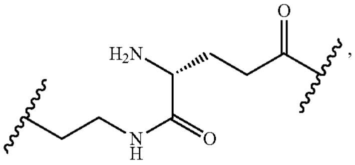 , $-C(O)CH_2CH_2C(O)NH-$ , 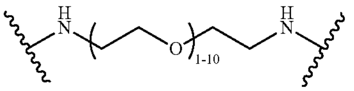 , 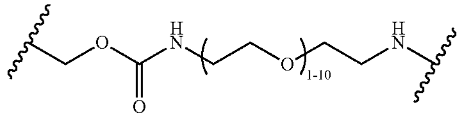 ,

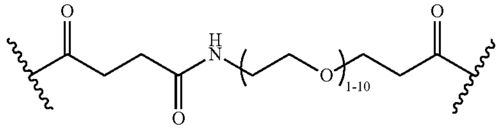 , 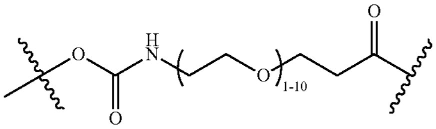 ,

—$OCH_2C(O)$—, or cyclodextrin residue (CD); or combinations thereof. In some embodiments L is -$L^1$-$L^2$-$(L^3)_{0-1}$- and $L^2$ may comprise
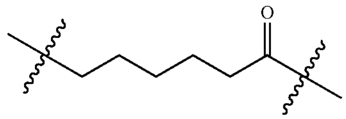
,
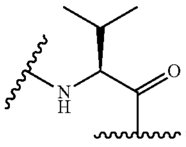
,
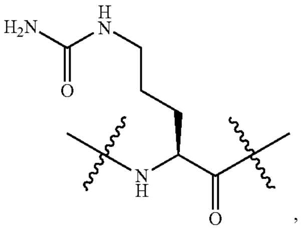
,
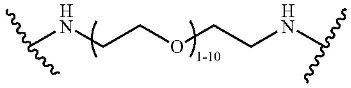
,
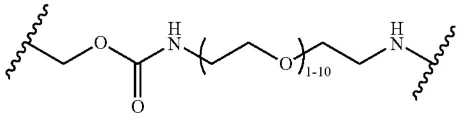
,
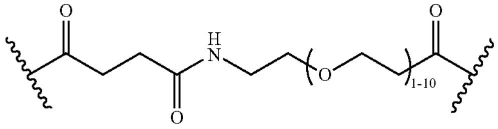
,
or CD, or combinations thereof. In some embodiments, L is -$L^1$-$L^2$-$(L^3)_{0-1}$- and $L^2$ may comprise CD wherein CD is selected from the group consisting of
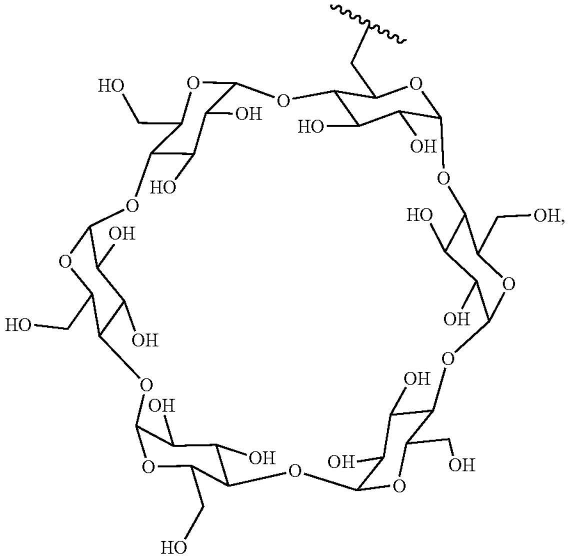
-continued
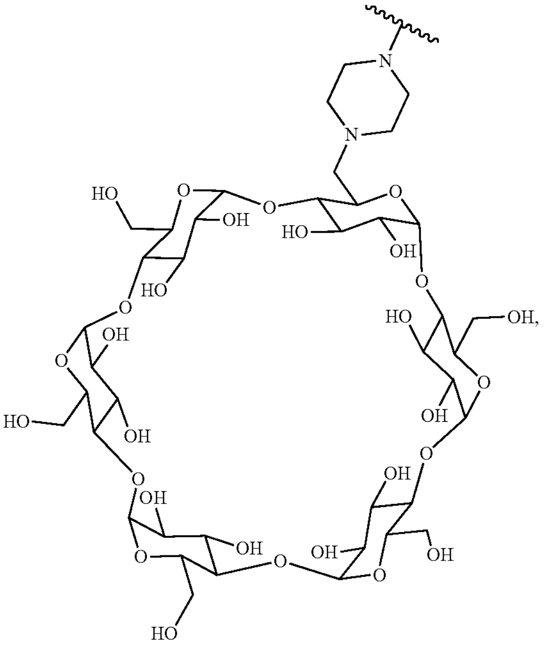
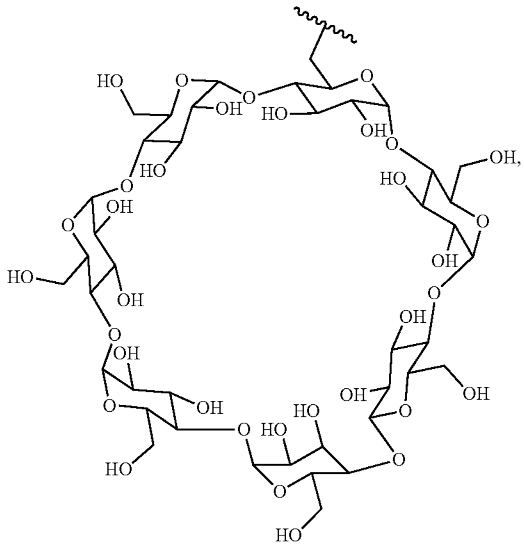

-continued
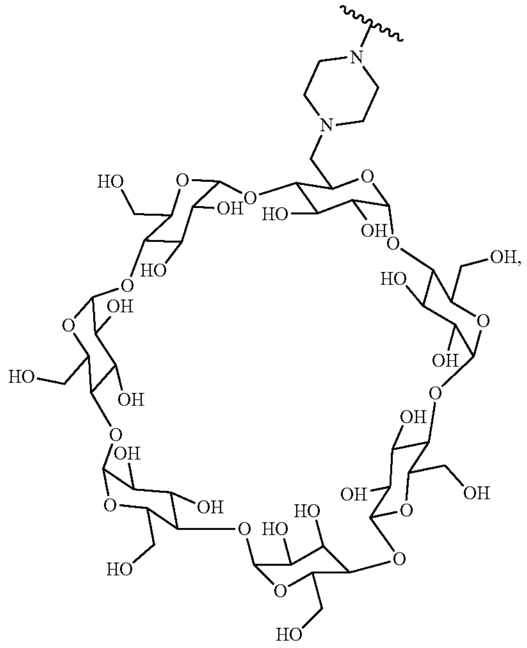
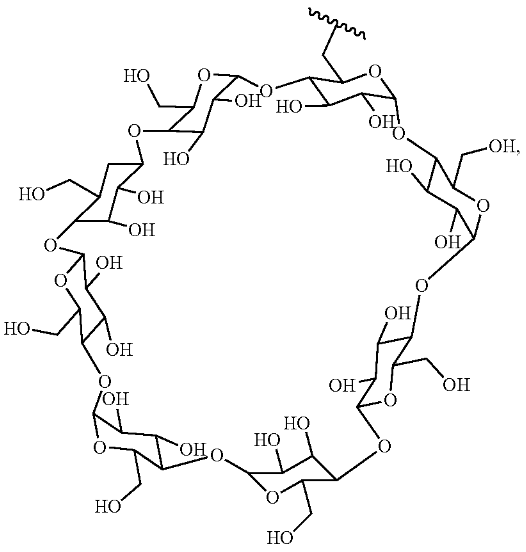
and
-continued
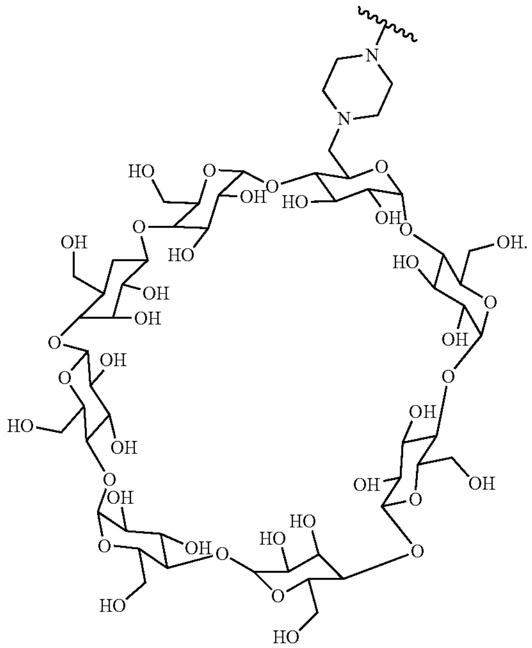
In some embodiments of Formula (XV), L is $-L^1-L^2-(L^3)_{0-1}-$ and $L^2$ may comprise
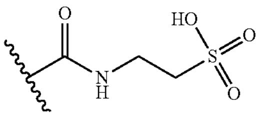
or
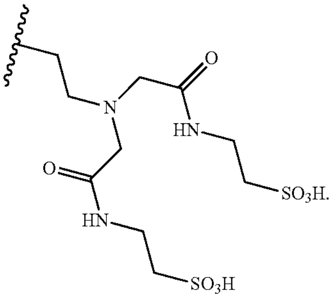
In some embodiments, L is $-L^1-L^2-(L^3)_{0.1}-$ and $-L^1$ may comprise $L^1$ is selected from
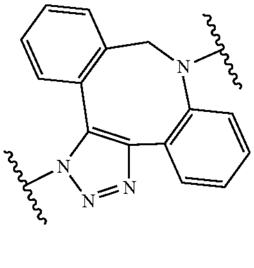 [SMILES: *N1Cc2ccccc2-c2c(nnn2*)-c2ccccc21]

or a regioisomer or mixture of isomers thereof;

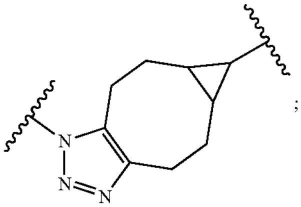
;
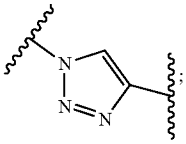
;
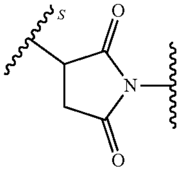

or a steroisomer or mixture of stereoisomers thereof, wherein S refers to the S atom on a cysteine residue through which the reactive group residue is attached to BA; and

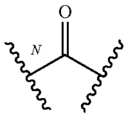

wherein N refers to the N atom on a lysine residue through which the reactive group residue is attached to BA.

In some embodiments, L is $-L^1-L^2-(L^3)_{0-1}-$ and $-L^2-(L^3)_{0-1}-$ may comprise

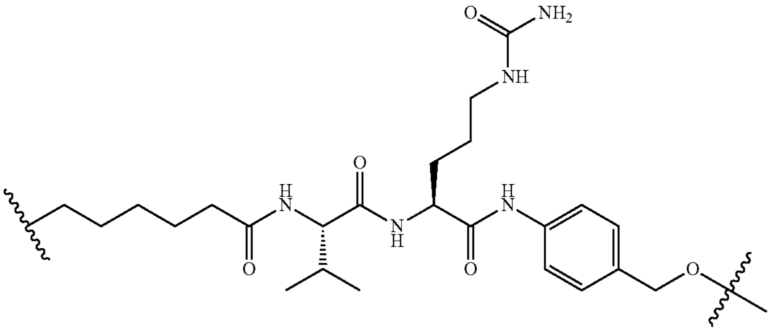

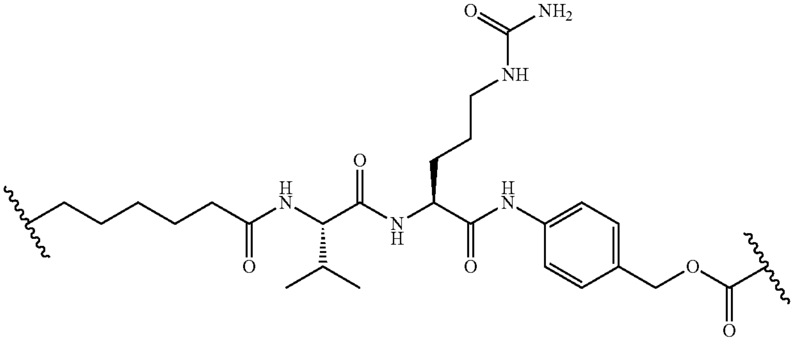

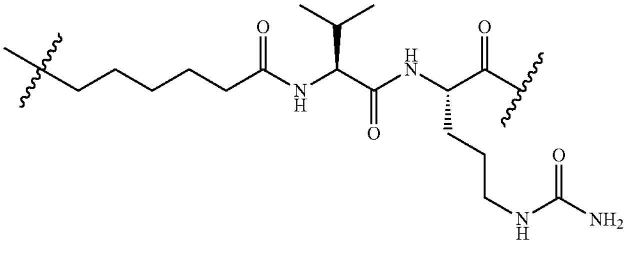

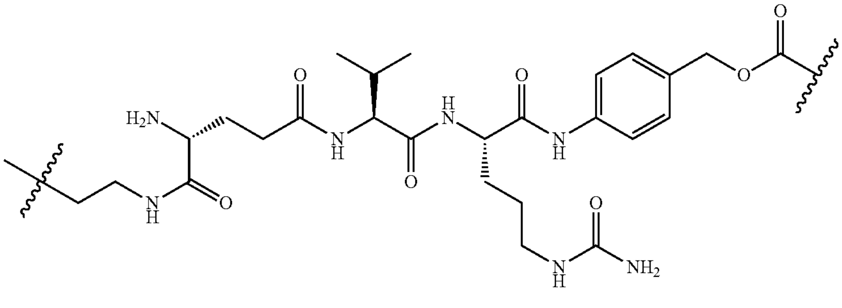

-continued
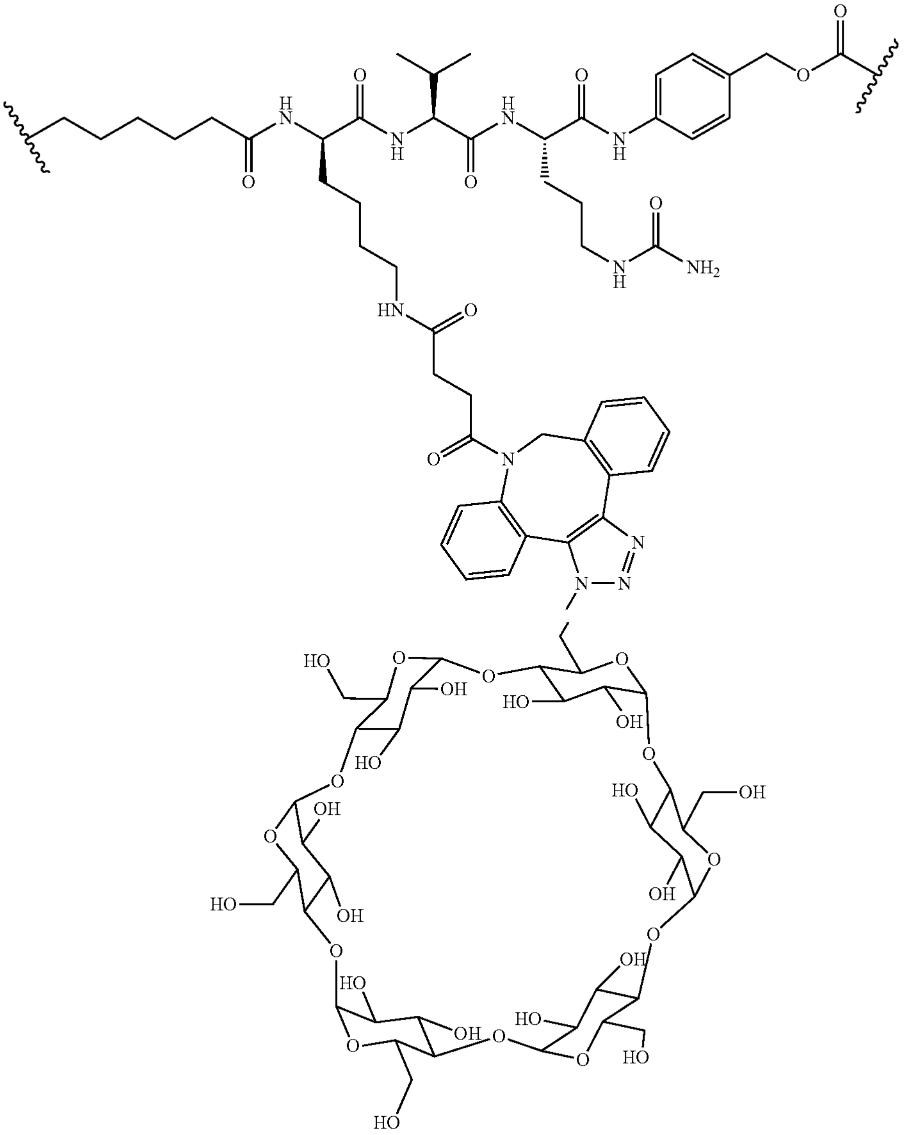
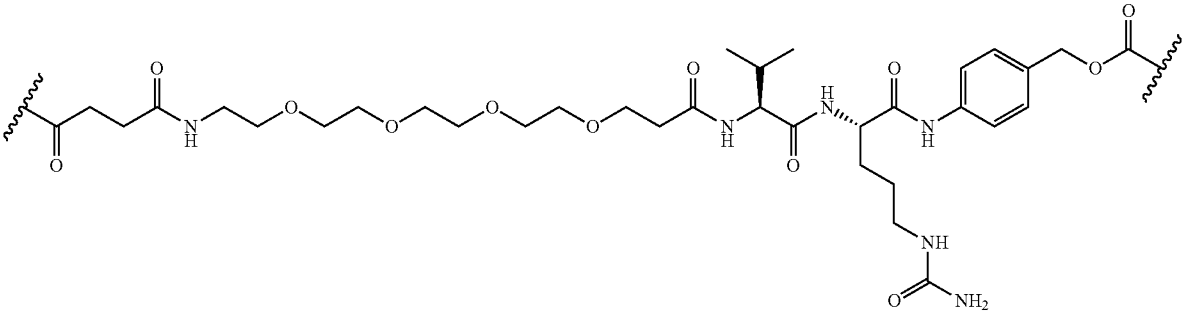
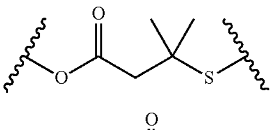
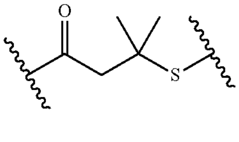
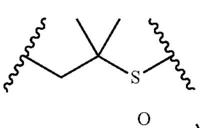
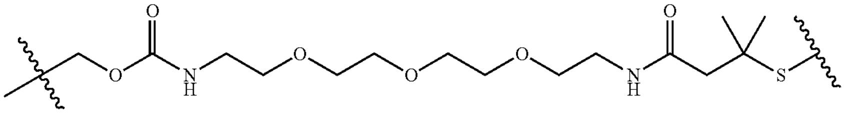

-continued
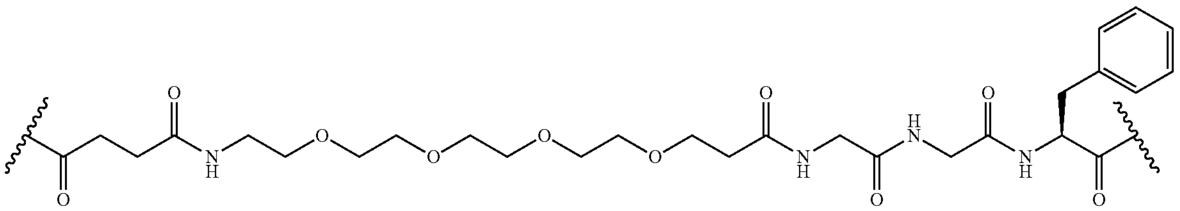
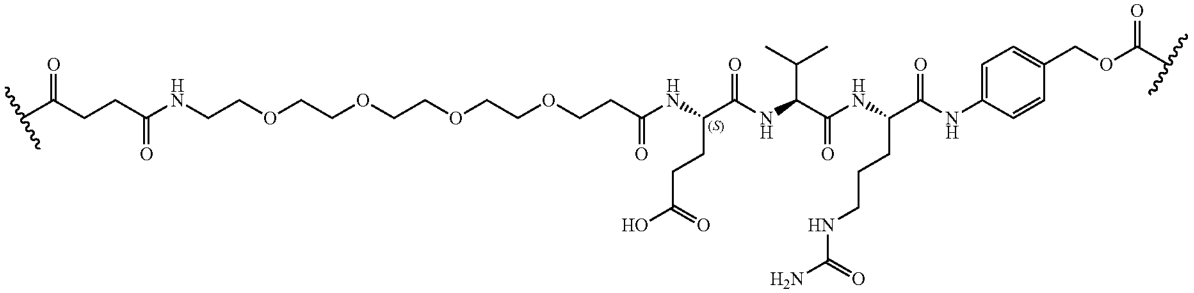
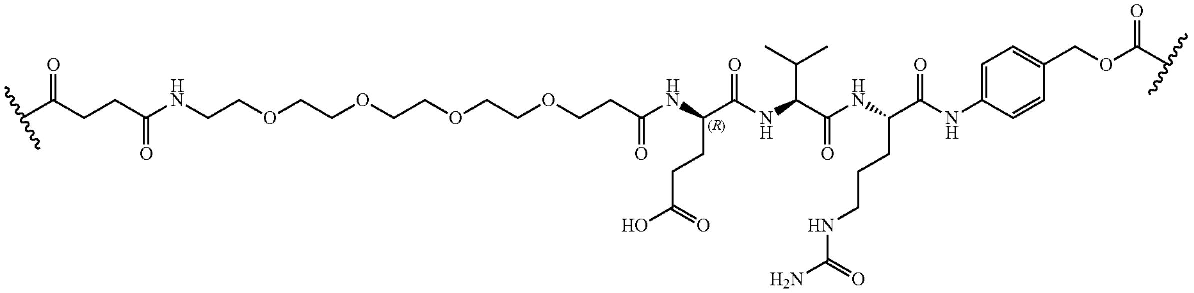
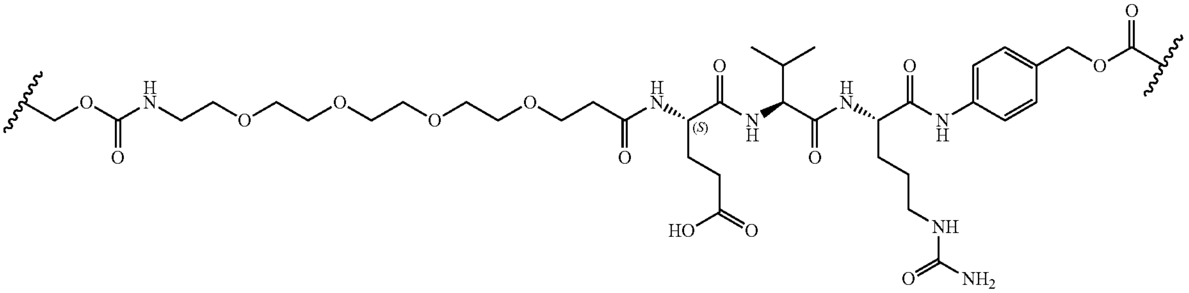
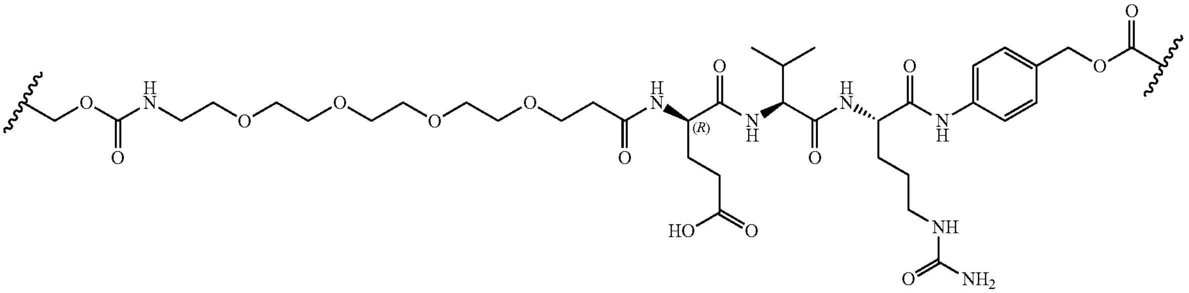
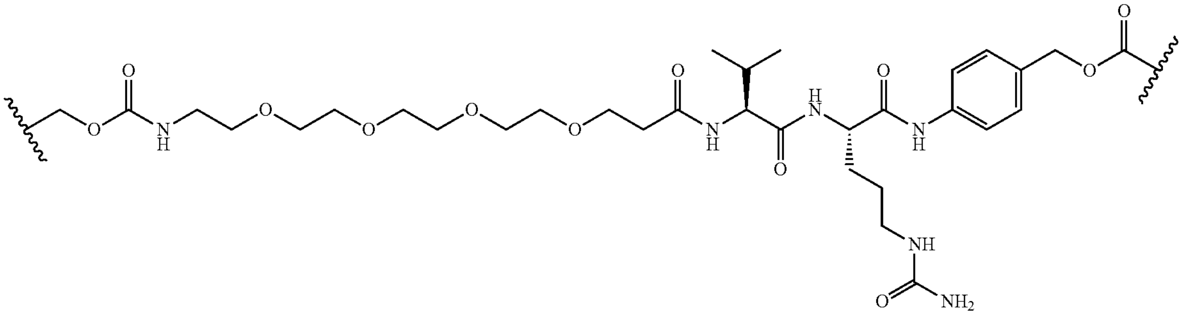

-continued
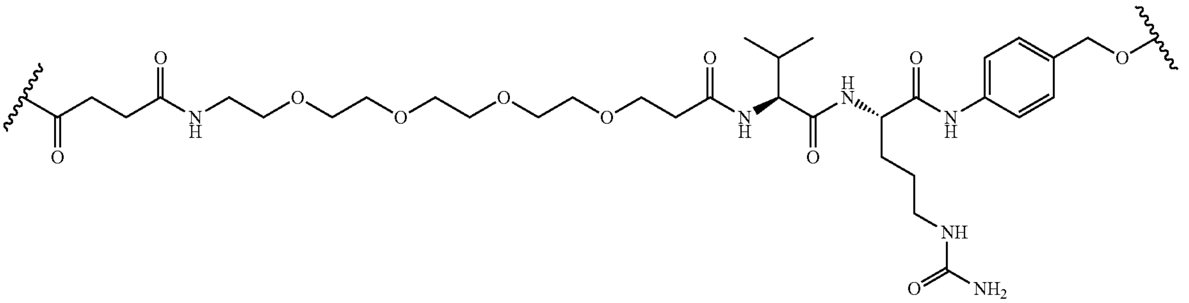
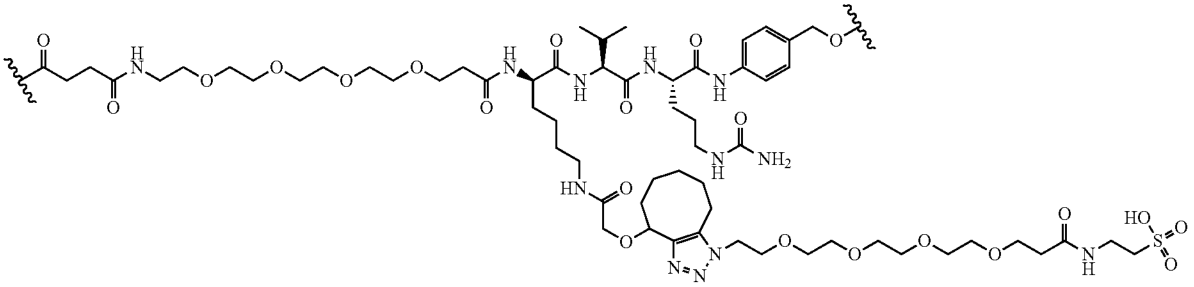
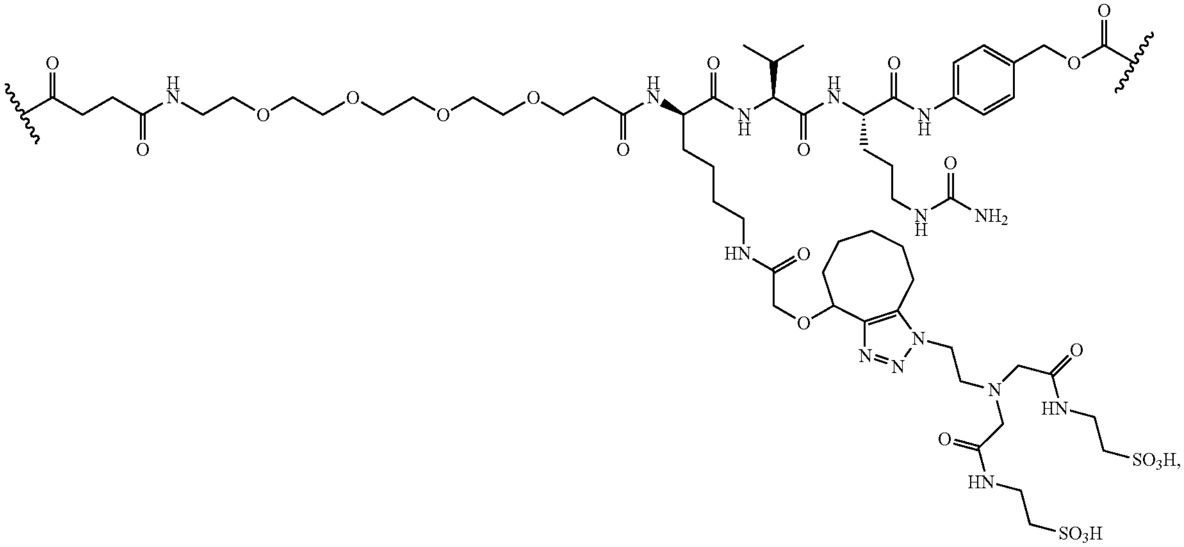
,
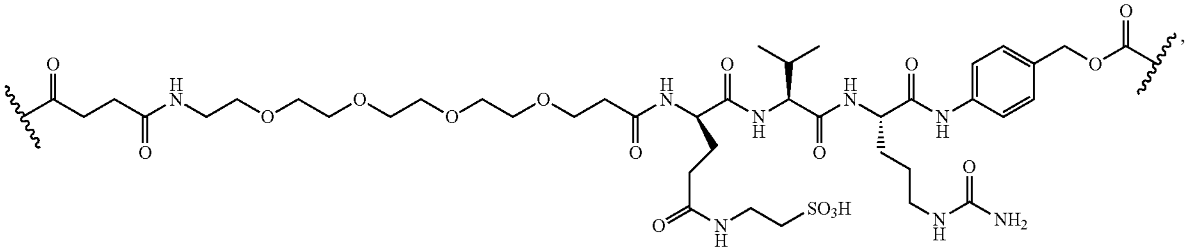
,
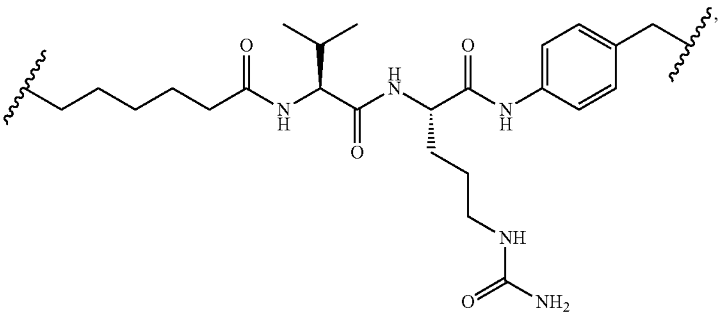
,

-continued

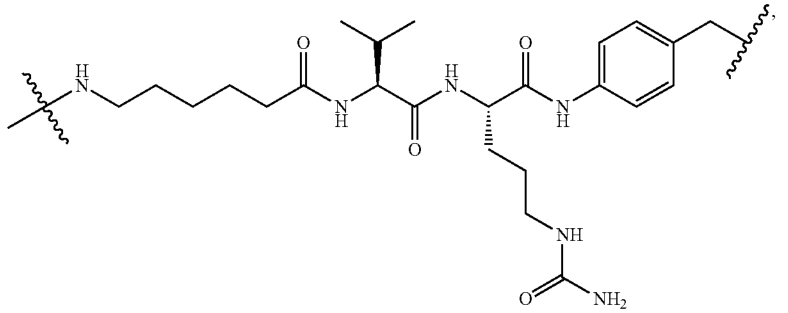

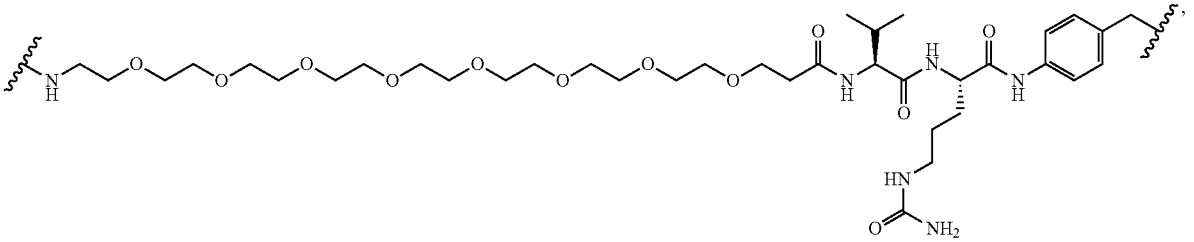

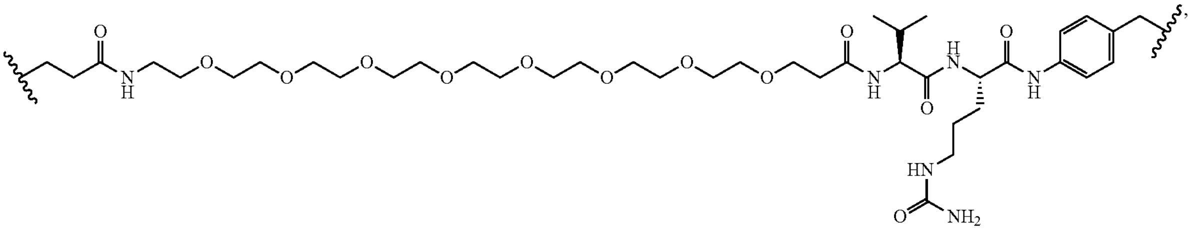

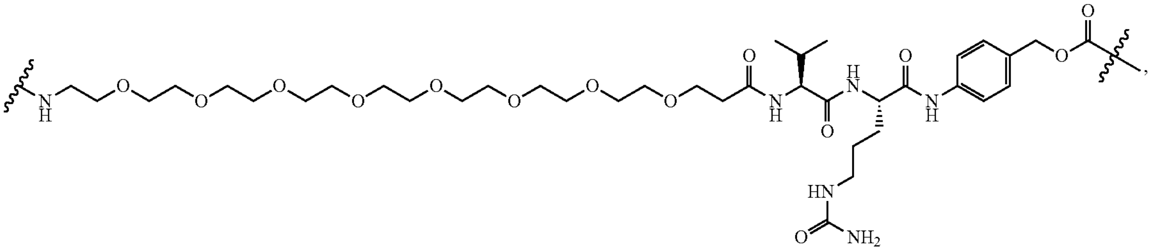

or.

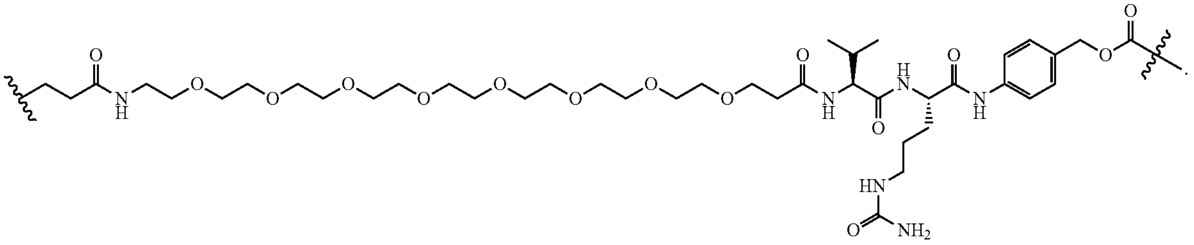

In the Formula (XV), BA-[L-PA]$_n$, PA may be linked to BA with any linker L deemed suitable. Linkers are any group or moiety that links, connects, or bonds the antibody or antigen-binding proteins described herein with a therapeutic moiety, e.g. a rifamycin analog. Suitable linkers may be found, for example, in *Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. Generally, suitable binding agent linkers for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers include linkers that are cleaved by intracellular metabolism following internalization, e.g., cleavage via hydrolysis, reduction, or enzymatic reaction. Non-cleavable linkers include linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citruline units, and para-aminobenzyl (PAB) units.

Any linker molecule or linker technology known in the art can be used to create or construct an ADC of the present disclosure. In certain embodiments, the linker is a cleavable linker. According to other embodiments, the linker is a non-cleavable linker. Exemplary linkers that can be used in the context of the present disclosure include, linkers that comprise or consist of e.g., MC (6-maleimidocaproyl), MP (maleimidopropanoyl), val-cit (valine-citrulline), val-ala (valine-alanine), dipeptide site in protease-cleavable linker, ala-phe (alanine-phenylalanine), dipeptide site in protease-cleavable linker, PAB (p-aminobenzyloxycarbonyl), SPP (N-Succinimidyl 4-(2-pyridylthio) pentanoate), SMCC (N-Succinimidyl 4-(N-maleimidomethyl)cyclohexane-1 carboxylate), SIAB (N-Succinimidyl (4-iodo-acetyl)amino-benzoate), and variants and combinations thereof. Additional examples of linkers that can be used in the context of the present disclosure are provided, e.g., in U.S. Pat. No. 7,754,681 and in Ducry, Bioconjugate Chem., 2010, 21:5-13, and the references cited therein, the contents of which are incorporated by reference herein in their entireties.

In certain embodiments, the linkers are stable in physiological conditions. In certain embodiments, the linkers are cleavable, for instance, able to release at least the payload portion in the presence of an enzyme or at a particular pH range or value. In some embodiments, a linker may comprise an enzyme-cleavable moiety. Illustrative enzyme-cleavable moieties include, but are not limited to, peptide bonds, ester linkages, hydrazones, and disulfide linkages. In some embodiments, the linker may comprise a cathepsin-cleavable linker.

In some embodiments, the linker may comprise a non-cleavable moiety.

Suitable linkers also include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker may comprise one or more amino acids. Suitable amino acids include natural, non-natural, standard, non-standard, proteinogenic, non-proteinogenic, and L- or D-α-amino acids. In some embodiments, the linker may comprise alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or combination thereof. In certain embodiments, one or more side chains of the amino acids is linked to a side chain group, described below. In some embodiments, the linker may comprise valine and citrulline. In some embodiments, the linker may comprise lysine, valine, and citrulline. In some embodiments, the linker may comprise lysine, valine, and alanine. In some embodiments, the linker may comprise valine and alanine.

In some embodiments, the linker may comprise a self-immolative group. The self-immolative group may be any such group known to those of skill. In particular embodiments, the self-immolative group may be p-aminobenzyl (PAB), or a derivative thereof. Useful derivatives include p-aminobenzyloxycarbonyl (PABC). Those of skill will recognize that a self-immolative group is capable of carrying out a chemical reaction which releases the remaining atoms of a linker from a payload.

In some embodiments, the linker may be:

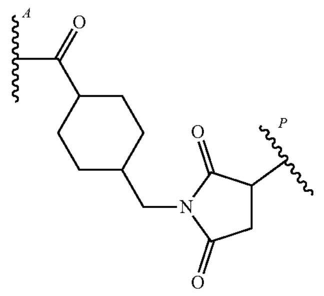

wherein

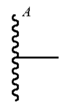

is a bond to the antibody or antigen-binding protein (e.g., via lysine residue) and

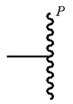

is a bond to the payload. In some embodiments, the linker may be:

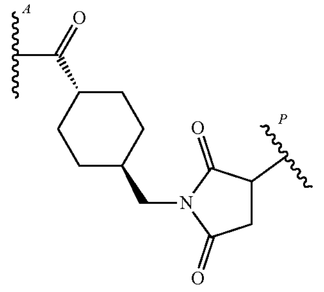

wherein

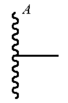

is a bond to the antibody or antigen-binding protein (e.g., via lysine residue) and

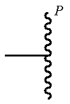
is a bond to the payload. In certain embodiments, the linker may be:
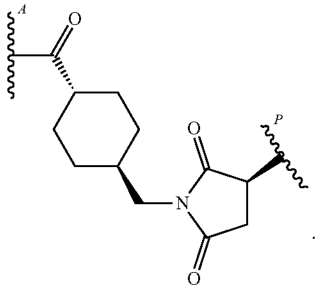
In certain embodiments, the linker may be:
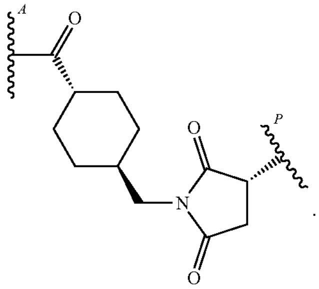
In some embodiments, the linker may be derived from maleimidylmethyl-4-trans-cyclohexanecarboxysuccinate:
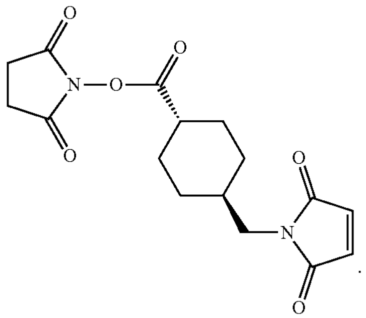 [SMILES: O=C1C=CC(=O)N1C[C@H]1CC[C@H](C(=O)ON2C(=O)CCC2=O)CC1]
In some embodiments, the linker may be:
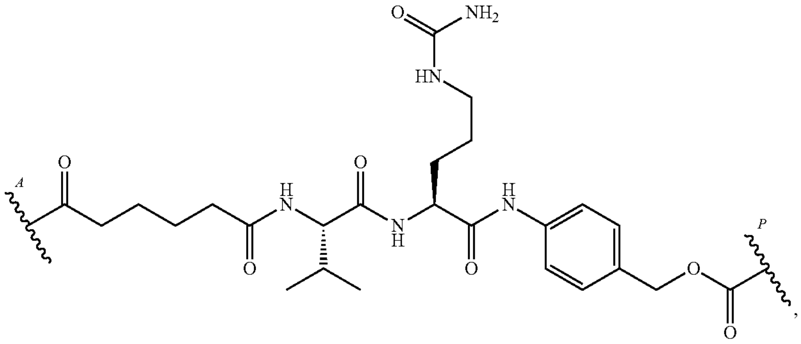
,
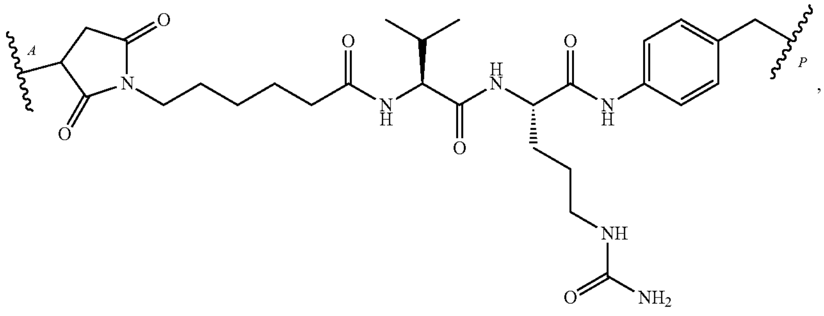
, -continued

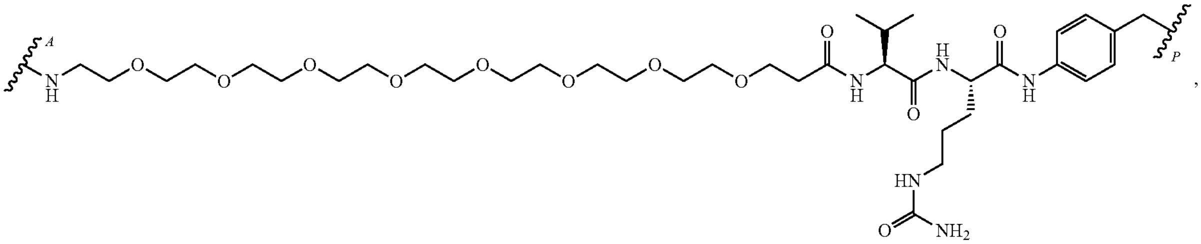

,

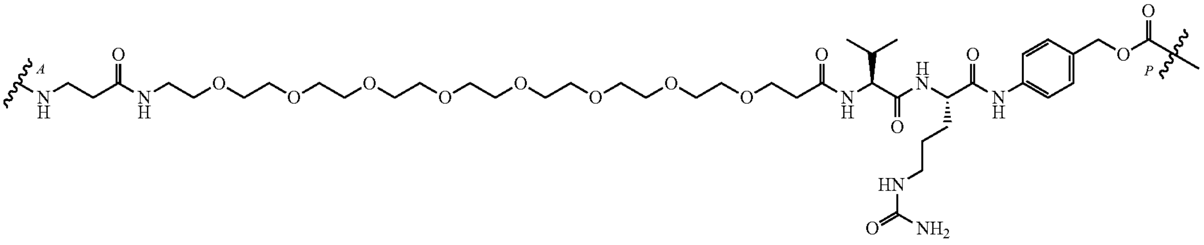

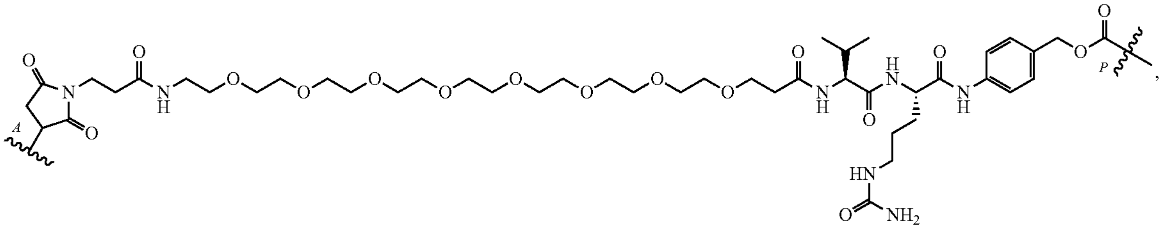

, or

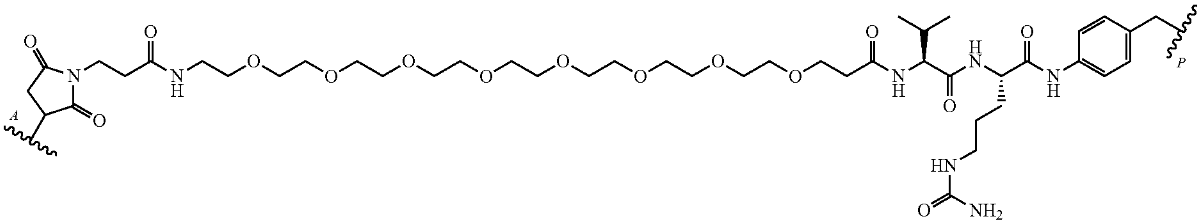

wherein

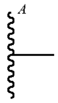

is a bond to the antibody or antigen-binding protein (e.g., via a lysine or a serine residue) and

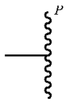

is a bond to the payload.

In some embodiments, L may be a cleavable linker. In some embodiments, L may be a non-cleavable linker. In some embodiments, L may comprise a dipeptide. In some embodiments, L may comprise a

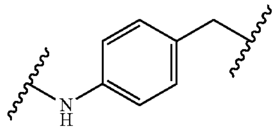 [SMILES: *Cc1ccc(N*)cc1]

moiety.

In some embodiments, L may comprise a moiety having the following structure:

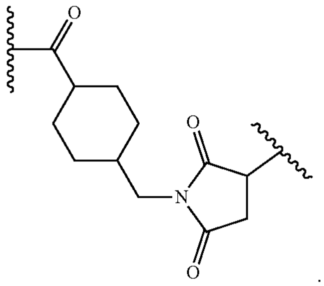 [SMILES: *C(=O)C1CCC(CN2C(=O)CC(*)C2=O)CC1]

.

In some embodiments, L may comprise a moiety having the following structure:

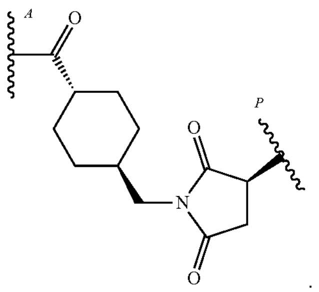
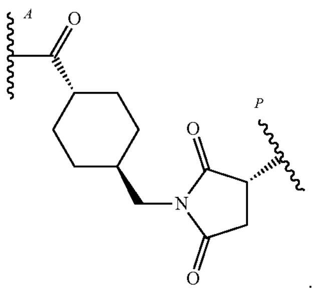
In some embodiments, L may comprise a moiety having the following structure:
In some embodiments, L may comprise a moiety having a structure selected from:
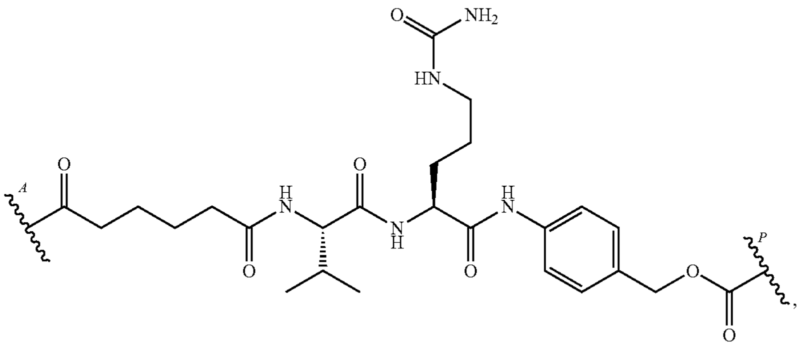
,
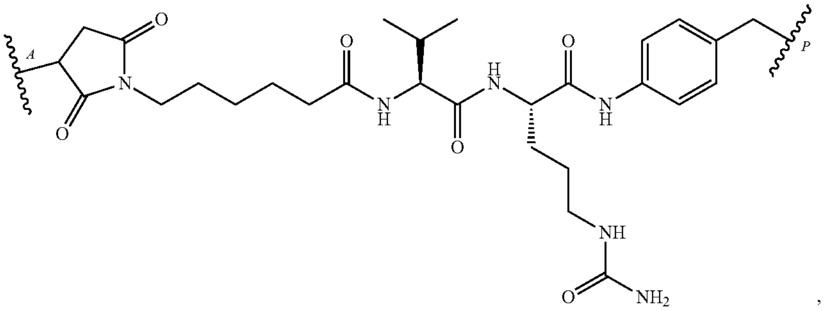
, or
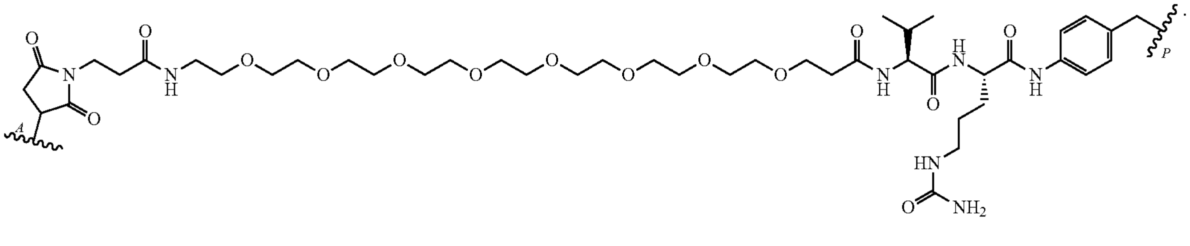
.

In certain embodiments, the linker may comprise a cyclodextrin group. In certain embodiments, the linker provides an ADC according to Formula (XVa):

(XVa)

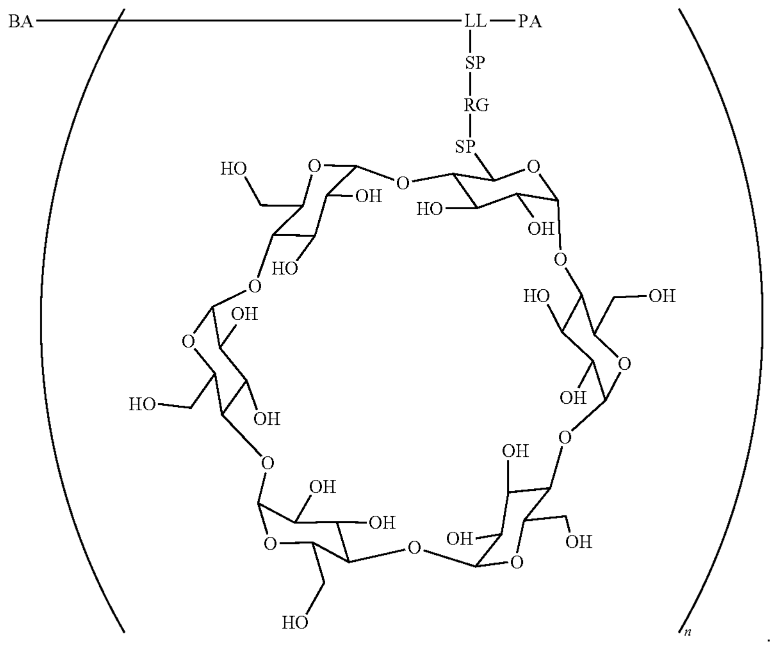

In Formula (XVa), BA is an antibody, or an antigen-binding fragment thereof, LL is a trivalent linker, RG is a reactive linker residue, SP is, independently in each instance, absent or a spacer group, subscript n is an integer from 1 to 30; and PA is a payload. In certain embodiments, n is from 1 to 4. In certain embodiments, n is 4. In certain embodiments, n is 2. In certain embodiments, n is 1. In certain embodiments, n is 3.

In certain embodiments, the linker may comprise a cyclodextrin group. In certain embodiments, the linker provides an ADC according to Formula (XVb):

(XVb)

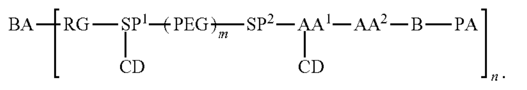

In Formula (XVb), BA is an antibody, or an antigen-binding fragment thereof, RG is a reactive group residue; $SP^1$ and $SP^2$ are each, independently in each instance, absent or a spacer group residue, and wherein $SP^1$ may comprise a trivalent linker; $AA^1$ is a trivalent linker comprising an amino acid residue; $AA^2$ is a di-peptide residue; PEG may comprise between 1 and 30 polyethylene glycol residues; B is absent,

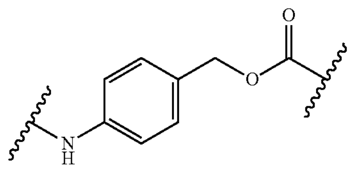

or

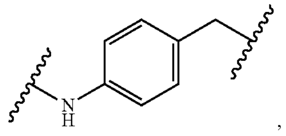

, wherein the

indicates the atom through which the B is bonded to the adjacent groups in the formula, CD is, independently in each instance, absent or a cyclodextrin residue, wherein at least one CD is present, subscript n is an integer from 1 to 30; subscript m is an integer from 0 to 5; and PA is a payload moiety. In these examples, subscript m is 0, 1, 2, 3, 4, or 5. In some examples, subscript m is 0. In some examples, subscript m is 1. In some examples, subscript m is 2. In some examples, subscript m is 3. In some examples, subscript m is 4. In some examples, subscript m is 5. In some examples, B is absent. In some examples, B is

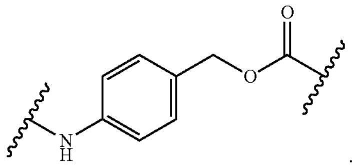 [SMILES: *Nc1ccc(COC(*)=O)cc1]

In some examples, B is

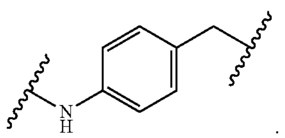 [SMILES: *Cc1ccc(N*)cc1]

In some examples, any one of $AA^1$ or $AA^2$ may comprise, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, and combinations thereof. In certain embodiments, $AA^1$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, and combinations thereof. In certain embodiments, $AA^1$ is lysine. In certain embodiments, $AA^1$ is lysine or a derivative of lysine. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In some embodiments, the $AA^1$-$AA^2$ glutamine-valine-citrulline. In some embodiments, the $AA^1$-$AA^2$ is glutamine-valine-citrulline. In some embodiments, the $AA^1$-$AA^2$ is lysine-valine-alanine. In some embodiments, the $AA^1$-$AA^2$ is lysine-valine-citrulline. In some embodiments, the $AA^1$-$AA^2$ is glutamine-valine-citrulline. In certain embodiments, the lysine is L-lysine. In certain embodiments, the lysine is D-lysine. In some examples, $SP^1$ is independently in each instance, selected from the group consisting of $C_{1-6}$ alkylene, —NH—, —C(O)—, $(—CH_2—CH_2\text{-}0)_e$, —NH—$CH_2$—$CH_2$—$(—O—CH_2—CH_2)_e$—C(O)—, —C(O)—$(CH_2)_u$-C(O)—, —C(O)—NH—$(CH_2)_v$—, and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, $(—CH_2—CH_2\text{-}0)_e$, —NH—$CH_2$—$CH_2$—$(—O—CH_2—CH_2)_e$—C(O)—, —C(O)—$(CH_2)_u$—C(O)—, —C(O)—NH—$(CH_2)_v$—, and combinations thereof, wherein subscript e is an integer from 0 to 4, subscript u is an integer from 1 to 8, and subscript v is an integer from 1 to 8.

In certain embodiments, the linker may comprise a terminal hydrophilic group (HG). In certain embodiments, the linker may comprise a taurine group. In certain embodiments, the linker may comprise a terminal sulfonic acid group. In certain embodiments, the linker provides an ADC according to Formula (XVI):

(XVI)

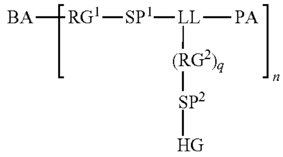

wherein, in Formula (XVI), BA is a binding agent; LL is a trivalent linker; $RG^1$ and $RG^2$ are reactive group residues; $SP^1$ and $SP^2$ are independently, in each instance, absent, or a spacer group residue; HG is a hydrophilic residue; PA is a payload residue; subscript n is an integer from 1 to 30; and subscript q is 0 or 1. In some instances more than one trivalent linker LL may be present. In some instances, n is an integer from 1 to 4. In some instances n is 1. In some instances n is 2. In some instances n is 3. In some instances n is 4. In some instances, HG is a terminal hydrophilic group. In some instances, HG may comprise one terminal sulfonic acid group or a salt thereof. In other instances, HG may comprise more than one terminal sulfonic acid groups or salts thereof. In some instances, HG may comprise one terminal phosphonic acid group or a salt thereof. In other instances, HG may comprise more than one terminal phosphonic acid groups or salts thereof. In some instances, HG may comprise one terminal tertiary amine group or a salt thereof. In other instances, HG may comprise more than one terminal tertiary amine groups or salts thereof. In some instances, HG may comprise one terminal polyol (e.g., glucose, maltose) or a derivative thereof. In other instances, HG may comprise more than one terminal polyol (e.g., glucose, maltose) or derivatives thereof.

In another example, the compound of Formula (XVI) is according to Formula (XVII):

(XVII)

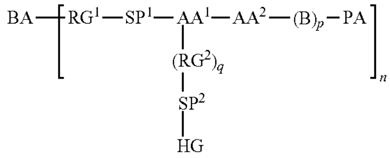

In Formula (XVII), BA, $RG^1$, $SP^1$, $RG^2$, $SP^2$ and HG are as defined above, $AA^1$ is a trivalent linker comprising an amino acid residue; $AA^2$ is a dipeptide residue; and B is

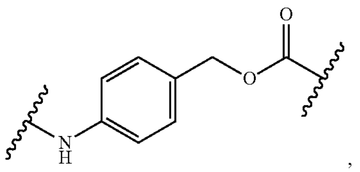 [SMILES: *Nc1ccc(COC(*)=O)cc1]

wherein the

indicates the atom through which the B is bonded to the adjacent groups in the formula; subscript p is 0 or 1; and subscript q is 0 or 1. In some instances, subscript p is 0 and subscript q is 0. In some instances, subscript p is 1; and subscript q is 0. In some instances, subscript p is 0; and subscript q is 1. In some instances, subscript p is 1; and subscript q is 1. In some instances $SP^1$ may comprise from 0-5 polyethylene glycol (PEG) residues. In some instances $SP^2$ may comprise from 0-5 PEG residues. In some examples, $SP^1$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8. In some examples, any one of $AA^1$ or $AA^2$ may comprise, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, and combinations thereof. In certain embodiments, $AA^1$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, and combinations thereof. In certain embodiments, $AA^1$ is lysine. In certain embodiments, $AA^1$ is lysine or a derivative of lysine. In certain embodiments, $AA^1$ is glutamic acid. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In some embodiments, the $AA^1$-$AA^2$ is glutamine-valine-citrulline. In some embodiments, the $AA^1$-$AA^2$ is lysine-valine-citrulline. In some embodiments, the $AA^1$-$AA^2$ is lysine-valine-alanine. In some embodiments, the $AA^1$-$AA^2$ is glutamine-valine-alanine. In certain embodiments, the lysine is L-lysine. In certain embodiments, the lysine is D-lysine.

In certain embodiments, the linker provides an ADC according to Formula (XVIII):

$$BA—[RG—SP—AA—B—PA]_n. \quad \text{(XVIII)}$$

In Formula (XVIII), BA is an antibody, or an antigen-binding fragment thereof, RG is a reactive group residue, e.g., a maleimide or a succinimide residue; SP is absent or a spacer group residue; AA is a di-peptide residue, e.g. a valine-citrulline linker; B is absent or

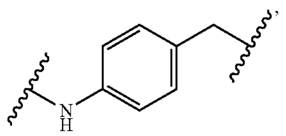 [SMILES: *Cc1ccc(N*)cc1]

wherein the

indicates the atom through which the B is bonded to the adjacent groups in the formula, subscript n is an integer from 1 to 30; and PA is a payload moiety, e.g. a rifamycin analog. In some examples, B is absent. In some examples, B is

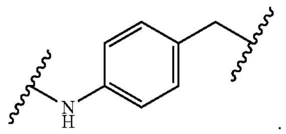 [SMILES: *Cc1ccc(N*)cc1]

in some examples, AA may comprise, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, and combinations thereof. In certain embodiments, the AA is valine-citrulline. In some embodiments, the AA is citrulline-valine. In some embodiments, the AA is valine-alanine. In some embodiments, the AA is alanine-valine. In some embodiments, the AA is valine-glycine. In some embodiments, the AA is glycine-valine. In some examples, SP is selected from the group consisting of $C_{1-6}$ alkyl, —NH—, —C(O)—, $—CH_2—CH_2—C(O)—NH—$, $—(CH)_u—C(O)—NH—$, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, $—(CH)_u—C(O)—NH—(CH_2—CH_2—O)_e—(CH)_u—C(O)—NH—$, $—(CH)_2—C(O)—NH—(CH_2—CH_2—O)_8—(CH)_2—C(O)—NH—$, and combinations thereof, wherein independently at each occurrence subscript e is an integer from 0 to 20, subscript u is an integer from 1 to 8, and subscript v is an integer from 1 to 8.

In certain embodiments, the linker may comprise a cyclodextrin group. In certain embodiments, the linker provides an ADC according to Formula (XIX):

$$BA—\left[RG—SP^1—(PEG)_m—SP^2—AA—B—PA\right]_n$$

(XIX)

In Formula (XIX), BA is an antibody, or an antigen-binding fragment thereof, RG is a reactive group residue, e.g., a maleimide or a succinimide residue; $SP^1$ and $SP^2$ are each, independently in each instance, absent or a spacer group residue, e.g.,

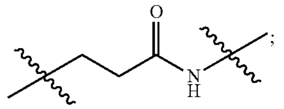 [SMILES: *CCC(=O)N*]

AA is a di-peptide residue, e.g. a valine-citrulline linker; PEG is a polyethylene glycol chain comprising between 1 and 30 polyethylene glycol residues; B is absent or

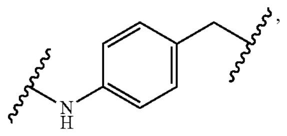 [SMILES: *Cc1ccc(N*)cc1]

wherein the

indicates the atom through which the B is bonded to the adjacent groups in the formula, subscript n is an integer from 1 to 30; subscript m is an integer from 0 to 20; subscript p is 0 or 1; and PA is a payload moiety, e.g. a rifamycin analog. In these examples, subscript m is 0, 1, 2, 3, 4, 5, 6, 7, 8, 9, 10, 11, 12, 13, 14, 15, 16, 17, 18, 19, or 20. In some examples, subscript m is 0. In some examples, subscript m is 1. In some examples, subscript m is 2. In some examples, subscript m is 5. In some examples, subscript m is 8. In some exam les, subscript m is 10. In some examples, B is absent. In some examples, B is

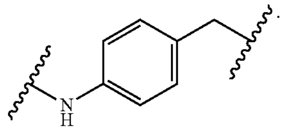 [SMILES: *Cc1ccc(N*)cc1]

In some examples, AA may comprise, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, and combinations thereof. In certain embodiments, the AA is valine-citrulline. In some embodiments, the AA is citrulline-valine. In some embodiments, the AA is valine-alanine. In some embodiments, the AA is alanine-valine. In some embodiments, the AA is valine-glycine. In some embodiments, the AA is glycine-valine. In some examples, $SP^1$ is independently in each instance, selected from the group consisting of $C_{1-6}$ alkyl, —NH—, —C(O)—, $—CH_2—CH_2—C(O)—NH—$, $—(CH)_u—C(O)—NH—$, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, $—CH_2—CH_2—C(O)—NH—$, $—(CH)_u—C(O)—NH—$, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8.

Also included in these examples, is a pharmaceutically acceptable salt, solvate, stereoisomeric form thereof, a regioisomer thereof, or mixture of regioisomers thereof, wherein each

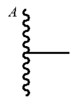

is a bond to the binding agent; and each

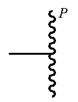

is a bond to the payload.

In some embodiments, antibody-drug conjugates comprising linker-rifamycin analog payloads comprise salts, e.g. ammonium salts, having one or more counterions. Any pharmaceutically acceptable counterion may be suitable. For example, in an embodiment of the disclosure a suitable counterion may be an anion selected from $F^-$, $Cl^-$, $Br^-$, $I^-$, $OH^-$, $^-BF_4$, $CF_3SO_3^-$, monobasic sulfate, dibasic sulfate, monobasic phosphate, dibasic phosphate, or tribasic phosphate, $NO_3^-$, $PF_6^-$, $NO_2^-$, carboxylate, $C_eF_fSO_3^-$, (wherein e=2-10 and f=2e+1), acetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, glycollyalarsanilate, hexanoate, hydrabamine, hydroxynaphthoate, isthionate, lactate, lactobionate, malate, maleate, mandelate, mesylate, methylbromide, methylnitrate, mucate, napsylate, octanoate, oleate, pamoate, pantothenate, polygalacturonate, propionate, salicylate, stearate, subacetate, succinate, tartrate, teoclate, tosylate, or triethiiodide.

The antibody drug conjugates described herein can be prepared using conjugation conditions known to those of ordinary skill in the art, (see, e.g., Doronina et al. *Nature Biotechnology* 2003, 21, 7, 778, which is incorporated herein by reference in its entirety). In some embodiments an ADC is prepared by contacting an antibody or an antigen-binding fragment thereof with a compound comprising the desired linker and payload, wherein said linker possesses a moiety that is reactive with the antibody or antigen-binding protein, e.g., at the desired residue of the antibody or antigen-binding protein. Exemplary conditions are described in the Examples below.

In some aspects, the payloads PA are rifamycin analogs as described in any of the above embodiments of compounds having a structure according to formulas (A), (B), (I), (I'), (II), (II'), (III), (III'), (IV), (IV'), (V), (V') as provided herein.

In one aspect, the payload PA is a rifamycin analog having the structure of Formula (XX):

(XX)

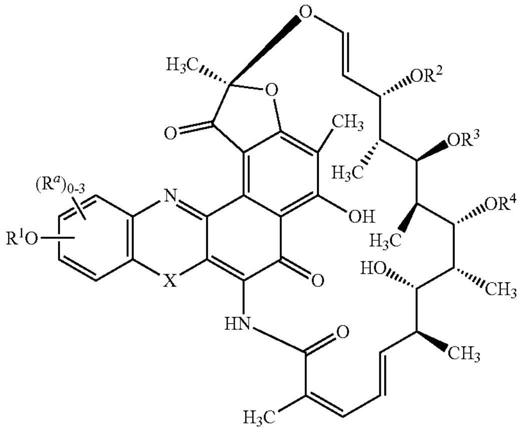

wherein:

X is selected from —O—, —S—, and —NR*—;

$R_1$ is selected from a bond; an aliphatic $C_1$-$C_{20}$ hydrocarbon; an aromatic $C_5$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, and combinations thereof, each of which further comprises 0-8 heteroatoms selected from halogen, O, N, and S, and wherein $R_1$ is optionally substituted with one or more of —F; —Cl; —Br; —I; —OH, —OR*; —NO; —$NO_2$; —$NO_3$; —O—NO; —$N_3$; —$NH_2$; —NHR*; —$N(R^*)_2$; —$N(R^*)_3^+$; —N(R*)—OH; —O—$N(R^*)_2$; —N(R*)—O—R*; —CN; —NC; —(C═O)—R*; —CHO; —$CO_2H$; —$CO_2R^*$; —(C═O)—S—R*; —O—(C═O)—H; —O—(C═O)—R*; —S—(C═O)—R*; —(C═O)—$NH_2$; —(C═O)—$N(R^*)_2$; —(C═O)—$NHNH_2$; —O—(C═O)—$NHNH_2$; —(C═S)—$NH_2$; —(C═S)—$N(R^*)_2$; —N(R*)—CHO; —N(R*)—(C═O)—R*; —SCN; —NCS; —NSO; —SSR*; —$SO_2R^*$; —$SO_2$—$N(R^*)_2$; —S(═O)—OR*; —S(═O)—R*; —$Si(R^*)_3$; —$CF_3$; —O—$CF_3$ and combinations thereof; $R_2$, $R_3$, and $R_4$ are independently selected from hydrogen, a straight chained, branched or cyclic aliphatic $C_1$-$C_{20}$ hydrocarbon, or —(C═O)—R*, each of which further comprises 0-8 heteroatoms selected from halogen, O, N, and S;

$R_a$ is independently at each occurrence selected from hydrogen, —F; —$C_1$; —Br; —I; —OH; OR*; —$NH_2$; —NHR*; —$N(R^*)_2$; —$N(R^*)_3^+$; —(C═O)—R*; —CHO; —$CO_2H$; —$CO_2R^*$ and an aliphatic $C_1$-$C_{20}$ hydrocarbon, which further comprises 0-8 heteroatoms selected from halogen, O, N, and S, and wherein $R_a$ and $R_b$ are optionally substituted with one or more of —F; —$C_1$; —Br; —I; —OH; —OR*;

R* is independently at each occurrence selected from hydrogen; an aliphatic $C_1$-$C_{20}$ hydrocarbon; an aromatic $C_5$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, and combinations thereof, which further comprises 0-8 heteroatoms selected from halogen, O, N, and S and combinations thereof, wherein the group $R_1$ is bonded to the linker.

It is to be understood that the group $R_1$ is either a bond (i.e., $R_1$ is absent), or a divalent group, i.e. a In another aspect, the payload PA is a rifamycin analog having the structure of Formula (XXI):

(XXI)

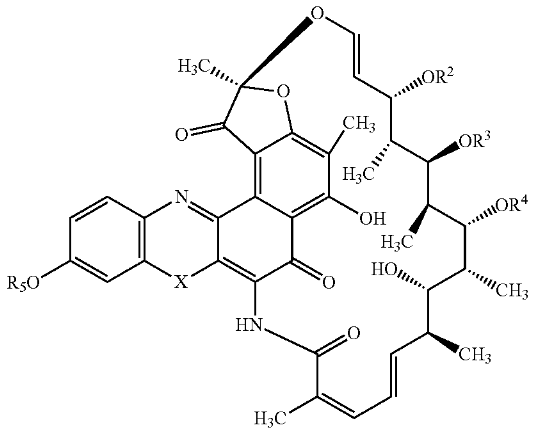

wherein:

X is selected from —O—, —S—, and —NR*—;

$R_5$ is selected from a bond; an aliphatic $C_1$-$C_{20}$ hydrocarbon which further comprises 0-8 heteroatoms selected from halogen, O, N, and S;

; or ;

wherein Y is C or N;

$R_2$, $R_3$, and $R_4$ are independently selected from a hydrogen, a straight chained, branched or cyclic aliphatic $C_1$-$C_{20}$ hydrocarbon, or —(C═O)—R*, each of which further comprises 0-8 heteroatoms selected from halogen, O, N, and S, and $R_{5c}$ is a bond or an aliphatic $C_1$-$C_8$ hydrocarbon;

wherein the group $R_5$ is bonded to the linker.

In another aspect, the payload PA is a rifamycin analog having the structure of Formula (XXI'):

(XXI')

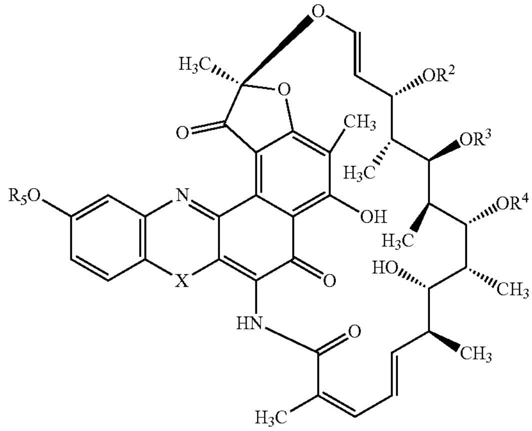

wherein:

X is selected from —O—, —S—, and —NR*—;

$R_5$ is selected from a bond; an aliphatic $C_1$-$C_{20}$ hydrocarbon which further comprises 0-8 heteroatoms selected from halogen, O, N, and S; from

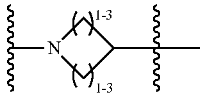
;
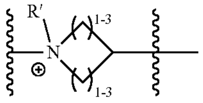
;
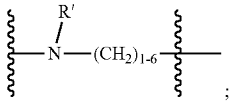
;
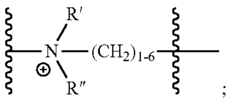
;
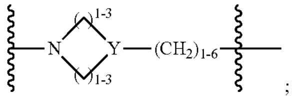
;
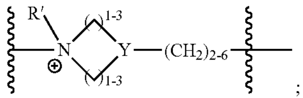
;
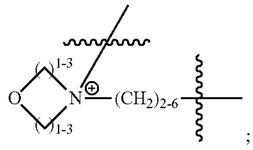
;
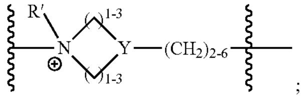
;
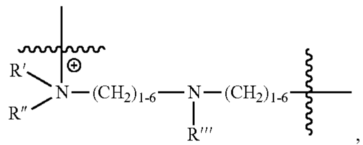
, and -continued

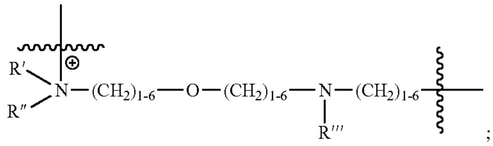
;

wherein Y is C or N;

$R_2$, $R_3$, and $R_4$ are independently selected from a hydrogen, a straight chained, branched or cyclic aliphatic $C_1$-$C_{20}$ hydrocarbon, or —(C═O)—R*, each of which further comprises 0-8 heteroatoms selected from halogen, O, N, and S, wherein the group $R_5$ is bonded to the linker.

It is to be understood that the group $R_5$ is either a bond (i.e., $R_5$ is absent), or a divalent group, i.e. $R_5$ capable of bonding to the —O— of rifamycin as well as to the linker.

In some or any embodiments of Formulas (A), (B), (I) through (XVI) and (I') through (XVI'), $R_a$ is hydrogen and/or $R_b$ is hydrogen. In some or any embodiments of Formulas (A), (I) through (XVI), and (I') through (XVI') $R_a$ is —OH. In some or any embodiments of Formulas (A), (I) through (XVI) and (I') through (XVI'), $R_2$ is methyl, ethyl, propyl or isopropyl. In one embodiment, $R_2$ is methyl. In some or any embodiments of Formulas (A), (I) through (XVI) and (I') through (XVI'), $R_3$ is $CH_3$—(C═O)-(acetyl group), $CH_3CH_2$—(C═O)— $CH_3CH_2CH_2$—(C═O)—, or $(CH_3)_2CH$—(C═O)—. In one embodiment, $R_3$ is acetyl. In some or any embodiments of Formulas (A), (I) through (XVI) and (I') through (XVI'), $R_4$ is hydrogen.

In some embodiments of Formula (XX) or (XX'), —$OR_1$ is —O— (i.e., $R_1$ is absent),

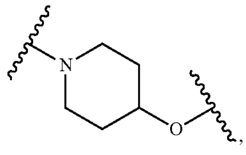
,
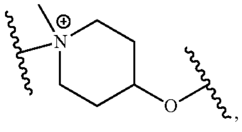
,
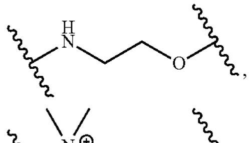
,
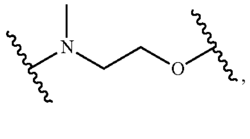
,
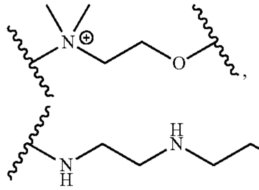
,
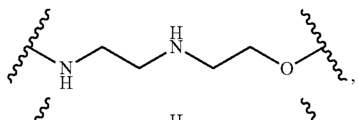
,
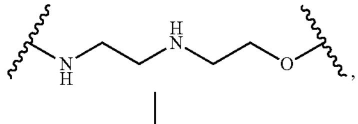
,
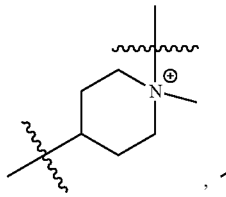
,
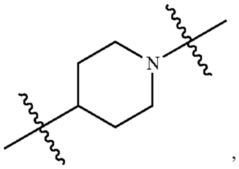
, -continued
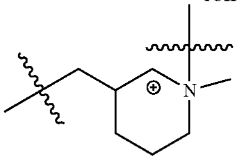,
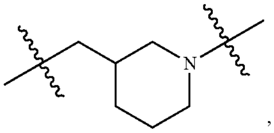,
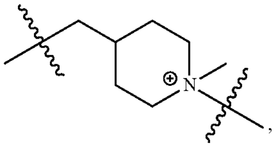,
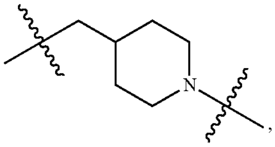,
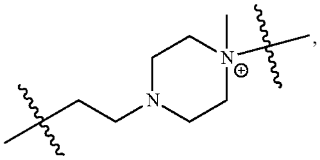,
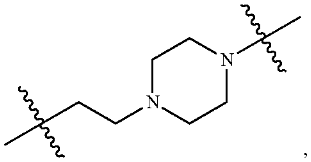,
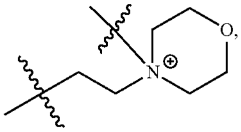
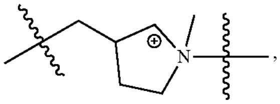,
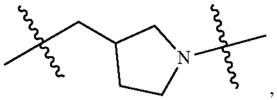,
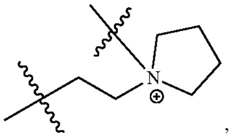,
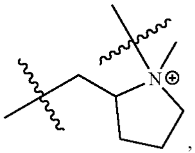,
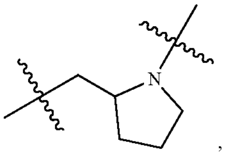,
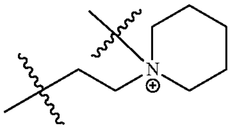,
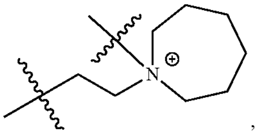,
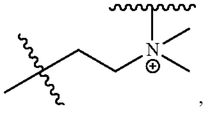,
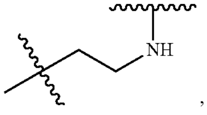,
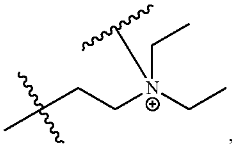,
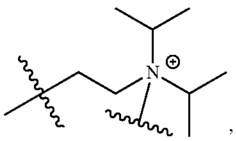,
-continued
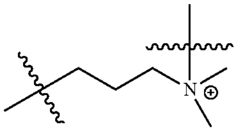,
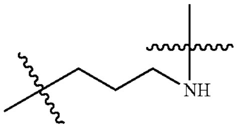,
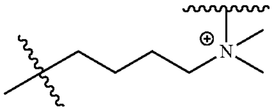,
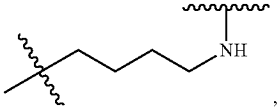,
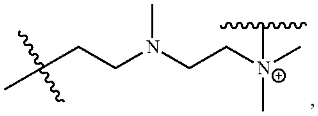,
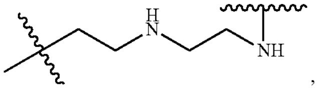,
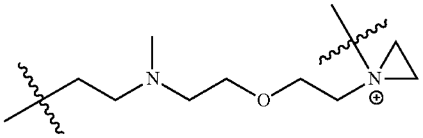,
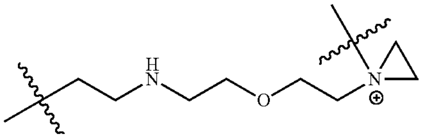,
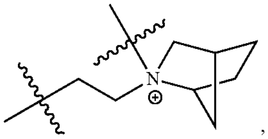,
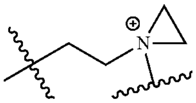, and
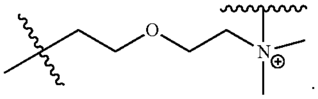.
In some embodiments of Formula (XXI) or (XXI'), —$OR_5$ is —O— (i.e., $R_5$ is absent),
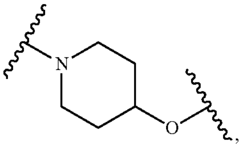,
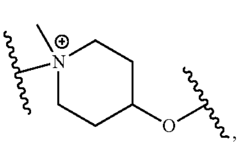,
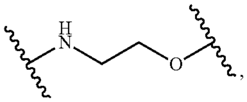,
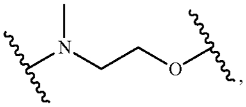,
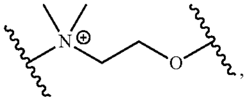,
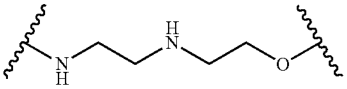

-continued
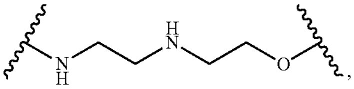,
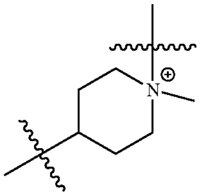, 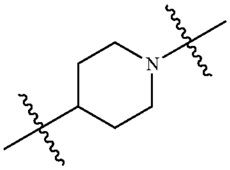,
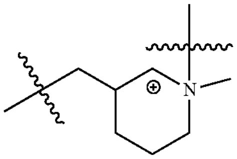, 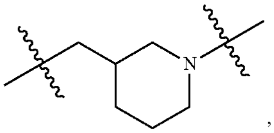,
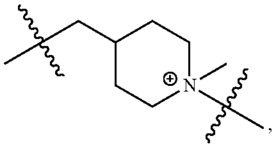,
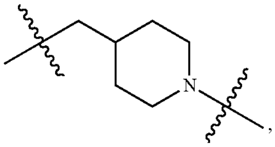,
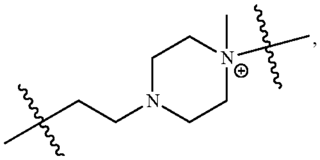,
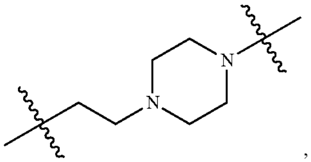,
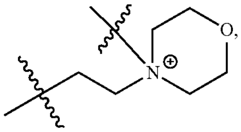
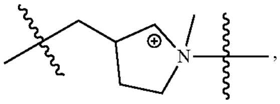,
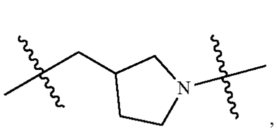, 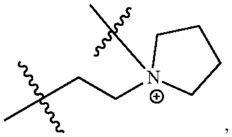,
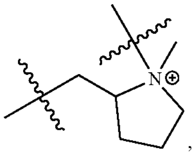, 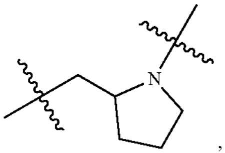,
-continued
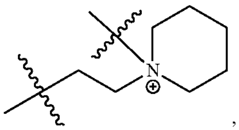, 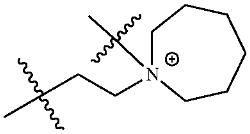,
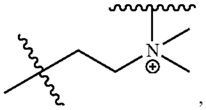, 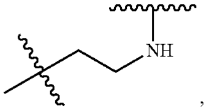,
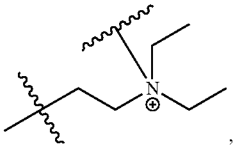, 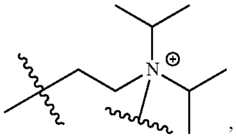,
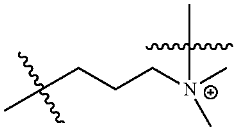, 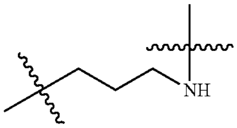,
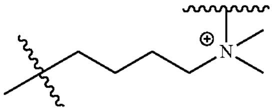,
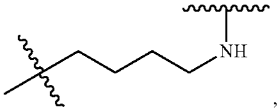,
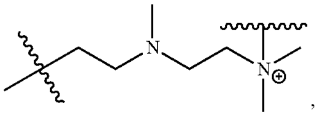,
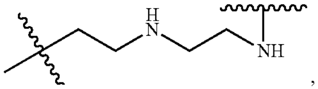,
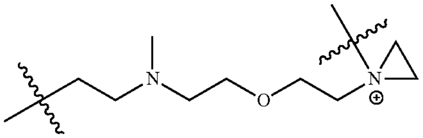
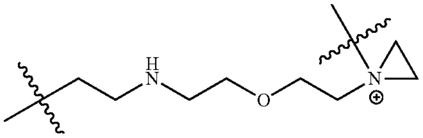
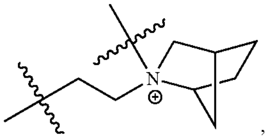, 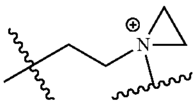, and
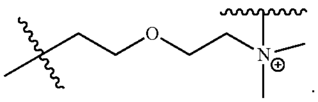.
In some or any embodiments of Formula (XX), X is —O—, and $—OR_1$ comprises a tertiary amine. In some of such embodiments, $—OR_1$ is

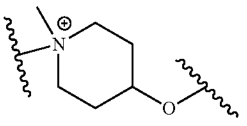
or
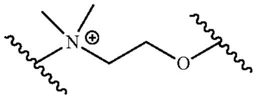
.
In some or any embodiments of Formula (XXI) or (XXI'), X is O, and —$OR_5$ comprises a tertiary amine. In some of such embodiments, —$OR_5$ is
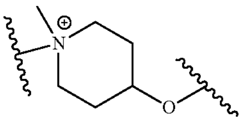
or
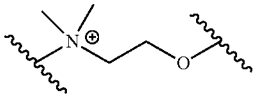
.
In some embodiments. a compound of Formulas (XX), (XXI), (XX') or (XXI') is selected from the group consisting of:
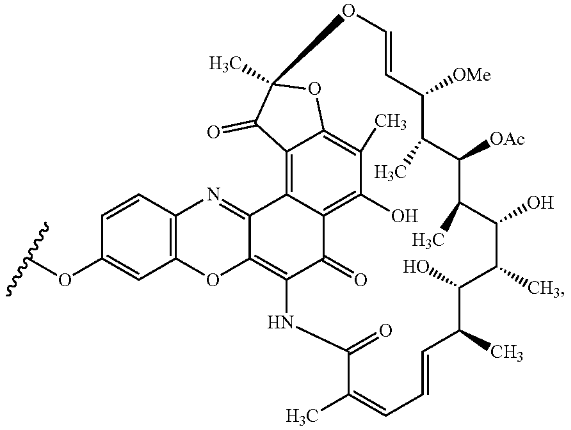
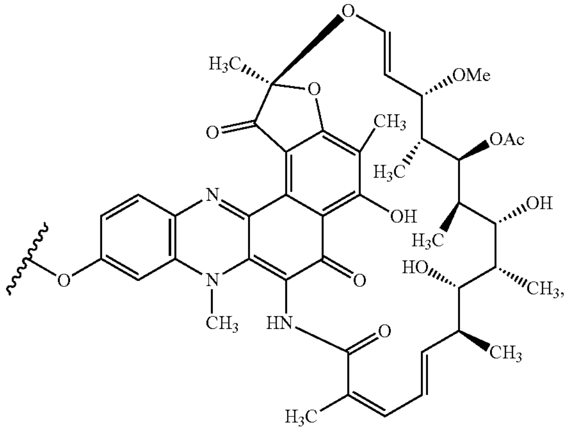
-continued
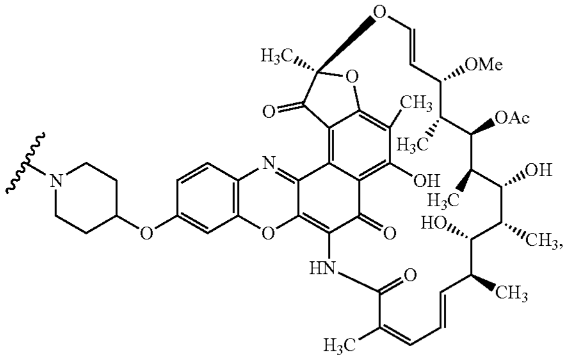
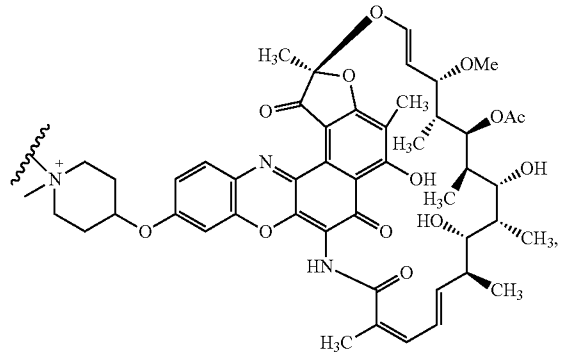
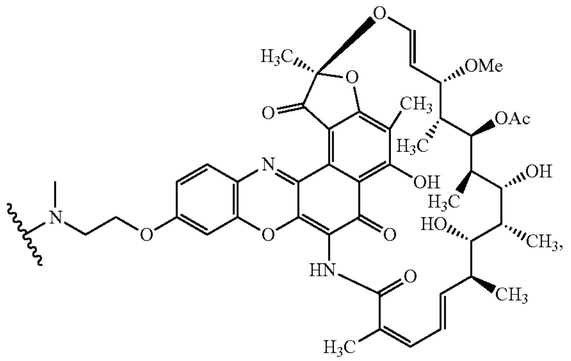
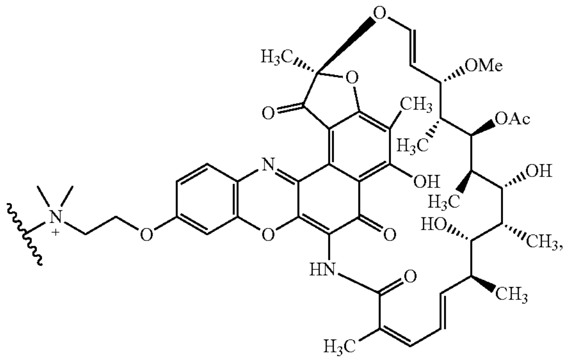

-continued
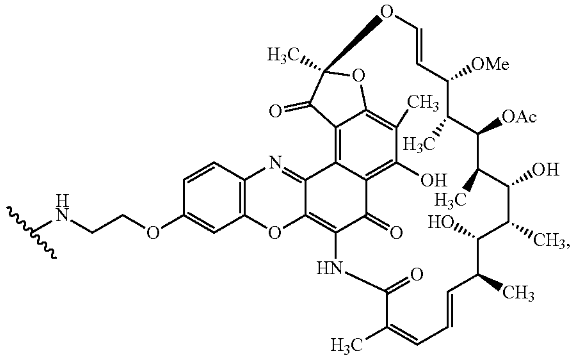
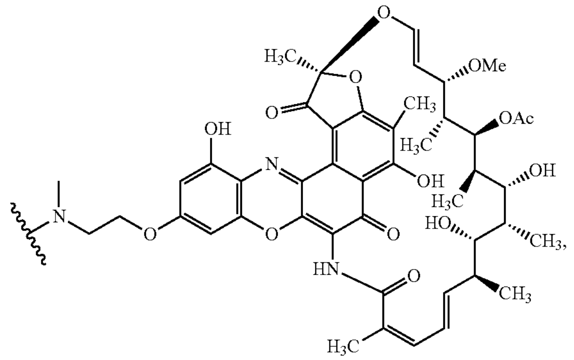
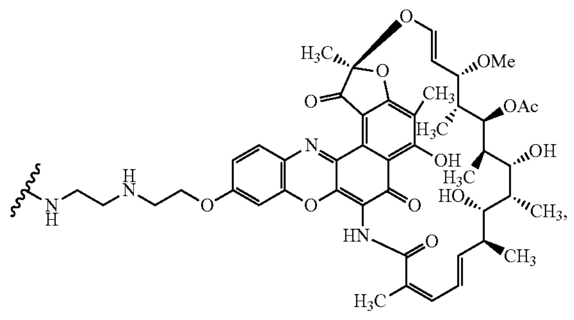
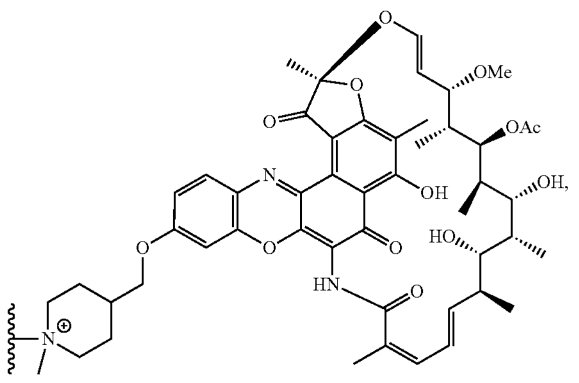
-continued
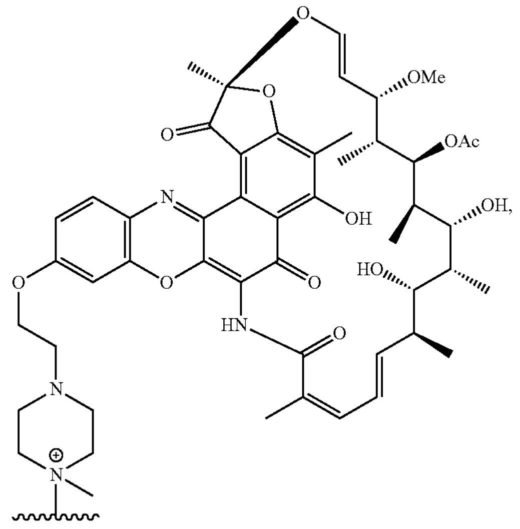
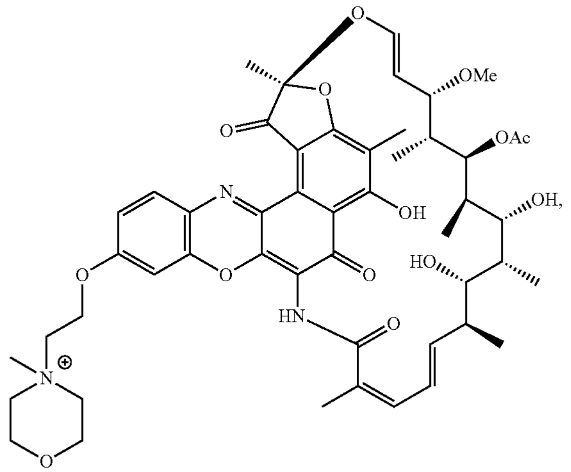
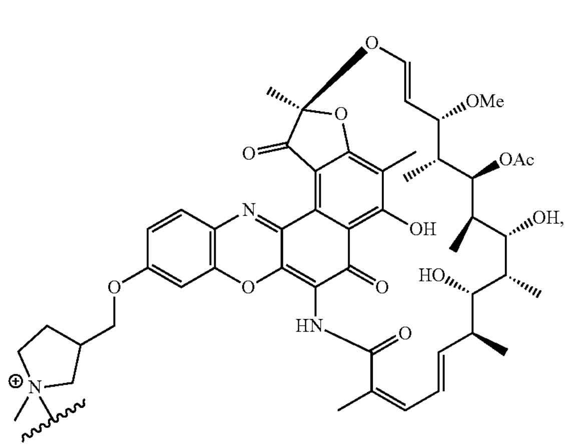

-continued
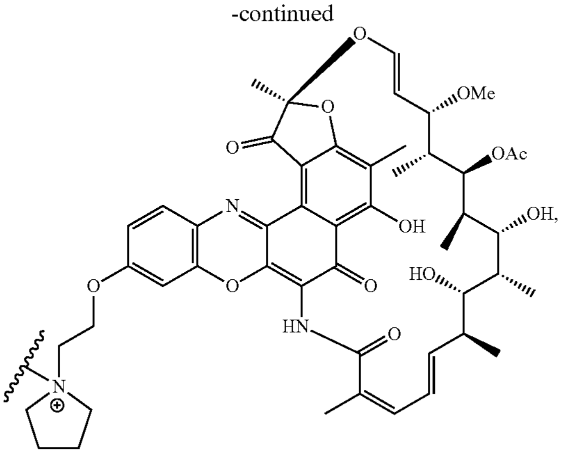
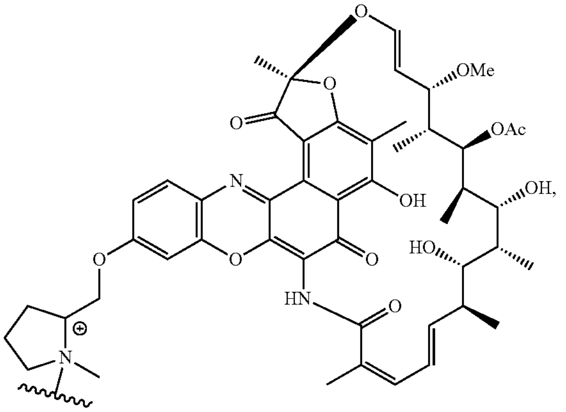
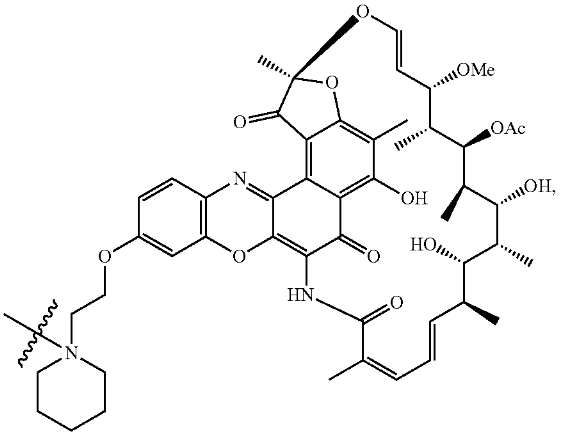
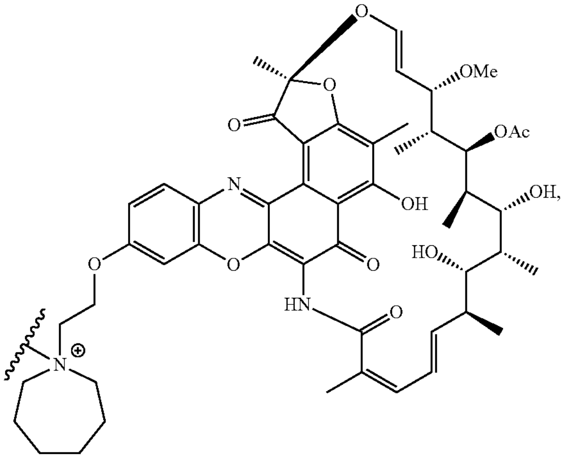
-continued
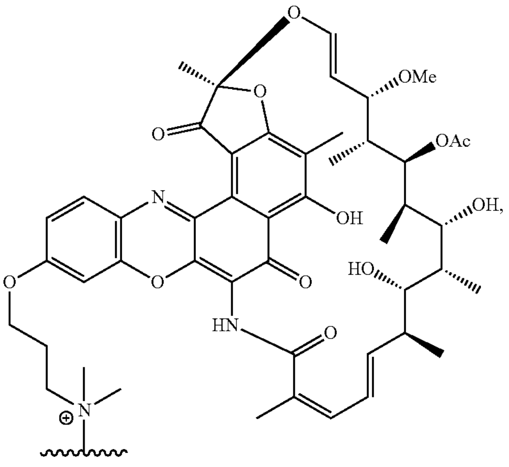
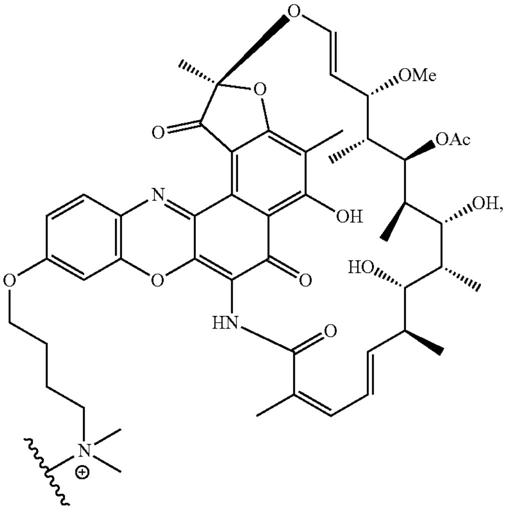
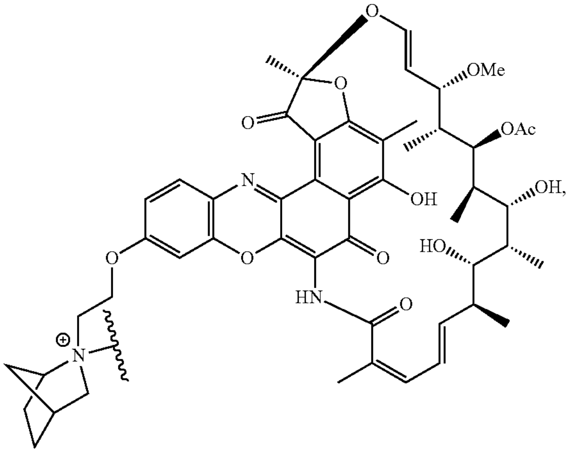

-continued
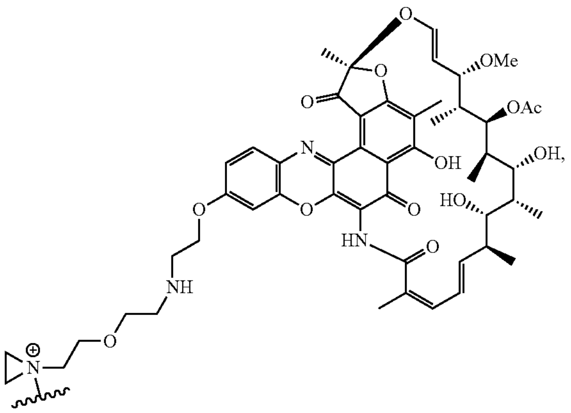
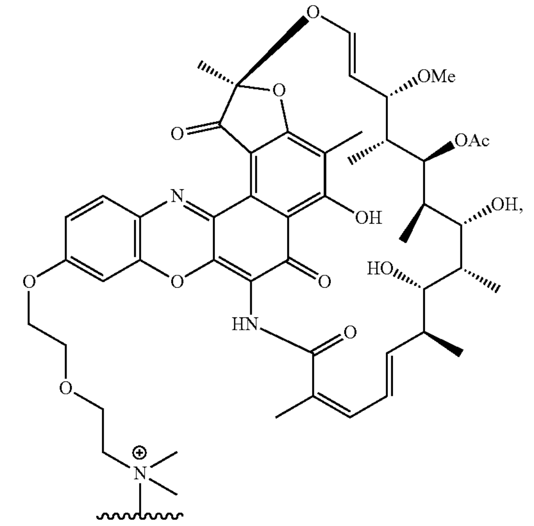
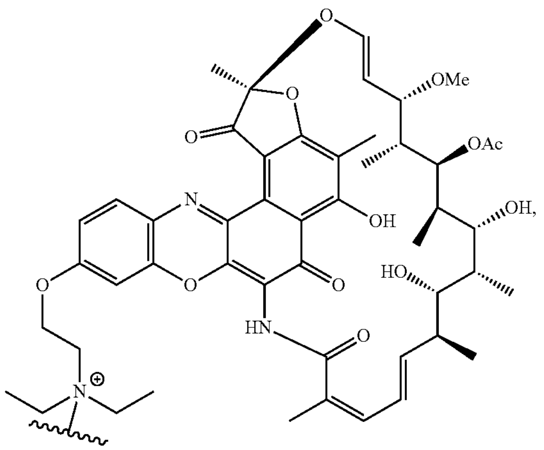
-continued
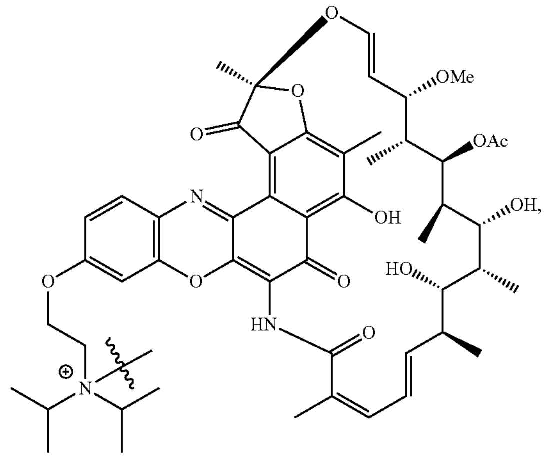
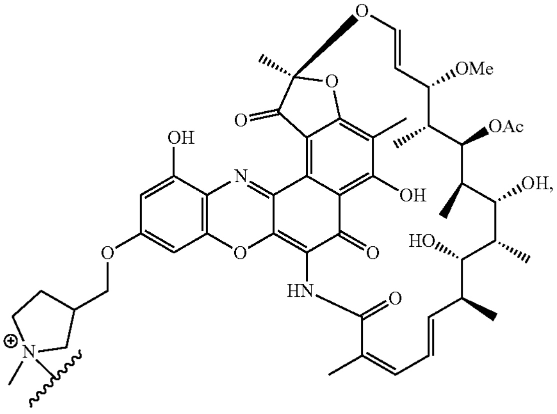
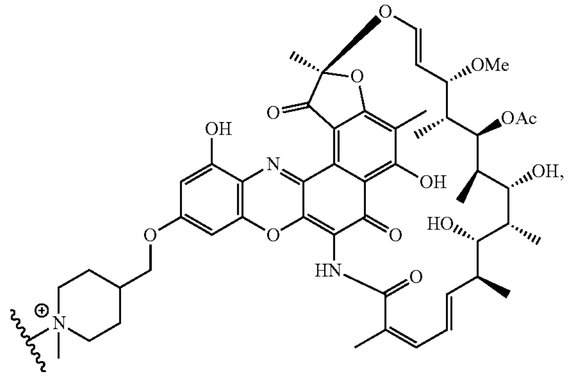
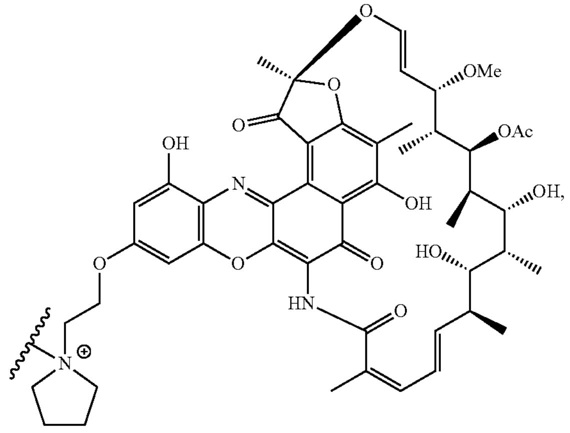

-continued
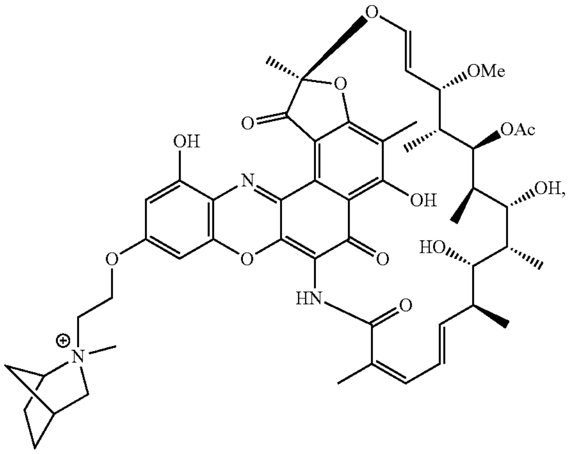
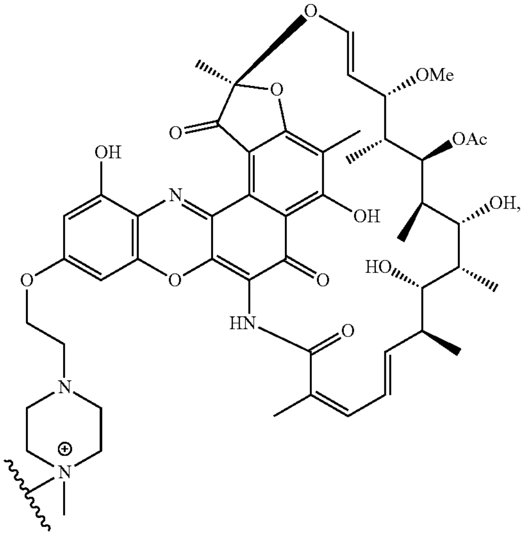
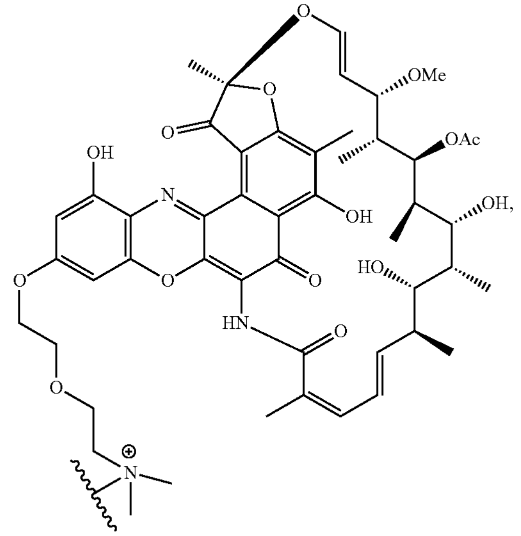
-continued
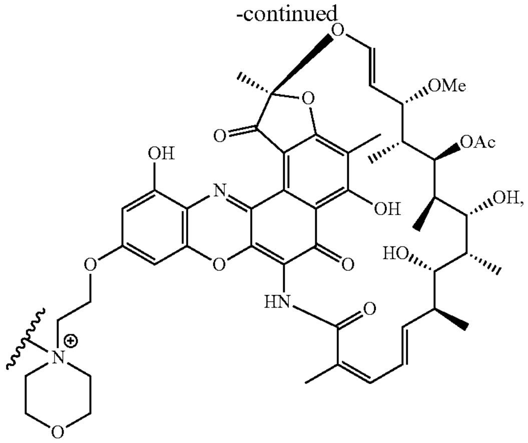
and
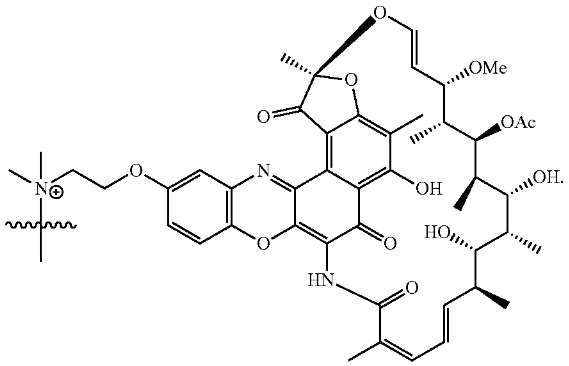
wherein the
is the bond to the linker.
In one aspect, the present disclosure provides an antibody-drug conjugate having the structure of Formula (XXII):

(XXII)

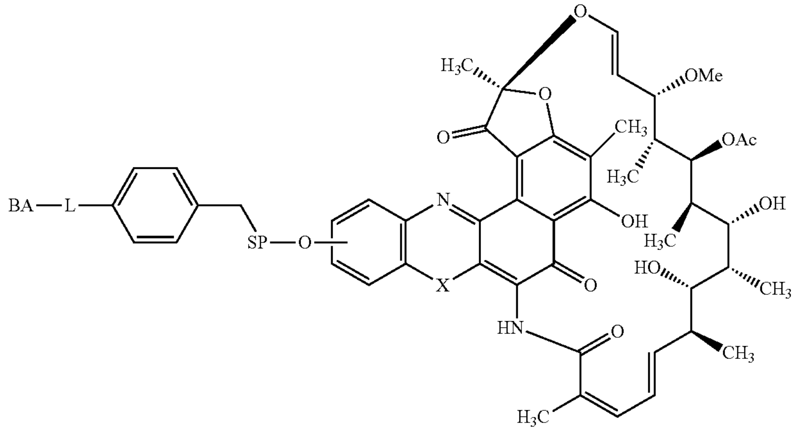

wherein:

BA is an antibody, or an antigen-binding fragment thereof;

L is a linker;

SP is a spacer group selected from

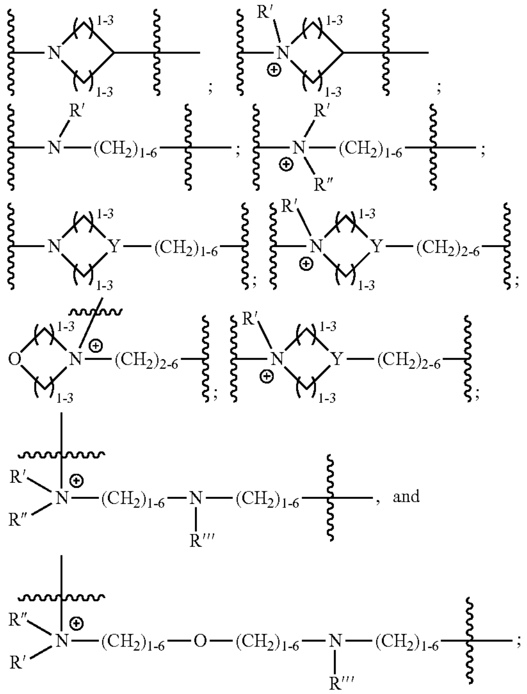

wherein Y is C or N; wherein the symbol represents the point of attachment; and R', R" and R'" are selected from a hydrogen, a $C_1$-$C_6$ aliphatic hydrocarbon, and a protecting group selected from Fluorenylmethyloxycarbonyl (FMOC) and tert-Butyloxycarbonyl (BOC), or wherein R' and R" together form an aliphatic monocyclic, an aliphatic bicyclic, or an aliphatic polycyclic structure;

R' and R" are independently at each occurrence selected from a hydrogen and a $C_{1-6}$ alkyl, and X is selected from —O—, —S—, and —NR*.

In some embodiments, the antibody, or antigen-binding fragment thereof, binds MSR1. In one embodiment, the anti-MSR1 antibody, or the antigen-binding fragment thereof, comprises: (a) the complementarity determining regions (CDRs) of a heavy chain variable region (HCVR) comprising an amino acid sequence as set forth in Table 9; and (b) the CDRs of a light chain variable region (LCVR) comprising an amino acid sequence as set forth in Table 9.

In one embodiment, the anti-MSR1 antibody, or the antigen-binding fragment thereof, comprises:

(i) a HCDR1 domain comprising an amino acid sequence selected from the group consisting of SEQ ID NOs: 4, 36, 52, 92, and 284;

(ii) a HCDR2 domain comprising an amino acid sequence selected from the group consisting of SEQ ID NOs: 6, 38, 54, 94, and 286;

(iii) a HCDR3 domain comprising an amino acid sequence selected from the group consisting of SEQ ID NOs: 8, 40, 56, 96, and 288;

(iv) a LCDR1 domain comprising an amino acid sequence selected from the group consisting of SEQ ID NOs: 12, 44, 60, 100, and 292;

(v) a LCDR2 domain comprising an amino acid sequence selected from the group consisting of SEQ ID NOs: 14, 46, 62, 102, and 294; and (vi) a LCDR3 domain comprising an amino acid sequence selected from the group consisting of SEQ ID NOs: 16, 48, 64, 104, and 296.

In one embodiment, the anti-MSR1 antibody, or the antigen-binding fragment thereof, comprises (i) a HCDR1 domain comprising an amino acid sequence of SEQ ID NO: 52;

(ii) a HCDR2 domain comprising an amino acid sequence of SEQ ID NO: 54;

(iii) a HCDR3 domain comprising an amino acid sequence of SEQ ID NO: 56;

(iv) a LCDR1 domain comprising an amino acid sequence of SEQ ID NO: 60;

(v) a LCDR2 domain comprising an amino acid sequence of SEQ ID NO: 62; and (vi) a LCDR3 domain comprising an amino acid sequence of SEQ ID NO: 64.

In one embodiment, the anti-MSR1 antibody, or the antigen-binding fragment thereof, comprises a N297Q mutation.

In some embodiments, the antibody, or antigen-binding fragment thereof, binds WTAα. In one embodiment, the anti-WTAα antibody, or the antigen-binding fragment thereof, comprises: (a) the complementarity determining regions (CDRs) of a heavy chain variable region (HCVR) comprising an amino acid sequence as set forth in Table 2A; and (b) the CDRs of a light chain variable region (LCVR) comprising an amino acid sequence as set forth in Table 2A.

In one embodiment, the anti-WTAα antibody, or an antigen-binding fragment thereof, comprises:

(i) a HCDR1 domain comprising an amino acid sequence selected from the group consisting of SEQ ID NOs: 470, 476, 482, and 488;
(ii) a HCDR2 domain comprising an amino acid sequence selected from the group consisting of SEQ ID NOs: 471, 477, 483, and 489;
(iii) a HCDR3 domain comprising an amino acid sequence selected from the group consisting of SEQ ID NOs: 472, 478, 484, and 490;
(iv) a LCDR1 domain comprising an amino acid sequence selected from the group consisting of SEQ ID NOs: 467, 473, 479, and 485;
(v) a LCDR2 domain comprising an amino acid sequence selected from the group consisting of SEQ ID NOs: 468, 474, 480, and 486; and
(vi) a LCDR3 domain comprising an amino acid sequence selected from the group consisting of SEQ ID NOs: 469, 475, 481, and 487.

In some embodiments, the antibody, or antigen-binding fragment thereof, binds WTAβ. In one embodiment, the anti-WTAβ antibody, or the antigen-binding fragment thereof, comprises: (a) the complementarity determining regions (CDRs) of a heavy chain variable region (HCVR) comprising an amino acid sequence as set forth in Table 2B; and (b) the CDRs of a light chain variable region (LCVR) comprising an amino acid sequence as set forth in Table 2B.

In one embodiment, the anti-WTA antibody, or an antigen-binding fragment thereof, comprises:

(i) a HCDR1 domain comprising an amino acid sequence selected from the group consisting of SEQ ID NOs: 502, 508, 514, 520, 526, 532, 538, 544, 550, 556, 562, 568, and 574;
(ii) a HCDR2 domain comprising an amino acid sequence selected from the group consisting of SEQ ID NOs: 503, 509, 515, 521, 527, 533, 539, 545, 551, 557, 563, 569, and 575;
(iii) a HCDR3 domain comprising an amino acid sequence selected from the group consisting of SEQ ID NOs: 504, 510, 516, 522, 528, 534, 540, 546, 552, 558, 564, 570, 576, and 584;
(iv) a LCDR1 domain comprising an amino acid sequence selected from the group consisting of SEQ ID NOs: 499, 505, 511, 517, 523, 529, 535, 541, 547, 553, 559, 565, and 571;
(v) a LCDR2 domain comprising an amino acid sequence selected from the group consisting of SEQ ID NOs: 500, 506, 512, 518, 524, 530, 536, 542, 548, 554, 560, 566, and 572; and
(vi) a LCDR3 domain comprising an amino acid sequence selected from the group consisting of SEQ ID NOs: 501, 507, 513, 519, 525, 531, 537, 543, 549, 555, 561, 567, and 573.

In some embodiments, the anti-WTA antibody, or the antigen-binding fragment thereof, comprises a V205C mutation.

In one embodiment, the anti-WTA antibody, or the antigen-binding fragment thereof, is derived from antibody 4497 described in US Patent Application Publication 20140356375 (which is incorporated herein by reference in its entirety). In one embodiment, the anti-WTA antibody is derived from antibody 4497 and further comprises a V205C mutation in the light chain.

In one embodiment, the anti-WTA antibody, or the antigen-binding fragment thereof, comprises the HCDR1-HCDR2-HCDR3-LCDR1-LCDR2-LCDR3 of SEQ ID Nos: 568-569-570-565-566-567.

In some embodiments, the anti-WTA antibody or antigen binding fragment thereof comprises three heavy chain complementarity determining regions (HCDR1, HCDR2, and HCDR3) within a heavy chain variable region (HCVR) amino acid sequence of SEQ ID NOs: 586; and three light chain complementarity determining regions (LCDR1, LCDR2, and LCDR3) within a light chain variable region (LCVR) amino acid sequence of SEQ ID NO: 585.

In some embodiments, the anti-WTA antibody or antigen binding fragment thereof comprises an HCVR amino acid sequence of SEQ ID NOs: 586, and an LCVR amino acid sequence of SEQ ID NO: 585.

In some embodiments, the anti-WTA antibody comprises a heavy chain amino acid sequence of SEQ ID NOs: 602 and a light chain amino acid sequence of SEQ ID NO: 587 or SEQ ID NO: 589. In some embodiments, the anti-WTA antibody, or the antigen-binding fragment thereof comprises a V205C mutation in the light chain.

In some embodiments, the antibody, or antigen-binding fragment thereof, binds Protein A. In one embodiment, the anti-Protein A antibody, or the antigen-binding fragment thereof, may comprise: (a) the complementarity determining regions (CDRs) of a heavy chain variable region (HCVR) comprising an amino acid sequence as set forth in Table 3A; and (b) the CDRs of a light chain variable region (LCVR) comprising an amino acid sequence as set forth in Table 3A.

In one embodiment, the anti-Protein A antibody, or the antigen-binding fragment thereof, may comprise:

(i) a HCDR1 domain comprising an amino acid sequence selected from the group consisting of SEQ ID NOs: 632, 652, and 672;
(ii) a HCDR2 domain comprising an amino acid sequence selected from the group consisting of SEQ ID NOs: 634, 654, and 674;
(iii) a HCDR3 domain comprising an amino acid sequence selected from the group consisting of SEQ ID NOs: 636, 656, and 676;
(iv) a LCDR1 domain comprising an amino acid sequence selected from the group consisting of SEQ ID NOs: 640, 660, and 680;
(v) a LCDR2 domain comprising an amino acid sequence selected from the group consisting of SEQ ID NOs: 642 and 662; and
(vi) a LCDR3 domain comprising an amino acid sequence selected from the group consisting of SEQ ID NOs: 644, 664, and 683.

In some embodiments, the anti-Protein A antibody, or the antigen-binding fragment thereof, comprises a H435R and a Y436F mutation (EU numbering) in the heavy chain Fc.

In one embodiment, the anti-Protein A antibody or antigen binding fragment thereof comprises three heavy chain complementarity determining regions (HCDR1, HCDR2, and HCDR3) within a heavy chain variable region (HCVR) amino acid sequence of SEQ ID NOs: 630; and three light chain complementarity determining regions (LCDR1, LCDR2, and LCDR3) within a light chain variable region (LCVR) amino acid sequence of SEQ ID NO: 638. In one embodiment, the anti-Protein A antibody or antigen binding fragment thereof comprises a set of six CDRs (HCDR1-

HCDR2-HCDR3-LCDR1-LCDR2-LCDR3) comprising SEQ ID NOs: 632-634-636-640-642-644.

In one embodiment, the anti-Protein A antibody or antigen binding fragment thereof comprises an HCVR amino acid sequence of SEQ ID NOs: 630; and an LCVR amino acid sequence of SEQ ID NO: 638.

In one embodiment, the anti-Protein A antibody comprises a heavy chain amino acid sequence of SEQ ID NOs: 666 and a light chain amino acid sequence of SEQ ID NO: 668. In one embodiments, the anti-Protein A antibody, further comprises a H435R and a Y436F mutation (EU numbering) in the heavy chain Fc. In one embodiment, anti-Protein A antibody further comprises a C103S mutation in the light chain. In one embodiment, the anti-Protein A antibody, or antigen-binding fragment thereof, is conjugated to a compound of the present disclosure at light chain position 103.

In various embodiments, the antibody, or antigen-binding fragment thereof, comprises a C103S mutation in the light chain.

The various embodiments, the antibody, or the antigen-binding fragment thereof, is conjugated to a compound of the present disclosure at position 103 of the light chain.

In one embodiment, L is a linker having the formula

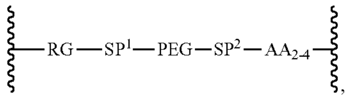, wherein

RG is selected from a maleimide, a N-hydroxysuccinimide, or a succinimide;

$SP^1$ and $SP^2$ are independently absent or a spacer group selected from the group consisting of

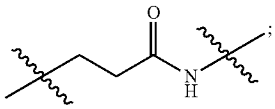 [SMILES: *CCC(=O)N*];

$C_{1-6}$ alkyl, $-NH-$, $-C(O)-$, $-CH_2-CH_2-C(O)-NH-$, $-(CH)_u-C(O)-NH-$, $(-CH_2-CH_2-O)_e$, $-NH-CH_2-CH_2-(-O-CH_2-CH_2)_e-C(O)-$, $-C(O)-(CH_2)_u-C(O)-$, $-C(O)-NH-(CH_2)_v-$, and combinations thereof, wherein subscript e is an integer from 0 to 4, subscript u is an integer from 1 to 8, and subscript v is an integer from 1 to 8;

$AA_{2-4}$ is a peptide unit comprising from 2 to 4 amino acids, and

PEG is a polyethylene glycol chain comprising between 1 and 30 polyethylene glycol residues.

In one embodiment, $AA_{2-4}$ is a dipeptide selected from valine-citrulline; citrulline-valine; valine-alanine; alanine-valine; valine-glycine, or glycine-valine.

In one embodiment, $AA_{2-4}$ is valine-citrulline.

In one embodiment, SP is

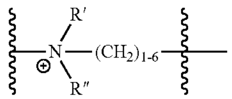

and R' and R" are each a $C_{1-6}$ alkyl.

In one embodiment, SP is

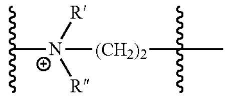

and R' and R" are each methyl.

In one embodiment, $SP^1$ and $SP^2$ are each

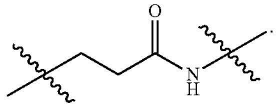.

In one embodiment, PEG comprises 8 polyethylene glycol units.

In one embodiment, the antibody-drug conjugate has a structure:

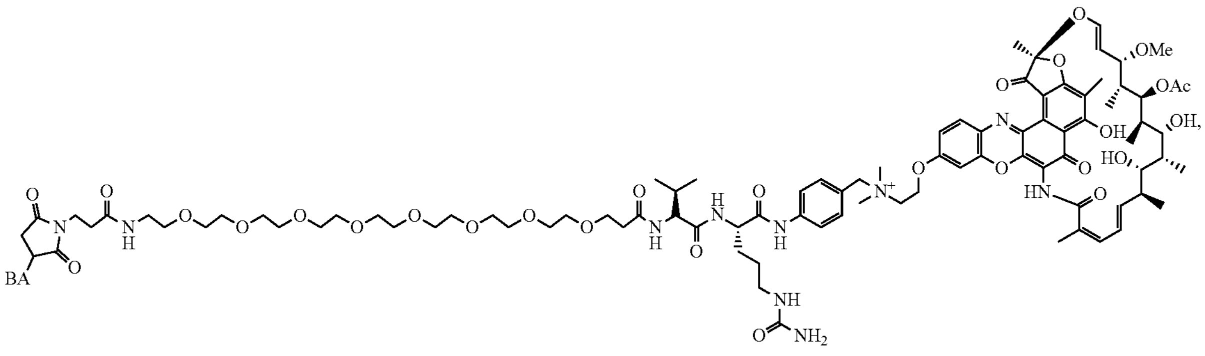

wherein BA is an antibody, or an antigen-binding fragment thereof.

In another aspect, the present disclosure provides an isolated antibody or antigen binding fragment thereof, wherein the antibody or antigen binding fragment thereof is conjugated, directly or through a linker or a linker-spacer, to a payload having the structure selected from the group consisting of:

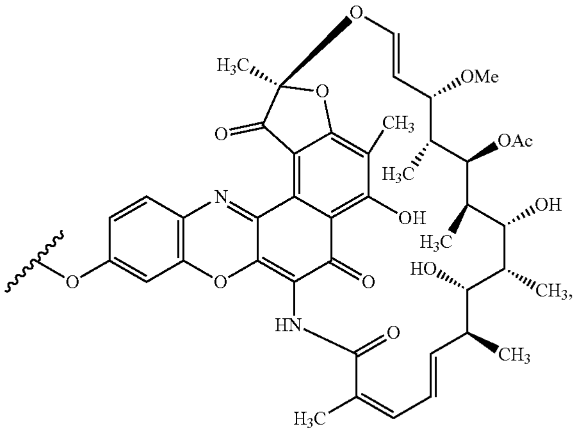

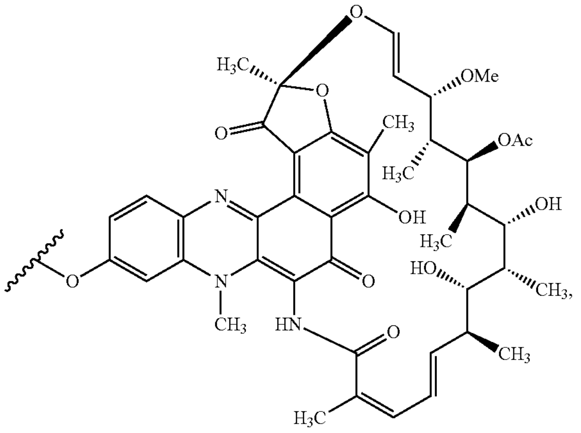

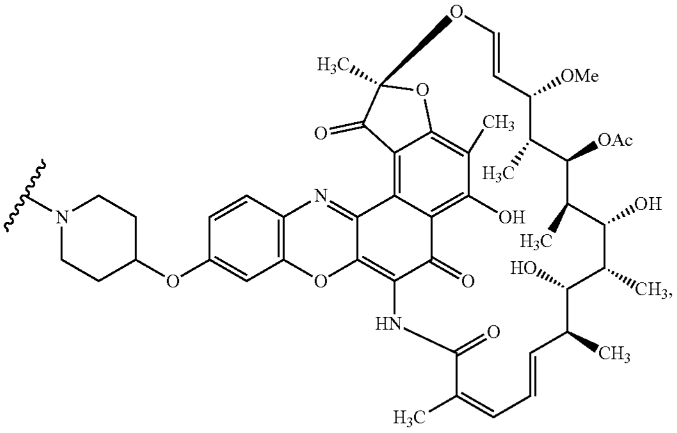

-continued
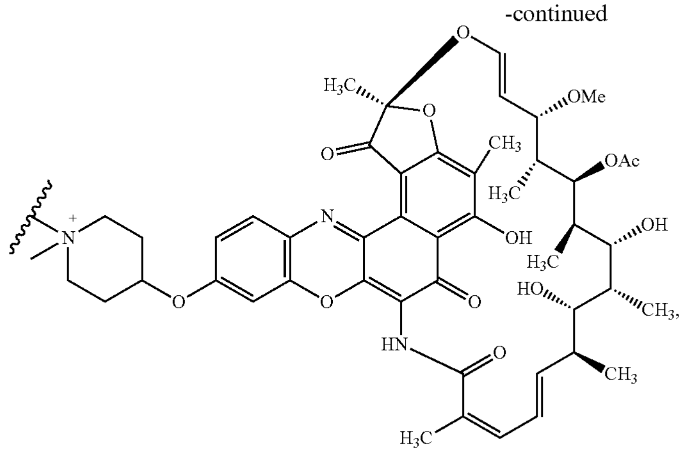
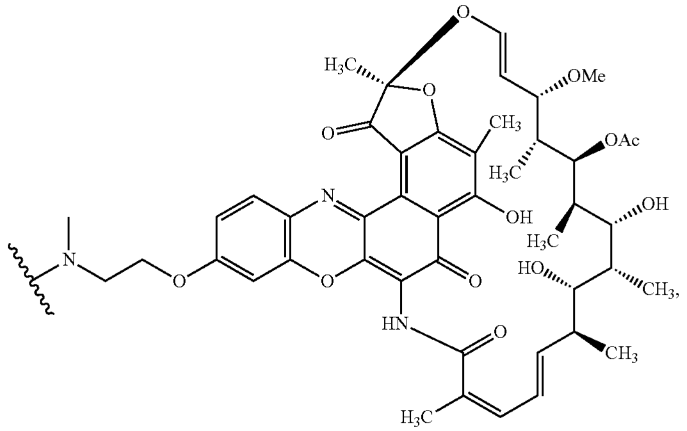
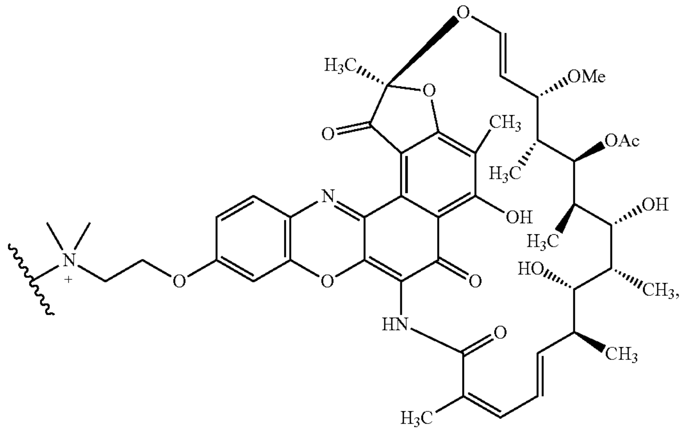
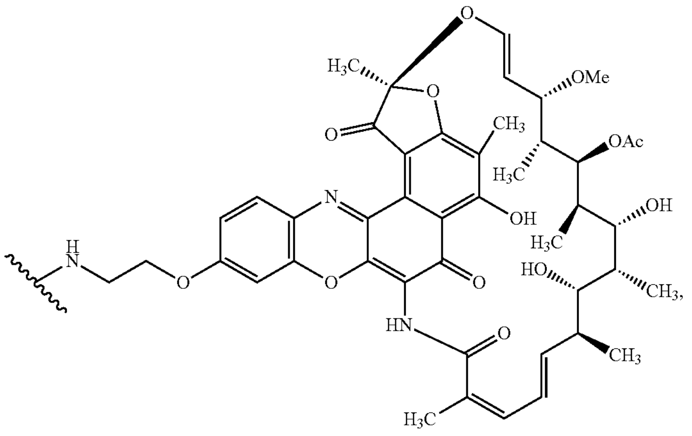

-continued
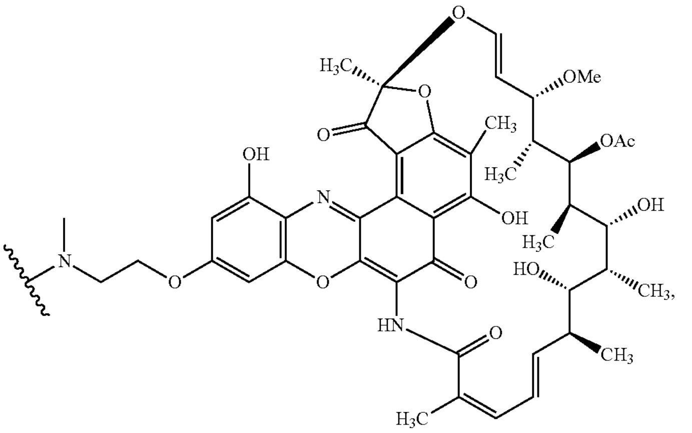
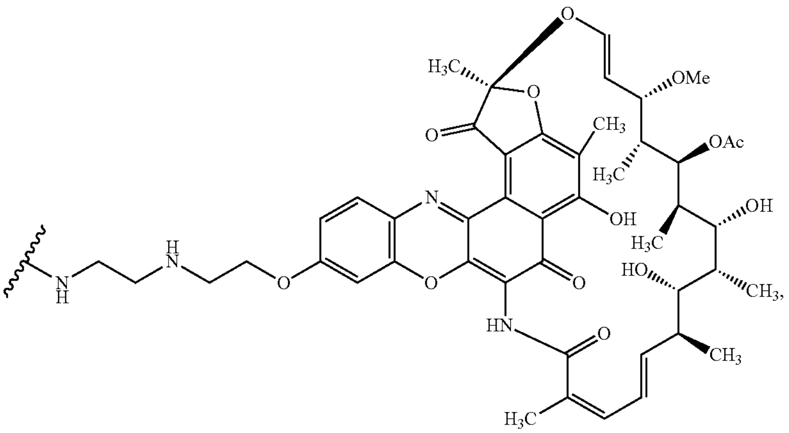
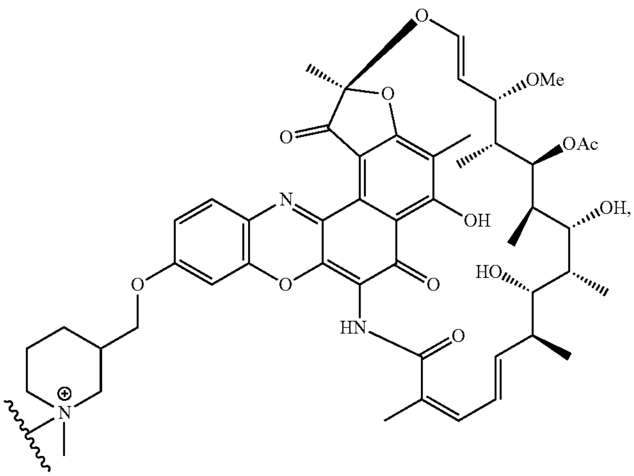

-continued
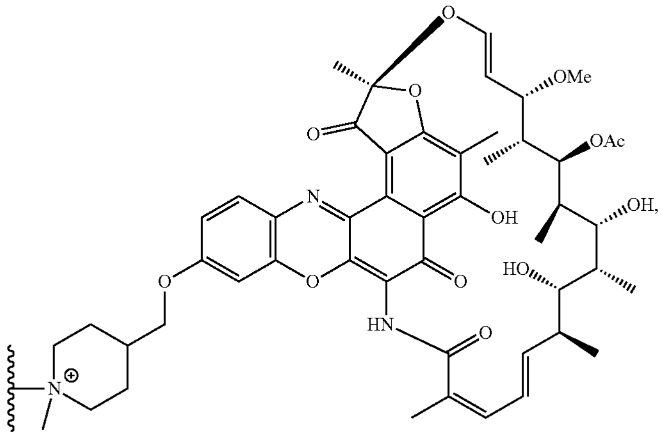
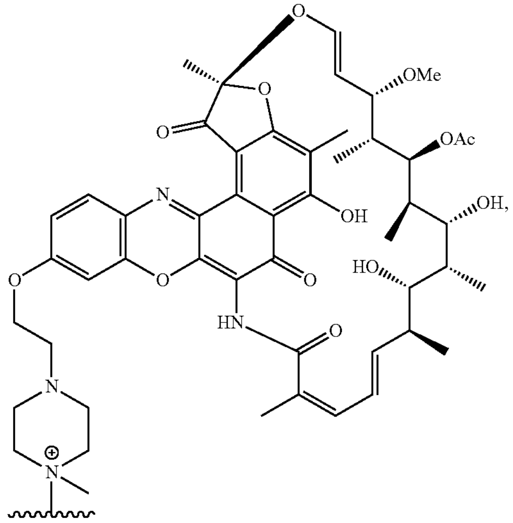
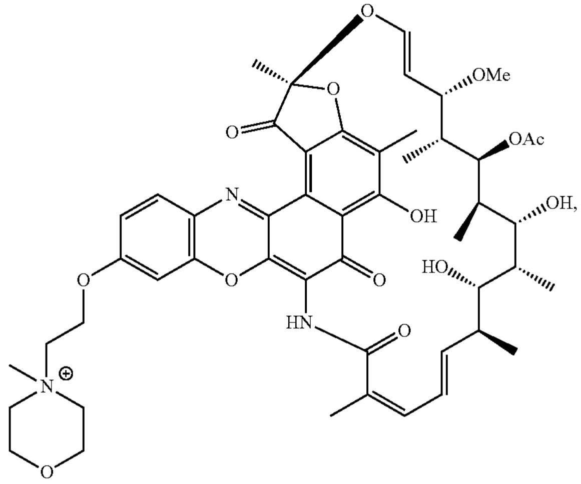
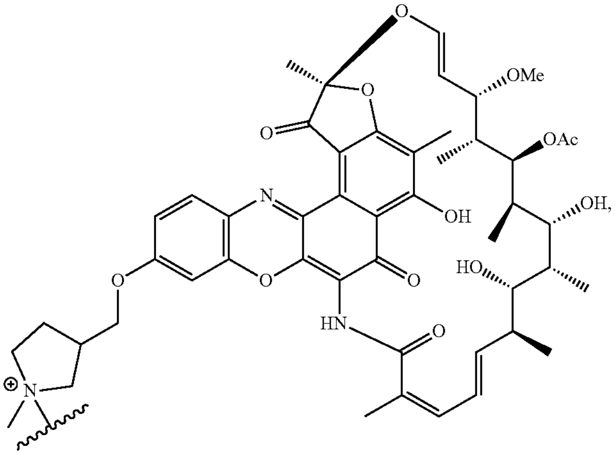

-continued
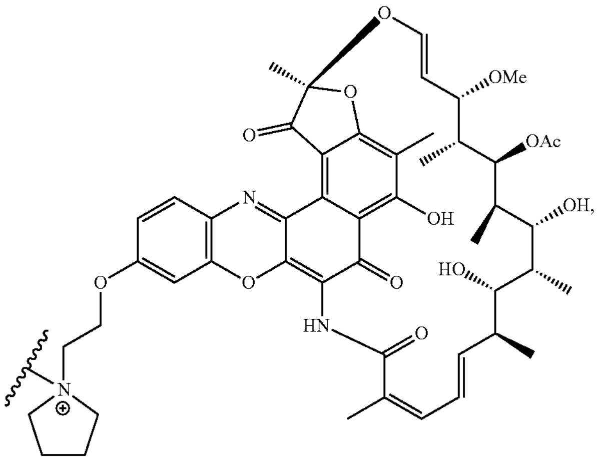
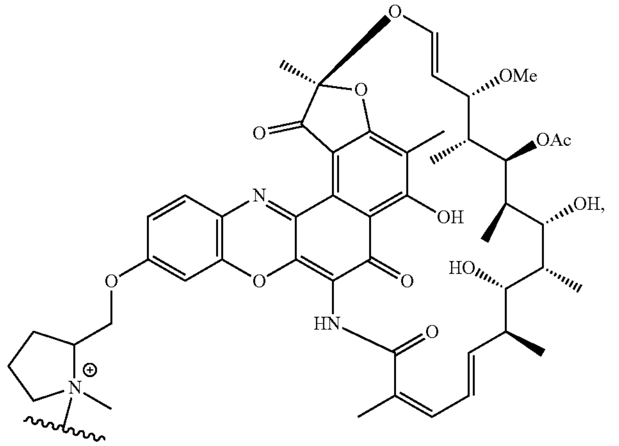
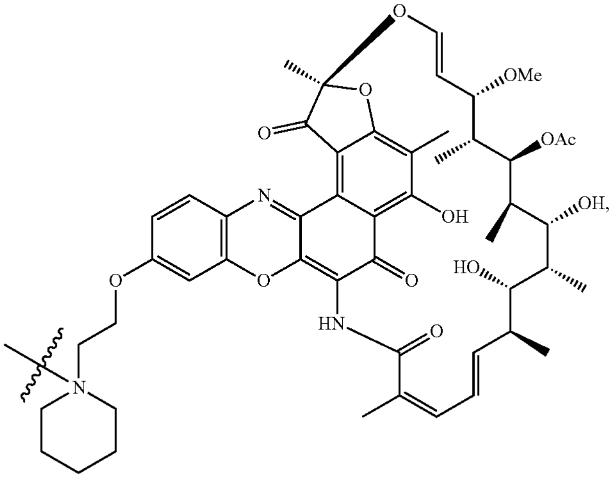

-continued
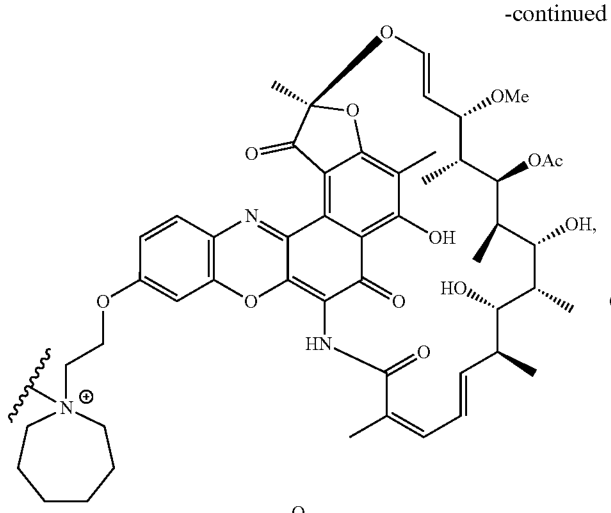
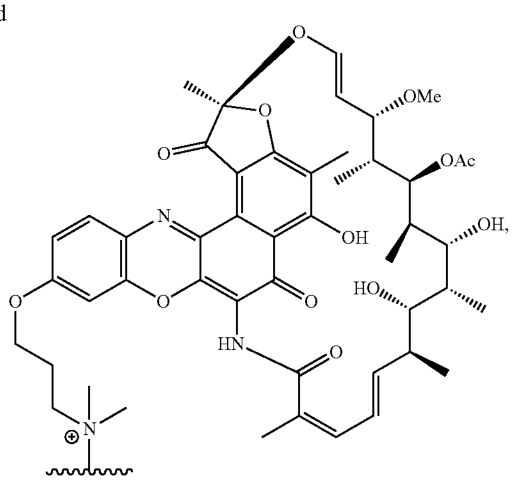
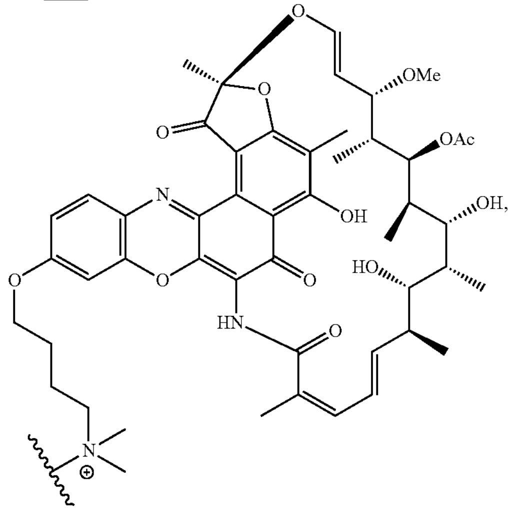
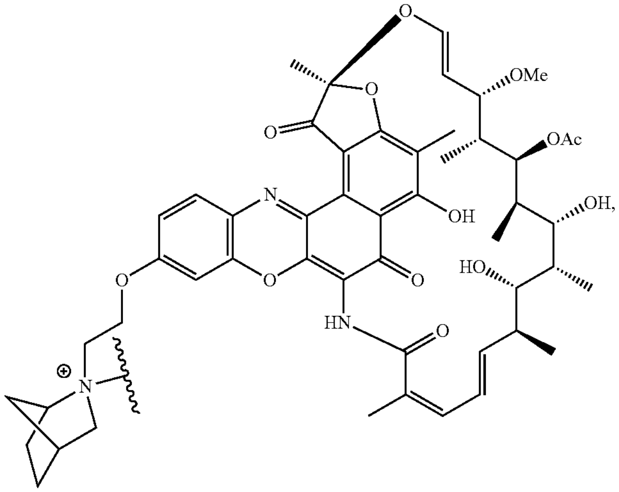
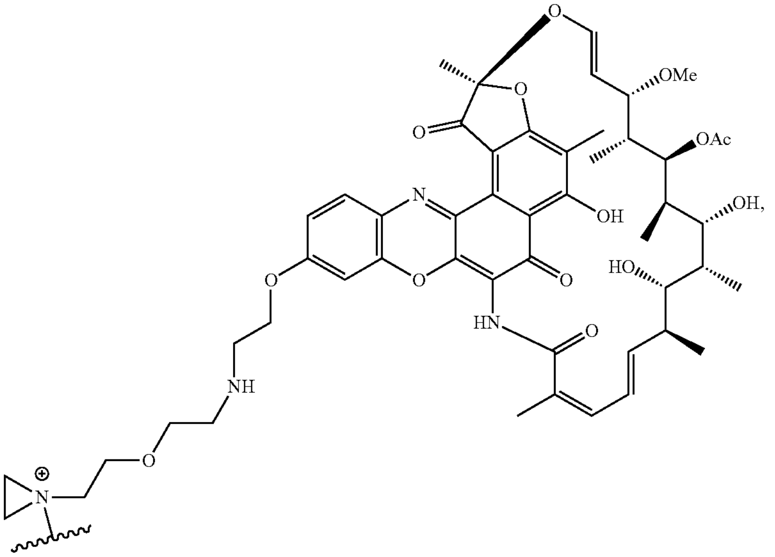

-continued
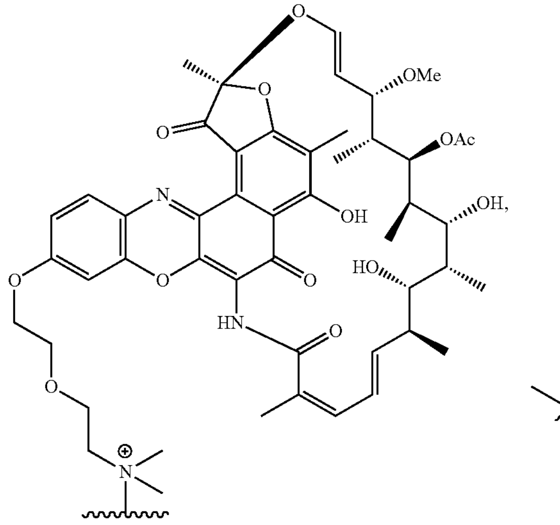
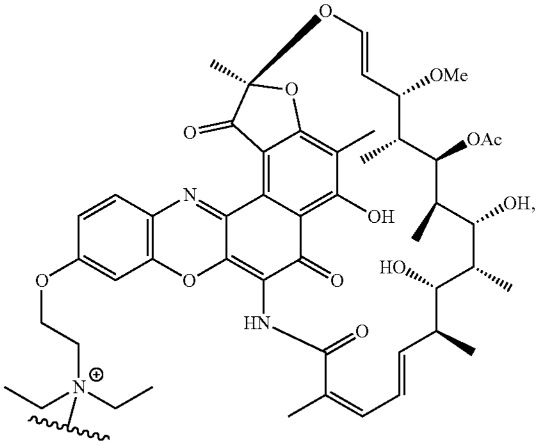
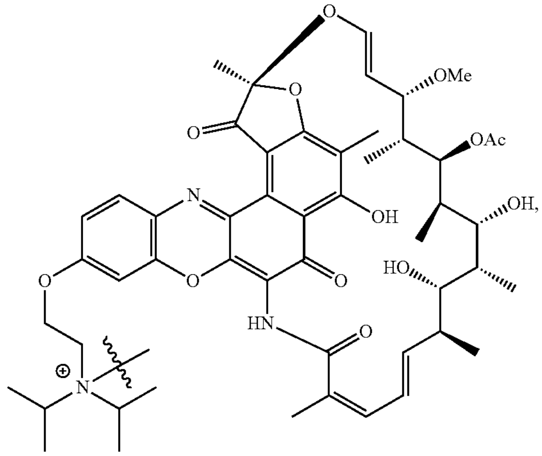
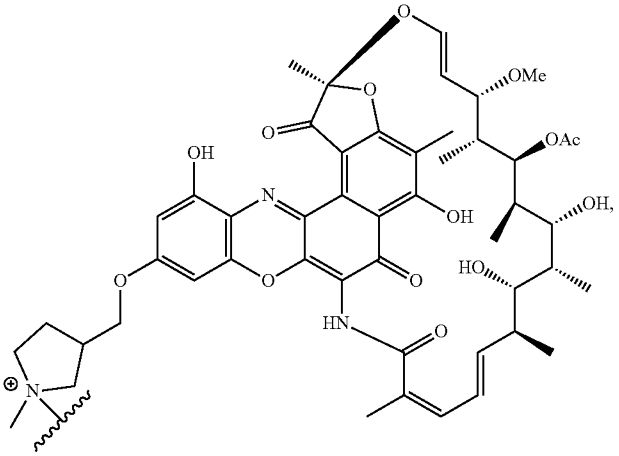

-continued
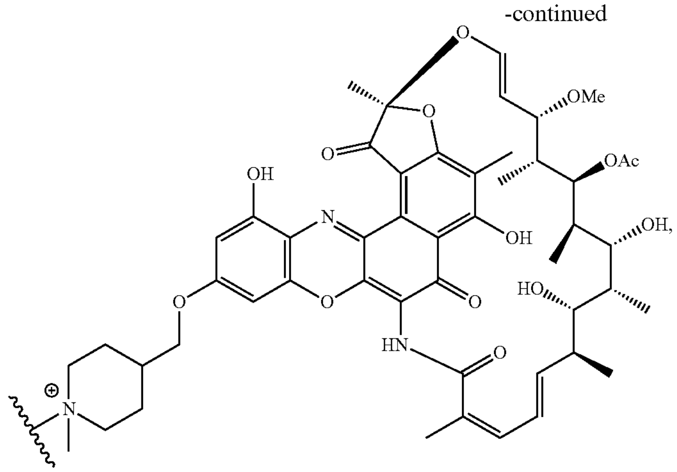
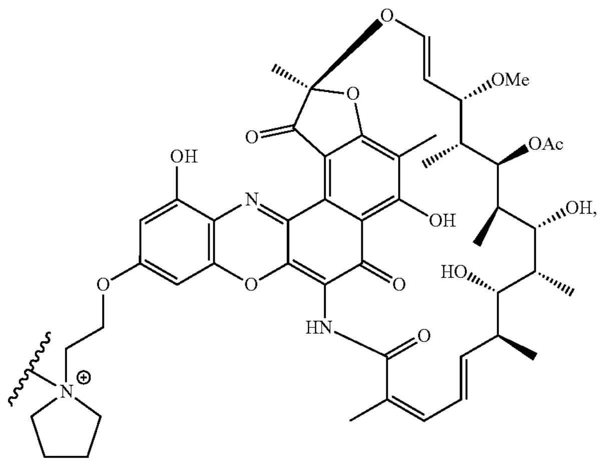
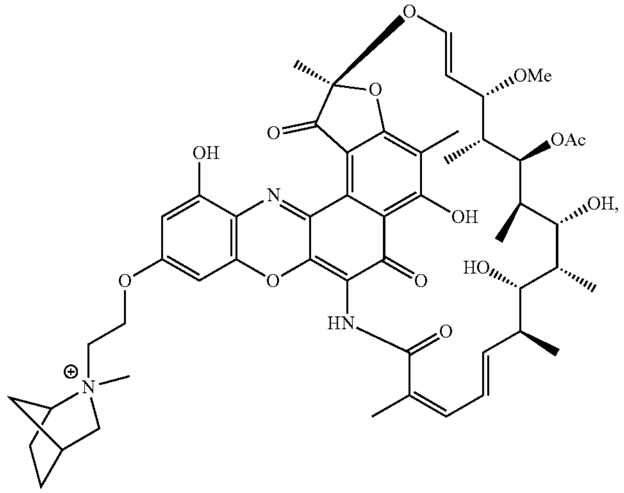
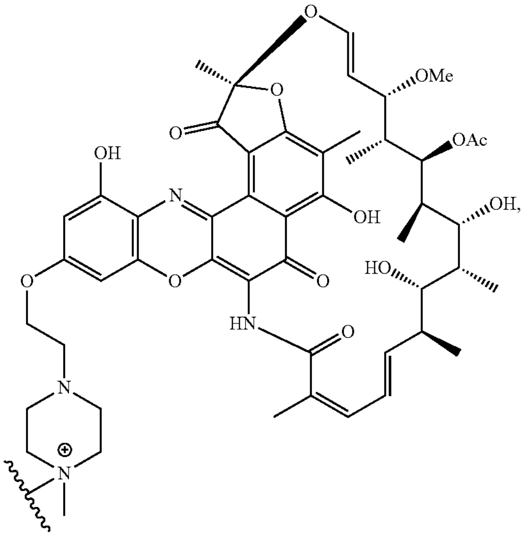

-continued
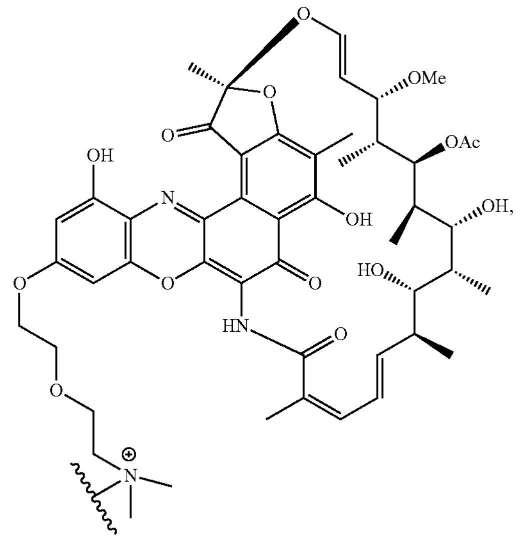
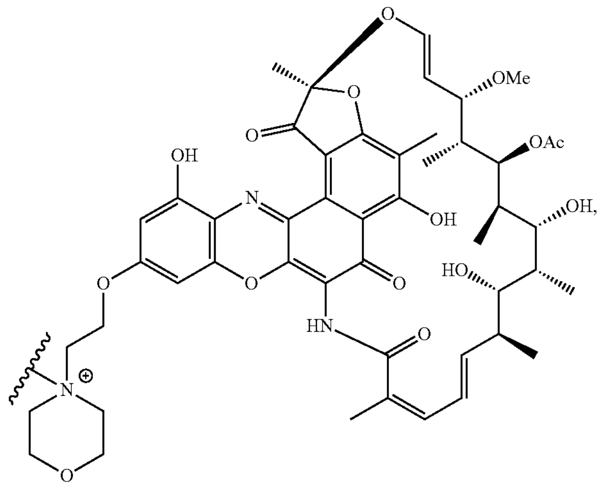
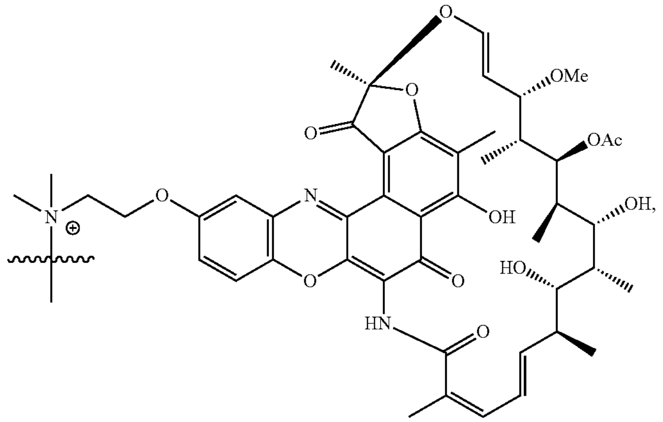
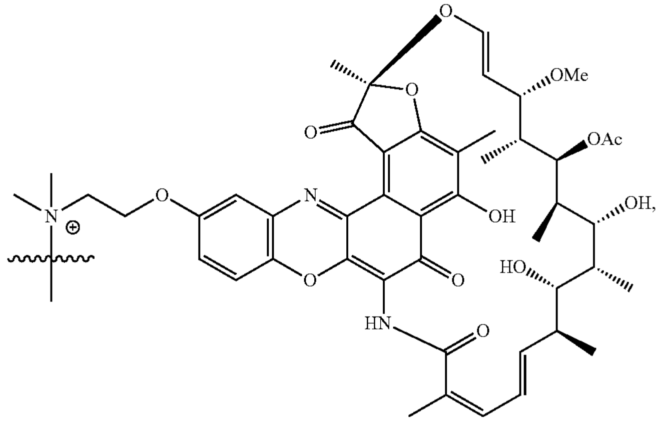

-continued
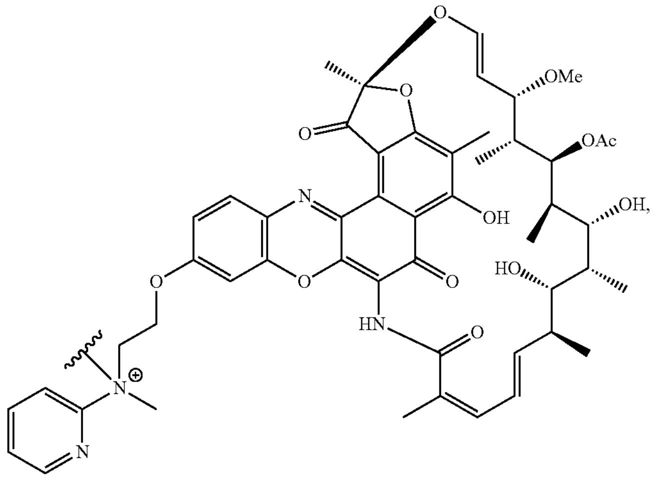
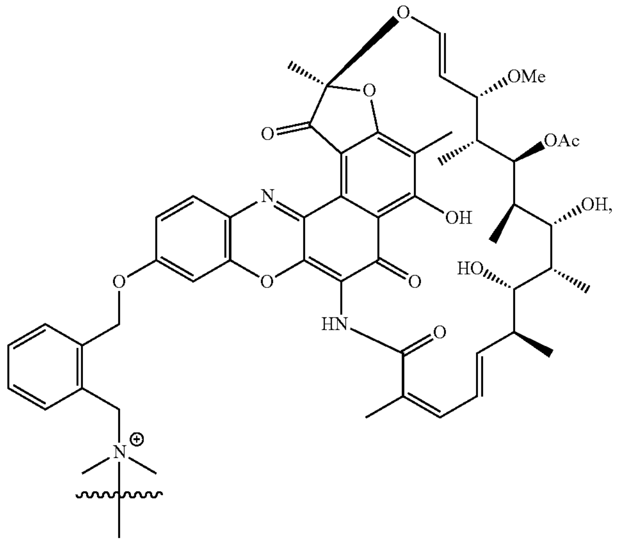
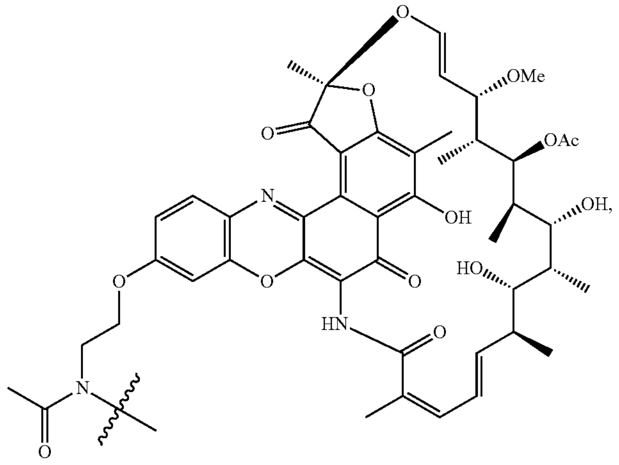

-continued
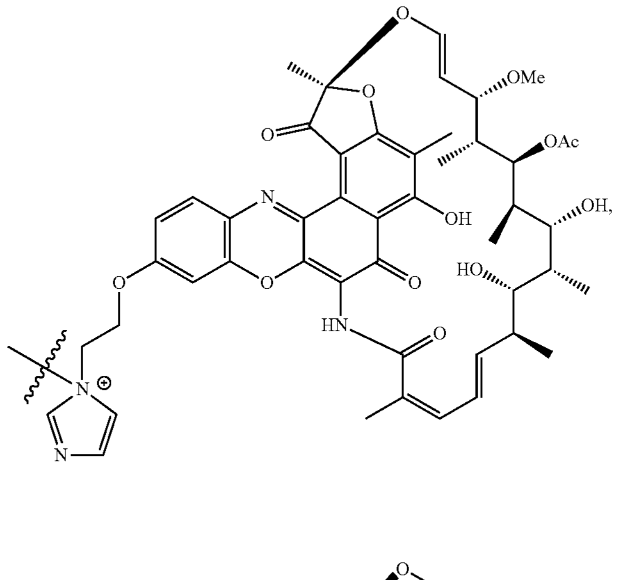
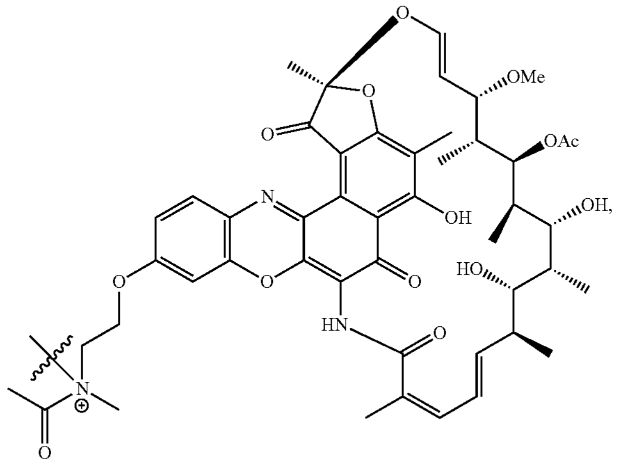
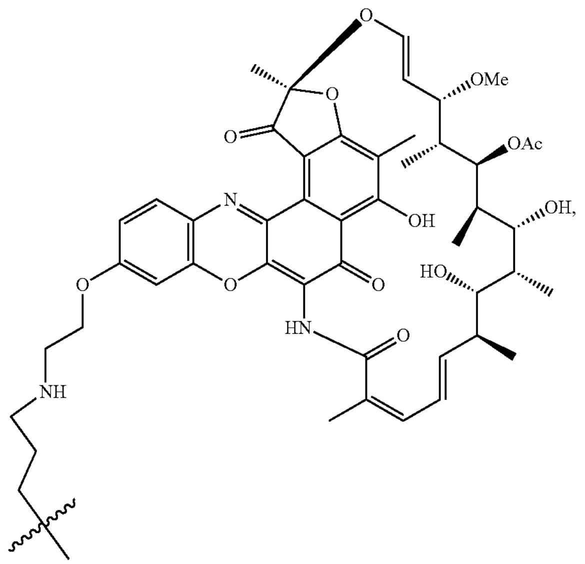

-continued
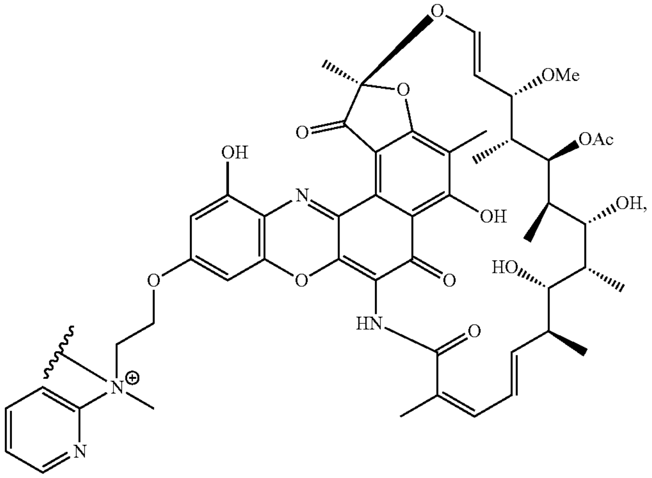
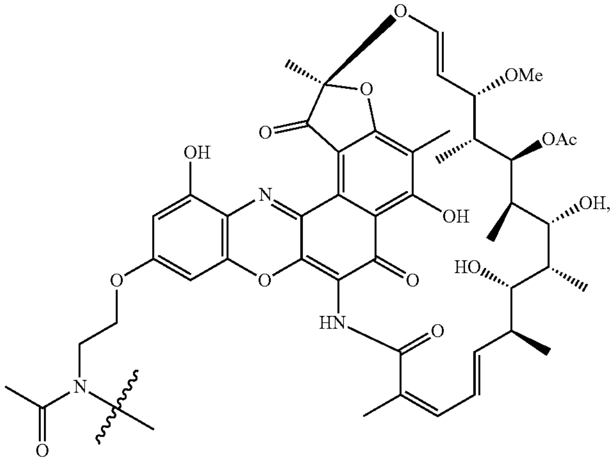
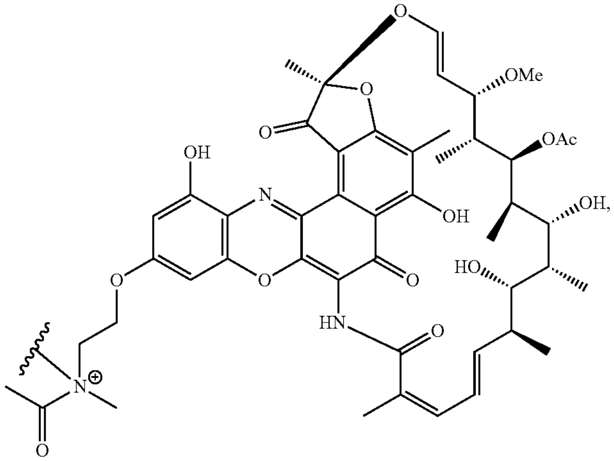

-continued
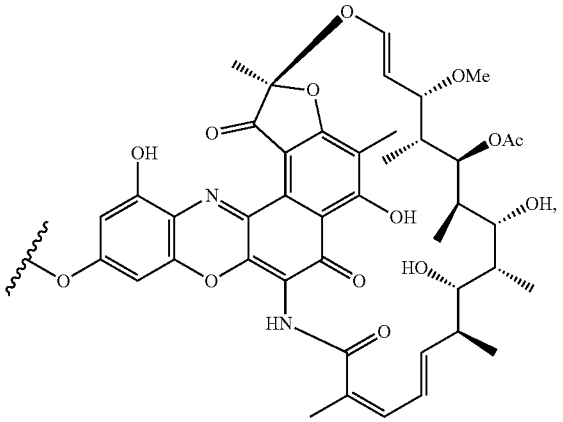
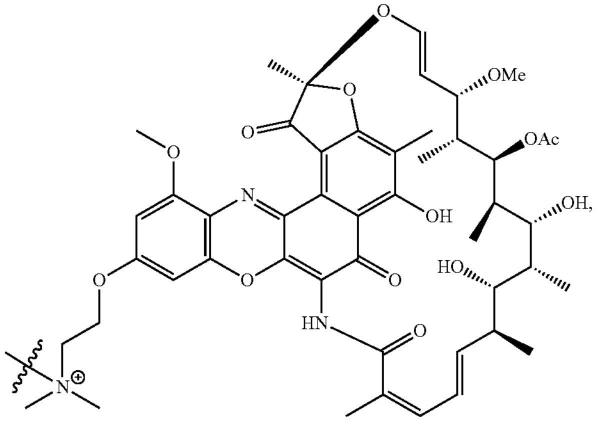
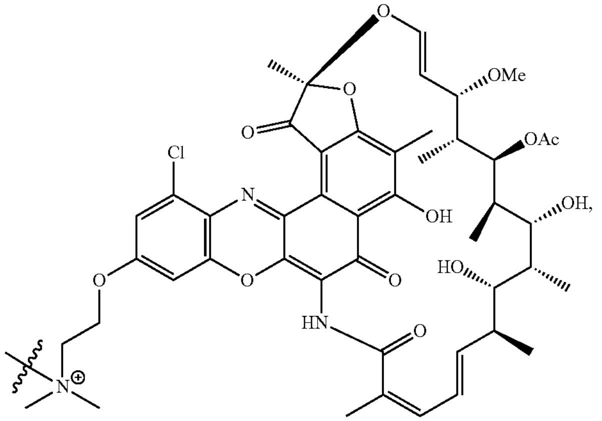
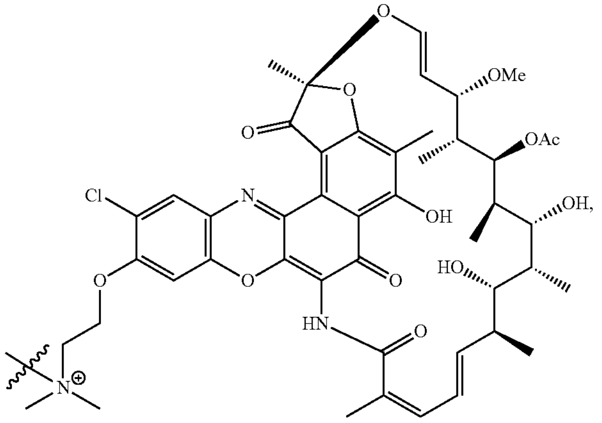

-continued
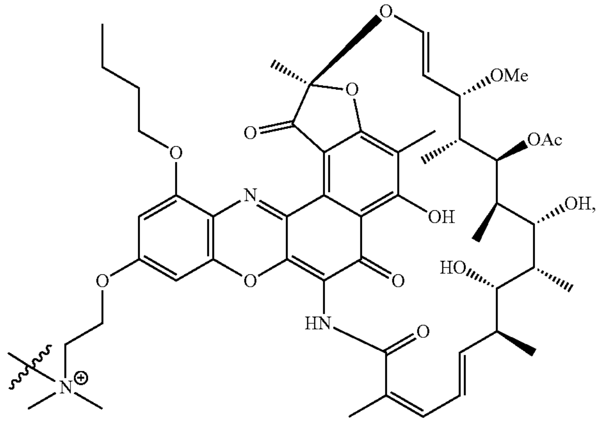
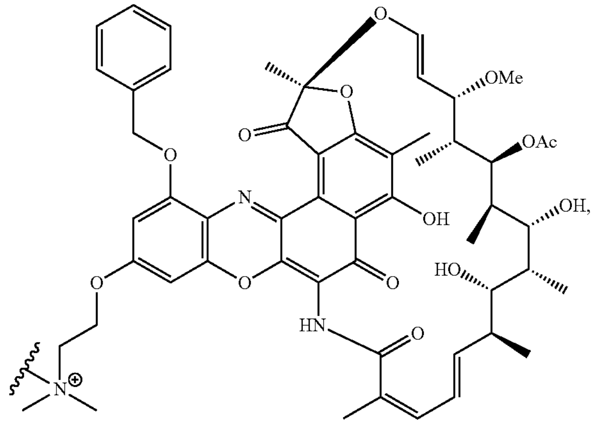
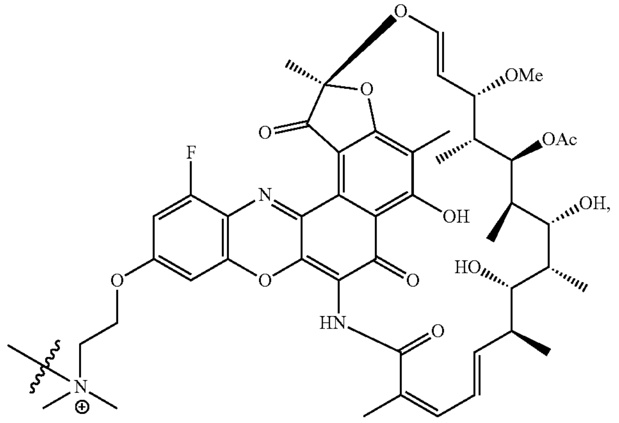
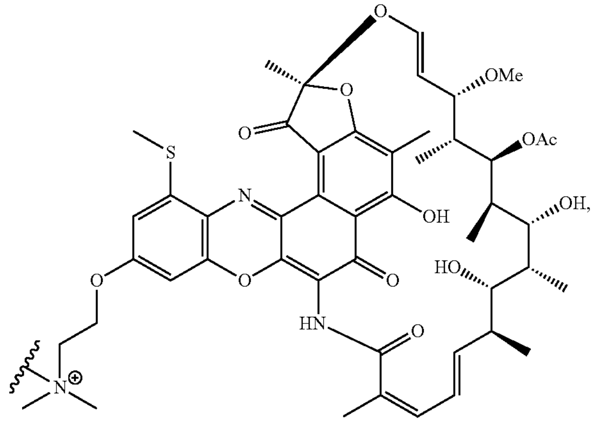

-continued
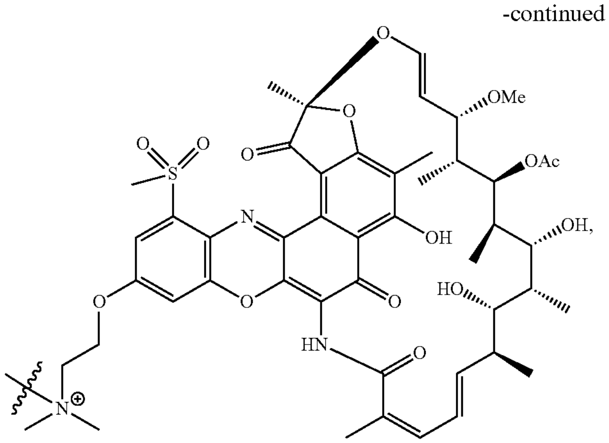
,
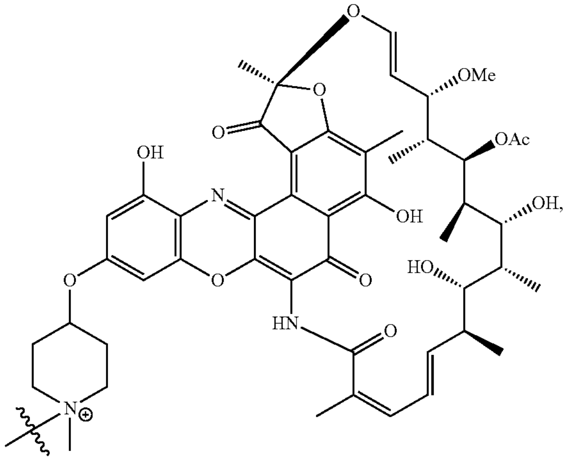
,
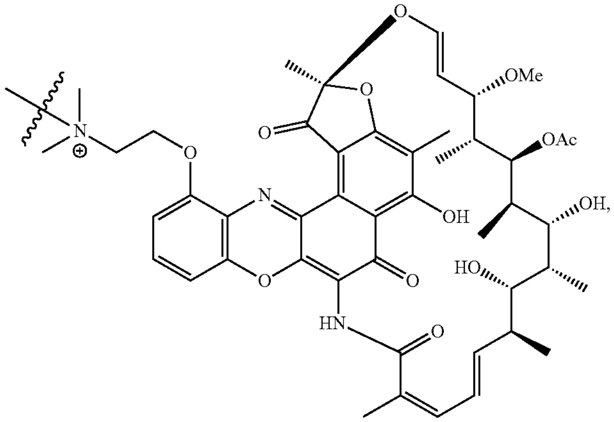
,
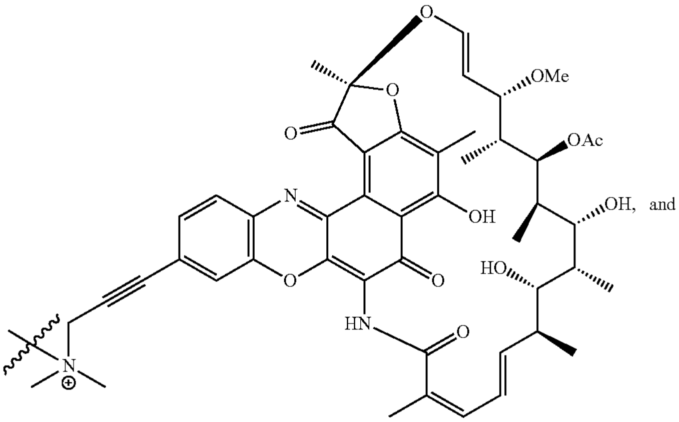
, and

-continued

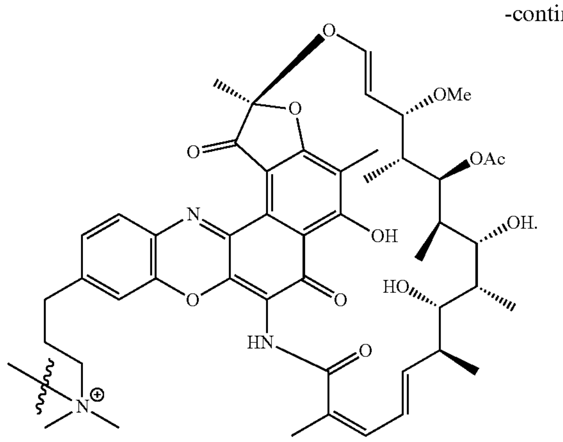

In one embodiment, the payload has the structure selected from:

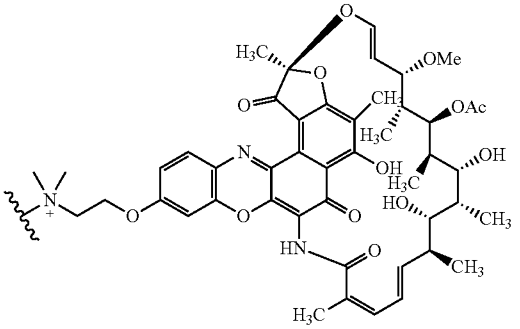

and

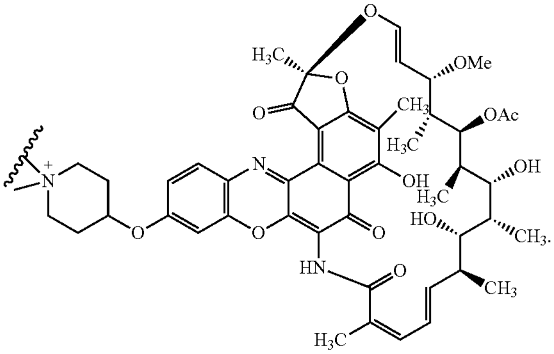

In one embodiment, the payload is conjugated through a linker, the linker having the structure:

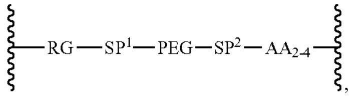

wherein

RG is selected from a maleimide, a N-hydroxysuccinimide, or a succinimide;

$SP^1$ and $SP^2$ are independently absent or a spacer group selected from the group consisting of

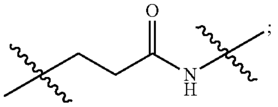 [SMILES: *CCC(=O)N*]

$C_{1-6}$ alkyl, —NH—, —C(O)—, —$CH_2$—$CH_2$—C(O)—NH—, —$(CH)_u$—C(O)—NH—, (—$CH_2$—$CH_2$—O)$_e$, —NH—$CH_2$—$CH_2$—(—O—$CH_2$—$CH_2$)$_e$—C(O)—, —C(O)—$(CH_2)_u$—C(O)—, —C(O)—NH—$(CH_2)_v$—, and combinations thereof, wherein subscript e is an integer from 0 to 4, subscript u is an integer from 1 to 8, and subscript v is an integer from 1 to 8;

$AA_{2-4}$ is a peptide unit comprising from 2 to 4 amino acids, and

PEG is a polyethylene glycol chain comprising between 1 and 30 polyethylene glycol residues.

In one embodiment, $AA_{2-4}$ is a dipeptide selected from valine-citrulline; citrulline-valine; valine-alanine; alanine-valine; valine-glycine, or glycine-valine.

In one embodiment, $AA_{2-4}$ is valine-citrulline.

In one embodiment, SP is

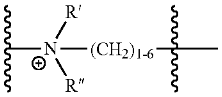

and R' and R" are each a $C_{1-6}$ alkyl.

In one embodiment, SP is

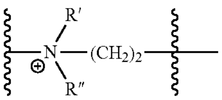

and R' and R" are each methyl.

In one embodiment, $SP^1$ and $SP^2$ are each
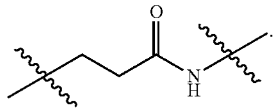 [SMILES: *CCC(=O)N*]
In one embodiment, PEG comprises 8 polyethylene glycol units.
In one embodiment, the payload is conjugated through a linker having the structure:
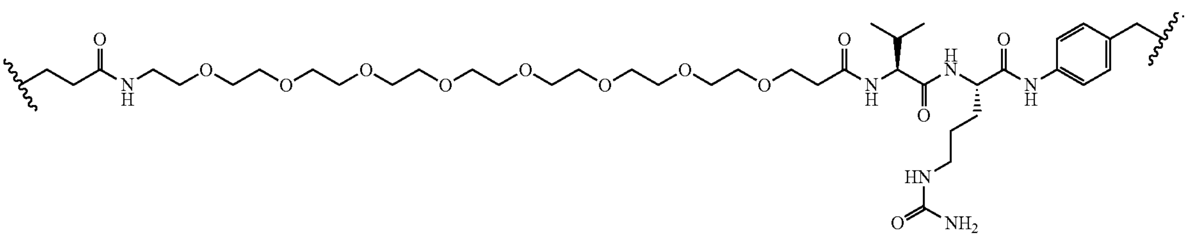 [SMILES: *CCC(=O)NCCOCCOCCOCCOCCOCCOCCOCCOCCC(=O)N[C@H](C(=O)N[C@@H](CCCNC(N)=O)C(=O)Nc1ccc(C*)cc1)C(C)C]
In one embodiment, the payload is conjugated through a linker, the linker-payload having the structure:
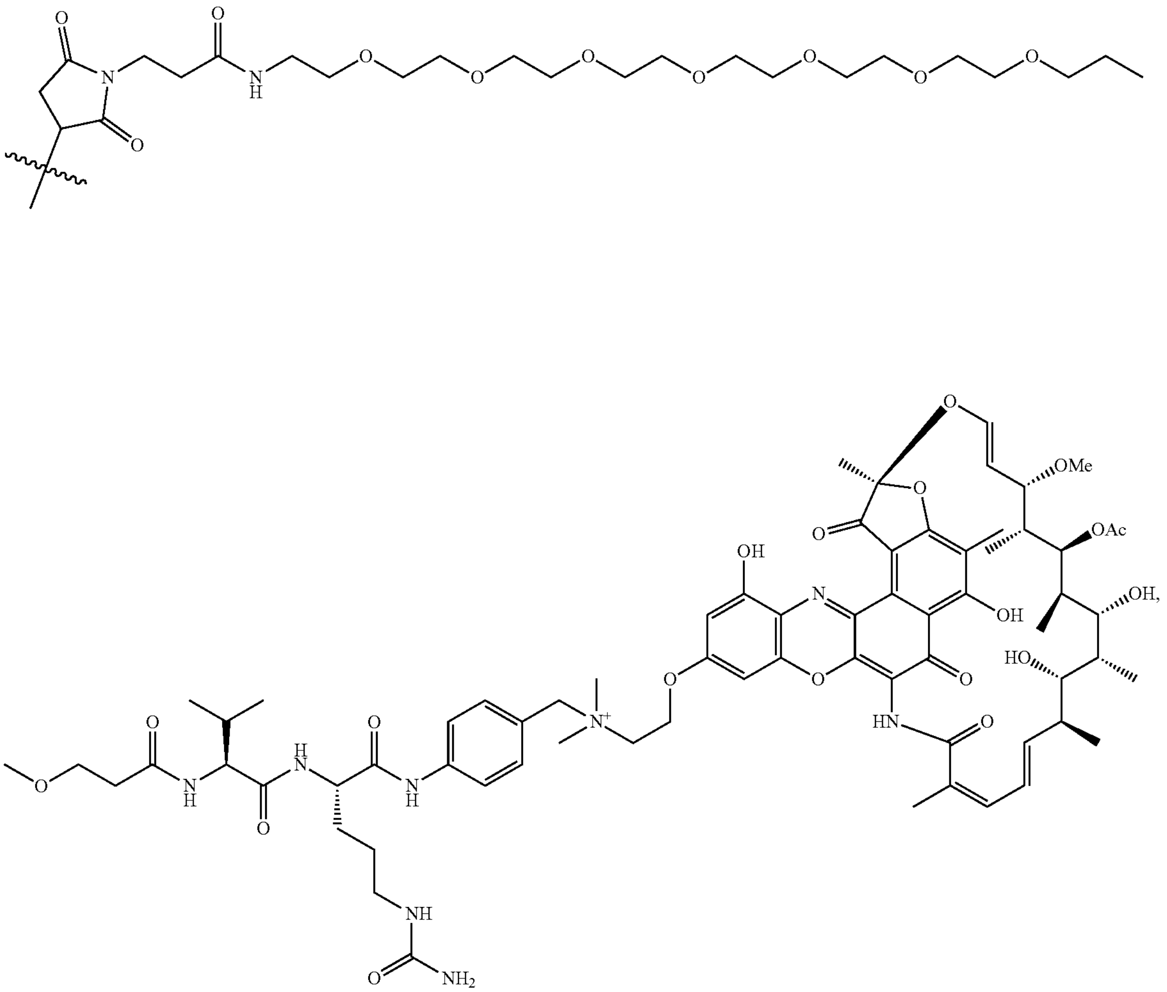

wherein the

is the bond to the antibody or the antigen-binding fragment thereof.

In one embodiment, the payload is conjugated through a linker, the linker-payload having the structure:

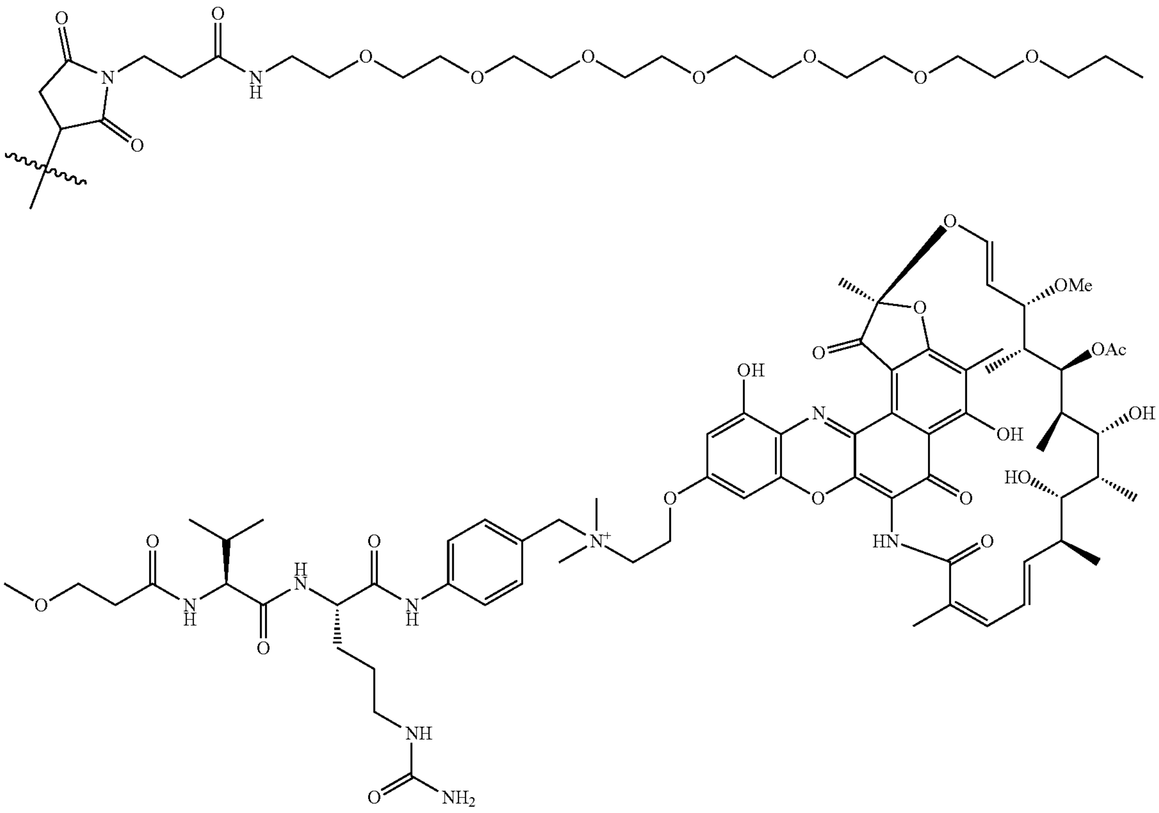

wherein the

is the bond to the antibody or the antigen-binding fragment thereof.

In one embodiment, the payload is conjugated through a linker, the linker-payload having the structure:

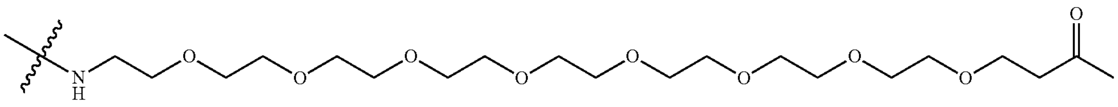

-continued
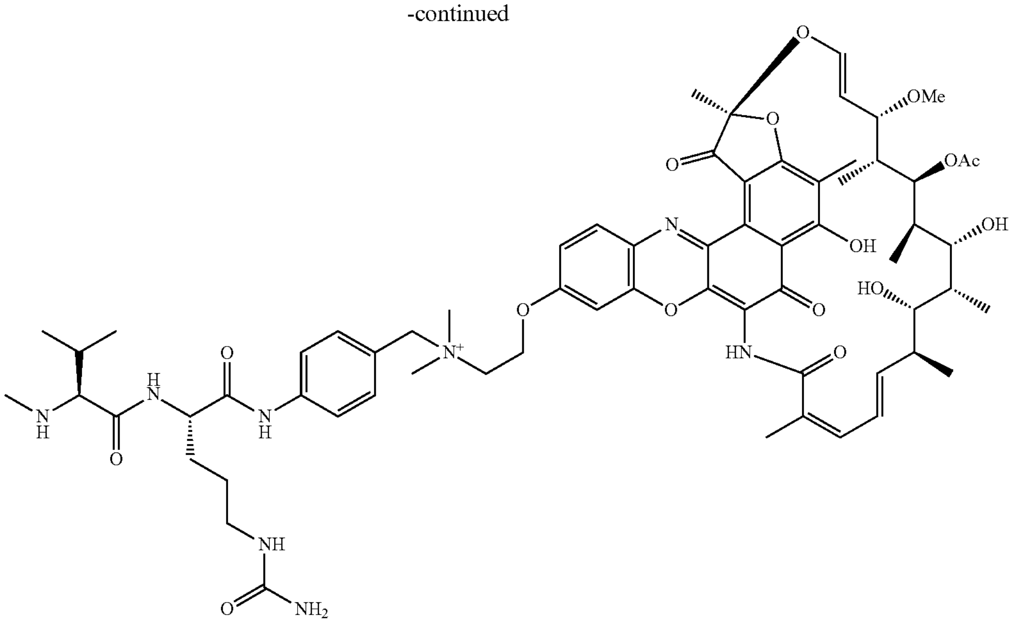
wherein the
is the bond to the antibody or the antigen-binding fragment thereof.
In one embodiment, the payload is conjugated through a linker, the linker-payload having the structure:
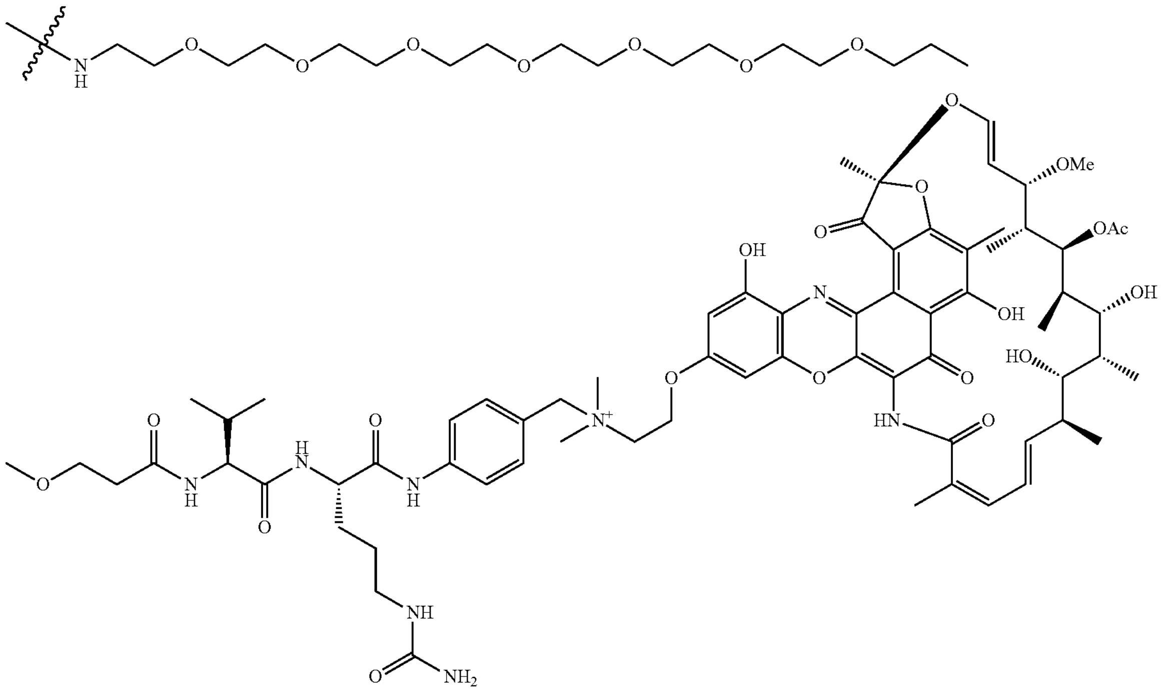

wherein the

is the bond to the antibody or the antigen-binding fragment thereof.

In one embodiment, the antibody, or the antigen-binding fragment thereof, that binds macrophage scavenger receptor 1 (MSR1) comprises: (a) the complementarity determining regions (CDRs) of a heavy chain variable region (HCVR) comprising an amino acid sequence as set forth in Table 9; and (b) the CDRs of a light chain variable region (LCVR) comprising an amino acid sequence as set forth in Table 9.

In some embodiments, the antibody, or antigen-binding fragment thereof, binds MSR1. In one embodiment, the anti-MSR1 antibody, or the antigen-binding fragment thereof, comprises: (a) the complementarity determining regions (CDRs) of a heavy chain variable region (HCVR) comprising an amino acid sequence as set forth in Table 9; and (b) the CDRs of a light chain variable region (LCVR) comprising an amino acid sequence as set forth in Table 9.

In one embodiment, the anti-MSR1 antibody, or the antigen-binding fragment thereof, comprises:

(i) a HCDR1 domain comprising an amino acid sequence selected from the group consisting of SEQ ID NOs: 4, 36, 52, 92, and 284;
(ii) a HCDR2 domain comprising an amino acid sequence selected from the group consisting of SEQ ID NOs: 6, 38, 54, 94, and 286;
(iii) a HCDR3 domain comprising an amino acid sequence selected from the group consisting of SEQ ID NOs: 8, 40, 56, 96, and 288;
(iv) a LCDR1 domain comprising an amino acid sequence selected from the group consisting of SEQ ID NOs: 12, 44, 60, 100, and 292;
(v) a LCDR2 domain comprising an amino acid sequence selected from the group consisting of SEQ ID NOs: 14, 46, 62, 102, and 294; and
(vi) a LCDR3 domain comprising an amino acid sequence selected from the group consisting of SEQ ID NOs: 16, 48, 64, 104, and 296.

In one embodiment, the anti-MSR1 antibody, or the antigen-binding fragment thereof, comprises (i) a HCDR1 domain comprising an amino acid sequence of SEQ ID NO: 52;
(ii) a HCDR2 domain comprising an amino acid sequence of SEQ ID NO: 54;
(iii) a HCDR3 domain comprising an amino acid sequence of SEQ ID NO: 56;
(iv) a LCDR1 domain comprising an amino acid sequence of SEQ ID NO: 60;
(v) a LCDR2 domain comprising an amino acid sequence of SEQ ID NO: 62; and
(vi) a LCDR3 domain comprising an amino acid sequence of SEQ ID NO: 64.

In one embodiment, the anti-MSR1 antibody, or the antigen-binding fragment thereof, comprises a N297Q mutation.

In some embodiments, the antibody, or antigen-binding fragment thereof, binds WTAα. In one embodiment, the anti-WTAα antibody, or the antigen-binding fragment thereof, comprises: (a) the complementarity determining regions (CDRs) of a heavy chain variable region (HCVR) comprising an amino acid sequence as set forth in Table 2A; and (b) the CDRs of a light chain variable region (LCVR) comprising an amino acid sequence as set forth in Table 2A.

In one embodiment, the anti-WTAα antibody, or an antigen-binding fragment thereof, comprises:

(i) a HCDR1 domain comprising an amino acid sequence selected from the group consisting of SEQ ID NOs: 470, 476, 482, and 488;
(ii) a HCDR2 domain comprising an amino acid sequence selected from the group consisting of SEQ ID NOs: 471, 477, 483, and 489;
(iii) a HCDR3 domain comprising an amino acid sequence selected from the group consisting of SEQ ID NOs: 472, 478, 484, and 490;
(iv) a LCDR1 domain comprising an amino acid sequence selected from the group consisting of SEQ ID NOs: 467, 473, 479, and 485;
(v) a LCDR2 domain comprising an amino acid sequence selected from the group consisting of SEQ ID NOs: 468, 474, 480, and 486; and
(vi) a LCDR3 domain comprising an amino acid sequence selected from the group consisting of SEQ ID NOs: 469, 475, 481, and 487.

In some embodiments, the antibody, or antigen-binding fragment thereof, binds WTAβ. In one embodiment, the anti-WTAβ antibody, or the antigen-binding fragment thereof, comprises: (a) the complementarity determining regions (CDRs) of a heavy chain variable region (HCVR) comprising an amino acid sequence as set forth in Table 2B; and (b) the CDRs of a light chain variable region (LCVR) comprising an amino acid sequence as set forth in Table 2B.

In one embodiment, the anti-WTAβ antibody, or an antigen-binding fragment thereof, comprises:

(i) a HCDR1 domain comprising an amino acid sequence selected from the group consisting of SEQ ID NOs: 502, 508, 514, 520, 526, 532, 538, 544, 550, 556, 562, 568, and 574;
(ii) a HCDR2 domain comprising an amino acid sequence selected from the group consisting of SEQ ID NOs: 503, 509, 515, 521, 527, 533, 539, 545, 551, 557, 563, 569, and 575;
(iii) a HCDR3 domain comprising an amino acid sequence selected from the group consisting of SEQ ID NOs: 504, 510, 516, 522, 528, 534, 540, 546, 552, 558, 564, 570, 576, and 584;
(iv) a LCDR1 domain comprising an amino acid sequence selected from the group consisting of SEQ ID NOs: 499, 505, 511, 517, 523, 529, 535, 541, 547, 553, 559, 565, and 571;
(v) a LCDR2 domain comprising an amino acid sequence selected from the group consisting of SEQ ID NOs: 500, 506, 512, 518, 524, 530, 536, 542, 548, 554, 560, 566, and 572; and
(vi) a LCDR3 domain comprising an amino acid sequence selected from the group consisting of SEQ ID NOs: 501, 507, 513, 519, 525, 531, 537, 543, 549, 555, 561, 567, and 573.

In some embodiments, the anti-WTA antibody, or the antigen-binding fragment thereof, comprises a V205C mutation.

In one embodiment, the anti-WTA antibody, or the antigen-binding fragment thereof, is derived from antibody 4497 described in US Patent Application Publication 20140356375 (which is incorporated herein by reference in its entirety). In one embodiment, the anti-WTA antibody is derived from antibody 4497 and further comprises a V205C mutation in the light chain.

In one embodiment, the anti-WTA antibody, or the antigen-binding fragment thereof, comprises the HCDR1-HCDR2-HCDR3-LCDR1-LCDR2-LCDR3 of SEQ ID Nos: 568-569-570-565-566-567.

In some embodiments, the anti-WTA antibody or antigen binding fragment thereof comprises three heavy chain complementarity determining regions (HCDR1, HCDR2, and HCDR3) within a heavy chain variable region (HCVR) amino acid sequence of SEQ ID NOs: 586; and three light chain complementarity determining regions (LCDR1, LCDR2, and LCDR3) within a light chain variable region (LCVR) amino acid sequence of SEQ ID NO: 585.

In some embodiments, the anti-WTA antibody or antigen binding fragment thereof comprises an HCVR amino acid sequence of SEQ ID NOs: 586; and an LCVR amino acid sequence of SEQ ID NO: 585.

In some embodiments, the anti-WTA antibody comprises a heavy chain amino acid sequence of SEQ ID NOs: 602 and a light chain amino acid sequence of SEQ ID NO: 587 or SEQ ID NO: 589. In some embodiments, the anti-WTA antibody, or the antigen-binding fragment thereof comprises a V205C mutation in the light chain.

In some embodiments, the antibody, or antigen-binding fragment thereof, binds Protein A. In one embodiment, the anti-Protein A antibody, or the antigen-binding fragment thereof, may comprise: (a) the complementarity determining regions (CDRs) of a heavy chain variable region (HCVR) comprising an amino acid sequence as set forth in Table 3A; and (b) the CDRs of a light chain variable region (LCVR) comprising an amino acid sequence as set forth in Table 3A.

In one embodiment, the anti-Protein A antibody, or the antigen-binding fragment thereof, may comprise:

(i) a HCDR1 domain comprising an amino acid sequence selected from the group consisting of SEQ ID NOs: 632, 652, and 672;

(ii) a HCDR2 domain comprising an amino acid sequence selected from the group consisting of SEQ ID NOs: 634, 654, and 674;

(iii) a HCDR3 domain comprising an amino acid sequence selected from the group consisting of SEQ ID NOs: 636, 656, and 676;

(iv) a LCDR1 domain comprising an amino acid sequence selected from the group consisting of SEQ ID NOs: 640, 660, and 680;

(v) a LCDR2 domain comprising an amino acid sequence selected from the group consisting of SEQ ID NOs: 642 and 662; and (vi) a LCDR3 domain comprising an amino acid sequence selected from the group consisting of SEQ ID NOs: 644, 664, and 683.

In some embodiments, the anti-Protein A antibody, or the antigen-binding fragment thereof, comprises a H435R and a Y436F mutation (EU numbering) in the heavy chain Fc.

In one embodiment, the anti-Protein A antibody or antigen binding fragment thereof comprises three heavy chain complementarity determining regions (HCDR1, HCDR2, and HCDR3) within a heavy chain variable region (HCVR) amino acid sequence of SEQ ID NOs: 630; and three light chain complementarity determining regions (LCDR1, LCDR2, and LCDR3) within a light chain variable region (LCVR) amino acid sequence of SEQ ID NO: 638. In one embodiment, the anti-Protein A antibody or antigen binding fragment thereof comprises a set of six CDRs (HCDR1-HCDR2-HCDR3-LCDR1-LCDR2-LCDR3) comprising SEQ ID NOs: 632-634-636-640-642-644.

In one embodiment, the anti-Protein A antibody or antigen binding fragment thereof comprises an HCVR amino acid sequence of SEQ ID NOs: 630; and an LCVR amino acid sequence of SEQ ID NO: 638.

In one embodiment, the anti-Protein A antibody comprises a heavy chain amino acid sequence of SEQ ID NOs: 666 and a light chain amino acid sequence of SEQ ID NO: 668. In one embodiments, the anti-Protein A antibody, further comprises a H435R and a Y436F mutation (EU numbering) in the heavy chain Fc. In one embodiment, anti-Protein A antibody further comprises a C103S mutation in the light chain. In one embodiment, the anti-Protein A antibody, or antigen-binding fragment thereof, is conjugated to a compound of the present disclosure at light chain position 103.

In various embodiments, the antibody, or antigen-binding fragment thereof, comprises a C103S mutation in the light chain.

The various embodiments, the antibody, or the antigen-binding fragment thereof, is conjugated to a compound of the present disclosure at position 103 of the light chain.

Exemplary Antibody-Drug Conjugates of the Disclosure

In one embodiment, the antibody-drug conjugate of the present disclosure comprises an anti-MSR1 antibody, or antigen-binding fragment thereof, comprising a set of six CDRs (HCDR1-HCDR2-HCDR3-LCDR1-LCDR2-LCDR3) comprising SEQ ID NOs: 52-54-56-60-62-64, and a N297Q mutation, said anti-MSR1 antibody, or antigen-binding fragment thereof, is conjugated to a compound having the structure of

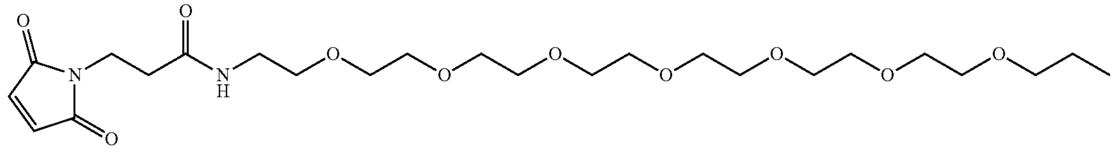

-continued
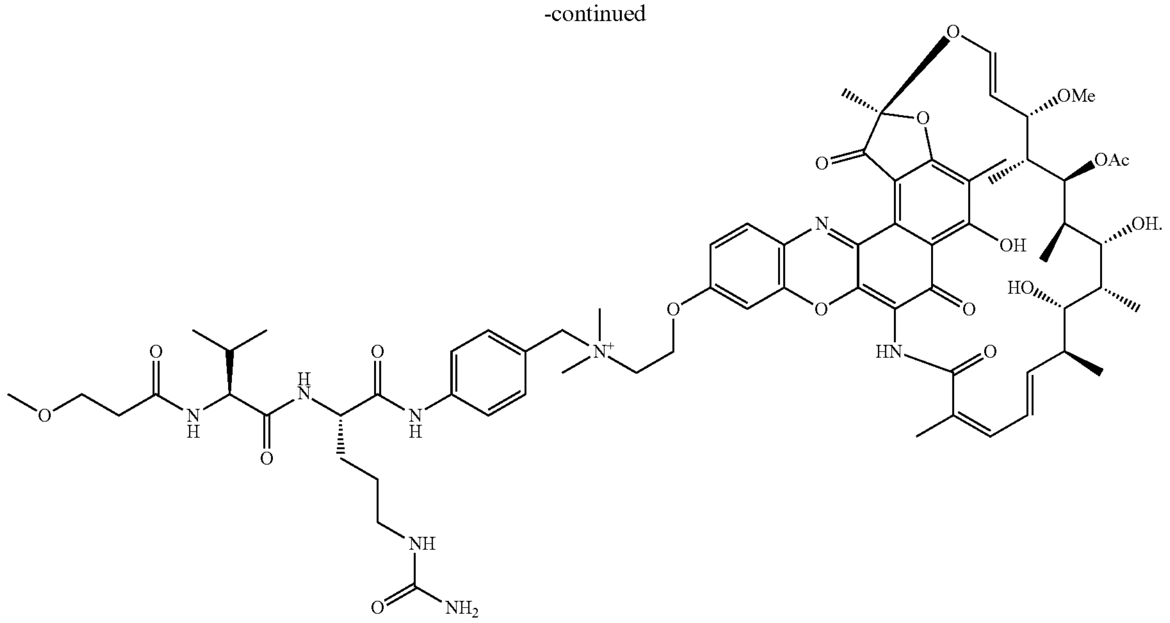
In one embodiment, the antibody-drug conjugate of the present disclosure comprises an anti-MSR1 antibody, or antigen-binding fragment thereof, comprising a set of six CDRs (HCDR1-HCDR2-HCDR3-LCDR1-LCDR2-LCDR3) comprising SEQ ID NOs: 52-54-56-60-62-64, and a N297Q mutation, said anti-MSR1 antibody, or antigen-binding fragment thereof, is conjugated to a compound having the structure of
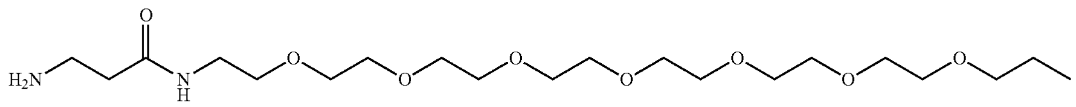
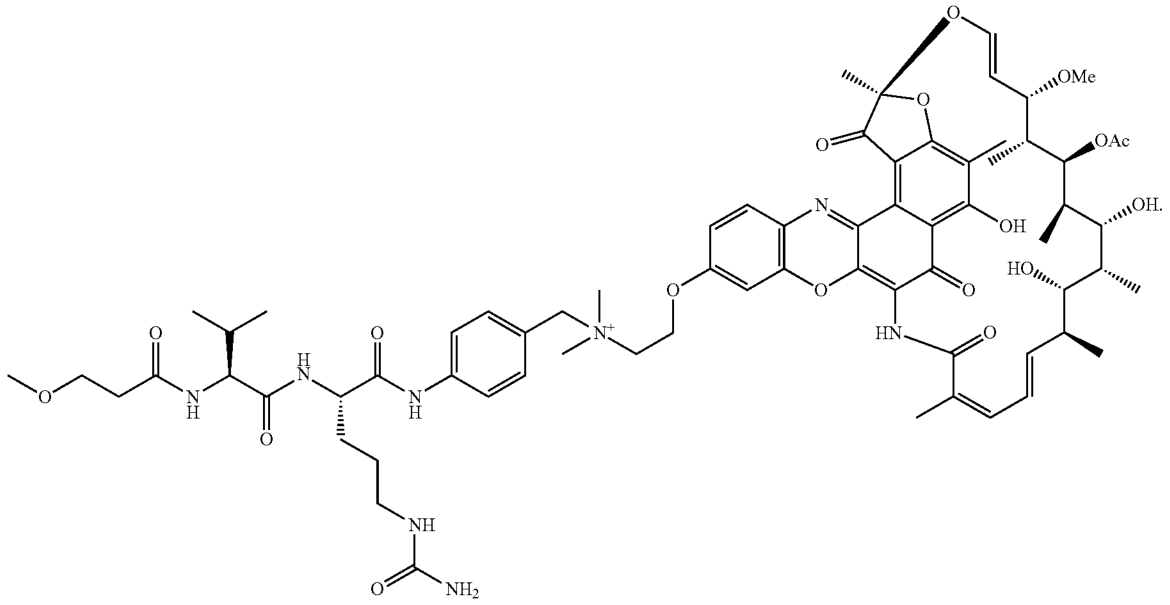

In one embodiment, the antibody-drug conjugate of the present disclosure comprises an anti-MSR1 antibody, or antigen-binding fragment thereof, comprising a set of six CDRs (HCDR1-HCDR2-HCDR3-LCDR1-LCDR2-LCDR3) comprising SEQ ID NOs: 52-54-56-60-62-64, and a N297Q mutation, said anti-MSR1 antibody, or antigen-binding fragment thereof, is conjugated to a compound having the structure of

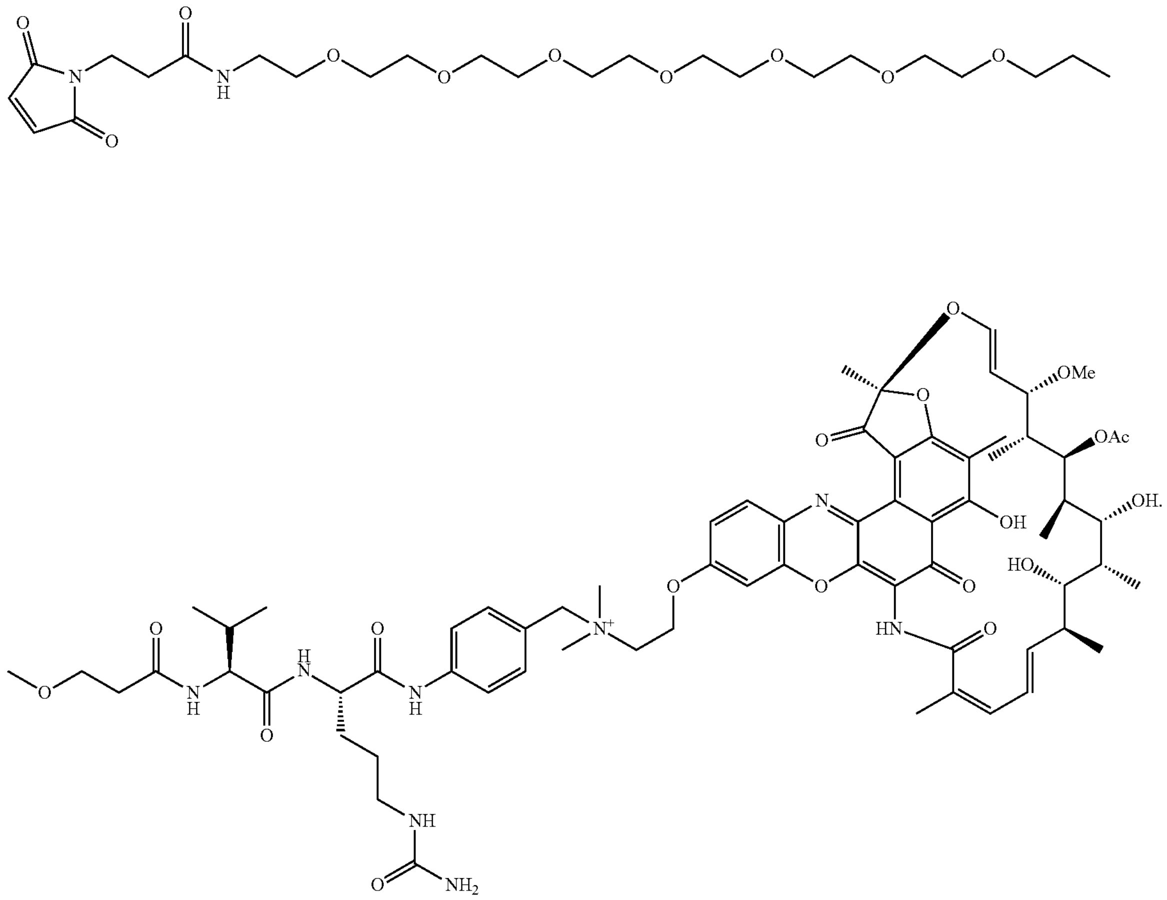

In one embodiment, the antibody-drug conjugate of the present disclosure comprises an anti-MSR1 antibody, or antigen-binding fragment thereof, comprising a set of six CDRs (HCDR1-HCDR2-HCDR3-LCDR1-LCDR2-LCDR3) comprising SEQ ID NOs: 52-54-56-60-62-64, and a N297Q mutation, said anti-MSR1 antibody, or antigen-binding fragment thereof, is conjugated to a compound having the structure of

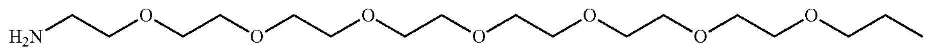

-continued

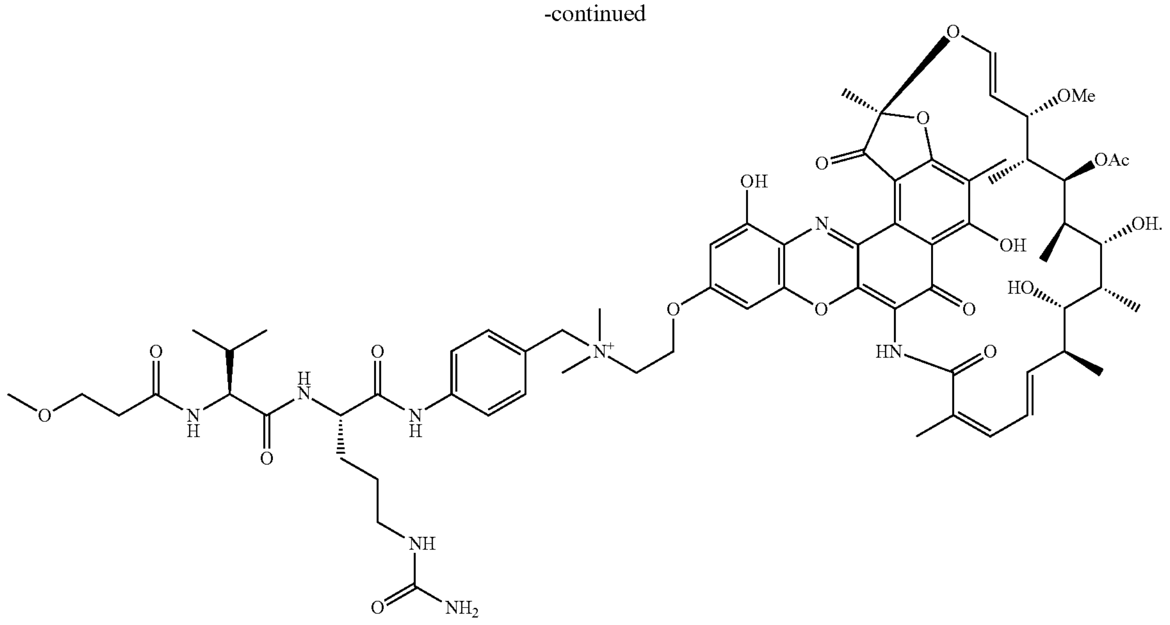

In one embodiment, the antibody-drug conjugate of the present disclosure comprises an anti-MSR1 antibody, or antigen-binding fragment thereof, comprising a set of six CDRs (HCDR1-HCDR2-HCDR3-LCDR1-LCDR2-LCDR3) comprising SEQ ID NOs: 52-54-56-60-62-64, and a N297Q mutation, said anti-MSR1 antibody, or antigen-binding fragment thereof, is conjugated to a compound having the structure of

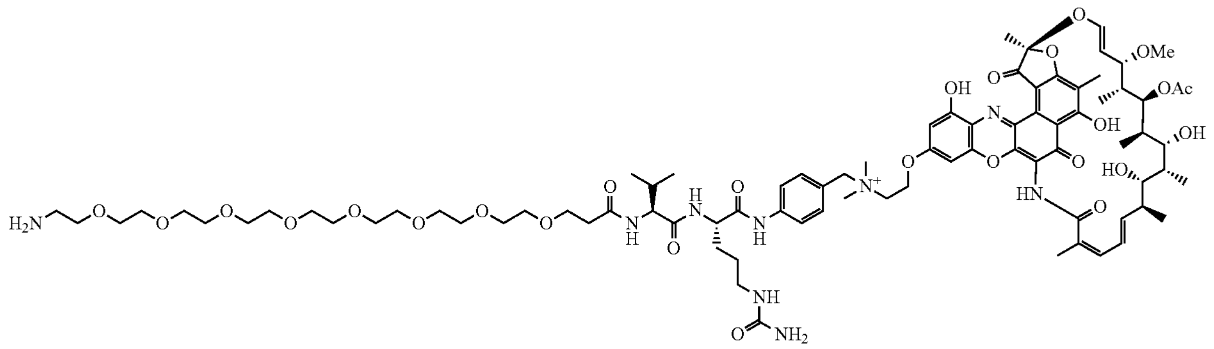

In one embodiment, the antibody-drug conjugate of the present disclosure comprises an anti-MSR1 antibody, or antigen-binding fragment thereof, comprising a set of six CDRs (HCDR1-HCDR2-HCDR3-LCDR1-LCDR2-LCDR3) comprising SEQ ID NOs: 52-54-56-60-62-64, and a N297Q mutation, said anti-MSR1 antibody, or antigen-binding fragment thereof, is conjugated to a compound having the structure of

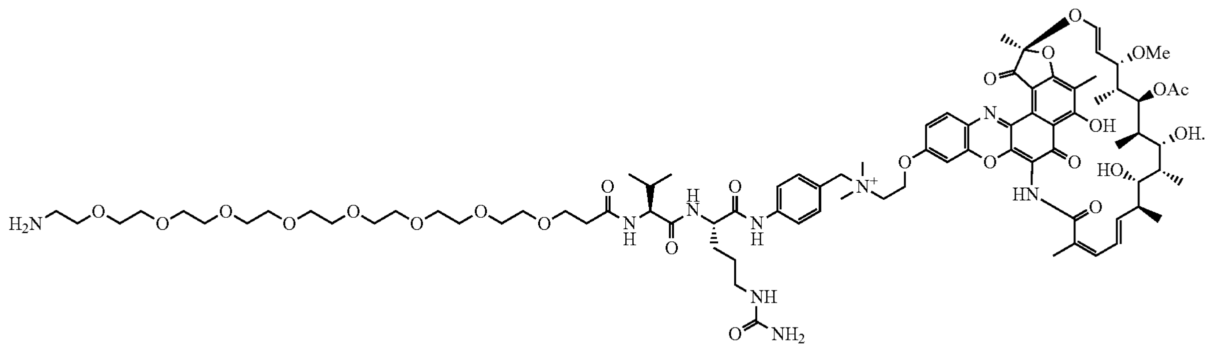

In some embodiments, the anti-MSR1 antibody or antigen binding fragment thereof comprises an HCVR amino acid sequence of SEQ ID NOs: 50; and an LCVR amino acid sequence of SEQ ID NO: 58.

In one embodiment, the antibody-drug conjugate of the present disclosure comprises an anti-WTA antibody, or antigen-binding fragment thereof, comprising a set of six CDRs (HCDR1-HCDR2-HCDR3-LCDR1-LCDR2-LCDR3) comprising SEQ ID NOs: 568-569-570-565-566-567, and a V205C mutation in the light chain, said anti-WTA antibody, or antigen-binding fragment thereof, is conjugated to a compound having the structure of

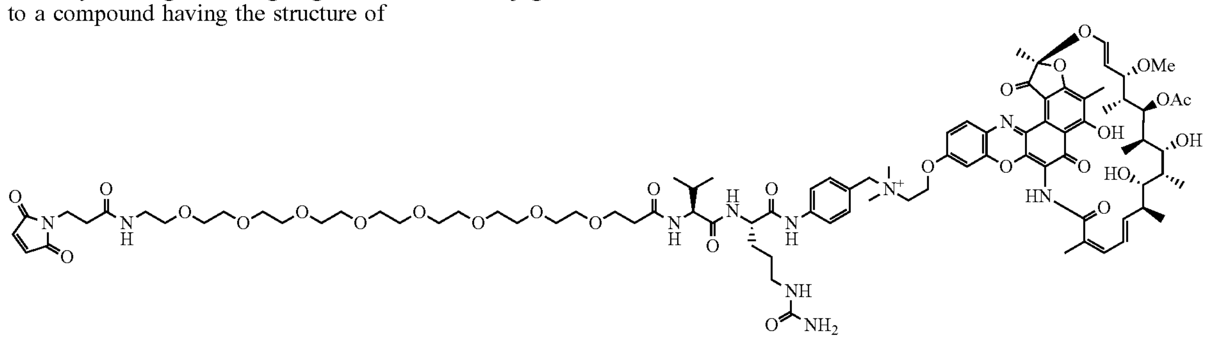

In one embodiment, the antibody-drug conjugate of the present disclosure comprises an anti-WTA antibody, or antigen-binding fragment thereof, comprising a set of six CDRs (HCDR1-HCDR2-HCDR3-LCDR1-LCDR2-LCDR3) comprising SEQ ID NOs. 568-569-570-565-566-567, and a V205C mutation in the light chain, said anti-WTA antibody, or antigen-binding fragment thereof, is conjugated to a compound having the structure of

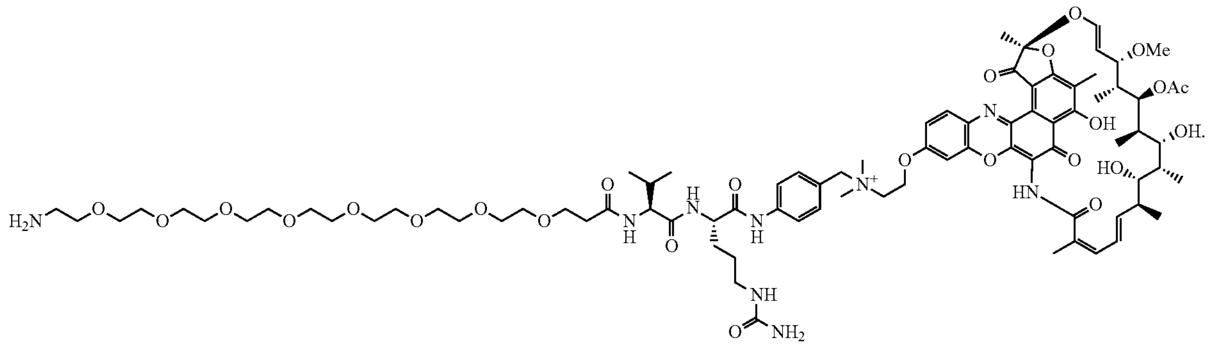 [SMILES: CO[C@H]1/C=C/O[C@@]2(C)Oc3c(C)c(O)c4c(=O)c(c5oc6cc(OCC[N+](C)(C)Cc7ccc(NC(=O)[C@H](CCCNC(N)=O)NC(=O)[C@@H](NC(=O)CCOCCOCCOCCOCCOCCOCCOCCOCCN)C(C)C)cc7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In one embodiment, the antibody-drug conjugate of the present disclosure comprises an anti-WTA antibody, or antigen-binding fragment thereof, comprising a set of six CDRs (HCDR1-HCDR2-HCDR3-LCDR1-LCDR2-LCDR3) comprising SEQ ID NOs: 568-569-570-565-566-567, and a V205C mutation in the light chain, said anti-WTA antibody, or antigen-binding fragment thereof, is conjugated to a compound having the structure of

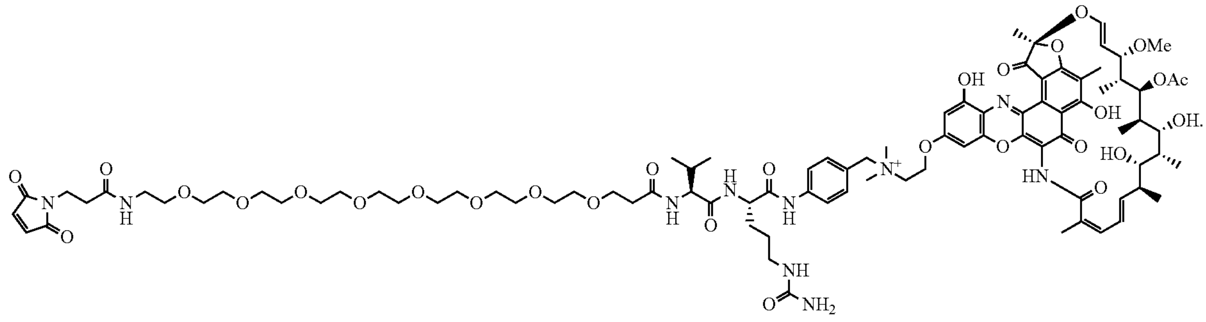 [SMILES: CO[C@H]1/C=C/O[C@@]2(C)Oc3c(C)c(O)c4c(=O)c(c5oc6cc(OCC[N+](C)(C)Cc7ccc(NC(=O)[C@H](CCCNC(N)=O)NC(=O)[C@@H](NC(=O)CCOCCOCCOCCOCCOCCOCCOCCOCCNC(=O)CCN8C(=O)C=CC8=O)C(C)C)cc7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In one embodiment, the antibody-drug conjugate of the present disclosure comprises an anti-WTA antibody, or antigen-binding fragment thereof, comprising a set of six CDRs (HCDR1-HCDR2-HCDR3-LCDR1-LCDR2-LCDR3) comprising SEQ ID NOs: 568-569-570-565-566-567, and a V205C mutation in the light chain, said anti-WTA antibody, or antigen-binding fragment thereof, is conjugated to a compound having the structure of

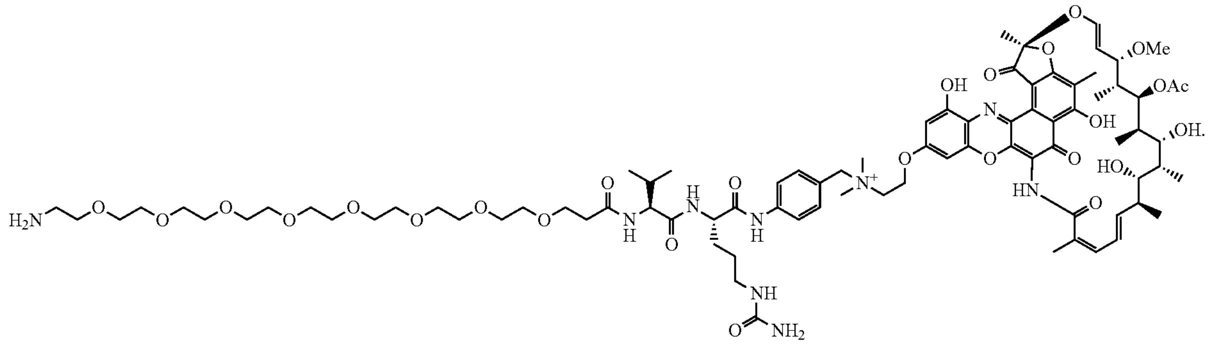 [SMILES: CO[C@H]1/C=C/O[C@@]2(C)Oc3c(C)c(O)c4c(=O)c(c5oc6cc(OCC[N+](C)(C)Cc7ccc(NC(=O)[C@H](CCCNC(N)=O)NC(=O)[C@@H](NC(=O)CCOCCOCCOCCOCCOCCOCCOCCOCCN)C(C)C)cc7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In one embodiment, the antibody-drug conjugate of the present disclosure comprises an anti-WTA antibody, or antigen-binding fragment thereof, comprising a set of six CDRs (HCDR1-HCDR2-HCDR3-LCDR1-LCDR2-LCDR3) comprising SEQ ID NOs: 568-569-570-565-566-567, and a V205C mutation in the light chain, said anti-WTA antibody, or antigen-binding fragment thereof, is conjugated to a compound having the structure of

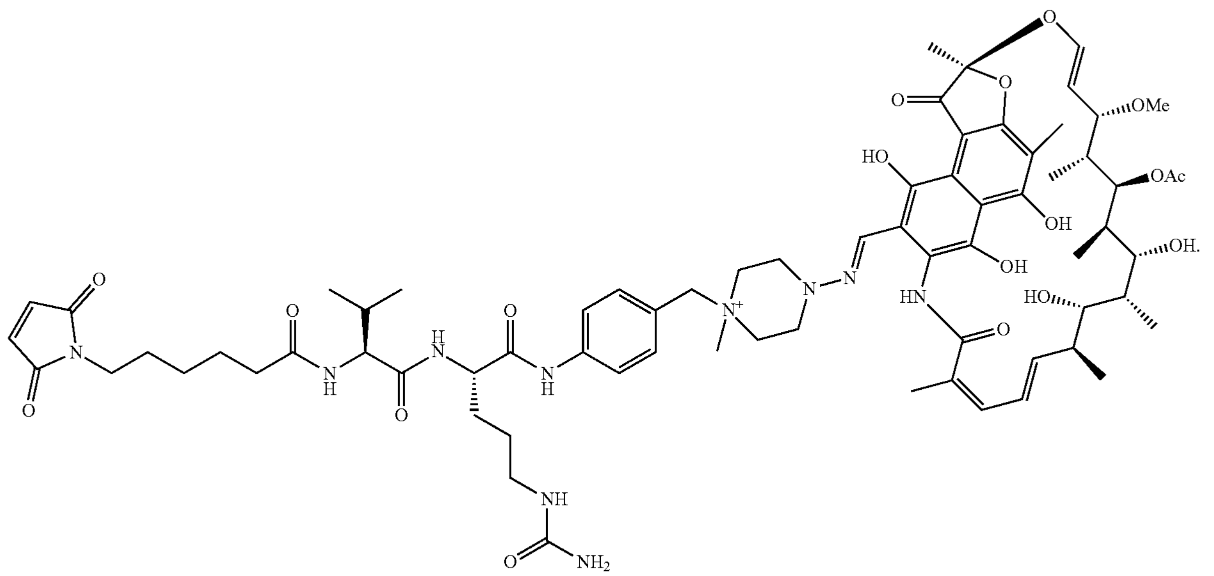

In some embodiments, the anti-WTA antibody or antigen binding fragment thereof comprises an HCVR amino acid sequence of SEQ ID NOs: 586, and an LCVR amino acid sequence of SEQ ID NO: 585.

In some embodiments, the anti-WTA antibody comprises a heavy chain amino acid sequence of SEQ ID NOs: 602 and a light chain amino acid sequence of SEQ ID NO: 587 or SEQ ID NO: 589.

In one embodiment, the antibody-drug conjugate of the present disclosure comprises an anti-Protein A antibody, or antigen-binding fragment thereof, comprising a set of six CDRs (HCDR1-HCDR2-HCDR3-LCDR1-LCDR2-LCDR3) comprising SEQ ID NOs: 632-634-636-640-642-644, and a H435R and a Y436F mutation in the heavy chain Fc, and a C103S mutation in the light chain, said anti-Protein A antibody, or antigen-binding fragment thereof, is conjugated to a compound having the structure of

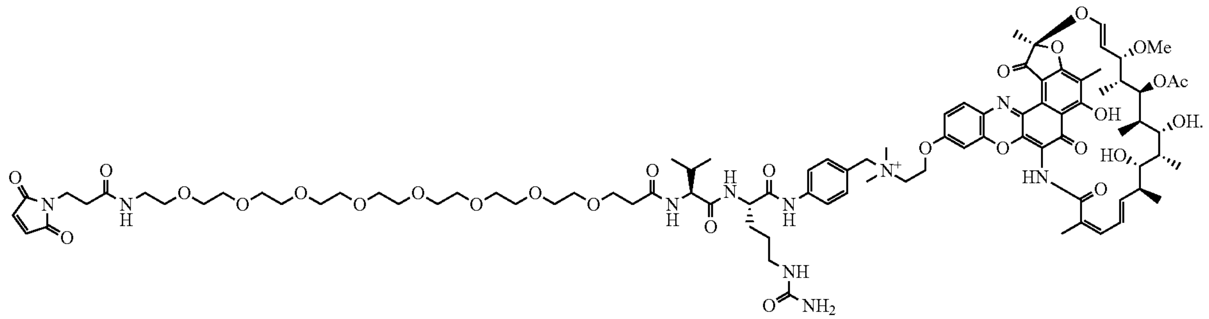 [SMILES: CO[C@H]1/C=C/O[C@@]2(C)Oc3c(C)c(O)c4c(=O)c(c5oc6cc(OCC[N+](C)(C)Cc7ccc(NC(=O)[C@H](CCCNC(N)=O)NC(=O)[C@@H](NC(=O)CCOCCOCCOCCOCCOCCOCCOCCOCCNC(=O)CCN8C(=O)C=CC8=O)C(C)C)cc7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In one embodiment, the antibody-drug conjugate of the present disclosure comprises an anti-Protein A antibody, or antigen-binding fragment thereof, comprising a set of six CDRs (HCDR1-HCDR2-HCDR3-LCDR1-LCDR2-LCDR3) comprising SEQ ID NOs: 632-634-636-640-642-644, and a H435R and a Y436F mutation in the heavy chain Fc, and a $C_{103}S$ mutation in the light chain, said anti-Protein A antibody, or antigen-binding fragment thereof, is conjugated to a compound having the structure of

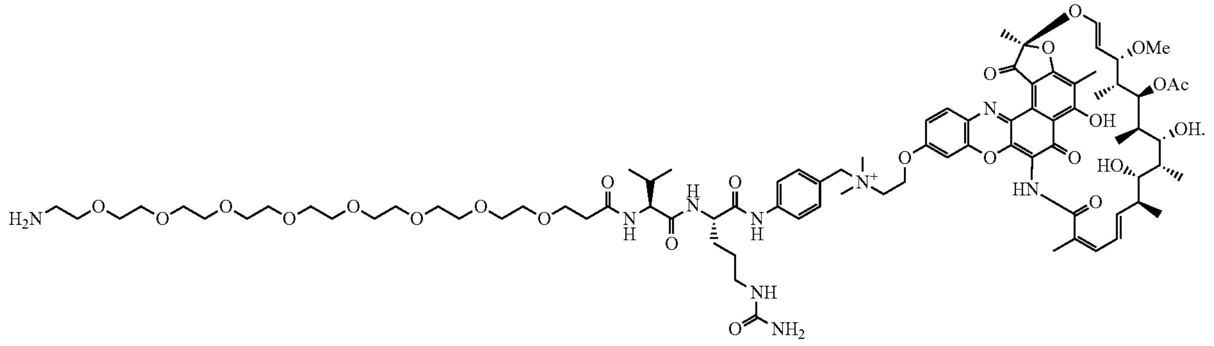 [SMILES: CO[C@H]1/C=C/O[C@@]2(C)Oc3c(C)c(O)c4c(=O)c(c5oc6cc(OCC[N+](C)(C)Cc7ccc(NC(=O)[C@H](CCCNC(N)=O)NC(=O)[C@@H](NC(=O)CCOCCOCCOCCOCCOCCOCCOCCOCCN)C(C)C)cc7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In one embodiment, the antibody-drug conjugate of the present disclosure comprises an anti-Protein A antibody, or antigen-binding fragment thereof, comprising a set of six CDRs (HCDR1-HCDR2-HCDR3-LCDR1-LCDR2-LCDR3) comprising SEQ ID NOs: 632-634-636-640-642-644, and a H435R and a Y436F mutation in the heavy chain Fc, and a $C_{103}S$ mutation in the light chain, said anti-Protein A antibody, or antigen-binding fragment thereof, is conjugated to a compound having the structure of

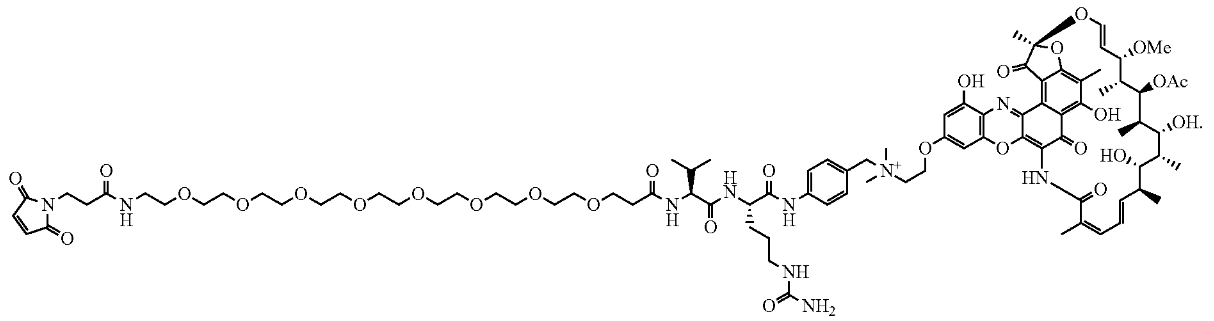

In one embodiment, the antibody-drug conjugate of the present disclosure comprises an anti-Protein A antibody, or antigen-binding fragment thereof, comprising a set of six CDRs (HCDR1-HCDR2-HCDR3-LCDR1-LCDR2-LCDR3) comprising SEQ ID NOs: 632-634-636-640-642-644, and a H435R and a Y436F mutation in the heavy chain Fc, and a C103S mutation in the light chain, said anti-Protein A antibody, or antigen-binding fragment thereof, is conjugated to a compound having the structure of

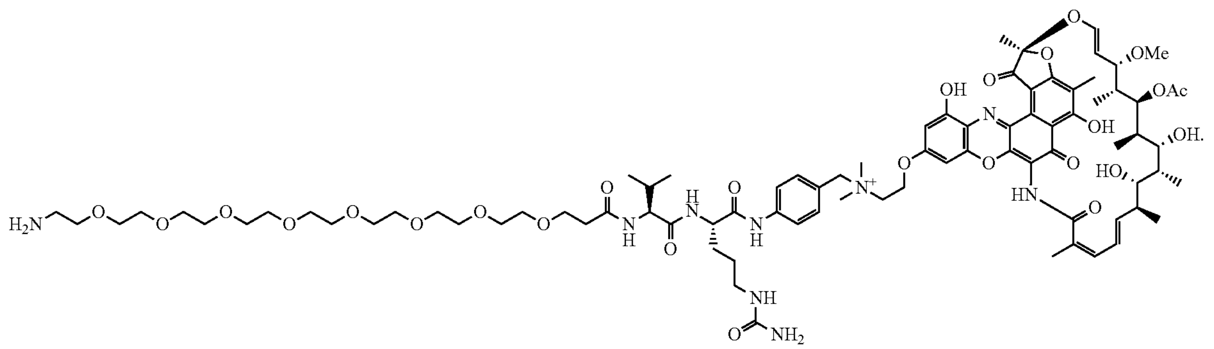 [SMILES: CO[C@H]1/C=C/O[C@@]2(C)Oc3c(C)c(O)c4c(=O)c(c5oc6cc(OCC[N+](C)(C)Cc7ccc(NC(=O)[C@H](CCCNC(N)=O)NC(=O)[C@@H](NC(=O)CCOCCOCCOCCOCCOCCOCCOCCOCCN)C(C)C)cc7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In one embodiment, the antibody-drug conjugate of the present disclosure comprises an anti-Protein A antibody, or antigen-binding fragment thereof, comprising a set of six CDRs (HCDR1-HCDR2-HCDR3-LCDR1-LCDR2-LCDR3) comprising SEQ ID NOs: 632-634-636-640-642-644, and a H435R and a Y436F mutation in the heavy chain Fc, and a C103S mutation in the light chain, said anti-Protein A antibody, or antigen-binding fragment thereof, is conjugated to a compound having the structure of

80

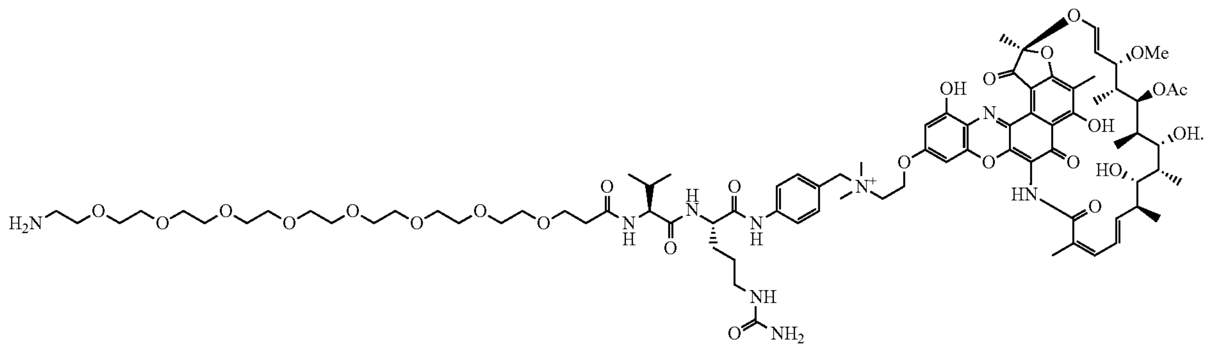

In one embodiment, the anti-Protein A antibody or antigen binding fragment thereof comprises an HCVR amino acid sequence of SEQ ID NOs: 630; and an LCVR amino acid sequence of SEQ ID NO: 638.

In one embodiment, the anti-Protein A antibody comprises a heavy chain amino acid sequence of SEQ ID NOs: 666 and a light chain amino acid sequence of SEQ ID NO: 668.

Epitope Mapping and Related Technologies

The epitope to which the antibody-drug conjugates comprising antibodies of the present disclosure bind may consist of a single contiguous sequence of 3 or more (e.g., 3, 4, 5, 6, 7, 8, 9, 10, 11, 12, 13, 14, 15, 16, 17, 18, 19, 20 or more) amino acids located within the antigen (e.g., an MSR1 protein or Protein A) (e.g. a linear epitope in a domain). Alternatively, the epitope may consist of a plurality of non-contiguous amino acids (or amino acid sequences) of MSR1. In some embodiments, the epitope is located on or near the modified LDL-binding domain of MSR1. In other embodiments, the epitope is located outside of the modified LDL-binding domain of MSR1, e.g., at a location on the surface of MSR1 at which an antibody, when bound to such an epitope, does not interfere with modified-LDL binding to the antigen (e.g. a conformational epitope).

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

Embodiments include antibody-drug conjugates comprising anti-MSR1 antibodies that bind to the same epitope as any of the specific exemplary antibodies described herein (e.g. anti-MSR1 antibodies comprising any of the amino acid sequences as set forth in Table 9 herein; anti-WTA antibodies comprising any of the amino acid sequences as set forth in Tables 2A and 2B herein; or anti-Protein A antibodies comprising any of the amino acid sequences as set forth in Table 3A herein). Likewise, embodiments also include antibody-drug conjugates comprising anti-MSR1 antibodies that compete for binding to the same antigen with any of the specific exemplary antibodies described herein (e.g. anti-MSR1 antibodies comprising any of the amino acid sequences as set forth in Table 9 herein; anti-WTA antibodies comprising any of the amino acid sequences as set forth in Tables 2A and 2B herein; or anti-Protein A antibodies comprising any of the amino acid sequences as set forth in Table 3A herein).

One can easily determine whether an antibody binds to the same epitope as, or competes for binding with, a reference antibody by using routine methods known in the art and exemplified herein at, e.g., Example 29. For example, to determine if a test antibody binds to the same epitope as a reference anti-MSR1 antibody disclosed herein, the reference antibody is allowed to bind to a MSR1 protein. Next, the ability of a test antibody to bind to the MSR1 molecule is assessed. If the test antibody is able to bind to MSR1 following saturation binding with the reference anti-MSR1 antibody, it can be concluded that the test antibody binds to a different epitope than the reference anti-MSR1 antibody. On the other hand, if the test antibody is not able to bind to the MSR1 molecule following saturation binding with the reference anti-MSR1 antibody, then the test antibody may bind to the same epitope as the epitope bound by the reference anti-MSR1 antibody of the disclosure. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present disclosure, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine, for example, if an antibody competes for binding (or cross-competes for binding) with a reference anti-MSR1 antibody, the above-described binding methodology is performed in two orientations. In a first orientation, the reference antibody is allowed to bind to a MSR1 protein under saturating conditions followed by assessment of binding of the test antibody to the MSR1 molecule. In a second orientation, the test antibody is allowed to bind to a MSR1 molecule under saturating conditions followed by assessment of binding of the reference antibody to the MSR1 molecule. If, in both orientations, only the first (saturating) antibody is capable of binding to the MSR1 molecule, then it is concluded that the test antibody and the reference antibody compete for binding to MSR1. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies Suitable for ADCs

Suitable antibodies for antibody-drug conjugates disclosed herein can be fully human antibodies. Methods for generating monoclonal antibodies, including fully human monoclonal antibodies are known in the art. Any such known methods can be used in the context of the present disclosure to make human antibodies that specifically bind to a target antigen, such as an infectious disease-related target (e.g., MSR1, WTA or Protein A).

Using VELOCIMMUNE™ technology, for example, or any other similar known method for generating fully human monoclonal antibodies, high affinity chimeric antibodies to MSR1 are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human antibody. While the constant region selected may vary according to specific use, high affinity antigen-binding and target specificity characteristics reside in the variable region. In certain instances, fully human antibodies are isolated directly from antigen-positive B cells.

Bioequivalents

The antibody-drug conjugates comprising antibodies and antibody fragments disclosed herein encompass proteins having amino acid sequences that vary from those of the described antibodies but that retain the ability to bind to a target antigen, such as an infectious disease-related target (e.g., MSR1, WTA or Protein A). Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences disclosed herein encompass sequences that comprise one or more additions, deletions, or substitutions of nucleotides when compared to the disclosed sequence, but that encode an antibody or antibody fragment that is essentially bioequivalent to an antibody or antibody fragment disclosed herein. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of antibodies suitable for antibody-drug conjugates disclosed herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes which modify the glycosylation characteristics of the antibodies, e.g., mutations which eliminate or remove glycosylation.

Species Selectivity and Species Cross-Reactivity

According to certain embodiments, provided herein are antibody-drug conjugates comprising anti-MSR1 antibodies that bind to human MSR1 but not to MSR1 from other species. Embodiments also include antibody-drug conjugates comprising anti-MSR1 antibodies that bind to human MSR1 and to MSR1 from one or more non-human species. For example, the antibody-drug conjugates comprising anti-MSR1 antibodies disclosed herein may bind to human MSR1 and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee MSR1. According to certain exemplary embodiments, antibody-drug conjugates comprising anti-MSR1 antibodies are provided which specifically bind human MSR1 and cynomolgus monkey (e.g., *Macaca fascicularis*) MSR1. Other antibody-drug conjugates comprising anti-MSR1 antibodies disclosed herein bind human MSR1 but do not bind, or bind only weakly, to cynomolgus monkey MSR1.

Multispecific Antibodies

The antibodies suitable for antibody-drug conjugates disclosed herein may be monospecific or multispecific (e.g., bispecific). Multispecific antibodies may be specific for different epitopes of one target polypeptide or may contain antigen-binding domains specific for more than one target polypeptide. See, e.g., Tutt et al., 1991, *J. Immunol.* 147: 60-69; Kufer et al., 2004, *Trends Biotechnol.* 22:238-244. The antibodies disclosed herein can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bispecific or a multispecific antibody with a second binding specificity.

Embodiments include antibody-drug conjugates comprising bispecific antibodies wherein one arm of an immunoglobulin binds a first antigen, and the other arm of the immunoglobulin is specific for a second antigen. The antigen may be an infectious disease-related target. As a non-limiting example, antibody-drug conjugates may comprise bispecific antibodies wherein one arm of an immunoglobulin binds human MSR1, and the other arm of the immunoglobulin is specific for WTA or Protein A. As another non-limiting example, antibody-drug conjugates may comprise bispecific antibodies wherein one arm of an immunoglobulin binds WTA, and the other arm of the immunoglobulin is specific for Protein A.

For example, the MSR1-binding arm can comprise any of the HCVR/LCVR or CDR amino acid sequences as set forth in Table 9 herein. In certain embodiments, the MSR1-binding arm binds human MSR1 and blocks modified LDL binding to MSR1. In other embodiments, the MSR1-binding arm binds human MSR1 but does not block modified LDL binding to MSR1. In some embodiments, the MSR1 binding arm binds human MSR1 and activates MSR1 signaling. In other embodiments, the MSR1 binding arm blocks MSR1-mediated receptor stimulation. Embodiments also include bispecific antibodies wherein one arm of an antibody binds a first epitope of human MSR1, and the other arm of said antibody binds a second distinct epitope of human MSR1.

An exemplary bispecific antibody format that can be used in the context of the antibody-drug conjugates according to the present disclosure involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bispecific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present disclosure.

Other exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and $Mab^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Combination Treatment

In one embodiment of any of the above methods, the method further comprises administering a second therapeutic agent.

In one embodiment, the second therapeutic agent is a second antibiotic.

In one embodiment, the second therapeutic agent is an antibiotic including an antibiotic against *S. aureus* in general and/or MRSA in particular.

In one embodiment, the second therapeutic agent is a second antibiotic selected from an aminoglycoside, a beta-lactam, a macrolide, a cyclic peptide, a tetracycline, a fluoroquinoline, a fluoroquinolone, and an oxazolidinone.

In one embodiment, the second therapeutic agent is a second antibiotic selected from clindamycin, novobiocin, retapamulin, daptomycin, sitafloxacin, teicoplanin, triclosan, napthyridone, radezolid, doxorubicin, ampicillin, vancomycin, imipenem, doripenem, gemcitabine, dalbavancin, and azithromycin.

Embodiments include compositions and therapeutic formulations comprising any of the antibodies or ADCs described herein in combination with one or more additional therapeutically active components, and methods of treatment comprising administering such combinations to subjects in need thereof.

The antibodies or ADCs disclosed herein may be co-formulated with and/or administered in combination with one or more additional therapeutically active component(s) selected from the group consisting of: cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The antibodies or ADCs disclosed herein may also be administered and/or co-formulated in combination with anti-inflammatory agents, immunomodulatory agents, analgesics, corticosteroids, steroids, antioxidants, COX inhibitors, cardioprotectants, metal chelators, IFN-gamma, and/or NSAIDs. In some embodiments, the antibodies or ADCs can be administered and/or co-formulated in combination with anti-PCSK9 antibodies, anti-ANGPTL3 antibodies, statins, ezetimibe and other lipid lowering therapies.

The additional therapeutically active component(s), e.g., any of the agents listed above or derivatives thereof, may be administered just prior to, concurrent with, or shortly after the administration of an antibody or ADC disclosed herein; (for purposes of the present disclosure, such administration regimens are considered the administration of an antibody or ADC "in combination with" an additional therapeutically active component). Embodiments include pharmaceutical compositions in which an antibody or ADC disclosed herein is co-formulated with one or more of the additional therapeutically active component(s) as described elsewherein-herein.

EXAMPLES

The following examples illustrate specific aspects of the instant description. The examples should not be construed as limiting, as the examples merely provide specific understanding and practice of the embodiments and their various aspects.

As used herein, the symbols and conventions used in the processes, and Examples, herein, are consistent with those used in the contemporary scientific literature, for example, the Journal of the American Chemical Society or the Journal of Biological Chemistry unless specified otherwise to the contrary. Specifically, but without limitation, the following abbreviations may be used in the Examples and throughout the specification:

| Abbreviation | Term |
|---|---|
| ADC | Antibody-drug conjugate |
| Aglycosylated antibody | Antibody does not have any glycan |
| aq | Aqueous |
| BARAC | Biarylazacyclooctynone |
| BCN | (1R,8S,9s)-Bicyclo[6.1.0]non-4-yn-9-yl |
| Boc | N-tert-butoxycarbonyl |
| BupHTM | Thermo Scientific Prod# 28372, containing 100 mM sodium phosphate and 150 mM sodium chloride, potassium free, pH was adjusted from 7.2 to 7.6-7.8 MQ, unless otherwise noted. |
| CD | Cyclodextrin |
| COT | Cyclooctynol |
| Da | Dalton |
| DAR | Drug to antibody ratio. |
| DCM | Dichloromethane |
| DIBAC | Dibenz[b,f]azocine,11,12-didehydro-5,6-dihydro- or Dibenzocyclooctyne or Dibenz[b,f]azocine-5(6H)-butanoic acid,11,12-didehydro |
| DIBAC-Suc | Dibenz[b,f]azocine-5(6H)-butanoic acid,11,12-didehydro |
| DIBACT | 3H-Benzo[c]-1,2,3-triazolo[4,5-e][1]benzazocine,8,9-dihydro- |
| DIBO | Dibenzocyclooctyne |
| DIFO | Difluorinated cyclooctyne |
| DIPEA | Diisopropylethylamine |
| DMF | N,N-dimethylformamide |
| DMSO | Dimethylsulfoxide |
| ESI | Electrospray ionization |
| g | Gram |
| HATU | 2-(7-Aza-1H-benzotriazole-1-yl)-1,1,3,3-tetramethyluronium hexafluorophosphate |
| HC | Heavy chain of immunoglobulin |
| HEK | Human embryonic kidney (cells) |
| HPLC | High performance liquid chromatography |
| hr or hrs | Hours |
| LC | Light chain of immunoglobulin |
| LC | Liquid chromatography |
| MC | Maleimidocaproyl |
| mg | Milligrams |
| min | Minutes |
| mL | Milliliters |
| mM | Millimolar |
| MMAE | Monomethyl auristatin E |

-continued

| Abbreviation | Term |
|---|---|
| MS | Mass spectrometry |
| MSD | Mass-selective detector |
| MTG | Microbial transglutaminase |
| MW | Molecular weight |
| ncADC | Non-Cytotoxic antibody drug conjugation |
| NHS | N-hydroxy succinimide |
| nM | nanomolar |
| NMR | Nuclear magnetic resonance |
| NOESY | Nuclear Overhauser effect spectroscopy |
| PAB | Para-aminobezyloxy(carbonyl) |
| PBS | 10 mM sodium phosphate buffer and 150 mM sodium chloride |
| PBSg | 10 mM phosphate, 150 mM sodium chloride, 5% glycerol |
| PEG | Polyethyleneglycol |
| ppm | Parts per million (chemical shift) |
| RP | Reversed phase |
| RT or rt | Room temperature |
| SDS-PAGE | Sodium dodecylsulfate polyacrylamide gel electrophoresis |
| SEC | Size exclusion chromatography |
| Suc | Succinic acid |
| TCEP | Tris(2-carboxyethyl)phosphine hydrochloride |
| TEA | Triethylamine |
| TFA | Trifluoroacetic acid |
| TG | Transglutaminase |
| THF | Tetrahydrofuran |
| TOF | Time-of-flight |
| UPLC | Ultra-Performance Liquid Chromatography |
| UV | Ultraviolet |
| VA | Valine-Aniline |
| VC | Valine-citrulline |
| μL | Microliters |
| μM | micromolar |

As use herein, the symbols an conventions use in these processes, schemes, an examples, regardless of whether a particular abbreviation is specifically defined, are consistent with those used in the contemporary scientific literature, for example, the Journal of the American Chemical Society or the Journal of Biological Chemistry.

General Methods

All the solvents used were purchased either from Sigma Aldrich or Fisher Scientific and were used without further purification. Rifamycin S was purchased from Bosche Scientific. $^1$H-NMR spectra were recorded on a Varian Inova 300 MHz and 500 MHz NMR instruments. The chemical shifts (δ) are reported in ppm with respect to the NMR solvents used for analysis and are reported as s—singlet, d—doublet, t—triplet, q—quartet, dd—doublet of doublet, dt—doublet of triplet, dq—doublet of quartet, and m—multiplet. Coupling constants (J) are reported in hertz (Hz). Chromatographic purities were determined on an Agilent 1100, 1260 Infinity, or 1200 Series LC/MS systems using Chromolith® FastGradient RP-18e analytical columns (50×2 mm, Merck KGaA, P/N 1.52007.0001) and the following analytical HPLC method: injection volume 5 or 10 μL; flow rate 1 mL/min; 5-95% acetonitrile in water over 4 min; Agilent diode array detector at λ=254 nm; room temperature. Low resolution mass spectrometry was performed on an Agilent system using electrospray ionization sources and analyzed with either single quadrupole or ion trap mass detectors.

Example 1: Synthesis of Analogs 1a-1d According to the Disclosure

Scheme 1,
below, depicts the synthesis of exemplary compounds 1a-1d according to the disclosure from commercially available starting materials.

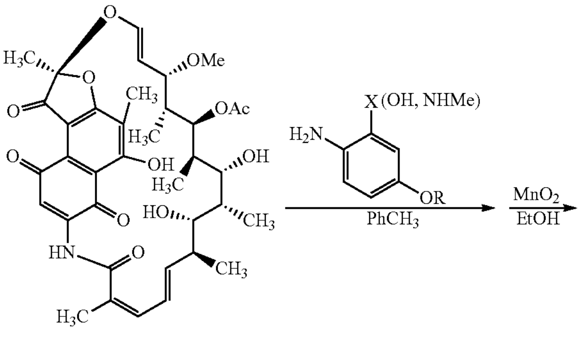

Rifamycin S

-continued

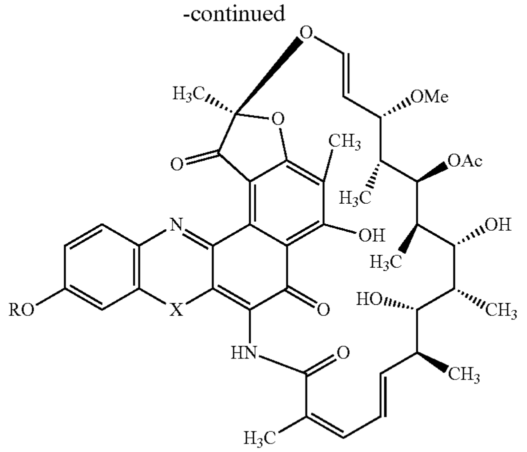

1a, R = Me X = O
1b, R = Bn X = O
1c, R = H X = O
1d, R = H X = NHMe

Example 1A: Rifamycin 4-MeO-Phenol Analogs (1a)

The general coupling procedure of Example 1 is used to prepare the title compound: To a stirring solution under argon of rifamycin S (200 mg, 0.287 mmol) in 15 mL of toluene at room temperature was added 2-amino-5-methoxyphenol (44 mg, 0.316 mmol). The mixture solution was stirred for 3 days at room temperature. The progress of reaction was monitored by LC/MS, then the mixture was evaporated to dryness. The dark residue was dissolved in 10 mL of ethanol, and 100 mg (1.14 mmol) of manganese oxide ($MnO_2$) was added in one portion to the ethanol solution. The sluggish mixture was stirred for 15 h at room temperature. After filtration of insoluble materials using a Celite pad, the filtrate was evaporated under reduced pressure. The dark residue was purified on a 40 g HP silica gel Gold RediSep column via ISCO (gradient elution: 5→95% EA in hexanes) and the pure fractions evaporated and dried in vacuo giving the title compound 1a as a dark reddish solid (85 mg, 37%). MS (ESI, pos.): calc'd for $C_{44}H_{50}N_2O_{13}$, 814.33; found 815.3 (M+H), 837.3 (M+Na). $^1$H NMR (500 MHz; $CDCl_3$) δ 7.96 (d, J=9.0 Hz, 1H), 7.47 (s, 1H), 7.05-7.01 (m, 2H), 6.86 (s, 1H), 5.99 (s, 2H), 4.97 (dd, J=12.4, 7.4 Hz, 2H), 3.93 (s, 3H), 3.08 (s, 3H), 3.00-2.99 (m, 1H), 2.30 (s, 3H), 2.13 (s, 3H), 2.03 (d, J=18.1 Hz, 3H), 1.81 (s, 3H), 1.70-1.67 (m, 1H), 1.59-1.54 (m, 16H), 1.53 (s, 3H), 0.96-0.95 (m, 3H).

Example 1B: Rifamycin 4-BnO-Phenol Analogs (1b)

Analog 1b was prepared using intermediate 2, the synthesis of which is depicted in Scheme 2, below.

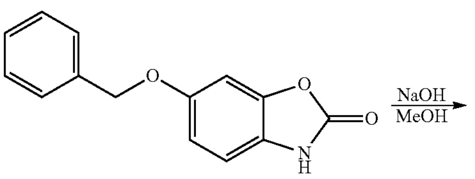

-continued

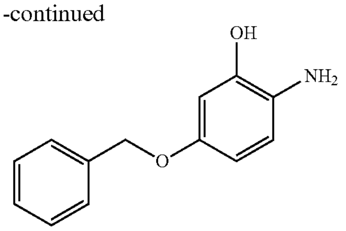

2

Synthesis of compound 2. The mixture of 6-(benzyloxy)benzo[d]oxazol-2(3H)-one (500 mg, 2.07 mmol) and methanol (6 mL) was treated with a solution of 1.2 g of NaOH in 6 mL of water. The suspension was heated at 90° C. overnight. After cooling at room temperature, the mixture was treated with 6N HCl (5 mL) then filtered. The filtrate was adjusted to afford pH=8-9 with sat. aq. $NaHCO_3$ and the precipitate was filtered, washed with water to give a dark solid, which was purified by 40 g HP silica gel Gold RediSep column (0→90% EA in hexanes) to afford 220 mg (49%) of compound 2. MS (ESI, pos.): calc'd for $C_{13}H_{13}NO_2$, 215.09; found 216.1 (M+H). $^1$H NMR (500 MHz; DMSO-$d_6$) δ 7.39-7.37 (m, 5H), 7.31 (d, J=7.0 Hz, 1H), 6.49 (d, J=8.4 Hz, 1H), 6.37 (d, J=2.7 Hz, 1H), 6.25 (dd, J=8.4, 2.7 Hz, 1H), 4.91 (s, 2H).

Synthesis of analog 1b. To a stirred solution of rifamycin S (20 mg, 0.0287 mmol) under argon in 1 mL of toluene at room temperature was treated with 2-amino-5-(benzyloxy)phenol 2 (6.8 mg, 0.0316 mmol). The solution was stirred for 3 days at room temperature and additional 2-amino-5-(benzyloxy)phenol (6.8 mg) was added. The progress of reaction was monitored by LC/MS. After 5 days, the mixture was evaporated to dryness. The dark residue was dissolved in 3.5 mL of ethanol and 10 mg (0.11 mmol) of manganese oxide ($MnO_2$) was added in one portion to the ethanol solution. The sluggish mixture was stirred for 3h at room temperature. After filtration of insoluble materials using a Celite pad, the filtrate was evaporated under reduced pressure. The dark residue was purified on a 24 g HP silica gel Gold RediSep column via ISCO (gradient elution: 5→98% EA in hexanes) and the pure fractions evaporated and dried in vacuo giving the title compound 1b as a dark reddish solid (8.5 mg, 33%). MS (ESI, pos.): calc'd for $C_{50}H_{54}N_2O_{13}$, 890.36; found 891.3 (M+H). $^1$H NMR (500 MHz; $CDCl_3$) δ 7.97 (s, 1H), 7.49 (s, 1H), 7.44-7.41 (m, 5H), 7.14-7.11 (m, 2H), 7.07 (s, 1H), 6.94 (s, 1H), 5.32 (s, 1H), 5.23 (s, 1H), 5.18 (d, J=11.9 Hz, 2H), 4.99 (s, 2H), 3.11 (s, 3H), 3.04 (dd, J=2.0, 0.6 Hz, 1H), 2.32 (s, 3H), 2.07 (s, 6H), 1.83 (s, 3H), 1.71-1.69 (m, 1H), 1.61 (d, J=0.4 Hz, 9H), 1.58-1.52 (m, 6H), 1.28 (s, 1H), 0.97 (td, J=1.9, 1.2 Hz, 3H), 0.79 (t, J=0.8 Hz, 1H).

Example 1C: Rifamycin 4-OH-Phenol Analogs (1c)

Analog 1c was prepared using intermediate 4, the synthesis of which is depicted in Scheme 3, below.

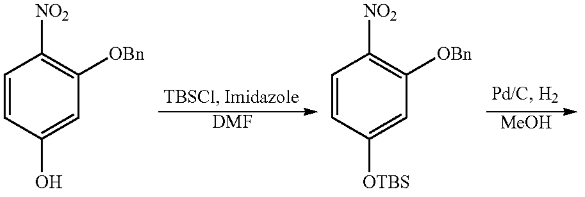

8

3

-continued

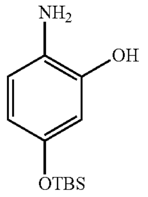

4

2-amino-5-((tert-butyldimethylsilyl) oxy)phenol (4)

Synthesis of compound 3. Compound 8 was prepared from the product in Example 1B. To the solution of 3-benzyloxy-4-nitrophenol 8 (400 mg, 1.63 mmol) under argon in DMF (2 mL) was added TBSCl (0.247 mL, 2.44 mmol), imidazole (222 mg, 3.26 mmol), and DMAP (0.5 mg). The mixture was stirred at room temperature overnight then diluted with ethyl acetate (25 mL), washed with water (2×10 mL), brine solution (10 mL), and dried over sodium sulfate. The crude was purified by 40 g HP silica gel Gold RediSep column via ISCO (gradient elution: 0→20% EA in hexanes) and the pure fractions evaporated to afford the desired compound 3 (540 mg, 92%). MS (ESI, pos.): calc'd for $C_{19}H_{25}N_2O_4Si$, 359.16; found 382.1 (M+Na).

Synthesis of compound 4. To the solution under argon of compound 3 (120 mg, 0.33 mmol) in 3 mL of methanol (degassed with argon three times) was added 10% Pd/C (10 mg). The mixture was again degassed and bubbled with hydrogen from a balloon. A hydrogen balloon was inserted through the septa and the mixture was aged for overnight. The mixture was filtered through Celite and concentrated to give a dark greenish solid (71 mg, 90%). MS (ESI, pos.): calc'd for $C_{12}H_{21}NO_2Si$, 239.13; found 240.2 (M+H).

Synthesis of analog 1c. To a stirring solution under argon of rifamycin S (120 mg, 0.172 mmol) in 10 mL of toluene at room temperature was added compound 4 (46 mg, 0.192 mmol). The mixture solution was stirred for 3 days at room temperature. The progress of the reaction was monitored by LC/MS, then the mixture was evaporated to dryness. The dark residue was dissolved in 10 mL of ethanol, and 50 mg (0.6 mmol) of manganese oxide ($MnO_2$) was added in one portion to the ethanol solution. The sluggish mixture was stirred for 12 h at room temperature. After filtration of insoluble materials using a Celite pad, the filtrate was evaporated under reduced pressure. The dark residue was purified on a 24 g HP silica gel Gold RediSep column via ISCO (gradient elution: 5-95% EA in hexanes). The pure fractions were evaporated and dried in vacuo giving the title compound 1c as a dark reddish solid (48 mg, 35%). MS: calc'd for $C_{43}H_{48}N_2O_{13}$, 800.32; found 801.3 (M+H), 799.2 (M−H). $^1H$ NMR (500 MHz; DMSO-$d_6$) δ 11.43 (d, J=1.7 Hz, 1H), 9.33-9.32 (m, 1H), 7.82 (dt, J=2.0, 1.0 Hz, 1H), 7.02-7.01 (m, 1H), 6.89 (t, J=1.3 Hz, 1H), 6.04 (dd, J=2.5, 0.9 Hz, 1H), 5.83 (dt, J=1.9, 1.0 Hz, 1H), 5.25-5.24 (m, 1H), 4.78-4.77 (m, 1H), 4.14-4.14 (m, 1H), 3.52 (d, J=0.8 Hz, 1H), 3.07 (d, J=0.7 Hz, 1H), 3.03 (t, J=0.6 Hz, 3H), 2.89 (s, 1H), 2.78 (t, J=2.7 Hz, 1H), 2.19 (d, J=16.7 Hz, 3H), 1.99 (d, J=12.2 Hz, 4H), 1.95 (t, J=0.5 Hz, 4H), 1.67 (d, J=1.9 Hz, 3H), 1.24 (s, 2H), 0.89 (dd, J=2.5, 1.1 Hz, 2H), 0.85 (d, J=6.5 Hz, 6H), 0.69 (d, J=1.5 Hz, 3H).

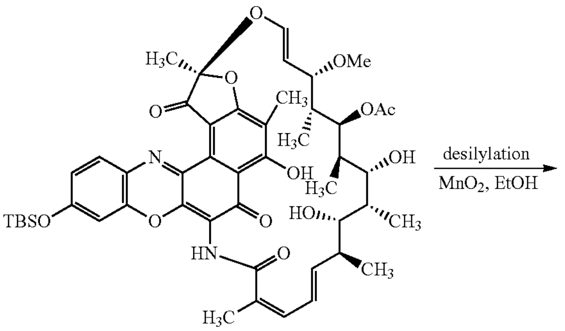

1c-TBS

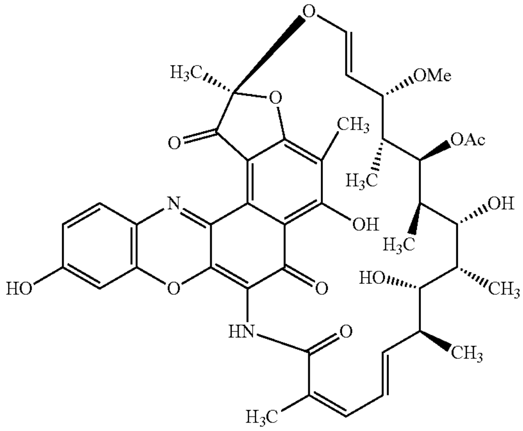

1c

Example 1D: Rifamycin 4-OH-Phenol N-Methyl Analogs (1d)

Analog 1d was prepared using intermediate 7, the synthesis of which is depicted in Scheme 4, below.

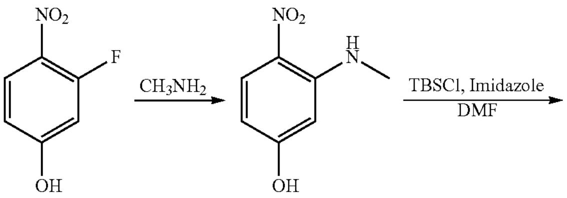

5

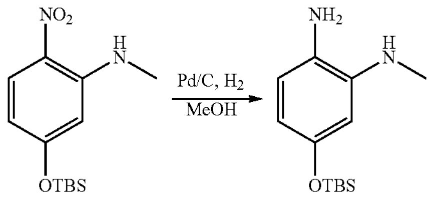

6 7

5-((tert-butyldimethylsilyl)oxy)-N1-methylbenzene-1,2-diamine (7)

Synthesis of compound 5. The title compound was prepared using the method disclosed in PTC *Int. Appl.* 2008051805. In a sealed tube were placed a mixture of 3-fluoro-4-nitrophenyl (1 g, 6.36 mmol) and 2 mL of a 40% methylamine aqueous solution. The flask was sealed via septum, purged with argon, and heated at 80° C. in an oil-bath for 18 h. The reaction was complete by LCMS analysis and cooled to room temperature. The solution was dissolved by the addition of water (15-20 mL) and extracted using ethyl acetate (3×30 mL). The combined organic layer was then washed with water, brine, dried ($Na_2SO_4$), and then concentrated to give a crude product, brown white solid (900 mg, 84%) of 5, which was used in the next step without further purification. MS (ESI, pos.): calc'd for $C_7H8N_2O_3$, 168.05; found 169.1 (M+H).

Synthesis of compound 6. Under argon 3-(methylamino)-4-nitrophenol 5 (200 mg, 1.19 mmol) and imidazole (162 mg, 2.38 mmol) were dissolved in anhydrous DMF in the presence of catalytic DMAP (0.7 mg). The stirred yellow solution was cooled in an ice-bath and TBSCl (269 mg, 1.79 mmol) was added in one portion to the yellow solution. After 5 min the bath was removed and the solution was allowed to warm to room temperature overnight. The mixture was quenched by saturated $NaHCO_3$ solution and extracted with ethyl acetate (2×25 mL). The combine organics were dried by addition of $Na_2SO_4$ and then concentrated to give a crude product. The residue was purified on a 24 g HP silica gel Gold RediSep column via ISCO (gradient elution: 0→90% EA in hexanes) and the pure fractions evaporated then dried in vacuo giving the title compound 6 as a yellow solid (220 mg, 66%). MS: calc'd for $C_{13}H_{22}N_2O_3Si$, 282.14; found 283.1 (M+H).

Synthesis of compound 7. Under argon 5-((tert-butyldimethylsilyl)oxy)-N1-methylbenzene-1,2-diamine 6 (50 mg, 0.177 mmol) was dissolved in 2 mL of methanol. The solution was degassed with argon three times followed by addition of Pd/C (5 mg). The mixture was further degassed with argon and connected to a hydrogen balloon via septum. After 2.5 h, the analysis by LC/MS from an in-process aliquot indicated the reaction was complete. The mixture was filtered through Celite and concentrated to afford 46 mg of compound 7 quantitatively, which was used in the next step instantly without further purification. MS: calc'd for $C_{13}H_{24}N_2OSi$, 252.17; found 253.2 (M+H).

Synthesis of analog 1d. To a stirring solution under argon of rifamycin S (58 mg, 0.083 mmol) in 3 mL of toluene at room temperature was added compound 7 (21 mg, 0.083 mmol). The solution was stirred for 2 days at room temperature. The progress of the reaction was monitored by LC/MS, then the solution was evaporated to dryness. The dark residue was dissolved in 5 mL of ethanol and 10 mg of manganese oxide ($MnO_2$) was added in one portion to the ethanol solution. The sluggish mixture was stirred for 12 h at room temperature. After filtration of insoluble materials using a Celite pad, the filtrate was evaporated under reduced pressure. The dark residue was purified on a 12 g HP silica gel Gold RediSep column via ISCO (gradient elution: 5→95% EA in hexanes) and the pure fractions evaporated then dried in vacuo giving the title compound 1d as a dark reddish solid (22.3 mg, 33%). This was found to be impure by LC/MS, so it was dissolved in MeCN/water and repurified on a 15.5 g C18 Aq Gold column (gradient elution: 10-95% MeCN in water, 0.05% acetic acid in both, over 20 min). The product fractions were combined, frozen on dry ice, and lyophilized giving the title compound 1d as a white solid (13.5 mg, 20%). MS: calc'd for $C_{44}H_{51}N_3O_{12}$, 813.35; found 814.3 (M+H), 812.3 (M−H). $^1H$ NMR (500 MHz; DMSO-$d_6$) δ 11.31 (b, J=0.8 Hz, 2H), 9.41 (s, 1H), 9.22 (s, 1H), 8.86 (s, 1H), 8.01-7.95 (m, 2H), 7.19-7.13 (m, 2H), 7.04 (s, 2H), 6.79-6.74 (m, 1H), 6.39-6.37 (m, 1H), 6.19 (t, J=11.4 Hz, 2H), 6.08 (d, J=12.4 Hz, 1H), 6.02-5.92 (m, 1H), 5.73 (d, J=26.4 Hz, 1H), 5.49 (d, J=11.2 Hz, 1H), 5.28 (d, J=0.6 Hz, 1H), 5.09-5.02 (m, 2H), 4.82 (dd, J=11.5, 10.2 Hz, 1H), 4.54 (d, J=6.6 Hz, 1H), 4.36 (d, J=2.6 Hz, 1H), 3.96 (d, J=4.4 Hz, 1H), 3.88 (s, 1H), 3.83 (s, 1H), 3.79 (s, 1H), 3.70 (s, 1H), 3.09 (s, 1H), 2.91 (s, 3H), 2.21 (s, 3H), 2.15 (d, J=5.9 Hz, 1H), 1.97 (s, 2H), 1.72 (s, 2H), 1.64 (s, 2H), 1.59 (s, 2H), 0.90 (d, J=7.0 Hz, 1H), 0.70 (d, J=6.6 Hz, 1H), 0.62 (d, J=6.8 Hz, 1H), 0.20-0.18 (m, 1H), 0.07 (d, J=0.7 Hz, 1H).

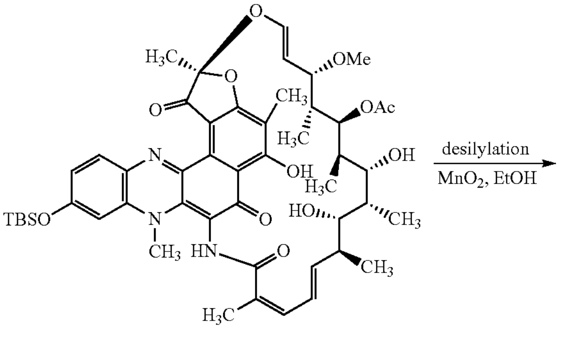

1d-TBS

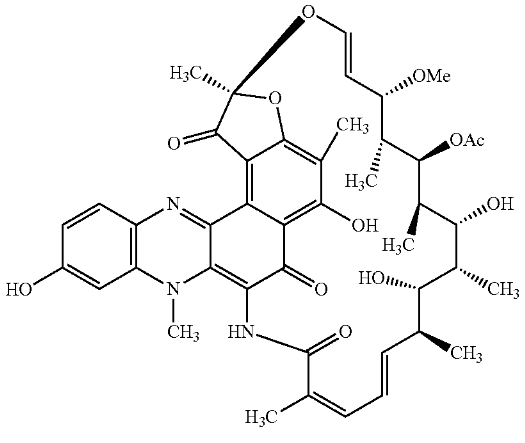

1d

Example 2: Synthesis of Analog 14 According to the Disclosure

Rifamycin analog 14 was synthesized from rifamycin S as shown in Scheme 5, below, and as described below.

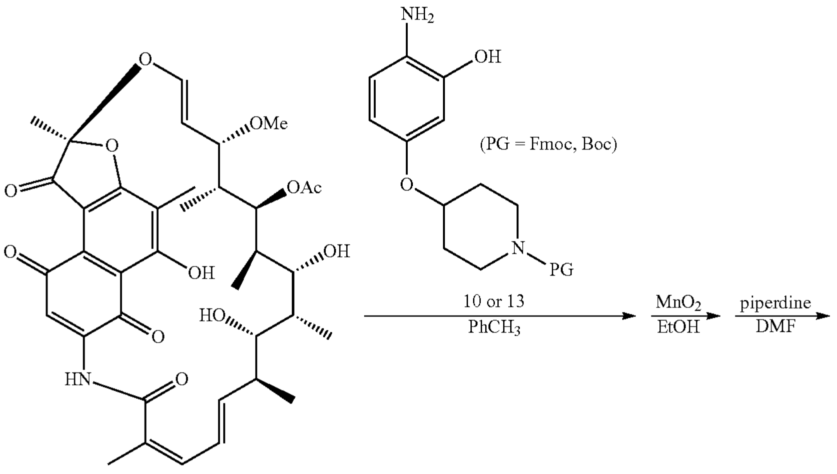
Rifamycin S
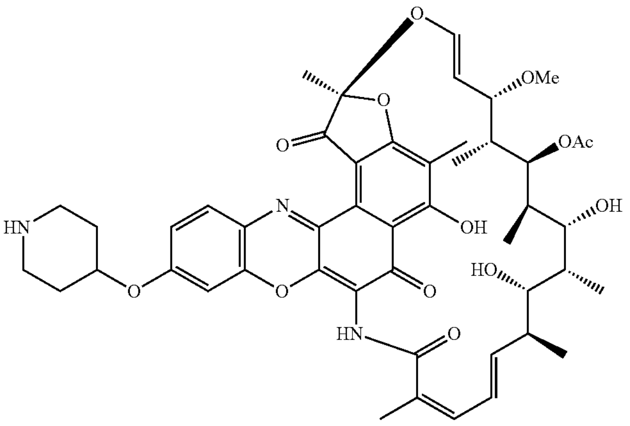
14
Example 2A: Preparation of Compounds (10 and 13)
Intermediates 10 and 13 were prepared according to Scheme 6, shown below.
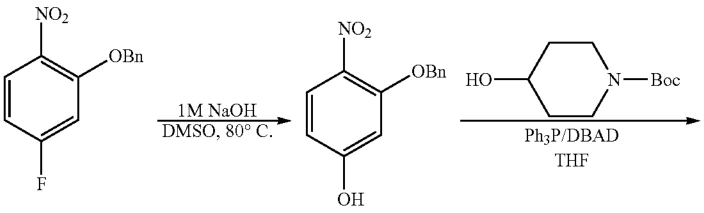
8

-continued

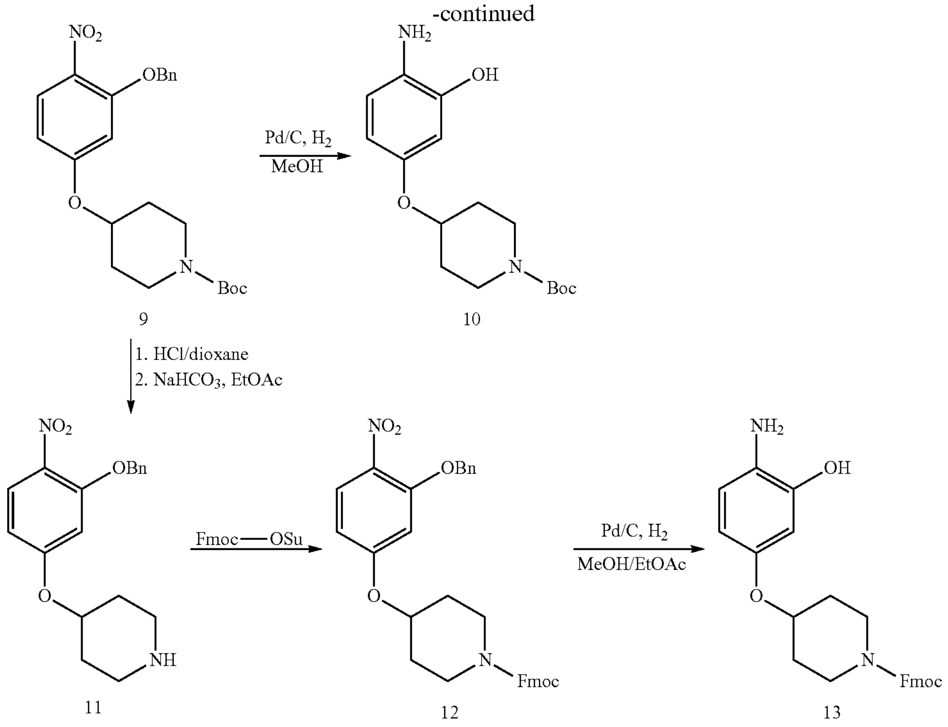

9 10 11 12 13

Synthesis of compound 8. The title compound was prepared using a slightly modified method reported by Otten et. al. (*Bioconjugate Chem.* 2001, 12, 76-83). To a solution of 3-fluoro-4-nitrophenyl (2.09 g, 8.45 mmol) in DMSO (10 mL) was added 1M NaOH (10 mL) and heated to 80° C. on a heating block for 18 h. The reaction was complete by LCMS and cooled to room temperature. The reaction was acidified with 1M HCl (15-20 mL) until the pH=3-4 and the resultant solution was extracted using ethyl acetate (3x30 mL). The combined organic layers were washed with water, brine, dried ($Na_2SO_4$), and concentrated in vacuo. The crude oil was then purified on an 80 g HP silica gel Gold RediSep column via ISCO (gradient elution: 0→100% ethyl acetate in hexanes) and the pure fractions evaporated then dried in vacuo giving the title compound 8 as a yellowish white solid (1.51 g, 73%). MS (ESI, pos.): calc'd for $C_{13}H_{11}NO_4$, 245.1; found 268.1 (M+Na), 244.1 (M−H).

Synthesis of compound 9. To a stirring solution under argon of compound 8 (1.51 g, 6.157 mmol) in THF (16 mL) at room temperature were added the BOC-piperidin-4-ol (1.61 g, 8.005 mmol) and $PPh_3$ (2.91 g, 11.083 mmol). A solution of DBAD (2.55 g, 11.083 mmol) in THF (9 mL) was added to the reaction mixture dropwise. After stirring for 16 h, the mixture was evaporated to dryness and the residue was purified on a 40 g HP silica gel Gold RediSep column via ISCO (gradient elution: 0→100% ethyl acetate in hexanes) and the pure fractions evaporated then dried in vacuo giving the title compound 9 as a yellowish white solid (2.41 g, 91%). MS: calc'd for $C_{23}H_{28}N_2O_6$, 428.2; found 451.1 (M+Na).

Synthesis of compound 10. To a degassed solution under argon of compound 9 (100 mg, 0.233 mmol) in 3 mL of methanol was added 5 mg of 10% Pd/C. The mixture was further degassed and connected to a hydrogen balloon. After 2.5 h, the analysis by LC/MS from in-process aliquot indicated the reaction was complete. The mixture was filtered through Celite and concentrated to afford 75 mg of compound 10 quantitatively, which was used in the next step instantly without further purification. MS: calc'd for $C_{16}H_{24}N_2O_4$, 308.17; found 331.2 (M+Na), 307.1 (M−H).

Synthesis of compound 11. To a solution of compound 9 (1100 mg, 2.561 mmol) in 1,4-dioxane (15 mL) was added 4 M HCl in 1,4-dioxane (5 mL). After stirring for 15 h an in-process aliquot indicated the reaction was complete. To the solution was added diethyl ether (50 mL), then the mixture was stirred vigorously for 1 h until a white precipitate formed. The solid was filtered and washed with ether to afford the HCl salt of 11. To the white solid was added EtOAc (10 mL) and sat. $NaHCO_3$ (15 mL) until pH=8-9 and stirred for 15 min. The two layers were separated and the aqueous layer was extracted with EtOAc (3x30 mL). The combined organic layers were dried ($Na_2SO_4$) and concentrated in vacuo to give compound 11 (372 mg, 44%) which was used in the next step instantly without further purification. MS: calc'd for $C_{18}H_{21}N_2O_4$, 328.1; found 329.1 (M+H).

Synthesis of compound 12. To a solution under argon of compound 11 (372 mg, 1.128 mmol) in 1,4-dioxane/water (v/v, 10:1, 11 mL) was added Fmoc-OSu (399 mg, 1.184 mmol). After stirring for 15 h an in-process LC/MS analysis indicated the reaction was complete. The reaction mixture was concentrated in vacuo to give compound 12 which was used in the next step instantly without further purification. MS: calc'd for $C_{33}H_{30}N_2O_6$, 550.2; found 551.2 (M+H).

Synthesis of compound 13. To a solution under argon of compound 12 (72 mg, 0.131 mmol) in 2 mL of methanol and degassed with argon was added 9 mg of 10% Pd/C. The mixture was further degassed with argon and connected to a hydrogen balloon. After 45 min, analysis by LC/MS from an in-process aliquot indicated the reaction was complete. The mixture was filtered through Celite and concentrated in vacuo to afford 55 mg of compound 13 quantitatively, which was used in the next step instantly without further purification. MS: calc'd for $C_{26}H_{26}N_2O_4$, 430.1; found 431.2 (M+H).

Example 2B: Preparation of Analog 14 from Intermediate 10

Synthesis of compound 14-Boc: To a stirring solution of rifamycin S (100 mg, 0.143 mmol) in 5 mL of toluene at room temperature was added compound 10 (44 mg, 0.143 mmol). The mixture solution was stirred for 4 days at room temperature. The progress of the reaction was monitored by LC/MS until complete, then the mixture was evaporated to dryness. The dark residue was dissolved in 10 mL of ethanol and 62 mg (0.715 mmol) of manganese oxide ($MnO_2$) was added at one portion to the ethanol solution. The sluggish mixture was stirred for 15 h at room temperature. After filtration of insoluble materials using Celite pad, the filtrate was evaporated under reduced pressure. The dark residue was purified on a 12 g HP silica gel Gold RediSep column via ISCO (gradient elution: 5%-95% ethyl acetate in hexanes). After concentrating under reduced pressure the crude product (ca. 85% pure) was repurified on a 50 g C18 Aq Gold column (gradient elution: 10-95% MeCN in water, 0.05% acetic acid in both). The pure fractions were combined, frozen on dry ice, and lyophilized to afford 14-Boc as a dark reddish solid (36 mg, 26%). MS: calc'd for $C_{53}H_{65}N_3O_{15}$, 983.44; found 984.4 (M+H).

14-Boc

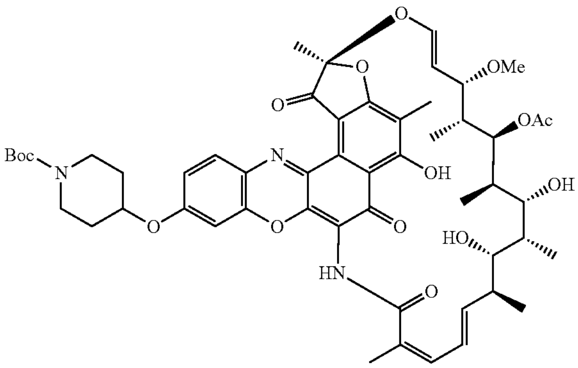

Synthesis of compound 14: 14-Boc (30 mg, 0.03 mmol) was treated with a mixture of TFA/acetonitrile/water (0.25 mL/5 mL/5 mL) at room temperature for 20 h to afford compound 14. The reaction mixture was purified on a 15.5 g C18 Aq. Gold column via ISCO system (gradient elution: 10%-100% MeCN in water, 0.05% acetic acid in both, over 30 min). The product-containing fractions were combined, frozen on dry ice, and lyophilized overnight giving the title compound 14 (10 mg, 37%) as dark reddish solid. MS: calc'd for $C_{48}H_{57}N_3O_{13}$, 883.4; found 884.3 (M+H).

Example 2C: Preparation of Analog 14 from Intermediate 13

Synthesis of compound 14: To a round-bottom flask with hydroxyaniline 13 (55 mg, 0.1278 mmol) were added toluene (1.5 mL) and rifamycin S (67 mg, 0.0956 mmol). The reaction mixture was sonicated for 1 min to dissolve the reaction mixture, sealed via rubber septum, purged with argon, and the reaction stirred at ambient temperature. After 2 days another portion of hydroxyaniline (45 mg, 0.1045 mmol) was added and stirred for 1 d. The reaction was concentrated in vacuo to remove toluene, dissolved in EtOH (6 mL) and $MnO_2$ (20 mg) was added. After stirring for 3 d, the reaction was concentrated in vacuo and purified by chromatography on a 40 g HP silica gel Gold RediSep column via ISCO (gradient elution: 0→100% ethyl acetate in hexanes). The pure fractions were evaporated and dried in vacuo giving the title compound 14-Fmoc as a dark reddish solid (35 mg, 33%). MS (ESI, pos.): calc'd for $C_{63}H_{67}N_3O_{15}$, 1105.4; found 1106.5 (M+H), 1128.5 (M+Na).

14-Fmoc

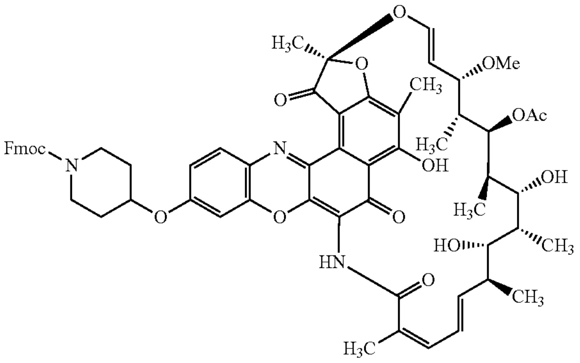

To a stirred solution under argon of Fmoc-rifamycin-piperidine-O-phenol 14-Fmoc of the preceding step (35 mg, 0.0361 mmol) in N,N-dimethylformamide (DMF, 1 mL), was treated with a solution of 2% piperidine (3.5 mg, 0.2 mL, 0.0411 mmol) in DMF and the reaction stirred at ambient temperature. After 2 h, the reaction was purified directly on a 50 g C18 RediSep Gold column via ISCO system (gradient elution: 0-100% MeCN in water, 0.05% acetic acid in both, over 30 min). The product-containing fractions were combined, frozen on dry ice, and lyophilized overnight giving the title compound 14 as dark reddish solid (12 mg, 43%). MS: calc'd for $C_{48}H_{57}N_3O_{13}$, 883.4; found 884.3 (M+H). $^1H$ NMR (500 MHz; DMSO-$d_6$) δ 9.40 (s, 1H), 7.87 (d, J=8.9 Hz, 1H), 7.16-7.23 (m, 4H), 5.99-6.05 (m, 2H), 5.76-5.85 (m, 2H), 5.18-5.23 (m, 2H), 4.83-4.95 (m, 2H), 4.80 (br. s, 2H), 4.12 (br. S., 1H), 2.91-3.18 (m, 13H), 2.88 (s, 1H), 2.78 (t, J=0.9 Hz, 2H), 2.67 (s, 2H), 2.22 (d, J=3.7 Hz, 4H), 2.15 (s, 2H), 2.02 (s, 2H), 1.96 (d, J=1.2 Hz, 2H), 1.90 (s, 1H), 1.68 (s, 2H), 0.85-0.92 (m, 12H), 0.69 (br. s, 9H).

Example 3: Synthesis of Analogs 16a-16z-1 According to the Disclosure

Rifamycin analogs 16a-16z-1 were synthesized from rifamycin S as shown in Scheme 7 and Scheme 7a, below, and as described below.

Scheme 7

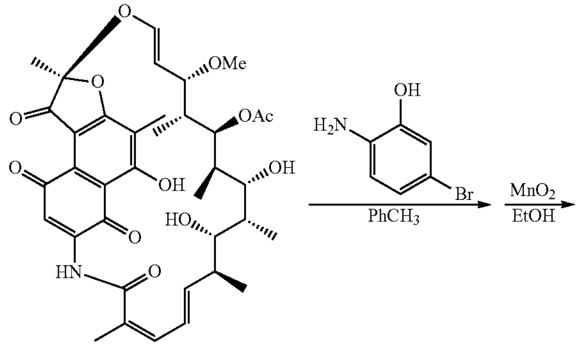

Rifamycin S

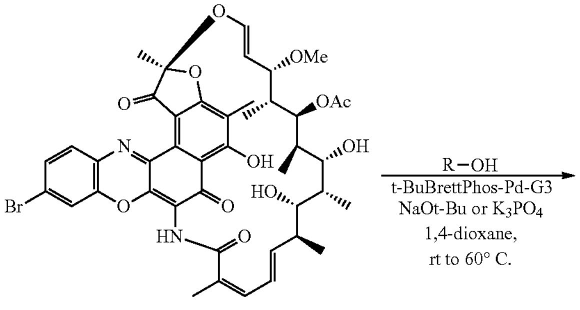

15

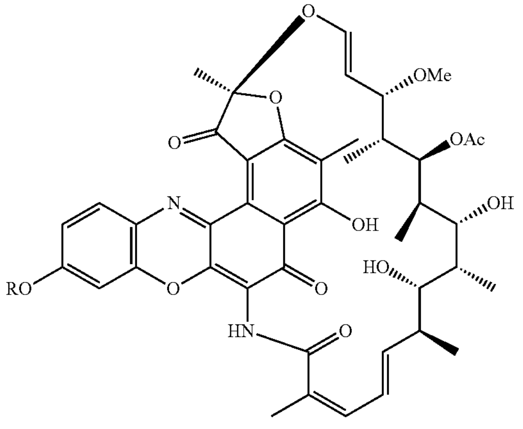

16

16a, R =

16b, R =

16c, R =

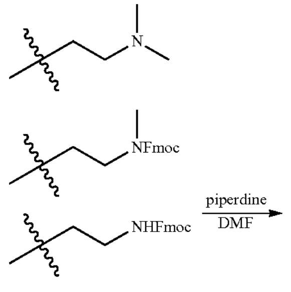

16d, R =

16e, R =

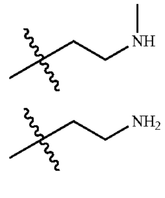

Pd-catalyzed O-alkylation (16a-16z-1)

Synthesis of compound 15. To a stirring solution under argon of rifamycin S (2.0 g, 2.87 mmol) in 80 mL of toluene at room temperature was added 2-amino-5-bromophenol (0.54 g, 2.87 mmol). The solution was stirred for 2 days at room temperature. The reaction mixture was then evaporated to dryness and the dark residue dissolved in 20 mL of ethanol and 300 mg of manganese oxide ($MnO_2$) was added in one portion to the ethanol solution. The sluggish mixture was stirred under argon for 15 h at room temperature. After filtration of insoluble materials using a Celite pad, the filtrate was evaporated under reduced pressure. The dark residue was purified on a 120 g HP silica gel Gold RediSep column via ISCO (gradient elution: 5→95% EA in hexanes). The pure fractions were evaporated and dried in vacuo giving the title compound 15 as a dark reddish solid (1.6 g, 65%). MS (ESI, pos.): calc'd for $C_{43}H_{47}BrN_2O_{13}$, 862.23; found 863.1 and 865.1 (M+H), 885.1 and 888.0 (M+Na). $^1$H NMR (500 MHz; DMSO-$d_6$): δ 9.49 (d, J=6.0 Hz, 1H), 7.92 (ddd, J=3.6, 2.9, 1.8 Hz, 1H), 7.86-7.85 (m, 1H), 7.75-7.74 (m, 1H), 6.06-6.05 (m, 1H), 5.84 (dt, J=2.6, 1.4 Hz, 2H), 5.25-5.23 (m, 2H), 4.80 (dt, J=2.5, 1.0 Hz, 1H), 4.23 (td, J=2.4, 1.0 Hz, 1H), 3.49 (d, J=1.1 Hz, 1H), 3.10-3.09 (m, 2H), 3.03 (s, 3H), 2.79 (s, 1H), 2.19 (s, 3H), 2.01 (s, 4H), 1.96 (s, 4H), 1.81 (d, J=2.2 Hz, 1H), 1.68 (s, 3H), 1.60 (dq, J=2.8, 0.9 Hz, 1H), 1.48 (t, J=1.4 Hz, 1H), 0.90 (dt, J=2.1, 1.1 Hz, 2H), 0.84 (d, J=7.1 Hz, 4H), 0.69 (dd, J=2.2, 1.2 Hz, 5H).

Synthesis of compound 16a. Using a similar method reported by Buchwald S. L. et al. (*Org. Lett.* 2018, 20, 1580), a palladium-catalyzed C—O coupling of primary alcohols with compound 15 was employed for title compounds 16a-16c. To a 2 dram screw-top oven-dried test tube, equipped with a stir bar, and sealed with a screw cap was charged compound 15 (40 mg, 0.0463 mmol, 1.00 eq.), 2-(dimethylamino)ethan-1-ol (42 mg, 0.462 mmol, 10 eq.), tBuBrettPhos Pd G3-palladacycle (11.8 mg, 30 mol %), and NaOt-Bu (5 mg, 0.051 mmol, 1.1 eq.). The reaction tube was recapped with a septum and pierced with a needle attached to evacuate and backfilled with argon (this process was repeated twice) followed by addition of 1,4-dioxane (2.0 mL) via syringe. The reaction was heated at 55° C.±5 in an oil bath under argon pressure for 15 h, the reaction was allowed to cool to room temperature before filtration through a pad of Celite® and rinsed with EtOAc. The crude material was concentrated in vacuo and purified on a 15.5 g C18 Aq Gold column (gradient elution: 10-95% MeCN in water, 0.05% acetic acid in both). The product fractions were combined, frozen on dry ice, and lyophilized giving the title compound 16a as a dark reddish solid (12.5 mg, 32%). MS: calc'd for $C_{47}H_{57}N_3O_{13}$, 871.39; found 872.3 (M+H), 870.2 (M−H). $^1$H NMR (300 MHz; DMSO-$d_6$) δ 9.40 (s, 1H), 7.87 (d, J=8.9 Hz, 1H), 7.23-7.16 (m, 2H), 6.83 (dt, J=2.3, 1.1 Hz, 1H), 6.23 (d, J=4.6 Hz, 1H), 6.06 (dd, J=5.9, 1.1 Hz, 1H), 5.82 (dd, J=2.3, 1.5 Hz, 2H), 5.24 (dt, J=1.4, 0.7 Hz, 1H), 4.83-4.75 (m, 1H), 4.24 (d, J=29.9 Hz, 3H), 3.80 (d, J=1.3 Hz, 1H), 3.03 (t, J=0.5 Hz, 3H), 2.88 (s, 1H), 2.78 (t, J=0.9 Hz, 2H), 2.67 (s, 2H), 2.22 (d, J=3.7 Hz, 4H), 2.15 (s, 2H), 2.02 (s, 2H), 1.96 (d, J=1.2 Hz, 2H), 1.90 (s, 1H), 1.68 (s, 2H), 0.85 (d, J=6.7 Hz, 3H), 0.69 (t, J=1.2 Hz, 3H).

Synthesis of compound 16b. To a 8 mL screw-top oven-dried vial, equipped with a stir bar, and sealed with a screw cap was charged compound 15 (40 mg, 0.0463 mmol, 1.00 eq.), Fmoc-glycinol (131 mg, 0.463 mmol, 10 eq.), t-Bu-BrettPhos-Pd-G3-palladacycle (16 mg, 0.4 eq.), and $K_3PO_4$ (20 mg, 0.0942 mmol, 2.0 eq.). The reaction vial was capped with a rubber septum, pierced with a needle attached to evacuate and backfilled with argon (this process was repeated twice), followed by the addition of 1,4-dioxane (2.0 mL). The reaction was heated at 60° C. in a heating block under argon pressure for 15h, the reaction was allowed to cool to room temperature before filtration through a pad of Celite® and rinsed with MeOH. The crude material was concentrated in vacuo and purified on a 50 g C18 Aq Gold column (gradient elution: 5-100% MeCN in water, 0.05% acetic acid in both). The product fractions were combined, frozen on dry ice, and lyophilized giving the title compound 16b as a dark reddish solid (19 mg, 38%). MS (ESI, pos.): calc'd for $C_{60}H_{63}N_3O_{15}$, 1065.4; found 1066.4 (M+H).

Synthesis of compound 16d. Compound 16b of the preceding step (26 mg, 0.0244 mmol) was dissolved in DMF (1 mL), treated with a solution of 2% piperidine (3.1 mg, 0.2 mL, 0.0366 mmol) in DMF and the reaction stirred under argon at ambient temperature. After 2 h, the reaction was purified directly on a 50 g C18 Aq Gold column via ISCO system (gradient elution: 0-100% MeCN in water, 0.05% acetic acid in both, over 30 min). The product-containing fractions were combined, frozen on dry ice, and lyophilized overnight giving the title compound 16d as dark blue solid (9 mg, 44%). MS: calc'd for $C_{45}H_{53}N_3O_{13}$, 843.4; found 844.4 (M+H), 842.3 (M−H). $^1H$ NMR (500 MHz; $CD_3OD$): δ 7.83 (d, J=8.8 Hz, 1H), 6.91-7.03 (m, 2H), 6.55 (s, 1H), 6.43 (d, J=11.2 Hz, 1H), 6.21-6.30 (m, 2H), 4.98-5.08 (m, 2H), 3.76 (br. s, 3H), 3.43-3.47 (m, 1H), 3.41 (d, J=5.37 Hz, 2H), 3.12 (br. s, 1H), 2.97-3.04 (m, 4H), 2.39 (br. s, 1H), 2.19-2.32 (m, 4H), 2.09-2.14 (m, 4H), 1.95-2.07 (m, 4H), 1.78 (s, 4H), 1.67 (d, J=6.84 Hz, 1H), 1.31 (br. s., 2H), 0.97 (br. s, 8H), 0.66-0.85 (m, 4H), 0.08 (d, J=5.5 Hz, 3H), −0.26 (d, J=6.5 Hz, 3H).

Synthesis of compound 16c. To a 8 mL screw-top oven-dried vial, equipped with a stir bar and sealed with a screw cap was charged compound 15 (80 mg, 0.0926 mmol, 1.00 eq.), Fmoc-sarcosinol (275 mg, 0.9262 mmol, 10 eq.), t-BuBrettPhos-Pd-G3-palladacycle (40 mg, 0.5 eq.), and $K_3PO_4$ (39 mg, 0.1852 mmol, 2 eq.). The reaction vial was capped with a rubber septum, pierced with a needle attached to evacuate and backfilled with argon (this process was repeated twice) followed by addition of 1,4-dioxane (3.0 mL) via syringe. The reaction was heated at 60° C. in a heating block under argon pressure for 15 h, the reaction was allowed to cool to room temperature before filtration through a pad of Celite® and rinsed with MeOH. The crude material was concentrated in vacuo and purified on a 50 g C18 Aq Gold column (gradient elution: 5-100% MeCN in water, 0.05% acetic acid in both). The product fractions were combined, frozen on dry ice, and lyophilized to give the title compound 16c as a dark reddish solid (49 mg, 49%). MS: calc'd for $C_{61}H_{65}N_3O_{15}$, 1079.4; found 1080.5 (M+H).

Synthesis of compound 16e. Compound 16c of the preceding step (49 mg, 0.045 mmol) was dissolved in DMF (1 mL), treated with a solution of 2% piperidine (7.7 mg, 0.45 mL, 0.091 mmol) in DMF and the reaction stirred under argon at ambient temperature. After 2 h, the reaction was purified directly on a 50 g C18 Aq Gold column via ISCO system (gradient elution: 0-100% MeCN in water, 0.05% acetic acid in both, over 30 min). The product-containing fractions were combined, frozen on dry ice, and lyophilized overnight giving the title compound 16e as a dark blue solid (18 mg, 46%). MS: calc'd for $C_{46}H_{55}N_3O_{13}$, 857.3; found 858.3 (M+H). $^1H$ NMR (500 MHz; $CD_3OD$): δ 7.84 (d, J=8.79 Hz, 1H), 7.11-7.20 (m, 1H), 6.88-6.96 (m, 1H), 6.64 (s, 1H), 6.42 (d, J=10.26 Hz, 1H), 6.17-6.28 (m, 2H), 4.93-5.06 (m, 2H), 3.86 (br. s, 1H), 3.66-3.84 (m, 8H), 3.18-3.31 (m, 7H), 3.10 (br. s, 2H), 2.94-3.05 (m, 6H), 2.37 (br. s, 1H), 2.25 (d, J=4.88 Hz, 4H), 2.05-2.22 (m, 7H), 1.85-2.05 (m, 7H), 1.78 (s, 6H), 1.65 (br. s, 1H), 1.30 (br. s., 2H), 0.95 (br. s, 8H), 0.82-0.92 (m, 4H), 0.78 (br. s., 1H), 0.70 (br. s, 1H), 0.03 (d, J=5.86 Hz, 3H), −0.28 (d, J=5.86 Hz, 3H).

Scheme 7a

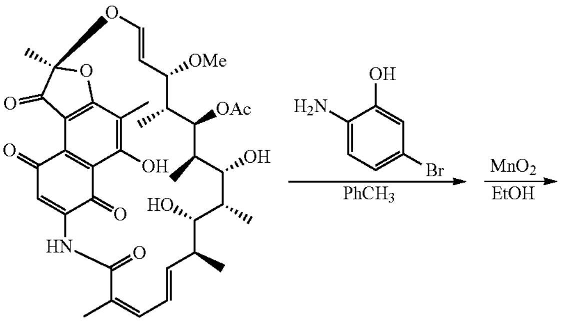

Rifamycin S

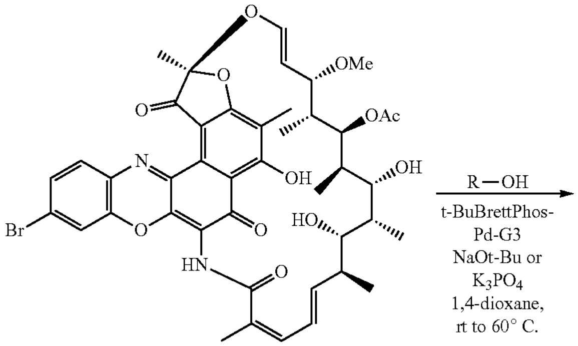

15

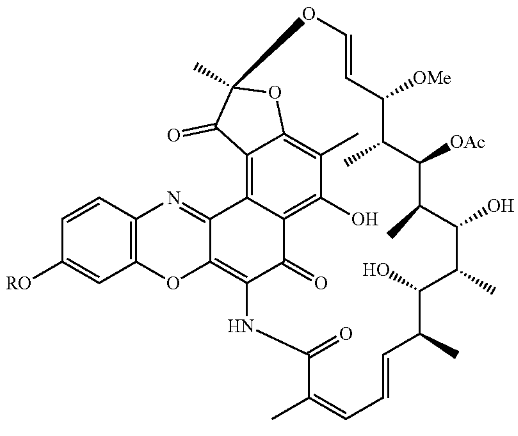

16

16f, R =

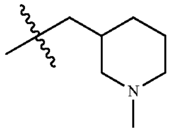

16g, R =

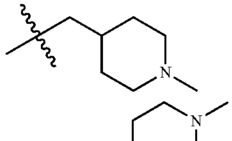

16h, R =

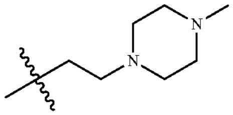

-continued

16i, R =

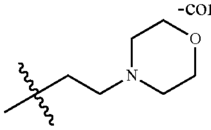

16j, R =

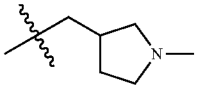

16k, R =

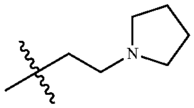

16l, R =

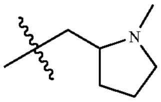

16m, R =

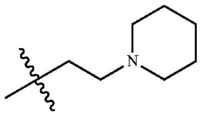

16n, R =

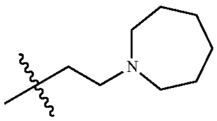

16o, R =

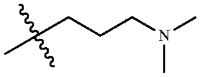

16p, R =

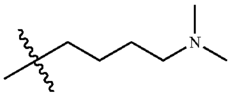

16q, R =

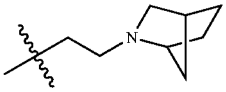

16r, R =

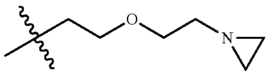

16s, R =

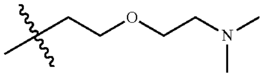

16t, R =

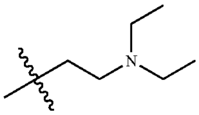

16u, R =

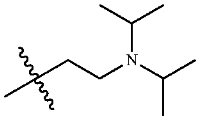

16v, R =

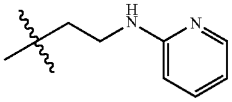

16w, R =

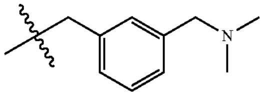

16x, R =

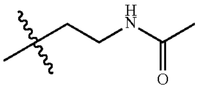

16y, R =

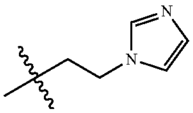

-continued

16z, R =

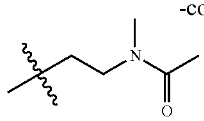

16z-1, R =

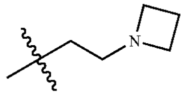

Compound 16f: To a 8 mL screw-top oven-dried vial, equipped with a stir bar and sealed with a screw cap was charged with compound 15 (40 mg, 0.0463 mmol, 1.00 eq.), (1-methylpiperidin-3-yl)methanol (60 mg, 0.463 mmol, 10 eq.), t-BuBrettPhos-Pd-G3-palladacycle (19 mg, 0.0222 mmol, 0.5 eq.), and $K_3PO_4$ (20 mg, 0.0942 mmol, 2.0 eq.). The reaction vial was capped with a rubber septum. The septum was pierced with a needle attached to evacuate and backfilled with argon (this process was repeated twice) followed by the addition of 1,4-dioxane (2.0 mL). The reaction was heated at 60° C. in a heating block under argon pressure for 15h, the reaction was allowed to cool to room temperature before filtration through a pad of Celite® and rinsed with MeOH. The crude material was concentrated in vacuo and purified on a 50 g C18 Aq Gold column (gradient elution: 5-100% MeCN in water, 0.05% acetic acid in both). Pure fractions were combined, frozen on dry ice, and lyophilized giving the title compound 16f as a dark reddish solid (16.2 mg, 39%). MS: calc'd for $C_{50}H_{61}N_3O_{13}$, 911.4; found 912.4 (M+H). $^1$H-NMR (500 MHz; DMSO-$d_6$): δ 9.38 (s, 1H), 7.86-7.84 (m, 1H), 7.19-7.18 (m, 2H), 6.06 (td, J=2.9, 1.9 Hz, 1H), 5.86-5.80 (m, 1H), 5.24-5.21 (m, 1H), 4.80-4.76 (m, 1H), 4.08-4.07 (m, 2H), 3.51 (ddq, J=5.7, 2.9, 1.0 Hz, 1H), 3.09 (t, J=0.6 Hz, 2H), 3.02-3.01 (m, 3H), 2.77 (d, J=0.7 Hz, 3H), 2.61-2.59 (m, 1H), 2.14 (s, 6H), 2.00 (s, 3H), 1.95-1.94 (m, 3H), 1.83-1.76 (m, 2H), 1.66 (s, 9H), 1.50-1.47 (m, 3H), 1.37 (d, J=15.9 Hz, 3H), 1.27-1.20 (m, 2H), 1.07 (d, J=6.5 Hz, 2H), 0.85 (d, J=6.5 Hz, 6H), 0.70-0.67 (m, 3H).

Compound 16g: 16 g was prepared using the general procedure as described for 16b: Compound 15 (40 mg, 0.0463 mmol, 1.00 eq.), (1-methylpiperidin-4-yl)-methanol (90 mg, 0.719 mmol, 15 eq.), t-BuBrettPhos-Pd-G3-palladacycle (21 mg, 0.0245 mmol, 0.5 eq.), and $K_3PO_4$ (23 mg, 0.108 mmol, 2.3 eq.) to afford the title compound 16g (5.6 mg, 13%). MS: calc'd for $C_{50}H_{61}N_3O_{13}$, 911.4; found 912.4 (M+H). $^1$H NMR (500 MHz, $CD_3OD$): δ 8.01 (br. s., 1H), 7.18 (br. s., 1H), 6.94 (br. s., 2H), 6.43 (br. s., 1H), 6.23 (br. s., 2H), 5.06 (br. s., 1H), 5.01 (br. s., 1H), 4.01-4.19 (m, 1H), 3.93 (br. s., 1H), 3.75 (br. s., 1H), 3.07 (br. s., 1H), 2.86-3.05 (m, 7H), 2.33-2.45 (m, 4H), 2.30 (br. s., 4H), 2.11-2.20 (m, 5H), 1.98 (br. s., 4H), 1.83-1.93 (m, 4H), 1.78 (br. s., 4H), 1.48 (d, J=11.72 Hz, 2H), 1.32 (d, J=18.07 Hz, 1H), 0.95 (br. s., 8H), 0.80 (br. s., 2H), 0.03 (br. s., 2H), −0.23 (br. s., 2H).

Compound 16h: 16h was prepared using the general procedure as described for 16b: Compound 15 (40 mg, 0.0463 mmol, 1.00 eq.), 2-(4-methylpiperazin-1-yl)ethan-1-ol (80 mg, 0.554 mmol, 12 eq.), t-BuBrettPhos-Pd-G3-palladacycle (20 mg, 0.0234 mmol, 0.5 eq.), and $K_3PO_4$ (23 mg, 0.108 mmol, 2.3 eq.) to afford the title compound 16h (9.6 mg, 22%). MS: calc'd for $C_{50}H_{62}N_4O_{13}$, 926.4; found 927.4 (M+H), 925.3 (M−H). $^1$H NMR (500 MHz; DMSO-$d_6$): δ 9.36-9.41 (m, 1H), 7.87 (br. s., 1H), 7.19 (br. s., 2H), 5.81 (br. s., 1H), 5.25 (br. s., 1H), 4.78 (br. s., 1H), 4.31 (br. s., 1H), 4.23 (br. s., 1H), 4.16 (br. s., 1H), 3.51 (br. s., 1H), 3.03 (br. s., 2H), 2.86 (d, J=10.75 Hz, 1H), 2.78 (br. s., 1H), 2.72 (br. s., 3H), 2.31 (br. s., 5H), 2.14 (br. s., 7H), 2.10 (br. s., 1H), 2.01 (br. s., 5H), 1.95 (br. s., 3H), 1.90 (br. s., 2H), 1.67 (br. s., 3H), 1.59 (br. s., 1H), 1.51 (br. s., 1H), 1.26-1.46 (m, 1H), 1.23 (br. s., 1H), 0.85 (br. s., 8H), 0.79 (br. s., 2H), 0.69-0.67 (m, 5H).

Compound 16i: 16i was prepared using the general procedure as described for 16b: Compound 15 (30 mg, 0.0347 mmol, 1.00 eq.), 2-morpholinoethan-1-ol (46 mg, 0.347 mmol, 10 eq.), t-BuBrettPhos-Pd-G3-palladacycle (15 mg, 0.0173 mmol, 0.5 eq.), and $K_3PO_4$ (15 mg, 0.0704 mmol, 2.0 eq.) to afford 69% (22 mg). MS: calc'd for $C_{49}H_{59}N_3O_{14}$, 913.40; found 914.3 (M+H). $^1$H NMR (500 MHz; DMSO-$d_6$): δ 9.41-9.40 (m, 1H), 7.86 (dd, J=5.2, 2.0 Hz, 1H), 7.23-7.18 (m, 2H), 6.06-6.03 (m, 1H), 5.83-5.81 (m, 1H), 5.25-5.24 (m, 1H), 4.79-4.78 (m, 1H), 4.33-4.31 (m, 1H), 4.33-4.16 (m, 3H), 3.58 (s, 5H), 3.09-3.03 (m, 4H), 2.73 (s, 2H), 2.16 (s, 4H), 1.99 (d, J=29.4 Hz, 8H), 1.67 (s, 3H), 1.52 (d, J=4.2 Hz, 2H), 1.13 (d, J=13.8 Hz, 1H), 0.85 (d, J=6.5 Hz, 10H), 0.69-0.67 (m, 8H).

Compound 16j: 16j was prepared using the general procedure as described for 16b: Compound 15 (30 mg, 0.0347 mmol, 1.00 eq.), (1-methylpyrrolidin-3-yl)methanol (40 mg, 0.347 mmol, 10 eq.), t-BuBrettPhos-Pd-G3-palladacycle (15 mg, 0.0173 mmol, 0.5 eq.), and $K_3PO_4$ (15 mg, 0.0704 mmol, 2.0 eq.) to afford 23% (7.0 mg). MS: calc'd for $C_{49}H_{59}N_3O_{13}$, 897.40; found 898.4 (M+H). $^1$H NMR (500 MHz; DMSO-$d_6$): δ 9.39-9.38 (m, 1H), 7.89-7.86 (m, 1H), 7.19 (t, J=7.0 Hz, 2H), 6.05-6.03 (m, 1H), 5.86-5.80 (m, 1H), 5.25-5.23 (m, 1H), 4.80-4.78 (m, 1H), 4.17-4.15 (m, 1H), 4.14-4.09 (m, 1H), 3.99 (s, 1H), 3.52-3.49 (m, 1H), 3.09-3.03 (m, 3H), 2.78-2.77 (m, 1H), 2.37 (dt, J=5.5, 2.7 Hz, 2H), 2.21 (d, J=35.5 Hz, 6H), 1.98 (d, J=31.1 Hz, 7H), 1.67-1.59 (m, 3H), 1.60-1.58 (m, 1H), 1.53-1.47 (m, 2H), 1.39-1.34 (m, 2H), 0.84 (d, J=6.8 Hz, 11H), 0.67 (t, J=2.9 Hz, 7H).

Compound 16k: 16k was prepared using the general procedure as described for 16b: Compound 15 (50 mg, 0.0579 mmol, 1.00 eq.), 2-(pyrrolidin-1-yl)ethan-1-ol (67 mg, 0.579 mmol, 10 eq.), t-BuBrettPhos-Pd-G3-palladacycle (25 mg, 0.0289 mmol, 0.5 eq.), and $K_3PO_4$ (25 mg, 0.1158 mmol, 2.0 eq.) to afford 46% (23.6 mg). MS: calc'd for $C_{49}H_{59}N_3O_{13}$, 897.40; found 898.4 (M+H), 896.3 (M−H). $^1$H NMR (500 MHz; DMSO-$d_6$): δ 9.38 (d, J=1.2 Hz, 1H), 7.88-7.87 (m, 1H), 7.21 (s, 1H), 6.05-6.03 (m, 1H), 5.82 (dd, J=1.3, 0.7 Hz, 1H), 5.25-5.20 (m, 1H), 4.81-4.79 (m, 1H), 4.33-4.30 (m, 1H), 4.24-4.15 (m, 1H), 3.54-3.50 (m, 2H), 3.09-3.03 (m, 6H), 2.85-2.78 (m, 6H), 2.18 (s, 4H), 1.99 (d, J=31.9 Hz, 5H), 1.70 (s, 6H), 1.15-1.05 (m, 1H), 0.85 (d, J=6.7 Hz, 11H), 0.68 (dt, J=3.6, 0.9 Hz, 9H).

Compound 16l: 16l was prepared using the general procedure as described for 16b: Compound 15 (50 mg, 0.0579 mmol, 1.00 eq.), (1-methylpyrrolidin-2-yl)methanol (67 mg, 0.579 mmol, 10 eq.), t-BuBrettPhos-Pd-G3-palladacycle (25 mg, 0.0289 mmol, 0.5 eq.), and $K_3PO_4$ (25 mg, 0.1158 mmol, 2.0 eq.) to afford 35% (17.7 mg). MS: calc'd for $C_{49}H_{59}N_3O_{13}$, 897.40; found 898.4 (M+H), 896.3 (M−H). $^1$H NMR (500 MHz; DMSO-$d_6$): δ 9.38-9.37 (m, 1H), 7.88-7.87 (m, 1H), 7.20-7.18 (m, 1H), 6.06-6.04 (m, 1H), 5.84-5.82 (m, 1H), 5.25-5.24 (m, 1H), 4.81-4.79 (m, 1H), 4.19-4.11 (m, 2H), 3.54-3.50 (m, 1H), 3.10-3.07 (m, 1H), 3.03 (s, 2H), 2.97-2.96 (m, 1H), 2.79-2.78 (m, 3H), 2.64-2.61 (m, 6H), 2.37 (s, 3H), 2.18 (s, 3H), 1.99 (d, J=32.7 Hz, 6H), 1.68 (s, 3H), 1.68-1.57 (m, 3H), 1.55-1.45 (m, 1H), 0.85 (d, J=6.7 Hz, 11H), 0.69-0.67 (m, 7H).

Compound 16m: 16m was prepared using the general procedure as described for 16b: Compound 15 (50 mg, 0.0579 mmol, 1.00 eq.), 2-(piperidin-1-yl)ethan-1-ol (75 mg, 0.579 mmol, 10 eq.), t-BuBrettPhos-Pd-G3-palladacycle (25 mg, 0.0289 mmol, 0.5 eq.), and $K_3PO_4$ (25 mg, 0.1158 mmol, 2.0 eq.) to afford 54% (28.3 mg). MS: calc'd for $C_{50}H_{61}N_3O_{13}$, 911.42; found 912.4 (M+H), 910.3 (M−H). $^1$H NMR (500 MHz; DMSO-$d_6$): δ 9.38-9.36 (m, 1H), 7.88-7.86 (m, 1H), 7.22 (dt, J=1.7, 0.8 Hz, 1H), 6.07-6.05 (m, 1H), 5.83-5.82 (m, 1H), 5.26-5.22 (m, 1H), 4.81-4.78 (m, 1H), 4.31 (dd, J=2.5, 1.0 Hz, 1H), 4.23-4.15 (m, 1H), 3.54-3.50 (m, 1H), 3.10-3.01 (m, 3H), 2.79-2.77 (m, 1H), 2.69 (s, 2H), 2.44 (d, J=0.7 Hz, 6H), 2.17 (s, 6H), 1.99 (d, J=32.3 Hz, 5H), 1.68 (s, 6H), 1.50 (s, 3H), 1.38-1.37 (m, 2H), 0.85 (d, J=6.7 Hz, 9H), 0.69-0.67 (m, 7H).

Compound 16n: 16n was prepared using the general procedure as described for 16b: Compound 15 (50 mg, 0.0579 mmol, 1.00 eq.), 2-(azepan-1-yl)ethan-1-ol (83 mg, 0.579 mmol, 10 eq.), t-BuBrettPhos-Pd-G3-palladacycle (25 mg, 0.0289 mmol, 0.5 eq.), and $K_3PO_4$ (25 mg, 0.1158 mmol, 2.0 eq.) to afford 53% (28.4 mg). MS: calc'd for $C_{51}H_{63}N_3O_{13}$, 925.44; found 926.5 (M+H), 924.3 (M−H). $^1$H NMR (500 MHz; DMSO-$d_6$): δ 9.42-9.34 (m, 1H), 7.85-7.84 (m, 1H), 7.16 (td, J=1.8, 0.5 Hz, 2H), 6.07-6.04 (m, 1H), 5.84-5.82 (m, 1H), 5.24 (s, 1H), 4.81-4.77 (m, 1H), 4.26-4.25 (m, 1H), 4.19-4.13 (m, 2H), 3.57-3.48 (m, 1H), 3.12-3.10 (m, 2H), 3.02-2.99 (m, 4H), 2.89 (s, 6H), 2.89-2.76 (m, 3H), 2.69 (s, 3H), 2.15-2.14 (m, 3H), 2.01 (s, 3H), 1.95 (s, 3H), 1.90 (s, 3H), 1.67 (s, 3H), 1.58-1.54 (m, 6H), 0.86 (d, J=6.5 Hz, 8H), 0.71-0.67 (m, 6H).

Compound 16o: 16o was prepared using the general procedure as described for 16b: Compound 15 (30 mg, 0.0347 mmol, 1.0 eq.), N,N-dimethylaminopropan-1-ol (35 mg, 0.339 mmol, 10 eq.), t-BuBrettPhos-Pd-G3-palladacycle (15 mg, 0.0176 mmol, 0.5 eq.), and $K_3PO_4$ (15 mg, 0.0707 mmol, 2.0 eq.) to afford 55% (17 mg). MS: calc'd for $C_{48}H_{59}N_3O_{13}$, 885.4; found 886.4 (M+H). $^1$H NMR (500 MHz, $CD_3OD$) δ 7.86-8.10 (m, 1H), 7.16 (s, 1H), 6.93 (br. s., 1H), 6.43 (br. s., 1H), 6.22 (br. s., 2H), 5.06 (br. s., 1H), 4.98 (br. s., 1H), 4.24 (br. s., 1H), 4.15 (br. s., 1H), 3.75 (br. s., 1H), 2.90-3.13 (m, 5H), 2.58 (br. s., 2H), 2.34 (br. s., 7H), 2.26 (br. s., 3H), 2.09-2.17 (m, 4H), 2.05 (br. s., 3H), 1.98 (br. s., 3H), 1.82-1.95 (m, 3H), 1.79 (s, 3H), 1.73 (s, 1H), 0.77-1.00 (m, 8H), 0.03 (s, 2H), −0.25 (s, 2H).

Compound 16p: 16p was prepared using the general procedure as described for 16b: Compound 15 (30 mg, 0.0347 mmol, 1.0 eq.), N,N-dimethylaminobutan-1-ol (40 mg, 0.341 mmol, 10 eq.), t-BuBrettPhos-Pd-G3-palladacycle (15 mg, 0.0176 mmol, 0.5 eq.), and $K_3PO_4$ (15 mg, 0.0707 mmol, 2.0 eq.) to afford 35% (11 mg). MS: calc'd for $C_{49}H_{61}N_3O_{13}$, 899.42; found 900.4 (M+H). $^1$H NMR (500 MHz, $CD_3OD$) δ 7.98 (br. s., 1H), 7.18 (br. s., 1H), 6.93 (br. s., 1H), 6.22 (br. s., 2H), 5.06 (br. s., 1H), 4.99 (br. s., 1H), 4.93 (br. s., 1H), 4.22 (br. s., 2H), 4.12 (br. s., 1H), 3.83-3.96 (m, 1H), 3.63-3.83 (m, 2H), 3.08 (br. s., 2H), 3.01 (d, J=8.79 Hz, 5H), 2.51 (br. s., 3H), 2.35 (br. s., 6H), 2.28 (br. s., 3H), 2.09-2.17 (m, 3H), 2.07 (br. s., 1H), 1.98 (br. s., 3H), 1.81-1.92 (m, 3H), 1.68-1.81 (m, 2H), 1.52-1.65 (m, 2H), 1.36-1.52 (m, 3H), 1.32 (d, J=18.56 Hz, 2H), 0.95 (br. s., 3H), 0.88 (d, J=6.84 Hz, 4H) 0.04 (s, 2H), −0.24 (s, 2H).

Compound 16q: 16q was prepared using the general procedure as described for 16b: Compound 15 (50 mg, 0.0579 mmol, 1.00 eq.), 2-(2-azabicyclo[2.2.1]heptan-2-yl)ethan-1-ol (82 mg, 0.579 mmol, 10 eq.), t-BuBrettPhos-Pd-G3-palladacycle (25 mg, 0.0289 mmol, 0.5 eq.), and $K_3PO_4$ (25 mg, 0.1158 mmol, 2.0 eq.) to afford 55% (29 mg). MS: calc'd for $C_{51}H_{61}N_3O_{13}$, 923.42; found 924.4 (M+H), 922.3 (M−H). $^1$H NMR (500 MHz; DMSO-$d_6$): δ 9.34-9.32 (m, 1H), 7.88-7.86 (m, 1H), 7.18-7.17 (m, 2H), 6.06-6.03 (m, 1H), 5.84-5.81 (m, 1H), 5.25-5.22 (m, 1H), 4.82-4.78 (m, 1H), 4.21-4.13 (m, 3H), 3.46-3.39 (m, 1H), 3.13 (t, J=2.6 Hz, 3H), 3.02-3.01 (m, 3H), 2.81-2.79 (m, 3H), 2.29 (d, J=0.8 Hz, 3H), 2.18 (s, 3H), 2.02 (s, 3H), 1.95 (s, 3H), 1.68 (s, 5H), 1.55-1.50 (m, 3H), 1.40 (s, 3H), 1.22 (d, J=9.2 Hz, 6H), 0.86 (d, J=6.8 Hz, 8H), 0.69-0.68 (m, 5H).

Compound 16r: 16r was prepared using the general procedure as described for 16b: Compound 15 (50 mg, 0.0579 mmol, 1.00 eq.), 2-(aziridin-1-yl)ethan-1-ol (50.4 mg, 0.579 mmol, 10 eq.), t-BuBrettPhos-Pd-G3-palladacycle (25 mg, 0.0289 mmol, 0.5 eq.), and $K_3PO_4$ (25 mg, 0.1158 mmol, 2.0 eq.) to afford 11% (5.6 mg). MS: calc'd for $C_{51}H_{64}N_4O_{14}$, 956.44; found 957.4 (M+H), 955.3 (M−H). $^1$H NMR (500 MHz; DMSO-$d_6$): δ 9.37-9.35 (m, 1H), 7.87-7.84 (m, 1H), 7.20-7.18 (m, 1H), 6.07-6.03 (m, 1H), 5.83-5.81 (m, 1H), 5.25-5.21 (m, 1H), 4.78 (dq, J=2.8, 0.9 Hz, 1H), 4.34-4.31 (m, 2H), 4.23-4.15 (m, 1H), 3.47 (d, J=5.8 Hz, 5H), 3.09-3.08 (m, 2H), 3.02 (dddd, J=3.6, 2.6, 2.4, 1.3 Hz, 3H), 2.78-2.77 (m, 1H), 2.71-2.70 (m, 2H), 2.63 (d, J=1.2 Hz, 2H), 2.41-2.34 (m, 8H), 2.17-2.15 (m, 3H), 2.01 (t, J=0.4 Hz, 3H), 1.94 (t, J=0.9 Hz, 3H), 1.89 (s, 2H), 1.66 (d, J=0.4 Hz, 3H), 1.61-1.53 (m, 1H), 1.38 (d, J=15.9 Hz, 2H), 0.86-0.84 (m, 9H), 0.69-0.67 (m, 6H).

Compound 16s: 16s was prepared using the general procedure as described for 16b: Compound 15 (30 mg, 0.0347 mmol, 1.0 eq.), 2-(2-(dimethylamino)ethoxy)ethan-1-ol (50 mg, 0.375 mmol, 10 eq.), t-BuBrettPhos-Pd-G3-palladacycle (15 mg, 0.0176 mmol, 0.5 eq.), and $K_3PO_4$ (15 mg, 0.0707 mmol, 2.0 eq.) to afford 35% (11 mg). MS: calc'd for $C_{49}H_{61}N_3O_{14}$, 915.4; found 916.4 (M+H). $^1$H NMR (500 MHz, $CD_3OD$) δ 8.01 (d, J=15.1 Hz, 1H), 7.20 (br. s., 1H), 6.96 (br. s., 1H), 6.44 (br. s., 1H), 6.15-6.32 (m, 2H), 5.07 (d, J=16.2 Hz, 1H), 4.34 (br. s., 2H), 4.24 (br. s., 1H), 3.86 (br. s., 3H), 3.78 (d, J=11.7 Hz, 1H), 3.69 (br. s., 3H), 3.18 (br. s., 1H), 3.06-3.15 (m, 2H), 3.02 (d, J=9.77 Hz, 5H), 2.51-2.70 (m, 2H), 2.32 (d, J=11.7 Hz, 6H), 2.11 (s., 3H), 1.94-2.07 (m, 6H), 1.90 (br. s., 1H), 1.75-1.86 (m, 5H), 1.73 (br. s., 1H), 1.67 (br. s., 2H), 1.24-1.45 (m, 3H), 0.89-0.96 (m, 8H), 0.06 (s, 2H), −0.20 (s, 2H).

Compound 16t: 16t was prepared using the general procedure as described for 16b: Compound 15 (30 mg, 0.0347 mmol, 1.0 eq.), 2-diethylaminoethan-1-ol (45 mg, 0.383 mmol, 11 eq.), t-BuBrettPhos-Pd-G3-palladacycle (15 mg, 0.0176 mmol, 0.5 eq.), and $K_3PO_4$ (15 mg, 0.0707 mmol, 2.0 eq.) to afford 14% (4.5 mg). MS: calc'd for $C_{49}H_{61}N_3O_{13}$, 899.4; found 900.4 (M+H), 898.3 (M−H). $^1$H NMR (500 MHz, $CD_3OD$) δ 8.06 (br. s., 1H), 7.26 (br. s., 1H), 7.02 (br. s., 1H), 6.44 (br. s., 1H), 6.23 (br. s., 2H), 5.10 (br. s., 1H), 5.00 (br. s., 2H), 4.48 (br. s., 1H), 4.38 (br. s., 1H), 3.77 (br. s., 1H), 3.46 (br. s., 2H), 3.15 (s, 4H), 3.18 (s, 3H), 3.03 (d, J=9.28 Hz, 6H), 2.32 (br. s., 4H), 2.09-2.16 (m, 4H), 1.99 (br. s., 4H), 1.78 (br. s., 4H), 1.38 (br. s., 1H), 1.30 (br. s., 10H), 0.96 (br. s., 8H), 0.11 (s, 2H), −0.20 (s, 2H).

Compound 16u: 16u was prepared using the general procedure as described for 16b: Compound 15 (30 mg, 0.0347 mmol, 1.0 eq.), 2-diisopropylaminoethan-1-ol (45 mg, 0.383 mmol, 11 eq.), t-BuBrettPhos-Pd-G3-palladacycle (15 mg, 0.0176 mmol, 0.5 eq.), and $K_3PO_4$ (15 mg, 0.0707 mmol, 2.0 eq.) to afford 31% (10 mg). MS: calc'd for $C_{51}H_{65}N_3O_{13}$, 927.45; found 928.4 (M+H), 926.3 (M−H). $^1$H NMR (500 MHz, $CD_3OD$) δ 8.03 (br. s., 1H), 7.10-7.29 (m, 1H), 6.94 (br. s., 1H), 6.23 (br. s., 1H), 5.01-5.06 (m, 2H), 4.23 (br. s., 1H), 3.18 (br. s., 1H), 3.12 (br. s., 2H), 2.91-3.06 (m, 4H), 2.31 (br. s., 4H), 2.11 (s, 4H), 1.98 (br. s., 4H), 1.78 (br. s., 4H), 1.64 (br. s., 1H), 1.28-1.41 (m, 2H), 1.18 (br. s., 14H), 1.06 (d, J=6.84 Hz, 1H), 0.95 (s, 9H), 0.81 (s, 2H), 0.07-0.13 (m, 1H), 0.04 (s, 2H), −0.23 (s, 2H).

Compound 16v: 16v was prepared using general procedure as described for 16b: Compound 15 (40 mg, 0.0463 mmol, 1.0 eq.), 2-(methyl(pyridin-2-yl)amino)ethan-1-ol (75 mg, 0.463 mmol, 10 eq.), t-BuBrettPhos-Pd-G3-palladacycle (20 mg, 0.0213 mmol, 0.5 eq.), and $K_3PO_4$ (20 mg, 0.094 mmol, 2.0 eq.) to afford the title compound 16v (15.6 mg, 36%). MS: calc'd for $C_{51}H_{58}N_4O_{13}$, 934.40; found 935.3 (M+H), 933.3 (M−H). $^1$H NMR (500 MHz, $CD_3OD$): δ 8.09 (t, J=1.4 Hz, 1H), 8.02-8.00 (m, 1H), 7.56-7.53 (m, 1H), 7.19-7.17 (m, 1H), 7.07 (s, 1H), 6.86-6.84 (m, 1H), 6.70-6.68 (m, 2H), 6.61 (td, J=1.8, 0.7 Hz, 2H), 6.42-6.41 (m, 1H), 6.22-6.20 (m, 2H), 5.04-5.02 (m, 1H), 4.59 (s, 2H), 4.39-4.36 (m, 1H), 4.32-4.29 (m, 1H), 4.01 (s, 2H), 3.72-3.68 (m, 1H), 3.15 (s, 7H), 3.00-2.99 (m, 4H), 2.31 (s, 4H), 2.11 (s, 4H), 1.95 (d, J=22.7 Hz, 3H), 1.77 (s, 3H), 1.63-1.60 (m, 1H), 1.30 (s, 2H), 0.94 (d, J=6.6 Hz, 4H), 0.80-0.79 (m, 4H), −0.03 (dd, J=2.4, 0.5 Hz, 2H), −0.24 (dd, J=2.3, 1.1 Hz, 2H).

Compound 16w: 16w was prepared using general procedure as described for 16b: Compound 15 (40 mg, 0.0463 mmol, 1.0 eq.), (2-((dimethylamino)methyl)phenyl)methanol (76 mg, 0.463 mmol, 10 eq.), t-BuBrettPhos-Pd-G3-palladacycle (20 mg, 0.0213 mmol, 0.5 eq.), and $K_3PO_4$ (20 mg, 0.094 mmol, 2.0 eq.) to afford the title compound 16w (5.6 mg, 18%). MS: calc'd for $C_{53}H_{61}N_3O_{13}$, 947.42; found 948.4 (M+H), 946.3 (M−H). $^1$H NMR (500 MHz, $CD_3OD$): δ 8.05-8.04 (m, 1H), 7.46-7.44 (m, 1H), 7.34-7.33 (m, 1H), 7.07-7.05 (m, 1H), 6.80 (d, J=4.2 Hz, 1H), 6.53-6.48 (m, 1H), 6.24-6.22 (m, 1H), 5.51 (d, J=12.1 Hz, 1H), 5.44-5.42 (m, 1H), 5.07-5.00 (m, 1H), 4.59 (s, 1H), 3.82-3.69 (m, 2H), 3.55 (d, J=8.6 Hz, 1H), 3.31-3.11 (m, 12H), 3.03-3.01 (m, 4H), 2.33 (s, 3H), 2.24 (s, 5H), 2.09 (dd, J=1.9, 1.0 Hz, 3H), 1.99 (s, 3H), 1.92 (s, 1H), 1.77 (d, J=0.5 Hz, 4H), 1.67-1.61 (m, 1H), 1.30 (d, J=0.3 Hz, 1H), 0.96-0.87 (m, 5H), 0.11 (d, J=2.8 Hz, 1H), 0.06-0.04 (m, 3H), −0.20-0.22 (m, 2H).

Compound 16x: 16x was prepared using general procedure as described for 16b: Compound 15 (40 mg, 0.0463 mmol, 1.0 eq.), N-(2-hydroxyethyl)acetamide (48 mg, 0.463 mmol, 10 eq.), t-BuBrettPhos-Pd-G3-palladacycle (20 mg, 0.0213 mmol, 0.5 eq.), and $K_3PO_4$ (20 mg, 0.094 mmol, 2.0 eq.) to afford the title compound 16x (20 mg, 41%). MS: calc'd for $C_{47}H_{55}N_3O_{14}$, 885.37; found 886.3 (M+H). $^1$H NMR (500 MHz, $CD_3OD$) δ 7.98 (br. s., 1H), 7.18 (s, 2H), 6.94 (br. s., 1H), 6.23 (br. s., 1H), 5.01-5.06 (m, 2H), 4.14 (br. s., 1H), 3.62 (br. s., 4H), 2.94-3.18 (m, 5H), 2.31 (br. s., 5H), 2.11 (s, 5H), 1.98 (br. s., 10H), 1.78 (br. s., 5H), 1.64 (br. s., 1H), 1.28-1.41 (m, 2H), 1.06 (d, J=6.84 Hz, 1H), 0.95 (s, 8H), 0.07-0.13 (m, 1H), 0.04 (s, 2H), −0.23 (s, 2H).

Compound 16y: 16y was prepared using general procedure as described for 16b: Compound 15 (40 mg, 0.0463 mmol, 1.0 eq.), 2-(1H-imidazol-1-yl)ethan-1-ol (52 mg, 0.463 mmol, 10 eq.), t-BuBrettPhos-Pd-G3-palladacycle (20 mg, 0.0213 mmol, 0.5 eq.), and $K_3PO_4$ (20 mg, 0.094 mmol, 2.0 eq.) to afford the title compound 16y (8 mg, 8%). MS: calc'd for $C_{48}H_{54}N_4O_{13}$, 894.37; found 895.3 (M+H). $^1$H NMR (500 MHz, $CD_3OD$) δ 7.75 (br. s., 1H), 7.16-7.26 (m, 2H), 6.98 (s, 1H), 6.94 (s, 1H), 4.58 (br. s., 5H), 4.44-4.54 (m, 3H), 4.31-4.35 (m, 1H), 3.83-3.90 (m, 2H), 3.72 (br. s., 1H), 3.66 (s, 1H), 3.55 (s, 1H), 3.33-3.36 (m, 1H), 3.00 (d, J=8.30 Hz, 3H), 2.30 (br. s., 3H), 2.00-2.11 (m, 4H), 1.92-2.00 (m, 3H), 1.90 (s, 2H), 1.76 (br. s., 3H), 1.70 (d, J=6.84 Hz, 1H), 1.52-1.65 (m, 2H), 1.49 (d, J=15.14 Hz, 2H), 1.32-1.41 (m, 2H), 1.11-1.32 (m, 3H), 0.83-1.00 (m, 6H), 0.09-0.10 (m, 1H), 0.00 (br. s., 2H), −0.23 (br. s., 1H).

Compound 16z: 16z was prepared using general procedure as described for 16b: Compound 15 (40 mg, 0.0463 mmol, 1.0 eq.), N-(2-hydroxyethyl)-N-methylacetamide (54 mg, 0.463 mmol, 10 eq.), t-BuBrettPhos-Pd-G3-palladacycle (20 mg, 0.0213 mmol, 0.5 eq.), and $K_3PO_4$ (20 mg, 0.094 mmol, 2.0 eq.) to afford the title compound 16z (6.5 mg, 16%). MS: calc'd for $C_{48}H_{57}N_3O_{14}$, 899.38; found 900.4 (M+H). $^1$H NMR (500 MHz, $CD_3OD$) δ 8.03 (br. s., 1H), 7.20 (br. s., 2H), 6.42 (br. s., 1H), 6.22 (br. s., 1H), 5.06 (br. s., 1H), 4.99 (br. s., 2H), 4.58 (s, 3H), 4.38 (d, J=3.91 Hz, 1H), 4.31 (br. s., 2H), 4.23 (br. s., 2H), 3.86 (br. s., 2H), 3.80 (br. s., 2H), 3.74 (br. s., 1H), 3.19 (s, 3H), 2.96-3.06 (m, 5H), 2.31 (br. s., 2H), 2.20 (s, 2H), 2.11 (d, J=6.84 Hz, 3H), 2.04 (s, 1H), 1.97 (br. s., 6H), 1.93 (s, 2H), 1.76 (br. s., 3H), 1.65 (br. s., 2H), 1.29 (s, 1H), 0.94 (br. s., 3H), 0.10 (d, J=2.93 Hz, 1H), 0.03 (br. s., 2H), −0.23 (br. s., 2H).

Compound 16z-1: 16z-1 was prepared using general procedure as described for 16b: Compound 15 (40 mg, 0.0463 mmol, 1.0 eq.), 2-(azetidin-1-yl)ethan-1-ol (47 mg, 0.463 mmol, 10 eq.), t-BuBrettPhos-Pd-G3-palladacycle (20 mg, 0.0213 mmol, 0.5 eq.), and $K_3PO_4$ (20 mg, 0.094 mmol, 2.0 eq.) to afford the title compound 16z-1 (8.7 mg, 21%). MS: calc'd for $C_{48}H_{57}N_3O_{13}$, 883.39; found 884.4 (M+H). $^1$H NMR (500 MHz, $CD_3OD$) δ 7.19 (br. s., 1H), 4.58 (br. s., 2H), 4.19 (br. s., 1H), 3.83-3.89 (m, 1H), 3.73-3.82 (m, 1H), 3.52 (s, 1H), 3.46 (br. s., 6H), 3.00 (br. s., 1H), 2.30 (br. s., 4H), 2.13-2.22 (m, 3H), 2.10 (br. s., 3H), 1.97 (br. s., 3H), 1.92 (s, 8H), 1.76 (br. s., 4H), 1.56-1.69 (m, 2H), 1.43 (s, 2H), 1.46 (s, 2H), 1.31-1.39 (m, 2H), 1.29 (br. s., 1H), 1.24 (d, J=14.17 Hz, 1H), 1.15 (d, J=5.86 Hz, 1H), 0.95 (br. s., 3H), 0.10 (d, J=2.44 Hz, 2H), 0.03 (br. s., 2H), −0.23 (br. s., 1H).

Example 4: Reductive Amination

Rifamycin analog (17) was synthesized from compound 14 by use of reductive amination as shown in Scheme 8, below.

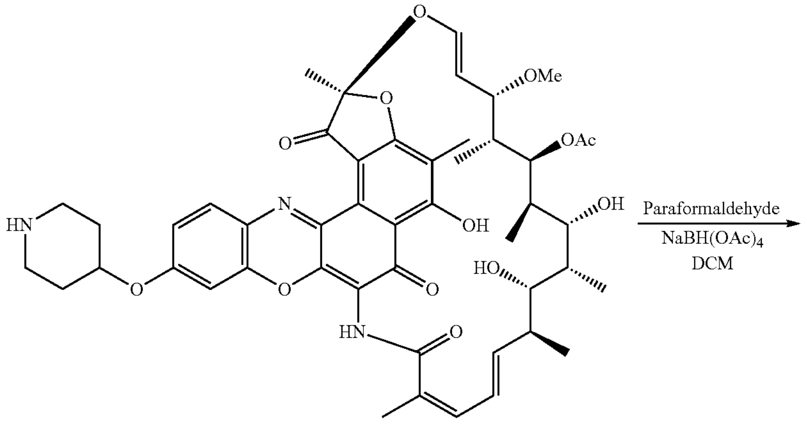

14

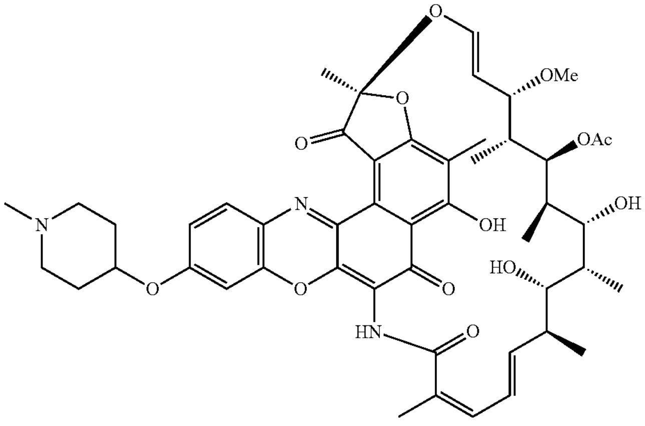

17

To a solution of compound 14 (9 mg, 0.0102 mmol) and paraformaldehyde (1.52 mg, 0.051 mmol) in 1.0 mL of anhydrous DCM at room temperature was added NaBH $(OAc)_3$ (4.3 mmol, 0.0204 mmol). The mixture was stirred for 1 h. The reaction progress was monitored by LC/MS to afford the desired product. The crude reaction mixture was quenched by addition of 2-3 drops of water. All volatiles were removed under reduced pressure, then diluted with DMSO (0.5 mL). The crude mixture was purified by preparative HPLC (Gemini, 5 μm, 150 mm×30 mm, eluents: 10-95% MeCN in water, 0.05% AcOH) pure fractions combined and lyophilized to give 6 mg (66%) of 17 as a reddish solid. MS (ESI, pos.): calc'd for $C_{49}H_{59}N_3O_{13}$, 897.40; found 898.4 (M+H). 1H NMR (500 MHz; DMSO-$d_6$): δ 9.38 (br. s., 1H), 7.86 (br. s., 1H), 7.17-7.25 (m, 4H), 6.04 (d, J=6.35 Hz, 1H), 5.81 (br. s., 2H), 4.79 (br. s., 2H), 4.70 (br. s., 2H), 4.15 (br. s., 1H), 3.53 (br. s., 1H), 3.30 (br. s., 5H), 3.09 (br. s., 3H), 3.03 (br. s., 4H), 2.87 (s, 1H), 2.78 (br. s., 2H), 2.58-2.66 (m, 6H), 2.54 (br. s., 8H), 2.37 (d, J=1.47 Hz, 2H), 2.15-2.27 (m, 20H), 2.12 (br. s., 1H), 2.03-2.09 (m, 3H), 2.00 (s, 9H), 1.95 (br. s., 10H), 1.91 (s, 3H), 1.72 (br. s., 3H), 1.67 (br. s., 8H), 1.58 (s, 1H), 1.50 (br. s., 1H), 1.24 (br. s., 2H), 0.81-0.94 (m, 15H), 0.78 (d, J=6.84 Hz, 3H), 0.69 (br. s., 9H).

Example 5: Preparation of Compound 29

Rifamycin analog 29 was prepared as shown in Scheme 9, below, and described below.

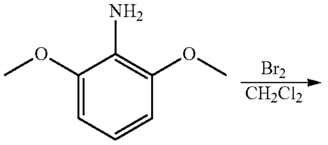

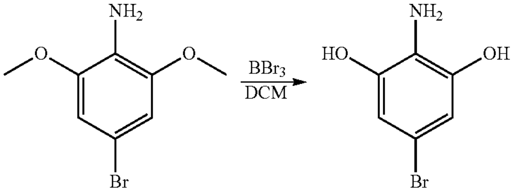

26 27

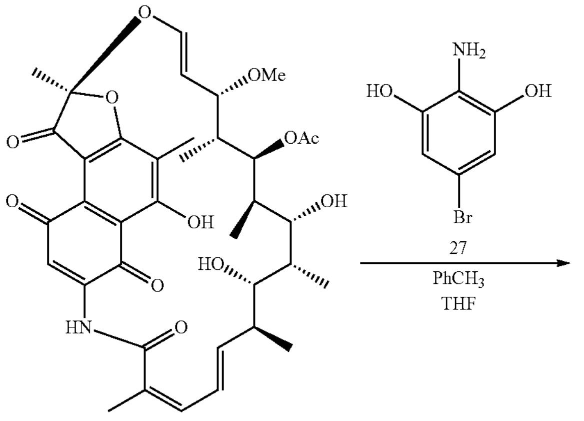

Rifamycin S

-continued

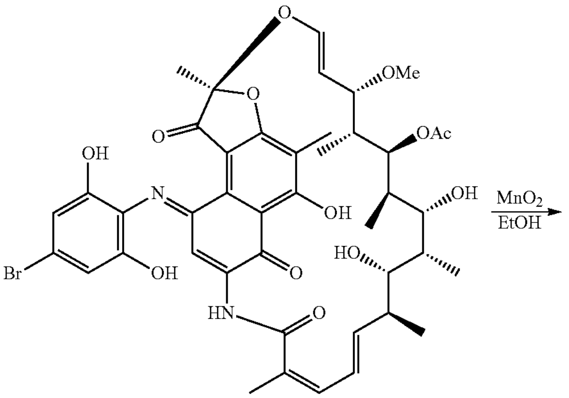

28a

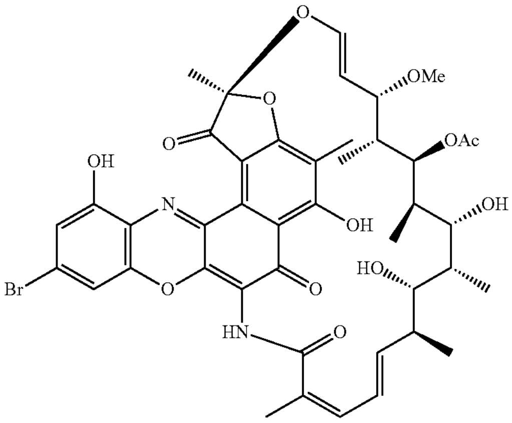

28

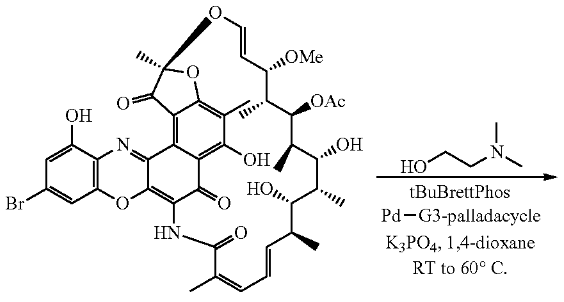

28

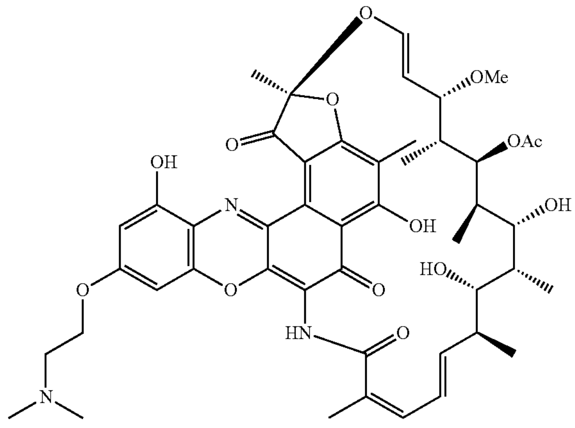

29

Synthesis of Compound 26. To a stirred solution of 2,6-dimethoxyaniline (9.0 g, 58.7 mmol, 1.0 eq) in 350 mL of anhydrous DCM was dropwise added over 30 min a $Br_2$ solution in 50 mL of anhydrous DCM at 4° C. An additional 200 mL was added to the slurry to achieve a semi-homogeneous solution. The reaction mixture was stirred overnight at room temperature. The dark brown mixture was cooled to 4° C. and basified by addition of 1.0 M NaOH solution (ca. 100 mL) to pH=10-11. The mixture was diluted with 200 mL of DCM and the layers are separated. The aqueous layer was extracted with DCM (200 mL total). The combined DCM layers were washed with water, brine, and dried over $Na_2SO_4$. After concentration in vacuo, the crude product was obtained as a slightly reddish solid. The residue was dissolved in DCM (8 mL) and loaded onto a 220 g HP silica gel Gold RediSep column and purified via ISCO (gradient elution: 5-95% EA in hexanes), pure fractions combined, and the solvent evaporated in vacuo. The solid was triturated with DCM and hexanes and filtered. The off-while solid was dried in vacuo giving the title compound 26 as an off-white solid (9.4 g, 70%). MS (ESI, pos.): calc'd for $C_8H_{10}BrNO_2$, 230.99; found 231.9 and 234.0 (M+H). $^1H$ NMR (500 MHz; $CDCl_3$) δ 6.66 (s, 2H), 3.84 (s, 6H).

Synthesis of Compound 27. Compound 26 (2.2 g, 9.47 mmol, 1.0 eq) was dissolved in 10 mL of anhydrous DCM and a $BBr_3$ solution was added dropwise over 10 min (10 mL, 1.0 M solution in DCM) at 4° C. The reaction was exothermic and produced a precipitate. An additional amount of $BBr_3$ (9 mL, 94.7 mmol, 10 eq) was added and the reaction mixture was stirred at room temperature overnight. The reddish suspension was checked by LC/MS to confirm the desired product. The reaction mixture was transferred to a 250 mL flask and cooled to 4° C. The mixture was carefully quenched with water followed by treatment with aqueous saturated $NaHCO_3$ solution to give a pH=7-8. The mixture was extracted with DCM and the aqueous layer cooled to 4° C. to afford a dark brown precipitate. The mixture was filtered and the brown solid was dissolved in 10 mL of methanol and dried over $Na_2SO_4$ to provide the desired product 27 (1.9 g, 100%). MS (ESI, pos.): calc'd for $C_6H_6BrNO_2$, 202.96; found 204.0 and 206.1 (M+H). 1H NMR (500 MHz; $CD_3OD$) δ 6.45 (s, 2H), 4.87 (s, 2H).

Synthesis of Compound 28. To a stirred solution of compound 27 (0.146 g, 0.72 mmol) in a mixture of toluene (20 mL) and THE (20 mL) at room temperature was added rifamycin S (0.5 g, 0.72 mmol). The solution was stirred for 3 days at room temperature to afford the desired product. The solvents were removed in vacuo, the dark residue was dissolved in 10 mL of ethanol followed by 100 mg of manganese dioxide ($MnO_2$). The sluggish mixture was stirred for 5 h at room temperature. After filtration of insoluble materials using a Celite pad, the filtrate was evaporated in vacuo. The dark residue was purified on a 120 g HP silica gel Gold RediSep column via ISCO (gradient elution: 5-95% EA in hexanes). The pure fractions combined and evaporated in vacuo giving the title compound 28 as a dark reddish solid (270 mg, 43%). MS (ESI, pos.): calc'd for $C_{43}H_{47}BrN_2O_{13}$, 878.23; found 879.2 and 880.2 (M+H), 878.1 and 879.1 (M−1). 1H NMR (500 MHz; DMSO-$d_6$) δ 10.22 (br. s., 1H), 9.52 (br. s., 1H), 7.43 (br. s., 1H), 7.35 (br. s., 1H), 6.04 (br. s., 1H), 5.83 (br. s., 2H), 5.21 (d, J=6.35 Hz, 2H), 4.89 (t, J=10.50 Hz, 1H), 4.16 (br. s., 1H), 3.51 (br. s., 1H), 3.15 (br. s., 2H), 3.02 (br. s., 4H), 2.80 (t, J=8.55 Hz, 1H), 2.21 (br. s., 3H), 2.08 (br. s., 1H), 1.96 (s, 4H), 1.99 (s, 4H), 1.78 (br. s., 1H), 1.71 (br. s., 3H), 1.60 (br. s., 1H), 1.47 (br. s., 1H), 0.84 (d, J=6.84 Hz, 6H), 0.69 (br. s., 6H).

Synthesis of Compound 29. To a 8 mL screw-top oven-dried vial, equipped with a stir bar was charged with compound 15 (60 mg, 0.069 mmol, 1.00 eq), 2-(dimethylamino)ethan-1-ol (61 mg, 0.69 mmol, 10 eq), t-BuBrett-Phos-Pd-G3-palladacycle (31 mg, 0.0345 mmol, 0.5 eq), and $K_3PO_4$ (30 mg, 0.141 mmol, 2.0 eq.). The reaction vial was capped with a rubber septum. The septum was pierced with a needle attached to evacuate and backfilled with argon (this process was repeated twice) followed by the addition of 1,4-dioxane (1.5 mL). The reaction was heated at 60° C. under argon pressure for 15 h, the reaction was allowed to cool to room temperature, filtered through a pad of Celite®, and rinsed with MeOH. The crude material was concentrated in vacuo and purified on a 50 g C18 Aq column (gradient elution: 10-95% MeCN in water, 0.05% acetic acid in both). The product fractions were combined and lyophilized giving the title compound 29 as a dark reddish solid (21 mg, 35%). MS (ESI, pos.): calc'd for $C_{47}H_{57}N_3O_{14}$, 887.38; found 888.3 (M+H). $^1H$ NMR (500 MHz; DMSO-$d_6$) δ 10.12 (br. s., 1H), 9.39 (br. s., 1H), 6.75 (br. s., 1H), 6.70 (br. s., 1H), 6.03 (br. s., 1H), 5.77 (d, J=15.14 Hz, 1H), 5.21 (br. s., 1H), 4.83-4.90 (m, 1H), 4.15-4.30 (m, 2H), 4.08 (br. s., 1H), 3.53 (br. s., 1H), 3.29 (s, 1H), 3.16 (br. s., 1H), 3.03 (br. s., 3H), 2.87 (br. s., 1H), 2.79 (br. s., 1H), 2.62-2.71 (m, 2H), 2.36 (s, 1H), 2.23 (s, 6H), 2.19 (br. s., 3H), 1.93-2.11 (m, 7H), 1.91 (s, 1H), 1.76 (br. s., 1H), 1.69 (br. s., 3H), 1.53-1.65 (m, 1H), 1.50 (br. s., 1H), 1.32-1.45 (m, 1H), 0.76-0.94 (m, 6H), 0.68 (br. s., 5H).

29a

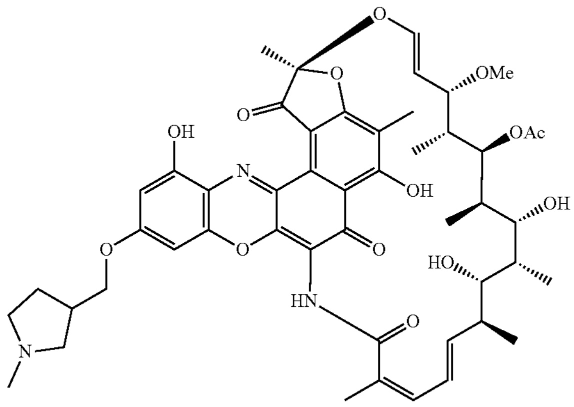

Compound 29a: 29a was prepared using the general procedure as described for 29: Compound 28 (50 mg, 0.0568 mmol, 1.00 eq.), (1-methylpyrrolidin-3-yl)methanol (65 mg, 0.568 mmol, 10 eq.), t-BuBrettPhos-Pd-G3-palladacycle (24 mg, 0.0284 mmol, 0.5 eq.), and $K_3PO_4$ (24 mg, 0.115 mmol, 2.0 eq.) to afford 19% (9.8 mg). MS: calc'd for $C_{49}H_{59}N_3O_{14}$, 913.40; found 914.4 (M+H), 912.3 (M−H). $^1H$ NMR (500 MHz; DMSO-$d_6$): δ 9.38-9.34 (m, 1H), 6.74-6.64 (m, 1H), 6.26 (s, 1H), 6.02-6.00 (m, 1H), 5.80-5.78 (m, 1H), 5.23-5.19 (m, 1H), 4.87-4.82 (m, 1H), 4.06-4.03 (m, 2H), 3.55-3.51 (m, 1H), 3.17-3.15 (m, 1H), 3.03 (dd, J=3.2, 1.1 Hz, 2H), 2.87 (s, 3H), 2.78 (tdd, J=2.8, 1.5, 0.6 Hz, 3H), 2.64-2.58 (m, 1H), 2.37 (s, 1H), 2.30 (s, 6H), 2.18 (s, 6H), 1.97 (d, J=16.7 Hz, 5H), 1.69 (t, J=0.4 Hz, 3H), 1.53-1.51 (m, 2H), 0.85 (dt, J=2.6, 1.3 Hz, 11H), 0.69-0.67 (m, 4H).

29b

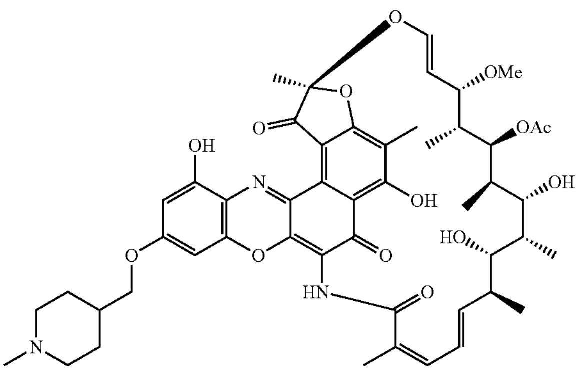

Compound 29b: 29b was prepared using the general procedure as described for 29: Compound 28 (60 mg, 0.068 mmol, 1.00 eq.), (1-methylpiperidin-4-yl)methanol (88 mg, 0.683 mmol, 10 eq.), t-BuBrettPhos-Pd-G3-palladacycle (29 mg, 0.034 mmol, 0.5 eq.), and $K_3PO_4$ (29 mg, 0.136 mmol, 2.0 eq.) to afford 9.5% (6.0 mg). MS: calc'd for $C_{50}H_{61}N_3O_{14}$, 927.42; found 928.4 (M+H), 926.3 (M−H). $^1$H NMR (500 MHz; DMSO-$d_6$): δ 8.84 (dd, J=1.5, 0.9 Hz, 1H), 7.13 (dd, J=1.7, 0.9 Hz, 1H), 6.92-6.88 (m, 1H), 6.29-6.26 (m, 1H), 6.21-6.18 (m, 1H), 5.67 (t, J=0.6 Hz, 1H), 5.00-4.99 (m, 1H), 4.75-4.73 (m, 1H), 3.92-3.90 (m, 1H), 3.81-3.79 (m, 4H), 2.85 (d, J=2.5 Hz, 2H), 2.75-2.72 (m, 1H), 2.63 (s, 2H), 2.36 (s, 3H), 2.12 (t, J=5.7 Hz, 6H), 1.93 (d, J=9.7 Hz, 4H), 1.81 (ddd, J=3.6, 3.0, 1.4 Hz, 2H), 1.72 (s, 6H), 1.66 (s, 6H), 1.37-1.34 (m, 5H), 0.88-0.85 (m, 7H), 0.69-0.64 (m, 4H).

29c

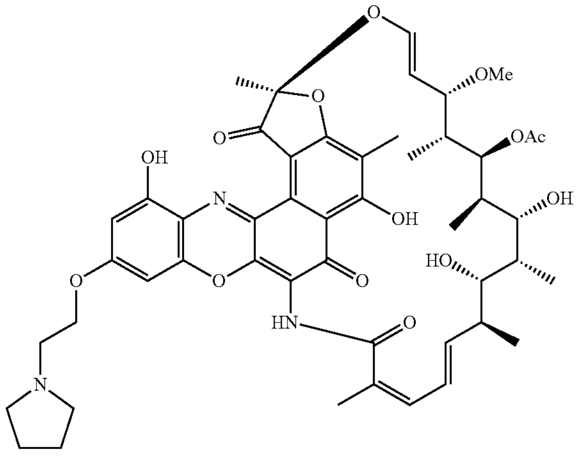

Compound 29c: 29c was prepared using the general procedure as described for 29: Compound 28 (60 mg, 0.068 mmol, 1.00 eq.), 2-(pyrrolidin-1-yl)ethan-1-ol (88 mg, 0.682 mmol, 10 eq.), t-BuBrettPhos-Pd-G3-palladacycle (29 mg, 0.034 mmol, 0.5 eq.), and $K_3PO_4$ (29 mg, 0.136 mmol, 2.0 eq.) to afford 26% (16.2 mg). MS: calc'd for $C_{49}H_{59}N_3O_{14}$, 913.40; found 914.4 (M+H), 912.3 (M−H). $^1$H NMR (500 MHz; DMSO-$d_6$): δ 9.40-9.39 (m, 1H), 6.77-6.76 (m, 1H), 6.67-6.65 (m, 1H), 6.02-6.00 (m, 1H), 5.78-5.76 (m, 1H), 5.21-5.19 (m, 1H), 4.86 (t, J=10.6 Hz, 1H), 4.27-4.20 (m, 2H), 4.08-4.06 (m, 1H), 3.54-3.50 (m, 1H), 3.17-3.14 (m, 1H), 3.03 (d, J=0.8 Hz, 3H), 2.86 (d, J=0.4 Hz, 3H), 2.79-2.77 (m, 1H), 2.64-2.57 (m, 4H), 2.18 (s, 8H), 1.97 (d, J=18.7 Hz, 7H), 1.70 (s, 7H), 1.60-1.56 (m, 1H), 1.51-1.46 (m, 1H), 0.84 (d, J=5.8 Hz, 7H), 0.67 (dt, J=1.5, 0.7 Hz, 5H).

29d

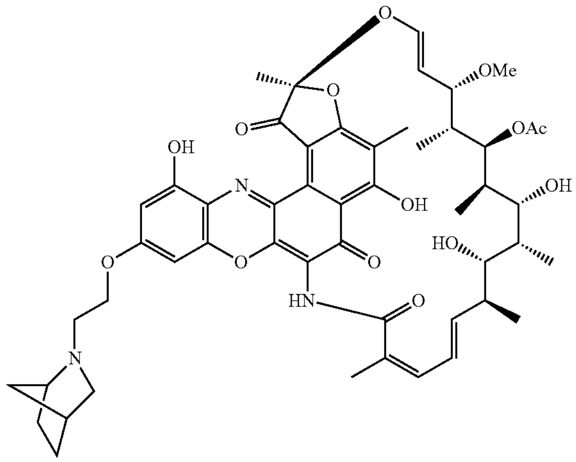

Compound 29d: 29d was prepared using the general procedure as described for 29: Compound 28 (60 mg, 0.068 mmol, 1.00 eq.), 2-(2-azabicyclo[2.2.1]heptan-2-yl)ethan-1-ol (96 mg, 0.682 mmol, 10 eq.), t-BuBrettPhos-Pd-G3-palladacycle (29 mg, 0.034 mmol, 0.5 eq.), and $K_3PO_4$ (29 mg, 0.136 mmol, 2.0 eq.) to afford 37% (23.7 mg). MS: calc'd for $C_{51}H_{61}N_3O_{14}$, 939.42; found 940.5 (M+H), 938.3 (M−H). $^1$H NMR (500 MHz; DMSO-$d_6$): δ 9.37-9.35 (m, 1H), 6.72-6.65 (m, 1H), 6.04-6.00 (m, 1H), 5.79 (tdd, J=3.6, 1.8, 1.1 Hz, 1H), 5.22-5.19 (m, 1H), 4.86-4.82 (m, 1H), 4.19-4.16 (m, 2H), 4.07-4.05 (m, 2H), 3.54-3.52 (m, 1H), 3.17-3.14 (m, 1H), 3.07-3.02 (m, 2H), 2.86-2.80 (m, 3H), 2.80-2.77 (m, 1H), 2.32 (d, J=1.2 Hz, 3H), 2.18 (s, 7H), 1.98-1.91 (m, 8H), 1.69 (d, J=0.5 Hz, 3H), 1.58 (ddd, J=5.0, 2.0, 0.9 Hz, 1H), 1.52-1.43 (m, 2H), 1.42-1.40 (m, 2H), 1.27-1.24 (m, 2H), 0.85 (dt, J=2.2, 1.1 Hz, 9H), 0.68-0.67 (m, 5H).

29e

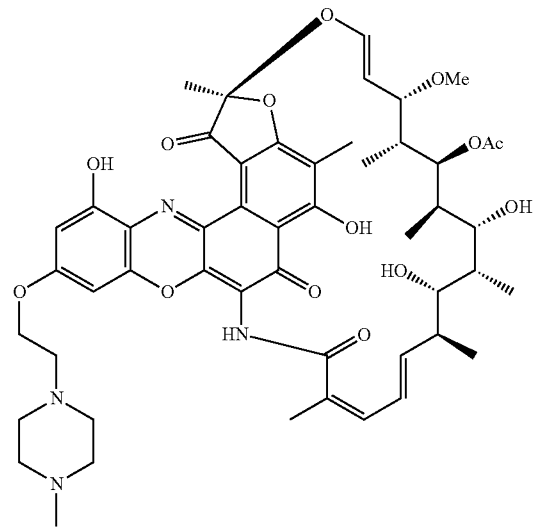

Compound 29e: 29e was prepared using the general procedure as described for 29: Compound 28 (60 mg, 0.068 mmol, 1.00 eq.), 2-(4-methylpiperazin-1-yl)ethan-1-ol (100 mg, 0.693 mmol, 10 eq.), t-BuBrettPhos-Pd-G3-palladacycle (30 mg, 0.0351 mmol, 0.5 eq.), and $K_3PO_4$ (30 mg, 0.141 mmol, 2.0 eq.) to afford 15% (9.8 mg). MS: calc'd for $C_{50}H_{62}N_4O_{14}$, 942.43; found 943.4 (M+H). $^1$H NMR (500 MHz, $CD_3OD$) δ 6.53-6.63 (m, 2H), 6.24 (br. s., 1H), 4.99-5.11 (m, 2H), 4.27-4.40 (m, 2H), 3.67 (s, 1H), 3.01 (d, J=8.30 Hz, 4H), 2.89 (br. s., 2H), 2.56-2.68 (m, 6H), 2.46 (br. s., 1H), 2.32 (s, 8H), 2.12 (br. s., 3H), 2.06 (s, 1H), 1.92-2.04 (m, 3H), 1.83 (s, 3H), 1.65 (d, J=8.79 Hz, 2H), 1.56 (s, 1H), 1.31 (br. s., 3H), 1.03 (br. s., 1H), 0.95 (s, 8H), 0.81 (s, 4H), 0.01 (s, 2H), −0.28 (s, 2H).

29f

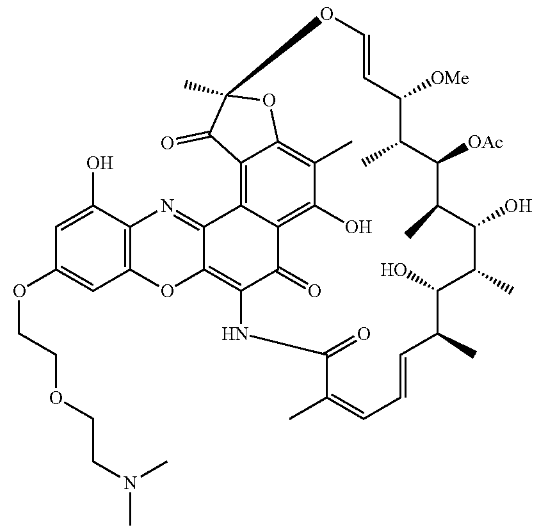

Compound 29f 29f was prepared using the general procedure as described for 29: Compound 28 (60 mg, 0.068 mmol, 1.00 eq.), 2-(2-(dimethylamino)ethoxy)ethan-1-ol (100 mg, 0.693 mmol, 10 eq.), t-BuBrettPhos-Pd-G3-palladacycle (30 mg, 0.0351 mmol, 0.5 eq.), and $K_3PO_4$ (30 mg, 0.141 mmol, 2.0 eq.) to afford 11% (7.1 mg). MS: calc'd for $C_{49}H_{61}N_3O_{15}$, 931.41; found 932.3 (M+H). $^1$H NMR (500 MHz, $CD_3OD$) δ 6.49-6.59 (m, 2H), 6.21 (br. s., 1H), 4.95-5.07 (m, 2H), 4.24-4.40 (m, 2H), 3.87 (br. s., 3H), 3.72 (br. s., 3H), 3.00 (d, J=8.79 Hz, 5H), 2.67 (d, J=4.88 Hz, 3H), 2.36 (s, 10H), 2.30 (s, 5H), 2.11 (s, 5H), 1.99 (s, 5H), 1.82 (s, 4H), 1.30 (s, 2H), 0.93 (s, 6H), 0.00 (s, 2H), −0.30 (s, 2H).

29g

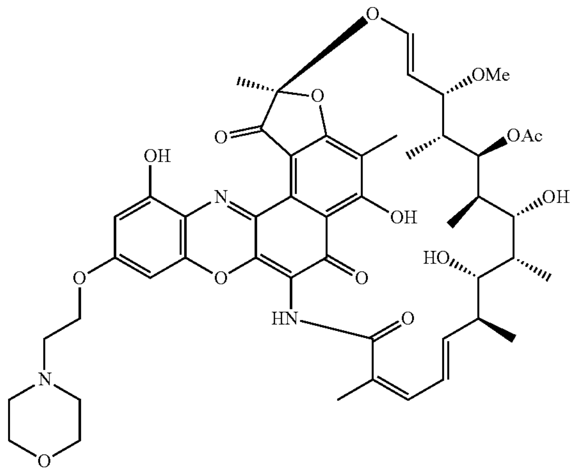

Compound 29g: 29g was prepared using the general procedure as described for 29: Compound 28 (50 mg, 0.0568 mmol, 1.00 eq.), 2-morpholinoethan-1-ol (75 mg, 0.568 mmol, 10 eq.), t-BuBrettPhos-Pd-G3-palladacycle (24 mg, 0.028 mmol, 0.5 eq.), and $K_3PO_4$ (24 mg, 0.115 mmol, 2.0 eq.) to afford 12% (5.8 mg). MS: calc'd for $C_{49}H_{59}N_3O_{15}$, 929.39; found 930.4 (M+H). $^1$H NMR (500 MHz; DMSO-$d_6$): δ 10.14-10.11 (m, 1H), 9.38-9.31 (m, 1H), 6.76-6.59 (m, 1H), 6.34-6.20 (m, 1H), 6.04-6.01 (m, 1H), 5.79-5.76 (m, 2H), 5.21 (td, J=2.0, 1.1 Hz, 1H), 4.83 (t, J=0.8 Hz, 1H), 4.27-4.22 (m, 1H), 4.06-4.05 (m, 1H), 3.57 (s, 6H), 3.15 (d, J=0.7 Hz, 3H), 3.03 (d, J=1.5 Hz, 4H), 2.86 (s, 1H), 2.71 (dt, J=2.0, 1.5 Hz, 4H), 2.17 (s, 3H), 1.97 (d, J=15.3 Hz, 6H), 1.69 (s, 3H), 1.60-1.59 (m, 3H), 1.50-1.44 (m, 3H), 1.37 (s, 1H), 1.24 (d, J=1.0 Hz, 2H), 1.15-1.14 (m, 1H), 0.85 (td, J=1.9, 0.8 Hz, 6H), 0.67 (dtd, J=4.1, 2.1, 0.9 Hz, 4H).

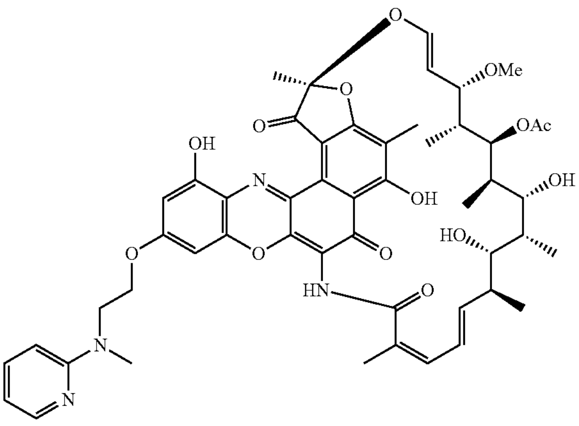 [SMILES: CO[C@H]1/C=C/O[C@@]2(C)Oc3c(C)c(O)c4c(=O)c(c5oc6cc(OCCN(C)c7ccccn7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

Compound 29h: 29h was prepared using general procedure as described for 29: Compound 28 (40 mg, 0.0454 mmol, 1.0 eq.), 2-(methyl(pyridin-2-yl)amino)ethan-1-ol (69 mg, 0.454 mmol, 10 eq.), t-BuBrettPhos-Pd-G3-palladacycle (20 mg, 0.0223 mmol, 0.5 eq.), and $K_3PO_4$ (20 mg, 0.0921 mmol, 2.0 eq.) to afford 29h (5.6 mg, 13%). MS: calc'd for $C_{51}H_{58}N_4O_{14}$, 950.39; found 951.3 (M+H). $^1$H NMR (500 MHz; $CD_3OD$): δ 8.07 (d, J=3.91 Hz, 1H), 7.53 (t, J=7.08 Hz, 1H), 6.69 (d, J=8.79 Hz, 1H), 6.59-6.66 (m, 2H), 6.44 (d, J=1.95 Hz, 1H), 6.22 (d, J=10.26 Hz, 1H), 5.95 (d, J=1.95 Hz, 1H), 5.74 (d, J=11.72 Hz, 1H), 5.13-5.18 (m, 2H), 4.58 (s, 5H), 4.30 (d, J=6.35 Hz, 2H), 4.22 (dd, J=2.93, 5.86 Hz, 1H), 4.00 (t, J=5.62 Hz, 2H), 3.86 (d, J=10.26 Hz, 1H), 3.35 (br. s., 2H), 3.13 (s, 2H), 2.95-3.03 (m, 3H), 2.11-2.17 (m, 2H), 2.03-2.11 (m, 4H), 1.92-2.00 (m, 8H), 1.71 (br. s., 1H), 1.42 (d, J=2.93 Hz, 1H), 1.35 (d, J=6.35 Hz, 2H), 1.22-1.32 (m, 5H), 0.85-1.00 (m, 3H), 0.33 (d, J=6.84 Hz, 2H), 0.09-0.10 (m, 1H), −0.33 (d, J=7.33 Hz, 2H).

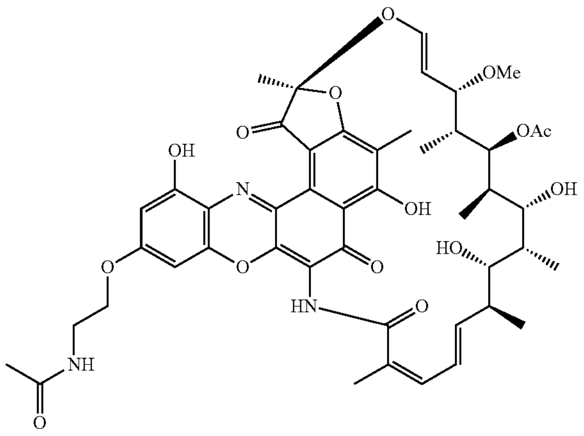 [SMILES: CO[C@H]1/C=C/O[C@@]2(C)Oc3c(C)c(O)c4c(=O)c(c5oc6cc(OCCNC(C)=O)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

Compound 29i: 29i was prepared using general procedure as described for 29: Compound 28 (40 mg, 0.0454 mmol, 1.0 eq.), 2N-(2-hydroxyethyl)acetamide (47 mg, 0.454 mmol, 10 eq.), t-BuBrettPhos-Pd-G3-palladacycle (20 mg, 0.0227 mmol, 0.5 eq.), and $K_3PO_4$ (20 mg, 0.0939 mmol, 2.0 eq.) to afford 29i (12.2 mg, 31%). MS: calc'd for $C_{47}H_{55}N_3O_{15}$, 901.36; found 902.3 (M+H), 900.3 (M−H). $^1$H NMR (500 MHz; $CD_3OD$): 6.65-6.84 (m, 1H), 6.43-6.64 (m, 3H), 6.31-6.43 (m, 1H), 6.07-6.28 (m, 2H), 4.92-5.10 (m, 2H), 4.08-4.24 (m, 4H), 3.62 (br. s., 5H), 2.91-3.09 (m, 4H), 2.29 (s, 5H), 2.11 (br. s., 5H), 2.04 (s, 2H), 1.90-2.02 (m, 7H), 1.82 (s, 5H), 0.91 (br. s., 5H), 0.10 (s, 3H), −0.34 (s, 2H).

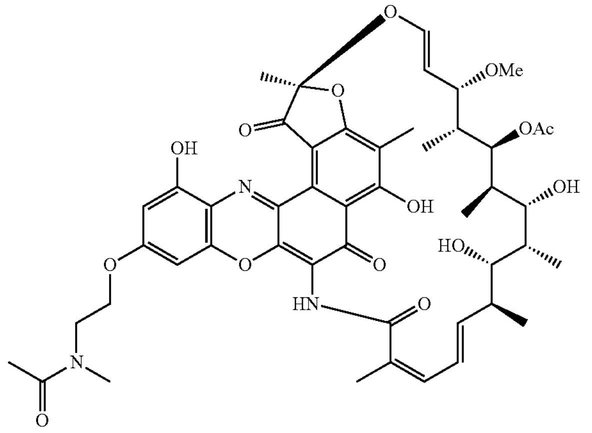 [SMILES: CO[C@H]1/C=C/O[C@@]2(C)Oc3c(C)c(O)c4c(=O)c(c5oc6cc(OCCN(C)C(C)=O)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

Compound 29j: 29j was prepared using general procedure as described for 29: Compound 28 (40 mg, 0.0454 mmol, 1.0 eq.), N-(2-hydroxyethyl)-N-methylacetamide (53 mg, 0.454 mmol, 10 eq.), t-BuBrettPhos-Pd-G3-palladacycle (20 mg, 0.0227 mmol, 0.5 eq.), and $K_3PO_4$ (20 mg, 0.0939 mmol, 2.0 eq.) to afford 29j (7 mg, 17%). MS: calc'd for $C_{48}H_{57}N_3O_{15}$, 915.38; found 916.3 (M+H). $^1$H NMR (500 MHz; $CD_3OD$): δ 6.45-6.68 (m, 2H), 6.30-6.45 (m, 1H), 6.11-6.30 (m, 1H), 5.09-5.34 (m, 1H), 4.95-5.09 (m, 5H), 4.58 (s, 3H), 4.18-4.40 (m, 2H), 3.73-3.90 (m, 2H), 3.14-3.23 (m, 2H), 2.99 (d, J=9.28 Hz, 6H), 2.31 (br. s., 5H), 2.10 (s, 5H), 2.13 (s, 2H), 2.04 (s, 1H), 1.98 (br. s., 3H), 1.93 (s, 1H), 1.81 (s, 6H), 0.79-1.02 (m, 6H), −0.10-0.04 (m, 2H), −0.21-0.41 (m, 2H).

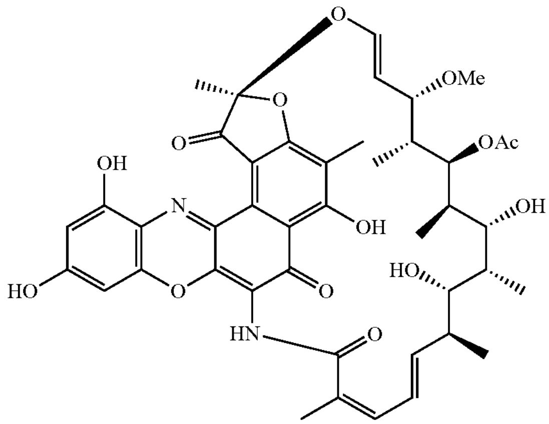 [SMILES: CO[C@H]1/C=C/O[C@@]2(C)Oc3c(C)c(O)c4c(=O)c(c5oc6cc(O)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

Compound 29k: 29k was the byproduct for all the C—O cross coupling reaction starting with compound 28. MS: calc'd for $C_{43}H_{48}N_2O_{14}$, 816.3; found 817.3 (M+H), 839.3 (M+Na). $^1$H NMR (500 MHz; DMSO-$d_6$): δ 10.09 (s, 1H), 9.31 (s, 1H), 6.44 (s, 2H), 6.00 (s, 1H), 5.77 (br. s., 2H), 5.20 (br. s., 1H), 4.81-4.88 (m, 2H), 4.05 (br. s., 1H), 3.48-3.54 (m, 1H), 3.16 (br. s., 1H), 3.02 (br. s., 3H), 2.97 (br. s., 1H), 2.77 (br. s., 1H), 2.51-2.54 (m, 1H), 2.12-2.21 (m, 4H), 2.00 (br. s., 1H), 1.92-1.98 (m, 5H), 1.90 (s, 1H), 1.74 (s, 3H), 1.61-1.71 (m, 6H), 1.43-1.61 (m, 3H), 1.22-1.24 (m, 1H), 0.83 (d, J=6.35 Hz, 2H), 0.66 (br. s., 3H), 0.06 (d, J=0.98 Hz, 1H).

Example 6: Preparation of Compound 35

Rifamycin analog 35 was synthesized from rifamycin S as shown in Scheme 10, below, and described below.

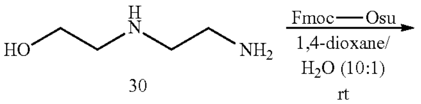

30

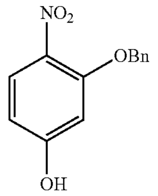

8

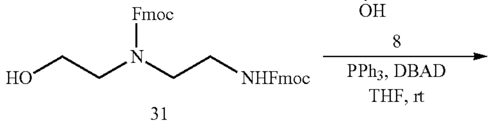

31

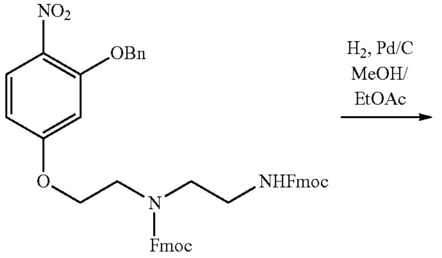

32

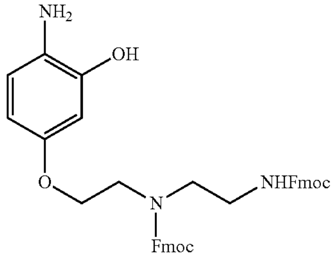

33

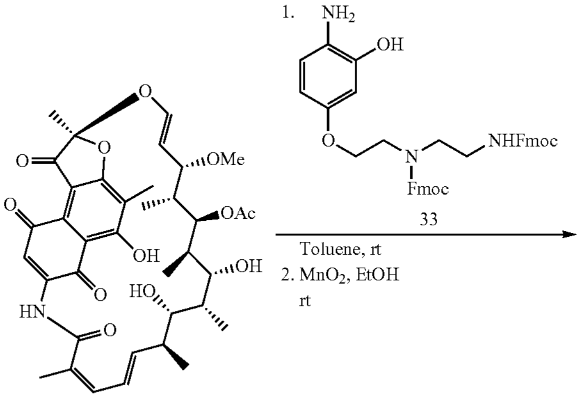

rifamycin S

-continued

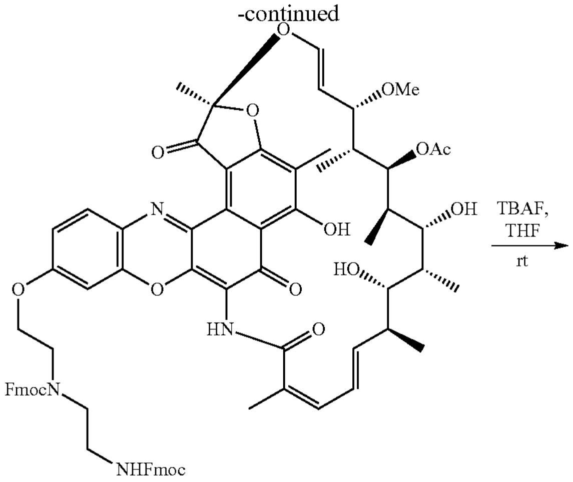

34

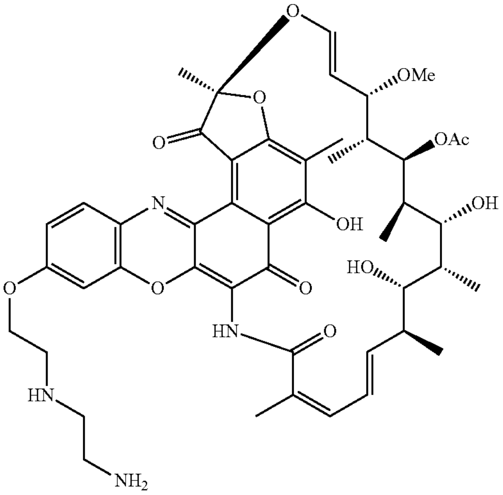

35

Synthesis of compound 31. To a solution of compound 30 (200 mg, 1.920 mmol) under argon in 1,4-dioxane/water (v/v, 10:1, 11 mL) was added Fmoc-OSu (1360 mg, 4.032 mmol). After stirring for 5 h an LC/MS analysis indicated the reaction was complete. The reaction mixture was treated with sat. $NaHCO_3$ (5 mL) and extracted with EtOAc (3×15 mL). The combined organic layer was then treated with brine (10 mL), dried ($Na_2SO_4$) and concentrated in vacuo to give crude compound 31 as a white foam (800 mg, 76%), which was used in the next step instantly without further purification. MS: calc'd for $C_{34}H_{32}N_2O_5$, 548.2; found 549.2 (M+H).

Synthesis of compound 32. To a stirring solution of compound 8 (160 mg, 0.652 mmol) under argon in THF (2 mL) at room temperature were added the alcohol 31 (432 mg, 0.788 mmol) and $PPh_3$ (308 mg, 1.174 mmol). Then a solution of DBAD (270 mg, 1.174 mmol) in THF (1 mL) was added to the reaction mixture dropwise. After stirring for 15 h, the mixture was evaporated to dryness and the residue was purified on a 40 g HP silica gel Gold RediSep column via ISCO (gradient elution: 0-100% ethyl acetate in hexanes), and the pure fractions evaporated and dried in vacuo giving the title compound 32 as a yellowish white solid (286 mg, 56%). MS: calc'd for $C_{47}H_{41}N_3O_8$, 775.3; found 776.3 (M+H), 798.2 (M+Na).

Synthesis of compound 33. To a solution under argon of compound 32 (220 mg, 0.284 mmol) in 5 mL of methanol/EtOAc (2:3) and degassed with argon was added 31 mg of 10% Pd/C. The mixture was further degassed with argon and connected to a hydrogen balloon. After 2 h, analysis by LC/MS from an in-process aliquot indicated the reaction was complete. The mixture was filtered through Celite and concentrated to afford 150 mg of compound 33 (85% pure by LC/MS) as yellowish oil, which was used in the next step instantly without further purification. MS: calc'd for $C_{40}H_{37}N_3O_6$, 655.3; found 656.3 (M+H).

Synthesis of compound 34. To a round-bottom flask with hydroxyaniline 33 (150 mg, 0.194 mmol, 85% pure), were added toluene (2 mL) and rifamycin S (129 mg, 0.185 mmol). The reaction mixture was sonicated for 1 min to dissolve the reaction mixture, sealed via rubber septum, purged with argon, and the reaction stirred at ambient temperature. After 1 day another portion of hydroxyaniline 33 (45 mg, 0.059 mmol, 86% pure, synthesized using same procedure describe before) in toluene (2 mL) was added and stirred for 5 d. The reaction was concentrated in vacuo to remove toluene, dissolved in EtOH (4 mL) and $MnO_2$ (20 mg) was added. After stirring for 4 d, the reaction was concentrated in vacuo and purified by chromatography on a 40 g HP silica gel Gold RediSep column via ISCO (gradient elution: 0-100% ethyl acetate in hexanes). The pure fractions were evaporated and dried in vacuo giving the title compound 34 as a dark reddish solid (65 mg, 26%). MS (ESI, pos.): calc'd for $C_{77}H_{78}N_4O_{17}$, 1330.5; found, 1353.5 (M+Na).

Synthesis of compound 35. To a stirred solution of compound 34 (28 mg, 0.021 mmol) under argon in THF (1 mL), was treated with a solution of TBAF (13 mg, 0.05 mL, 0.050 mmol, 1M in THF) and the reaction was stirred at ambient temperature. After 2 h, the reaction was purified directly on a 50 g C18 RediSep Gold column via ISCO system (gradient elution: 0-100% MeCN in water, 0.05% acetic acid in both, over 30 min). The product-containing fractions were combined, frozen on dry ice, and lyophilized overnight giving the title compound 35 as dark reddish solid (9 mg, 48%). MS: calc'd for $C_{47}H_{58}N_4O_{13}$, 886.4; found 887.3 (M+H). $^1$H-NMR (500 MHz; $CD_3OD$): δ 7.86-7.74 (m, 1H), 7.18-7.08 (m, 1H), 6.98-6.84 (m, 1H), 6.78-6.68 (m, 1H), 6.53-6.40 (m, 1H), 6.23-6.15 (m, 1H), 6.23-6.15 (m, 1H), 6.00-5.79 (m, 1H), 6.00-5.79 (m, 1H), 5.30-4.95 (m, 2H), 3.81-3.65 (m, 6H), 3.35 (s, 3H), 3.09-2.93 (m, 7H), 2.25-2.20 (m, 2H), 2.17-2.03 (m, 4H), 2.00-1.87 (m, 5H), 1.76-1.68 (m, 4H), 1.03-0.85 (m, 7H), 0.78-0.65 (m, 2H), 0.14-0.03 (m, 4H), 0.13-0.00 (m, 3H), −0.30 (m, 2H).

Example 7: Synthesis of Analog 38 According to the Disclosure

Rifamycin analog 38 was synthesized from rifamycin S as shown in Scheme 11 below, and as described below.

Scheme 11

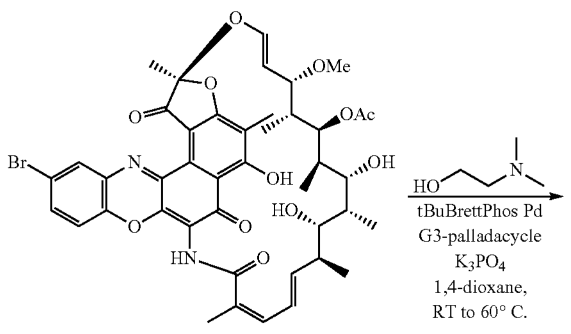

37

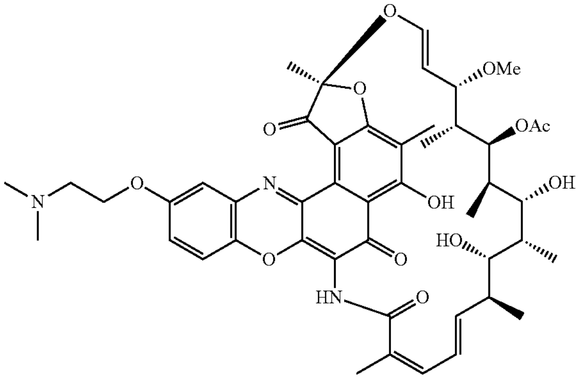

38

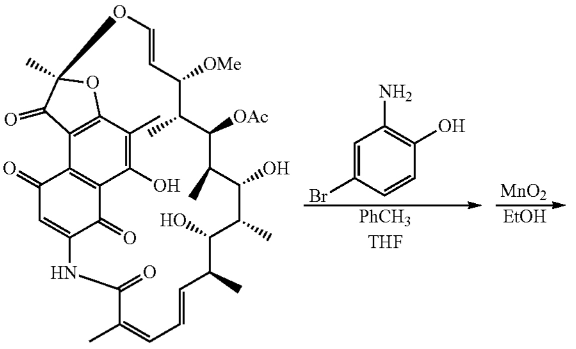

Rifamycin S

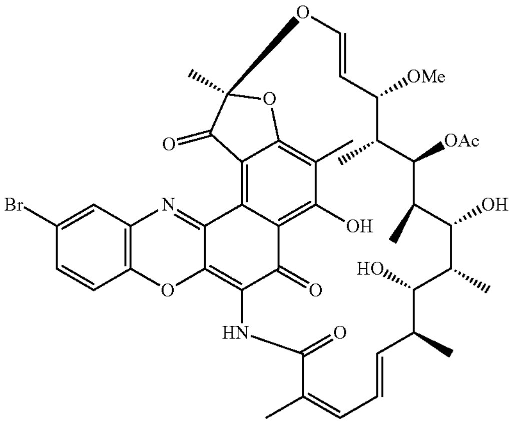

37

Example 6A: Pd-Catalyzed O-Alkylation (37)

Compound 37: As described in the Example 3, rifamycin S (2.0 g, 2.87 mmol) in 80 mL of toluene at room temperature was treated with 2-amino-4-bromophenol (0.54 g, 2.87 mmol). The mixture solution was stirred for 2 days at room temperature. The mixture was then evaporated to dryness and the residue dissolved in 20 mL of ethanol and 300 mg of manganese oxide ($MnO_2$) was added in one portion to the ethanol solution. The mixture was stirred under argon for 15 h at room temperature. After filtration of insoluble materials using a Celite pad, the filtrate was evaporated under reduced pressure. The dark residue was purified on a 120 g HP silica gel Gold RediSep column via ISCO (gradient elution: 5-95% EA in hexanes). The pure fractions were evaporated and dried in vacuo giving the title compound 37 as a dark reddish solid (1.5 g, 60%). MS (ESI, pos.): calc'd for $C_{43}H_{47}BrN_2O_{12}$, 862.23; found 863.1 and 865.1 (M+H), 885.1 and 888.0 (M+Na). $^1H$ NMR $^1H$-NMR (500 MHz; $CDCl_3$): δ 8.19-8.19 (m, 1H), 7.66-7.64 (m, 1H), 7.48 (s, 2H), 7.06 (s, 1H), 6.23-6.18 (m, 1H), 6.01 (d, J=12.3 Hz, 2H), 5.06-5.05 (m, 1H), 4.98 (dd, J=12.2, 7.1 Hz, 2H), 3.11 (s, 3H), 3.03-3.00 (m, 2H), 2.33 (s, 6H), 2.13 (s, 3H), 2.07 (s, 6H), 1.83 (s, 6H), 1.70 (s, 2H), 1.54 (s, 1H), 0.97 (d, J=6.6 Hz, 3H), 0.80 (d, J=5.2 Hz, 6H), 0.58-0.57 (m, 4H).

Compound 38: A palladium-catalyzed C—O coupling of primary alcohols similar to title compounds 15 and 29 was employed. To compound 37 (60 mg, 0.069 mmol, 1.00 eq) was added 2-(dimethylamino)ethan-1-ol (62 mg, 0.69 mmol, 10 eq), t-BuBrettPhos-Pd-G3-palladacycle (30 mg, 0.0345 mmol, 0.5 eq), and $K_3PO_4$ (30 mg, 0.141 mmol, 2.0 eq.). The septum was pierced with a needle to evacuate and backfill with argon (this process was repeated twice) followed by the addition of 1,4-dioxane (1.5 mL). The reaction was heated at 60° C. in an oil bath under argon pressure for 15 h. The crude material was concentrated in vacuo and purified on a 50 g C18 Aq column (gradient elution: 10-95% MeCN in water, 0.05% acetic acid in both). The product fractions were combined, frozen on dry ice, and lyophilized giving the title compound 38 as a dark reddish solid (6.8 mg, 12%). Another purification by preparative HPLC (Gemini, 5 μm, 150 mm×30 mm, eluents: 10-95% MeCN in water, 0.05% AcOH) was conducted and lyophilized to afford pure product (4.5 mg). MS (ESI, pos.): calc'd for $C_{47}H_{57}N_3O_{13}$, 871.39; found 872.4 (M+H). 1H NMR (500 MHz; DMSO-$d_6$) δ 9.48-9.32 (m, 2H), 7.68-7.49 (m, 2H), 7.44-7.27 (m, 1H), 6.11-5.95 (m, 1H), 5.88-5.76 (m, 2H), 5.28-5.16 (m, 2H), 4.84-4.71 (m, 1H), 4.21-4.18 (m, 1H), 3.57-3.43 (m, 2H), 3.09-3.01 (m, 1H), 2.82-2.75 (m, 1H), 2.67 (dd, J=15.5, 10.1 Hz, 3H), 2.29-2.23 (m, 13H), 2.19 (d, J=0.6 Hz, 9H), 1.99-1.91 (m, 1H), 1.69 (s, 1H), 1.64-1.56 (m, 1H), 1.55-1.43 (m, 1H), 1.24 (s, 1H), 0.85-0.84 (m, 7H), 0.69-0.68 (m, 4H).

Example 8: Preparation of Compound 43

Rifamycin analog 43 was synthesized from rifamycin S as shown in Scheme 12 below, and as described below.

Scheme 12

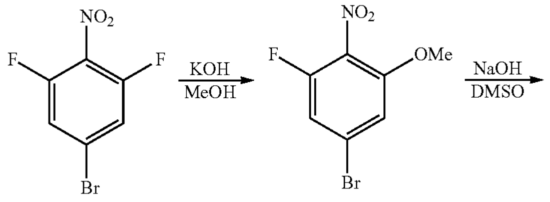

39

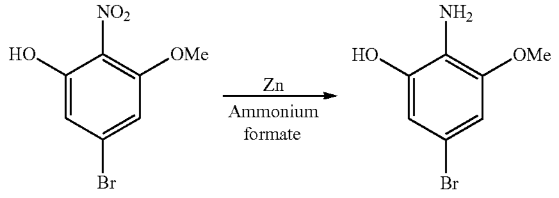

40 41

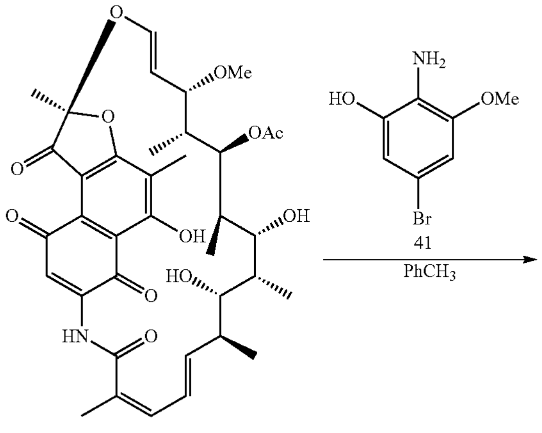

rifamycin S

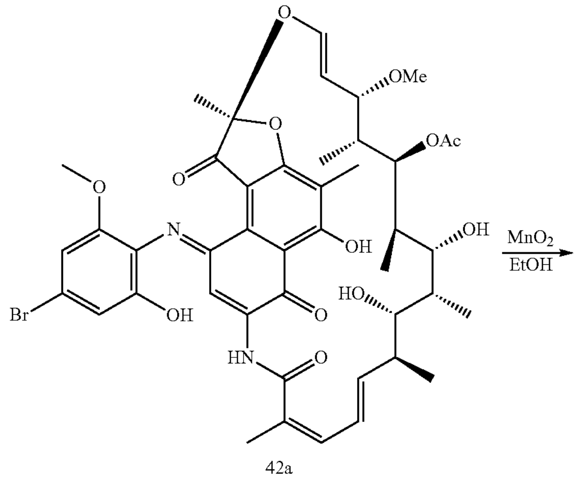

42a

-continued

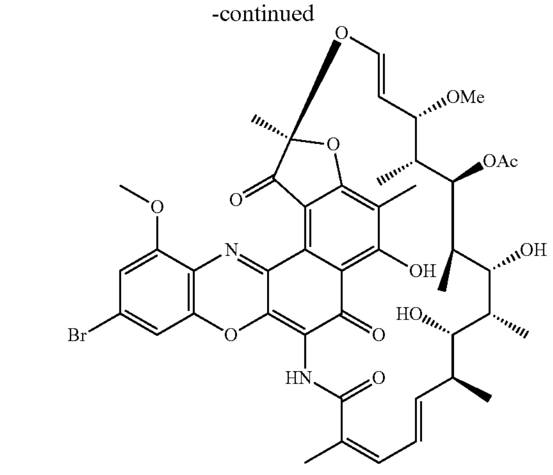

42

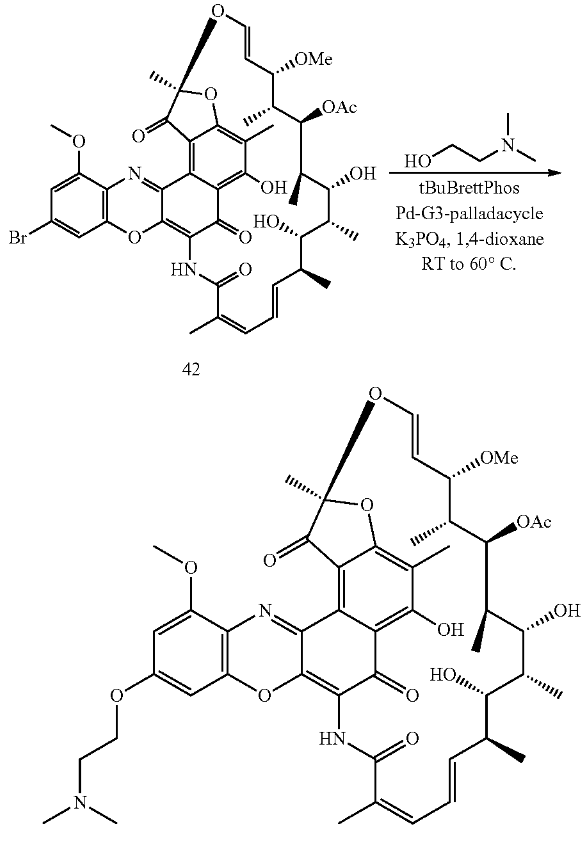

42

43

Compound 39: To a stirred solution of 5-bromo-1,3-difluoro-2-nitrobenzene (2.0 g, 8.40 mmol, 1.0 eq.) in 15 mL of methanol at room temperature was added KOH (504 mg, 8.98 mmol, 1.07 eq.). The resulting mixture was refluxed at 90° C. for 1 h. After reaction completion, the mixture was cooled at room temperature and concentrated under reduced pressure. The residue was diluted with ethyl acetate (20 mL) and washed with water, brine, and dried over $Na_2SO_4$. After concentration in vacuo, the crude product was obtained as a dark solid. The residue was dissolved in DCM (5 mL) and loaded on a 80 g HP silica gel Gold RediSep column via ISCO (gradient elution: hexanes—90% EA in hexanes), and the pure fractions evaporated to afford light yellow solid of 39 (1.48g, 70%). MS (ESI, pos.): calc'd for $C_7H_5BrFNO_3$, 250.02; found 273.2 (M+Na). $^1$H-NMR (500 MHz; $CDCl_3$): δ 7.06 (dd, J=8.6, 1.5 Hz, 1H), 7.02 (s, 1H), 3.95 (s, 3H).

Compound 40: To a stirred solution of 5-bromo-1-fluoro-3-methoxy-2-nitrobenzene 39 (400 mg, 1.56 mmol) in DMSO (3 mL) was added 1M NaOH (2 mL, 2 mmol) and heated to 85° C. in an oil bath for 15 h. The reaction was complete by LCMS and cooled to room temperature then acidified with 1M HCl until the pH=2-3. The resultant solution was extracted using ethyl acetate (2×10 mL). The combined organic layers were washed with water, brine, dried ($Na_2SO_4$), and then concentrated. The crude oil was then purified on a 24 g HP silica gel Gold RediSep column via ISCO (gradient elution: 0-100% ethyl acetate in hexanes), and the pure fractions evaporated and dried in vacuo giving 40 as a yellowish white solid (0.35 g, 89%). MS (ESI, pos.): calc'd for $C_7H_6BrNO_4$, 248.03; found 247.9 and 248.9 isotopes (M+H). $^1$H-NMR (500 MHz; $CDCl_3$): δ10.50 (t, J=0.4 Hz, 1H), 6.94 (s, 1H), 6.71 (s, 1H), 3.97 (s, 3H).

Compound 41: To a stirred solution of 5-bromo-3-methoxy-2-nitrophenol 40 (150 mg, 0.605 mmol, 1.0 eq.) and ammonium acetate (114 mg, 1.814 mmol, 3.0 eq.) in anhydrous THF (3 mL) at room temperature was added Zn dust (593 mg, 9.07 mmol, 15 eq.) and degassed by nitrogen. The mixture was heated to 50° C. in an oil bath for overnight. The reaction was complete by LCMS. The reaction was cooled to room temperature and the crude was filtered through a Celite pad and concentrated. The crude oil was then purified on a 24 g HP silica gel Gold RediSep column via ISCO (gradient elution: 0-20% DCM in methanol), and the pure fractions evaporated and dried in vacuo giving 41 as a brown solid (40 mg, 31%). MS (ESI, pos.): calc'd for $C_7H_8BrNO_2$, 218.05; found 219.9 and 220.9 isotopes (M+H). $^1$H-NMR (500 MHz; $CDCl_3$): δ 6.65 (s, 1H), 6.62 (s, 1H), 3.85 (s, 3H), 1.45 (s, 2H).

Compound 42: Following the general procedure in Example 3, To a stirring solution under argon of rifamycin S (118 mg, 0.169 mmol) in 4 mL of toluene at room temperature was added 2-amino-5-bromo-3-methoxyphenol 41 (37 mg, 0.169 mmol). The mixture solution was stirred for 2 days at room temperature. The mixture was then evaporated to dryness and the dark residue dissolved in 5 mL of ethanol and 30 mg of manganese oxide ($MnO_2$) was added at one portion to the ethanol solution. The sluggish mixture was stirred under argon for 15 h at room temperature. After filtration of insoluble materials using a Celite pad, the filtrate was evaporated under reduced pressure. The dark residue was purified on a 24 g HP silica gel Gold RediSep column via ISCO (gradient elution: 5-95% EA in hexanes). The pure fractions were evaporated and dried in vacuo giving the title compound 42 as a dark reddish solid (70 mg, 47%). MS (ESI, pos.): calc'd for $C_{44}H_{49}BrN_2O_{13}$, 893.78; found 893.7 and 895.7 (M+H), 891.3 and 893.1 (M−H). $^1$H-NMR (500 MHz; $CDCl_3$): δ 7.06 (d, J=9.8 Hz, 1H), 6.00-5.98 (m, 1H), 5.32 (s, 1H), 5.10-5.05 (m, 1H), 5.00-4.96 (m, 1H), 4.13 (s, 4H), 3.11 (s, 3H), 3.03-3.01 (m, 1H), 2.32 (s, 3H), 2.13 (s, 3H), 2.07 (d, J=4.3 Hz, 4H), 1.85 (s, 3H), 1.74 (dtd, J=6.2, 1.7, 1.2 Hz, 1H), 1.67-1.65 (m, 1H), 1.54 (s, 2H), 1.29-1.26 (m, 1H), 0.99-0.97 (m, 3H), 0.85-0.80 (m, 3H), 0.63-0.59 (m, 3H).

Compound 43: 43 was prepared using general procedure as described for 16b: Compound 42 (37 mg, 0.0447 mmol, 1.0 eq.), 2-(dimethylamino)ethan-1-ol (40 mg, 0.447 mmol, 10 eq.), t-BuBrettPhos-Pd-G3-palladacycle (20 mg, 0.0223 mmol, 0.5 eq.), and $K_3PO_4$ (20 mg, 0.091 mmol, 2.0 eq.) to afford the title compound 43 (15.0 mg, 40%). MS: calc'd for $C_{48}H_{59}N_3O_{14}$, 901.40; found 902.3 (M+H), 900.3 (M−H). $^1$H-NMR (500 MHz; DMSO-$d_6$): δ 9.31-9.30 (m, 1H), 6.79-6.76 (m, 1H), 6.70 (d, J=6.2 Hz, 2H), 6.05-6.03 (m, 1H), 5.81-5.80 (m, 2H), 5.25-5.22 (m, 2H), 4.77-4.77 (m, 2H), 4.29 (dt, J=1.9, 1.0 Hz, 2H), 4.21-4.13 (m, 3H), 4.00 (s, 3H), 3.57-3.54 (m, 1H), 3.04 (t, J=0.9 Hz, 4H), 2.96-2.87 (m, 1H), 2.80-2.76 (m, 2H), 2.66 (s, 6H), 2.22 (s, 2H), 2.15 (s, 3H), 2.00 (s, 3H), 1.95 (s, 3H), 1.80-1.78 (m, 1H), 1.66-1.59 (m, 3H), 0.85-0.84 (m, 6H), 0.69-0.66 (m, 6H).

Example 9: Preparation of Compound 45

Rifamycin analog 45 was synthesized from rifamycin S as shown in Scheme 13 below, and as described below.

Scheme 13

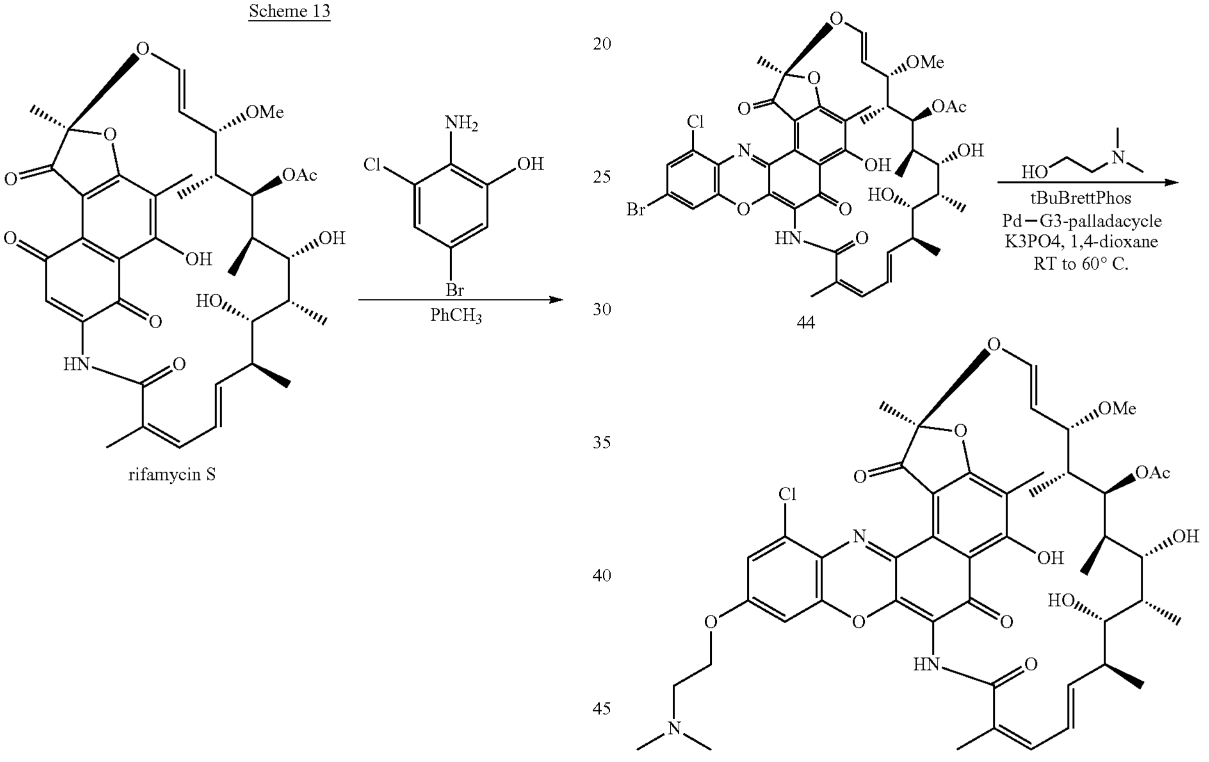

rifamycin S

44

45

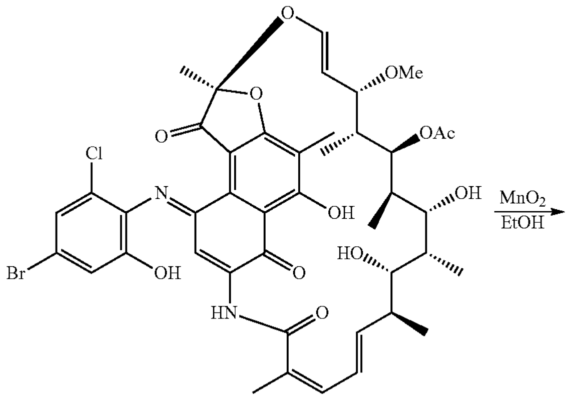

44a

-continued

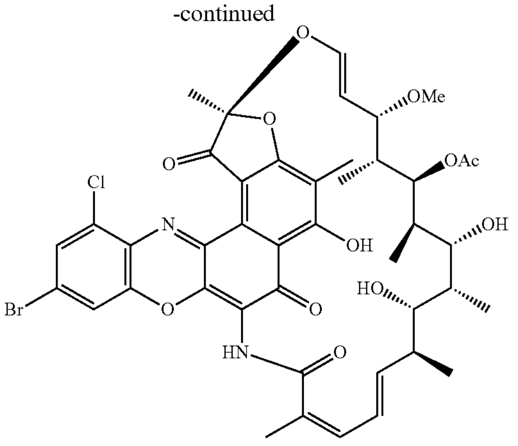

44

Compound 44: Following the general procedure in Example 3, To a stirring solution under argon of rifamycin S (250 mg, 0.359 mmol) in 5 mL of toluene at room temperature was added commercially available 2-amino-5-bromo-3-chlorophenol (80 mg, 0.359 mmol). The mixture solution was stirred overnight at room temperature. The mixture was then evaporated to dryness and the dark reddish residue dissolved in 15 mL of ethanol and 300 mg of manganese oxide ($MnO_2$) was added in one portion to the ethanol solution. The sluggish mixture was stirred under argon for 15 h at room temperature. After filtration of insoluble materials using a Celite pad, the filtrate was evaporated under reduced pressure. The dark residue was purified on a 40 g HP silica gel Gold RediSep column via ISCO (gradient elution: hexanes—95% EA in hexanes). The pure fractions were evaporated and dried in vacuo giving the title compound 44 as a dark reddish solid (161 mg, 50%). MS (ESI, pos.): calc'd for $C_{43}H_{46}BrClN_2O_{12}$, 898.19; found 899.1 (M+H). $^1$H-NMR (500 MHz; $CDCl_3$): δ 13.81 (s, 1H), 7.65 (d, J=1.7 Hz, 1H), 7.44 (s, 1H), 6.24-6.22 (m, 1H), 6.01 (d, J=12.2 Hz, 1H), 5.07-5.05 (m, 1H), 4.99 (dd, J=12.3, 6.8 Hz, 1H), 3.11 (s, 3H), 3.04-3.02 (m, 1H), 2.32 (s, 3H), 2.13 (s, 3H), 2.08 (s, 4H), 1.84 (s, 3H), 1.74-1.71 (m, 1H), 1.71-1.66 (m, 1H), 1.60 (s, 9H), 0.98 (d, J=6.5 Hz, 4H), 0.82-0.81 (m, 4H), 0.63 (d, J=0.5 Hz, 4H).

Compound 45: 45 was prepared using general procedure as described for 16b: Compound 44 (20 mg, 0.0222 mmol, 1.0 eq.), 2-(dimethylamino)ethan-1-ol (20 mg, 0.222 mmol, 10 eq.), t-BuBrettPhos-Pd-G3-palladacycle (9.5 mg, 0.0111 mmol, 0.5 eq.), and $K_3PO_4$ (9.6 mg, 0.045 mmol, 2.0 eq.) to afford the title compound 45 (6.8 mg, 34%). MS: calc'd for $C_{47}H_{56}ClN_3O_{13}$, 905.35; found 906.3 (M+H). $^1$H-NMR (500 MHz; $CD_3OD$): δ 7.30 (d, J=0.4 Hz, 1H), 6.93-6.92 (m, 1H), 6.78-6.76 (m, 1H), 6.39-6.37 (m, 1H), 6.20 (dd, J=12.5, 0.4 Hz, 2H), 5.09-5.07 (m, 1H), 4.58 (dq, J=2.2, 0.6 Hz, 1H), 4.30 (dd, J=9.1, 4.5 Hz, 1H), 4.21 (dtd, J=2.8, 1.4, 0.7 Hz, 1H), 3.04 (d, J=9.5 Hz, 6H), 2.83 (s, 3H), 2.36 (s, 6H), 2.31 (s, 3H), 2.11 (s, 1H), 2.00 (s, 2H), 1.91 (s, 4H), 1.76 (s, 3H), 1.73-1.62 (m, 2H), 1.30 (s, 1H), 0.96 (d, J=5.4 Hz, 6H), 0.88 (d, J=6.4 Hz, 4H), 0.25 (d, J=6.6 Hz, 1H), 0.11 (s, 2H), −0.16-0.19 (m, 2H).

Example 10: Preparation of Compound 48

Rifamycin analog 48 was synthesized from rifamycin S as shown in Scheme 14 below, and as described below.

Scheme 14

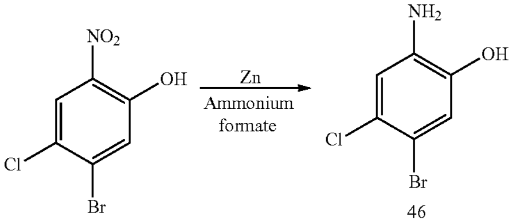

46

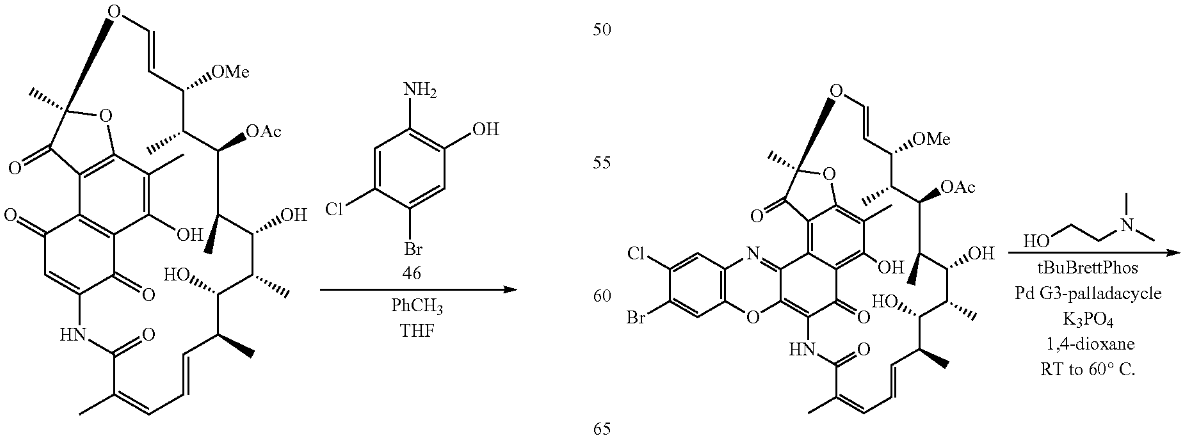

Rifamycin S

47

-continued

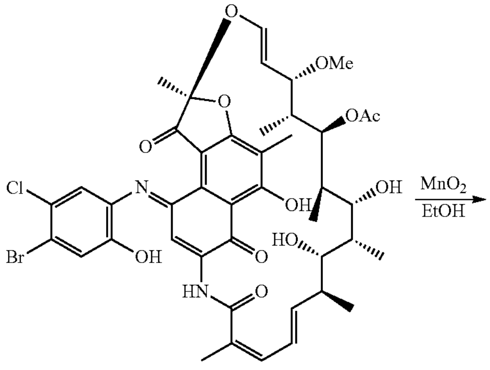

47a

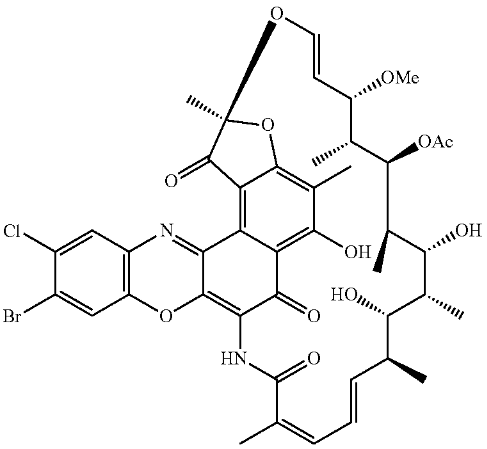

47

-continued

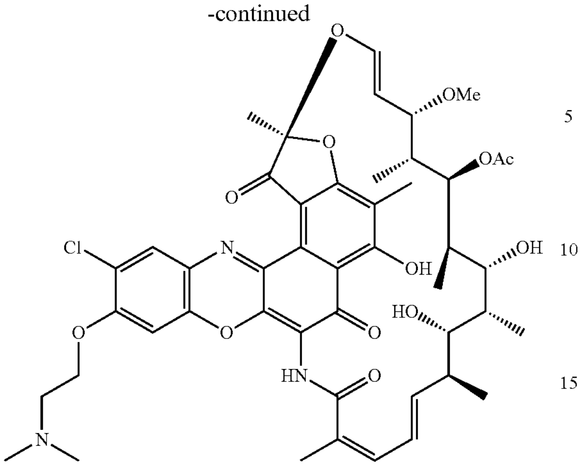

48

Compound 46: To a stirred solution of commercially available 5-bromo-4-chloro-2-nitrophenol (100 mg, 0.396 mmol, 1.0 eq.) and ammonium acetate (75 mg, 1.188 mmol, 3.0 eq.) in anhydrous THF (5 mL) at room temperature was added Zn dust (388 mg, 5.94 mmol, 15 eq.) and degassed by nitrogen. The mixture was heated to 50° C. in an oil bath for 2h. The reaction was complete by LCMS and cooled to room temperature. The crude was filtered through Celite pad and concentrated. The crude oil was then purified on a 24 g HP silica gel Gold RediSep column via ISCO (gradient elution: 0-20% DCM in methanol), and the pure fractions evaporated and dried in vacuo giving 46 as a brown solid (37 mg, 42%). MS (ESI, pos.): calc'd for $C_6H_5BrClNO$, 222.47; found 222.9 and 223.9 isotopes (M+H). $^1$H-NMR (500 MHz; $CD_3OD$): δ 6.89 (s, 1H), 6.81 (s, 1H) $NH_2$ and OH not seen.

Compound 47: Following the general procedure in Example 3, To a stirring solution under argon of rifamycin S (62 mg, 0.0899 mmol) in 1.5 mL of toluene and 0.25 mL of THF at room temperature was added 2-amino-5-bromo-4-chlorophenol 46 (20 mg, 0.0899 mmol). The mixture solution was stirred for 7 days at room temperature. The mixture was then evaporated to dryness and the dark reddish residue dissolved in 10 mL of ethanol and 100 mg of manganese oxide ($MnO_2$) was added at one portion to the ethanol solution. The sluggish mixture was stirred under argon for 15 h at room temperature. After filtration of insoluble materials using a Celite pad, the filtrate was evaporated under reduced pressure. The dark residue was purified on a 40 g HP silica gel Gold RediSep column via ISCO (gradient elution: hexanes—95% EA in hexanes). The pure fractions were evaporated and dried in vacuo giving the title compound 47 as a dark reddish solid (40 mg, 51%). MS (ESI, pos.): calc'd for $C_{43}H_{46}BrClN_2O_{12}$, 898.19; found 899.1 (M+H). $^1$H-NMR (500 MHz; $CDCl_3$): δ 13.87 (s, 1H), 8.11 (s, 1H), 7.67 (s, 1H), 6.32 (s, 1H), 6.01 (d, J=12.4 Hz, 2H), 5.04-5.04 (m, 1H), 4.98 (dd, J=12.2, 6.5 Hz, 2H), 3.11 (s, 6H), 3.03-3.01 (m, 2H), 2.34 (s, 6H), 2.14 (s, 7H), 2.07 (s, 6H), 1.83 (s, 6H), 1.73 (dt, J=6.4, 0.6 Hz, 3H), 1.65-1.56 (m, 17H), 0.99 (d, J=6.2 Hz, 6H), 0.83-0.82 (m, 6H), 0.60 (t, J=0.7 Hz, 5H).

Compound 48: 48 was prepared using general procedure as described for 16b: Compound 47 (20 mg, 0.0222 mmol, 1.0 eq.), 2-(dimethylamino)ethan-1-ol (20 mg, 0.222 mmol, 10 eq.), t-BuBrettPhos-Pd-G3-palladacycle (9.5 mg, 0.0111 mmol, 0.5 eq.), and $K_3PO_4$ (9.6 mg, 0.045 mmol, 2.0 eq.) to afford the title compound 48 (2.8 mg, 12%). MS: calc'd for $C_{47}H_{56}ClN_3O_{13}$, 905.35; found 906.3 (M+H). $^1$H-NMR (500 MHz; $CD_3OD$): δ 8.04 (t, J=0.6 Hz, 1H), 7.15-7.14 (m, 1H), 6.90-6.89 (m, 2H), 6.42-6.41 (m, 2H), 6.22-6.20 (m, 1H), 5.02-4.99 (m, 1H), 4.59 (s, 1H), 4.42-4.41 (m, 1H), 4.24-4.21 (m, 1H), 3.77-3.74 (m, 1H), 3.04-3.02 (m, 1H), 2.94 (d, J=0.4 Hz, 1H), 2.43 (s, 6H), 2.31 (s, 5H), 2.12 (s, 6H), 1.99 (s, 5H), 1.92 (s, 4H), 1.79 (s, 1H), 1.69 (t, J=1.4 Hz, 1H), 1.31 (s, 1H), 0.96 (t, J=0.5 Hz, 6H), 0.85-0.70 (m, 4H), 0.11 (s, 1H), −0.22 (td, J=2.3, 1.2 Hz, 1H).

Example 11: Preparation of Compound 50

Rifamycin analog 50 was synthesized from compound 28 as shown in Scheme 15 below, and as described below.

Scheme 15

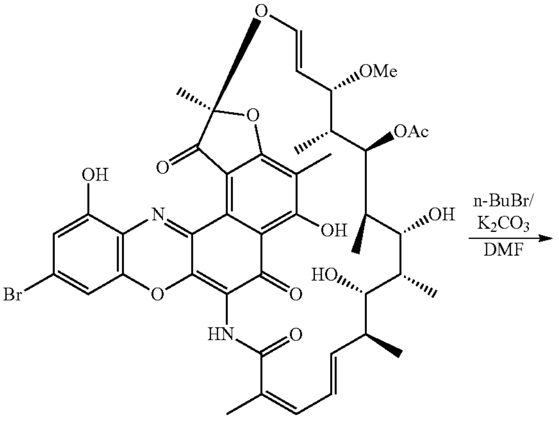

28

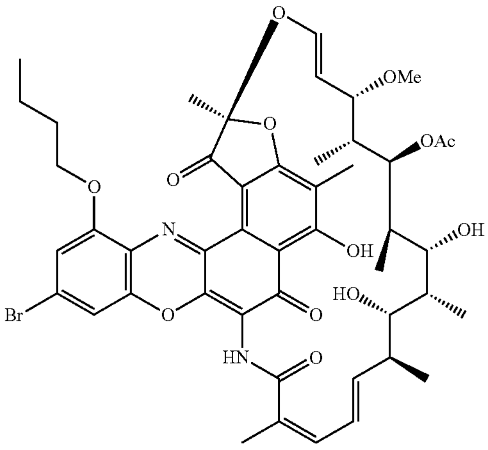

49

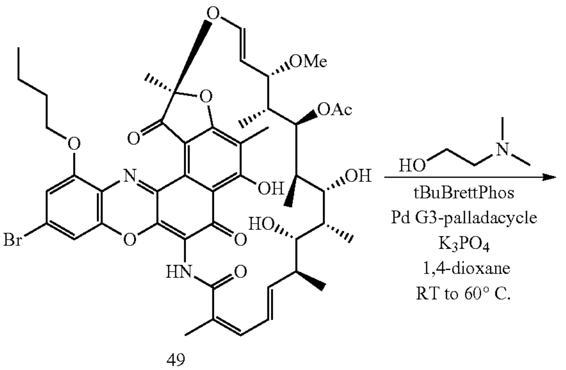

49

-continued

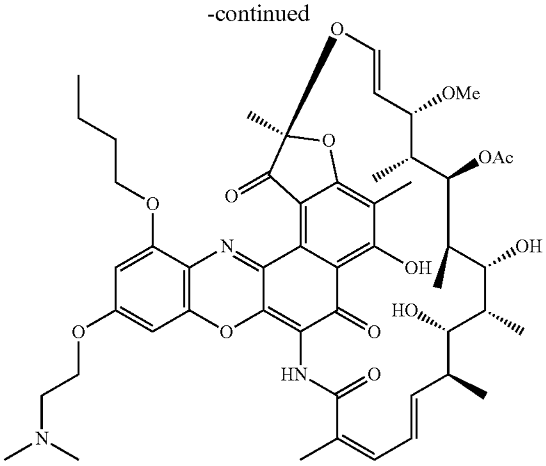

50

Scheme 16

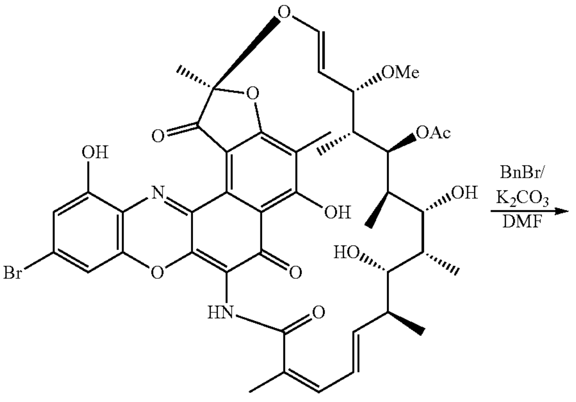

28

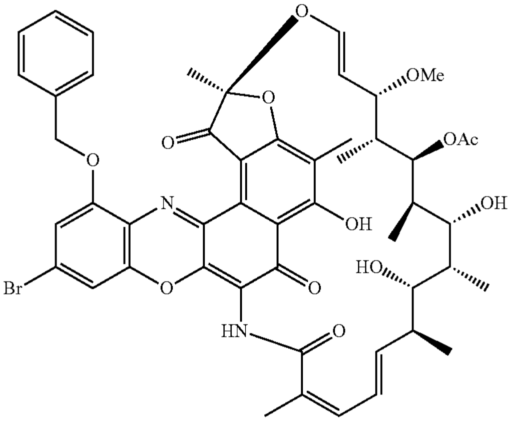

51

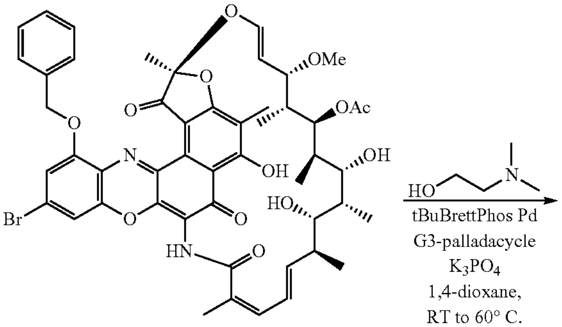

51

Compound 49: To a stirred solution of compound 28 (50 mg, 0.0568 mmol, 1.0 eq.) in 1.5 mL of anhydrous DMF at room temperature was added $K_2CO_3$ (12 mg, 0.0852 mmol, 1.5 eq.) followed by addition of n-BuBr (15.5 mg, 0.1136 mmol, 2.0 eq.) The resulting mixture was refluxed at 50° C. for overnight. The crude product was diluted with acetonitrile/water and purified on an ISCO system by an EZ preparative column (eluents: 10-95% MeCN in water, 0.05% in AcOH). Pure fractions by LC/MS were collected, frozen at dry-ice/acetone bath, and lyophilized for 30 h to afford 34 mg (65%) of 49. MS (ESI, pos.): calc'd for $C_{47}H_{55}BrN_2O_{13}$, 935.85; found 935.2 and 937.2(M+H). $^1$H-NMR (500 MHz; $CDCl_3$): δ 7.48 (s, 2H), 7.13 (s, 1H), 7.07 (s, 2H), 7.02 (s, 1H), 5.92-6.07 (m, 1H), 4.98 (dd, J=6.84, 12.21 Hz, 1H), 4.18-4.25 (m, 2H), 3.11 (s, 3H), 3.02 (br. s., 1H), 2.31 (s, 3H), 2.13 (s, 3H), 2.07 (s, 4H), 1.95-2.03 (m, 2H), 1.80 (s, 4H), 1.74 (br. s., 2H), 1.60-1.71 (m, 2H), 1.50-1.59 (m, 12H), 1.05 (t, J=7.33 Hz, 4H), 0.98 (br. s., 3H), 0.81 (br. s., 2H), 0.62 (br. s., 2H)

Compound 50: 50 was prepared using general procedure as described for 16b: Compound 49 (20 mg, 0.0213 mmol, 1.0 eq.), 2-(dimethylamino)ethan-1-ol (19 mg, 0.213 mmol, 10 eq.), t-BuBrettPhos-Pd-G3-palladacycle (9.1 mg, 0.01065 mmol, 0.5 eq.), and $K_3PO_4$ (9.2 mg, 0.043 mmol, 2.0 eq.) to afford the title compound 50 (6.1 mg, 30%). An ISCO EZ preparative column (Gemini) was used to purify the desired product (eluents: 10-95% MeCN in water, 0.05% in AcOH). MS: calc'd for $C_{51}H_{65}N_3O_{14}$, 943.45; found 944.4 (M+H), 942.3 (M−H). $^1$H-NMR (500 MHz; $CD_3OD$): δ 6.82-6.81 (m, 2H), 6.70 (s, 1H), 6.58-6.55 (m, 1H), 6.38-6.37 (m, 2H), 6.23 (ddd, J=3.0, 1.6, 0.8 Hz, 2H), 5.07 (bs, 2H), 4.59 (s, 6H), 4.29 (t, J=5.3 Hz, 4H), 4.20-4.14 (m, 2H), 3.74-3.71 (m, 2H), 3.03 (s, 6H), 2.83 (d, J=0.3 Hz, 2H), 2.36 (s, 6H), 2.31 (s, 1H), 2.11 (s, 3H), 1.98 (s, 2H), 1.76 (s, 3H), 1.69-1.60 (m, 1H), 1.30 (s, 2H), 1.08 (s, 6H), 0.97-0.91 (m, 4H), 0.11 (s, 3H), −0.21 (dd, J=2.2, 0.9 Hz, 2H).

Example 12: Preparation of Compound 52

Rifamycin analog 52 was synthesized from compound 28 as shown in Scheme 16 below, and as described below.

-continued

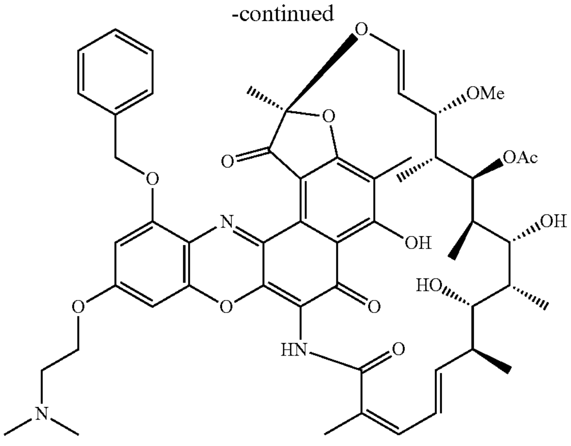

52

Compound 51: To a stirred solution of compound 28 (50 mg, 0.0568 mmol, 1.0 eq.) in 1.5 mL of anhydrous DMF at room temperature was added $K_2CO_3$ (12 mg, 0.0852 mmol, 1.5 eq.) followed by addition of benzyl bromide (19.4 mg, 0.1136 mmol, 2.0 eq.) The resulting mixture was stirred at room temperature overnight. An ISCO system EZ preparative column was used to purify the desired product (eluents: 10-95% MeCN in water, 0.05% in AcOH). Pure fractions by LC/MS were collected, frozen at dry-ice/acetone bath, and lyophilized for 30 h to afford 25 mg (45%) of 51. MS (ESI, pos.): calc'd for $C_{50}H_{53}BrN_2O_{13}$, 969.88; found 969.2 and 971.2 (M+H). $^1$H-NMR (500 MHz; $CDCl_3$): δ 7.68-7.66 (m, 1H), 7.45-7.42 (m, 2H), 7.39-7.37 (m, 2H), 7.19 (dt, J=1.0, 0.5 Hz, 2H), 7.14 (t, J=0.4 Hz, 2H), 5.99 (dd, J=12.2, 0.4 Hz, 1H), 5.44-5.38 (m, 1H), 5.29-5.22 (m, 2H), 5.00-4.96 (m, 2H), 3.10 (s, 3H), 3.03-3.01 (m, 1H), 2.31 (s, 6H), 2.14 (s, 3H), 2.07 (s, 3H), 1.78 (d, J=0.4 Hz, 3H), 1.66-1.64 (m, 3H), 1.54 (s, 3H), 1.27 (s, 3H), 1.00-0.98 (m, 3H), 0.90 (dd, J=8.5, 4.8 Hz, 3H), 0.83 (dddd, J=2.9, 2.1, 1.5, 0.7 Hz, 2H), 0.63-0.61 (m, 1H), 0.14 (s, 1H).

Compound 52: 52 was prepared using general procedure as described for 16b: Compound 51 (26 mg, 0.0268 mmol, 1.0 eq.), 2-(dimethylamino)ethan-1-ol (24 mg, 0.268 mmol, 10 eq.), t-BuBrettPhos-Pd-G3-palladacycle (11.4 mg, 0.0134 mmol, 0.5 eq.), and $K_3PO_4$ (11.5 mg, 0.054 mmol, 2.0 eq.) to afford the title compound 52 (7.0 mg, 27%). An ISCO EZ preparative column (Gemini) was used to purify the desired product (eluents: 10-95% MeCN in water, 0.05% in AcOH). MS: calc'd for $C_{54}H_{63}N_3O_{14}$, 977.43; found 978.4 (M+H), 976.3 (M−H). $^1$H-NMR (500 MHz; $CD_3OD$): δ 7.73 (d, J=7.0 Hz, 2H), 7.43 (d, J=4.3 Hz, 2H), 7.38-7.37 (m, 1H), 6.81 (s, 2H), 6.58 (d, J=0.9 Hz, 1H), 6.42-6.40 (m, 1H), 6.21-6.18 (m, 1H), 6.03 (d, J=12.6 Hz, 1H), 5.41-5.36 (m, 2H), 5.05-5.01 (m, 1H), 4.59 (s, 1H), 4.29 (d, J=5.1 Hz, 1H), 4.18 (dt, J=2.6, 1.3 Hz, 1H), 3.72-3.70 (m, 1H), 3.00 (d, J=9.9 Hz, 4H), 2.83 (s, 2H), 2.37 (s, 7H), 2.29 (s, 3H), 2.11 (s, 3H), 2.03 (d, J=18.5 Hz, 6H), 1.74 (s, 4H), 1.64-1.63 (m, 1H), 1.30 (s, 1H), 0.96-0.90 (m, 10H), 0.11-0.09 (m, 2H), −0.25 (t, J=0.6 Hz, 2H).

Example 13: Preparation of Compound 55

Rifamycin analog 55 was synthesized from Rifamycin S as shown in Scheme 17 below, and as described below.

Scheme 17

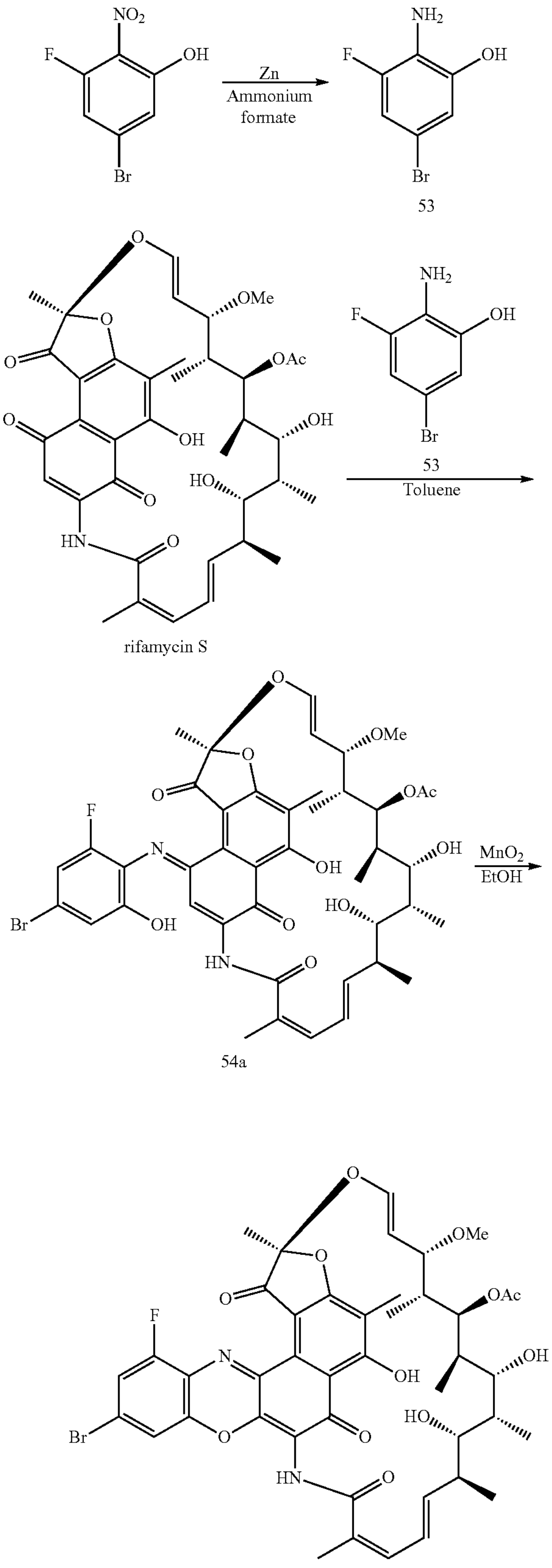

53 rifamycin S

54a

54

-continued

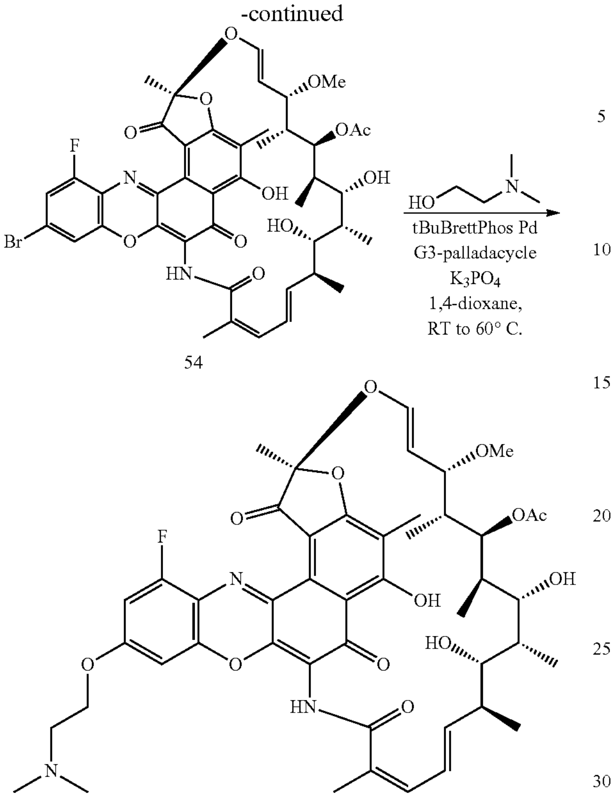

54

55

Compound 53: To a solution of commercially available 5-bromo-3-fluoro-2-nitrophenol (150 mg, 0.635 mmol, 1.0 eq.) and ammonium acetate (120 mg, 1.906 mmol, 3.0 eq.) in anhydrous THE (5 mL) at room temperature, degassed with nitrogen, was added Zn dust (622 mg, 9.52 mmol, 15 eq.). The mixture was heated to 50° C. in an oil bath for 2h. The reaction was complete by LCMS and cooled to room temperature. The crude was filtered through a Celite pad and concentrated. The crude oil was then purified on a 24 g HP silica gel Gold RediSep column via ISCO system (gradient elution: 0-20% DCM in methanol), and the pure fractions evaporated and dried in vacuo giving 53 as a brown solid (67 mg, 52%). MS (ESI, pos.): calc'd for $C_6H_5BrFNO$, 206.01; found 205.9 and 207.9 isotopes (M+H). $^1$H-NMR (500 MHz; $CD_3OD$): δ 6.71-6.67 (m, 2H). $NH_2$ and OH not seen.

Compound 54: Following the general procedure in Example 9, To a stirring solution under argon of rifamycin S (120 mg, 0.172 mmol) in 1.5 mL of toluene at room temperature was added compound 53 (36 mg, 0.172 mmol) to afford the title compound 54 as a dark reddish solid (92 mg, 61%). MS (ESI, pos.): calc'd for $C_{43}H_{46}BrFN_2O_{12}$, 881.75; found 882.1 and 883.2 (M+H), 880.1 and 881.1 (M−H). $^1$H-NMR (500 MHz; DMSO-$d_6$): δ 9.54 (s, 1H), 7.80-7.79 (m, 2H), 6.04-6.01 (m, 1H), 5.74 (s, 1H), 5.22 (s, 2H), 4.80-4.76 (m, 1H), 4.23 (dt, J=1.4, 0.6 Hz, 1H), 3.09-3.02 (m, 5H), 2.78 (td, J=10.0, 1.8 Hz, 1H), 2.16 (s, 3H), 1.99 (s, 4H), 1.95 (s, 4H), 1.65 (s, 3H), 1.60-1.59 (m, 2H), 1.46 (dt, J=1.9, 0.9 Hz, 1H), 0.88-0.85 (m, 2H), 0.83 (t, J=7.8 Hz, 4H), 0.67 (s, 5H).

Compound 55: 55 was prepared using general procedure as described for 16b: Compound 54 (40 mg, 0.0453 mmol, 1.0 eq.), 2-(dimethylamino)ethan-1-ol (40 mg, 0.453 mmol, 10 eq.), t-BuBrettPhos-Pd-G3-palladacycle (19.3 mg, 0.0226 mmol, 0.5 eq.), and $K_3PO_4$ (19.6 mg, 0.0919 mmol, 2.0 eq.) to afford the title compound 55 (16.8 mg, 42%). MS: calc'd for $C_{47}H_{56}FN_3O_{13}$, 889.38; found 890.4 (M+H), 888.3 (M−H). $^1$H-NMR (500 MHz; DMSO-$d_6$): δ 9.43-9.42 (m, 1H), 7.15-7.12 (m, 1H), 7.05-7.03 (m, 1H), 6.04 (dtd, J=4.5, 2.2, 1.1 Hz, 1H), 5.85-5.80 (m, 1H), 5.23 (dtd, J=3.5, 1.8, 1.0 Hz, 1H), 4.79-4.75 (m, 1H), 4.27 (s, 1H), 4.19-4.18 (m, 2H), 3.52-3.51 (m, 1H), 3.09-2.99 (m, 4H), 2.80-2.75 (m, 1H), 2.64-2.63 (m, 2H), 2.15 (s, 9H), 1.99 (s, 3H), 1.94 (s, 2H), 1.64 (s, 2H), 1.48-1.44 (m, 1H), 1.36-1.33 (m, 1H), 1.23-1.22 (m, 1H), 1.14-1.13 (m, 1H), 1.05 (d, J=12.0 Hz, 1H), 0.83 (d, J=6.8 Hz, 6H), 0.68-0.66 (m, 5H).

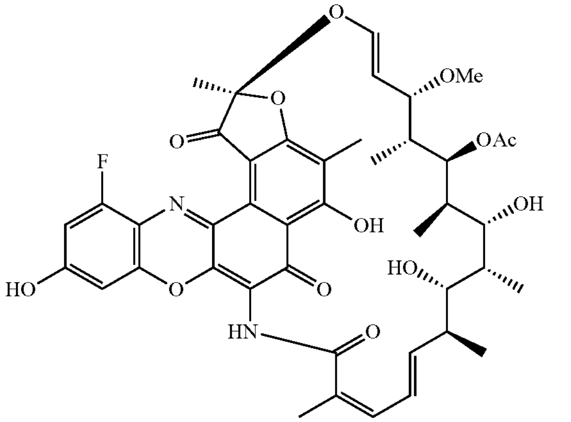 [SMILES: CO[C@H]1/C=C/O[C@@]2(C)Oc3c(C)c(O)c4c(=O)c(c5oc6cc(O)cc(F)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

Compound 55a: 55a was the byproduct for the C—O cross coupling reaction starting with compound 54. MS: calc'd for $C_{43}H_{47}N_2O_{13}$, 818.3; found 819.3 (M+H), 817.2 (M−H). $^1$H NMR (500 MHz; DMSO-$d_6$): δ 9.31 (s, 1H), 5.82 (s, 2H), 4.76 (s, 2H), 4.13 (br. s., 1H), 3.52 (d, J=5.86 Hz, 1H), 3.08 (br. s., 2H), 3.02 (br. s., 3H), 2.97 (s, 1H), 2.88 (s, 1H), 2.77 (br. s., 2H), 2.72 (s, 1H), 2.52 (d, J=8.79 Hz, 1H), 2.19 (br. s., 1H), 2.14 (br. s., 3H), 1.92-2.01 (m, 7H), 1.90 (s, 1H), 1.64 (br. s., 3H), 1.58 (br. s., 2H), 1.22 (s, 1H), 0.72-0.95 (m, 6H), 0.67 (br. s., 3H), 0.06 (s, 2H).

Example 14: Preparation of Compounds 60 and 61

Rifamycin analogs 60 and 61 were synthesized from Rifamycin S as shown in Scheme 18 below, and as described below.

Scheme 18

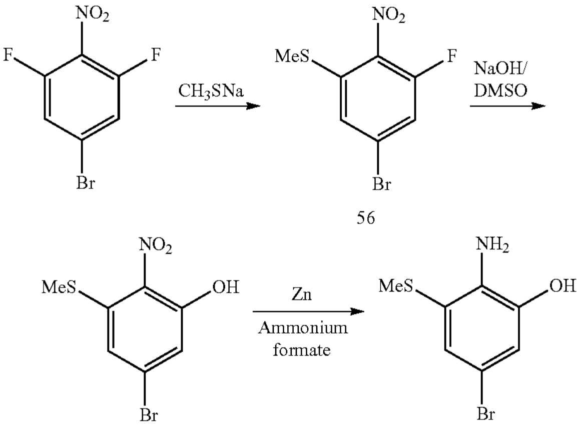

56

57

58

-continued

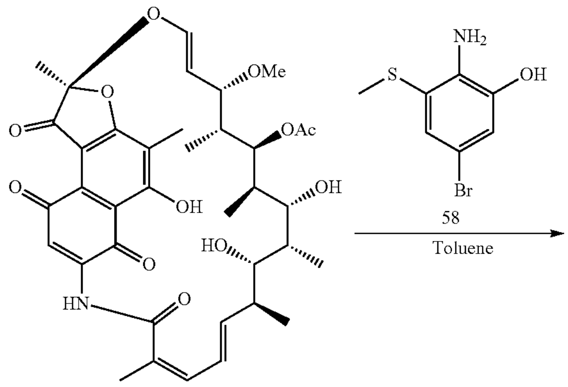

rifamycin S

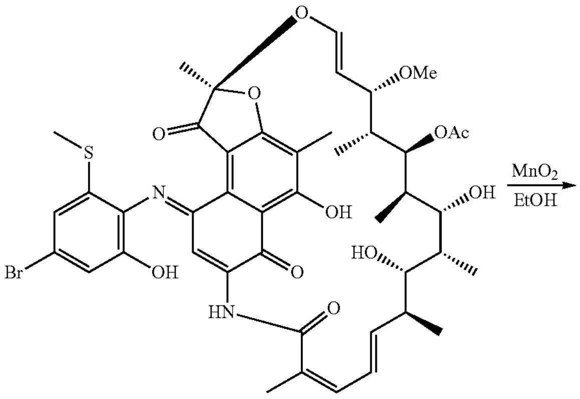

59a

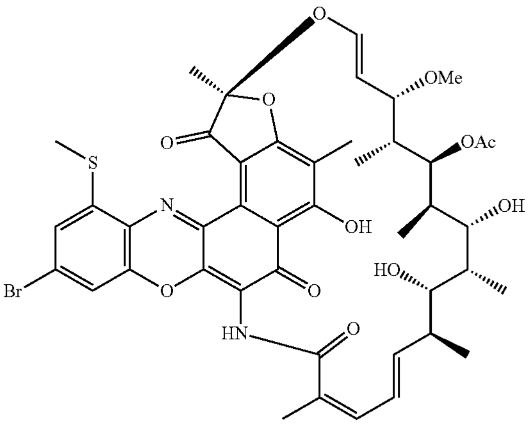

59

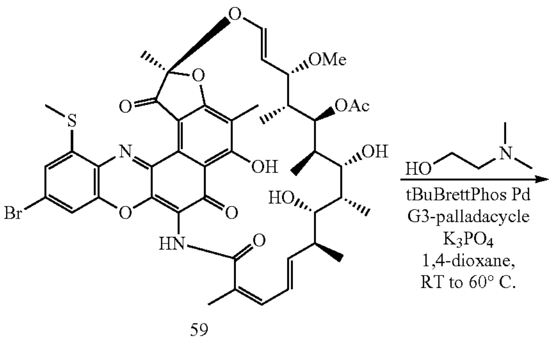

59

-continued

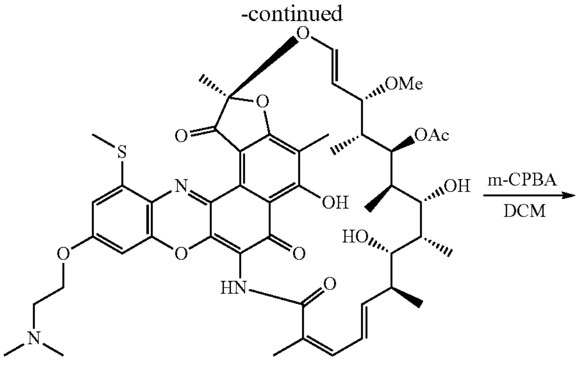

60

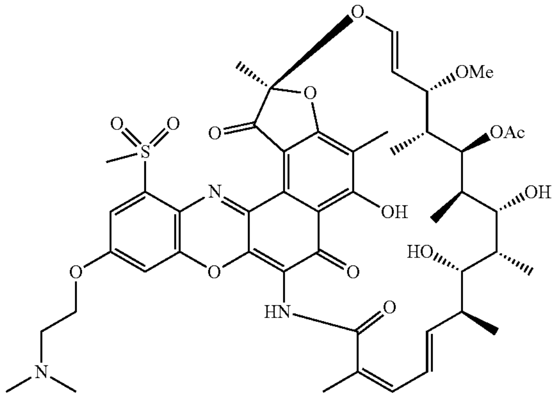

61

Compound 56: To a stirred solution of 5-bromo-1,3-difluoro-2-nitrobenzene (1.0 g, 4.2 mmol, 1.0 eq.) in 7.5 mL of DMF in an ice-bath was added $CH_3SNa$ (320 mg, 4.6 mmol, 1.1 eq.) in 2.5 mL of water. The resulting mixture was stirred at room temperature for 1 h. The yellow suspension was diluted with water (5 mL) and filtered to obtain yellow solid (0.91g) with an impurity of di-sulfide byproducts. MS (ESI, pos.): calc'd for $C_7H_5BrFNO_2S$, 266.08; found 299.1 (M+Na).

Compound 57: The crude 56 (900 mg) in DMSO (10 mL) was treated with 1M NaOH (6 mL, 6 mmol) and heated to 85° C. in oil bath for 1.5 h. The reaction was complete by LCMS and cooled to room temperature. The reaction was acidified with 1M HCl until the pH=2-3 and the resultant solution was extracted using ethyl acetate (2×10 mL). The combined organic layers were washed with water, brine, dried ($Na_2SO_4$), and then concentrated. The crude product was then purified on a 24 g HP silica gel Gold RediSep column via ISCO system (gradient elution: 0-100% ethyl acetate in hexanes), and the pure fractions evaporated and dried in vacuo giving 57 as a yellowish white solid (0.51 g, 46%). MS (ESI, pos.): calc'd for $C_7H6BrNO_3S$, 264.09; found 263.9 and 262.9 isotopes (M−H). $^1H$-NMR (500 MHz; $CDCl_3$): δ 11.40 (s, 1H), 7.10 (dd, J=2.0, 1.1 Hz, 1H), 6.91 (d, J=1.1 Hz, 1H), 6.91 (d, J=1.1 Hz, 1H), 2.48 (s, 3H).

Compound 58: To a solution of compound 57 (200 mg, 0.757 mmol, 1.0 eq.) and ammonium acetate (143 mg, 2.271 mmol, 3.0 eq.) in anhydrous THF (7 mL) at room temperature was added Zn dust (495 mg, 7.57 mmol, 10 eq.) and degassed by nitrogen. The mixture was heated to 50° C. in an oil bath for 2h. The reaction was complete by LCMS and cooled to room temperature. The crude was filtered through a Celite pad and concentrated. The crude was then purified on a 24 g HP silica gel Gold RediSep column via ISCO system (gradient elution: 0-20% DCM in methanol), and the pure fractions evaporated and dried in vacuo giving 58 as a pale brown solid (120 mg, 68%). MS (ESI, pos.): calc'd for $C_7H_8BrNOS$, 234.11; found 235.9 and 236.9 isotopes (M+H), 232.9 and 231.9 isotopes (M−H). $^1$H-NMR (300 MHz; $CDCl_3$): δ 7.09 (d, J=2.0 Hz, 1H), 6.84 (d, J=2.1 Hz, 1H), 5.07-5.06 (m, 1H), 4.15-4.09 (m, 2H), 2.42 (s, 3H).

Compound 59: Following the general procedure in Example 9, to a stirred solution under argon of rifamycin S (267 mg, 0.384 mmol) in 5 mL of toluene at room temperature was added compound 58 (90 mg, 0.384 mmol). After 2 days, the reaction was concentrated in vacuo to remove toluene, dissolved in EtOH (10 mL) and $MnO_2$ (30 mg) was added. After stirring for 1 day, the reaction was concentrated in vacuo. The crude was purified on a 40 g HP silica gel Gold RediSep column via ISCO system (gradient elution: 0-100% ethyl acetate in hexanes) to afford the title compound 59 as a dark reddish solid (181 mg, 52%). MS (ESI, pos.): calc'd for $C_{44}H_{49}BrN_2O_{12}S$, 909.84; found 910.2 and 911.2 (M+H), 908.1 and 907.1 (M−H). $^1$H-NMR (500 MHz; $CD_3OD$): δ 7.35 (s, 1H), 7.25-7.23 (m, 1H), 6.74 (dt, J=1.7, 0.9 Hz, 1H), 6.37-6.35 (m, 1H), 6.26-6.22 (m, 2H), 5.20 (ddt, J=7.1, 2.9, 1.1 Hz, 1H), 5.09-5.08 (m, 1H), 3.70-3.68 (m,), 3.05-3.03 (m, 4H), 2.57 (s, 3H), 2.30 (s, 3H), 2.09 (s, 3H), 1.99 (s, 3H), 1.75 (s, 3H), 1.67-1.64 (m, 1H), 0.94 (d, J=6.9 Hz, 3H), 0.87-0.86 (m, 3H), 0.07-0.06 (m, 2H), −0.17-0.18 (m, 1H).

Compound 60: 60 was prepared using general procedure as described for 16b: Compound 59 (40 mg, 0.044 mmol, 1.0 eq.), 2-(dimethylamino)ethan-1-ol (40 mg, 0.439 mmol, 10 eq.), t-BuBrettPhos-Pd-G3-palladacycle (19 mg, 0.022 mmol, 0.5 eq.), and $K_3PO_4$ (19 mg, 0.089 mmol, 2.0 eq.) to afford the title compound 60 (22 mg, 55%). MS: calc'd for $C_{48}H_{59}N_3O_{13}S$, 917.38; found 918.4 (M+H), 916.3 (M−H). $^1$H-NMR (500 MHz; $CD_3OD$): δ 6.85-6.81 (m, 2H), 6.68-6.67 (m, 1H), 6.41-6.39 (m, 1H), 6.27 (dt, J=1.5, 0.7 Hz, 1H), 6.19-6.16 (m, 1H), 5.25-5.22 (m, 1H), 5.03-5.02 (m, 1H), 4.30 (t, J=5.1 Hz, 1H), 4.19-4.17 (m, 1H), 3.68 (ddd, J=5.5, 2.2, 1.0 Hz, 1H), 3.48-3.44 (m, 1H), 3.02 (d, J=8.9 Hz, 6H), 2.81 (d, J=4.9 Hz, 3H), 2.56 (s, 3H), 2.43-2.37 (m, 6H), 2.29 (s, 4H), 2.14-2.04 (m, 3H), 1.98 (s, 3H), 1.79-1.71 (m, 3H), 1.63-1.59 (m, 2H), 1.25-1.22 (m, 2H), 1.08-1.05 (m, 2H), 0.94 (d, J=7.0 Hz, 6H), 0.89-0.87 (m, 3H), 0.05-0.03 (m, 2H), −0.24 (ddt, J=2.8, 2.2, 1.4 Hz, 2H).

Compound 61: To a stirring solution of compound 60 (12 mg, 0.013 mmol) in 3 mL of anhydrous DCM in an ice-bath was added m-CPBA (6.8 mg, 0.039 mmol). The resulting solution was allowed to warm to room temperature for 3h to afford the title compound 61. The crude was concentrated and purified by ISCO system EZ preparative HPLC column (Gemini, 5 μm, 150 mm×30 mm, eluents: 10-95% MeCN in water, 0.05% AcOH). Pure fractions were collected, frozen in a dry-ice/acetone bath, and dried by lyophilizer for 30 h to afford 6.5 mg (52%) of 61 as a red purple solid. MS (ESI, pos.): calc'd for $C_{48}H_{59}N_3O_{15}S$, 949.37; found 950.37 (M+H), 948.2 (M−H). $^1$H-NMR (500 MHz; $CD_3OD$): δ 7.94-7.85 (m, 1H), 7.59 (d, J=0.7 Hz, 1H), 7.42 (d, J=7.9 Hz, 1H), 7.37 (dd, J=7.2, 0.6 Hz, 1H), 7.18-7.15 (m, 1H), 6.85-6.81 (m, 1H), 6.41-6.36 (m, 1H), 6.23-6.21 (m, 1H), 5.11-5.08 (m, 1H), 4.74-4.72 (m, 2H), 3.83-3.81 (m, 4H), 3.14-3.06 (m, 2H), 3.03 (dd, J=10.2, 2.1 Hz, 6H), 2.33 (s, 6H), 2.11 (d, J=5.2 Hz, 4H), 2.04 (s, 3H), 1.98 (s, 3H), 1.77 (d, J=10.6 Hz, 2H), 1.70-1.65 (m, 1H), 1.29 (s, 1H), 0.94 (d, J=6.9 Hz, 6H), 0.87-0.86 (m, 3H), 0.10 (d, J=2.8 Hz, 3H), 0.05-0.02 (m, 2H), −0.17-0.19 (m, 2H).

Example 15: Preparation of Compound 68

Rifamycin analog 68 was synthesized from Rifamycin S as shown in Scheme 19 below, and as described below.

Scheme 19

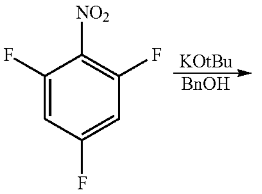

-continued
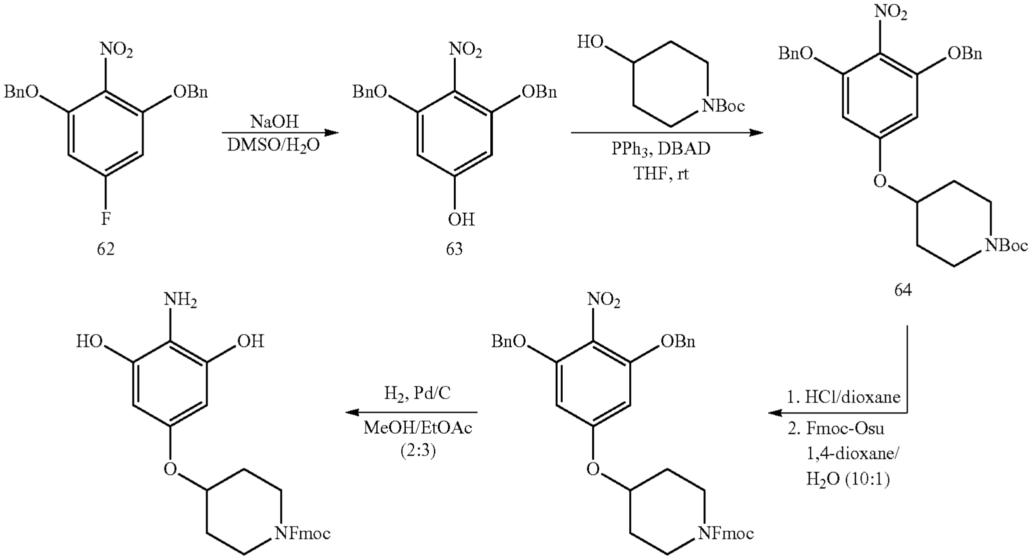
62 63 64
66 65
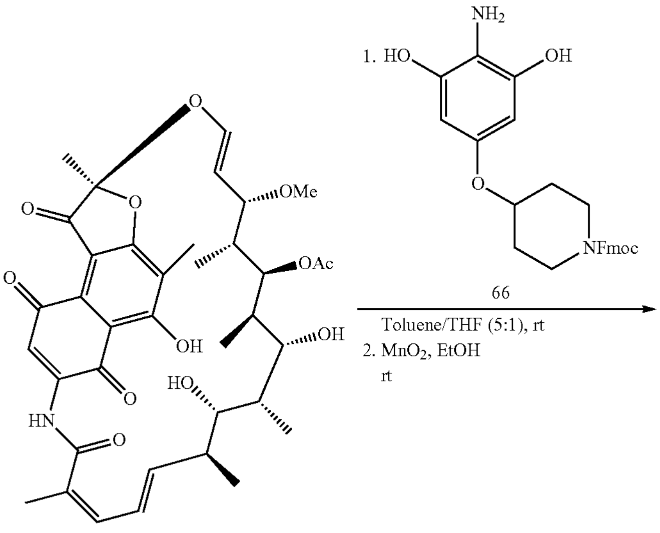
rifamycin S
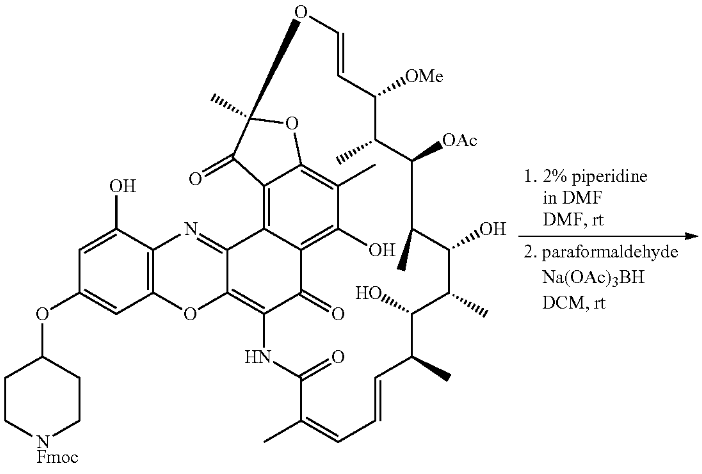
67

-continued

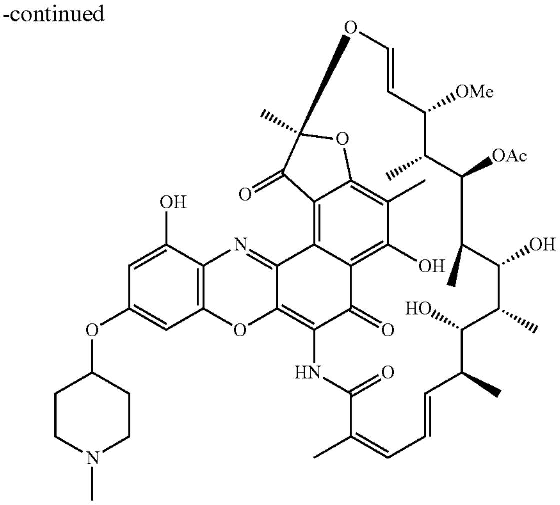

68

Compound 62: To a stirred solution of 1,3,5-trifluoro-2-nitrobenzene (1.0 g, 5.65 mmol, 1.0 eq.) in 5 mL of anhydrous THF in an ice-bath was dropwise added a solution of benzyl alcohol (1.34 g, 12.42 mmol, 2.2 eq.) in 7 mL of THF, which was then treated with a solution of KO$^t$Bu (12 mL, 11.86 mmol, 2.1 eq.) in THF under Argon. The resulting mixture was stirred at room temperature for 4h. The resultant solution was extracted using ethyl acetate (2×40 mL). The combined organic layers were washed with water, brine, dried ($Na_2SO_4$), and then concentrated. The crude product was recrystallized by THF/ethanol to afford an off-white solid of compound 62 (1.63 g, 82%). MS (ESI, pos.): calc'd for $C_{20}H_{16}FNO_4$, 353.35; found 376.1 (M+Na). $^1$H-NMR (500 MHz; $CDCl_3$): δ 7.40-7.35 (m, 10H), 6.40 (d, J=10.1 Hz, 2H), 5.16 (s, 4H).

Compound 63: Compound 62 (1.4g, 3.96 mmol) in DMSO (7 mL) was treated with 2M NaOH (5 mL, 10 mmol) and heated to 85° C. in oil bath overnight. The reaction was complete by LCMS and cooled to room temperature. The reaction was acidified with 1M HCl until the pH=2-3 and the resultant solution was extracted using ethyl acetate (2×30 mL). The combined organic layers were washed with water, brine, dried ($Na_2SO_4$), and then concentrated. The crude product was then purified on a 80 g HP silica gel Gold RediSep column via ISCO system (gradient elution: 0-100% ethyl acetate in hexanes), and the pure fractions evaporated and dried in vacuo giving 63 as a yellow solid (1.29 g, 82%). MS (ESI, pos.): calc'd for $C_{20}H_{17}NO_5$, 351.11; found 374.1 (M+H) and 350.1 (M−H). $^1$H-NMR (300 MHz; $CDCl_3$): δ 7.40-7.35 (m, 10H), 6.20 (d, J=10.1 Hz, 2H), 5.15 (s, 4H).

Compound 64: The title compound was prepared using the same method reported in Example 2. To a stirred solution under argon of compound 63 (200 mg, 0.569 mmol) in THF (5 mL) at room temperature were added BOC-piperidin-4-ol (115 mg, 0.569 mmol) and $PPh_3$ (224 mg, 0.853 mmol) followed by a dropwise addition of DBAD (157 mg, 0.682 mmol) in THE (2 mL). After stirring overnight, the mixture was evaporated to dryness and the residue was purified on a 40 g HP silica gel Gold RediSep column via ISCO system (gradient elution: 0-100% ethyl acetate in hexanes), and the pure fractions evaporated and dried in vacuo giving the title compound 64 as an off-white solid (285 mg, 93%). MS: calc'd for $C_{30}H_{34}N_2O_7$, 534.24; found 557.2 (M+Na). $^1$H-NMR (500 MHz; $CDCl_3$): δ 7.39 (d, J=4.3 Hz, 6H), 7.34 (d, J=4.7 Hz, 4H), 6.14 (s, 2H), 5.15 (s, 4H), 4.29 (dd, J=3.6, 3.0 Hz, 1H), 3.67-3.63 (m, 2H), 3.28-3.26 (m, 2H), 1.79-1.76 (m, 2H), 1.63-1.56 (m, 2H), 1.49 (d, J=2.0 Hz, 9H.

Compound 65: To a solution of compound 64 (285 mg, 0.54 mmol) in 1,4-dioxane (2.0 mL) was added 4 M HCl in 1,4-dioxane (1.4 mL). After stirring for 15 h an in-process aliquot indicated the reaction was complete. To the solution was added diethyl ether (50 mL), then the mixture was stirred vigorously for 1 h until a white precipitate formed. The solid was filtered and washed with ether to afford the HCl salt of corresponding amine, which was used in the next step instantly without further purification. MS: calc'd for $C_{25}H_{26}N_2O_5$, 434.18; found 435.2 (M+H).

To the solution of HCl salt in 1,4-dioxane/water (v/v, 1:1, 6 mL) was added $NaHCO_3$ (182 mg, 2.17 mmol, 4.0 eq.) followed by addition of Fmoc-OSu (219 mg, 0.65 mmol, 1.2 eq.). After stirring for 5 h an in-process LC/MS analysis indicated the reaction was complete. The reaction mixture was treated with water (5 mL) and extracted with EtOAc (3×15 mL). The combined organic layers were then treated with brine (10 mL), dried ($Na_2SO_4$) and concentrated in vacuo. The crude compound was purified on a 24g HP silica gel Gold RediSep column via ISCO system (gradient elution: 0-100% ethyl acetate in hexanes), and the pure fractions evaporated to afford off-white foam (250 mg, 70%). MS: calc'd for $C_{40}H_{36}N_2O_7$, 656.25; found 657.2 (M+H), 689.3 (M+Na). $^1$H-NMR (500 MHz; $CDCl_3$): δ 7.79 (d, J=7.5 Hz, 2H), 7.59 (d, J=7.4 Hz, 2H), 7.40 (quintet, J=5.6

Hz, 10H), 7.34 (t, J=6.9 Hz, 4H), 6.13 (s, 2H), 5.15 (s, 4H), 4.48-4.47 (m, 2H), 4.31-4.30 (m, 1H), 4.26 (t, J=6.5 Hz, 1H), 3.63 (dddt, J=5.1, 2.7, 1.7, 0.9 Hz, 2H), 3.35-3.32 (m, 2H), 1.74-1.72 (m, 2H), 1.62-1.58 (m, 2H).

Compound 66: To a solution of compound 65 (220 mg, 0.304 mmol) in 5 mL of methanol/EtOAc (2:3), degassed with argon, was added 28 mg of 10% Pd/C. The mixture was further degassed with argon and connected to a hydrogen balloon. After 2 h, analysis by LC/MS from an in-process aliquot indicated the reaction was complete. The mixture was filtered through Celite, washed with MeOH (2×10 mL) and EtOAc (10 mL) and concentrated to afford 130 mg of compound 66 (70% pure by LC/MS) as yellowish oil which was used in the next step instantly without further purification. MS: calc'd for $C_{26}H_{26}N_2O_5$, 446.1; found 447.1 (M+H).

Compound 67: To a round-bottom flask with hydroxyaniline 66 (130 mg, 0.204 mmol, 70% pure), was added THE (1 mL) and sonicated for 1 min. Then rifamycin S (135 mg, 0.194 mmol) and toluene (5 mL) were added and the reaction mixture was sonicated for 2 min to dissolve the dark yellow solid, sealed via rubber septum, purged with argon, and the reaction stirred vigorously at ambient temperature. After 10 days, the reaction was concentrated in vacuo to remove toluene/THF, dissolved in EtOH (10 mL) and $MnO_2$ (70 mg, 0.805 mmol) was added. After stirring for 4 days, the reaction was concentrated in vacuo and purified by chromatography on a 24 g HP silica gel Gold RediSep column via ISCO system (gradient elution: 0-50% MeOH/DCM). The relatively pure fractions were evaporated and dried in vacuo giving the title compound 67 as a dark reddish solid (120 mg, 38%). Compound 67 did not ionize in the LCMS.

Compound 68: To a stirred solution of crude compound 67 (120 mg, 0.041 mmol, 38% pure) under argon in DMF (2 mL), was treated with a solution of piperidine (0.5 mL, 2% in DMF) and the reaction was stirred at ambient temperature. After 1 h, the reaction was purified directly on a 50 g C18 RediSep Gold column via ISCO system (gradient elution: 0-100% MeCN in water, 0.05% acetic acid in both, over 30 min). The product-containing fractions were combined, frozen on dry ice, and lyophilized overnight giving the Fmoc deprotected product as dark reddish solid (9 mg, 25%). MS: calc'd for $C_{48}H_{57}N_3O_{14}$, 899.4; found 900.4 (M+H).

To a stirred solution of the product (7 mg, 0.0078 mmol) under argon in DCM (2 mL), was added paraformaldehyde (3.5 mg, 0.1167 mmol) and $Na(OAc)_3BH$ (6.6 mg, 0.0312 mmol) at ambient temperature. After 4h, another portion of paraformaldehyde (3.5 mg, 0.1167 mmol) and $Na(OAc)_3BH$ (6.0 mg, 0.0283 mmol) was added to the reaction mixture. After 1 h, the reaction was filtered through Celite, washed with MeOH (2×10 mL), concentrated and purified directly on a 15.5 g C18 RediSep Gold column via ISCO system (gradient elution: 0-100% MeCN in water, 0.05% acetic acid in both, over 30 min). The product-containing fractions were combined, frozen on dry ice, and lyophilized overnight giving the title compound 68. The compound was re-purified by EZ preparative HPLC column (Gemini, 5 μm, 150 mm×30 mm, eluents: 10-95% MeCN in water, 0.05% AcOH). Pure fractions were combined, frozen on dry ice/Acetone, and lyophilized overnight giving the title compound 68 as dark reddish solid. (2 mg, 28%). MS: calc'd for $C_{49}H_{59}N_3O_{14}$, 913.4; found 914.4 (M+H). $^1$H-NMR (500 MHz; $CD_3OD$): δ 6.68 (br. s., 1H), 6.47-6.58 (m, 1H), 6.32-6.46 (m, 1H), 6.13-6.32 (m, 1H), 4.64-4.75 (m, 1H), 4.59 (br. s., 1H), 3.46 (s, 1H), 3.18 (br. s., 1H), 2.91-3.12 (m, 4H), 2.76 (br. s., 2H), 2.51 (br. s., 2H), 2.35-2.42 (m, 3H), 2.31 (br. s., 2H), 2.22 (br. s., 2H), 2.04-2.17 (m, 3H), 1.97-2.04 (m, 3H), 1.94 (s, 6H), 1.90 (br. s., 2H), 1.72-1.83 (m, 6H), 1.55-1.71 (m, 3H), 1.39-1.52 (m, 3H), 1.25-1.37 (m, 3H), 0.76-1.06 (m, 4H), 0.02 (br. s., 2H), −0.25 (br. s., 3H).

Example 16: Preparation of Compound 71

Rifamycin analog 71 was synthesized from Rifamycin S as shown in Scheme 20 below, and as described below.

Scheme 20

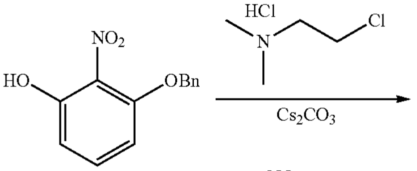

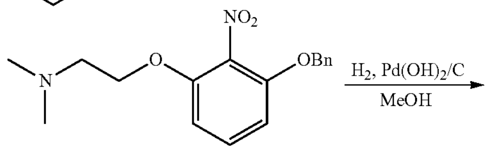

69

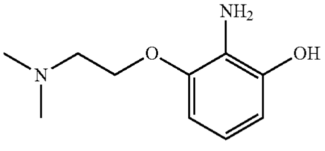

70

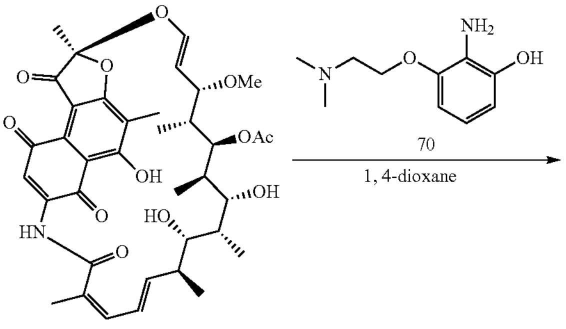

rifamycin S

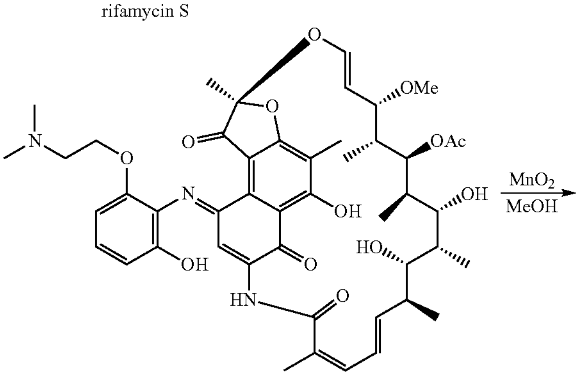

71a

-continued

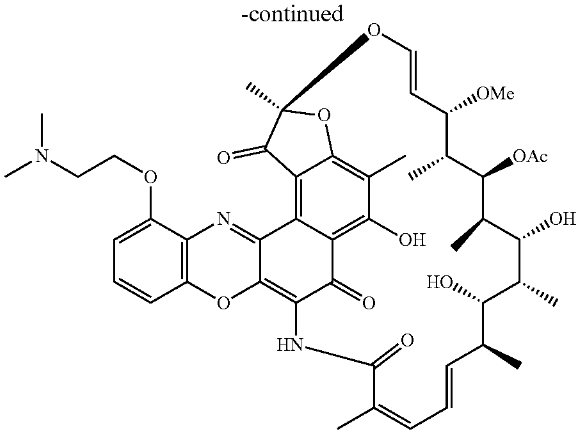

71

Compound 69: To a stirred mixture of 3-(benzyloxy)-2-nitrophenol (500 mg, 2.03 mmol, 1.0 eq.), 2-chloro-N,N-dimethylethan-1-amine HCl salt (380 mg, 2.65 mmol, 1.3 eq.), and $Cs_2CO_3$ (1.65 g, 5.07 mmol, 2.5 eq.) was added anhydrous acetone (7 mL) and heated at 50° C. overnight. The reaction was complete by LC/MS and cooled to room temperature. The crude was filtered through a Celite pad and concentrated. The crude was then purified on a 40 g HP silica gel Gold RediSep column via ISCO (gradient elution: 0-20% DCM in methanol), and the pure fractions evaporated and dried in vacuo giving 69 as a dark oil (428 mg, 67%). MS (ESI, pos.): calc'd for $C_{17}H_{20}N_2O_4$, 316.36; found 317.2 (M+H). $^1$H-NMR (500 MHz; $CDCl_3$): δ 7.39-7.29 (m, 6H), 6.65 (t, J=8.5 Hz, 2H), 5.18 (s, 2H), 4.17 (t, J=5.9 Hz, 2H), 2.75 (t, J=5.9 Hz, 2H), 2.33 (s, 6H).

Compound 70: To a stirred solution, under argon, of compound 69 (185 mg, 0.585 mmol) in methanol (3 mL) was added 37 mg of 20% $Pd(OH)_2/C$ (contains ~50% water). The mixture was further degassed with argon and connected to a hydrogen balloon. After 2 h, analysis by LC/MS from an in-process aliquot indicated the reaction was complete. The mixture was filtered through Celite and concentrated to afford 110 mg of the title compound 70 (85% pure by LC/MS) as dark yellow oil, which was used in the next step instantly without further purification. MS: calc'd for $C_{10}H_{16}N_2O_2$, 196.1; found 197.1 (M+H).

Compound 71: To a round-bottom flask with hydroxyaniline 70 (110 mg, 0.476 mmol, 85% pure), were added 1,4-dioxane (6.8 mL) and rifamycin S (663 mg, 0.953 mmol). The reaction mixture was sealed via rubber septum, purged with argon, and the reaction stirred vigorously at ambient temperature. After 7 days, the reaction was concentrated in vacuo, dissolved in MeOH (10 mL) and $MnO_2$ (104 mg, 1.191 mmol) was added. After stirring for 4 weeks, the reaction was filtered through Celite, washed with MeOH (2×20 mL) concentrated in vacuo and purified by chromatography on a 40 g HP silica gel Gold RediSep column via ISCO system (gradient elution: 0-10% then 10-50% MeOH/DCM). The pure fractions were evaporated and dried in vacuo. The concentrated fractions were dissolved in MeCN/$H_2O$ (1:1), frozen on dry ice/Acetone, and lyophilized overnight to give the title compound 71 as a dark reddish solid (48 mg, 12%). MS (ESI, pos.): calc'd for $C_{47}H_{57}N_3O_{13}$, 871.4; found, 872.4 (M+H). $^1$H-NMR (500 MHz; DMSO-$d_6$): δ 9.37 (s, 1H), 7.65 (t, J=8.55 Hz, 1H), 7.15 (d, J=8.30 Hz, 1H), 5.23 (br. s., 1H), 4.33 (br. s., 2H), 4.28 (br. s., 1H), 3.13 (br. s., 1H), 3.01 (br. s., 4H), 2.95 (br. s., 1H), 2.91 (br. s., 3H), 2.78 (t, J=9.28 Hz, 1H), 2.31 (br. s., 9H), 2.17 (br. s., 4H), 1.98 (s, 5H), 1.94 (br. s., 4H), 1.67 (br. s., 3H), 1.59 (br. s., 1H), 0.80-0.93 (m, 8H), 0.78 (br. s., 1H), 0.67 (br. s., 6H).

Example 17: Preparation of Compound 72

Rifamycin analog 72 was synthesized from compound 15 as shown in Scheme 21 below, and as described below.

Scheme 21

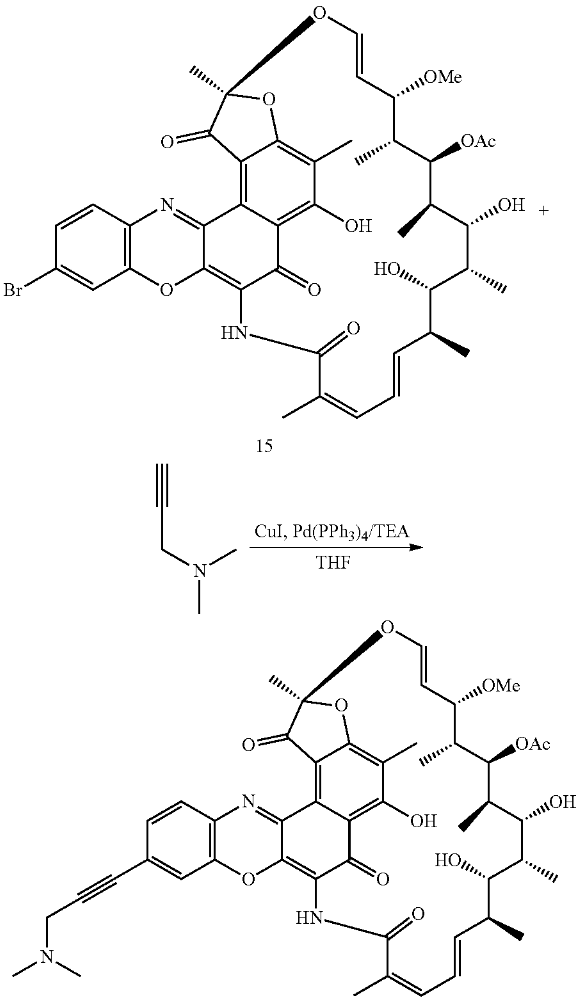

Compound 72: The title compound was prepared using a Sonogashira coupling reaction. A mixture of compound 15 (100 mg, 0.115 mmol, 1.0 eq.), N,N-dimethylprop-2-yn-1-amine (19 μL, 0.173 mmol, 1.5 eq.), CuI (1.1 mg, 0.00575 mmol, 0.05 eq.), $Pd(PPh_3)_4$(3.3 mg, 0.00287 mmol, 0.025 eq.), and triethylamine (64 μL, 0.46 mmol, 4.0 eq.) in anhydrous THF (3 mL), degassed, at room temperature, was stirred overnight. The progress of the reaction was monitored by LC/MS and additional catalyst (10 mg) was added. The mixture was heated to 40° C. in an oil bath for overnight. The reaction was complete by LC/MS. The crude was filtered through a Celite pad and concentrated. The crude was then purified by a C18 50g column followed by another purification by ISCO EZ preparative HPLC column (Gemini, 5 μm, 150 mm×30 mm, eluents: 10-95% MeCN in water, 0.05% AcOH). Pure fractions were collected, frozen in a dry-ice/acetone bath, and dried by lyophilizer for 20 h to afford 12 mg (9%) of 72 as a reddish solid. MS (ESI, pos.): calc'd for $C_{48}H_{55}N_3O_{12}$, 865.38; found 866.4 (M+H), 864.4 (M−H). $^1$H-NMR (500 MHz; $CD_3OD$): δ 7.97-7.94 (m, 1H), 7.54 (t, J=1.7 Hz, 1H), 7.39-7.35 (m, 1H), 6.89-6.86 (m, 1H), 6.38-6.35 (m, 1H), 6.17-6.15 (m, 2H), 5.12-5.09 (m, 1H), 4.95-4.93 (m, 2H), 3.82-3.79 (m, 1H), 3.58 (s, 2H), 3.02 (s, 6H), 2.40 (s, 3H), 2.27-2.27 (m, 4H), 2.12-2.01 (m, 3H), 1.97 (d, J=10.6 Hz, 8H), 1.74 (s, 4H), 1.72-1.68 (m, 2H), 1.54-1.49 (m, 1H), 1.29 (d, J=2.3 Hz, 1H), 0.95 (s, 3H), 0.89 (dd, J=5.2, 1.5 Hz, 3H), 0.21-0.17 (m, 2H), −0.08-0.12 (m, 2H).

Example 18: Preparation of Compound 75

Rifamycin analog 75 was synthesized from Rifamycin S as shown in Scheme 22 below, and as described below.

Scheme 22

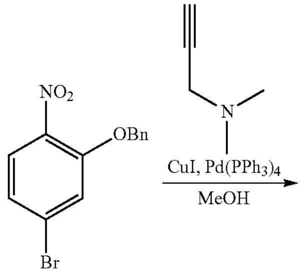

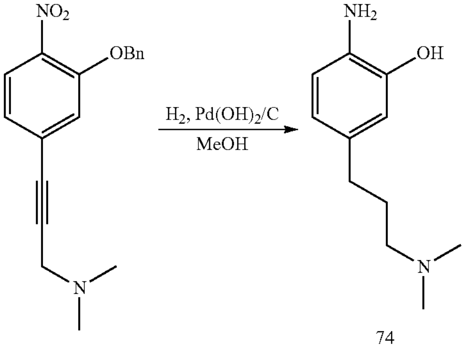

73

74

-continued

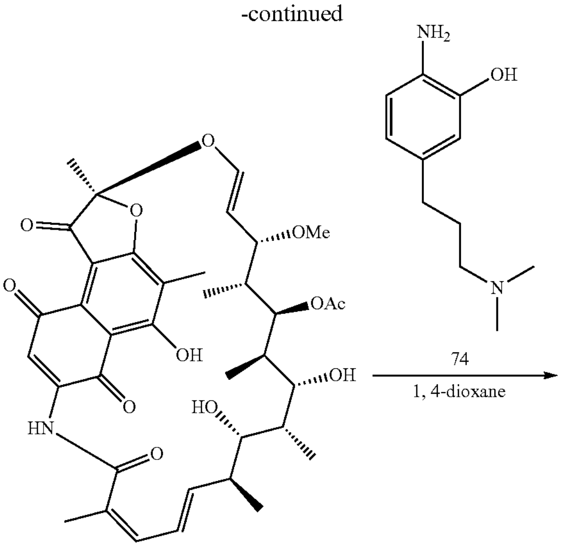

rifamycin S

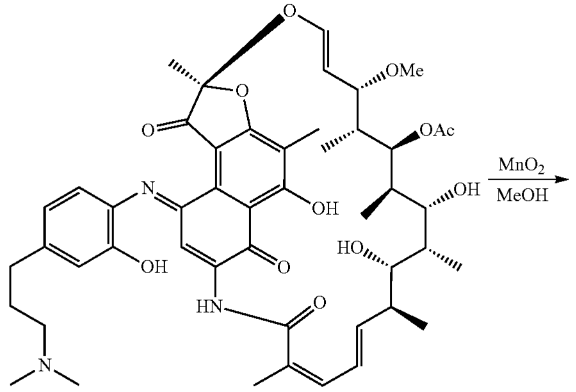

75a

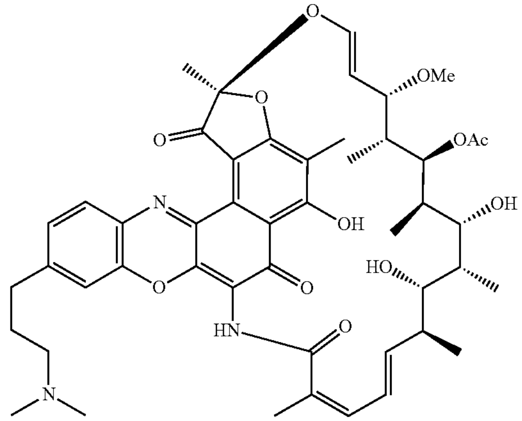

75

Compound 73: The mixture of 2-(benzyloxy)-4-bromo-1-nitrobenzene (500 mg, 1.622 mmol, 1.0 eq.), N,N-dimethylprop-2-yn-1-amine (262 μL, 2.433 mmol, 1.5 eq.), CuI (15.4 mg, 0.0811 mmol, 0.05 eq.), $Pd(PPh_3)_4$(47 mg, 0.0405 mmol, 0.025 eq.), and triethylamine (904 L, 6.488 mmol, 4.0 eq.) in anhydrous THE (15 mL) at room temperature, was degassed and stirred for 5h. The progress of reaction was monitored by LC/MS. The crude was filtered through a Celite pad and concentrated. The crude was then purified on a 40 g HP silica gel Gold RediSep column via ISCO system (gradient elution: 0-20% DCM in methanol), and the pure fractions evaporated and dried in vacuo giving 73 (492 mg, 98%). MS (ESI, pos.): calc'd for $C_{18}H_{18}N_2O_3$, 310.13; found 311.2 (M+H). $^1$H-NMR (500 MHz; $CD_3OD$): δ 7.81 (d, J=8.3 Hz, 1H), 7.47 (d, J=7.6 Hz, 2H), 7.38 (dd, J=8.4, 1.4 Hz, 4H), 7.14 (dd, J=8.3, 1.5 Hz, 1H), 5.28 (s, 2H), 3.52 (s, 2H), 2.36 (dd, J=1.3, 0.6 Hz, 6H).

Compound 74: To a solution of compound 73 (100 mg, 0.322 mmol) under argon in methanol (4 mL) was added 20 mg of 20% $Pd(OH)_2/C$. The mixture was further degassed with argon and connected to a hydrogen balloon. After 16 h, analysis by LC/MS from an in-process aliquot indicated the reaction was complete. The mixture was filtered through Celite, washed with MeOH (2×10 mL) and concentrated to afford 72 mg of the title compound 74 as reddish yellow oil, which was used in the next step instantly without further purification. MS: calc'd for $C_{11}H_{18}N_2O$, 194.1; found 195.2 (M+H).

Compound 75: To a round-bottom flask with hydroxyaniline 74 (72 mg, 0.304 mmol, 82% pure), were added 1,4-dioxane (3 mL) and rifamycin S (423 mg, 0.608 mmol). The reaction mixture was sealed via rubber septum, purged with argon, and the reaction stirred vigorously at ambient temperature. After 12 days, the reaction was concentrated in vacuo to remove dioxane, dissolved in MeOH (6 mL) and $MnO_2$ (106 mg, 1.216 mmol) was added. After stirring for 20 h, the reaction was filtered through Celite, washed with MeOH (2×10 mL), concentrated in vacuo and purified directly on a 50 g C18 RediSep Gold column via ISCO system (gradient elution: 0-100% MeCN in water, 0.05% acetic acid in both). The product-containing fractions were combined, frozen on dry ice/acetone, and lyophilized overnight giving the title compound 75. The compound was re-purified by EZ preparative HPLC column (Gemini, 5 μm, 150 mm×30 mm, eluents: 10-95% MeCN in water, 10 mM $NH_4OAc$ in both). Pure fractions were combined, frozen on dry ice/acetone, and lyophilized overnight giving the title compound 75 as a reddish brown solid (6 mg, 2.2%). MS: calc'd for $C_{48}H_{59}N_3O_{12}$, 869.4; found 870.4 (M+H). $^1$H-NMR (500 MHz; $CD_3OD$): δ 8.46 (s, 1H), 7.67 (s, 1H), 7.00 (s, 1H), 6.28 (d, J=8.79 Hz, 1H), 6.20 (s, 1H), 5.98-6.11 (m, 2H), 5.21 (dd, J=6.11, 12.46 Hz, 1H), 5.11 (d, J=10.26 Hz, 1H), 3.85-3.99 (m, 2H), 3.76 (s, 3H), 3.65-3.70 (m, 3H), 3.58 (s, 3H), 3.45 (br. s., 3H), 3.04-3.15 (m, 3H), 2.35 (br. s., 3H), 2.03 (s, 3H), 1.99 (s, 3H), 1.77 (s, 3H), 1.61-1.69 (m, 3H), 1.29 (s, 3H), 1.00 (d, J=6.84 Hz, 3H), 0.92 (d, J=7.33 Hz, 3H), 0.75-0.89 (m, 3H), 0.63 (d, J=6.84 Hz, 3H), 0.10 (s, 3H), 0.00 (d, J=6.84 Hz, 2H).

Example 19: Preparation of Linker-Payload Compounds

The linker-payload chemistry is used to prepare compound 20, as shown in Scheme 23, below, and described below.

Scheme 23

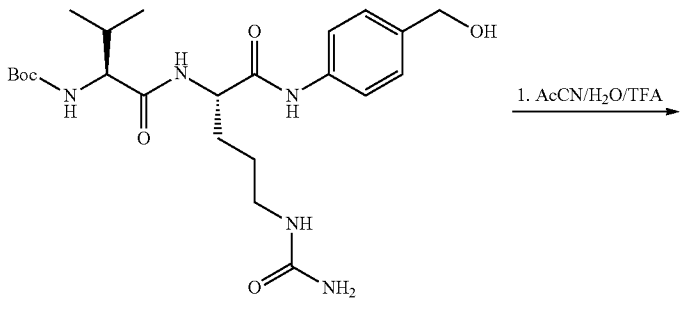

18a

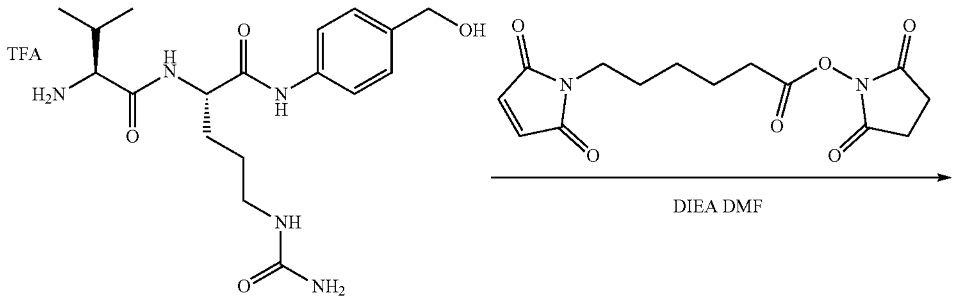

18b

-continued
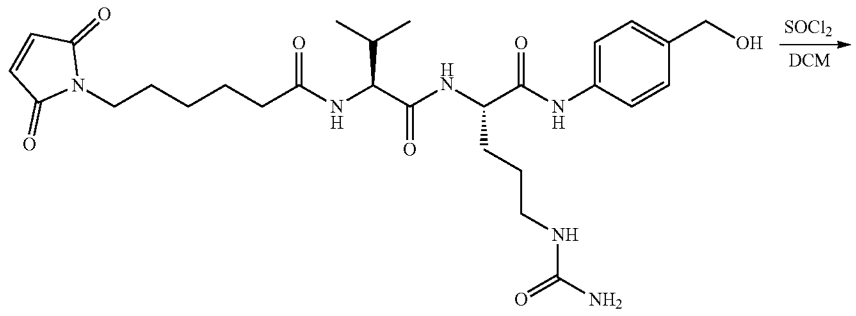
18
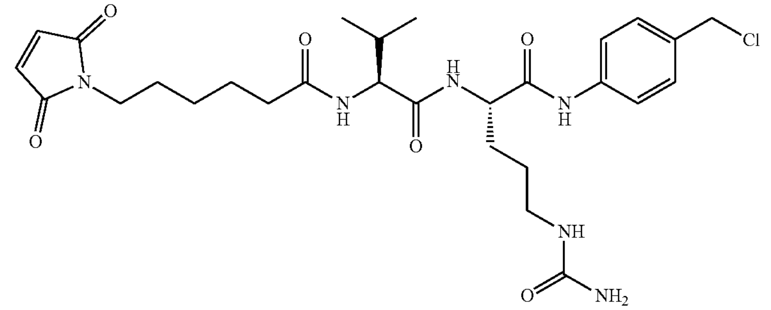
+
19
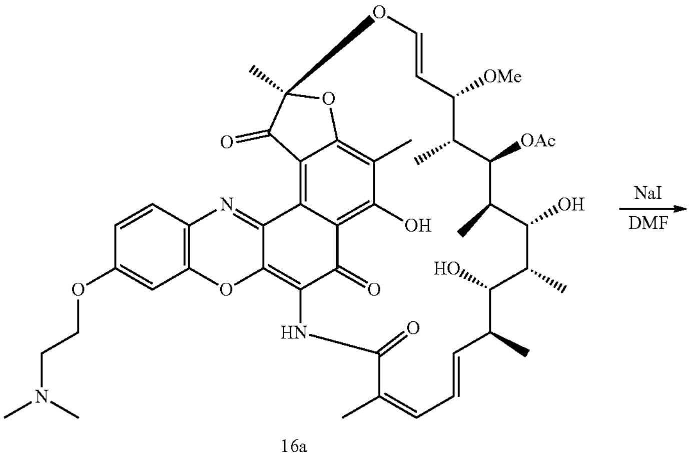
16a

-continued

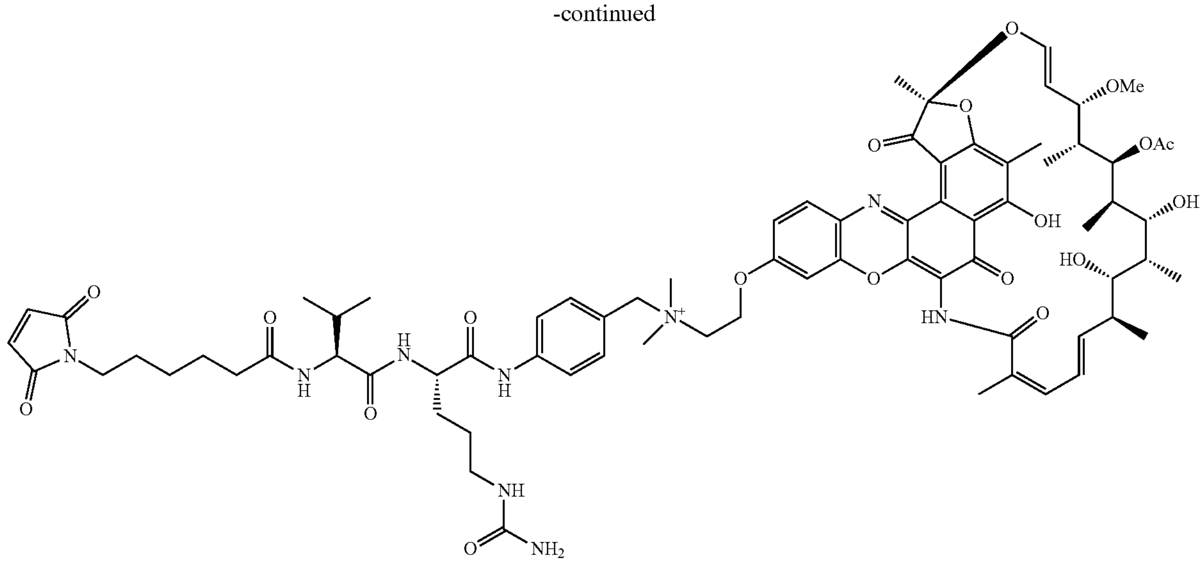

Synthesis of Compound 18. The title compound was prepared using a procedure in PCT Int. Appl., 2014145090. tert-butyl ((S)-1-(((S)-1-((4-(hydroxymethyl) phenyl) amino)-1-oxo-5-ureidopentan-2-yl)amino)-3-methyl-1-oxobutan-2-yl)carbamate 18a, (500 mg, 1.04 mmol) was dissolved in a mixture of $CH_3CN/H_2O$/TFA (3:1:1=v/v/v, 12 mL/4 mL/4 mL). The reaction mixture was stirred at room temperature for 48 h. The progress of the reaction was determined to be complete by LCMS. After concentrating in vacuo, the crude product 18b (0.9 g wet) was used directly for the next step without further purification. MS (ESI, pos.): calc'd for $C_{18}H_{29}N_5O_4$, 379.22; found 380.2 (M+H).

A solution of 18b (700 mg, 1.47 mmol, 1.0 eq) in water (8 mL) was diluted with 2 mL of aqueous $NaHCO_3$ solution at 4° C. and the mixture (pH=8.0) was treated with commercially available 2,5-dioxopyrrolidin-1-yl 6-(2,5-dioxo-2,5-dihydro-1H-pyrrol-1-yl)hexanoate (408 mg, 0.9 eq) in 10 mL of acetonitrile. The suspension was stirred at room temperature for 16 h until the reaction was complete. The crude product was concentrated under reduced pressure and diluted with DMSO (5 mL). The crude product was purified by an ISCO 150g C18 column (eluents: 10-95% MeCN in water, 0.05% in AcOH). Pure fractions were combined and lyophilized to afford 368 mg (44%) of compound 18 as a white solid. MS (ESI, pos.): calc'd for $C_{28}H_{40}N_6O_7$, 572.30; found 573.6 (M+H), (2M+H), 1145.9. $^1H$ NMR (500 MHz; DMSO-$d_6$): δ 9.89 (s, 1H), 8.05 (d, J=7.33 Hz, 1H), 7.81 (d, J=8.79 Hz, 1H), 7.52-7.57 (m, J=8.79 Hz, 2H), 7.21-7.26 (m, J=8.79 Hz, 2H), 6.99-7.02 (m, 2H), 5.98 (br. s., 1H), 5.40 (s, 2H), 5.10 (t, J=5.62 Hz, 1H), 4.35-4.45 (m, 3H), 4.18 (dd, J=6.84, 8.30 Hz, 1H), 3.26-3.33 (m, 2H), 2.91-3.06 (m, 2H), 2.08-2.22 (m, 2H), 1.93-2.01 (m, 1H), 1.66-1.74 (m, 1H), 1.59 (dd, J=4.40, 9.28 Hz, 1H), 1.43-1.55 (m, 5H), 1.32-1.43 (m, 1H), 1.19 (quin, J=7.57 Hz, 2H), 0.84 (d, J=8.30 Hz, 3H), 0.80-0.89 (m, 3H).

Synthesis of Compound 19. To a stirred suspension of 18 (100 mg, 0.174 mmol, 1.0 eq) at room temperature was slowly added $SOCl_2$ (14 μL, 0.192 mmol, 1.1 eq) using a micro syringe. The slurry reaction mixture was stirred for 1.5 h and an aliquot analyzed by LC/MS indicated the formation of the desired. The crude mixture was concentrated to remove all volatiles under reduced pressure. The mixture was diluted with 2 mL of DMSO and loaded on to an ISCO C18 Aq 50g column for purification (10-95% MeCN in water, 0.05% AcOH). The pure fractions were combined and lyophilized to give 72 mg (71%) of 19 as an off-white solid. MS (ESI, pos.): calc'd for $C_{28}H_{39}ClN_6O_6$, 590.26; found 591.3 (M+H), 1181.5 (2M+H). 1H NMR (500 MHz; DMSO-$d_6$) δ 10.03 (s, 1H), 8.03-8.11 (m, 1H), 7.79 (d, J=8.30 Hz, 1H), 7.57-7.63 (m, J=8.79 Hz, 2H), 7.34-7.38 (m, J=8.79 Hz, 2H), 6.99-7.02 (m, 2H), 5.97 (br. s., 1H), 5.40 (br. s., 2H), 4.71 (s, 2H), 4.34-4.43 (m, 2H), 4.16-4.21 (m, 1H), 3.36-3.42 (m, 3H), 2.90-3.06 (m, 3H), 2.07-2.22 (m, 3H), 1.91-2.00 (m, 1H), 1.66-1.73 (m, 1H), 1.31-1.41 (m, 1H), 1.18 (quin, J=7.69 Hz, 3H), 0.79-0.89 (m, 7H).

Synthesis of Compound 20. The mixture of 19 (13.5 mg, 0.0228 mmol, 1.2 eq), 16a (16.6 mg, 0.0190 mmol, 1.0 eq), and NaI (14.2 mg, 0.095 mmol) in a 2 dram vial was dissolved in 1 mL of anhydrous DMF. A catalytic amount (10 μL) of 0.5 M DIPEA solution in DMF was added by syringe. The mixture was heated at 55° C. in an oil bath overnight. The reaction was complete by LC/MS to afford the desired product. The mixture was cooled to 4° C. and diluted with 1 mL of water. After filtration, the dark crude mixture was purified by an EZ preparative HPLC column (Gemini, 5 μm, 150 mm×30 mm, eluents: 10-95% MeCN in water, 0.05% AcOH). Pure fractions were combined and lyophilized to afford 14.6 mg (55%) of 20 as a dark red solid. MS (ESI, pos.): calc'd for $C_{75}H_{96}N_9O_{19}^+$, 1426.68; found 1427.3 (M+1) and 1425.5 (M-1). $^1H$ NMR (500 MHz; DMSO-$d_6$) δ 10.25 (s, 1H), 8.19 (d, J=6.84 Hz, 1H), 7.82 (d, J=8.30 Hz, 2H), 7.76 (d, J=8.79 Hz, 3H), 7.50 (d, J=8.30 Hz, 3H), 7.00 (s, 2H), 6.12 (d, J=12.70 Hz, 1H), 6.03 (br. s., 1H), 5.43 (s, 2H), 4.70-4.80 (m, 2H), 4.58 (br. s., 3H), 4.36-4.41 (m, 1H), 4.18 (t, J=7.82 Hz, 1H), 3.77 (br. s., 2H), 3.36-3.45 (m, 8H), 3.13 (d, J=8.30 Hz, 1H), 2.89-3.06 (m, 12H), 2.78 (t, J=9.04 Hz, 1H), 2.06-2.22 (m, 3H), 2.03 (br. s., 1H), 1.91-2.00 (m, 10H), 1.85 (s, 3H), 1.66-1.74 (m, 1H), 1.56-1.64 (m, 6H), 1.42-1.56 (m, 8H), 1.38 (d, J=6.84 Hz, 2H), 1.15-1.25 (m, 3H), 0.75-0.88 (m, 14H), 0.07 (s, 1H).

Linker-payload compound 25 was prepared as shown in Scheme 24, below, and described below.

Scheme 24
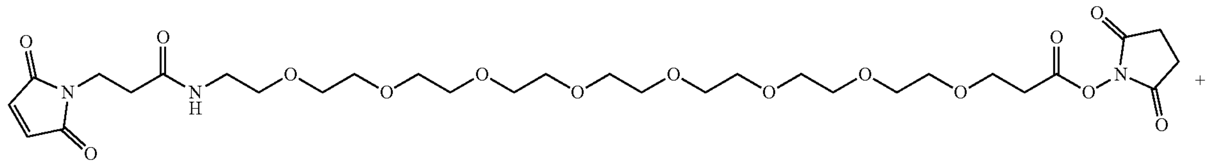
22
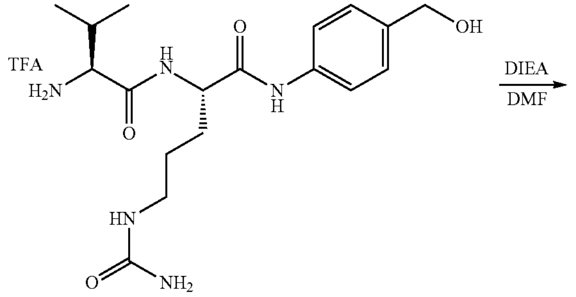
18b
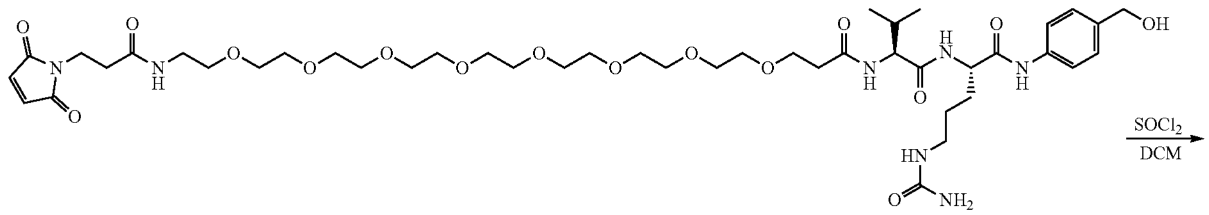
23
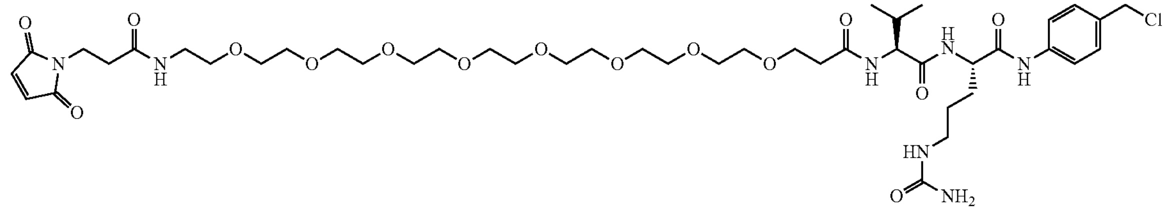
24
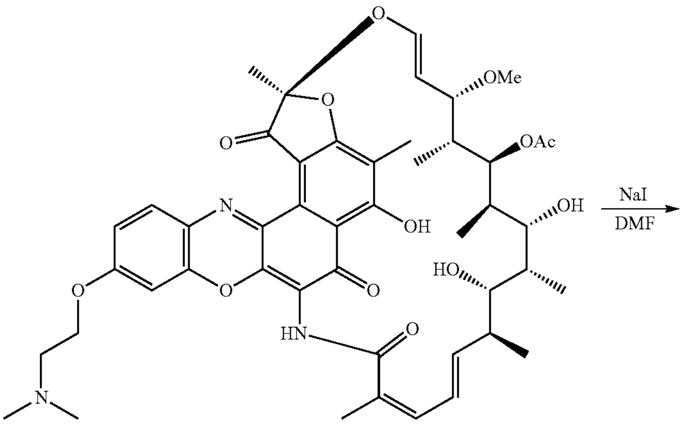
16a -continued

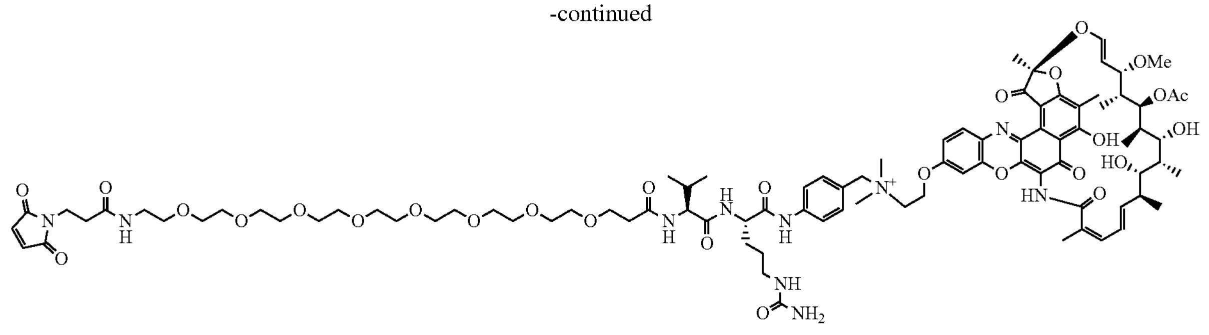

25

Synthesis of Compound 23. To a mixture of 22 (100 mg, 0.144 mmol) and 18b (82 mg, 0.217 mmol) in anhydrous DMF (1.5 mL) was then treated with DIEA (50 μL, 0.288 mmol) via micro syringe. The reaction mixture was stirred for 2 h at room temperature and determined to afford 23 by LC/MS. The crude mixture was purified by an ISCO C18 100g Aq column (eluents: 10-95% MeCN in water, 0.05% in AcOH), pure factions combined and lyophilized to yield 84.4 mg (62%) of 23. MS (ESI, pos.): calc'd for $C_{44}H_{71}N_7O_{16}$, 953.50; found 954.4 (M+H), 976.4 (M+Na), 952.4 (M−H). $^1$H NMR (500 MHz; DMSO-$d_6$) δ 9.88 (s, 1H), 8.08 (d, J=7.2 Hz, 1H), 8.00 (s, 1H), 7.86 (d, J=8.5 Hz, 1H), 7.55 (d, J=8.4 Hz, 2H), 7.23 (d, J=8.3 Hz, 2H), 7.00 (s, 2H), 5.98 (s, 1H), 5.40 (s, 1H), 4.43 (s, 2H), 4.39 (d, J=5.4 Hz, 1H), 4.23 (dd, J=8.3, 6.8 Hz, 2H), 3.60 (d, J=6.9 Hz, 6H), 3.44-3.54 (m, 30H), 3.37 (t, J=5.8 Hz, 3H), 3.15 (d, J=5.7 Hz, 2H), 2.99 (d, J=29.6 Hz, 2H), 2.33 (t, J=7.3 Hz, 3H), 1.98 (d, J=6.7 Hz, 1H), 1.71-1.70 (m, 1H), 1.61-1.58 (m, 1H), 1.44-1.36 (m, 2H), 0.85 (dd, J=15.5, 6.7 Hz, 7H).

Synthesis of Compound 24. To a stirred suspension of 23 (15 mg, 0.0157 mmol, 1.0 eq) in a vial at room temperature was slowly added $SOCl_2$ (1.3 μL, 0.0173 mmol, 1.1 eq) via a micro syringe. After 1 h, an aliquot analyzed by LC/MS indicated the formation of the desired product. The crude mixture was concentrated to remove all volatiles under reduced pressure. The crude mixture was diluted with 0.8 mL of MeCN and loaded onto an EZ preparative HPLC column and eluted (Gemini, 5 μm, 150 mm×30 mm, eluents: 10-95% MeCN in water, 0.05% AcOH). Pure fractions were combined and lyophilized to afford 9.5 mg (63%) of 24 as an off-white solid. MS (ESI, pos.): calc'd for $C_{44}H_{70}ClN_7O_{15}$, 971.46; found 972.4 (M+H), 994.4 (M+Na), 970.3 (M−1).

Synthesis of linker-payload Compound 25. To a mixture of 24 (9.5 mg, 0.00976 mmol, 1.0 eq), 16a (8.51 mg, 0.00976 mmol, 1.0 eq), and NaI (7.3 mg, 0.0488 mmol) in a 1 dram vial was dissolved in 1 mL of anhydrous DMF. A catalytic amount (20 μL) of 0.5M DIEA solution in DMF was added by syringe. The mixture was heated at 55° C. in an oil bath overnight. The reaction was complete by LC/MS to afford the desired product. The mixture was cooled in an ice-bath and diluted with 1 mL of water. After filtration, the dark crude mixture was purified by an EZ preparative HPLC column (Gemini, 5 μm, 150 mm×30 mm, eluents: 10-95% MeCN in water, 0.05% AcOH). Pure fractions were combined and lyophilized to afford 7.4 mg (42%) of 25 as a dark red solid. MS (ESI, pos.): calc'd for $C_{91}H_{127}N_{10}O_{28}^+$, 1807.88; found 1808.8 (M+H) and 1806.5 (M−1). $^1$H NMR (500 MHz; DMSO-$d_6$) δ 10.23 (s, 1H), 8.22-8.17 (m, 1H), 8.03-7.98 (m, 1H), 7.86 (d, J=8.3 Hz, 1H), 7.75 (d, J=8.2 Hz, 4H), 7.50 (d, J=8.3 Hz, 3H), 7.00 (s, 2H), 6.01 (s, 1H), 5.76 (s, 1H), 5.43 (s, 1H), 4.80-4.80 (m, 1H), 4.58 (s, 1H), 4.43-4.41 (m, 1H), 4.27-4.23 (m, 1H), 3.76 (t, J=0.6 Hz, 2H), 3.59 (t, J=7.3 Hz, 5H), 3.49 (d, J=2.9 Hz, 54H), 3.14 (d, J=5.8 Hz, 4H), 3.03 (s, 8H), 2.90 (t, J=0.7 Hz, 3H), 2.77 (d, J=0.7 Hz, 1H), 2.33 (t, J=7.3 Hz, 4H), 2.08 (d, J=6.1 Hz, 4H), 1.94 (d, J=18.9 Hz, 10H), 1.83 (s, 5H), 1.59 (s, 8H), 0.85 (dd, J=16.1, 6.7 Hz, 8H).

Linker-payload compound 36 was prepared as shown in Scheme 25, below, and described below.

Scheme 25

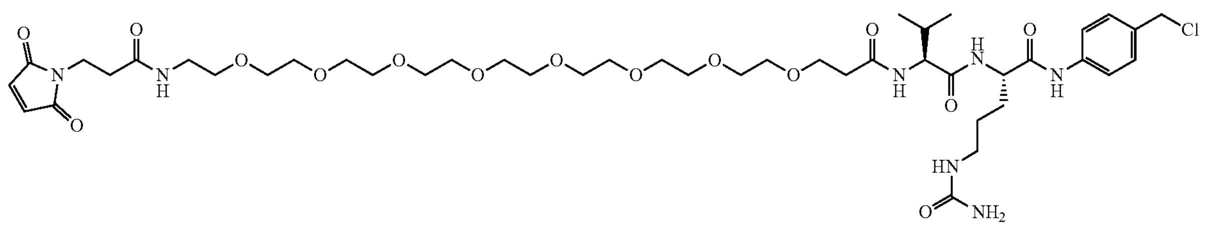

24

-continued

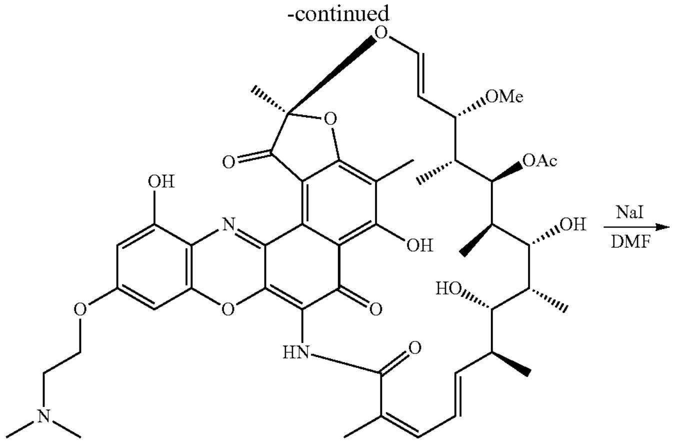

29

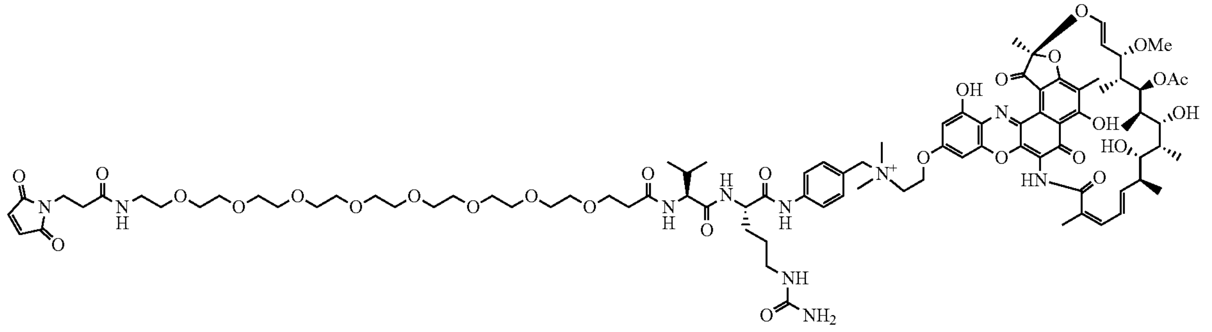

36

Compound 36: The mixture of 24 (14.4 mg, 0.00149 mmol, 1.2 eq), 16a (11.0 mg, 0.00123 mmol, 1.0 eq), and NaI (9.1 mg, 0.0615 mmol) in a 1 dram vial was dissolved in 1 mL of anhydrous DMF. A catalytic amount of 0.5M DIEA solution in DMF (10 μL) was added via a syringe. The mixture was heated at 55° C. in an oil bath overnight. The reaction was complete when assayed by LC/MS to afford the desired product. The mixture was cooled in an ice-bath and diluted with 0.5 mL of water. After filtration, the dark crude mixture was purified by EZ preparative HPLC column (Gemini, 5 μm, 150 mm×30 mm, eluents: 10-95% MeCN in water, 0.05% AcOH). Pure fractions were collected, frozen, and lyophilized to afford 11.7 mg (53%) of 36 as a dark red solid. MS (ESI, pos.): calc'd for $C_{91}H_{127}N_{10}O_{29}^+$, 1823.88; found 1824.8 (M+H) and 1821.7 (M−1). $^1H$ NMR (500 MHz; DMSO-$d_6$): δ 10.22 (s, 1H), 8.85 (d, J=0.8 Hz, 1H), 8.18-8.17 (m, 1H), 8.01 (s, 1H), 7.86 (d, J=8.1 Hz, 1H), 7.75-7.73 (m, 2H), 7.49-7.47 (m, 2H), 7.00 (s, 2H), 6.28 (dd, J=9.9, 0.9 Hz, 1H), 6.21 (dd, J=12.4, 0.6 Hz, 1H), 6.00-5.98 (m, 1H), 5.86 (s, 1H), 5.48 (s, 1H), 5.42 (d, J=8.4 Hz, 2H), 5.04-4.99 (m, 1H), 4.72-4.69 (m, 1H), 4.58-4.50 (m, 3H), 4.40-4.38 (m, 1H), 4.25-4.22 (m, 1H), 3.89-3.87 (m, 1H), 3.73-3.70 (m, 4H), 3.62-3.58 (m, 7H), 3.54-3.47 (m, 29H), 3.36 (t, J=5.8 Hz, 7H), 3.15 (d, J=5.7 Hz, 4H), 3.03-2.98 (m, 4H), 2.85 (s, 3H), 2.66 (d, J=23.9 Hz, 3H), 2.34 (dd, J=16.4, 9.2 Hz, 4H), 2.12-2.05 (m, 3H), 1.92 (d, J=18.7 Hz, 13H), 1.67 (s, 3H), 1.61 (t, J=0.6 Hz, 3H), 1.47-1.37 (m, 3H), 1.24 (d, J=0.6 Hz, 1H), 0.88-0.78 (m, 8H), 0.78-0.65 (m, 4H), 0.17-0.16 (m, 1H), 0.07 (s, 1H), −0.41 (td, J=2.5, 0.9 Hz, 1H).

Linker-payload compound 25a was prepared as shown in Scheme 26, below, and described below.

Scheme 26

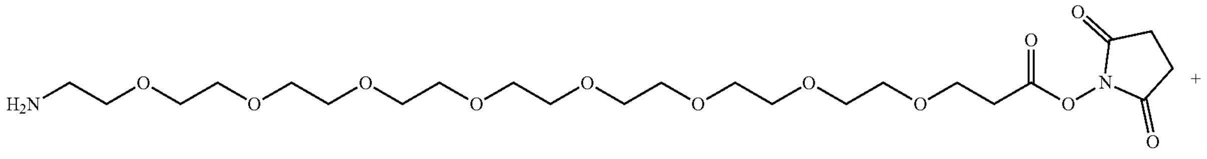

22a

-continued
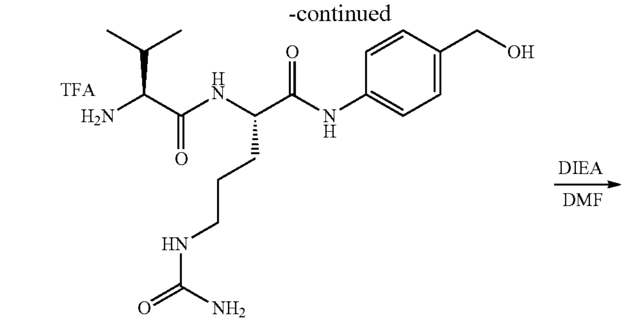
18b
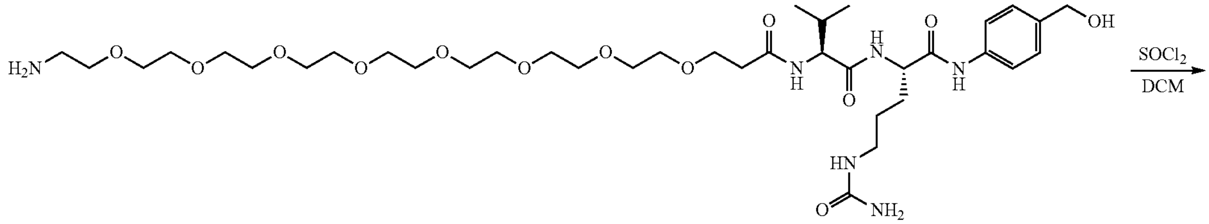
23a
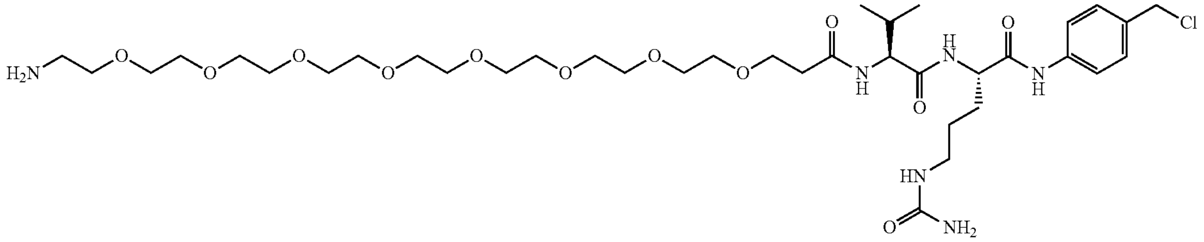
24a
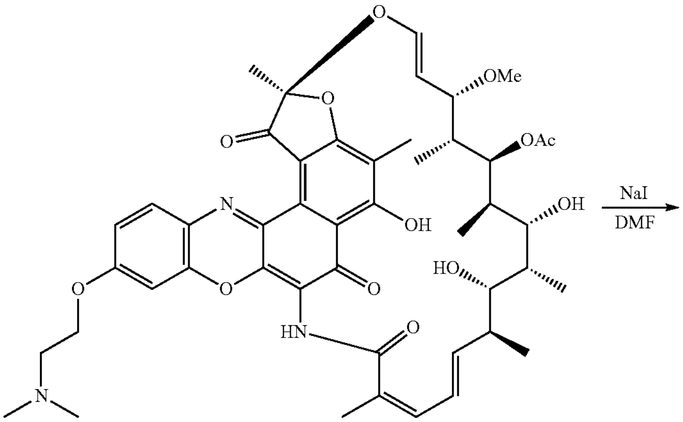
16a

-continued

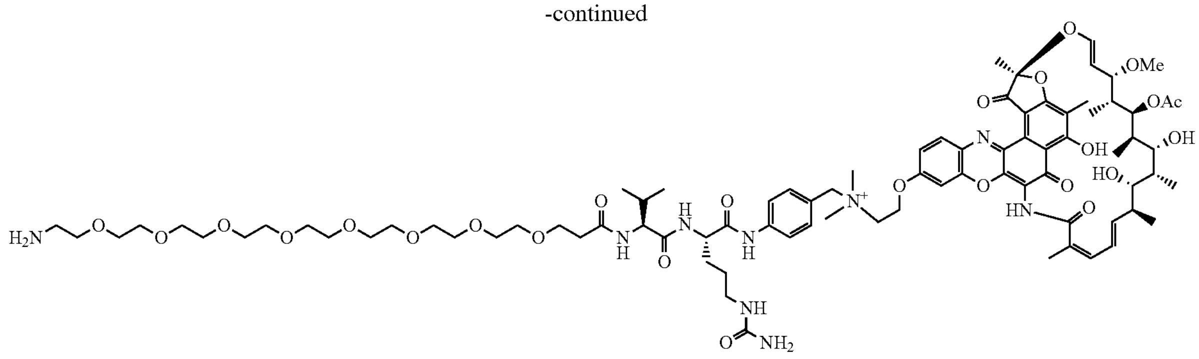

25a

Synthesis of Compound 23a. To a mixture of 22a (100 mg, 0.144 mmol) and 18b (82 mg, 0.217 mmol) in anhydrous DMF (1.5 mL) was then treated with DIEA (50 μL, 0.288 mmol) via micro syringe. The reaction mixture was stirred for 2 h at room temperature and determined to afford 23a by LC/MS. The crude mixture was purified by an ISCO C18 100g Aq column (eluents: 10-95% MeCN in water, 0.05% in AcOH), pure factions combined and lyophilized to yield 84.4 mg (62%) of 23. MS (ESI, pos.): calc'd for $C_{44}H_{71}N_7O_{16}$, 953.50; found 954.4 (M+H), 976.4 (M+Na), 952.4 (M−H). $^1$H NMR (500 MHz; DMSO-$d_6$) δ 9.88 (s, 1H), 8.08 (d, J=7.2 Hz, 1H), 8.00 (s, 1H), 7.86 (d, J=8.5 Hz, 1H), 7.55 (d, J=8.4 Hz, 2H), 7.23 (d, J=8.3 Hz, 2H), 7.00 (s, 2H), 5.98 (s, 1H), 5.40 (s, 1H), 4.43 (s, 2H), 4.39 (d, J=5.4 Hz, 1H), 4.23 (dd, J=8.3, 6.8 Hz, 2H), 3.60 (d, J=6.9 Hz, 6H), 3.44-3.54 (m, 30H), 3.37 (t, J=5.8 Hz, 3H), 3.15 (d, J=5.7 Hz, 2H), 2.99 (d, J=29.6 Hz, 2H), 2.33 (t, J=7.3 Hz, 3H), 1.98 (d, J=6.7 Hz, 1H), 1.71-1.70 (m, 1H), 1.61-1.58 (m, 1H), 1.44-1.36 (m, 2H), 0.85 (dd, J=15.5, 6.7 Hz, 7H).

Synthesis of Compound 24a. To a stirred suspension of 23a (15 mg, 0.0157 mmol, 1.0 eq) in a vial at room temperature was slowly added $SOCl_2$ (1.3 μL, 0.0173 mmol, 1.1 eq) via a micro syringe. After 1 h, an aliquot analyzed by LC/MS indicated the formation of the desired product. The crude mixture was concentrated to remove all volatiles under reduced pressure. The crude mixture was diluted with 0.8 mL of MeCN and loaded onto an EZ preparative HPLC column and eluted (Gemini, 5 μm, 150 mm×30 mm, eluents: 10-95% MeCN in water, 0.05% AcOH). Pure fractions were combined and lyophilized to afford 9.5 mg (63%) of 24 as an off-white solid. MS (ESI, pos.): calc'd for $C_{44}H_{70}ClN_7O_{15}$, 971.46; found 972.4 (M+H), 994.4 (M+Na), 970.3 (M−1).

Synthesis of linker-payload Compound 25a. To a mixture of 24a (9.5 mg, 0.00976 mmol, 1.0 eq), 16a (8.51 mg, 0.00976 mmol, 1.0 eq), and NaI (7.3 mg, 0.0488 mmol) in a 1 dram vial was dissolved in 1 mL of anhydrous DMF. A catalytic amount (20 μL) of 0.5M DIEA solution in DMF was added by syringe. The mixture was heated at 55° C. in an oil bath overnight. The reaction was complete by LC/MS to afford the desired product. The mixture was cooled in an ice-bath and diluted with 1 mL of water. After filtration, the dark crude mixture was purified by an EZ preparative HPLC column (Gemini, 5 μm, 150 mm×30 mm, eluents: 10-95% MeCN in water, 0.05% AcOH). Pure fractions were combined and lyophilized to afford 7.4 mg (42%) of 25 as a dark red solid. MS (ESI, pos.): calc'd for $C_{91}H_{127}N_{10}O_{28}^+$, 1807.88; found 1808.8 (M+H) and 1806.5 (M−1). $^1$H NMR (500 MHz; DMSO-$d_6$) δ 10.23 (s, 1H), 8.22-8.17 (m, 1H), 8.03-7.98 (m, 1H), 7.86 (d, J=8.3 Hz, 1H), 7.75 (d, J=8.2 Hz, 4H), 7.50 (d, J=8.3 Hz, 3H), 7.00 (s, 2H), 6.01 (s, 1H), 5.76 (s, 1H), 5.43 (s, 1H), 4.80-4.80 (m, 1H), 4.58 (s, 1H), 4.43-4.41 (m, 1H), 4.27-4.23 (m, 1H), 3.76 (t, J=0.6 Hz, 2H), 3.59 (t, J=7.3 Hz, 5H), 3.49 (d, J=2.9 Hz, 54H), 3.14 (d, J=5.8 Hz, 4H), 3.03 (s, 8H), 2.90 (t, J=0.7 Hz, 3H), 2.77 (d, J=0.7 Hz, 1H), 2.33 (t, J=7.3 Hz, 4H), 2.08 (d, J=6.1 Hz, 4H), 1.94 (d, J=18.9 Hz, 10H), 1.83 (s, 5H), 1.59 (s, 8H), 0.85 (dd, J=16.1, 6.7 Hz, 8H).

Linker-payload compound 36a was prepared as shown in Scheme 27, below, and described below.

Scheme 27

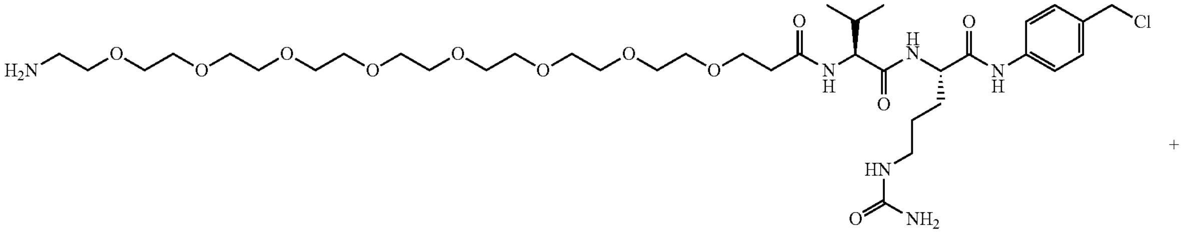

24a

-continued

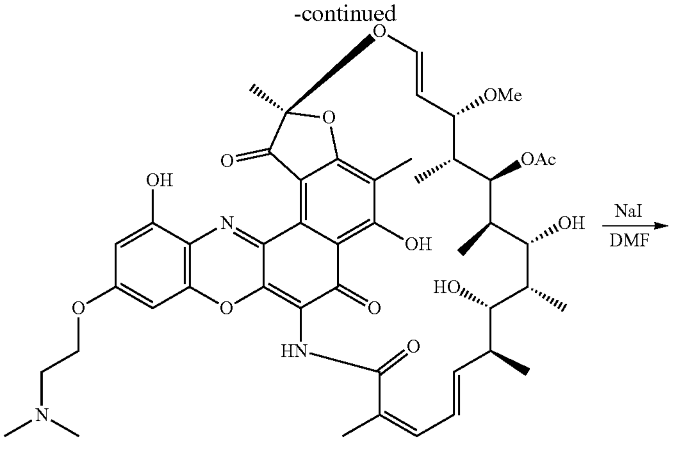

29

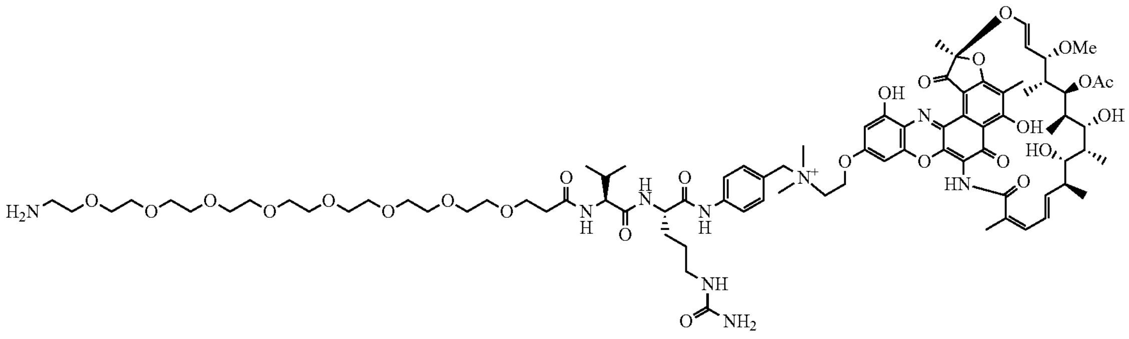

36a

Compound 36a: The mixture of 24a (14.4 mg, 0.00149 mmol, 1.2 eq), 16a (11.0 mg, 0.00123 mmol, 1.0 eq), and NaI (9.1 mg, 0.0615 mmol) in a 1 dram vial was dissolved in 1 mL of anhydrous DMF. A catalytic amount of 0.5M DIEA solution in DMF (10 μL) was added via a syringe. The mixture was heated at 55° C. in an oil bath overnight. The reaction was complete when assayed by LC/MS to afford the desired product. The mixture was cooled in an ice-bath and diluted with 0.5 mL of water. After filtration, the dark crude mixture was purified by EZ preparative HPLC column (Gemini, 5 μm, 150 mm×30 mm, eluents: 10-95% MeCN in water, 0.05% AcOH). Pure fractions were collected, frozen, and lyophilized to afford 11.7 mg (53%) of 36 as a dark red solid. MS (ESI, pos.): calc'd for $C_{91}H_{127}N_{10}O_{29}^{+}$, 1823.88; found 1824.8 (M+H) and 1821.7 (M−1). 1H NMR (500 MHz; DMSO-$d_6$): δ 10.22 (s, 1H), 8.85 (d, J=0.8 Hz, 1H), 8.18-8.17 (m, 1H), 8.01 (s, 1H), 7.86 (d, J=8.1 Hz, 1H), 7.75-7.73 (m, 2H), 7.49-7.47 (m, 2H), 7.00 (s, 2H), 6.28 (dd, J=9.9, 0.9 Hz, 1H), 6.21 (dd, J=12.4, 0.6 Hz, 1H), 6.00-5.98 (m, 1H), 5.86 (s, 1H), 5.48 (s, 1H), 5.42 (d, J=8.4 Hz, 2H), 5.04-4.99 (m, 1H), 4.72-4.69 (m, 1H), 4.58-4.50 (m, 3H), 4.40-4.38 (m, 1H), 4.25-4.22 (m, 1H), 3.89-3.87 (m, 1H), 3.73-3.70 (m, 4H), 3.62-3.58 (m, 7H), 3.54-3.47 (m, 29H), 3.36 (t, J=5.8 Hz, 7H), 3.15 (d, J=5.7 Hz, 4H), 3.03-2.98 (m, 4H), 2.85 (s, 3H), 2.66 (d, J=23.9 Hz, 3H), 2.34 (dd, J=16.4, 9.2 Hz, 4H), 2.12-2.05 (m, 3H), 1.92 (d, J=18.7 Hz, 13H), 1.67 (s, 3H), 1.61 (t, J=0.6 Hz, 3H), 1.47-1.37 (m, 3H), 1.24 (d, J=0.6 Hz, 1H), 0.88-0.78 (m, 8H), 0.78-0.65 (m, 4H), 0.17-0.16 (m, 1H), 0.07 (s, 1H), −0.41 (td, J=2.5, 0.9 Hz, 1H).

Linker-payload compound 80 was prepared as shown in Scheme 28, below, and described below.

Scheme 28

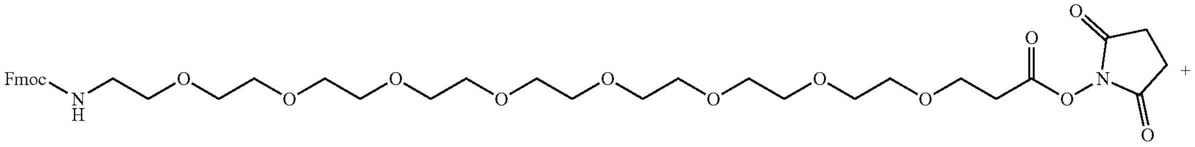

76

-continued
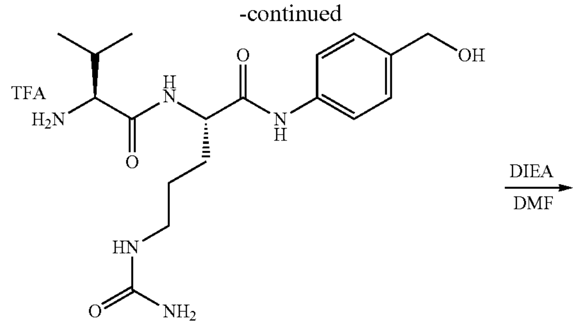
18b
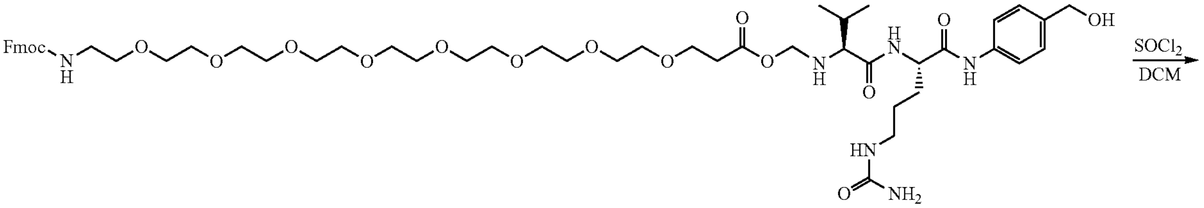
77
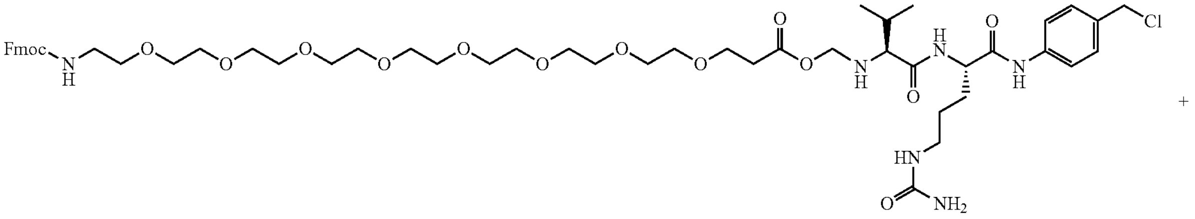
78
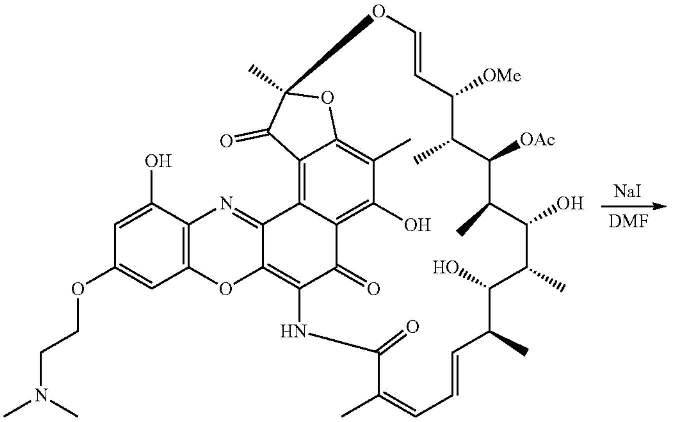
29
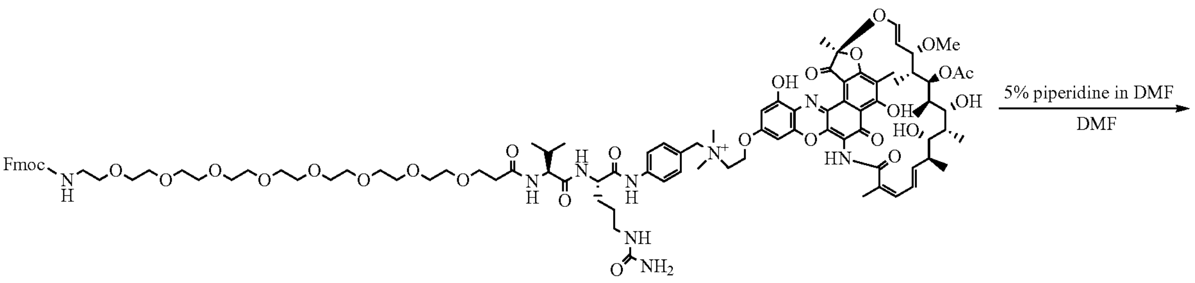
79

-continued

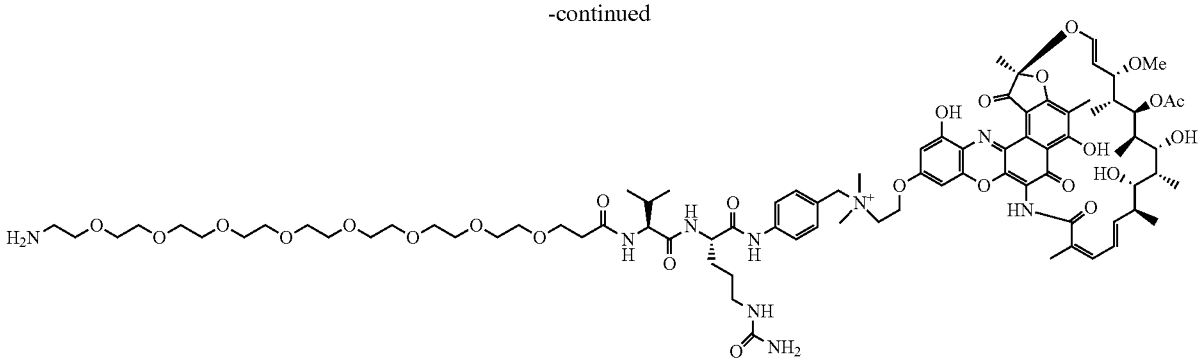

80

Compound 77: To a solution of commercially available compound 76 (100 mg, 0.131 mmol) and 18b (71 mg, 0.144 mmol) in anhydrous DMF (1.5 mL) was added DIEA (34 μL, 0.197 mmol) via micro syringe. The reaction mixture was stirred for 1 h at room temperature. The reaction was complete by LC/MS and concentrated in vacuo. The crude product was purified by ISCO system using a C18 100g Aq column (eluents: 10-95% MeCN in water, 0.05% in AcOH). Pure fractions by LC/MS were collected, frozen in a dry-ice/acetone bath, and lyophilized for 24 h to afford 114 mg (85%) of 77. MS (ESI, pos.): calc'd for $C_{52}H_{76}N_6O_{15}$, 1024.54; found 1025.5 (M+H), 1047.4 (M+Na).

Compound 78: To a stirred suspension of 77 (46 mg, 0.0448 mmol, 1.0 eq) in 1.5 mL of anhydrous DCM at room temperature was slowly added $SOCl_2$ (3.6 μL, 0.0493 mmol, 1.1 eq) using a micro syringe. After 30 min, an in process aliquot was analyzed by LC/MS to indicate the formation of desired product. The crude mixture was concentrated in vacuo and diluted with 1 mL of MeCN. The solution was loaded on to a ISCO system C18 50 g Ag column (eluents: 10-95% MeCN in water, 0.05% AcOH). Pure fractions were collected, frozen in a dry-ice/acetone bath, and lyophilized to afford 40 mg (85%) of 77 as an off-white solid. MS (ESI, pos.): calc'd for $C_{52}H_{75}ClN_6O_{14}$, 1042.50; found 1043.4 (M+H), 1065.4 (M+Na).

Compound 79: To a mixture of 78 (35 mg, 0.0337 mmol, 1.2 eq), 29 (25 mg, 0.0281 mmol, 1.0 eq), and NaI (21 mg, 0.145 mmol, 5.0 eq.) in 2 dram vial was added 1.5 mL of anhydrous DMF. A catalytic amount of 0.5M DIEA solution in DMF (20 μL) was added by syringe via septa. The mixture was heated at 55° C. in an oil bath for overnight. The reaction was complete by LC/MS to afford the desired product. The mixture was cooled with an ice-bath and diluted with 1 mL of water. After filtration, the dark crude mixture was purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized to afford 42 mg (79%) of 79 as a dark red solid. MS (ESI, pos.): calc'd for $C_{99}H_{132}N_9O_{28}^+$, 1894.92; found 1895.9 (M+H). $^1H$-NMR (500 MHz; DMSO-$d_6$): δ 10.22 (s, 1H), 8.85 (s, 1H), 8.19-8.17 (m, 1H), 7.89-7.84 (m, 2H), 7.74-7.73 (m, 2H), 7.70-7.68 (m, 2H), 7.48-7.46 (m, 2H), 7.41 (t, J=7.5 Hz, 2H), 7.32 (t, J=7.4 Hz, 2H), 6.91-6.87 (m, 1H), 6.28-6.26 (m, 1H), 6.20 (dd, J=12.8, 0.7 Hz, 1H), 6.09-6.07 (m, 1H), 6.06-5.97 (m, 2H), 5.85 (t, J=0.7 Hz, 1H), 5.72-5.65 (m, 1H), 5.48 (d, J=0.7 Hz, 1H), 5.42 (s, 3H), 5.23-5.22 (m, 1H), 5.04-4.98 (m, 2H), 4.71-4.69 (m, 1H), 4.51 (t, J=0.8 Hz, 6H), 4.39-4.38 (m, 12H), 4.29 (d, J=6.9 Hz, 3H), 4.23-4.20 (m, 2H), 3.87 (dd, J=8.2, 1.1 Hz, 1H), 3.70 (dd, J=1.7, 0.9 Hz, 4H), 3.59 (d, J=5.7 Hz, 4H), 3.46 (s, 12H), 3.40 (d, J=5.8 Hz, 3H), 3.13-3.11 (m, 2H), 3.03-2.97 (m, 6H), 2.85 (s, 3H), 2.68 (dd, J=1.3, 0.8 Hz, 2H), 2.63 (d, J=1.7 Hz, 5H), 2.36 (dd, J=3.5, 1.7 Hz, 4H), 2.22-2.18 (m, 1H), 2.12 (s, 3H), 2.05 (dd, J=1.4, 0.7 Hz, 1H), 1.98-1.93 (m, 3H), 1.86 (s, 1H), 1.67 (s, 1H), 1.60 (t, J=0.8 Hz, 3H), 1.45-1.44 (m, 2H), 1.38-1.37 (m, 1H), 1.24-1.20 (m, 1H), 0.85 (dd, J=16.5, 6.6 Hz, 2H), 0.78-0.76 (m, 3H), 0.70-0.60 (m, 2H), 0.17-0.16 (m, 2H), −0.42 (dd, J=5.2, 0.8 Hz, 2H).

Compound 80: To a stirred solution of compound 79 (25 mg, 0.0131 mmol) in 2 mL of DMF was added a solution of 5% piperidine (400 μL) in DMF and the reaction stirred at ambient temperature. After 1 h, the reaction was complete by LC/MS. The crude was then purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized to afford 18.6 mg (82%) of 80 as a reddish solid. MS (ESI, pos.): calc'd for $C_{84}H_{122}N_9O_{26}^+$, 1672.85 (free base); found 1673.8 (M+H). $^1H$-NMR (500 MHz; DMSO-$d_6$): δ 10.26 (s, 1H), 8.85 (d, J=0.9 Hz, 1H), 8.23 (dd, J=6.3, 0.4 Hz, 1H), 7.89-7.87 (m, 1H), 7.75-7.74 (m, 2H), 7.48-7.47 (m, 2H), 6.90-6.87 (m, 1H), 6.28-6.26 (m, 1H), 6.21-6.19 (m, 1H), 6.04 (t, J=10.3 Hz, 2H), 5.88-5.85 (m, 1H), 5.74-5.72 (m, 1H), 5.50 (ddt, J=3.3, 1.0, 0.8 Hz, 1H), 5.43 (s, 2H), 5.03-4.98 (m, 1H), 4.71-4.69 (m, 1H), 4.52 (s, 4H), 4.38 (d, J=5.4 Hz, 1H), 4.23 (t, J=7.6 Hz, 1H), 3.89-3.87 (m, 1H), 3.70 (d, J=0.7 Hz, 3H), 3.60 (d, J=5.2 Hz, 4H), 3.48 (s, 24H), 3.00-2.97 (m, 12H), 2.85 (s, 2H), 2.64 (s, 2H), 2.39-2.36 (m, 1H), 2.23-2.20 (m, 1H), 2.11 (d, J=0.4 Hz, 3H), 1.93 (s, 9H), 1.83 (s, 3H), 1.67-1.60 (m, 6H), 1.46-1.38 (m, 3H), 1.24 (s, 1H), 0.85 (dd, J=16.2, 6.6 Hz, 12H), 0.76 (d, J=8.3 Hz, 5H), 0.15-0.15 (m, 2H), 0.07 (s, 1H), −0.40 (d, J=1.9 Hz, 1H).

Linker-payload compound 82 was prepared as shown in Scheme 29, below, and described below.

Scheme 29
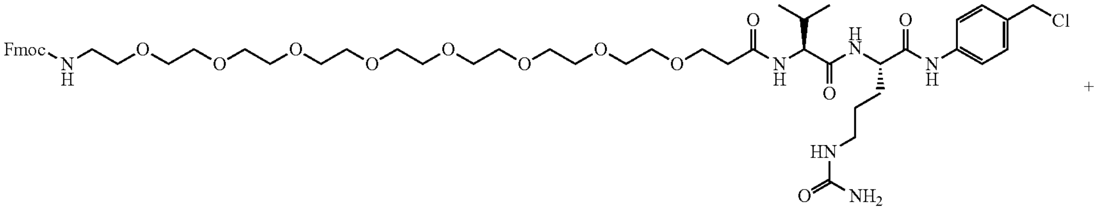
78
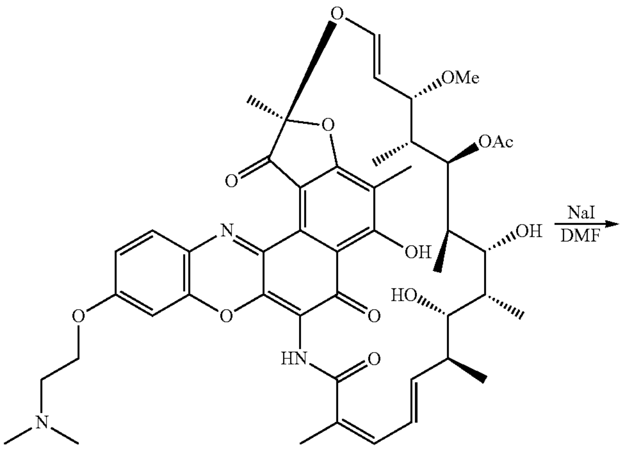
16a
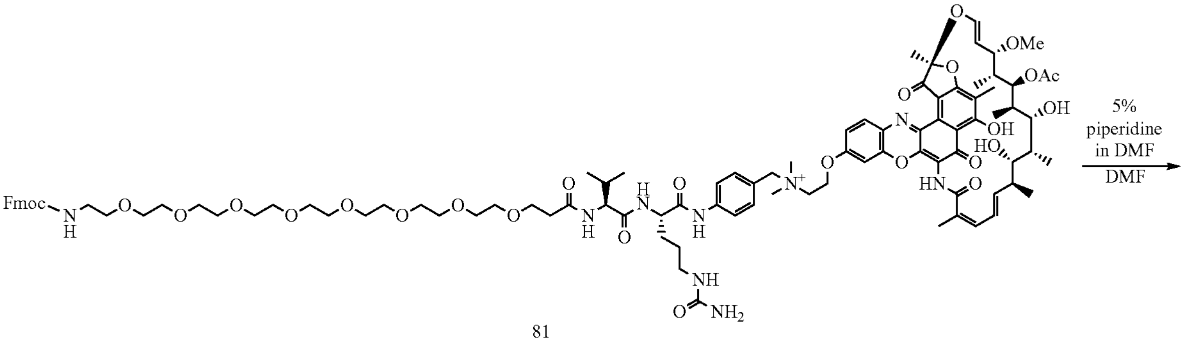
81
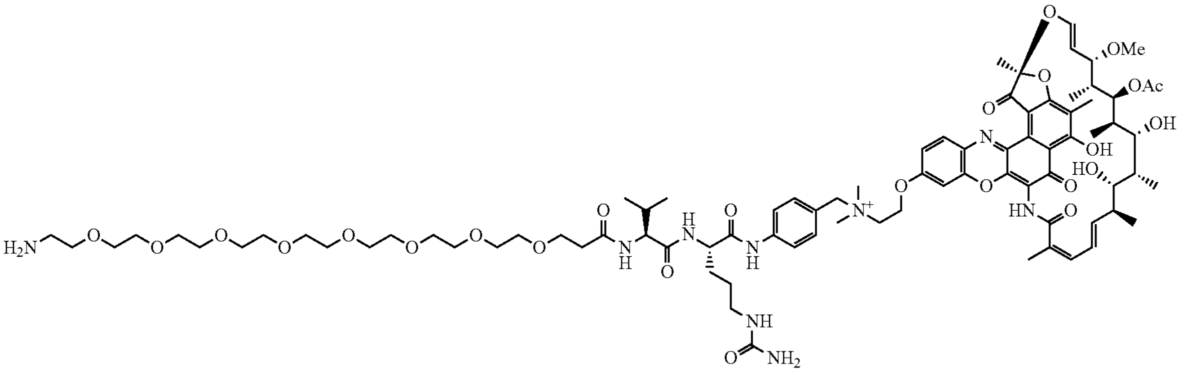
82

Compound 81: The mixture of 78 (43 mg, 0.0414 mmol, 1.0 eq), 16a (36 mg, 0.0412 mmol, 1.0 eq), and NaI (30 mg, 0.206 mmol, 5.0 eq.) in 2 dram vial was dissolved in 2 mL of anhydrous DMF. A catalytic amount (20 μL) of 0.5M DIEA solution in DMF was added via syringe. The mixture was heated at 55° C. in an oil bath overnight. The reaction was complete by LC/MS. The mixture was cooled in an ice-bath and diluted with 1 mL of water. After filtration, the dark crude mixture was purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized to afford 48 mg (62%) of 81 as a dark red solid. MS (ESI, pos.): calc'd for $C_{99}H_{132}N_9O_{27}^+$, 1878.92; found 1879.9 (M+H). $^1$H-NMR (500 MHz; DMSO-$d_6$): δ 10.35 (s, 1H), 8.86-8.81 (m, 1H), 8.34-8.33 (m, 1H), 7.93 (d, J=8.7 Hz, 1H), 7.89 (t, J=12.9 Hz, 3H), 7.75 (d, J=8.7 Hz, 3H), 7.68 (d, J=7.5 Hz, 2H), 7.48 (d, J=8.6 Hz, 2H), 7.40 (t, J=7.4 Hz, 2H), 7.31 (td, J=7.4, 0.8 Hz, 3H), 7.05-7.03 (m, 1H), 6.81-6.74 (m, 1H), 6.70-6.67 (m, 1H), 6.22-6.19 (m, 1H), 6.13-6.08 (m, 2H), 5.44 (s, 2H), 5.12-5.09 (m, 1H), 4.75 (dd, J=12.8, 8.4 Hz, 1H), 4.71-4.68 (m, 1H), 4.56 (s, 3H), 4.37-4.35 (m, 1H), 4.28 (d, J=6.9 Hz, 2H), 4.20 (dd, J=9.5, 2.8 Hz, 2H), 3.75 (s, 3H), 3.58 (d, J=5.5 Hz, 4H), 3.49-3.46 (m, 32H), 3.12 (d, J=6.0 Hz, 4H), 3.02 (s, 8H), 2.88 (d, J=0.4 Hz, 3H), 2.78-2.74 (m, 1H), 2.62 (quintet, J=1.8 Hz, 1H), 2.37-2.34 (m, 1H), 1.95-1.91 (m, 10H), 1.74 (s, 5H), 1.58 (s, 5H), 1.45-1.43 (m, 2H), 1.37-1.34 (m, 1H), 0.83 (dd, J=16.3, 6.8 Hz, 13H), 0.29 (s, 1H), 0.21-0.16 (m, 2H), 0.03-0.02 (m, 1H).

Compound 82: To a stirred solution of compound 81 (26 mg, 0.0138 mmol) of the preceding step in 1.5 mL of DMF was added a solution of 5% piperidine (500 μL) in DMF and the reaction was stirred at ambient temperature. After 50 min, the reaction was complete by LC/MS. The crude was then purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized to afford 17.6 mg (77%) of 82 as a reddish solid. MS (ESI, pos.): calc'd for $C_{84}H_{122}N_9O_{25}^+$, 1656.85 (free base); found 1658.7 (M+H), 1655.7 (M−H). $^1$H-NMR (500 MHz; DMSO-$d_6$): δ 10.25 (d, J=1.1 Hz, 1H), 8.26-8.17 (m, 1H), 7.89-7.87 (m, 1H), 7.75 (d, J=8.4 Hz, 3H), 7.49 (d, J=8.4 Hz, 2H), 7.08-7.05 (m, 1H), 6.12-6.09 (m, 1H), 6.04-6.01 (m, 1H), 5.42 (s, 2H), 5.13-5.09 (m, 1H), 4.76 (dd, J=12.6, 8.7 Hz, 1H), 4.70 (dq, J=3.2, 1.0 Hz, 1H), 4.57 (s, 3H), 4.37-4.36 (m, 1H), 4.23-4.20 (m, 1H), 3.75 (s, 2H), 3.58 (t, J=5.5 Hz, 3H), 3.48 (t, J=1.9 Hz, 32H), 3.14-3.07 (m, 3H), 3.02 (d, J=9.5 Hz, 10H), 2.96-2.93 (m, 4H), 2.91-2.87 (m, 4H), 2.78-2.76 (m, 1H), 2.63-2.62 (m, 3H), 2.38-2.35 (m, 1H), 1.95 (dd, J=3.4, 0.7 Hz, 8H), 1.92 (s, 3H), 1.83 (s, 3H), 1.68 (dd, J=2.2, 1.6 Hz, 1H), 1.59 (s, 5H), 1.45-1.43 (m, 2H), 1.38-1.35 (m, 1H), 1.22 (s, 1H), 0.84 (dt, J=12.6, 5.0 Hz, 10H), 0.79-0.77 (m, 2H), 0.06-0.01 (m, 1H).

Linker-payload compound 84 was prepared as shown in Scheme 30, below, and described below.

Scheme 30

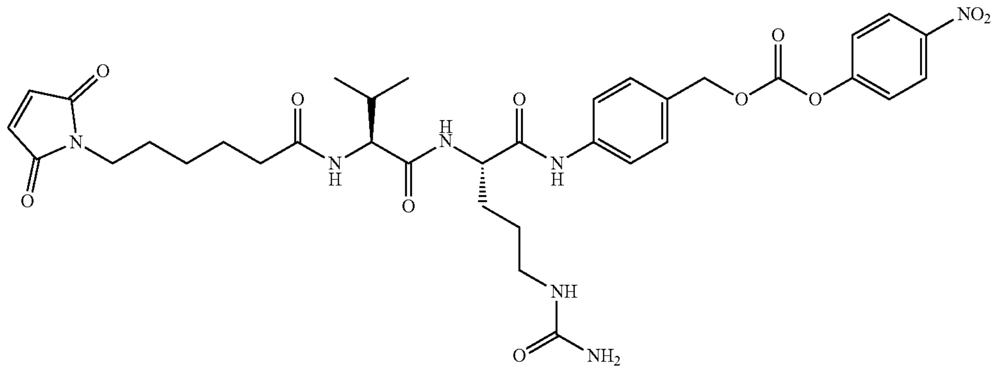

+

-continued

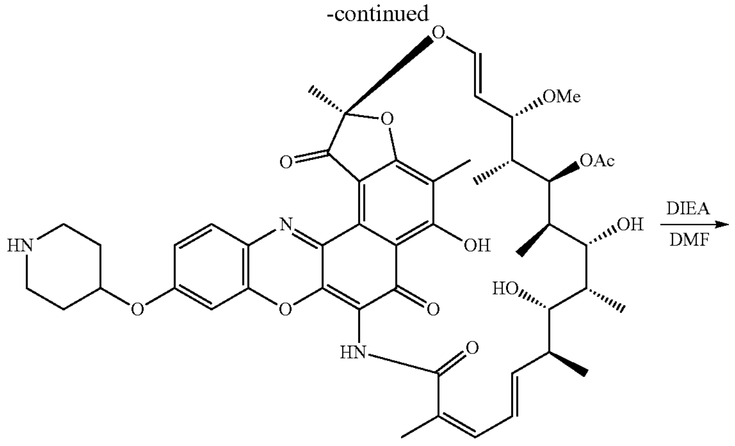

14

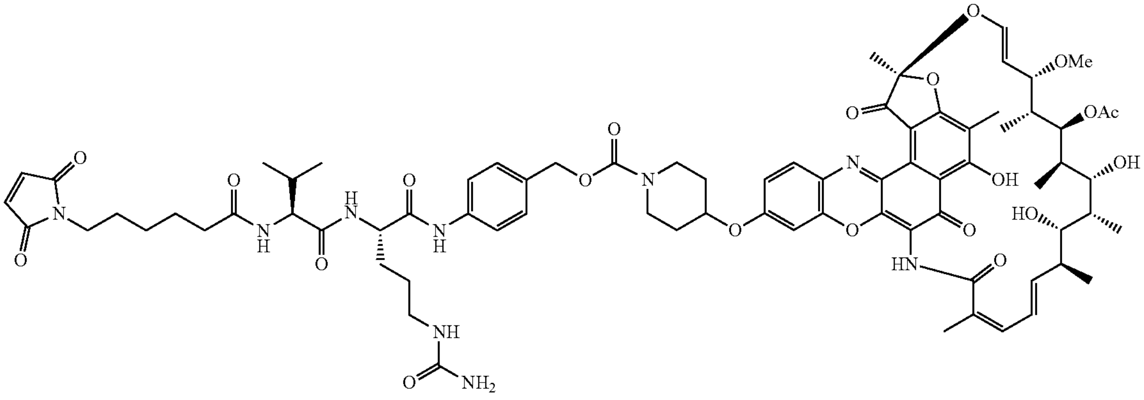

84

Compound 84: To a stirred solution of commercially available compound 83 (14 mg, 0.0186 mmol, 1.5 eq.) and compound 14 (11 mg, 0.0124 mmol, 1.0 eq.) in anhydrous 2.5 mL DMF was added DIEA (4.3 μL, 0.0248 mmol, 2.0 eq.) and the reaction was stirred at ambient temperature. After 15 min, the reaction was complete by LC/MS. The crude was then purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized to afford 11.4 mg (64%) of 84 as a reddish solid. MS (ESI, pos.): calc'd for $C_{77}H_{95}N_9O_{21}$, 1481.66; found 1482.6 (M+H), 1480.6 (M−H). $^1$H-NMR (500 MHz; DMSO-$d_6$): δ 9.99 (s, 1H), 8.08 (d, J=7.33 Hz, 1H), 7.87 (br. s., 1H), 7.80 (d, J=8.30 Hz, 1H), 7.60 (d, J=8.30 Hz, 2H), 7.24-7.34 (m, 3H), 7.21 (d, J=8.79 Hz, 1H), 7.00 (s, 2H), 5.95-6.00 (m, 1H), 5.81 (br. s., 1H), 5.40 (s, 2H), 5.02 (s, 2H), 4.91 (br. s., 1H), 4.79 (br. s., 1H), 4.35-4.41 (m, 1H), 4.19 (t, J=7.57 Hz, 2H), 3.73 (br. s., 2H), 3.38 (br. s., 2H), 3.08 (s, 3H), 3.10 (s, 3H), 2.82-3.05 (m, 6H), 2.78 (br. s., 1H), 2.64 (br. s., 1H), 2.54 (br. s., 1H), 2.37 (d, J=4.40 Hz, 6H), 2.25 (br. s., 1H), 2.02-2.23 (m, 6H), 1.93-2.02 (m, 9H), 1.90 (s, 2H), 1.67 (br. s., 5H), 1.60 (br. s., 4H), 1.43-1.55 (m, 6H), 1.28-1.43 (m, 2H), 1.14-1.28 (m, 3H), 0.72-0.95 (m, 6H), 0.67 (br. s., 2H), 0.07 (s, 1H).

Linker-payload compound 86 was prepared as shown in Scheme 31, below, and described below.

Scheme 31

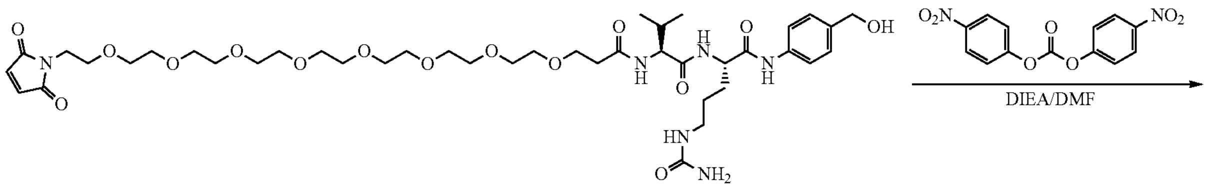

23

-continued

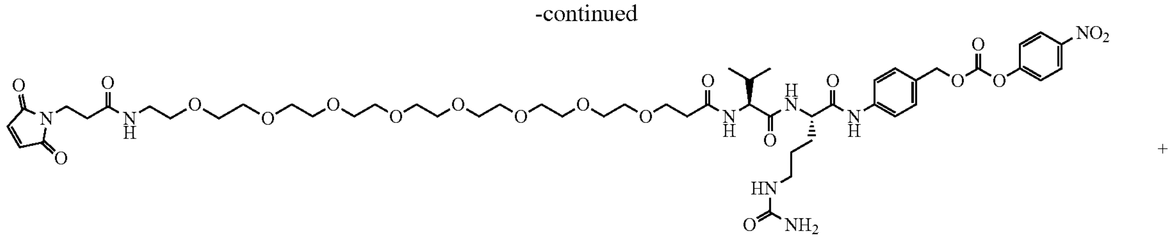

85

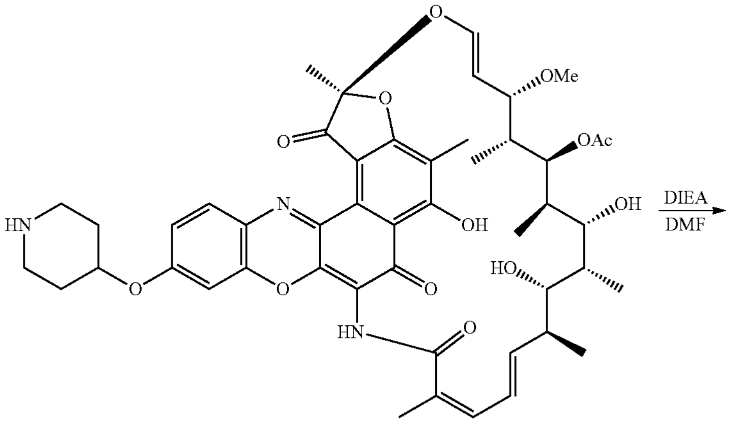

14

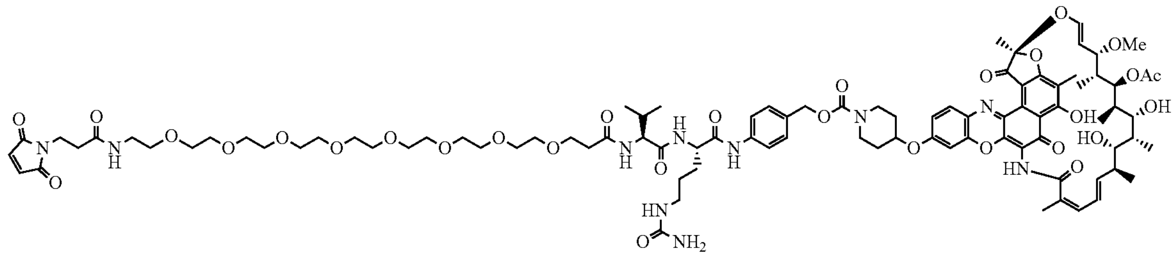

86

Compound 85: To a stirred solution of compound 23 (85 mg, 0.0894 mmol, 1.0 eq.) and bis(4-nitrophenyl) carbonate (82 mg, 0.2682 mmol, 3.0 eq.) under argon in anhydrous DMF (2.5 mL), was added DIEA (31 μL, 0.1788 mmol, 2.0 eq.) and the reaction was stirred at ambient temperature overnight. The reaction was complete by LC/MS analysis. The resulting mixture was purified directly on a 100 g C18 Aq. column via ISCO system (gradient elution: 10-100% MeCN in water, 0.05% acetic acid in both, over 30 min). The product-containing fractions were combined, frozen on dry ice, and lyophilized overnight giving the title compound 85 as a dark reddish solid. (68 mg, 69%). MS: calc'd for $C_{51}H_{74}N_8O_{20}$, 1118.50; found 1120.0 (M+H).

Compound 86: The title compound was prepared using linker-payload chemistry described in compound 84. To a stirred solution of compound 85 (12 mg, 0.01085 mmol, 1.2 eq.) and compound 14 (8 mg, 0.00905 mmol, 1.0 eq.) in anhydrous DMF (1.5 mL), was added with DIEA (3.2 μL, 0.0180 mmol, 2.0 eq.) and the reaction was stirred at ambient temperature. After 30 min, the reaction was complete to afford a desired product by LC/MS. The crude was then purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized to afford 12.5 mg (74%) of 86 as a reddish solid. MS (ESI, pos.): calc'd for $C_{93}H_{126}N_{10}O_{30}$, 1862.86; found 1863.8 (M+H), 1886.8 (M+Na). $^1$H-NMR (500 MHz; DMSO-$d_6$): δ 9.99 (s, 1H), 9.38 (s, 1H), 8.11 (d, J=7.33 Hz, 1H), 8.00 (t, J=5.37 Hz, 1H), 7.86 (d, J=8.79 Hz, 2H), 7.60 (d, J=8.30 Hz, 2H), 7.25-7.34 (m, 3H), 7.21 (d, J=8.79 Hz, 1H), 7.00 (s, 2H), 5.97 (t, J=5.62 Hz, 1H), 5.81 (br. s., 1H), 5.40 (s, 2H), 5.24 (br. s., 1H), 5.02 (s, 2H), 4.91 (br. s., 1H), 4.78 (br. s., 1H), 4.35-4.41 (m, 1H), 4.21-4.25 (m, 1H), 3.74 (br. s., 2H), 3.53-3.69 (m, 5H), 3.43-3.53 (m, 38H), 3.34-3.39 (m, 3H), 3.29 (br. s., 1H), 3.06-3.18 (m, 4H), 2.84-3.06 (m, 5H), 2.78 (br. s., 1H), 2.45-2.49 (m, 1H), 2.30-2.40 (m, 3H), 2.17 (br. s., 2H), 1.93-2.05 (m, 9H), 1.90 (s, 1H), 1.72 (br. s., 1H), 1.53-1.69 (m, 7H), 1.42-1.53 (m, 1H), 1.33-1.42 (m, 1H), 0.86 (d, J=6.84 Hz, 6H), 0.82 (d, J=6.84 Hz, 6H), 0.67 (br. s., 4H).

Linker-payload compound 89 was prepared as shown in Scheme 32, below, and described below.

Scheme 32
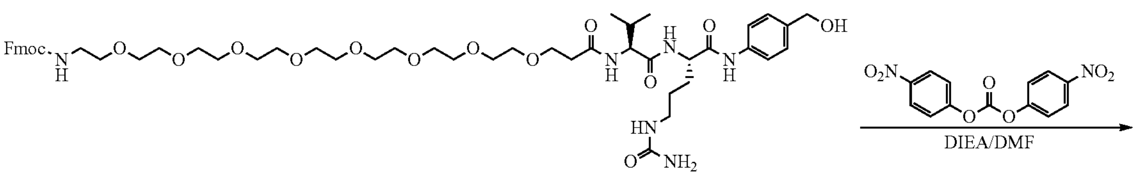
77
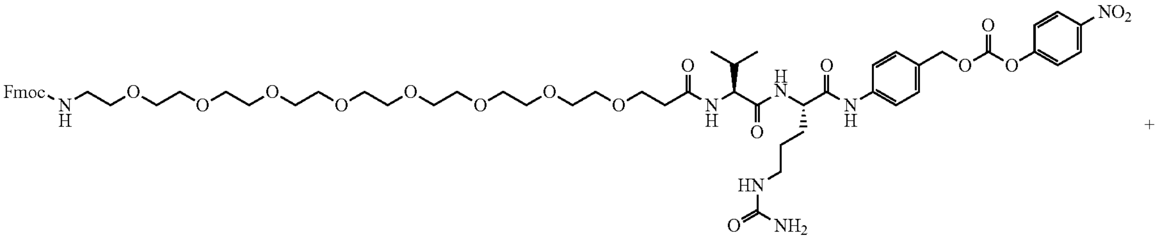
87
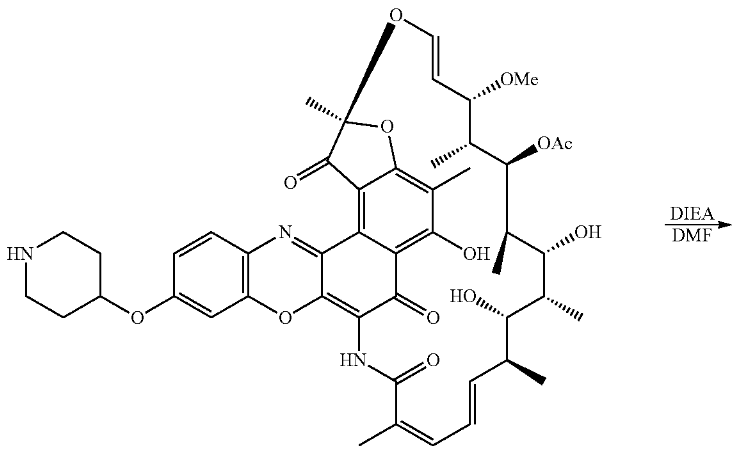
14
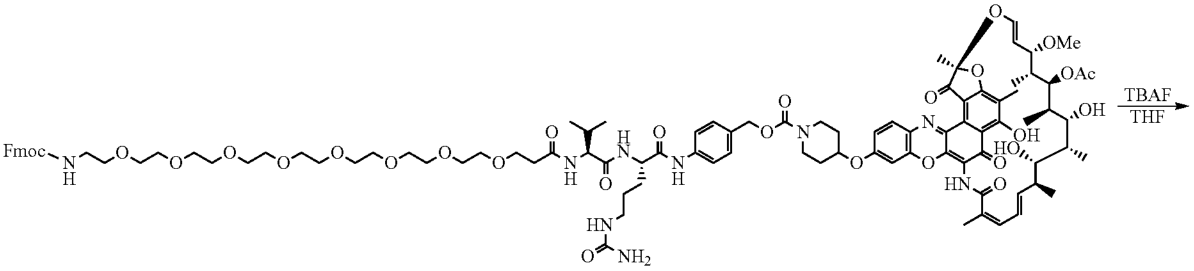
88
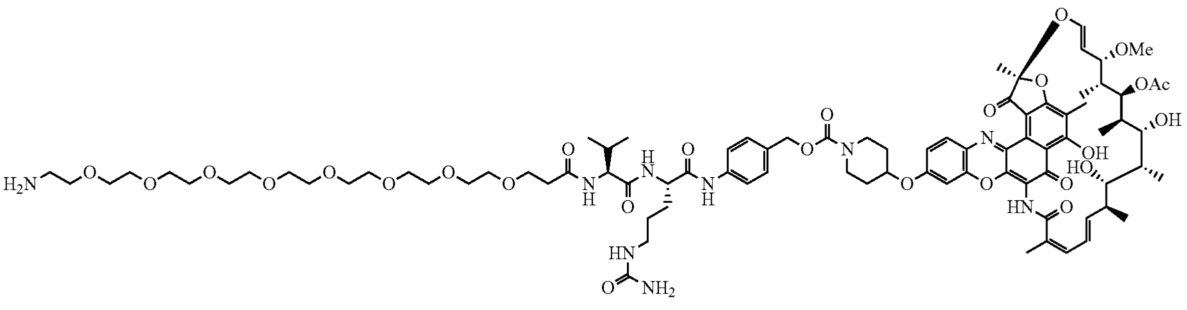
89

Compound 87: The title compound was prepared using the same procedure described for compound 85. To a stirred solution of compound 77 (56 mg, 0.0546 mmol, 1.0 eq.) and bis(4-nitrophenyl) carbonate (50 mg, 0.1638 mmol, 3.0 eq.) under argon in anhydrous DMF (1.5 mL), was added DIEA (19 μL, 0.1092 mmol, 2.0 eq.) to afford a dark reddish solid. (43 mg, 67%). MS: calc'd for $C_{59}H_{79}N_7O_{19}$, 1189.54; found 1190.5 (M+H), 1212.5 (M+Na).

Compound 88: The title compound was prepared using linker-payload chemistry described for compound 86. The solution of compound 87 (40.3 mg, 0.0339 mmol, 1.0 eq.) and compound 14 (30 mg, 0.0339 mmol, 1.0 eq.) in anhydrous DMF (3 mL) was stirred at room temperature to afford 50.7 mg (77%) of 88 as a reddish solid. MS: calc'd for $C_{101}H_{131}N_9O_{29}$, 1933.91; found 1935.7 (M+H), 1957.8 (M+Na).

Compound 89: To a stirred solution of compound 88 (34 mg, 0.0175 mmol, 1.0 eq.) in anhydrous THF (2.5 mL) was added TBAF (1.0 M solution in THF, 35 μL, 0.0351 mmol, 2.0 eq.) and the reaction was stirred at ambient temperature. After 30 min, the reaction was complete by LC/MS. The crude was purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized for 30 h to afford 23.5 mg (79%) of 89 as a reddish solid. MS (ESI, pos.): calc'd for $C_{86}H_{121}N_9O_{27}$, 1711.84; found 1713.7 (M+H), 1711.6 (M−H). $^1H$-NMR (500 MHz; DMSO-$d_6$): 9.99 (s, 1H), 8.11 (d, J=7.33 Hz, 1H), 7.83-7.89 (m, 2H), 7.58-7.62 (m, J=8.79 Hz, 2H), 7.29-7.33 (m, J=8.30 Hz, 2H), 7.18 (br. s., 1H), 5.97 (t, J=5.37 Hz, 1H), 5.40 (s, 2H), 5.02 (s, 2H), 4.89 (br. s., 1H), 4.76-4.83 (m, 1H), 4.35-4.41 (m, 1H), 4.21-4.25 (m, 1H), 3.73 (br. s., 2H), 3.44-3.68 (m, 39H), 3.38 (t, J=5.62 Hz, 3H), 3.29 (br. s., 2H), 2.90-3.14 (m, 7H), 2.75-2.81 (m, 1H), 2.68 (t, J=5.62 Hz, 2H), 2.64 (d, J=1.95 Hz, 1H), 2.45-2.48 (m, 1H), 2.35-2.41 (m, 2H), 2.15 (br. s., 3H), 1.92-2.02 (m, 10H), 1.90 (s, 1H), 1.63-1.72 (m, 5H), 1.59 (d, J=9.28 Hz, 3H), 1.45 (d, J=6.84 Hz, 1H), 1.37 (dd, J=6.35, 16.12 Hz, 1H), 0.73-0.93 (m, 13H), 0.68 (br. s., 3H).

Example 20: Broth Minimum Inhibitory Concentration (MIC) Assay 1

To test the potency of rifamycin analogs of the disclosure in vitro, a broth growth inhibition assay was developed. For the assay, *S. aureus* NRS384 was grown in Tryptic Soy Broth (TSB) overnight, then sub-cultured 1:50 in fresh TSB and grown for an additional two hours. The culture was then pelleted via centrifugation and washed twice in PBS. The culture was then diluted to $1\times10^4$ cfu/mL in TSB and 50 μL of the suspension was added per well to a 96 well microtiter dish in duplicate. A dilution series of the indicated antibiotic (an analog according to the disclosure or a previously known analog Rifampicin) was added 1:1 for a final starting concentration of $1\times10^{-5}$ M with 1:3 dilutions. The plates were incubated at 37° C. with shaking for 24h and then the OD600 nm was read on a Spectramax i3 Minimax 300.

The reagents used and lot numbers are shown in Table 4, below.

TABLE 4

Reagents and Lot Numbers for MIC Assay

| Reagent | Vendor | Catalogue # | Lot |
|---|---|---|---|
| PBS | Gibco | 20012-043 | 2003838 |
| *S. aureus* NRS384 | BEI resources | NR-46070 | |
| Tryptic Soy Broth (TSB) | Teknova | T1525 | T014420G1801 |
| Dilution plates | Greiner Bio one | 780261 | B17073CP |

The lowest concentrations that inhibited growth of *S. aureus* (minimum inhibitory concentration, MIC) are listed in Table 5. A plot of the *S. aureus* inhibition assay conducted with rifamycin analogs according to the disclosure is shown as FIG. 1.

TABLE 5

Minimum inhibitory concentration (MIC) of antibiotics in a broth growth inhibition assay.

| Rifamycin analog tested | Mol. Wt. (Da) | *S. aureus* Broth MIC (M) |
|---|---|---|
| Rifampicin | 823 | 4.6E−09 |
| 1a | 815 | 1.4E−08 |
| 1b | 890 | 1.2E−07 |
| 1d | 813 | 3.7E−07 |
| 14 | 883 | 4.1E−08 |
| 16a | 823 | 1.5E−09 |
| 16d | 843 | 4.1E−08 |
| 16e | 858 | 4.6E−09 |

As shown in Table 5, all rifamycin analogs according to the disclosure are effective at inhibiting growth of *aureus* at sub-micromolar to nanomolar concentrations. Analog 16a inhibited growth of *S. aureus* more potently than rifampicin with an MIC of $1.5\times10^{-9}$M.

Example 21: Intracellular Killing Assay 1

The rifamycin analog compounds' activity against *S. aureus* was tested in an intracellular "killing" assay.

The reagents used and lot numbers are shown in Table 6, below.

TABLE 6

Reagents and Lot Numbers for Intracellular Assay

| Reagent | Vendor | Catalogue # | Lot |
|---|---|---|---|
| TSB | Teknova | T1525 | T152517E1701 |
| PBS | Gibco | 20012-043 | 1951145 |
| Triton X-100 | Sigma | TX1568-1 | |
| RPMI | Gibco | 11875-093 | 1989237 |
| FBS | Gibco | 172667 | 138252-100 |
| PMA | Sigma | P8139 | MkBV849TV |
| Costa 96 well plate | Corning | 3904 | 16618025 |
| TSA plates | Teknova | T0144 | T014420G1801 |
| Pen/Strep | Gibco | 15140-122 | 1953095 |
| Dilution plates | Greiner Bio one | 780261 | B17073CP |
| Gentamicin | Gibco | 10131-035 | 1729122 |

THP-1 monocytic cell line was grown in media (RMPI+10% FBS+1% Penicillin/Streptomycin), then seeded at a density of 1e5 cells/well in a 96 well plate and differentiated into macrophages for three days prior to infection using 200 nM PMA. An overnight culture of *S. aureus* NRS384 was grown in RPMI, washed twice with PBS and resuspended at 1e7 cfu/mL in PBS. THP-1 were washed with warm media (RMPI without FBS) to remove the Penicillin/Streptomycin and then infected with the *S. aureus* suspension at a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing 2× with warm media and remaining extracellular *S. aureus* were killed by addition of media containing gentamicin (50 ug/mL). After 1 h, media was aspirated and the indicated compound was added to infected macrophages in media containing 50 pg/mL gentamicin to prevent extracellular growth of *S. aureus*. After 2h, plates were washed 2× with warm RPMI without FBS, and 100 ul of THP-1 lysis buffer (0.1% Triton in PBS) was added to each well. *S. aureus* survival was enumerated by colony forming units through serial dilution and plating onto TSA.

Figure 2:
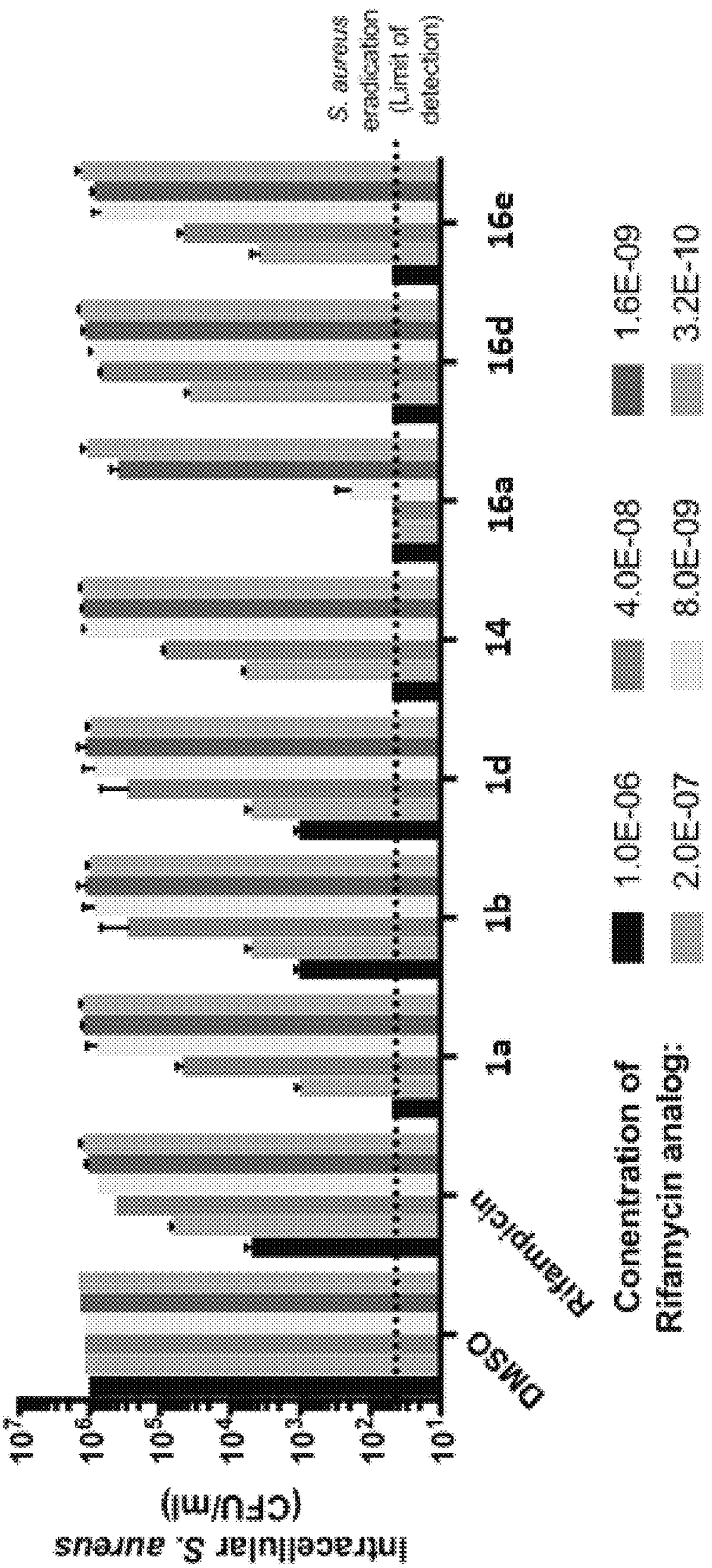
FIG. 2 is a bar graph of the results of the *S. aureus* intracellular killing assay conducted with rifamycin analogs according to the disclosure.
Figure 3:
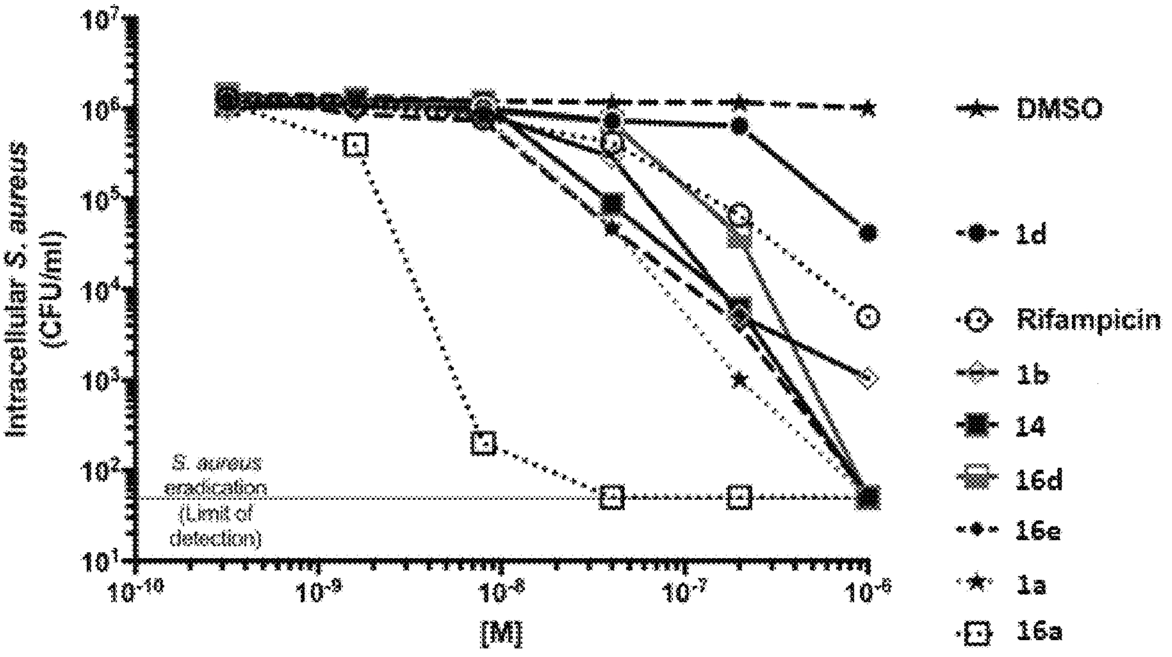
FIG. 3 is a plot of the results of the *S. aureus* intracellular killing assay conducted with rifamycin analogs according to the disclosure.

The results of the intracellular killing assay are shown in Table 7 and FIGS. 2 and 3. The minimum inhibitory concentration (MIC) corresponds to the lowest concentration of each compound that resulted in intracellular *S. aureus* eradication.

TABLE 7

Results of Intracellular Killing Assay

| Rifamycin Analog Tested | Intracellular killing MIC |
|---|---|
| Rifampicin | >1.0E−06 |
| 1a | 1.0E−06 |
| 1b | >1.0E−06 |
| 1d | >1.0E−06 |
| 14 | 1.0E−06 |
| 16a | 4.0E−08 |
| 16d | 1.0E−06 |
| 16e | 1.0E−06 |

As the above table and FIGS. 2 and 3 demonstrate, compounds 1a, 14, 16a, 16d, and 16e had increased intracellular *S. aureus* killing capacity compared to rifampicin, with compound 16a having the highest activity.

Example 22: MSR1 Antibody-Drug Conjugation

The MSR1 antibody (1-10 mg/ml) in 50 mM HEPES, 150 mM NaCl, pH 7.5, was treated with 1 mM dithiothreitol at 37° C. for 30 min. After gel filtration (G-25, pH 4.5 sodium acetate), the maleimido linker payload derivative compound 25 (1.2 equivalents/SH group) in DMSO (10 mg/ml) was added to the reduced antibody and the mixture adjusted to pH 7.0 with 1 M HEPES (pH 7.4). After 1 h the reaction was quenched with excess N-ethyl maleimide. The conjugates were purified using PBS with 5% glycerol by size exclusion chromatography and sterile filtered. Protein concentrations and payload to antibody ratios were determined by UV spectral analysis. Size-exclusion HPLC established that all conjugates used were >90% monomeric, and RP-HPLC established that there was <1% unconjugated linker payload. All conjugated antibodies were analyzed by HIC for linker payload loading values. Payload to antibody ratios are reported in Table 8.

TABLE 8

Percent yield and payload to antibody ratios for each of the antibody drug conjugates

| Antibody | Yield (%) | DAR (HIC) |
|---|---|---|
| MSR1 ncADC H1H21234N-N297Q-25 | 50 | 3 |
| Isotype Control Antibody N297Q-25 | 50 | 2 |

Characterization of Conjugates by Hydrophobic Interaction Chromatography (HIC)

To determine the loading of the linker-payloads on the antibody, the conjugates were run on Agilent 1260 using a TSK-NPR Butyl HIC column using a linear gradient of 1M potassium phosphate pH 8.5 to water over 60 min. The payload loading was determined by integration of peak areas corresponding to the species of conjugated and unconjugated antibody.

Example 23: Generation of Anti-MSR1 Antibodies

Anti-MSR1 antibodies were obtained by immunizing a genetically engineered mouse comprising DNA encoding human immunoglobulin heavy and kappa light chain variable regions with an immunogen comprising recombinant human MSR1 extracellular domain fused to an N-terminal nonahistidine tag (SEQ ID NO: 688) (R&D Systems, Catalog #2708-MS-050, Minneapolis, MN). The mice used for the immunizations were Velocimmune mice or mice which expressed a “universal light chain” (“ULC” mice). Antibodies produced ULC mouse have different heavy chain variable regions but essentially identical light chain variable domains.

The antibody immune response was monitored by a MSR1-specific immunoassay. When a desired immune response was achieved splenocytes were harvested and fused with mouse myeloma cells to preserve their viability and form hybridoma cell lines. The hybridoma cell lines were screened and selected to identify cell lines that produce MSR1-specific antibodies. Using this technique several anti-MSR1 chimeric antibodies (i.e., antibodies possessing human variable domains and mouse constant domains) were obtained. In addition, several fully human anti-MSR1 antibodies were isolated directly from antigen-positive B cells without fusion to myeloma cells, as described in US 2007/0280945A1.

Certain biological properties of the exemplary anti-MSR1 antibodies generated in accordance with the methods of this Example are described in detail in the Examples set forth below.

Example 24: Heavy and Light Chain Variable Region Amino Acid and Nucleic Acid Sequences Table 9 sets forth the amino acid sequence identifiers of the heavy and light chain variable regions and CDRs of selected anti-MSR1 antibodies described herein. The corresponding nucleic acid sequence identifiers are set forth in Table 10.

TABLE 9

| Antibody Designation | SEQ ID NOs: HCVR | HCDR1 | HCDR2 | HCDR3 | LCVR | LCDR1 | LCDR2 | LCDR3 |
|---|---|---|---|---|---|---|---|---|
| Amino Acid Sequence Identifiers | | | | | | | | |
| H1H21227N | 2 | 4 | 6 | 8 | 10 | 12 | 14 | 16 |
| H1H21228N | 18 | 20 | 22 | 24 | 26 | 28 | 30 | 32 |
| H1H21231N | 34 | 36 | 38 | 40 | 42 | 44 | 46 | 48 |
| H1H21234N | 50 | 52 | 54 | 56 | 58 | 60 | 62 | 64 |
| H1H21235N | 66 | 68 | 70 | 72 | 74 | 76 | 78 | 80 |
| H1H25685N | 82 | 84 | 86 | 88 | 90 | 92 | 94 | 96 |
| H1H25690N | 98 | 100 | 102 | 104 | 106 | 108 | 110 | 112 |
| H1H25695N | 114 | 116 | 118 | 120 | 122 | 124 | 126 | 128 |
| H1H25700N | 130 | 132 | 134 | 136 | 138 | 140 | 142 | 144 |
| H1H27729P | 146 | 148 | 150 | 152 | 154 | 156 | 158 | 160 |
| H1H27731P | 162 | 164 | 166 | 168 | 170 | 172 | 174 | 176 |
| H1H27732P | 178 | 180 | 182 | 184 | 186 | 188 | 190 | 192 |
| H1H27734P | 194 | 196 | 198 | 200 | 202 | 204 | 206 | 208 |
| H1H27736P | 210 | 212 | 214 | 216 | 218 | 220 | 222 | 224 |
| H1H27739P | 226 | 228 | 230 | 232 | 234 | 236 | 238 | 240 |
| H1H27747P | 242 | 244 | 246 | 248 | 250 | 252 | 254 | 256 |
| H1H27749P | 258 | 260 | 262 | 264 | 266 | 268 | 270 | 272 |
| H1H27751P | 274 | 276 | 278 | 280 | 282 | 284 | 286 | 288 |
| H1H27754P | 290 | 292 | 294 | 296 | 298 | 300 | 302 | 304 |
| H1H27756P | 306 | 308 | 310 | 312 | 314 | 316 | 318 | 320 |
| H1H27760P2 | 322 | 324 | 326 | 328 | 90 | 92 | 94 | 96 |
| H1H27761P2 | 330 | 332 | 334 | 336 | 90 | 92 | 94 | 96 |
| H1H27762P2 | 338 | 340 | 342 | 344 | 90 | 92 | 94 | 96 |
| H1H27766P2 | 346 | 348 | 350 | 352 | 90 | 92 | 94 | 96 |
| H1H27771P2 | 354 | 356 | 358 | 360 | 362 | 364 | 366 | 368 |
| H1xH27759P2 | 370 | 372 | 374 | 376 | 90 | 92 | 94 | 96 |
| H1xH27773P2 | 378 | 380 | 382 | 384 | 362 | 364 | 366 | 368 |
| H1xH27778P2 | 386 | 388 | 390 | 392 | 362 | 364 | 366 | 368 |
| H1xH29273P2 | 394 | 396 | 397 | 400 | 90 | 92 | 94 | 96 |
| H1xH29282P2 | 402 | 404 | 406 | 408 | 90 | 92 | 94 | 96 |
| H1xH29283P2 | 410 | 412 | 414 | 416 | 90 | 92 | 94 | 96 |
| H2M21229N | 420 | 422 | 424 | 426 | 428 | 430 | 432 | 434 |
| H2M21230N | 436 | 438 | 440 | 442 | 444 | 446 | 448 | 450 |
| H2M21232N | 452 | 454 | 456 | 458 | 460 | 462 | 464 | 466 |

TABLE 10

| Antibody Designation | SEQ ID NOs: HCVR | HCDR1 | HCDR2 | HCDR3 | LCVR | LCDR1 | LCDR2 | LCDR3 |
|---|---|---|---|---|---|---|---|---|
| Nucleic Acid Sequence Identifiers | | | | | | | | |
| H1H21227N | 1 | 3 | 5 | 7 | 9 | 11 | 13 | 15 |
| H1H21228N | 17 | 19 | 21 | 23 | 25 | 27 | 29 | 31 |
| H1H21231N | 33 | 35 | 37 | 39 | 41 | 43 | 45 | 47 |
| H1H21234N | 49 | 51 | 53 | 55 | 57 | 59 | 61 | 63 |
| H1H21235N | 65 | 67 | 69 | 71 | 73 | 75 | 77 | 79 |
| H1H25685N | 81 | 83 | 85 | 87 | 89 | 91 | 93 | 95 |
| H1H25690N | 97 | 99 | 101 | 103 | 105 | 107 | 109 | 111 |
| H1H25695N | 113 | 115 | 117 | 119 | 121 | 123 | 125 | 127 |
| H1H25700N | 129 | 131 | 133 | 135 | 137 | 139 | 141 | 143 |
| H1H27729P | 145 | 147 | 149 | 151 | 153 | 155 | 157 | 159 |
| H1H27731P | 161 | 163 | 165 | 167 | 169 | 171 | 173 | 175 |
| H1H27732P | 177 | 179 | 181 | 183 | 185 | 187 | 189 | 191 |
| H1H27734P | 193 | 195 | 197 | 199 | 201 | 203 | 205 | 207 |
| H1H27736P | 209 | 211 | 213 | 215 | 217 | 219 | 221 | 223 |
| H1H27739P | 225 | 227 | 229 | 231 | 233 | 235 | 237 | 239 |
| H1H27747P | 241 | 243 | 245 | 247 | 249 | 251 | 253 | 255 |
| H1H27749P | 257 | 259 | 261 | 263 | 265 | 267 | 269 | 271 |
| H1H27751P | 273 | 275 | 277 | 279 | 281 | 283 | 285 | 287 |
| H1H27754P | 289 | 291 | 293 | 295 | 297 | 299 | 301 | 303 |
| H1H27756P | 305 | 307 | 309 | 311 | 313 | 315 | 317 | 319 |
| H1H27760P2 | 321 | 323 | 325 | 327 | 89 | 91 | 93 | 95 |
| H1H27761P2 | 329 | 331 | 333 | 335 | 89 | 91 | 93 | 95 |
| H1H27762P2 | 337 | 339 | 341 | 343 | 89 | 91 | 93 | 95 |
| H1H27766P2 | 345 | 347 | 349 | 351 | 89 | 91 | 93 | 95 |
| H1H27771P2 | 353 | 355 | 357 | 359 | 361 | 363 | 365 | 367 |
| H1xH27759P2 | 369 | 371 | 373 | 375 | 89 | 91 | 93 | 95 |
| H1xH27773P2 | 377 | 379 | 381 | 383 | 361 | 363 | 365 | 367 |

TABLE 10-continued

| Nucleic Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1xH27778P2 | 385 | 387 | 389 | 391 | 361 | 363 | 365 | 367 |
| H1xH29273P2 | 393 | 395 | 397 | 399 | 89 | 91 | 93 | 95 |
| H1xH29282P2 | 401 | 403 | 405 | 407 | 89 | 91 | 93 | 95 |
| H1xH29283P2 | 409 | 411 | 413 | 415 | 89 | 91 | 93 | 95 |
| H2M21229N | 419 | 421 | 423 | 425 | 427 | 429 | 431 | 433 |
| H2M21230N | 435 | 437 | 439 | 441 | 443 | 445 | 447 | 449 |
| H2M21232N | 451 | 453 | 455 | 457 | 459 | 461 | 463 | 465 |

Antibodies are typically referred to herein according to the following nomenclature: Fc prefix (e.g. "H1H," "H2aM," etc.), followed by a numerical identifier (e.g. "21227," "21228," "21231," etc.), followed by a "P," "N," or "P2" suffix, as shown in Tables 9 and 10. Thus, according to this nomenclature, an antibody may be referred to herein as, e.g., "H1H21227N," "H2aM21228N," "H1H27729P," "H1H27760P2," etc. The prefix on the antibody designations used herein indicate the particular Fc region isotype of the antibody. In particular, an "H1H" antibody has a human IgG1 Fc (all variable regions are fully human as denoted by the first 'H' in the antibody designation), while an "H2aM" antibody has a mouse IgG2a Fc. As will be appreciated by a person of ordinary skill in the art, an antibody having a particular Fc isotype can be converted to an antibody with a different Fc isotype (e.g., an antibody with a mouse IgG4 Fc can be converted to an antibody with a human IgG1, etc.), but in any event, the variable domains (including the CDRs)—which are indicated by the numerical identifiers shown in Tables 9 and 10—will remain the same, and the binding properties are expected to be identical or substantially similar regardless of the nature of the Fc domain.

Antibody Modifications. Three anti-MSR1 antibodies described in Example 23 (21227N, 21231N, 21234N) were produced with the original human Fcγ portion, as well as a version with an N297Q single point mutation for all three anti-MSR1 antibodies. All other antibodies described herein were made with an N297Q single point mutation in human Fcγ portion. A third version, an N297D mutation was produced for the 21227N antibody only.

Example 25: Surface Plasmon Resonance Derived Binding Affinities and Kinetic Constants of Human Monoclonal Anti-MSR1 Antibodies Binding affinities and kinetic constants of human anti-MSR1 antibodies for different MSR1 reagents were determined by real-time surface plasmon resonance (Biacore 4000). All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore CM4 sensor chip surface was first derivatized by amine coupling with the goat anti-human Fcγ specific polyclonal antibody (Jackson ImmunoResearch Laboratories, Cat #BR-1008-39) to capture anti-MSR1 monoclonal antibodies. Binding studies were performed on human MSR1 extracellular domain expressed with a N-terminal nonahistidine tag (SEQ ID NO: 688) (His9-hMSR1; R&D Systems, Cat #2708-MS), and monkey MSR1 extracellular domain expressed with a N-terminal hexahistidine-myc-myc tag ("hexahistidine" disclosed as SEQ ID NO: 689) (HMM-mfMSR1; SEQ ID NO: 418). Different concentrations of His9-hMSR1 and HMM-mfMSR1 (100 nM-3.7 nM; 3-fold serial dilution) were first prepared in HBS-ET running buffer and were injected over anti-human Fcγ captured anti-MSR1 monoclonal antibody surface for 3 minutes at a flow rate of 30 μL/minute, while the dissociation of monoclonal antibody bound MSR1 reagent was monitored for 10 minutes in HBS-ET running buffer.

The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\text{min}) = \frac{\ln(2)}{60*kd}$$

Binding kinetics parameters for His9-hMSR1 or HMM-mfMSR1 binding to different anti-MSR1 monoclonal antibodies at 25° C. and 37° C. are shown in Tables 11 and 12, respectively.

TABLE 11

| Biacore Binding Affinities of Anti-MSR1 mAbs at 25° C. Binding at 25° C./Antibody-Capture Format | | | | | |
|---|---|---|---|---|---|
| Antibody | Analyte | ka ($M^{-1}s^{-1}$) | kd ($s^{-1}$) | $K_D$ (Molar) | t½ (min) |
| H1H21227N-N297Q | His9-hMSR1 | 1.23E+06 | 4.89E−05 | 3.97E−11 | 236 |
| | HMM-mfMSR1 | 1.36E+06 | 7.51E−05 | 5.53E−11 | 154 |
| H1H21227N-N297D | His9-hMSR1 | 1.14E+06 | 3.79E−05 | 3.33E−11 | 305 |
| | HMM-mfMSR1 | 1.35E+06 | 4.03E−05 | 2.99E−11 | 287 |
| H1H21231N-N297Q | His9-hMSR1 | 3.99E+05 | 5.88E−05 | 1.47E−10 | 196 |
| | HMM-mfMSR1 | 2.40E+05 | 9.03E−05 | 3.76E−10 | 128 |
| H1H21234N-N297Q | His9-hMSR1 | 4.97E+05 | 1.00E−05* | 2.01E−11 | 1155 |
| | HMM-mfMSR1 | 4.08E+05 | 1.95E−05 | 4.66E−11 | 593 |
| H1H27729P- | His9-hMSR1 | 1.97E+05 | 1.07E−03 | 5.45E−09 | 11 |

TABLE 11-continued

Biacore Binding Affinities of Anti-MSR1 mAbs at 25° C.
Binding at 25° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| N297Q | HMM-mfMSR1 | 2.69E+05 | 2.12E−03 | 7.90E−09 | 5 |
| H1H27731P- | His9-hMSR1 | 1.29E+05 | 2.24E−05 | 1.74E−10 | 515 |
| N297Q | HMM-mfMSR1 | 9.82E+04 | 4.69E−05 | 4.77E−10 | 247 |
| H1H27732P- | His9-hMSR1 | 1.25E+05 | 1.00E−05* | 8.01E−11 | 1155 |
| N297Q | HMM-mfMSR1 | 1.28E+05 | 3.17E−05 | 2.48E−10 | 364 |
| H1H27734P- | His9-hMSR1 | 4.20E+05 | 1.11E−03 | 2.64E−09 | 10 |
| N297Q | HMM-mfMSR1 | 4.23E+05 | 2.91E−03 | 6.88E−09 | 4 |
| H1H27736P- | His9-hMSR1 | 5.15E+05 | 2.31E−04 | 4.48E−10 | 50 |
| N297Q | HMM-mfMSR1 | 4.64E+05 | 5.87E−04 | 1.27E−09 | 20 |
| H1H27739P- | His9-hMSR1 | 3.75E+05 | 1.03E−03 | 2.74E−09 | 11 |
| N297Q | HMM-mfMSR1 | 3.52E+05 | 1.44E−04 | 4.10E−10 | 80 |
| H1H27747P- | His9-hMSR1 | 2.43E+05 | 6.52E−04 | 2.69E−09 | 18 |
| N297Q | HMM-mfMSR1 | 2.31E+05 | 8.74E−04 | 3.78E−09 | 13 |
| H1H27749P- | His9-hMSR1 | 3.18E+05 | 1.76E−05 | 5.54E−11 | 656 |
| N297Q | HMM-mfMSR1 | 2.49E+05 | 4.27E−05 | 1.71E−10 | 271 |
| H1H27751P- | His9-hMSR1 | 1.78E+06 | 3.05E−04 | 1.72E−10 | 38 |
| N297Q | HMM-mfMSR1 | 7.44E+05 | 7.49E−04 | 1.01E−09 | 15 |
| H1H27754P- | His9-hMSR1 | 2.90E+05 | 1.00E−05* | 3.44E−11 | 1155 |
| N297Q | HMM-mfMSR1 | 2.35E+05 | 1.76E−05 | 7.50E−11 | 657 |
| H1H27756P- | His9-hMSR1 | 3.00E+05 | 1.22E−04 | 4.06E−10 | 94 |
| N297Q | HMM-mfMSR1 | 3.58E+05 | 2.44E−03 | 6.81E−09 | 5 |
| H1H27760P- | His9-hMSR1 | 4.54E+05 | 9.09E−04 | 2.00E−09 | 13 |
| N297Q | HMM-mfMSR1 | 3.63E+05 | 7.01E−04 | 1.93E−09 | 16 |
| H1H27759P- | His9-hMSR1 | 5.99E+05 | 1.22E−03 | 2.03E−09 | 9 |
| N297Q | HMM-mfMSR1 | 4.17E+05 | 9.19E−04 | 2.20E−09 | 13 |
| H1H27761P- | His9-hMSR1 | 3.12E+05 | 5.10E−04 | 1.63E−09 | 23 |
| N297Q | HMM-mfMSR1 | 3.18E+05 | 5.97E−04 | 1.88E−09 | 19 |
| H1H27762P- | His9-hMSR1 | 9.89E+05 | 1.83E−03 | 1.85E−09 | 6 |
| N297Q | HMM-mfMSR1 | 1.25E+06 | 1.99E−03 | 1.59E−09 | 6 |
| H1H27766P- | His9-hMSR1 | 2.34E+05 | 1.86E−05 | 7.96E−11 | 620 |
| N297Q | HMM-mfMSR1 | 1.57E+05 | 7.94E−05 | 5.06E−10 | 145 |
| H1H27771P- | His9-hMSR1 | 6.86E+05 | 9.58E−04 | 1.40E−09 | 12 |
| N297Q | HMM-mfMSR1 | 5.19E+05 | 5.26E−03 | 1.01E−08 | 2.2 |
| H1H27773P- | His9-hMSR1 | 6.58E+05 | 2.63E−03 | 3.99E−09 | 4 |
| N297Q | HMM-mfMSR1 | 6.43E+05 | 1.96E−03 | 3.05E−09 | 6 |
| H1H27778P- | His9-hMSR1 | 5.75E+05 | 3.94E−04 | 6.85E−10 | 29 |
| N297Q | HMM-mfMSR1 | 4.67E+05 | 1.36E−03 | 2.91E−09 | 8 |
| H1H21234N | His9-hMSR1 | 6.04E+05 | 1.00E−05* | 1.66E−11 | 1155 |
| | HMM-mfMSR1 | 3.36E+05 | 1.00E−05* | 2.98E−11 | 1155 |
| H1H21231N | His9-hMSR1 | 4.77E+05 | 1.00E−05* | 2.10E−11 | 1155 |
| | HMM-mfMSR1 | 2.74E+05 | 6.39E−05 | 2.33E−10 | 181 |
| H1H21227N | His9-hMSR1 | 1.20E+06 | 1.44E−05 | 1.20E−11 | 800 |
| | HMM-mfMSR1 | 1.27E+06 | 4.41E−05 | 3.48E−11 | 262 |
| Non-binding | His9-hMSR1 | NB$ | NB$ | NB$ | NB$ |
| Control | HMM-mfMSR1 | NB$ | NB$ | NB$ | NB$ |

*indicates that no dissociation of His9-hMSR1 or HMM-mfMSR1 was observed under the current experimental conditions and the $k_d$ value was manually fixed at 1.00E−05 while fitting the data
$indicates that no binding was observed under the current experimental conditions.

TABLE 12

Biacore Binding Affinities of Anti-MSR1 mAbs at 37° C.
Binding at 37° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H1H21227N- | His9-hMSR1 | 2.67E+06 | 1.23E−05 | 4.60E−12 | 941 |
| N297Q | HMM-mfMSR1 | 2.74E+06 | 1.08E−05 | 3.95E−12 | 1069 |
| H1H21227N- | His9-hMSR1 | 2.73E+06 | 1.00E−05* | 3.66E−12 | 1155 |
| N297D | HMM-mfMSR1 | 2.68E+06 | 2.42E−05 | 9.03E−12 | 477 |
| H1H21231N- | His9-hMSR1 | 5.34E+05 | 1.15E−04 | 2.15E−10 | 101 |
| N297Q | HMM-mfMSR1 | 5.87E+05 | 1.09E−04 | 1.86E−10 | 106 |
| H1H21234N- | His9-hMSR1 | 7.87E+05 | 1.00E−05* | 1.27E−11 | 1155 |
| N297Q | HMM-mfMSR1 | 7.50E+05 | 1.00E−05* | 1.33E−11 | 1155 |
| H1H27729P- | His9-hMSR1 | 2.39E+05 | 2.04E−03 | 8.53E−09 | 6 |
| N297Q | HMM-mfMSR1 | 4.07E+05 | 3.49E−03 | 8.58E−09 | 3.3 |
| H1H27731P- | His9-hMSR1 | 2.86E+05 | 1.32E−04 | 4.62E−10 | 88 |
| N297Q | HMM-mfMSR1 | 2.78E+05 | 1.87E−04 | 6.74E−10 | 62 |
| H1H27732P- | His9-hMSR1 | 2.81E+05 | 3.12E−05 | 1.11E−10 | 370 |
| N297Q | HMM-mfMSR1 | 3.34E+05 | 1.06E−04 | 3.17E−10 | 109 |
| H1H27734P- | His9-hMSR1 | 1.09E+06 | 1.90E−03 | 1.74E−09 | 6 |
| N297Q | HMM-mfMSR1 | 9.49E+05 | 3.20E−03 | 3.37E−09 | 4 |
| H1H27736P- | His9-hMSR1 | 1.02E+06 | 7.33E−04 | 7.17E−10 | 16 |

TABLE 12-continued

| Biacore Binding Affinities of Anti-MSR1 mAbs at 37° C. Binding at 37° C./Antibody-Capture Format | | | | | |
|---|---|---|---|---|---|
| Antibody | Analyte | ka ($M^{-1}s^{-1}$) | kd ($s^{-1}$) | $K_D$ (Molar) | t½ (min) |
| N297Q | HMM-mfMSR1 | 2.01E+06 | 1.28E−03 | 6.37E−10 | 9 |
| H1H27739P- | His9-hMSR1 | 7.76E+05 | 2.88E−03 | 3.72E−09 | 4 |
| N297Q | HMM-mfMSR1 | 2.25E+06 | 8.42E−04 | 3.74E−10 | 14 |
| H1H27747P- | His9-hMSR1 | 5.13E+05 | 2.76E−03 | 5.37E−09 | 4 |
| N297Q | HMM-mfMSR1 | 6.57E+05 | 2.28E−03 | 3.47E−09 | 5 |
| H1H27749P- | His9-hMSR1 | 4.97E+05 | 2.42E−04 | 4.86E−10 | 48 |
| N297Q | HMM-mfMSR1 | 4.77E+05 | 1.72E−04 | 3.61E−10 | 67 |
| H1H27751P- | His9-hMSR1 | 1.45E+06 | 9.43E−04 | 6.50E−10 | 12 |
| N297Q | HMM-mfMSR1 | 1.17E+06 | 1.80E−03 | 1.55E−09 | 6 |
| H1H27754P- | His9-hMSR1 | 6.63E+05 | 2.53E−05 | 3.81E−11 | 457 |
| N297Q | HMM-mfMSR1 | 7.01E+05 | 3.53E−05 | 5.04E−11 | 327 |
| H1H27756P- | His9-hMSR1 | 6.63E+05 | 7.71E−04 | 1.16E−09 | 15 |
| N297Q | HMM-mfMSR1 | 8.02E+05 | 3.19E−03 | 3.97E−09 | 4 |
| H1H27760P- | His9-hMSR1 | 1.08E+06 | 1.89E−03 | 1.74E−09 | 6 |
| N297Q | HMM-mfMSR1 | 1.52E+06 | 1.59E−03 | 1.05E−09 | 7 |
| H1H27759P- | His9-hMSR1 | 1.03E+06 | 2.30E−03 | 2.24E−09 | 5 |
| N297Q | HMM-mfMSR1 | 1.46E+06 | 1.88E−03 | 1.28E−09 | 6 |
| H1H27761P- | His9-hMSR1 | 6.81E+05 | 2.22E−03 | 3.26E−09 | 5 |
| N297Q | HMM-mfMSR1 | 9.20E+05 | 2.14E−03 | 2.32E−09 | 5 |
| H1H27762P- | His9-hMSR1 | 3.06E+06 | 1.96E−03 | 6.40E−10 | 6 |
| N297Q | HMM-mfMSR1 | 2.82E+06 | 1.97E−03 | 6.98E−10 | 6 |
| H1H27766P- | His9-hMSR1 | 3.40E+05 | 7.72E−05 | 2.27E−10 | 150 |
| N297Q | HMM-mfMSR1 | 3.43E+05 | 5.89E−04 | 1.72E−09 | 20 |
| H1H27771P- | His9-hMSR1 | 1.35E+06 | 2.04E−03 | 1.51E−09 | 6 |
| N297Q | HMM-mfMSR1 | 4.94E+05 | 9.07E−03 | 1.84E−08 | 1.3 |
| H1H27773P- | His9-hMSR1 | 9.19E+05 | 3.07E−03 | 3.34E−09 | 4 |
| N297Q | HMM-mfMSR1 | 9.60E+05 | 5.06E−03 | 5.27E−09 | 2.3 |
| H1H27778P- | His9-hMSR1 | 1.19E+06 | 6.55E−04 | 5.49E−10 | 18 |
| N297Q | HMM-mfMSR1 | 1.19E+06 | 1.25E−03 | 1.05E−09 | 9 |
| H1H21234N | His9-hMSR1 | 6.76E+05 | 1.00E−05* | 1.48E−11 | 1155 |
| | HMM-mfMSR1 | 7.26E+05 | 1.00E−05* | 1.38E−11 | 1155 |
| H1H21231N | His9-hMSR1 | 7.02E+05 | 9.09E−05 | 1.30E−10 | 127 |
| | HMM-mfMSR1 | 7.12E+05 | 7.82E−05 | 1.10E−10 | 148 |
| H1H21227N | His9-hMSR1 | 2.56E+06 | 1.85E−05 | 7.24E−12 | 624 |
| | HMM-mfMSR1 | 2.76E+06 | 1.00E−05* | 3.62E−12 | 1155 |
| Non-binding | His9-hMSR1 | NB$ | NB$ | NB$ | NB$ |
| Control | HMM-mfMSR1 | NB$ | NB$ | NB$ | NB$ |

*indicates that no dissociation of His9-hMSR1 or HMM-mfMSR1 was observed under the current experimental conditions and the $k_d$ value was manually fixed at 1.00E−05 while fitting the data
$indicates that no binding was observed under the current experimental conditions.

At 25° C., all of the anti-MSR1 monoclonal antibodies according to the disclosure bound to His9-hMSR1 with $K_D$ values ranging from 12 pM to 5.45 nM, as shown in Table 11. At 37° C., all of the anti-MSR1 monoclonal antibodies of the disclosure bound to His9-hMSR1 with $K_D$ values ranging from 3.66 pM to 8.53 nM, as shown in Table 12.

At 25° C., all of the anti-MSR1 monoclonal antibodies according to the disclosure bound to HMM-mfMSR1 with $K_D$ values ranging from 29.9 pM to 10.1 nM, as shown in Table 11. At 37° C., all of the anti-MSR1 monoclonal antibodies of the disclosure bound to HMM-mfMSR1 with $K_D$ values ranging from 3.62 pM to 18.4 nM, as shown in Table 12.

Example 26: Octet-Derived Binding Affinities and Kinetic Constants of Human Monoclonal Anti-MSR1 Antibodies Binding affinities and kinetic constants of human anti-MSR1 antibodies for different MSR1 reagents were determined using a real time, label-free bio-layer interferometry assay on an OCTET® HTX biosensor platform (Pall FortéBio Corp., Menlo Park, CA). The experiment was performed at 25° C. in 10 mM HEPES, 150 mM NaCl, 3 mM EDTA, 0.05% v/v Surfactant Tween-20, and 1 mg/mL BSA, pH7.4 (HBS-EBT) buffer with the plate shaking at the speed of 1000 rpm. Binding studies were performed on human MSR1 extracellular domain expressed with a N-terminal nonahistidine tag (SEQ ID NO: 688) (His9-hMSR1; R&D Systems, Cat #2708-MS), monkey MSR1 extracellular domain expressed with a N-terminal myc-myc-hexahistidine tag (HMM-mfMSR1; SEQ ID NO: 418), and mouse MSR1 extracellular domain expressed with a N-terminal nonahistidine tag (SEQ ID NO: 688) ("hexahistidine" disclosed as SEQ ID NO: 689) (His9-mMSR1; R&D Systems, Cat #1797-MS). The anti-MSR1 monoclonal antibodies were captured by dipping either anti-human Fc (AHC) or anti-mouse Fc (AMC) Octet biosensors in wells containing 5 µg/mL or 10 µg/mL of anti-MSR1 monoclonal antibody for 45-90 seconds. The AHC captured anti-MSR1 monoclonal antibodies were then dipped in wells containing 50 nM of His9-mMSR1, while the AMC captured anti-MSR1 monoclonal antibodies were dipped in wells containing different concentrations of His9-hMSR1 or HMM-mfMSR1 (100 nM, 25 nM) or 100 nM His9-mMSR1. The binding of different MSR1 reagents to the captured anti-MSR1 monoclonal antibody was measured for 4 minutes and the dissociation of monoclonal antibody bound MSR1 reagent was monitored for 8-10 minutes in HBS-EBT buffer.

The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\text{min}) = \frac{\ln(2)}{60 * kd}$$

Binding kinetics parameters for His9-hMSR1, HMM-mfMSR1 or His9-mMSR1binding to different anti-MSR1 monoclonal antibodies of the disclosure at 25° C. are shown in Tables 13 and 14.

TABLE 13

OCTET ® Binding Affinities of Anti-MSR1 mAbs at 25° C.
Binding at 25° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H2aM21228N | His9-hMSR1 | 1.22E+05 | 1.16E−04 | 9.54E−10 | 100 |
| | HMM-mfMSR1 | 1.00E+05 | 1.46E−04 | 1.45E−09 | 79 |
| H2aM21229N | His9-hMSR1 | 3.00E+05 | 2.10E−04 | 7.00E−10 | 55 |
| | HMM-mfMSR1 | 1.35E+05 | 2.22E−03 | 1.64E−08 | 5 |
| H2aM21230N | His9-hMSR1 | 6.47E+05 | 2.87E−04 | 4.43E−10 | 40 |
| | HMM-mfMSR1 | 2.37E+05 | 3.76E−04 | 1.59E−09 | 31 |
| H2aM21232N | His9-hMSR1 | 1.30E+05 | 2.86E−04 | 2.20E−09 | 40 |
| | HMM-mfMSR1 | 9.75E+04 | 3.27E−04 | 3.35E−09 | 35 |
| H2aM21235N | His9-hMSR1 | 1.21E+05 | 4.58E−05 | 3.78E−10 | 252 |
| | HMM-mfMSR1 | 1.02E+05 | 6.27E−05 | 6.12E−10 | 184 |
| H2aM25700N | His9-hMSR1 | 5.58E+05 | 1.14E−04 | 2.05E−10 | 101 |
| | HMM-mfMSR1 | 5.53E+05 | 1.15E−04 | 2.08E−10 | 100 |
| H2aM25690N | His9-hMSR1 | 2.29E+05 | 3.11E−04 | 1.36E−09 | 37 |
| | HMM-mfMSR1 | 1.64E+05 | 5.47E−04 | 3.35E−09 | 21 |
| H2aM25695N | His9-hMSR1 | 3.60E+05 | 5.27E−04 | 1.46E−09 | 22 |
| | HMM-mfMSR1 | 3.12E+05 | 5.71E−04 | 1.83E−09 | 20 |
| H2aM25685N | His9-hMSR1 | 2.01E+05 | 3.97E−04 | 1.98E−09 | 29 |
| | HMM-mfMSR1 | 6.49E+04 | 1.28E−03 | 1.97E−08 | 9 |
| mIgG Isotype | His9-hMSR1 | NB$ | NB$ | NB$ | NB$ |
| Control | HMM-mfMSR1 | NB$ | NB$ | NB$ | NB$ |

$indicates that no binding was observed under the current experimental conditions.

TABLE 14

OCTET ® Binding Affinities of Anti-MSR1 mAbs at 25° C.
Binding at 25° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H2aM21228N | His9-mMSR1 | NB$ | NB$ | NB$ | NB$ |
| H2aM21229N | His9-mMSR1 | NB$ | NB$ | NB$ | NB$ |
| H2aM21230N | His9-mMSR1 | NB$ | NB$ | NB$ | NB$ |
| H2aM21232N | His9-mMSR1 | NB$ | NB$ | NB$ | NB$ |
| H2aM21235N | His9-mMSR1 | NB$ | NB$ | NB$ | NB$ |
| H2aM25700N | His9-mMSR1 | 3.60E+04 | 1.85E−04 | 5.20E−09 | 63 |
| H2aM25690N | His9-mMSR1 | NB$ | NB$ | NB$ | NB$ |
| H2aM25695N | His9-mMSR1 | NB$ | NB$ | NB$ | NB$ |
| H2aM25685N | His9-mMSR1 | NB$ | NB$ | NB$ | NB$ |
| mIgG Isotype Control | His9-mMSR1 | NB$ | NB$ | NB$ | NB$ |
| H1H21227N-N297Q | His9-mMSR1 | 3.74E+05 | 7.08E−04 | 1.89E−09 | 16 |
| H1H21227N-N297D | His9-mMSR1 | 4.6IE+05 | 7.86E−04 | 1.71E−09 | 15 |
| H1H21231N-N297Q | His9-mMSR1 | IC# | IC# | IC# | IC# |
| H1H21234N-N297Q | His9-mMSR1 | 3.82E+04 | 5.00E−05* | 1.31E−09 | 231 |
| H1H27729P-N297Q | His9-mMSR1 | NB$ | NB$ | NB$ | NB$ |
| H1H27731P-N297Q | His9-mMSR1 | NB$ | NB$ | NB$ | NB$ |
| H1H27732P-N297Q | His9-mMSR1 | NB$ | NB$ | NB$ | NB$ |
| H1H27734P-N297Q | His9-mMSR1 | NB$ | NB$ | NB$ | NB$ |
| H1H27736P-N297Q | His9-mMSR1 | IC# | IC# | IC# | IC# |
| H1H27739P-N297Q | His9-mMSR1 | NB$ | NB$ | NB$ | NB$ |
| H1H27747P-N297Q | His9-mMSR1 | NB$ | NB$ | NB$ | NB$ |
| H1H27749P-N297Q | His9-mMSR1 | IC# | IC# | IC# | IC# |
| H1H27751P-N297Q | His9-mMSR1 | NB$ | NB$ | NB$ | NB$ |
| H1H27754P-N297Q | His9-mMSR1 | NB$ | NB$ | NB$ | NB$ |
| H1H27756P-N297Q | His9-mMSR1 | NB$ | NB$ | NB$ | NB$ |
| H1H27760P-N297Q | His9-mMSR1 | NB$ | NB$ | NB$ | NB$ |
| H1H27759P-N297Q | His9-mMSR1 | NB$ | NB$ | NB$ | NB$ |
| H1H27761P-N297Q | His9-mMSR1 | IC# | IC# | IC# | IC# |
| H1H27762P-N297Q | His9-mMSR1 | NB$ | NB$ | NB$ | NB$ |
| H1H27766P-N297Q | His9-mMSR1 | NB$ | NB$ | NB$ | NB$ |
| H1H27771P-N297Q | His9-mMSR1 | IC# | IC# | IC# | IC# |

TABLE 14-continued

OCTET ® Binding Affinities of Anti-MSR1 mAbs at 25° C.
Binding at 25° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H1H27773P-N297Q | His9-mMSR1 | $NB^{\$}$ | $NB^{\$}$ | $NB^{\$}$ | $NB^{\$}$ |
| H1H27778P-N297Q | His9-mMSR1 | $NB^{\$}$ | $NB^{\$}$ | $NB^{\$}$ | $NB^{\$}$ |
| H1H21234N | His9-mMSR1 | 4.60E+04 | 5.00E−05* | 1.09E−09 | 231 |
| H1H21231N | His9-mMSR1 | $IC^{\#}$ | $IC^{\#}$ | $IC^{\#}$ | $IC^{\#}$ |
| H1H21227N | His9-mMSR1 | 4.15E+05 | 8.16E−04 | 1.97E−09 | 14 |
| Non-binding Control | His9-mMSR1 | $NB^{\$}$ | $NB^{\$}$ | $NB^{\$}$ | $NB^{\$}$ |

*indicates that no dissociation of His9-mMSR1 was observed under the current experimental conditions and the $k_d$ value was manually fixed at 5.00E−05 while fitting the data
$^{\$}$indicates that no binding was observed under the current experimental conditions.
$^{\#}$indicates that the binding data is inconclusive (IC)

The anti-MSR1 monoclonal antibodies bound to His9-hMSR1 with $K_D$ values ranging from 205 pM to 2.2 nM, as shown in Table 13. The anti-MSR1 monoclonal antibodies bound to HMM-mfMSR1 with $K_D$ values ranging from 208 pM to 19.7 nM, as shown in Table 13.

As shown in Table 14, 23 out of 35 anti-MSR1 monoclonal antibodies did not bind to His9-mMSR1, while the binding data for 6 anti-MSR1 monoclonal antibodies was inconclusive. Six (6) out of 35 anti-MSR1 monoclonal antibodies bound to His9-mMSR1 with $K_D$ values ranging from 1.09 nM to 5.2 nM, as shown in Table 14.

Example 27: Anti-MSR1 Antibodies Display Specific Binding to Cell Surface-Expressed Human and Monkey MSR1

The ability of anti-MSR1 monoclonal antibodies to bind to human or monkey MSR1 expressing cells was determined using electrochemiluminescence (ECL) based detection.

Generation of MSR1-expressing cell lines. Two cell lines overexpressing either human or monkey MSR1 were generated. To generate the human MSR1 overexpressing cell line, human embryonic kidney (HEK) 293 cells were engineered by transduction with hygromycin resistant lentiviral vector encoding full length human MSR1 (hMSR1, amino acids M1-L451 of accession number NP_619729.1) with a C-terminal Myc tag. The resulting cell line is referred to as HEK293.Myc.hMSR1. Similarly, to generate the monkey MSR1 overexpressing cell line, HEK293 cells were engineered by transfection with the geneticin resistant expression plasmid encoding full length monkey MSR1 (*Macaca fascicularis*, mfMSR1, amino acids M1-L451 of accession number XP_005562705.1). The resulting cell line is referred to as HEK293.mfMSR1 cells. To measure the ability of antibodies to bind to endogenously expressed human MSR1, THP-1 human monocytic cells were treated with 200 nM of phorbol 12-myristate 13-acetate (PMA; Sigma, Cat #P8139) for 72 hours to induce high MSR1 expression prior to antibody binding. Non-transfected HEK293 cells were included as non-specific binding controls as they have no detectable expression of MSR1 by next-generation sequencing of gene expression (data not shown).

Antibody binding assay. To perform the antibody binding assay, cells from each of the cell lines described above were rinsed once in PBS buffer without $Ca^{2+}/Mg^{2+}$ and incubated for 5 minutes at 37° C. with Enzyme Free Cell Dissociation Solution (Millipore, Cat. #S-004-C, Burlington, MA) to detach cells from a flask. All cells were washed once with 1×PBS with $Ca^{2+}/Mg^{2+}$ and counted with a Cellometer™ Auto T4 cell counter (Nexcelom Bioscience). Approximately $1.0\times10^4$ cells were seeded separately onto 96-well carbon electrode plates [MULTI-ARRAY high bind plate, Meso Scale Diagnostics] and incubated for 1 hour at 37° C. Non-specific binding sites were then blocked by 2% BSA (w/v) in PBS with $Ca^{2+}/Mg^{2+}$ for 1 hour at room temperature. THP-1 cells were pre-incubated for 0.5 hours at room temperature in sample dilution buffer with: 1) 1 mg/mL Fc receptor block reagents to block Fc gamma receptors on THP-1 cell surface [whole molecule human IgG (Jackson Immunoresearch, Cat #009-000-003) for wells being tested with anti-MSR1-mFc antibodies or 2) whole molecule mIgG (Jackson Immunoresearch, Cat #015-000-003) for wells being tested with anti-MSR1-hFc antibodies. Antibody binding on HEK293.Myc.hMSR1, HEK293.mfMSR1 and HEK293 cells was tested without Fc receptor block reagents. To the plate-bound HEK293.Myc.hMSR1, HEK293.mfMSR1 and HEK293 cells or THP-1+Fc block, solutions of anti-MSR1 or control antibodies in serial dilutions ranging from 1.7 pM to 100 nM, and solutions without the presence of antibodies were added in duplicate, and the plates were incubated for 1 hour at room temperature. Plates were then washed to remove unbound antibodies an AquaMax2000 plate washer with a cell washing head (MDS Analytical Technologies). The plate-bound antibodies were detected with either a SULFO-TAG™-conjugated goat polyclonal anti-human IgG antibody specific for Fcγ fragment (Jackson Immunoresearch, Cat #109-005-098) or a SULFO-TAG™-conjugated goat polyclonal anti-mouse IgG antibody specific for Fcγ fragment (Jackson Immunoresearch, Cat #115-005-164) for 1 hour at room temperature. Plates were washed and developed with Read Buffer (Meso Scale Diagnostics, Cat #R92TD-2) according to manufacturer's recommended procedure and luminescent signals were recorded with a SECTOR Imager 600 (Meso Scale Diagnostics). Luminescence intensity, measured in relative light units (RLU), was recorded to indicate the binding intensity of each antibody at the range of concentrations. The ratio of signal detected for cell-surface binding of each anti-MSR antibody compared to isotype control antibody (both at 11 nM) was reported as an indication of specificity of MSR1 binding. Antibodies with the binding ratio on MSR-1 expressing cells of greater than or equal to 2-fold compared to the ratio on parental HEK293 cells were classified as specific binders. Antibodies with a binding ratio of less than 2-fold compared to the ratio on parental HEK293 cells were classified as non-binders as shown in. (See Table 15).

TABLE 15

Binding of Anti-MSR1 Antibodies to MSR1-Expressing Cells

| Antibody | Ratio of 11 nM Antibody Binding Signal (RLU) on MSR1-expressing cells and parental HEK293 to isotype control HEK293.Myc.h MSR1 | PMA-treated THP-1 | HEK293.mf MSR1 | HEK293 |
|---|---|---|---|---|
| Specific Human and monkey MSR1 binders | | | | |
| H1H21227N-N297Q | 37 | 5 | 23 | 1 |
| H1H21227N-N297D | 34 | 6 | 25 | 1 |
| H1H21227N | 37 | 7 | 26 | 1 |
| H1H21231N-N297Q | 64 | 45 | 69 | 4 |
| H1H21231N | 61 | 42 | 75 | <1 |
| H1H21234N-N297Q | 43 | 25 | 35 | 9 |
| H1H21234N | 32 | 18 | 31 | 3 |
| H1H27729P-N297Q | 17 | 8 | 6 | 3 |
| H1H27731P-N297Q | 48 | 38 | 43 | 7 |
| H1H27732P-N297Q | 72 | 56 | 46 | 6 |
| H1H27734P-N297Q | 40 | 21 | 28 | 14 |
| H1H27736P-N297Q | 58 | 48 | 45 | 12 |
| H1H27739P-N297Q | 22 | 9 | 20 | 1 |
| H1H27747P-N297Q | 26 | 13 | 21 | 5 |
| H1H27749P-N297Q | 27 | 33 | 24 | 3 |
| H1H27751P-N297Q | 63 | 54 | 49 | 15 |
| H1H27754P-N297Q | 55 | 66 | 53 | 18 |
| H1H27756P-N297Q | 38 | 21 | 20 | 6 |
| H1H27759P2-N297Q | 23 | 9 | 25 | 2 |
| H1H27760P2-N297Q | 29 | 15 | 25 | 3 |
| H1H27761P2-N297Q | 23 | 10 | 15 | 3 |
| H1H27762P2-N297Q | 33 | 11 | 25 | 3 |
| H1H27771P2-N297Q | 42 | 21 | 7 | 2 |
| H1H27773P2-N297Q | 5 | 3 | 10 | 2 |
| H1H27778P2-N297Q | 51 | 32 | 29 | 4 |
| H1xH27759P2 | 22 | 6 | 21 | <1 |
| H1xH29283P2 | 26 | 9 | 24 | 1 |
| H2aM25685N | 75 | 11 | 25 | 2 |
| H2aM25690N | 166 | 25 | 77 | 5 |
| H2aM25695N | 35 | 8 | 45 | 5 |
| H2aM25700N | 46 | 3 | 39 | 1 |
| H2aM21228N | 66 | 16 | 60 | 2 |
| H2aM21230N | 78 | 21 | 55 | 5 |
| H2aM21232N | 86 | 21 | 51 | 1 |
| H2aM21235N | 68 | 20 | 40 | 6 |
| Specific Human MSR1 only binders | | | | |
| H2aM21229N | 78 | 56 | 27 | 36 |
| H1xH29282P2 | 9 | 3 | 1 | <1 |
| H1H27766P2-N297Q | 20 | 9 | 13 | 8 |
| Non-specific binder | | | | |
| H1xH29273P2 | 20 | 24 | 27 | |
| Isotype controls | | | | |
| hIgG1 Isotype Control | 1 | 1 | 1 | 1 |
| mIgG Isotype Control | 1 | 1 | 1 | 1 |

As illustrated in Table 15, thirty-eight of thirty-nine tested anti-MSR1 antibodies bound specifically to HEK293.Myc.hMSR1 cells with binding ratios ranging from 5- to 166-fold above isotype control at 11 nM anti-MSR1 antibody concentration. Thirty-three of these anti-MSR1 antibodies specifically bound to THP-1 cells endogenously expressing human MSR1 after PMA cell differentiation with cell binding ratios ranging from 3- to 66-fold above isotype control at 11 nM. Thirty-five anti-MSR1 antibodies that bound to engineered hMSR1 cells also bound specifically to mfMSR1 engineered cells with cell binding ratios ranging from 6- to 77-fold above isotype control at 11 nM. Twelve anti-MSR1 antibodies (H1H21234N-N297Q, H1H27731P-N297Q, H1H27732P-N297Q, H1H27734P-N297Q, H1H27736P-N297Q, H1H27751P-N297Q, H1H27754P-N297Q, H1H27756P-N297Q, H2aM25695N, H2aM21235N, H2aM21229N, H1H27766P2-N297Q) bound to parental HEK293 cells with ratios 5-fold or greater above isotype control. Anti-MSR1 antibodies produced with a human IgG1 containing a N297Q or a N297D single point mutation bound cells comparable to their corresponding unmodified parental antibodies.

One anti-MSR1 antibody, H1xH29273P2, was characterized as a non-specific binder, as it bound to MSR1 cells with ratios less than 2 compared to the HEK293 cells at 11 nM antibody concentration. The hIgG1 and mIgG1 isotype controls were not specific, as expected.

Example 28: Relative Binding of Anti-MSR1 Antibodies to Cell Surface-Expressed Mouse MSR1

Relative cell surface binding of the anti-MSR1 antibodies to mouse MSR1 expressing cells was determined by flow cytometry using MSR1 positive RAW264.7 cells (ATCC, Catalog #TIB-71) and MSR1 negative B16F10.9 cells (Lin et al. 1998. *PNAS* 95:8829-8834). For the assay, cells were plated in PBS without calcium and magnesium (VWR Cat #45000-446) and 2% FBS (Saradigm Cat #1500-500) (Staining Buffer) in 96 well V-bottom plates (Axygen Scientific, Cat #P-96-450-V-C-S). To block binding to Fc receptors, RAW264.7 cells were incubated for 30 minutes at 4° C. with 500 μg/mL mouse IgG (Jackson ImmunoResearch, Cat #015-000-003) diluted in staining buffer, while B16F10.9 cells remained in staining buffer. Following Fc receptor blocking, 10 μg/mL of anti-MSR1 antibodies or an isotype control antibody were added to the cells and were subsequently incubated for 30 minutes on ice. For a positive control, a commercial anti-mouse MSR1 (Sino Biological, Cat #50129-R004) antibody was used, while a rabbit IgG antibody (Thermo Scientific, Cat #26102) was used as a negative control. The cells were then washed once with staining buffer and were incubated with either an APC conjugated anti-human Fc secondary antibody (Jackson ImmunoResearch, Cat #109-136-170) or an Alexa-Flour 647 conjugated anti-rabbit Fc secondary antibody [Jackson ImmunoResearch Cat #111-606-046] at 10 μg/mL for 30 minutes at 4° C. Cells were subsequently washed and fixed using a 50% solution of Cytofix (BD Biosciences, Cat #554655) diluted in PBS. Samples were run on the Beckman Coulter Cytoflex and results were analyzed in Flowjo 10.2 software (BD) to calculate the mean fluorescent intensity (MFI; Table 16). The signal to noise (S/N) was determined by calculating the ratio of the anti-MSR1 antibodies or the control antibodies MFI to the unstained sample MFI (Table 16).

TABLE 16

Binding of Anti-MSR1 Antibodies to RAW264.7 Cells (Flow Cytometry)

| Antibody | RAW264.7 MFI | B16F10.9 MFI | RAW264.7 S/N | B16F10.9 S/N |
|---|---|---|---|---|
| Unstained | 2524 | 3657 | 1 | 1 |
| Anti-human IgG secondary antibody only | 3095 | 3174 | 1 | 1 |
| Non-binding control | 3402 | 3829 | 1 | 1 |
| H1H21227N-N297Q | 12810 | 3287 | 5 | 1 |
| H1H21231N-N297Q | 3582 | 3374 | 1 | 1 |
| H1H21234N-N297Q | 7052 | 3499 | 3 | 1 |
| Anti-mouse MSR antibody | 245149 | 6161 | 97 | 2 |
| Anti-rabbit IgG secondary antibody only | 8720 | 5389 | 3 | 1 |
| H1H27729P-N297Q | 3484 | 3459 | 1 | 1 |
| H1H27731P-N297Q | 3510 | 3688 | 1 | 1 |
| H1H27732P-N297Q | 3425 | 3730 | 1 | 1 |
| H1H27734P-N297Q | 4783 | 4505 | 1 | 1 |
| H1H27736P-N297Q | 3554 | 3759 | 1 | 1 |
| H1H27739P-N297Q | 3271 | 3580 | 1 | 1 |
| H1H27747P-N297Q | 3630 | 3875 | 1 | 1 |
| H1H27749P-N297Q | 3789 | 3693 | 1 | 1 |
| H1H27751P-N297Q | 3823 | 4992 | 1 | 1 |
| H1H27754P-N297Q | 5406 | 4091 | 1 | 1 |
| H1H27756P-N297Q | 4573 | 3782 | 1 | 1 |
| H1H27759P-N297Q | 3288 | 3425 | 1 | 1 |
| H1H27760P-N297Q | 3429 | 3521 | 1 | 1 |
| H1H27761P-N297Q | 3837 | 3734 | 1 | 1 |
| H1H27762P-N297Q | 3519 | 3608 | 1 | 1 |
| H1H27766P-N297Q | 3812 | 3793 | 1 | 1 |
| H1H27771P-N297Q | 4055 | 3865 | 1 | 1 |
| H1H27773P-N297Q | 3367 | 3735 | 1 | 1 |
| H1H27778P-N297Q | 3648 | 4138 | 1 | 1 |

As illustrated in Table 16, two anti-MSR1 antibodies (H1H21227N-N297Q and H1H21234N-N297Q) bound weakly to RAW264.7 cells with S/N values of 5 and 3, respectively. The non-binding control antibody did not bind RAW264.7 cells. None of the 22 anti-MSR1 antibodies bound to B16F10.9 cells. A reference positive control (mouse MSR1/CD204 antibody, Sino Biological, Cat. #50129-R004) bound Raw 264.7 cells with a S/N of 97.

Example 29: Anti-MSR1 Antibodies Bind to Distinct Epitopes on MSR1 Receptor/Cross-Competition Between Anti-MSR1 Antibodies Binding competition between different anti-MSR1 antibodies was assessed using a real time, label-free bio-layer interferometry assay on an OCTET® HTX biosensor platform (Pall FortéBio Corp., Menlo Park, CA). The experiment was performed at 25° C. in 10 mM HEPES, 150 mM NaCl, 3 mM EDTA, 0.05% v/v Surfactant Tween-20, and 1 mg/mL BSA, pH 7.4 (HBS-EBT) buffer with the plate shaking at the speed of 1000 rpm.

To assess whether different antibodies are able to compete with one another for binding to their respective epitopes on the recombinant human MSR1 extracellular domain expressed with a N-terminal nonahistidine tag (SEQ ID NO: 688) (His9-hMSR1; R&D Systems, Cat #2708-MS), around 0.59-0.79 nM of His9-hMSR1 was first captured onto anti-Penta-His antibody coated OCTET® biosensor tips ("Penta-His" disclosed as SEQ ID NO: 690) (Pall FortéBio Corp., #18-5122) by submerging the biosensor tips for 45 seconds into wells containing a 20 pg/mL solution of His9-hMSR1. The antigen-captured biosensor tips were then saturated with a first anti-MSR1 monoclonal antibody (subsequently referred to as "mAb-1") by immersion into wells containing a 50 pg/mL solution of mAb-1 for 4 minutes. The biosensor tips were then submerged into wells containing a 50 pg/mL solution of a second anti-MSR1 monoclonal antibody (subsequently referred to as "mAb-2") for 4 minutes. All of the biosensor tips were washed in HBS-EBT buffer in between each step of the experiment. The real-time binding response was monitored during the course of the experiment and the binding response at the end of each step was recorded. The response of mAb-2 binding to His9-hMSR1 pre-complexed with mAb-1 was compared, and the competitive/non-competitive behavior of the different anti-MSR1 monoclonal antibodies was determined using a 50% inhibition threshold. Table 17 explicitly defines the relationships of antibodies competing in both directions, independent of the order of binding.

TABLE 17

Cross-competition of Anti-MSR1 Antibodies for Binding to His9-hMSR1

| First mAb (mAb-1) Captured using Anti-Penta-His Octet Biosensors ("Penta-His" disclosed as SEQ ID NO: 690) | mAb-2 antibodies which Compete with mAb-1 |
|---|---|
| H1H27756P-N297Q | H1H21231N |
| | H1H27760P-N297Q |
| | H1H27762P-N297Q |

TABLE 17-continued

Cross-competition of Anti-MSR1 Antibodies for Binding to His9-hMSR1

| First mAb (mAb-1) Captured using Anti-Penta-His Octet Biosensors ("Penta-His" disclosed as SEQ ID NO: 690) | mAb-2 antibodies which Compete with mAb-1 |
|---|---|
| | H1H21231N-N297Q |
| | H1H27747P-N297Q |
| | H1H27749P-N297Q |
| H1H21231N | H1H27756P-N297Q |
| | H1H27760P-N297Q |
| | H1H27762P-N297Q |
| | H1H21231N-N297Q |
| | H1H27747P-N297Q |
| | H1H27749P-N297Q |
| H1H27760P-N297Q | H1H27756P-N297Q |
| | H1H21231N |
| | H1H27762P-N297Q |
| | H1H21231N-N297Q |
| | H1H27747P-N297Q |
| | H1H27749P-N297Q |
| H1H27762P-N297Q | H1H27756P-N297Q |
| | H1H21231N |
| | H1H27760P-N297Q |
| | H1H21231N-N297Q |
| | H1H27747P-N297Q |
| | H1H27749P-N297Q |
| | H1H27766P-N297Q |
| H1H21231N-N297Q | H1H27756P-N297Q |
| | H1H21231N |
| | H1H27760P-N297Q |
| | H1H27762P-N297Q |
| | H1H27747P-N297Q |
| | H1H27749P-N297Q |
| H1H27747P-N297Q | H1H27760P-N297Q |
| | H1H27762P-N297Q |
| | H1H21231N-N297Q |
| H1H27749P-N297Q | H1H27760P-N297Q |
| | H1H27762P-N297Q |
| | H1H21231N-N297Q |
| H1H21234N-N297Q | H1H21234N |
| H1H21234N | H1H21234N-N297Q |
| H1H27734P-N297Q | H1H21234N-N297Q |
| | H1H27751P-N297Q |
| | H1H27732P-N297Q |
| | H1H27731P-N297Q |
| | H1H27754P-N297Q |
| | H1H27766P-N297Q |
| | H1H21227N-N297D |
| H1H27766P-N297Q | No mAb* |
| H1H21227N-N297D | H1H21234N-N297Q |
| | H1H21234N |
| | H1H27766P-N297Q |
| H1H27739P-N297Q | H1H27759P-N297Q |
| H1H21227N | Data Inconclusive** |
| H1H27751P-N297Q | H1H21234N-N297Q |
| | H1H27734P-N297Q |
| | H1H27732P-N297Q |
| | H1H27731P-N297Q |
| | H1H27754P-N297Q |
| | H1H27766P-N297Q |
| | H1H21227N-N297D |
| H1H27732P-N297Q | H1H27734P-N297Q |
| | H1H27751P-N297Q |
| | H1H27731P-N297Q |
| | H1H27754P-N297Q |
| H1H27731P-N297Q | H1H27734P-N297Q |
| | H1H27751P-N297Q |
| | H1H27732P-N297Q |
| | H1H27754P-N297Q |
| H1H27754P-N297Q | H1H27734P-N297Q |
| | H1H27751P-N297Q |
| | H1H27732P-N297Q |
| | H1H27731P-N297Q |

TABLE 17-continued

Cross-competition of Anti-MSR1 Antibodies for Binding to His9-hMSR1

| First mAb (mAb-1) Captured using Anti-Penta-His Octet Biosensors ("Penta-His" disclosed as SEQ ID NO: 690) | mAb-2 antibodies which Compete with mAb-1 |
|---|---|
| H1H27761P-N297Q | H1H27736P-N297Q |
| | H1H27771P-N297Q |
| | H1H27778P-N297Q |
| | H1H27773P-N297Q |
| | H1H27739P-N297Q |
| H1H27736P-N297Q | H1H27761P-N297Q |
| | H1H27771P-N297Q |
| | H1H27778P-N297Q |
| | H1H27759P-N297Q |
| | H1H27773P-N297Q |
| | H1H27773P-N297Q |
| H1H27771P-N297Q | H1H27761P-N297Q |
| | H1H27736P-N297Q |
| | H1H27778P-N297Q |
| | H1H27759P-N297Q |
| | H1H27773P-N297Q |
| | H1H27739P-N297Q |
| H1H27778P-N297Q | H1H27761P-N297Q |
| | H1H27736P-N297Q |
| | H1H27771P-N297Q |
| | H1H27759P-N297Q |
| | H1H27773P-N297Q |
| | H1H27739P-N297Q |
| H1H27759P-N297Q | H1H27736P-N297Q |
| | H1H27771P-N297Q |
| | H1H27778P-N297Q |
| | H1H27773P-N297Q |
| | H1H27739P-N297Q |
| H1H27773P-N297Q | H1H27749P-N297Q |
| | H1H27766P-N297Q |
| | H1H21227N-N297D |
| H1H27729P-N297Q | Data Inconclusive** |
| H1H21227N-N297Q | Data Inconclusive** |

*Does not cross compete with any other mAb for binding to MSR1 when captured as 'mAb-1'

**mAb failed to saturate MSR1 surface or did not bind to MSR1 surface

Example 30: Ligand Uptake of Anti-MSR1 Antibodies

MSR1 can binds and internalize chemically modified or altered polyanionic molecules, including modified low density lipoproteins (LDL) (Platt, N. and S. Gordon. 2001. *J Clin Invest.* 108(5):649-654). A bioassay was generated to assess the ability of the exemplary anti-MSR1 antibodies to regulate the uptake of certain MSR1 ligands.

Generation of MSR1-expressing cell lines for assay. Human embryonic kidney cells (HEK293) were transduced to stably express human MSR1 (amino acids 1-451 of UniProtKB accession number NP_619729.1) with a C-terminal Myc tag. The resulting cell line, referred to here as "HEK293.Myc.hMSR1", was selected and maintained in DMEM containing 10% FBS, NEAA, penicillin/streptomycin, L-glutamine, and 100 pg/mL hygromycin.

Ligand uptake assay. For the bioassay, HEK293.Myc.hMSR1 cells were plated onto 96-well poly-D-lysine-coated assay plates (Greiner Bio One, Cat #655946) at 20,000 cells per well in Opti-MEM containing 0.1% FBS, penicillin/streptomycin, and L-Glutamine (assay media) and incubated at 37° C. in 5% $CO_2$ overnight. The following day, antibodies were serially diluted from 300 nM to 5.08 pM (1:3 serial dilution) and pre-incubated with the cells, along with a negative control consisting of assay media alone, for 30 minutes at 37° C. in 5% $CO_2$. After 30 minutes, either oxidized or acetylated low-density lipoprotein (LDL) labeled with 1,1'dioctadecyl-3,3,3',3'-tetramethylindocarbocyanine perchlorate (referred to as "DiI-OxLDL" or "DiI-AcLDL," respectively) was added to the cells at a constant concentration of 10 μg/mL. To determine the dose response of ligand uptake, DiI-OxLDL or DiI-AcLDL was serially diluted from 25 pg/mL to 24.4 pg/mL (plus assay media alone without LDL) and added to cells not with antibodies. After an overnight incubation at 37° C. in 5% $CO_2$, cells were fixed with BD CytoFix™ (BD Biosciences, Cat #554655) for 2 hours at 4° C., and ligand uptake was evaluated using a Flexstation3 plate reader (Molecular Devices) with excitation at 514 nm and emission at 565 nm. Results were analyzed using nonlinear regression (4-parameter logistics) with the Prism 7 program to obtain $EC_{50}$ and $C_{50}$ values. The percentage of inhibition was calculated with the Relative Fluorescent Unit (RFU) values by using the following equation:

$$\text{Max \% Inhibition} = 100 \times \frac{RLU_{Baseline} - RLU_{Inhibition}}{RLU_{Baseline} - RLU_{Background}}$$

In the equation, "$RFU_{Baseline}$" is the fluorescence value from the cells treated with 10 μg/mL ligand without antibodies, "$RFU_{Inhibition}$" is the minimum fluorescence value with for a particular antibody with 10 μg/mL ligand, and "$RFU_{Background}$" is the fluorescence value from cells without any ligand or antibodies. The results and calculated values of the ligand uptake assay are provided in Table 18.

TABLE 18

Antibody Inhibition of DiI-OxLDL and DiI-AcLDL Uptake in HEK293.Myc.hMSR1 Cells

| | | DiI-Oxidized LDL | | DiI-Acetylated LDL | |
|---|---|---|---|---|---|
| Row | Antibodies | % Inhibition | $IC_{50}$ (M) | % Inhibition | $IC_{50}$ (M) |
| 1 | H2aM21227N | 90 | 3.1E−09 | 62 | 3.7E−09 |
| 2 | H2aM21228N | 79 | 3.1E−09 | 10 | >1.0E−07 |
| 3 | H2aM21229N | 26 | >1.0E−07 | no inhibition | no inhibition |
| 4 | H2aM21230N | 70 | 2.3E−09 | 47 | >1.0E−08 |
| 5 | H1M21231N | 79 | 3.7E−09 | 50 | >2.0E−08 |
| 6 | H2aM21232N | 79 | 4.8E−09 | 54 | >1.0E−08 |
| 7 | H2bM21234N | 61 | 4.5E−09 | 19 | 1.8E−09 |
| 8 | H2aM21235N | 64 | 3.2E−09 | 24 | >1.0E−07 |
| 9 | Mouse IgG2a Isotype control mAb 1 | no inhibition | no inhibition | no inhibition | no inhibition |

TABLE 18-continued

Antibody Inhibition of DiI-OxLDL and DiI-AcLDL Uptake in HEK293.Myc.hMSR1 Cells

| Row | Antibodies | DiI-Oxidized LDL % Inhibition | DiI-Oxidized LDL $IC_{50}$ (M) | DiI-Acetylated LDL % Inhibition | DiI-Acetylated LDL $IC_{50}$ (M) |
|---|---|---|---|---|---|
| 10 | Mouse IgG1 Isotype control mAb | no inhibition | no inhibition | no inhibition | no inhibition |
| 11 | H2aM25685N | 43 | >1.0E−07 | 22 | >1.0E−07 |
| 12 | H2aM25690N | 83 | 1.7E−09 | 53 | 2.1E−09 |
| 13 | H2aM25695N | 69 | >1.6E−08 | 40 | >1.7E−07 |
| 14 | H2aM25700N | 91 | 2.2E−09 | 79 | 2.4E−09 |
| 15 | Mouse IgG2a isotype control mAb 2 | no inhibition | no inhibition | no inhibition | no inhibition |
| 16 | H1H21227N-N297Q | 94 | 1.8E−09 | 65 | 2.4E−09 |
| 17 | H1H21231N-N297Q | 88 | 3.7E−09 | 62 | 3.7E−09 |
| 18 | H1H21234N-N297Q | 52 | 6.1E−09 | 34 | 1.3E−09 |
| 19 | H1H21227N | 89 | 2.0E−09 | 65 | 2.1E−09 |
| 20 | H1H21231N | 78 | 3.6E−09 | 63 | 3.5E−09 |
| 21 | H1H21234N | 64 | 4.3E−09 | 36 | 7.1E−10 |
| 22 | H1H27729P-N297Q | no inhibition | no inhibition | 28 | 1.2E−09 |
| 23 | H1H27731P-N297Q | 62 | >1.0E−08 | 37 | 1.8E−09 |
| 24 | H1H27732P-N297Q | 86 | 1.7E−09 | 62 | 2.2E−09 |
| 25 | H1H27734P-N297Q | 22 | 5.5E−09 | no inhibition | no inhibition |
| 26 | H1H27736P-N297Q | 83 | 3.2E−09 | 49 | 3.4E−09 |
| 27 | H1H27739P-N297Q | 55 | >1.0E−07 | no inhibition | no inhibition |
| 28 | H1H27747P-N297Q | 42 | >1.0E−07 | 26 | >1.0E−07 |
| 29 | H1H27749P-N297Q | 42 | 1.7E−09 | 35 | 4.2E−10 |
| 30 | H1H27751P-N297Q | 85 | 2.9E−09 | 59 | 1.6E−09 |
| 31 | H1H27754P-N297Q | 73 | 4.6E−09 | 38 | 1.8E−09 |
| 32 | H1H27756P-N297Q | 76 | 3.4E−09 | 42 | >1.0E−07 |
| 33 | H1H27759P-N297Q | 74 | >1.0E−08 | 48 | >1.0E−07 |
| 34 | H1H27760P-N297Q | 70 | 4.9E−09 | 46 | 2.6E−09 |
| 35 | H1H27761P-N297Q | 43 | 9.5E−09 | 29 | >1.0E−07 |
| 36 | H1H27762P-N297Q | 78 | 4.0E−09 | 38 | 2.9E−09 |
| 37 | H1H27766P-N297Q | 72 | 3.7E−09 | 38 | 3.5E−09 |
| 38 | H1H27771P-N297Q | 73 | 3.0E−09 | 49 | 1.9E−09 |
| 39 | H1H27773P-N297Q | 41 | >1.0E−07 | 31 | >1.0E−07 |
| 40 | H1H27778P-N297Q | 88 | 2.2E−09 | 54 | 1.5E−09 |
| 41 | Human IgG1-N297Q, Isotype Control mAb | no inhibition | no inhibition | no inhibition | no inhibition |
| 42 | Human IgG1 Isotype Control mAb | no inhibition | no inhibition | no inhibition | no inhibition |

Suitable antibody candidates illustrate relatively efficient inhibition (e.g., an $IC_{50}$ value of less than about 10 nM). In some embodiments, suitable antibody candidates also illustrate less than about 65% maximum inhibition of ligand uptake.

As shown in Table 18 (rows 1-10), eight antibodies showed inhibition of DiI-OxLDL uptake on the HEK293.Myc.hMSR1 cells with maximum inhibition ranging from 2600 to 90% and $IC_{50}$ values ranging from 2.3 nM to >100 nM. Seven of the 8 antibodies showed inhibition of DiI-AcLDL uptake with maximum inhibition ranging from 10% to 62% and $IC_{50}$ values ranging from 1.8 nM to >100 nM. Antibody H2aM21229N showed no inhibition of DiI-AcLDL uptake.

As shown in Table 18 (rows 11-15), four antibodies showed inhibition of MSR1-mediated DiI-OxLDL uptake with maximum inhibition ranging from 43% to 91% and $IC_{50}$ values ranging from 1.7 nM to >100 nM. Four antibodies of the disclosure showed inhibition of MSR1-mediated DiI-AcLDL uptake with maximum inhibition ranging from 22% to 79% and $IC_{50}$ values ranging from 2.1 nM to >100 nM.

As shown in Table 18 (rows 16-42), twenty-four out of 25 antibodies showed inhibition of MSR1-mediated uptake of DiI-OxLDL with maximum inhibition ranging from 22% to 94% and $IC_{50}$ values ranging from 1.7 nM to >100 nM. Twenty-three of the 25 antibodies showed inhibition of DiI-AcLDL uptake with maximum inhibition ranging from 26% to 65% and $IC_{50}$ values ranging from 0.42 nM to >100 nM. Antibody H1H27729P-N297Q showed no inhibition of DiI-OxLDL uptake while antibodies H1H27739P-N297Q and H1H27734P-N297Q showed no inhibition of DiI-AcLDL uptake on HEK293.Myc.hMSR1 cells.

Human and mouse Isotype control antibodies did not show inhibition of DiI-OxLDL and DiI-AcLDL uptake by HEK293.Myc.hMSR1 cells in any of the assays.

Example 31: Binding and Internalization of Cell-Surface Expressed MSR1 by Anti-MSR1 Antibodies Exemplary anti-MSR1 antibodies were assessed for their ability to bind and internalize MSR1 on MSR1-expressing cells.

For the assay, THP-1 cells [ATCC, Cat #TIB-202] were seeded into 96 well PDL coated plates (Perkin Elmer, Cat #6055500) in RPMI (Irvine Scientific, Cat #9160) containing 10% FBS (ATCC, Cat #30-2020), pencillin/streptomycin/L-glutamine (Gibco, Cat #10378-016), 50 μM Beta-Mercaptoethanol (Sigma, Cat #M7522) (growth media) plus 200 nM Phorbol Myristate Acetate (PMA; Sigma, Cat #P1585). The THP-1 cells were allowed to differentiate for 4 days at 37° C. in 5% $CO_2$. To stain, quadruplicate plates of cells were incubated with 10 μg/mL of anti-MSR1 antibodies diluted in 2% FBS in PBS, without Calcium and Magnesium (Irving, Cat #9240) (staining buffer) for 30 minutes at 4° C. Cells were washed twice with staining buffer incubated with an Alexa-Flour 488 conjugated secondary Ab (Jackson Immunoresearch, Cat #115-547-003 or Jackson Immunoresearch, Cat #109-547-003) at 10 μg/mL for 30 minutes at 4° C., and subsequently washed twice more with staining buffer. Two plates were immediately fixed and stained with 4% paraformaldehyde (PFA; ThermoFisher, Cat #28908)+5 μM DRAQ5 (ThermoFisher, Cat #62251) in PBS for 20 minutes (non-internalization plates). The remaining two plates were incubated at 37° C. for 1 hour followed by fixation and staining for 20 minutes using a solution of 4% PFA+5 μM DRAQ5 diluted in PBS (internalization plates). After fixation, all plates were washed once with PBS. One non-internalization plate and one internalization plate were incubated with an anti-Alexa Fluor 488 antibody (Regeneron) at 50 μg/mL in PBS overnight at 4° C. to quench surface Alexa Fluor 488 fluorescence. The remaining plates were incubated with PBS only. Confocal images were acquired on the Opera Phenix (Perkin Elmer) at 40× magnification. Harmony analysis software (Perkin Elmer) was utilized to identify DRAQ5-labeled cells and the total Alexa-Fluor 488 relative fluorescent units (RFU) per cell was determined. The total binding at 4° C. (RFU values of 4° C. unquenched wells), total binding at 37° C. (RFU values of 37° C. unquenched wells), the total internalized RFU, and % Internalization were determined for each antibody as shown in Table 19.

For all calculations, background fluorescence from unstained wells was subtracted from every well. Total internalized RFU was calculated as follows: Total RFU of 37° C. unquenched samples—Surface RFU at 37° C. Surface RFU is defined as unquenched RFU at 37° C.—quenched RFU at 37° C.)/QE. QE (quenching efficiency) is defined as: 1-(Total RFU of 4° C. quenched sample/Total RFU of 4° C. unquenched sample). The % Internalization was determined from the following formula: (Total internalized RFU at 37° C./Total RFU at 37° C.)*100.

TABLE 19

Internalization and Surface Binding of Anti-MSR1 Antibodies in Differentiated THP-1 Cells

| Antibody | Total Binding at 4° C. | Total Binding at 37° C. | Total Internalized RFU | % Internalization |
|---|---|---|---|---|
| H1H27729P-N297Q | 1930685 | 6607625 | 3763127 | 57.0 |
| H1H27731P-N297Q | 1215319 | 1802404 | 977543 | 54.2 |
| H1H27732P-N297Q | 2513511 | 4924734 | 2414132 | 49.0 |
| H1H27734P-N297Q | 482859 | 1151348 | 737425 | ND* |
| H1H27736P-N297Q | 9514681 | 12267400 | 14468087 | 117.9** |
| H1H27739P-N297Q | 3702857 | 5608380 | 4016378 | 71.6 |
| H1H27747P-N297Q | 2518361 | 5917858 | 3444330 | 58.2 |
| H1H27749P-N297Q | 4478384 | 12799899 | 5704834 | 44.6 |
| H1H27751P-N297Q | 5831744 | 7998767 | 6787876 | 84.9 |
| H1H27754P-N297Q | 3077308 | 7161570 | 6446236 | 90.0 |
| H1H27756P-N297Q | 6691792 | 11904608 | 9039171 | 75.9 |
| H1H27759P-N297Q | 4028970 | 2480463 | 1861578 | 75.0 |
| H1H27760P-N297Q | 1297337 | 6011876 | 3707164 | 61.7 |
| H1H27761P-N297Q | 1940392 | 2764577 | 1625899 | 58.8 |
| H1H27762P-N297Q | 2529645 | 3856573 | 3767717 | 97.7 |
| H1H27766P-N297Q | 1877240 | 3224247 | 2062539 | 64.0 |
| H1H27771P-N297Q | 6272656 | 7535203 | 6991358 | 92.8 |
| H1H27773P-N297Q | 490905 | 962752 | −67811 | ND* |
| H1H27778P-N297Q | 9910952 | 16552831 | 12518725 | 75.6 |
| H1H21227N-N297Q | 1800012 | 4110990 | 3226161 | 78.5 |
| H1H21234N-N297Q | 1953248 | 5451125 | 722651 | 13.3 |
| Isotype control | 185971 | 1087469 | 1704047 | ND* |

ND*: % internalization could not be determined due to weak binding and/or inability to determine quenching efficiency

**A % internalized value >100% is due to the total internalized values being slightly higher than total values at 37° C. An internalization of 100% was confirmed visually by the appearance of all Alex488 fluorescence into vesicular structures at 37° C.

As shown in Table 19, 19 of 21 assayed anti-MSR1 antibodies demonstrated internalization into differentiated THP-1 cells ranging from 13.3% to 117.9% internalization. For two of the 21 anti-MSR1 antibodies, internalization could not be determined due to weak binding and/or inability to determine quenching efficiency. As a control, the isotype control did not demonstrate any measurable internalization.

Example 32: Assessing Blocking Ability of Anti-MSR1 Antibodies for Human MSR1

The ability of anti-MSR1 antibodies disclosed herein to block the binding of various ligands to human MSR1 was measured using three competition sandwich ELISA assays. The ligands used in the assays were: (1) acetylated LDL (Ac-LDL), (2) oxidized LDL (Ox-LDL), and (3) advanced glycation end-products of bovine serum albumin (AGE-BSA).

For the assay, recombinant monomeric human MSR1 protein comprised of a portion of the human MSR1 extracellular domain expressed with a N-terminal 9-Histidine tag (SEQ ID NO: 688) (His9-hMSR1; R&D Systems, Cat #2708-MS) was coated at a concentration of 2 μg/mL in PBS on a 96-well microtiter plate overnight at 4° C. for use in competition ELISA assays with Ac-LDL, Ox-LDL, or biotinylated-AGE-BSA ("biot-AGE-BSA"). Nonspecific binding sites were subsequently blocked using a 0.5% (w/v) solution of bovine serum albumin (BSA) in phosphate-buffered saline (PBS). Anti-MSR1 antibodies or isotype control antibodies were serially diluted as appropriate for each tested ligand and added in duplicate for each serial dilution set to microtiter plates coated with His9-hMSR1. Buffer alone was also added to wells on each coat. After 1 hour incubation at room temperature, without wash, a final constant concentration of 50 pM Ac-LDL (Life Technologies/ThermoFisher Scientific, Cat #L-35354), 5 nM or 10 nM Ox-LDL (Alfa Aesar, Cat #J65591), or 400 pM biot-AGE-BSA (R&D Systems, Cat #BT4127) were added to plates with His9-hMSR1, and the plates were incubated for an additional 1 hour at room temperature. (Concentrations of Ac-LDL, Ox-LDL and biot-AGE-BSA for antibody inhibition assays were selected from the approximate midway point within the linear portion of individual binding curves of Ac-LDL, Ox-LDL or biot-AGE-BSA to plate-coated His9-hMSR1.) Wells were washed, and plate-bound Ac-LDL or Ox-LDL were detected with anti-LDL rabbit antibody (Alfa Aesar, Cat #J64398) in combination with anti-rabbit IgG (H+L) specific donkey polyclonal antibodies conjugated with horseradish peroxidase (HRP) (JacksonImmunoResearch, Cat #711-035-152) and biot-AGE-BSA was detected with a streptavidin-HRP (ThermoFisher Scientific, Cat #N200). Plates were developed using TMB substrate solution (BD Biosciences, Cat #51-2606KC & Cat #51-2607KC) according to manufacturer's recommendation and absorbance at 450 nm was measured on a Victor™ Multilabel Plate Reader (PerkinElmer™). This assay was conducted in four different assay runs.

Data analysis was performed using a sigmoidal dose-response model within Prism™ software (GraphPad). Percent blockade at maximum concentration of the antibody tested in each assay was calculated as an indicator of the ability of the antibodies to block the binding of Ac-LDL, Ox-LDL or biot-AGE-BSA to His9-hMSR1 on the plate relative to the baseline of the assay. In the calculation, binding signal of the same concentrations of Ac-LDL, Ox-LDL, or biot-AGE-BSA used for the assays in the absence of antibody was referenced as 100% binding or 0% blocking, while the baseline of the assay, defined as binding signal of the sample of buffer without MSR1 ligands or antibody, was referenced as 0% binding or 100% blocking. The maximum percent blockade at the highest concentration of antibody tested in each assay are reported for all antibodies. Negative percent blockade numbers reflected higher MSR1 ligands binding to plate coated His9-hMSR1 in the presence of antibodies. The blocking results are summarized in Table 20.

TABLE 20

Blocking Ability of Anti-MSR1 Antibodies in Competition ELISA Assays

| | anti-MSR1 antibody blocking of Ox-LDL binding to His9-hMSR1 | | | Anti-MSR1 antibody (100 nM) blocking of Ac-LDL binding to | Anti-MSR1 antibody (300 nM) blocking of biot-AGE-BSA binding to |
|---|---|---|---|---|---|
| Antibody | anti-MSR1 antibody concentration | Ox-LDL concentration | % Blocking | His9-hMSR1 % Blocking | His9-hMSR1 % Blocking |
| Blocked >50% in all assay formats | | | | | |
| H2aM25700N | 500 nM | 10 nM | 98 | 104 | 101 |
| H1H21227N-N297Q | 500 nM | 10 nM | 97 | 105 | 96 |
| H1H21227N-N297D | 500 nM | 10 nM | 99 | 101 | 97 |
| H1H21227N | 500 nM | 10 nM | 100 | 105 | 99 |
| Blocked >50% in some assay formats | | | | | |
| H2aM25695N | 500 nM | 10 nM | 96 | 65 | 16 |
| H1H27766P2-N297Q | 1 μM | 10 nM | 54 | 52 | 27 |
| H1H21234N-N297Q | 500 nM | 10 nM | 49 | 75 | −27 |
| H1H21234N | 500 nM | 10 nM | 98 | 70 | 21 |
| Blocked <50% in all assay formats | | | | | |
| H2aM21228N | 500 nM | 5 nM | 41 | −32 | −1 |
| H2aM21229N | 500 nM | 5 nM | 38 | −11 | 3 |
| H2aM21230N | 500 nM | 5 nM | 45 | −14 | 9 |

TABLE 20-continued

Blocking Ability of Anti-MSR1 Antibodies in Competition ELISA Assays

| Antibody | anti-MSR1 antibody blocking of Ox-LDL binding to His9-hMSR1 anti-MSR1 antibody concentration | Ox-LDL concentration | % Blocking | Anti-MSR1 antibody (100 nM) blocking of Ac-LDL binding to His9-hMSR1 % Blocking | Anti-MSR1 antibody (300 nM) blocking of biot-AGE-BSA binding to His9-hMSR1 % Blocking |
|---|---|---|---|---|---|
| H2aM21232N | 500 nM | 5 nM | 16 | 25 | −50 |
| H2aM21235N | 500 nM | 5 nM | −4 | 24 | −24 |
| H2aM25685N | 500 nM | 10 nM | 28 | −33 | −86 |
| H2aM25690N | 500 nM | 10 nM | 8 | −76 | −96 |
| H1H21231N-N297Q | 500 nM | 10 nM | 26 | −60 | −50 |
| H1H21231N | 500 nM | 10 nM | 22 | −62 | −44 |
| H1H27729P-N297Q | 1 μM | 10 nM | 36 | 8 | 15 |
| H1H27731P-N297Q | 1 μM | 10 nM | −1 | −41 | 4 |
| H1H27732P-N297Q | 1 μM | 10 nM | −60 | −61 | −9 |
| H1H27734P-N297Q | 1 μM | 10 nM | −15 | −38 | −4 |
| H1H27736P-N297Q | 1 μM | 10 nM | 3 | −31 | −3 |
| H1H27739P-N297Q | 1 μM | 10 nM | −41 | −47 | −9 |
| H1H27747P-N297Q | 1 μM | 10 nM | −31 | −44 | −2 |
| H1H27749P-N297Q | 1 μM | 10 nM | −21 | −51 | −1 |
| H1H27751P-N297Q | 1 μM | 10 nM | −31 | −51 | −11 |
| H1H27754P-N297Q | 1 μM | 10 nM | −44 | −42 | −9 |
| H1H27756P-N297Q | 1 μM | 10 nM | −45 | −54 | −8 |
| H1H27759P2-N297Q | 1 μM | 10 nM | −62 | −45 | −19 |
| H1H27760P2-N297Q | 1 μM | 10 nM | −47 | −43 | −4 |
| H1H27761P2-N297Q | 1 μM | 10 nM | −21 | −36 | −4 |
| H1H27762P2-N297Q | 1 μM | 10 nM | −65 | −58 | −16 |
| H1H27771P2-N297Q | 1 μM | 10 nM | −23 | −21 | −1 |
| H1H27773P2-N297Q | 1 μM | 10 nM | 2 | −11 | 1 |
| H1H27778P2-N297Q | 1 μM | 10 nM | −59 | −40 | −8 |
| Isotype control antibodies | | | | | |
| hIgG1 isotype control | 1 μM | 10 nM | 3 | −8 | 4 |
| mIgG1 isotype control | 1 μM | 10 nM | 16 | −4 | 7 |

Four of 35 assayed anti-MSR1 antibodies were identified as blocking >50% o of Ac-LDL, Ox-LDL, and biot-AGE-BSA binding to hMSR1. These four anti-MSR1 antibodies blocked greater than 95% o of 50 pM Ac-LDL, 10 nM Ox-LDL and 400 pM biot-AGE-BSA binding to His9-hMSR1.

At the maximum concentration of antibody tested, four of the 35 anti-MSR1 antibodies blocked >50% Ac-LDL and/or Ox-LDL binding to hMSR1 but did not block biot-AGE-BSA binding to hMSR1. Three of these antibodies blocked both 50 pM Ac-LDL and 10 nM Ox-LDL binding to hMSR1 with 52% to 98% blockade. One antibody (H1H21234N-N297Q) blocked only 50 pM Ac-LDL binding to hMSR1 with 7500 blockade.

Twenty-seven (27) of the 35 anti-MSR1 antibodies and the irrelevant isotype control antibodies blocked <5000 of Ac-LDL, Ox-LDL, and biot-AGE-BSA binding to hMSR1.

Three anti-MSR1 antibodies (21227N, 21231N, 21234N) were produced both with the original human Fcγ portion and a version with a N297Q single point mutation. The 21227N antibody was also produced as a third version with a N297D mutation. The modified versions of 21227N (H1H21227N-N297Q and H1H21227N-N297D) and 21231N (H1H21231N-N297Q) anti-MSR1 antibodies retained parental characteristics. Antibodies H1H21227N-N297Q and H1H21227N-N297D blocked >50% of Ac-LDL, Ox-LDL, and biot-AGE-BSA binding to hMSR1, while antibody H1H21231N-N297Q blocked <50% of Ac-LDL, Ox-LDL, and biot-AGE-BSA binding to hMSR1. Anti-MSR1 modified antibody H1H21234N-N297Q blocked only 50 pM Ac-LDL binding to hMSR1 in comparison to unmodified H1H21234N antibody, which blocked >50% for both Ac-LDL and Ox-LDL binding to hMSR1.

Example 33: Intracellular *S. aureus* Antibody-Drug Conjugate Killing Assay 1 (MSR1)

The reagents used are shown in Table 21, below.

TABLE 21

Reagents for Intracellular Assay

| Reagent | Vendor | Catalogue # |
|---|---|---|
| RPMI | Gibco | 11835-030 |
| PBS | Gibco | 20012-043 |
| Triton X-100 | Sigma | TX1568-1 |
| RPMI | Gibco | 11875-093 |
| FBS | Gibco | 10082-147 |
| PMA | Sigma | P8139 |
| Costa 48 well plate | Corning | 3548 |
| TSA plates | Teknova | T0144 |
| Pen/Strep | Gibco | 15140-122 |
| Dilution plates | Greiner Bio one | 780271-FD |
| Gentamicin | BioWhittaker | 17-519Z |

To test the efficacy of an anti-MSR1 Ab-antibiotic ncADC according to the disclosure in vitro, an intracellular *S. aureus* killing assay was utilized. For the assay, a THP-1 monocytic cell line was grown in media comprised of RPMI containing 10% FBS and 1% Penicillin/Streptomycin, then was seeded at a density of $1\times10^5$ cells/well in a 96 well plate and differentiated into macrophages for three days prior to infection using 200 nM Phorbol Myristate Acetate (PMA). An overnight culture of *S. aureus* MRSA strain NRS384 was grown in RPMI, washed twice with PBS and subsequently resuspended at $1\times10^7$ cfu/mL in PBS. THP-1 cells were washed with warm media (RPMI without FBS) to remove the Penicillin/Streptomycin and then infected with the *S. aureus* suspension at a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing twice with warm media and remaining extracellular *S. aureus* were killed by addition of media containing 100 pg/mL of gentamicin. After 1 hour, media was aspirated and the anti-MSR1 Ab-antibiotic ncADCs (H1H21234N-N297Q-25 and H1H21234N-N297Q-80), which is an anti-MSR1 antibody according to the disclosure conjugated to the maleimido linker payload derivative compounds 25 and 80 according to the disclosure via interchain cysteines, at different doses (10 μg/mL, 3.3 μg/mL, 1.1 μg/mL, 0.4 μg/mL, 0.1 μg/mL, and 0.04 μg/mL) and the isotype control-antibiotic ncADC (Isotype control-N297Q-25 and Isotype control-N297Q-80) at 10 pg/mL were added to infected macrophages in media containing 50 pg/mL gentamicin to prevent extracellular growth of *S. aureus*. A sample without any ncADC was also included for reference. After 24 hours, plates were washed twice with warm RPMI without FBS, and then 100 μL of 0.1% Triton X-100 in PBS was added and incubated for 10 minutes to lyse the THP-1. *S. aureus* survival was enumerated by colony forming units through serial dilution in PBS and plating onto trypticase soy agar plates.

The DARs are summarized in Table 22, below.

TABLE 22

Drug-antibody-ratios for the antibody-drug conjugates used

| Antibody | DAR |
|---|---|
| MSR1 ncADC H1H21234N-N297Q-25 | 3 (HIC) |
| Isotype Control-N297Q-25 | 2 (HIC) |
| MSR1 ncADC H1H21234N-N297Q-80 | 3 (HIC) |
| Isotype Control-N297Q-80 | 3 (HIC) |

The results are summarized in Table 23, below.

TABLE 23

Average colony forming units of anti-MSR1 Ab-Antibiotic

| | ncADC dose (ug/mL) | Average cfu/mL | Standard Deviation |
|---|---|---|---|
| *S. aureus* control | none | 1,350,000 | 139,194 |
| Isotype Control-N297Q-25 | 10 | 608,333 | 52,042 |
| MSR1 ncADC | 10 | 1,325 | 87 |
| H1H21234N-N297Q-25 | 3.3 | 4,917 | 722 |
| | 1.1 | 13,250 | 1,887 |
| | 0.4 | 56,667 | 7,638 |
| | 0.1 | 82,500 | 17,500 |
| | 0.04 | 1,025,000 | 43,301 |
| Isotype Control-N297Q-80 | 10 | 1,208,333 | 94,648 |
| MSR1 ncADC | 10 | 50 (limit of detection) | 0 |
| H1H21234N-N297Q-80 | 3.3 | 50 (limit of detection) | 0 |
| | 1.1 | 50 (limit of detection) | 0 |
| | 0.4 | 7,417 | 2,876 |
| | 0.1 | 75,833 | 15,275 |
| | 0.04 | 758,333 | 230,940 |

As shown in Table 23, the anti-MSR1 Ab-antibiotic ncADCs (H1H21234N-N297Q-25 and H1H21234N-N297Q-80) demonstrated the ability to reduce intracellular *S. aureus* from infected macrophages in vitro in a dose-dependent manner compared to the untreated control. Macrophages treated with the isotype control-antibiotic ncADC (Isotype control-N297Q-25 and Isotype control-N297Q-80) at 10 pg/mL harbored intracellular *S. aureus* at a similar level to the untreated control. These data demonstrate that an anti-MSR1 Ab-antibiotic ncADC according to the disclosure can be used to effectively kill pathogens residing within a macrophage reservoir.

Example 34: *S. aureus* IV Disseminated Infection Mouse Model

To test the efficacy of an anti-MSR1 Ab-antibiotic ncADC according to the disclosure in vivo, an intravenous disseminated infection model was utilized. *S. aureus* MRSA strain NRS384 was grown overnight in tryptic soy broth (TSB) and sub-cultured to mid-logarithmic phase. Bacteria were then washed twice with PBS and resuspended in PBS at a concentration of 1.2×10ˆ8 cfu/mL. Mice homozygously expressing human MSR1 extracellular domain and transmembrane domain in place of mouse MSR1 extracellular and transmembrane domains (humanized MSR, MAID 7343-MSR1 HumIn delHyg) were then infected intravenously through the tail vein with 100 μL of the bacterial suspension, for a final infectious dose of 1.2×10ˆ7 cfu/mouse. From one to three days post infection, mice were treated with 110 mg/kg vancomycin subcutaneously twice daily wherein indicated. Either the anti-MSR1 monoclonal antibody (H1H21234N-N297Q), anti-MSR1 Ab-antibiotic ncADC (H1H21234N-N297Q-25), which is an anti-MSR1 antibody according to the disclosure conjugated to the maleimido linker payload derivative compound 25 according to the disclosure via interchain cysteines, the Isotype control antibody or the ncADC Isotype control conjugated to the maleimido linker payload derivative compound 25, was administered subcutaneously at the indicated dose, as described in Table 24, one day after infection. Mice were monitored for weight loss and body conditioning score throughout the infection. At four days post infection, mice were euthanized and the *S. aureus* kidney burden was quantified by tissue homogenization followed by enumeration of colony forming units through serial dilution in PBS and plating onto trypicase soy agar plates.

TABLE 24

Average *S. aureus* kidney burden in mice treated with anti-MSR1 Ab-Antibiotic ncADC in combination with vancomycin

| Treatment | Vancomycin treatment | mAb or conjugate dose (mg/kg) | Average cfu/kidney pair | # of mice with *S. aureus* below the limit of detection | Standard Deviation |
|---|---|---|---|---|---|
| Infected Control | − | (−) | 4.33E+08 | 0/5 | 2.32E+08 |
| Vancomycin | + | (−) | 2.07E+06 | 0/6 | 2.76E+06 |
| Isotype Control 1 mg/kg | + | 1 | 2.44E+06 | 0/4 | 1.51E+06 |
| ncADC Isotype control (Isotype control-25) | + | 1 | 4.01E+05 | 1/5 | 6.49E+05 |
| anti-MSR1 Ab (H1H21234N-N297Q) | + | 1 | 1.55E+05 | 4/8 | 2.72E+05 |
| anti-MSR1 Ab (H1H21234N-N297Q) | + | 0.1 | 2.43E+05 | 0/6 | 2.64E+05 |
| anti-MSR1 Ab-antibiotic ncADC (H1H21234N-N297Q-25) | + | 1 | 6.17E+03 | 7/9 | 1.69E+04 |
| anti-MSR1 Ab-antibiotic ncADC (H1H21234N-N297Q-25) | + | 0.1 | 1.16E+03 | 6/8 | 1.78E+03 |

Limit of detection = 250 colony forming units (cfu)

As shown in Table 24, above, intravenous infection with *S. aureus* MRSA strain NRS5384 results in high bacterial burden in the kidneys, and treatment of mice with the standard of care antibiotic vancomycin reduces the *S. aureus* kidney burden by approximately 2 logs, but none of the mice had levels of *S. aureus* reduced below the limit of detection (LOD). The anti-MSR1 Ab-antibiotic ncADC (H1H21234N-N297Q-25) at doses of 1 and 0.1 mg/kg in combination with vancomycin resulted in 77% and 75% of mice with *S. aureus* levels below the LOD, demonstrating a marked improvement in *S. aureus* clearance in mice treated with the Ab-antibiotic ncADC combination therapy. *S. aureus* clearance was less pronounced in mice treated with the isotype control ncADC conjugate (Isotype Control-N297Q-25) plus vancomycin, demonstrating the benefit of payload targeting to macrophages.

Example 35: Conjugation Method for Aglycosylated Antibodies to Amino-Linker-Payloads Bacterial Transglutaminase Conjugation of Compound 80 and 82

An anti-MSR1 antibody H1H21234N containing a N297Q mutation, which eliminates N-linked glycosylation of the Fc at this site, was used. The mutation allowed the antibodies to be conjugated to a maximum loading of 4 at 295Q and 297Q of the heavy chains. A nontargeting antibody control, containing the same N297Q mutation, was used as a non-binding isotype control.

Deglycosylated control and MSR1 antibodies were conjugated at 1 mg/mL in PBS pH 7.4. Compound 80 or 82 was added in a 10-40 fold molar excess over antibody and the enzymatic reaction was initiated by addition of 12 units of bacterial transglutaminase (Zedira, T1001) per mg antibody and incubated at 37° C. for 4-16 hours. Samples were purified by SEC into PBS. The conjugates were analyzed by ESI-MS for the determination of the drug to antibody ratio (DAR) and by hydrophobic interaction chromatography (HIC). The results are listed in Table 25.

TABLE 25

Percent yield and payload to antibody ratios for each of the antibody drug conjugates

| Antibody | Purity (by SEC) | Yield (%) | DAR (HIC) | DAR (ESI-MS) |
|---|---|---|---|---|
| H1H21234N-82 | >95% | 50 | 3 | 3.6 |
| Nontargeting Antibody Control-82 | >95% | 50 | 3 | 3.5 |
| H1H21234N-80 | >95% | 50 | 2 | 3.4 |
| Nontargeting Antibody Control-80 | >95% | 50 | 2 | 3.0 |

Characterization of Conjugates by Hydrophobic Interaction Chromatography (HIC)

To determine the loading of the linker-payloads on the antibody, the conjugates were run on an Agilent 1260 using a TSK-NPR Butyl HIC column using a linear gradient of 1M potassium phosphate pH 8.5 in water over 60 min. The payload loading was determined by integration of peak areas corresponding to the species of conjugated and unconjugated antibody.

Characterization of Conjugates by ESI-MS

The chromatographic separation was achieved on a C4 column (0.3×50 mm ACQUITY UPLC BEH protein C4, 1.7 um, 300 A) in a 10 min gradient (minute: percentage of mobile phase B; 0:5%, 2:50%, 2.1:26%, 6.5:40%, 6.6:90%, 8.5:90%, 8.6:5%, 10:5%, 10.5:90%, 12.5:90%, 12.9:5%, 15:5%). The mobile phase A was 0.1% formic acid in water and mobile phase B was 0.1% formic acid in acetonitrile. The flow rate was set at 8 μL/min. The detector TOF scan was set from m/z 500-4500 with major parameters as listed (Capillary voltage 3.0 kV; Sampling Cone 80V; Source Offset at 100V; Source temperatures 150° C.; Desolvation temperature 400° C.; Cone gas 0 L/hr; Desolvation gas 600 L/hr). The spectra were deconvoluted with MaxEnt function within MassLynx software.

Average drug to antibody ratio (DAR) calculation based on deconvoluted mass spectra peak intensity using the following equation, where PI=Peak Intensity and D=Individual DAR.

$$DAR = \frac{\Sigma(PI_o + PI_1 * D_1 + PI_2 * D_2 + PI_n * D_n)}{\Sigma(PI_o + PI_1 + PI_2 + PI_n)}$$

Example 36: Antibody Engineered Cysteine Deblocking

Anti-Protein A (H1×H15140P*/*) and a nontargeting antibody control engineered antibodies were created by mutating the interchain disulfide forming heavy chain C103S. The antibodies are expressed in CHO cells and need to be deblocked on the native light chain cysteine using mild reduction in PBS at room temperature by the addition of a thirty fold molar excess of reducing agent, TCEP followed by buffer exchange. To reform the two heavy interchain disulfide bonds, the antibody was incubated for three hours at room temperature with $CuSO_4$ or with dhAA at a two to twenty fold molar excess. The reduced and oxidized antibody was buffer exchanged into PBS to remove oxidizing agent. This process produces two free thiols that reside on the light chain and are available for maleimide conjugation.

The anti-WTA engineered antibody was taken from the literature (Lehar et al, *Nature* 2015 527, 323-328; antibody 4497 described in US20140356375 and WO2016090038, the content of which is incorporated herein by reference in its entirety) and has a light chain mutation V205C to provide 2 sites for maleimide conjugation. The same procedure above was used to deblock the engineered cysteines.

Conjugation of Antibody Engineered Deblocked Cysteine to Linker Payload

To the reduced and oxidized antibody (1-10 mg/ml) in PBS pH7.5, the maleimido linker payload (2 equivalents/SH group, Lehar et al, *Nature* 527, 323-328), or the linker payloads of this filing, in DMSO (10 mg/ml) was added. The reaction proceeded for 2 hrs. The conjugates were purified into PBS by size exclusion chromatography and sterile filtered. Protein concentrations and payload to antibody ratios were determined by UV spectral analysis. Size-exclusion HPLC established that all conjugates used were >95% monomeric, and RP-HPLC established that there was <1% unconjugated linker payload. All conjugated antibodies were analyzed by HIC for linker payload loading values. Payload to antibody ratios are reported in Table 26.

Conjugation Method for Aglycosylated Antibodies (H1H21234N and a Nontargeting Antibody Control The antibody (1-10 mg/ml) in 50 mM HEPES, 150 mM NaCl, pH 7.5, was treated with 1 mM dithiothreitol at 37° C. for 30 min. After gel filtration (G-25, pH 4.5 sodium acetate), the maleimido linker payload derivative compound 25 (1.2 equivalents/SH group) in DMSO (10 mg/ml) was added to the reduced antibody and the mixture adjusted to pH 7.0 with 1 M HEPES (pH 7.4). The conjugates were purified using PBS with 5% glycerol by size exclusion chromatography and sterile filtered. Protein concentrations and payload to antibody ratios were determined by UV spectral analysis. Size-exclusion HPLC established that all conjugates used were >95% monomeric. All conjugated antibodies were analyzed by HIC for linker payload loading values. Payload to antibody ratios are reported in Table 26.

TABLE 26

Purity and drug to antibody ratios (DAR) of conjugates.

| Antibody Drug Conjugate | DAR (by HIC) | DAR (by ESI-MS) | Purity (by SEC) | Yield (%) |
|---|---|---|---|---|
| Anti-WTA-rifalog | 1.8 | 1.8 | >95% | 53% |
| Anti-WTA-21 (rifampicin control) | 2.0 | 1.5 | >95% | 70% |
| Anti-WTA-compound 25 | 1.7 | 1.6 | >95% | 50% |
| Anti-WTA-compound 36 | 1.8 | 1.4 | >95% | 40% |
| Anti-Protein A-rifalog | 1.9 | Not available | >95% | 30% |
| Anti-Protein A-compound 36 | 1.1 | 1.1 | >95% | 40% |
| H1H21234N-compound 25 | 3 | 3.2 | >95% | 50% |
| Nontargeting antibody control 1-rifalog | 1.7 | 1.6 | >95% | 60% |
| Nontargeting antibody control 1-rifampicin | 2.0 | 1.7 | >95% | 70% |
| Nontargeting antibody control 1- 25 | 1.3 | 0.6 | >95% | 50% |
| Nontargeting antibody control 1- 36 | 1.2 | 0.7 | >95% | 40% |
| Nontargeting antibody control 2- 25 | 2 | 2.0 | >95% | 50% |

Rifalog (Lehar et al, *Nature* 2015 527, 323-328; WO2016090038):

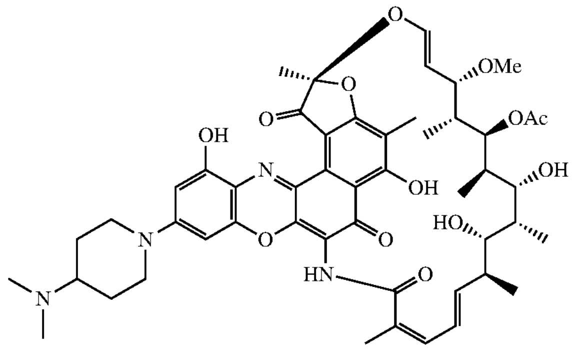 [SMILES: CO[C@H]1/C=C/O[C@@]2(C)Oc3c(C)c(O)c4c(=O)c(c5oc6cc(N7CCC(N(C)C)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

Characterization of Conjugates by Hydrophobic Interaction Chromatography (HIC)

To determine the loading of the linker-payloads on the antibody, the conjugates were run on Agilent 1260 using a TSK-NPR Butyl HIC column using a linear gradient of 1M potassium phosphate pH 8.5 to water over 60 min. The payload loading was determined by integration of peak areas corresponding to the species of conjugated and unconjugated antibody.

Characterization of Conjugates by ESI-MS

To determine the loading of the linker-payloads on the antibody (cysteine conjugates), the conjugates were deglycosylated, reduced, and analyzed by LC-MS.

For the assay, 50 pg of the conjugate was diluted with mili-Q water to a final concentration of 1 mg/mL. Ten µL of PNGase F solution [PNGase F solution was prepared by adding 150 µL of PNGase F stock (New England Biolabs, Cat #P0704L) and 850 µL of mili-Q water and mixed well] was added to the diluted conjugate solution and then incubated at 37° C. overnight. 2.4 µL of 0.5 M TCEP was added to the sample such that the resulting material had a final TCEP concentration of 20 mM and this was then incubated at 50° C. for 30 minutes. Injections of 10 µL of each sample were made onto LC-MS (Waters Synat G2-Si) and eluted with 0.1 mL/minute of a gradient mobile phase 20-40% of mobile phase B over 25 minutes (Mobile Phase A: 0.1% v/v FA in H2O; Mobile Phase B: 0.1% v/v FA in Acetonitrile).

The LC separation was achieved on Waters Acquity BEH C18 column (1.0×50 mM, 1.7 µM).

The mass spectrometry spectra were deconvoluted and the identified light and heavy chain peaks represent the light chain (L) with linker-payload values=0 and 1, heavy chain (H) with linker-payload values=0, 1, 2, and 3. From the intensity values of each species, the drug to antibody ratio (DAR) was calculated using the equation below for a homo-dimer antibody conjugate.

$$DAR = 2*\left[\frac{L1}{L0+L1} + \frac{H1+2*H2+3*H3}{H0+H1+H2+H3}\right]$$

Example 37: Broth Minimum Inhibitory Concentration (MIC) Assay 2

To test the potency of rifamycin analogs of the disclosure in vitro, a broth growth inhibition assay was developed. For the assay, *S. aureus* NRS384 was grown in Tryptic Soy Broth (TSB) overnight, then sub-cultured 1:50 in fresh TSB and grown for an additional two hours. The culture was then pelleted via centrifugation and washed twice in PBS. The culture was then diluted to $1\times10^{6}$ cfu/mL in TSB and 100 µL of the suspension was added per well to a 2 mL dilution plate in triplicate. A dilution series of the indicated antibiotic (an analog according to the disclosure or a previously known analog Rifampicin) was added 1:1 for a final starting concentration of $1\times10^{-5}$ M, then a 1:10 dilution for $1\times10^{-6}$ M followed with 1:4 dilutions to include $2.5\times10^{-7}$ M, $6.25\times10^{-8}$ M, $1.56\times10^{-8}$ M, $3.91\times10^{-9}$ M, $9.77\times10^{-10}$ M, $2.44\times10^{-11}$ M, $6.1\times10^{-11}$ M, $1.53\times10^{-11}$ M, and $3.81\times10^{-12}$ M for a total of 11 points. The plates were sealed and incubated at 37° C. with shaking for 24 hours, then 150 µL of each sample was added to 96 well microtiter plates and the OD600 nm was read on a Spectramax i3 Minimax 300.

The reagents used are shown in Table 27, below.

TABLE 27

| Reagents for MIC Assay | | |
|---|---|---|
| Reagent | Vendor | Catalogue # |
| PBS | Gibco | 20012-043 |
| *S. aureus* NRS384 | BEI resources | NR-46070 |
| Tryptic Soy Broth (TSB) | Teknova | T1525 |
| Dilution plates | Greiner Bio one | 780261 |
| 250 mL Flask | Thermo Scientific | 4116-0250 |
| 50 mL bioreactor tube | TPP | 87050 |
| Tryptic Soy agar (TSA) | Teknova | T0144 |
| DMSO | VWR | WN182 |
| Reagent Reservoir | VWR | 89094-658 |
| Costa 96 well plate | Corning | 3904 |

The lowest concentrations that inhibited growth of *S. aureus* (minimum inhibitory concentration, MIC) are listed in Table 28. As shown in Table 28, all rifamycin analogs according to the disclosure are effective at inhibiting growth of *S. aureus* at sub-micromolar to nanomolar concentrations. The broth MIC experiments were assessed in at least two independent experiments and the median value is captured below unless indicated otherwise.

TABLE 28

| Minimum inhibitory concentration (MIC) of antibiotics in a broth growth inhibition assay. | |
|---|---|
| Antibiotic tested | *S. aureus* Broth MIC (M) |
| Rifampicin | 3.91E−09 |
| Rifalog | 9.77E−10 |
| P1 | 6.25E−08 |
| P2 | 6.25E−08 |
| P3 | 1.56E−08 |
| 16f | 1.56E−08 |
| 16g | 1.56E−08 |
| 16h | 1.56E−08 |
| 16i | 1.56E−08 |
| 16j | 6.25E−08 |
| 16k | 9.77E−10 |
| 16l | 3.91E−09 |
| 16m | 3.91E−09 |
| 16n | 1.56E−08 |
| 16o | 3.91E−09 |
| 16p | 1.56E−08 |
| 16q | 3.91E−09 |
| 16r | 1.56E−08 |
| 16s | 6.25E−08 |
| 16t | 6.25E−08 |
| 16u | 1.00E−06 |
| 16v | 6.25E−08 |
| 16w | 6.25E−08 |
| 16x | 9.77E−10 |
| 16y | 1.56E−08 |
| 16z | 3.91E−09 |
| 16z-1 | 3.91E−09 |
| 17 | 1.56E−08 |
| 29 | 3.91E−09 |
| 29a | 3.91E−09 |
| 29b | 3.91E−09 |
| 29c | 3.91E−09 |
| 29d | 3.91E−09 |
| 29e | 1.56E−08 |
| 29f | 1.56E−08 |
| 29g | 3.91E−09 |
| 29h | 6.25E−08 |
| 29i | 2.44E−09 |
| 29j | 9.77E−10 |
| 29k | 6.25E−08 |
| 35 | 2.50E−07 |
| 38 | 6.25E−08 |

TABLE 28-continued

| Minimum inhibitory concentration (MIC) of antibiotics in a broth growth inhibition assay. | |
|---|---|
| Antibiotic tested | *S. aureus* Broth MIC (M) |
| 43 | 3.91E−09 |
| 45 | 3.91E−09 |
| 48 | 1.56E−08 |
| 50 | 1.56E−08 |
| 52 | 6.25E−08 |
| 55 | 1.56E−08 |
| 55a | 6.25E−08 |
| 60 | 3.91E−09 |
| 68 | 1.56E−08 |
| 71 | 1.56E−08 |
| 72 | 6.25E−08 |
| 75 | 2.90E−07 |

Example 38: Intracellular Killing Assay 2

The rifamycin analog compounds' activity against *S. aureus* was tested in an intracellular "killing" assay.

The reagents used are shown in Table 29, below.

TABLE 29

| Reagents for Intracellular Assay | | |
|---|---|---|
| Reagent | Vendor | Catalogue # |
| RPMI | Gibco | 11835-030 |
| PBS | Gibco | 20012-043 |
| Triton X-100 | Sigma | TX1568-1 |
| RPMI | Gibco | 11875-093 |
| FBS | Gibco | 10082-147 |
| PMA | Sigma | P8139 |
| Costa 96 well plate | Corning | 3904 |
| TSA plates | Teknova | T0144 |
| Pen/Strep | Gibco | 15140-122 |
| Dilution plates | Greiner Bio one | 780271-FD |
| DMSO | VWR | WN182 |
| Rifampicin | Sigma | R3501 |
| Gentamicin | BioWhittaker | 17-519Z |

THP-1 monocytic cell line was grown in media (RMPI+10% FBS+1% Penicillin/Streptomycin), then seeded at a density of 1e5 cells/well in a 96 well plate and differentiated into macrophages for three days prior to infection using 200 nM PMA. An overnight culture of *S. aureus* NRS384 was grown in RPMI, washed twice with PBS and resuspended at 1e7 cfu/mL in PBS. THP-1 were washed with warm media (RMPI without FBS) to remove the Penicillin/Streptomycin and then infected with the *S. aureus* suspension at a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing 2× with warm media and remaining extracellular *S. aureus* were killed by addition of media containing gentamicin (50 ug/mL). After 1 hour, media was aspirated and the indicated compound was added to infected macrophages in a dilution series starting at 1e-6 M, with 1:5 dilutions for 6 points ($1.0\times10^{-6}$ M, $2.0\times10^{-7}$ M, $4.0\times10^{-8}$ M, $8.0\times10^{-9}$ M, $1.6\times10^{-9}$ M, and $3.2\times10^{10}$ M). The compounds were added in media containing 50 μg/mL gentamicin to prevent extracellular growth of *S. aureus*. After 2 hours, plates were washed 2× with warm RPMI without FBS, and 100 ul of THP-1 lysis buffer (0.1% Triton in PBS) was added to each well. *S. aureus* survival was enumerated by colony forming units through serial dilution and plating onto TSA.

The results of the intracellular killing assay are shown in Table 30. The minimum inhibitory concentration (MIC) corresponds to the lowest concentration of each compound that resulted in intracellular *S. aureus* below the limit of detection (50 cfu/mL). The intracellular MIC value indicated represents the median value of at least two independent experiments, unless indicated otherwise.

TABLE 30

Minimum inhibitory concentration (MIC) of antibiotics of the invention in an intracellular killing assay using THP cells

| Antibiotic tested | *S. aureus* Intracellular killing MIC (M) |
|---|---|
| Rifampicin | 1.0E−06 |
| P1 | 2.0E−07 |
| P2 | >1.0E−06 |
| 16f | 1.0E−06 |
| 16g | 2.0E−07 |
| 16h | 1.0E−06 |
| 16i | 1.0E−06 |
| 16j | 1.0E−06 |
| 16k | 1.0E−06 |
| 16l | 1.0E−06 |
| 16m | 1.0E−06 |
| 16n | 1.0E−06 |
| 16o | 2.0E−07 |
| 16p | 1.0E−06 |
| 16q | 1.0E−06 |
| 16r | 1.0E−06 |
| 16s | 1.0E−06 |
| 16t | 1.0E−06 |
| 16u | 1.0E−06 |
| 16v | 1.0E−06 |
| 16w | >1.0E−06 |
| 16x | >1.0E−06 |
| 16y | >1.0E−06 |
| 16z | >1.0E−06 |
| 16z-1 | 1.0E−06 |
| 17 | 2.0E−07 |
| 29 | 4.0E−08 |
| 29a | 4.0E−08 |
| 29b | 4.0E−08 |
| 29c | 4.0E−08 |
| 29d | 4.0E−08 |
| 29e | 4.0E−08 |
| 29f | 2.0E−07 |
| 29g | 2.0E−07 |
| 29h | 1.0E−06 |
| 29i | 2.0E−07 |
| 29j | 4.0E−08 |
| 29k | >1.0E−06 |
| 35 | >1.0E−06 |
| 38 | 1.0E−06 |
| 43 | 4.0E−08 |
| 45 | 1.0E−06 |
| 48 | 1.0E−06 |
| 50 | 1.0E−06 |
| 52 | 1.0E−06 |
| 55 | 2.0E−07 |
| 55a | >1.0E−06 |
| 60 | 2.0E−07 |
| 68 | 2.0E−07 |
| 71 | >1.0E−06 |
| 72 | >1.0E−06 |
| 75 | >1.0E−06 |

As Table 30 demonstrates, the intracellular killing MIC for rifamycin analogs according to the disclosure (and rifampicin) ranged from >1e-6 M to 4e-8 M, with 8 novel rifamycin analogs exhibiting potent intracellular killing activity.

Example 39: Intracellular *S. aureus* Antibody-Drug Conjugate Killing Assay 2 (Anti-WTA and Anti-Protein A)

The reagents used are shown in Table 31, below.

TABLE 31

Reagents for Intracellular Assay

| Reagent | Vendor | Catalogue # |
|---|---|---|
| RPMI | Gibco | 11835-030 |
| PBS | Gibco | 20012-043 |
| Triton X-100 | Sigma | TX1568-1 |
| RPMI | Gibco | 11875-093 |
| FBS | Gibco | 10082-147 |
| PMA | Sigma | P8139 |
| Costa 48 well plate | Corning | 3548 |
| TSA plates | Teknova | T0144 |
| Pen/Strep | Gibco | 15140-122 |
| Dilution plates | Greiner Bio one | 780271-FD |
| Gentamicin | BioWhittaker | 17-519Z |

Rifamycin analog compounds of the disclosure were conjugated to either an anti-WTA antibody (Anti-WTA mAb, hIgG1), an anti-Protein A antibody (anti-Protein A mAb, hIgG1 C103S), or a control antibody (Non-targeting isotype control, hIgG1).

To test the efficacy of Anti-*Staphylococcus aureus* antibody-drug conjugates (ADCs) of the present disclosure in vitro, an *S. aureus* intracellular killing assay was developed. For the assay, THP-1 monocytic cell line was grown in media (RMPI+10% FBS+1% Penicillin/Streptomycin), then seeded at a density of 1e5 cells/well in a 48 well plate and differentiated into macrophages for three days prior to infection using 200 nM PMA. An overnight culture of *S. aureus* NRS384 was grown in RPMI, washed twice with PBS and resuspended at 1e7 cfu/mL in PBS. The *S. aureus* suspension was preincubated with the indicated anti-*S. aureus* ADC in a dilution series starting at 10 ug/mL, with 1:3 dilutions for 6 points (10, 3.3, 1.1, 0.37, 0.12, and 0.041 μg/mL final concentrations) and the isotype control ADCs were tested at the highest concentration only. THP-1 were washed with warm media (RMPI without FBS) to remove the Penicillin/Streptomycin and then infected with the pre-incubated *S. aureus* suspension and the ADC, naked antibody or no mAb at a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing 2× with warm media and remaining extracellular *S. aureus* were killed by addition of media containing gentamicin (50 g/mL). After 24 hours, media was aspirated and wells washed 2× with warm RPMI without FB S, and 100 μl of THP-1 lysis buffer (0.1% Triton in PBS) and 150 μl of PBS were added to each well. *S. aureus* survival was enumerated by colony forming units through serial dilution and plating onto TSA.

Figure 5:
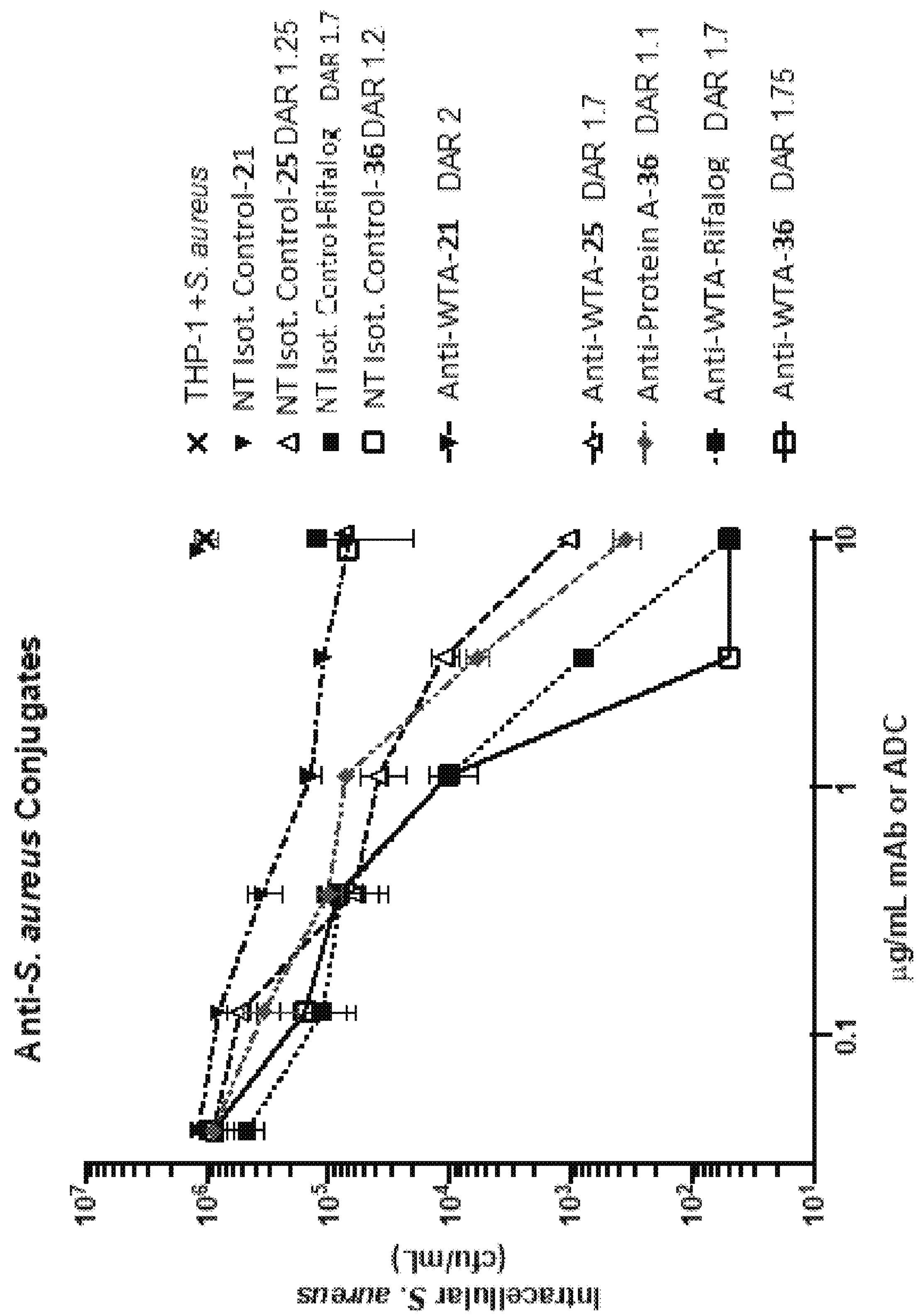
FIG. 5 is a plot of colony forming units of Anti-*Staphylococcus aureus* ADCs according to the disclosure in an intracellular killing assay using THP cells.

The results of the intracellular killing assay are shown in FIG. 5 and Table 32, with a limit of detection of 50 cfu/mL.

TABLE 32

Colony forming units of Anti-*Staphylococcus aureus* ADCs of the disclosure in an intracellular killing assay using THP cells

| | ncADC or mAb dose (ug/mL) | Average cfu/mL | Standard Deviation | Fold Reduction compared to *S. aureus* control |
|---|---|---|---|---|
| *S. aureus* control | none | 1,025,000 | 212,132 | 1 |
| Non-targeting isotype control | 10 | 600,000 | 141,421 | 2 |
| Anti-Protein A mAb | 10 | 500,000 | 70,711 | 2 |
| Anti-WTA mAb | 10 | 750,000 | 70,711 | 1 |
| Non-targeting isotype control-21 | 10 | 1,175,000 | 70,711 | 1 |
| Non-targeting isotype control-25 | 10 | 73,750 | 8,839 | 14 |
| Non-targeting isotype control-Rifalog | 10 | 128,750 | 22,981 | 8 |
| Non-targeting isotype control-36 | 10 | 70,000 | 0 | 15 |
| Anti-WTA mAb-21 | 10 | 65,833 | 46,256 | 16 |
| | 3.3 | 109,167 | 3,819 | 9 |
| | 1.1 | 138,333 | 26,732 | 7 |
| | 0.4 | 350,000 | 108,972 | 3 |
| | 0.1 | 800,000 | 108,972 | 1 |
| | 0.04 | 1,175,000 | 139,194 | 1 |
| Anti-WTA mAb-25 | 10 | 1,067 | 113 | 961 |
| | 3.3 | 11,250 | 2,883 | 91 |
| | 1.1 | 38,333 | 16,073 | 27 |
| | 0.4 | 61,667 | 28,976 | 17 |
| | 0.1 | 533,333 | 152,753 | 2 |
| | 0.04 | 883,333 | 289,756 | 1 |
| Anti-WTA mAb-Rifalog | 10 | 50 | 0 | 20,500 |
| | 3.3 | 808 | 138 | 1,268 |
| | 1.1 | 10,250 | 4,265 | 100 |
| | 0.4 | 78,333 | 40,646 | 13 |
| | 0.1 | 110,833 | 39,713 | 9 |
| | 0.04 | 466,667 | 125,831 | 2 |
| Anti-Protein A mAb-36 | 10 | 350 | 87 | 2,929 |
| | 3.3 | 5,917 | 1,258 | 173 |
| | 1.1 | 71,667 | 8,780 | 14 |
| | 0.4 | 100,000 | 22,220 | 10 |
| | 0.1 | 341,667 | 166,458 | 3 |
| | 0.04 | 883,333 | 128,290 | 1 |
| Anti-WTA mAb-36 | 10 | 50 | 0 | 20,500 |
| | 3.3 | 50 | 0 | 20,500 |
| | 1.1 | 10,250 | 1,521 | 100 |
| | 0.4 | 82,500 | 32,692 | 12 |
| | 0.1 | 156,667 | 97,511 | 7 |
| | 0.04 | 883,333 | 189,297 | 1 |

Control ADCs (Non-targeting isotype control conjugates), which are a human IgG1 isotype and therefore able to bind to Protein A on *S. aureus*, reduced intracellular *S. aureus* viability by ~1 log or less compared to the untreated control. Anti-WTA mAb-21, which releases a rifampicin payload, reduced the bacterial burden similarly to the control ADCs. Anti-*S. aureus* ADCs which delivered a payload with potent intracellular killing activity (Anti-WTA mAb-25, Anti-Protein A mAb-36, Anti-WTA mAb-Rifalog, and Anti-WTA mAb-36), were more effective than the rifampicin conjugate (Anti-WTA mAb-21) at reducing intracellular *S. aureus*, with reductions of 3 log or greater compared to the untreated control. Anti-WTA mAb-36 consistently reduced *S. aureus* viability more than Anti-WTA mAb-Rifalog in multiple experiments.

Example 40: Intracellular *S. aureus* Antibody-Drug Conjugate Killing Assay 3 (MSR1)

The reagents used are shown in Table 33, below.

TABLE 33

Reagents for Intracellular Assay

| Reagent | Vendor | Catalogue # |
|---|---|---|
| RPMI | Gibco | 11835-030 |
| PBS | Gibco | 20012-043 |
| Triton X-100 | Sigma | TX1568-1 |
| RPMI | Gibco | 11875-093 |
| FBS | Gibco | 10082-147 |
| PMA | Sigma | P8139 |
| Costa 48 well plate | Corning | 3548 |
| TSA plates | Teknova | T0144 |
| Pen/Strep | Gibco | 15140-122 |
| Dilution plates | Greiner Bio one | 780271-FD |
| Gentamicin | BioWhittaker | 17-519Z |

To test the efficacy of an anti-MSR1 Ab-antibiotic ncADC of the disclosure in vitro, an intracellular *S. aureus* killing assay was utilized. For the assay, a THP-1 monocytic cell line was grown in media comprised of RPMI containing 10% FBS and 1% Penicillin/Streptomycin, then was seeded at a density of $1\times10^5$ cells/well in a 48 well plate and differentiated into macrophages for three days prior to infection using 200 nM Phorbol Myristate Acetate (PMA). An overnight culture of *S. aureus* MRSA strain NRS384 was grown in RPMI, washed twice with PBS and subsequently resuspended at $1\times10^7$ cfu/mL in PBS. THP-1 cells were washed with warm media (RPMI without FBS) to remove the Penicillin/Streptomycin and then infected with the *S. aureus* suspension at a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing twice with warm media and remaining extracellular *S. aureus* were killed by addition of media containing 50 μg/mL of gentamicin. After 1 hour, media was aspirated and the anti-MSR1 Ab-antibiotic ncADCs (H1H21234N-N297Q-25 and H1H21234N-N297Q-80) at different doses (10 μg/mL, 3.3 μg/mL, 1.1 μg/mL, 0.4 μg/mL, 0.1 μg/mL and 0.04 μg/mL) and the isotype control-antibiotic ncADC (Isotype control-N297Q-25 and Isotype Control-N297Q-80) at 10 μg/mL were added to infected macrophages in media containing 50 μg/mL gentamicin to prevent extracellular growth of *S. aureus*. A sample without any ncADC was also included for reference. After 24 hours, plates were washed twice with warm RPMI without FBS and then 100 μL of 0.1% o Triton X-100 in PBS was added and incubated for 10 minutes to lyse the THP-1. *S. aureus* survival was enumerated by colony forming units through serial dilution in PBS and plating onto trypticase soy agar plates.

The results are summarized in Table 34, below.

TABLE 34

Average colony forming units of anti-MSRl Ab-Antibiotic

| | ncADC dose (μg/mL) | Average cfu/mL | Standard Deviation | Fold Reduction compared to *S. aureus* control |
|---|---|---|---|---|
| *S. aureus* control | none | 1,350,000 | 139,194 | 1 |
| Isotype Control-N297Q-25 | 10 | 608,333 | 52,042 | 2 |
| MSR1 ncADC | 10 | 1,325 | 87 | 1,019 |
| H1H21234N- | 3.3 | 4,917 | 722 | 275 |
| N297Q-25 | 1.1 | 13,250 | 1,887 | 102 |
| | 0.4 | 56,667 | 7,638 | 24 |
| | 0.1 | 82,500 | 17,500 | 16 |
| | 0.04 | 1,025,000 | 43,301 | 1 |
| Isotype Control-N297Q-80 | 10 | 1,208,333 | 94,648 | 1 |
| MSR1 ncADC | 10 | 50 | 0 | 27,000 |
| H1H21234N- | 3.3 | 50 | 0 | 27,000 |
| N297Q-80 | 1.1 | 50 | 0 | 27,000 |
| | 0.4 | 7,417 | 2,876 | 182 |
| | 0.1 | 75,833 | 15,275 | 18 |
| | 0.04 | 758,333 | 230,940 | 2 |

As shown in Table 34, the anti-MSR1 Ab-antibiotic ncADCs (H1H21234N-N297Q-25 and H1H21234N-N297Q-80) demonstrated the ability to reduce intracellular *S. aureus* in macrophages in vitro in a dose-dependent manner compared to the untreated control. Macrophages treated with the isotype control-antibiotic ncADC (Isotype control-N297Q-25 and Isotype control-N297Q-80) at 10 μg/mL harbored intracellular *S. aureus* at a similar level to the untreated control. These data demonstrate that an anti-MSR1 Ab-antibiotic ncADC according to the disclosure can be used to effectively kill pathogens residing within a macrophage reservoir.

Example 41: *S. aureus* IV Disseminated Infection Mouse Model (4 Day Model)

Figure 4:
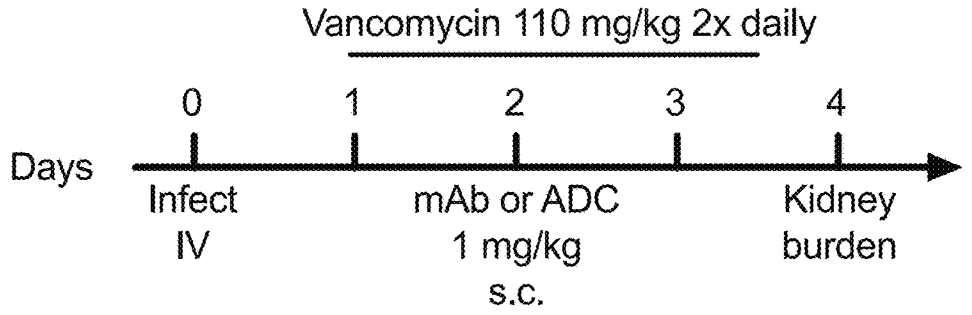
FIG. 4 is a schematic of four day *S. aureus* infection model.

To test the efficacy of an anti-*S. aureus* Ab-antibiotic ncADC of the disclosure alone and in combination with the standard of care MRSA antibiotic vancomycin in vivo, a four day intravenous disseminated infection model was utilized. *S. aureus* MSRA strain NRS384 was grown overnight in Tryptic soy broth (TSB) and sub-cultured to mid-logarithmic phase. Bacteria were then washed twice with PBS and resuspended in PBS at a concentration of 1.5×10^8 cfu/mL. Balb/c mice were then infected intravenously through the tail vein with 100 μL of the bacterial suspension, for a final infectious dose of 1.5×10^7 cfu/mouse. In the study, mice were treated with either vancomycin alone, an isotype control Ab-Antibiotic ncADC (Isotype control Ab-Antibiotic ncADC-Rifalog), which is an anti-WTA antibody conjugated to Rifalog, an anti-WTA antibody, an anti-WTA Ab-Antibiotic ncADC (anti-WTA Ab-Antibiotic ncADC-36), which is an anti-WTA antibody conjugated to compound 36 according to the disclosure, a second anti-WTA Ab-Antibiotic ncADC (anti-WTA Ab-Antibiotic ncADC-25), which is an anti-WTA antibody conjugated to compound 25 according to the disclosure, or a third anti-WTA Ab-Antibiotic ncADC (anti-WTA Ab-Antibiotic ncADC-Rifalog), an isotype control Ab-Antibiotic ncADC (Isotype control Ab-Antibiotic ncADC-Rifalog) plus vancomycin, an anti-WTA antibody plus vancomycin, an anti-WTA Ab-Antibiotic ncADC (anti-WTA Ab-Antibiotic ncADC-36), a second anti-WTA Ab-Antibiotic ncADC (anti-WTA Ab-Antibiotic ncADC-25) plus vancomycin, or a third anti-WTA Ab-Antibiotic ncADC (anti-WTA Ab-Antibiotic ncADC-Rifalog) plus vancomycin. For treatment groups that included vancomycin, it was dosed from 1 day to 3 days post infection at 110 mg/kg subcutaneously twice daily. For treatment groups that included antibodies and ncADCs, they were administered 2 days after infection subcutaneously at 1 mg/kg. A no treatment infected control and an uninfected control were included in the study. Mice were monitored for weight loss and body conditioning score throughout the infection. At four days post infection, mice were euthanized, and the *S. aureus* kidney burden was quantified. For quantification, the kidneys were homogenized followed by enumeration of colony forming units through serial dilution in PBS and plating onto trypticase soy agar plates. Infection scheme is represented in FIG. 4. Data is represented in Table 35 as median *S. aureus* kidney burden in mice.

TABLE 35

Median *S. aureus* kidney burden in mice treated with anti-*S. aureus* Ab-Antibiotic ncADC at 1 mg/kg alone and in combination with vancomycin (4 day infection model).

| mAb or conjugate dose (1 mg/kg) | Vancomycin treatment | Median cfu/kidney pair | Standard Deviation | Mortality (n) |
|---|---|---|---|---|
| Uninfected Control | – | 250 (limit of detection) | — | 0/1 |
| Infected Control | – | 3.63E+07 | 3.72E+07 | 2/5 |
| Non-targeting Isotype Control Ab-Antibiotic ncADC-Rifalog | – | 1.50E+08 | 8.32E+07 | 2/5 |
| Anti-WTA mAb | – | 2.19E+08 | 3.78E+08 | 1/5 |
| Anti-WTA Ab-Antibiotic ncADC-Rifalog | – | 5.38E+07 | 1.34E+08 | 0/5 |
| Anti-WTA Ab-Antibiotic ncADC-25 | – | 1.06E+06 | 2.77E+06 | 1/5 |
| Anti-WTA Ab-Antibiotic ncADC-36 | – | 1.61E+06 | 8.10E+07 | 1/5 |
| Vancomycin control | + | 4.38E+05 | 6.92E+05 | 0/5 |
| Non-targeting Isotype Control Ab-Antibiotic ncADC-Rifalog | + | 3.13E+06 | 5.70E+06 | 0/5 |
| Anti-WTA mAb | + | 4.50E+05 | 8.12E+06 | 0/5 |

TABLE 35-continued

Median *S. aureus* kidney burden in mice treated with anti-*S. aureus* Ab-Antibiotic ncADC at 1 mg/kg alone and in combination with vancomycin (4 day infection model).

| mAb or conjugate dose (1 mg/kg) | Vancomycin treatment | Median cfu/kidney pair | Standard Deviation | Mortality (n) |
|---|---|---|---|---|
| Anti-WTA Ab-Antibiotic ncADC-Rifalog | + | 2.50E+02 | 3.24E+06 | 0/5 |
| Anti-WTA Ab-Antibiotic ncADC-25 | + | 3.75E+02 | 1.55E+04 | 0/5 |
| Anti-WTA Ab-Antibiotic ncADC-36 | + | 2.50E+02 | 2.21E+05 | 0/5 |

Limit of detection = 250 colony forming units (cfu)

Limit of detection=250 colony forming units (cfu)

As shown in Table 35, intravenous infection with *S. aureus* MRSA strain NRS384 results in high median bacterial burden in the kidneys of 3.63E+07 cfus/kidney pair. As a monotherapy, anti-WTA Ab Antibiotic ncADC-25 and anti-WTA Ab Antibiotic ncADC-36 reduced the kidney bacterial burden by ~2 logs. When the anti-WTA Ab antibiotic ncADCs tested were administered in combination with vancomycin, all treatment groups had a further reduction in kidney bacterial burden by ~3 logs compared to the vancomycin treated control.

Example 42: *S. aureus* IV Advanced Disseminated Infection Mouse Model (8 Day Model)

To test the efficacy of anti-*S. aureus* Ab-antibiotic ncADCs of the disclosure in combination therapy with standard of care vancomycin in vivo, two different 8 day intravenous disseminated infection models was performed. In this model, treatment was initiated at an advanced infection stage where abscesses have already formed. *S. aureus* MSRA strain NRS384 was grown overnight in Tryptic soy broth (TSB) and sub-cultured to mid-logarithmic phase. Bacteria were then washed twice with PBS and resuspended in PBS at a concentration of 1.5×10^8 cfu/mL. Balb/c mice were then infected intravenously through the tail vein with 100 uL of the bacterial suspension, for a final infectious dose of 1.5×10^7 cfu/mouse. In the first study, mice were treated either vancomycin alone, an isotype control antibody plus vancomycin, an isotype control Ab-ncADC (Isotype control-36) plus vancomycin, an anti-WTA antibody plus vancomycin, an anti-WTA Ab-Antibiotic ncADC (anti-WTA Ab-Antibiotic ncADC-36), or a different anti-WTA Ab-Antibiotic ncADC (anti-WTA Ab-Antibiotic ncADC-25) plus vancomycin. Mice were also treated either vancomycin alone, an isotype control antibody plus vancomycin, an isotype control Ab-Antibiotic ncADC (Isotype control Ab-Antibiotic ncADC-36) plus vancomycin, an anti-Protein A antibody plus vancomycin, or an anti-Protein A Ab-Antibiotic ncADC (anti-Protein A Ab-Antibiotic ncADC-36).

In the second study, mice were treated either vancomycin alone, an isotype control antibody plus vancomycin, an isotype control Ab-Antibiotic ncADC (Isotype control Ab-Antibiotic ncADC-36) plus vancomycin, a second isotype control Ab-Antibiotic ncADC (Isotype control Ab-Antibiotic ncADC-25) plus vancomycin, a third isotype control Ab-Antibiotic ncADC (Isotype control Ab-Antibiotic ncADC-21) plus vancomycin, an anti-WTA antibody plus vancomycin, an anti-WTA Ab-Antibiotic ncADC (anti-WTA Ab-Antibiotic ncADC-36), a second anti-WTA Ab-Antibiotic ncADC (anti-WTA Ab-Antibiotic ncADC-25) plus vancomycin, or a third anti-WTA Ab-Antibiotic ncADC (anti-WTA Ab-Antibiotic ncADC-21) plus vancomycin. In all studies, for treatment groups that included vancomycin, it was dosed from three to seven days post infection at 110 mg/kg subcutaneously twice daily. For treatment groups that included antibodies and ncADCs, they were administered four days after infection subcutaneously at 2 mg/kg for the first study or 5 mg/kg for the second study. A no treatment infected control and an uninfected control were included in each of the studies. Mice were monitored for weight loss and body conditioning score throughout the infection. At eight days post infection, mice were euthanized, and the *S. aureus* kidney burden was quantified. For quantification, the kidneys were homogenized followed by enumeration of colony forming units through serial dilution in PBS and plating onto trypticase soy agar plates. Data points represent the kidney burden from individual mice tested.

TABLE 36

Average *S. aureus* kidney burden in mice treated with isotype control and anti-WTA Ab-Antibiotic ncADC at 2 mg/kg in combination with vancomycin

| mAb or conjugate dose (2 mg/kg) | Vancomycin treatment | Median cfu/kidney pair | Standard Deviation | Mortality (n) |
|---|---|---|---|---|
| Uninfected Control | − | 2.50E+02 (limit of detection) | 0.00E+00 | 0/5 |
| Infected Control | − | 4.63E+08 | 2.56E+08 | 3/6 |
| Vancomycin Control | + | 7.25E+06 | 1.83E+07 | 7/11 |
| Isotype Control mAb | + | 6.50E+06 | 1.12E+08 | 1/6 |
| Non-targeting Isotype Control Ab-Antibiotic ncADC-Rifalog | + | 1.56E+06 | 1.12E+06 | 1/5 |

TABLE 36-continued

Average *S. aureus* kidney burden in mice treated with isotype control and anti-WTA Ab-Antibiotic ncADC at 2 mg/kg in combination with vancomycin

| mAb or conjugate dose (2 mg/kg) | Vancomycin treatment | Median cfu/kidney pair | Standard Deviation | Mortality (n) |
|---|---|---|---|---|
| Non-targeting Isotype Control Ab-Antibiotic ncADC-36 | + | 4.56E+06 | 1.21E+07 | 2/7 |
| anti-WTA mAb | + | 3.50E+06 | 8.78E+06 | 0/5 |
| Anti-WTA Ab-Antibiotic ncADC-Rifalog | + | 2.25E+05 | 1.45E+06 | 1/6 |
| Anti-WTA Ab-Antibiotic ncADC-25 | + | 2.50E+02 | 1.84E+05 | 0/6 |
| Anti-WTA Ab-Antibiotic ncADC-36 | + | 4.13E+04 | 1.25E+05 | 0/5 |

Figure 6:
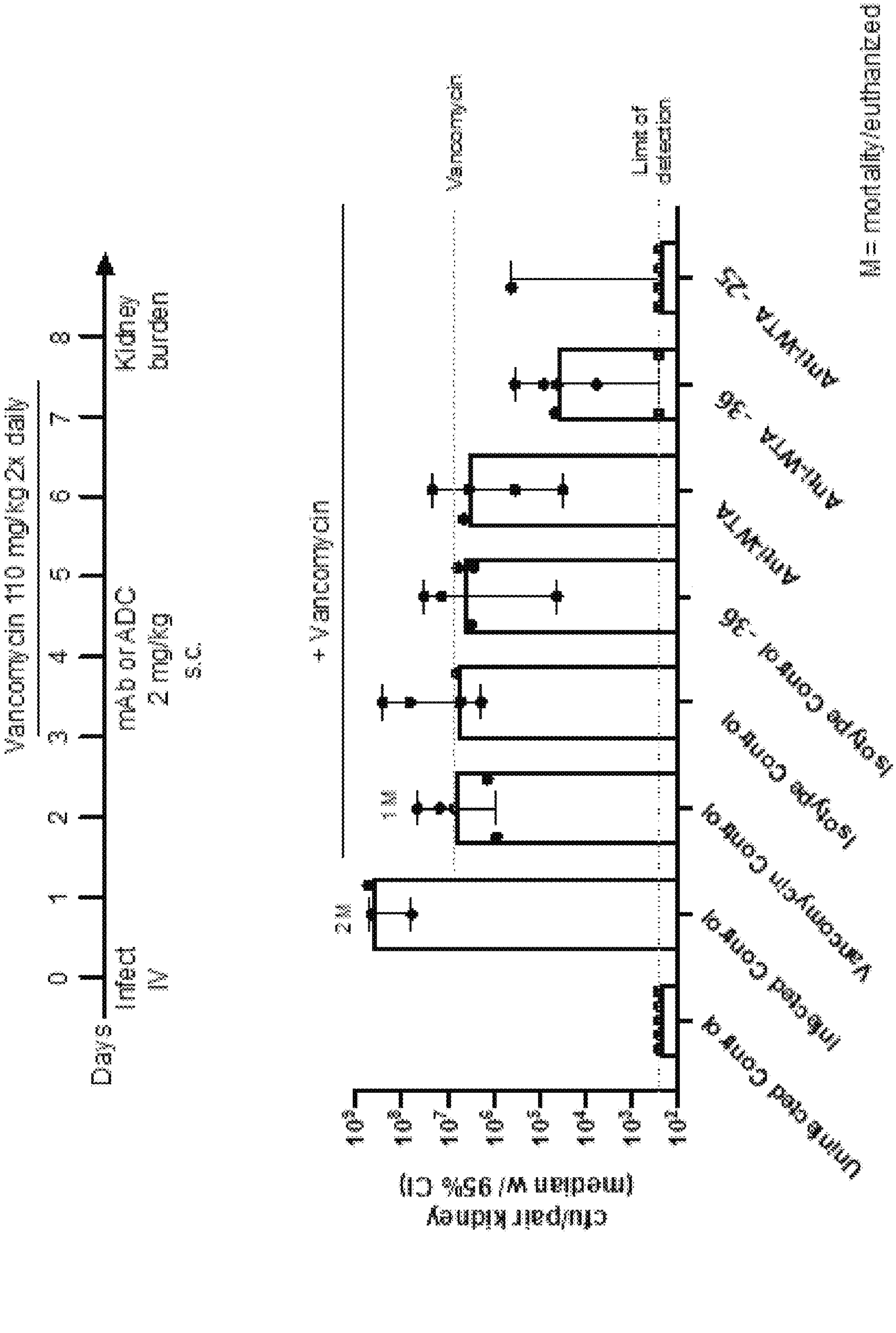
FIG. 6 depicts the average *S. aureus* kidney burden in mice treated with isotype control and anti-WTA Ab-Antibiotic ncADC (antibody-drug conjugates) according to the disclosure at 2 mg/kg in combination with vancomycin.

For the first study, as shown in FIG. 6 and Table 36, intravenous infection with *S. aureus* MRSA strain NRS384 results in high median bacterial burden in the kidneys of 4.63E+08 cfu/kidney pair. Vancomycin treatment alone reduced *S. aureus* kidney burden by 1-2 logs. Combination treatment of vancomycin with the isotype control mAb, anti-WTA monoclonal mAb, and isotype control Ab-Antibiotic ncADC-36 did not result in a further reduction in kidney bacterial burden compared to vancomycin treated mice. When the anti-WTA Ab-Antibiotic ncADC-36 and anti-WTA Ab-Antibiotic ncADC-25 were administered in combination with vancomycin, there was a further ~100 and ~10,000 times reduction in median kidney bacterial burden, respectively.

TABLE 37

Average *S. aureus* kidney burden in mice treated with isotype control and anti-Protein A Ab-Antibiotic ncADC at 2 mg/kg in combination with vancomycin

| mAb or conjugate dose (2 mg/kg) | Vancomycin treatment | Median cfu/kidney pair | Standard Deviation | Mortality (n) |
|---|---|---|---|---|
| Uninfected Control | – | 2.50E+02 | 0.00E+00 | 0/5 |
| Infected Control | – | 4.63E+08 | 2.56E+08 | 3/6 |
| Vancomycin Control | + | 7.25E+06 | 1.83E+07 | 7/11 |
| Non-targeting Isotype Control mAb | + | 6.50E+06 | 1.12E+08 | 1/6 |

TABLE 37-continued

Average *S. aureus* kidney burden in mice treated with isotype control and anti-Protein A Ab-Antibiotic ncADC at 2 mg/kg in combination with vancomycin

| mAb or conjugate dose (2 mg/kg) | Vancomycin treatment | Median cfu/kidney pair | Standard Deviation | Mortality (n) |
|---|---|---|---|---|
| Non-targeting Isotype Control Ab-Antibiotic ncADC 36 | + | 4.56E+06 | 1.21E+07 | 2/7 |
| Anti-Protein A Ab | + | 5.69E+04 | 1.22E+07 | 0/6 |
| Anti-Protein A Ab-Antibiotic ncADC - Rifalog | + | 7.08E+04 | 2.13E+05 | 0/6 |
| Anti-Protein A Ab-Antibiotic ncADC - 36 | + | 6.25E+03 | 3.64E+05 | 1/6 |

Figure 7:
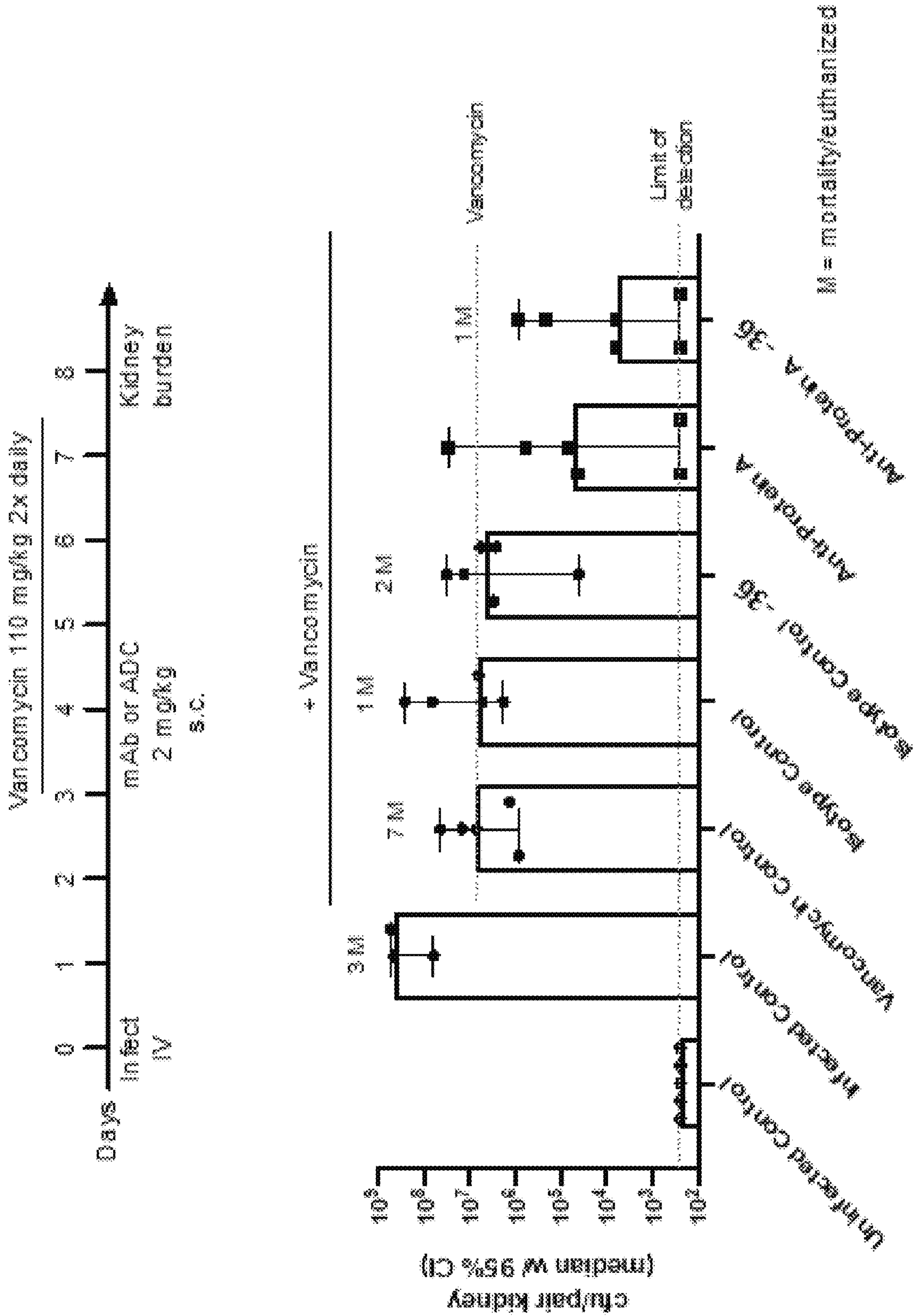
FIG. 7 depicts the average *S. aureus* kidney burden in mice treated with isotype control and anti-Protein A Ab-Antibiotic ncADC according to the disclosure at 2 mg/kg in combination with vancomycin.

Also in the first study, as shown in FIG. 7 and Table 37, intravenous infection with *S. aureus* MRSA strain NRS384 results in high median bacterial burden in the kidneys of 4.63E+08 cfu/kidney pair. Vancomycin treatment alone reduced *aureus* kidney bacterial burden by 1-2 logs. Combination treatment of vancomycin with the isotype control mAb and isotype control Ab-Antibiotic ncADC-36 did not result in a further reduction in kidney bacterial burden compared to vancomycin treated mice. When anti-Protein A mAb and anti-Protein A Ab-Antibiotic ncADC-36 were administered in combination with vancomycin, there was a further ~100 and ~1,000 times reduction in median kidney bacterial burden, respectively.

TABLE 38

Average *S. aureus* kidney burden in mice treated with isotype control and anti-WTA Ab-Antibiotic ncADC at 5 mg/kg in combination with vancomycin

| mAb or conjugate dose (5 mg/kg) | Vancomycin treatment | Median cfu/kidney pair | Standard Deviation | Mortality (n) |
|---|---|---|---|---|
| Uninfected Control | – | 2.50E+02 | 0.00E+00 | 0/2 |
| Infected Control | – | 2.50E+07 | 1.00E+07 | 2/5 |
| Vancomycin Control | + | 1.88E+06 | 6.17E+05 | 2/5 |
| Non-targeting Isotype Control mAb | + | 3.13E+06 | 1.28E+07 | 1/4 |
| Non-targeting Isotype Control Ab-Antibiotic ncADC-Rifalog | + | 2.77E+06 | 1.28E+07 | 1/4 |
| Non-targeting Isotype Control Ab-Antibiotic ncADC-36 | + | 1.50E+06 | 5.78E+06 | 0/5 |

TABLE 38-continued

Average *S. aureus* kidney burden in mice treated with isotype control and anti-WTA Ab-Antibiotic ncADC at 5 mg/kg in combination with vancomycin

| mAb or conjugate dose (5 mg/kg) | Vancomycin treatment | Median cfu/kidney pair | Standard Deviation | Mortality (n) |
|---|---|---|---|---|
| Non-targeting Isotype Control Ab-Antibiotic ncADC 25 | + | 4.13E+05 | 1.68E+06 | 0/5 |
| Non-targeting Isotype Control Ab-Antibiotic ncADC-21 | + | 2.50E+06 | 1.56E+07 | 0/5 |
| Anti-WTA mAb | + | 2.13E+06 | 1.95E+06 | 0/5 |
| Anti-WTA mAb-Antibiotic ncADC-Rifalog | + | 3.50E+04 | 1.99E+04 | 2/5 |
| Anti-WTA mAb-Antibiotic ncADC-36 | + | 2.25E+06 | 3.21E+06 | 0/5 |
| Anti-WTA mAb-Antibiotic ncADC 25 | + | 8.56E+03 | 2.02E+04 | 1/5 |
| Anti-WTA mAb-Antibiotic ncADC 21 | + | 2.13E+06 | 1.48E+07 | 0/5 |

Figure 8:
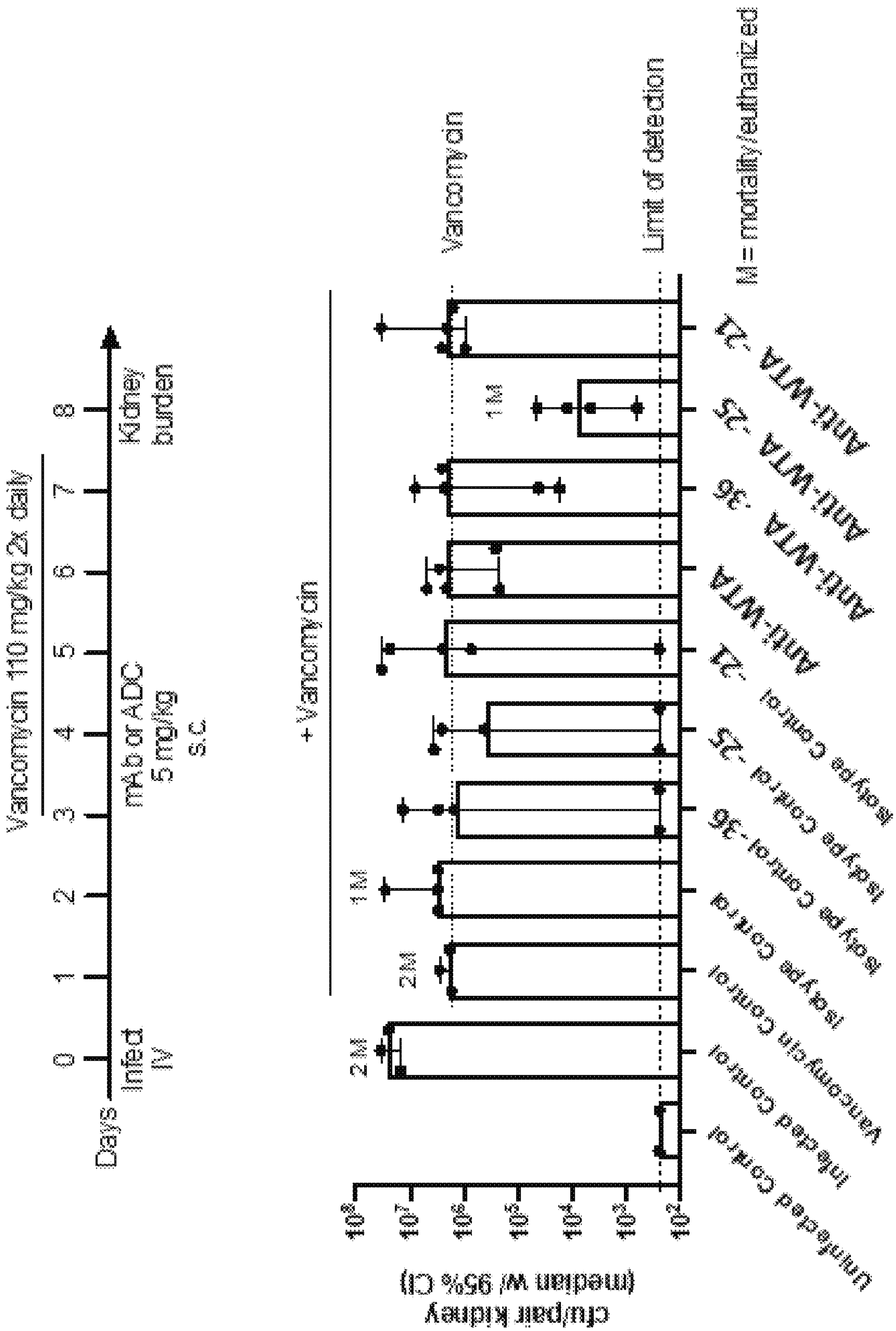
FIG. 8 depicts the average *S. aureus* kidney burden in mice treated with isotype control and anti-WTA Ab-Antibiotic ncADC according to the disclosure at 5 mg/kg in combination with vancomycin.

For the second study, as shown in FIG. 8 and Table 38, intravenous infection with *S. aureus* MRSA strain NRS384 results in high median bacterial burden in the kidneys of 2.50E+07 cfus/kidney pair. Vancomycin treatment alone reduced *S. aureus* kidney bacterial burden by 1-2 logs. Combination treatments with vancomycin and isotype control mAb, anti-WTA mAb, isotype control Ab-antibiotic ncADCs, anti-WTA Ab-antibiotic ncADC-36, or anti-WTA-Ab-antibiotic ncADC-21 (Rifampicin ADC) did not result in a further reduction in kidney bacterial burden compared to vancomycin treated mice. However, when the anti-WTA Ab-Antibiotic ncADC-25 tested were administered in combination with vancomycin, there was a further ~100 times reduction in median kidney bacterial burden.

Example 43: Antibody Engineered Cysteine Deblocking

Anti-Protein A (H1×H15140P*/*) and a nontargeting antibody control engineered antibodies were created by mutating the interchain disulfide forming heavy chain C103S. The antibodies are expressed in CHO cells and need to be deblocked on the native light chain cysteine using mild reduction in PBS at room temperature by the addition of a thirty fold molar excess of reducing agent, TCEP followed by buffer exchange. To reform the two heavy interchain disulfide bonds, the antibody was incubated for three hours at room temperature with $CuSO_4$ or with dhAA at a two to twenty fold molar excess. The reduced and oxidized antibody was buffer exchanged into PBS to remove oxidizing agent. This process produces two free thiols that reside on the light chain and are available for maleimide conjugation.

The anti-WTA engineered antibody was taken from the literature (Lehar et al, *Nature* 2015 527, 323-328; antibody 4497 described in US20140356375 and WO2016090038, the content of which is incorporated herein by reference in its entirety) and has a light chain mutation V205C to provide 2 sites for maleimide conjugation. The same procedure above was used to deblock the engineered cysteines.

Conjugation of Antibody Engineered Deblocked Cysteine to Linker Payload

To the reduced and oxidized antibody (1-10 mg/ml) in PBS pH7.5, the maleimido linker payload (2 equivalents/SH group, Lehar et al, Nature 527, 323-328), or the linker payloads of this filing, in DMSO (10 mg/ml) was added. The reaction proceeded for 2 hrs. The conjugates were purified into PBS by size exclusion chromatography and sterile filtered. Protein concentrations and payload to antibody ratios were determined by UV spectral analysis. Size-exclusion HPLC established that all conjugates used were >95% monomeric, and RP-HPLC established that there was <1% unconjugated linker payload. All conjugated antibodies were analyzed by HIC for linker payload loading values. Payload to antibody ratios are reported in Table 39.

Conjugation Method for Aglycosylated Antibodies (H1H21234N and Nontargeting Antibody Control 2)

The antibody (1-10 mg/ml) in 50 mM HEPES, 150 mM NaCl, pH 7.5, was treated with 1 mM dithiothreitol at 37° C. for 30 min. After gel filtration (G-25, pH 4.5 sodium acetate), the maleimido linker payload derivative compound 25 (Rifanalog M2767) (1.2 equivalents/SH group) in DMSO (10 mg/ml) was added to the reduced antibody and the mixture adjusted to pH 7.0 with 1 M HEPES (pH 7.4). The conjugates were purified using PBS with 5% glycerol by size exclusion chromatography and sterile filtered. Protein concentrations and payload to antibody ratios were determined by UV spectral analysis. Size-exclusion HPLC established that all conjugates used were >95% monomeric. All conjugated antibodies were analyzed by HIC for linker payload loading values. Payload to antibody ratios are reported in Table 39.

TABLE 39

Purity and drug to antibody ratios (DAR) of conjugates.

| Antibody Drug Conjugate | DAR (by HIC) | DAR (by ESI-MS) | Purity (by SEC) | Yield |
|---|---|---|---|---|
| Anti-WTA-rifalog | 1.8 | | >95% | 53% |
| Anti-WTA-21 (rifampicin control) | 2.0 | | >95% | 70% |
| Anti-WTA-25 | 1.7 | | >95% | 50% |
| Anti-WTA-36 | 1.8 | | >95% | 40% |
| Anti-Protein A-rifalog | 1.9 | | >95% | 30% |
| Anti-Protein A-36 | 1.1 | | >95% | 40% |
| H1H21234N-25 | 3 | | >95% | 50% |
| nontargeting antibody control 1- rifalog | 1.7 | | >95% | 60% |
| nontargeting antibody control 1-21 (Rifampicin) | 2.0 | | >95% | 70% |
| nontargeting antibody control 1-25 | 1.3 | | >95% | 50% |

TABLE 39-continued

| Purity and drug to antibody ratios (DAR) of conjugates. | | | | |
|---|---|---|---|---|
| Antibody Drug Conjugate | DAR (by HIC) | DAR (by ESI-MS) | Purity (by SEC) | Yield |
| nontargeting antibody control 1-36 | 1.2 | | >95% | 40% |
| nontargeting antibody control 2-25 | 2 | | >95% | 50% |

Characterization of Conjugates by Hydrophobic Interaction Chromatography (HIC)

To determine the loading of the linker-payloads on the antibody, the conjugates were run on Agilent 1260 using a TSK-NPR Butyl HIC column using a linear gradient of 1M potassium phosphate pH 8.5 to water over 60 min. The payload loading was determined by integration of peak areas corresponding to the species of conjugated and unconjugated antibody.

Characterization of Conjugates by ESI-MS

To determine the loading of the linker-payloads on the antibody (cysteine conjugates), the conjugates were deglycosylated, reduced, and analyzed by LC-MS.

For the assay, 50 μg of the conjugate was diluted with mili-Q water to a final concentration of 1 mg/mL. Ten μL of PNGase F solution [PNGase F solution was prepared by adding 150 μL of PNGase F stock (New England Biolabs, Cat #P0704L) and 850 μL of mili-Q water and mixed well] was added to the diluted conjugate solution and then incubated at 37° C. overnight. 2.4 μL of 0.5 M TCEP was added to the sample such that the resulting material had a final TCEP concentration of 20 mM and this was then incubated at 50° C. for 30 minutes. Injections of 10 μL of each sample were made onto LC-MS (Waters Synat G2-Si) and eluted with 0.1 mL/minute of a gradient mobile phase 20-40% of mobile phase B over 25 minutes (Mobile Phase A: 0.1% v/v FA in $H_2O$; Mobile Phase B: 0.1% v/v FA in Acetonitrile). The LC separation was achieved on Waters Acquity BEH C18 column (1.0×50 mM, 1.7 μM).

The mass spectrometry spectra were deconvoluted and the identified light and heavy chain peaks represent the light chain (L) with linker-payload values=0 and 1, heavy chain (H) with linker-payload values=0, 1, 2, and 3. From the intensity values of each species, the drug to antibody ratio (DAR) was calculated using equation below for a homodimer antibody conjugate.

$$DAR = 2 * \left[ \frac{L1}{L0 + L1} + \frac{H1 + 2 * H2 + 3 * H3}{H0 + H1 + H2 + H3} \right]$$

As various changes can be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

SEQUENCE LISTING

```
Sequence total quantity: 690
SEQ ID NO: 1              moltype = DNA  length = 363
FEATURE                   Location/Qualifiers
misc_feature              1..363
                          note = Synthetic
source                    1..363
                          mol_type = other DNA
                          organism = synthetic construct
SEQUENCE: 1
caggtccaat tggtacagtc tggggctgag gtgaagaagc ctggggcctc agtgaaggtg  60
tcctgcaagg tttccggata caccctcact gaattatcca tacactgggt gcgccaggtt  120
cctggaaaag gacttgagtg gatgggaggt tttgatcctg aagagggtga aacaatcttc  180
gcacaggagt tccgggacag agtcaccttg accgaggaca catctccaga cacagcctac  240
atggagttga gcagcctgaa atctgaggac gcggccgtat attactgtac aaccccccga  300
tattgtaata atggtatatg ttatgactac tggggccagg gaaccctggt caccgtctct  360
tca                                                                363

SEQ ID NO: 2              moltype = AA  length = 121
FEATURE                   Location/Qualifiers
REGION                    1..121
                          note = Synthetic
source                    1..121
                          mol_type = protein
                          organism = synthetic construct
SEQUENCE: 2
QVQLVQSGAE VKKPGASVKV SCKVSGYTLT ELSIHWVRQV PGKGLEWMGG FDPEEGETIF  60
AQEFRDRVTL TEDTSPDTAY MELSSLKSED AAVYYCTTPR YCNNGICYDY WGQGTLVTVS  120
S                                                                  121

SEQ ID NO: 3              moltype = DNA  length = 24
FEATURE                   Location/Qualifiers
misc_feature              1..24
                          note = Synthetic
source                    1..24
                          mol_type = other DNA
```

```
                        organism = synthetic construct
SEQUENCE: 3
ggatacaccc tcactgaatt atcc                                        24

SEQ ID NO: 4            moltype = AA  length = 8
FEATURE                 Location/Qualifiers
REGION                  1..8
                        note = Synthetic
source                  1..8
                        mol_type = protein
                        organism = synthetic construct
SEQUENCE: 4
GYTLTELS                                                          8

SEQ ID NO: 5            moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 5
tttgatcctg aagagggtga aaca                                        24

SEQ ID NO: 6            moltype = AA  length = 8
FEATURE                 Location/Qualifiers
REGION                  1..8
                        note = Synthetic
source                  1..8
                        mol_type = protein
                        organism = synthetic construct
SEQUENCE: 6
FDPEEGET                                                          8

SEQ ID NO: 7            moltype = DNA  length = 42
FEATURE                 Location/Qualifiers
misc_feature            1..42
                        note = Synthetic
source                  1..42
                        mol_type = other DNA
                        organism = synthetic construct
SEQUENCE: 7
acaacccccc gatattgtaa taatggtata tgttatgact ac                    42

SEQ ID NO: 8            moltype = AA  length = 14
FEATURE                 Location/Qualifiers
REGION                  1..14
                        note = Synthetic
source                  1..14
                        mol_type = protein
                        organism = synthetic construct
SEQUENCE: 8
TTPRYCNNGI CYDY                                                   14

SEQ ID NO: 9            moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 9
gacatccaga tgacccagtc gccttcctcc ctgtctgcat ctgtgggaga cagagtcacc  60
atcacttgcc gggcaagtca gagcattagc aactatttaa attggtatca gcagaaacca  120
gggaaagccc ctaagctcct gatctatact gcatccagtt tgcaaagtgg ggtcccatca  180
aggttcagtg gcagtggatc tgggacagat ttcactctca ccatcagcag tcttcaaact  240
gaagattttg caacttacta ttgtcaacag agttacagta attttccgat caccttcggc  300
caagggacac gactggagat taaacga                                     327

SEQ ID NO: 10           moltype = AA  length = 109
FEATURE                 Location/Qualifiers
REGION                  1..109
                        note = Synthetic
source                  1..109
                        mol_type = protein
                        organism = synthetic construct
SEQUENCE: 10
DIQMTQSPSS LSASVGDRVT ITCRASQSIS NYLNWYQQKP GKAPKLLIYT ASSLQSGVPS  60
RFSGSGSGTD FTLTISSLQT EDFATYYCQQ SYSNFPITFG QGTRLEIKR             109
```

```
SEQ ID NO: 11          moltype = DNA  length = 18
FEATURE                Location/Qualifiers
misc_feature           1..18
                       note = Synthetic
source                 1..18
                       mol_type = other DNA
                       organism = synthetic construct
SEQUENCE: 11
cagagcatta gcaactat                                                18

SEQ ID NO: 12          moltype = AA  length = 6
FEATURE                Location/Qualifiers
REGION                 1..6
                       note = Synthetic
source                 1..6
                       mol_type = protein
                       organism = synthetic construct
SEQUENCE: 12
QSISNY                                                             6

SEQ ID NO: 13          moltype =   length =
SEQUENCE: 13
000

SEQ ID NO: 14          moltype =   length =
SEQUENCE: 14
000

SEQ ID NO: 15          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 15
caacagagtt acagtaattt tccgatcacc                                   30

SEQ ID NO: 16          moltype = AA  length = 10
FEATURE                Location/Qualifiers
REGION                 1..10
                       note = Synthetic
source                 1..10
                       mol_type = protein
                       organism = synthetic construct
SEQUENCE: 16
QQSYSNFPIT                                                         10

SEQ ID NO: 17          moltype = DNA  length = 360
FEATURE                Location/Qualifiers
misc_feature           1..360
                       note = Synthetic
source                 1..360
                       mol_type = other DNA
                       organism = synthetic construct
SEQUENCE: 17
gtgcagctgg tggagtctgg gggaggcttg gtccagcctg gagggtccct gagactctcc  60
tgtgcagcct ctggattcac cttcagtgac cactacatgg actgggtccg tcaggctcct  120
gggaaggggc tggagtgggt tggccgaacc agaaacaaag ctaatagtca caccacagaa  180
tacgccgcgt ctgtgagtgg cagattcacc atctcaagag atgattcaaa gaactcattg  240
tatctgcaaa tgaacagcct gaaaaccgag gacacggccg tgtattattg cactagagcc  300
ggtataattg gaaccctctt tgactactgg ggccagggaa ccctggtcac cgtctcctca  360

SEQ ID NO: 18          moltype = AA  length = 120
FEATURE                Location/Qualifiers
REGION                 1..120
                       note = Synthetic
source                 1..120
                       mol_type = protein
                       organism = synthetic construct
SEQUENCE: 18
VQLVESGGGL VQPGGSLRLS CAASGFTFSD HYMDWVRQAP GKGLEWVGRT RNKANSHTTE  60
YAASVSGRFT ISRDDSKNSL YLQMNSLKTE DTAVYYCTRA GIIGTLFDYW GQGTLVTVSS  120

SEQ ID NO: 19          moltype = DNA  length = 24
FEATURE                Location/Qualifiers
misc_feature           1..24
                       note = Synthetic
```

```
source                  1..24
                        mol_type = other DNA
                        organism = synthetic construct
SEQUENCE: 19
ggattcacct tcagtgacca ctac                                        24

SEQ ID NO: 20           moltype = AA  length = 8
FEATURE                 Location/Qualifiers
REGION                  1..8
                        note = Synthetic
source                  1..8
                        mol_type = protein
                        organism = synthetic construct
SEQUENCE: 20
GFTFSDHY                                                          8

SEQ ID NO: 21           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 21
accagaaaca aagctaatag tcacaccaca                                  30

SEQ ID NO: 22           moltype = AA  length = 10
FEATURE                 Location/Qualifiers
REGION                  1..10
                        note = Synthetic
source                  1..10
                        mol_type = protein
                        organism = synthetic construct
SEQUENCE: 22
TRNKANSHTT                                                        10

SEQ ID NO: 23           moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 23
actagagccg gtataattgg aaccctcttt gactac                           36

SEQ ID NO: 24           moltype = AA  length = 12
FEATURE                 Location/Qualifiers
REGION                  1..12
                        note = Synthetic
source                  1..12
                        mol_type = protein
                        organism = synthetic construct
SEQUENCE: 24
TRAGIIGTLF DY                                                     12

SEQ ID NO: 25           moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 25
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaacga                                     327

SEQ ID NO: 26           moltype = AA  length = 109
FEATURE                 Location/Qualifiers
REGION                  1..109
                        note = Synthetic
source                  1..109
                        mol_type = protein
                        organism = synthetic construct
SEQUENCE: 26
```

```
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIKR             109

SEQ ID NO: 27          moltype = DNA  length = 18
FEATURE                Location/Qualifiers
misc_feature           1..18
                       note = Synthetic
source                 1..18
                       mol_type = other DNA
                       organism = synthetic construct
SEQUENCE: 27
cagagcatta gcagctat                                               18

SEQ ID NO: 28          moltype = AA  length = 6
FEATURE                Location/Qualifiers
REGION                 1..6
                       note = Synthetic
source                 1..6
                       mol_type = protein
                       organism = synthetic construct
SEQUENCE: 28
QSISSY                                                            6

SEQ ID NO: 29          moltype =   length =
SEQUENCE: 29
000

SEQ ID NO: 30          moltype =   length =
SEQUENCE: 30
000

SEQ ID NO: 31          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 31
caacagagtt acagtacccc tccgatcacc                                  30

SEQ ID NO: 32          moltype = AA  length = 10
FEATURE                Location/Qualifiers
REGION                 1..10
                       note = Synthetic
source                 1..10
                       mol_type = protein
                       organism = synthetic construct
SEQUENCE: 32
QQSYSTPPIT                                                        10

SEQ ID NO: 33          moltype = DNA  length = 363
FEATURE                Location/Qualifiers
misc_feature           1..363
                       note = Synthetic
source                 1..363
                       mol_type = other DNA
                       organism = synthetic construct
SEQUENCE: 33
gaggtgcagc tggtggagtc tgggggaggc ttggtccagc ctggagggtc cctgagactc  60
tcctgtgcag cctctggatt caccttcagt gaccactata tggactgggt ccgccaggct  120
ccagggaagg ggctggaatg ggttggccgt actcgaaaca aagctaatag tcacaccaca  180
gaatacaccg cgtctgtgac aggcagattc accatctcaa gagatgattc aagaaactca  240
ctatatctgc aaatgaacag cctgaaaacc gaggacacgg ccgtatatta ctgtgttaga  300
gccggtataa ttggaaccct ctttgactat tggggccagg gaaccctggt caccgtctcc  360
tca                                                               363

SEQ ID NO: 34          moltype = AA  length = 121
FEATURE                Location/Qualifiers
REGION                 1..121
                       note = Synthetic
source                 1..121
                       mol_type = protein
                       organism = synthetic construct
SEQUENCE: 34
EVQLVESGGG LVQPGGSLRL SCAASGFTFS DHYMDWVRQA PGKGLEWVGR TRNKANSHTT  60
EYTASVTGRF TISRDDSRNS LYLQMNSLKT EDTAVYYCVR AGIIGTLFDY WGQGTLVTVS  120
S                                                                 121
```

```
SEQ ID NO: 35           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 35
ggattcacct tcagtgacca ctat                                        24

SEQ ID NO: 36           moltype = AA  length = 8
FEATURE                 Location/Qualifiers
REGION                  1..8
                        note = Synthetic
source                  1..8
                        mol_type = protein
                        organism = synthetic construct
SEQUENCE: 36
GFTFSDHY                                                          8

SEQ ID NO: 37           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 37
actcgaaaca aagctaatag tcacaccaca                                  30

SEQ ID NO: 38           moltype = AA  length = 10
FEATURE                 Location/Qualifiers
REGION                  1..10
                        note = Synthetic
source                  1..10
                        mol_type = protein
                        organism = synthetic construct
SEQUENCE: 38
TRNKANSHTT                                                        10

SEQ ID NO: 39           moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 39
gttagagccg gtataattgg aaccctcttt gactat                           36

SEQ ID NO: 40           moltype = AA  length = 12
FEATURE                 Location/Qualifiers
REGION                  1..12
                        note = Synthetic
source                  1..12
                        mol_type = protein
                        organism = synthetic construct
SEQUENCE: 40
VRAGIIGTLF DY                                                     12

SEQ ID NO: 41           moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 41
gacatccaga tgacccagtt tccatcctcc ctgtctgcat ctgtaggaga cagagtcacc  60
atcacttgcc gggcaagtca gagcattagc agctttttaa attggtttca gcagaaacca  120
gggaaagccc ctaagttcct gatctatgct gcatccagtt tgcaaagtgg ggtcccatca  180
aggttcagtg gcagtgggtc tgggacagat ttcactctca ccatcagcag tctacaacct  240
gaagattttg caacttacta ctgtcaacag agttacagtt cccctccgat caccttcggc  300
caagggacac gactggagat taaacga                                     327

SEQ ID NO: 42           moltype = AA  length = 109
FEATURE                 Location/Qualifiers
REGION                  1..109
                        note = Synthetic
```

-continued

```
source                  1..109
                        mol_type = protein
                        organism = synthetic construct
SEQUENCE: 42
DIQMTQFPSS LSASVGDRVT ITCRASQSIS SFLNWFQQKP GKAPKFLIYA ASSLQSGVPS  60
RFSGSGSGTD FTLTISSLQP EDFATYYCQQ SYSSPPITFG QGTRLEIKR             109

SEQ ID NO: 43           moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 43
cagagcatta gcagcttt                                               18

SEQ ID NO: 44           moltype = AA  length = 6
FEATURE                 Location/Qualifiers
REGION                  1..6
                        note = Synthetic
source                  1..6
                        mol_type = protein
                        organism = synthetic construct
SEQUENCE: 44
QSISSF                                                            6

SEQ ID NO: 45           moltype =   length =
SEQUENCE: 45
000

SEQ ID NO: 46           moltype =   length =
SEQUENCE: 46
000

SEQ ID NO: 47           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 47
caacagagtt acagttcccc tccgatcacc                                  30

SEQ ID NO: 48           moltype = AA  length = 10
FEATURE                 Location/Qualifiers
REGION                  1..10
                        note = Synthetic
source                  1..10
                        mol_type = protein
                        organism = synthetic construct
SEQUENCE: 48
QQSYSSPPIT                                                        10

SEQ ID NO: 49           moltype = DNA  length = 357
FEATURE                 Location/Qualifiers
misc_feature            1..357
                        note = Synthetic
source                  1..357
                        mol_type = other DNA
                        organism = synthetic construct
SEQUENCE: 49
caggtgcagc tgcaggagtc gggcccagga ctggtgaagc cttcggagac cctgtccctc  60
acctgcactg tcactggtgg ctccatcagt aggaactact ggagttggat ccggcagccc  120
ccagggaagg gactggaatg gattggatat atctattaca gtgggagtat cgactacaat  180
ccctccctca agagtcgagt caccatatca gtagacacgt ccaagaacca gttctccctg  240
aagctgagtt ctatgaccgc tgcggacacg gccgtatact actgtgcgag agatcggtgg  300
aactggaaat acggtatgga cgtctggggc caagggacca cggtcatcgt ctcgtca     357

SEQ ID NO: 50           moltype = AA  length = 119
FEATURE                 Location/Qualifiers
REGION                  1..119
                        note = Synthetic
source                  1..119
                        mol_type = protein
                        organism = synthetic construct
SEQUENCE: 50
QVQLQESGPG LVKPSETLSL TCTVTGGSIS RNYWSWIRQP PGKGLEWIGY IYYSGSIDYN  60
```

-continued

```
PSLKSRVTIS VDTSKNQFSL KLSSMTAADT AVYYCARDRW NWKYGMDVWG QGTTVIVSS   119

SEQ ID NO: 51          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 51
ggtggctcca tcagtaggaa ctac                                         24

SEQ ID NO: 52          moltype = AA  length = 8
FEATURE                Location/Qualifiers
REGION                 1..8
                       note = Synthetic
source                 1..8
                       mol_type = protein
                       organism = synthetic construct
SEQUENCE: 52
GGSISRNY                                                           8

SEQ ID NO: 53          moltype = DNA  length = 21
FEATURE                Location/Qualifiers
misc_feature           1..21
                       note = Synthetic
source                 1..21
                       mol_type = other DNA
                       organism = synthetic construct
SEQUENCE: 53
atctattaca gtgggagtat c                                            21

SEQ ID NO: 54          moltype = AA  length = 7
FEATURE                Location/Qualifiers
REGION                 1..7
                       note = Synthetic
source                 1..7
                       mol_type = protein
                       organism = synthetic construct
SEQUENCE: 54
IYYSGSI                                                            7

SEQ ID NO: 55          moltype = DNA  length = 39
FEATURE                Location/Qualifiers
misc_feature           1..39
                       note = Synthetic
source                 1..39
                       mol_type = other DNA
                       organism = synthetic construct
SEQUENCE: 55
gcgagagatc ggtggaactg gaaatacggt atggacgtc                         39

SEQ ID NO: 56          moltype = AA  length = 13
FEATURE                Location/Qualifiers
REGION                 1..13
                       note = Synthetic
source                 1..13
                       mol_type = protein
                       organism = synthetic construct
SEQUENCE: 56
ARDRWNWKYG MDV                                                     13

SEQ ID NO: 57          moltype = DNA  length = 327
FEATURE                Location/Qualifiers
misc_feature           1..327
                       note = Synthetic
source                 1..327
                       mol_type = other DNA
                       organism = synthetic construct
SEQUENCE: 57
gaaattgtgt tgacgcagtc tccaggcacc ctgtctttgt ctccagggga aagagccacc  60
ctctcctgca gggccagtca gactgttaga aacaactact tagcctggta ccaccagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttacagtgta ttactgtcac cagtatggta actcaccttg gacgttcggc  300
caagggacca aaatggaaat caaacga                                      327

SEQ ID NO: 58          moltype = AA  length = 109
FEATURE                Location/Qualifiers
```

```
REGION                  1..109
                        note = Synthetic
source                  1..109
                        mol_type = protein
                        organism = synthetic construct
SEQUENCE: 58
EIVLTQSPGT LSLSPGERAT LSCRASQTVR NNYLAWYHQK PGQAPRLLIY GASSRATGIP  60
DRFSGSGSGT DFTLTISRLE PEDFTVYYCH QYGNSPWTFG QGTKMEIKR              109

SEQ ID NO: 59           moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 59
cagactgtta gaaacaacta c                                            21

SEQ ID NO: 60           moltype = AA  length = 7
FEATURE                 Location/Qualifiers
REGION                  1..7
                        note = Synthetic
source                  1..7
                        mol_type = protein
                        organism = synthetic construct
SEQUENCE: 60
QTVRNNY                                                            7

SEQ ID NO: 61           moltype =   length =
SEQUENCE: 61
000

SEQ ID NO: 62           moltype =   length =
SEQUENCE: 62
000

SEQ ID NO: 63           moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 63
caccagtatg gtaactcacc ttggacg                                      27

SEQ ID NO: 64           moltype = AA  length = 9
FEATURE                 Location/Qualifiers
REGION                  1..9
                        note = Synthetic
source                  1..9
                        mol_type = protein
                        organism = synthetic construct
SEQUENCE: 64
HQYGNSPWT                                                          9

SEQ ID NO: 65           moltype = DNA  length = 363
FEATURE                 Location/Qualifiers
misc_feature            1..363
                        note = Synthetic
source                  1..363
                        mol_type = other DNA
                        organism = synthetic construct
SEQUENCE: 65
gaggtgcagc tggtggagtc tgggggaggc ttggtccagc ctggagggtc cctgagactc  60
tcctgtgcag cctctggatt caccttcagt gaccactaca tggactgggt ccgccaggct  120
cctgggaagg ggctggagtg ggttggccga actagaaaca aagctaatag ttacaccaca  180
gaatacgccg cgtctgtgag tggcagattc accatctcaa gagatgattc aaagaactca  240
ttatatctgc aaatgaacag cctgaaaacc gaggacacgg ccgtgtatta ttgcactaga  300
gccggtataa ttggaaccct ctttgactac tggggccagg gaaccctggt caccgtctcc  360
tca                                                                363

SEQ ID NO: 66           moltype = AA  length = 121
FEATURE                 Location/Qualifiers
REGION                  1..121
                        note = Synthetic
source                  1..121
                        mol_type = protein
```

```
                         organism = synthetic construct
SEQUENCE: 66
EVQLVESGGG LVQPGGSLRL SCAASGFTFS DHYMDWVRQA PGKGLEWVGR TRNKANSYTT  60
EYAASVSGRF TISRDDSKNS LYLQMNSLKT EDTAVYYCTR AGIIGTLFDY WGQGTLVTVS  120
S                                                                  121

SEQ ID NO: 67            moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 67
ggattcacct tcagtgacca ctac                                         24

SEQ ID NO: 68            moltype = AA  length = 8
FEATURE                  Location/Qualifiers
REGION                   1..8
                         note = Synthetic
source                   1..8
                         mol_type = protein
                         organism = synthetic construct
SEQUENCE: 68
GFTFSDHY                                                           8

SEQ ID NO: 69            moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 69
actagaaaca aagctaatag ttacaccaca                                   30

SEQ ID NO: 70            moltype = AA  length = 10
FEATURE                  Location/Qualifiers
REGION                   1..10
                         note = Synthetic
source                   1..10
                         mol_type = protein
                         organism = synthetic construct
SEQUENCE: 70
TRNKANSYTT                                                         10

SEQ ID NO: 71            moltype = DNA  length = 36
FEATURE                  Location/Qualifiers
misc_feature             1..36
                         note = Synthetic
source                   1..36
                         mol_type = other DNA
                         organism = synthetic construct
SEQUENCE: 71
actagagccg gtataattgg aaccctcttt gactac                            36

SEQ ID NO: 72            moltype = AA  length = 12
FEATURE                  Location/Qualifiers
REGION                   1..12
                         note = Synthetic
source                   1..12
                         mol_type = protein
                         organism = synthetic construct
SEQUENCE: 72
TRAGIIGTLF DY                                                      12

SEQ ID NO: 73            moltype = DNA  length = 327
FEATURE                  Location/Qualifiers
misc_feature             1..327
                         note = Synthetic
source                   1..327
                         mol_type = other DNA
                         organism = synthetic construct
SEQUENCE: 73
gacatccaga tgacccagtc tccatcctcc ctgtctgcat ctgtaggaga cagagtcacc  60
atcacttgcc gggcaagtca gatcattggt agatatttaa attggtttca gcagaaacca  120
gggaaagtcc ctaagctcct gatctatgct gcatccagtt tgcaacgtgg ggtcccatca  180
aggttcagtg gcagtggatc tgggacagat ttcactctca ccatcagcag tctgcaacct  240
gaagattttg caacttacta ctgtcaacag agttacaata cccctccgat caccttcggc  300
```

-continued

```
caagggacac gactggagat taaacga                                    327

SEQ ID NO: 74          moltype = AA  length = 109
FEATURE                Location/Qualifiers
REGION                 1..109
                       note = Synthetic
source                 1..109
                       mol_type = protein
                       organism = synthetic construct
SEQUENCE: 74
DIQMTQSPSS LSASVGDRVT ITCRASQIIG RYLNWFQQKP GKVPKLLIYA ASSLQRGVPS  60
RFSGSGSGTD FTLTISSLQP EDFATYYCQQ SYNTPPITFG QGTRLEIKR             109

SEQ ID NO: 75          moltype = DNA  length = 18
FEATURE                Location/Qualifiers
misc_feature           1..18
                       note = Synthetic
source                 1..18
                       mol_type = other DNA
                       organism = synthetic construct
SEQUENCE: 75
cagatcattg gtagatat                                              18

SEQ ID NO: 76          moltype = AA  length = 6
FEATURE                Location/Qualifiers
REGION                 1..6
                       note = Synthetic
source                 1..6
                       mol_type = protein
                       organism = synthetic construct
SEQUENCE: 76
QIIGRY                                                           6

SEQ ID NO: 77          moltype =   length =
SEQUENCE: 77
000

SEQ ID NO: 78          moltype =   length =
SEQUENCE: 78
000

SEQ ID NO: 79          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 79
caacagagtt acaatacccc tccgatcacc                                 30

SEQ ID NO: 80          moltype = AA  length = 10
FEATURE                Location/Qualifiers
REGION                 1..10
                       note = Synthetic
source                 1..10
                       mol_type = protein
                       organism = synthetic construct
SEQUENCE: 80
QQSYNTPPIT                                                       10

SEQ ID NO: 81          moltype = DNA  length = 363
FEATURE                Location/Qualifiers
misc_feature           1..363
                       note = Synthetic
source                 1..363
                       mol_type = other DNA
                       organism = synthetic construct
SEQUENCE: 81
caggtccagc tggtgcagtc tggggctgag gtgagggagc ctggggcctc agtgaagctc  60
tcctgcaagg tttccggata caccctcact gaattatcca tccactgggt gcgacaggct  120
cctggaaaag gacttgagtg gatgggaggt tttgatcctg aagagggtga aacagtctac  180
gcacagaagt tccggggcag agtcaccctg accgaggaca taagtccaga cacggcctac  240
atggagctga gcagcctgac ctctgaggac acggccgtat attattgtgc aacccccgc  300
tattgtaata atggtatatg ttatgactac tggggccagg gaaccctaat caccgtctcc  360
tca                                                              363

SEQ ID NO: 82          moltype = AA  length = 121
FEATURE                Location/Qualifiers
```

-continued

```
REGION                  1..121
                        note = Synthetic
source                  1..121
                        mol_type = protein
                        organism = synthetic construct
SEQUENCE: 82
QVQLVQSGAE VREPGASVKL SCKVSGYTLT ELSIHWVRQA PGKGLEWMGG FDPEEGETVY  60
AQKFRGRVTL TEDISPDTAY MELSSLTSED TAVYYCATPR YCNNGICYDY WGQGTLITVS  120
S                                                                 121

SEQ ID NO: 83           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 83
ggatacaccc tcactgaatt atcc                                        24

SEQ ID NO: 84           moltype = AA  length = 8
FEATURE                 Location/Qualifiers
REGION                  1..8
                        note = Synthetic
source                  1..8
                        mol_type = protein
                        organism = synthetic construct
SEQUENCE: 84
GYTLTELS                                                          8

SEQ ID NO: 85           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 85
tttgatcctg aagagggtga aaca                                        24

SEQ ID NO: 86           moltype = AA  length = 8
FEATURE                 Location/Qualifiers
REGION                  1..8
                        note = Synthetic
source                  1..8
                        mol_type = protein
                        organism = synthetic construct
SEQUENCE: 86
FDPEEGET                                                          8

SEQ ID NO: 87           moltype = DNA  length = 42
FEATURE                 Location/Qualifiers
misc_feature            1..42
                        note = Synthetic
source                  1..42
                        mol_type = other DNA
                        organism = synthetic construct
SEQUENCE: 87
gcaacccccc gctattgtaa taatggtata tgttatgact ac                    42

SEQ ID NO: 88           moltype = AA  length = 14
FEATURE                 Location/Qualifiers
REGION                  1..14
                        note = Synthetic
source                  1..14
                        mol_type = protein
                        organism = synthetic construct
SEQUENCE: 88
ATPRYCNNGI CYDY                                                   14

SEQ ID NO: 89           moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 89
gacatccaga tgacccagtc tccatcctcc ctgtctgcat ctgtaggaga cagagtcacc  60
```

-continued

```
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                        324

SEQ ID NO: 90          moltype = AA  length = 108
FEATURE                Location/Qualifiers
REGION                 1..108
                       note = Synthetic
source                 1..108
                       mol_type = protein
                       organism = synthetic construct
SEQUENCE: 90
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK              108

SEQ ID NO: 91          moltype = DNA  length = 18
FEATURE                Location/Qualifiers
misc_feature           1..18
                       note = Synthetic
source                 1..18
                       mol_type = other DNA
                       organism = synthetic construct
SEQUENCE: 91
cagagcatta gcagctat                                               18

SEQ ID NO: 92          moltype = AA  length = 6
FEATURE                Location/Qualifiers
REGION                 1..6
                       note = Synthetic
source                 1..6
                       mol_type = protein
                       organism = synthetic construct
SEQUENCE: 92
QSISSY                                                            6

SEQ ID NO: 93          moltype =   length =
SEQUENCE: 93
000

SEQ ID NO: 94          moltype =   length =
SEQUENCE: 94
000

SEQ ID NO: 95          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 95
caacagagtt acagtacccc tccgatcacc                                  30

SEQ ID NO: 96          moltype = AA  length = 10
FEATURE                Location/Qualifiers
REGION                 1..10
                       note = Synthetic
source                 1..10
                       mol_type = protein
                       organism = synthetic construct
SEQUENCE: 96
QQSYSTPPIT                                                        10

SEQ ID NO: 97          moltype = DNA  length = 363
FEATURE                Location/Qualifiers
misc_feature           1..363
                       note = Synthetic
source                 1..363
                       mol_type = other DNA
                       organism = synthetic construct
SEQUENCE: 97
gaggtgcagc tgttggagtc tgggggaggc ttggtacagc ctggggggtc cctgagactc  60
tcctgtgcag cctctggatt cacctttagt aattatgcca tgacctgggt ccgccaggct  120
ccagggacgg ggctggagtg ggtctcagct attagtggtc gtggtagtaa cacatactac  180
acagactccg tgaagggccg gttcaccatc tccagagaca attccaagaa catgctgtat  240
ctgcaaatga acagcctgag agccgaggac acggcctcat attactgtgc gaaagatcgt  300
tttactacag tggggaactg gttcgacccc tggggccagg gaaccctggt caccgtctcc  360
```

```
tca                                                                    363

SEQ ID NO: 98          moltype = AA  length = 121
FEATURE                Location/Qualifiers
REGION                 1..121
                       note = Synthetic
source                 1..121
                       mol_type = protein
                       organism = synthetic construct
SEQUENCE: 98
EVQLLESGGG LVQPGGSLRL SCAASGFTFS NYAMTWVRQA PGTGLEWVSA ISGRGSNTYY  60
TDSVKGRFTI SRDNSKNMLY LQMNSLRAED TASYYCAKDR FTTVGNWFDP WGQGTLVTVS  120
S                                                                  121

SEQ ID NO: 99          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 99
ggattcacct ttagtaatta tgcc                                         24

SEQ ID NO: 100         moltype = AA  length = 8
FEATURE                Location/Qualifiers
REGION                 1..8
                       note = Synthetic
source                 1..8
                       mol_type = protein
                       organism = synthetic construct
SEQUENCE: 100
GFTFSNYA                                                           8

SEQ ID NO: 101         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 101
attagtggtc gtggtagtaa caca                                         24

SEQ ID NO: 102         moltype = AA  length = 8
FEATURE                Location/Qualifiers
REGION                 1..8
                       note = Synthetic
source                 1..8
                       mol_type = protein
                       organism = synthetic construct
SEQUENCE: 102
ISGRGSNT                                                           8

SEQ ID NO: 103         moltype = DNA  length = 42
FEATURE                Location/Qualifiers
misc_feature           1..42
                       note = Synthetic
source                 1..42
                       mol_type = other DNA
                       organism = synthetic construct
SEQUENCE: 103
gcgaaagatc gttttactac agtggggaac tggttcgacc cc                     42

SEQ ID NO: 104         moltype = AA  length = 14
FEATURE                Location/Qualifiers
REGION                 1..14
                       note = Synthetic
source                 1..14
                       mol_type = protein
                       organism = synthetic construct
SEQUENCE: 104
AKDRFTTVGN WFDP                                                    14

SEQ ID NO: 105         moltype = DNA  length = 327
FEATURE                Location/Qualifiers
misc_feature           1..327
                       note = Synthetic
source                 1..327
```

```
                        mol_type = other DNA
                        organism = synthetic construct
SEQUENCE: 105
gacatccaga tgacccagtc tccatcctcc ctgtctgcat ctgtaggaga cagagtcacc  60
atcacttgcc gggcaagtca gagtattagc agctatttaa attggtatca gcagaaacca  120
gggaaagccc ctaagctcct gatctatgct gcgtccagtt tgcaaaatgg ggtcccatca  180
aggttcagtg gcagtggatc tgggacagat ttcactctca ccatcagcag tctgcagcct  240
gaagattttg caacttacta ctgtcaacag agttacagta gtcttccgat caccttcggc  300
caagggacac gactggatat taaacga                                      327

SEQ ID NO: 106          moltype = AA  length = 109
FEATURE                 Location/Qualifiers
REGION                  1..109
                        note = Synthetic
source                  1..109
                        mol_type = protein
                        organism = synthetic construct
SEQUENCE: 106
DIQMTQSPSS LSASVGDRVT ITCRASQSIS SYLNWYQQKP GKAPKLLIYA ASSLQNGVPS  60
RFSGSGSGTD FTLTISSLQP EDFATYYCQQ SYSSLPITFG QGTRLDIKR              109

SEQ ID NO: 107          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 107
cagagtatta gcagctat                                                18

SEQ ID NO: 108          moltype = AA  length = 6
FEATURE                 Location/Qualifiers
REGION                  1..6
                        note = Synthetic
source                  1..6
                        mol_type = protein
                        organism = synthetic construct
SEQUENCE: 108
QSISSY                                                             6

SEQ ID NO: 109          moltype =   length =
SEQUENCE: 109
000

SEQ ID NO: 110          moltype =   length =
SEQUENCE: 110
000

SEQ ID NO: 111          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 111
caacagagtt acagtagtct tccgatcacc                                   30

SEQ ID NO: 112          moltype = AA  length = 10
FEATURE                 Location/Qualifiers
REGION                  1..10
                        note = Synthetic
source                  1..10
                        mol_type = protein
                        organism = synthetic construct
SEQUENCE: 112
QQSYSSLPIT                                                         10

SEQ ID NO: 113          moltype = DNA  length = 357
FEATURE                 Location/Qualifiers
misc_feature            1..357
                        note = Synthetic
source                  1..357
                        mol_type = other DNA
                        organism = synthetic construct
SEQUENCE: 113
caggtgcagc tgcaggagtc gggcccagga ctggtgaagc cttcggagac cctgtccctc  60
acctgcactg tcactggtgg ctccatcagt aggaactact ggagttggat ccggcagccc  120
```

-continued

```
ccagggaagg gactggaatg gattggatat atctattaca gtgggagtat caactacaat  180
ccctccctca agagtcgagt caccatatca gtggacatgt ctaagaacca gttctcccta  240
aagctgaatt ctgtgaccgc tgcggacacg gccgtgtact actgtgcgag agatcgatgg  300
aactggaaat acggtatgga cgtctggggc caagggacca cggtcatcgt ctcgtca     357

SEQ ID NO: 114          moltype = AA  length = 119
FEATURE                 Location/Qualifiers
REGION                  1..119
                        note = Synthetic
source                  1..119
                        mol_type = protein
                        organism = synthetic construct
SEQUENCE: 114
QVQLQESGPG LVKPSETLSL TCTVTGGSIS RNYWSWIRQP PGKGLEWIGY IYYSGSINYN  60
PSLKSRVTIS VDMSKNQFSL KLNSVTAADT AVYYCARDRW NWKYGMDVWG QGTTVIVSS   119

SEQ ID NO: 115          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 115
ggtggctcca tcagtaggaa ctac                                         24

SEQ ID NO: 116          moltype = AA  length = 8
FEATURE                 Location/Qualifiers
REGION                  1..8
                        note = Synthetic
source                  1..8
                        mol_type = protein
                        organism = synthetic construct
SEQUENCE: 116
GGSISRNY                                                           8

SEQ ID NO: 117          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 117
atctattaca gtgggagtat c                                            21

SEQ ID NO: 118          moltype = AA  length = 7
FEATURE                 Location/Qualifiers
REGION                  1..7
                        note = Synthetic
source                  1..7
                        mol_type = protein
                        organism = synthetic construct
SEQUENCE: 118
IYYSGSI                                                            7

SEQ ID NO: 119          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 119
gcgagagatc gatggaactg gaaatacggt atggacgtc                         39

SEQ ID NO: 120          moltype = AA  length = 13
FEATURE                 Location/Qualifiers
REGION                  1..13
                        note = Synthetic
source                  1..13
                        mol_type = protein
                        organism = synthetic construct
SEQUENCE: 120
ARDRWNWKYG MDV                                                     13

SEQ ID NO: 121          moltype = DNA  length = 327
FEATURE                 Location/Qualifiers
misc_feature            1..327
```

```
                        note = Synthetic
source                  1..327
                        mol_type = other DNA
                        organism = synthetic construct
SEQUENCE: 121
gaaattgtgt tgacgcagtc tccaggcacc ctgtctttgt ctccagggga aagagccacc  60
ctctcctgca gggccagtca gactgttaga aacagctact tagcctggta ccaccagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gttcatattg gacgttcggc  300
caagggacca aaatggaaat caaacga                                      327

SEQ ID NO: 122          moltype = AA  length = 109
FEATURE                 Location/Qualifiers
REGION                  1..109
                        note = Synthetic
source                  1..109
                        mol_type = protein
                        organism = synthetic construct
SEQUENCE: 122
EIVLTQSPGT LSLSPGERAT LSCRASQTVR NSYLAWYHQK PGQAPRLLIY GASSRATGIP  60
DRFSGSGSGT DFTLTISRLE PEDFAVYYCQ QYGSSYWTFG QGTKMEIKR              109

SEQ ID NO: 123          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 123
cagactgtta gaaacagcta c                                            21

SEQ ID NO: 124          moltype = AA  length = 7
FEATURE                 Location/Qualifiers
REGION                  1..7
                        note = Synthetic
source                  1..7
                        mol_type = protein
                        organism = synthetic construct
SEQUENCE: 124
QTVRNSY                                                            7

SEQ ID NO: 125          moltype =   length =
SEQUENCE: 125
000

SEQ ID NO: 126          moltype =   length =
SEQUENCE: 126
000

SEQ ID NO: 127          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 127
cagcagtatg gtagttcata ttggacg                                      27

SEQ ID NO: 128          moltype = AA  length = 9
FEATURE                 Location/Qualifiers
REGION                  1..9
                        note = Synthetic
source                  1..9
                        mol_type = protein
                        organism = synthetic construct
SEQUENCE: 128
QQYGSSYWT                                                          9

SEQ ID NO: 129          moltype = DNA  length = 363
FEATURE                 Location/Qualifiers
misc_feature            1..363
                        note = Synthetic
source                  1..363
                        mol_type = other DNA
                        organism = synthetic construct
SEQUENCE: 129
```

```
caggtccagc tggtgcagtc tgggtctgag gtgaagaagc ctggggcctc agtgaaggtc  60
tcctgcaagg tttccggata caccctcact gaattatcca tacactgggt gcgacaggct  120
cctggaaaag gacttgagtg gatgggaggt tttgatcctg aagatggtga aacaatctac  180
gcacagaagt tccggggcag agtcaccatg accgaggaca tatctccaga cacagcctac  240
atggagctga gcagcctgag atctgaagac acggccgtat attactgtgc aaccccccgc  300
tattgtaata atggtatatg ttatgactat tggggccagg gaaccctggt caccgtctcc  360
tca                                                                 363

SEQ ID NO: 130          moltype = AA  length = 121
FEATURE                 Location/Qualifiers
REGION                  1..121
                        note = Synthetic
source                  1..121
                        mol_type = protein
                        organism = synthetic construct
SEQUENCE: 130
QVQLVQSGSE VKKPGASVKV SCKVSGYTLT ELSIHWVRQA PGKGLEWMGG FDPEDGETIY  60
AQKFRGRVTM TEDISPDTAY MELSSLRSED TAVYYCATPR YCNNGICYDY WGQGTLVTVS  120
S                                                                   121

SEQ ID NO: 131          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 131
ggatacaccc tcactgaatt atcc                                          24

SEQ ID NO: 132          moltype = AA  length = 8
FEATURE                 Location/Qualifiers
REGION                  1..8
                        note = Synthetic
source                  1..8
                        mol_type = protein
                        organism = synthetic construct
SEQUENCE: 132
GYTLTELS                                                            8

SEQ ID NO: 133          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 133
tttgatcctg aagatggtga aaca                                          24

SEQ ID NO: 134          moltype = AA  length = 8
FEATURE                 Location/Qualifiers
REGION                  1..8
                        note = Synthetic
source                  1..8
                        mol_type = protein
                        organism = synthetic construct
SEQUENCE: 134
FDPEDGET                                                            8

SEQ ID NO: 135          moltype = DNA  length = 42
FEATURE                 Location/Qualifiers
misc_feature            1..42
                        note = Synthetic
source                  1..42
                        mol_type = other DNA
                        organism = synthetic construct
SEQUENCE: 135
gcaacccccc gctattgtaa taatggtata tgttatgact at                      42

SEQ ID NO: 136          moltype = AA  length = 14
FEATURE                 Location/Qualifiers
REGION                  1..14
                        note = Synthetic
source                  1..14
                        mol_type = protein
                        organism = synthetic construct
SEQUENCE: 136
ATPRYCNNGI CYDY                                                     14
```

```
SEQ ID NO: 137         moltype = DNA  length = 327
FEATURE                Location/Qualifiers
misc_feature           1..327
                       note = Synthetic
source                 1..327
                       mol_type = other DNA
                       organism = synthetic construct
SEQUENCE: 137
gacatccaga tgacccagtc tccatcctcc ctgtctgcat ctataggaga cagagtcacc  60
atcacttgcc gggcaagtca gagcattagc agctatttaa attggtatca gcagaaacca  120
gggaaagccc ctatgctcct gatctatgct gcatccagtt tgcaaagtgg ggtcccatca  180
aggttcagtg gcagtggatc tgggacagat ttcactctca ccatcagcag tctgcaaact  240
gaagattttg caacttacta ctgtcaacag agttacagta cccctccgat caccttcggc  300
caagggacac gactggagat taaacga                                      327

SEQ ID NO: 138         moltype = AA  length = 109
FEATURE                Location/Qualifiers
REGION                 1..109
                       note = Synthetic
source                 1..109
                       mol_type = protein
                       organism = synthetic construct
SEQUENCE: 138
DIQMTQSPSS LSASIGDRVT ITCRASQSIS SYLNWYQQKP GKAPMLLIYA ASSLQSGVPS  60
RFSGSGSGTD FTLTISSLQT EDFATYYCQQ SYSTPPITFG QGTRLEIKR              109

SEQ ID NO: 139         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 139
cagagcatta gcagctat                                                18

SEQ ID NO: 140         moltype = AA  length = 6
FEATURE                Location/Qualifiers
REGION                 1..6
                       note = Synthetic
source                 1..6
                       mol_type = protein
                       organism = synthetic construct
SEQUENCE: 140
QSISSY                                                             6

SEQ ID NO: 141         moltype =   length =
SEQUENCE: 141
000

SEQ ID NO: 142         moltype =   length =
SEQUENCE: 142
000

SEQ ID NO: 143         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 143
caacagagtt acagtacccc tccgatcacc                                   30

SEQ ID NO: 144         moltype = AA  length = 10
FEATURE                Location/Qualifiers
REGION                 1..10
                       note = Synthetic
source                 1..10
                       mol_type = protein
                       organism = synthetic construct
SEQUENCE: 144
QQSYSTPPIT                                                         10

SEQ ID NO: 145         moltype = DNA  length = 345
FEATURE                Location/Qualifiers
misc_feature           1..345
                       note = Synthetic
```

-continued

```
source                  1..345
                        mol_type = other DNA
                        organism = synthetic construct
SEQUENCE: 145
caggtgcagc tggtggagtc tgggggaggc ttggtcaagc ctggagggtc cctgagactc  60
tcctgtgcag cctctggatt catttttagt gactactaca tgagctggat ccgccaggct  120
ccagggaagg ggctggagtg ggtttcatac attagtagta gtggtactac catatatgga  180
gactctgtga agggccgatt caccatgtcc agggacaacg ccaagaactc actgtatctg  240
caaatgaaca gcctgagagc cgaggacacg gccgtgtatt actgtgcgag gaactacgct  300
ctctttgact actggggcca gggaaccctg gtcaccgtct cctca                  345

SEQ ID NO: 146          moltype = AA  length = 115
FEATURE                 Location/Qualifiers
REGION                  1..115
                        note = Synthetic
source                  1..115
                        mol_type = protein
                        organism = synthetic construct
SEQUENCE: 146
QVQLVESGGG LVKPGGSLRL SCAASGFIFS DYYMSWIRQA PGKGLEWVSY ISSSGTTIYG  60
DSVKGRFTMS RDNAKNSLYL QMNSLRAEDT AVYYCARNYA LFDYWGQGTL VTVSS       115

SEQ ID NO: 147          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 147
ggattcattt ttagtgacta ctac                                         24

SEQ ID NO: 148          moltype = AA  length = 8
FEATURE                 Location/Qualifiers
REGION                  1..8
                        note = Synthetic
source                  1..8
                        mol_type = protein
                        organism = synthetic construct
SEQUENCE: 148
GFIFSDYY                                                           8

SEQ ID NO: 149          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 149
attagtagta gtggtactac cata                                         24

SEQ ID NO: 150          moltype = AA  length = 8
FEATURE                 Location/Qualifiers
REGION                  1..8
                        note = Synthetic
source                  1..8
                        mol_type = protein
                        organism = synthetic construct
SEQUENCE: 150
ISSSGTTI                                                           8

SEQ ID NO: 151          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 151
gcgaggaact acgctctctt tgactac                                      27

SEQ ID NO: 152          moltype = AA  length = 9
FEATURE                 Location/Qualifiers
REGION                  1..9
                        note = Synthetic
source                  1..9
                        mol_type = protein
                        organism = synthetic construct
```

```
SEQUENCE: 152
ARNYALFDY                                                        9

SEQ ID NO: 153         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 153
gacatccaga tgacccagtc tccatcctcc ctgtctgcat ctgtaggaga cagagtcacc  60
atcacttgcc aggcgagtca ggacattagc aaatatttaa attggtatca gcagaaacca  120
gggaaagccc ctaagctcct gatctactat acatccaatt tggaaacagg ggtcccatca  180
aggttcagtg gaagtggatc tgggacagat tttactttca ccatcagcag cctgcagcct  240
gaagatattg caacatatta ctgtcaccag tctgattatc tcccattcac tttcggccct  300
gggaccaaag tggatatcaa acga                                         324

SEQ ID NO: 154         moltype = AA  length = 108
FEATURE                Location/Qualifiers
REGION                 1..108
                       note = Synthetic
source                 1..108
                       mol_type = protein
                       organism = synthetic construct
SEQUENCE: 154
DIQMTQSPSS LSASVGDRVT ITCQASQDIS KYLNWYQQKP GKAPKLLIYY TSNLETGVPS  60
RFSGSGSGTD FTFTISSLQP EDIATYYCHQ SDYLPFTFGP GTKVDIKR               108

SEQ ID NO: 155         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 155
caggacatta gcaaatat                                                18

SEQ ID NO: 156         moltype = AA  length = 6
FEATURE                Location/Qualifiers
REGION                 1..6
                       note = Synthetic
source                 1..6
                       mol_type = protein
                       organism = synthetic construct
SEQUENCE: 156
QDISKY                                                           6

SEQ ID NO: 157         moltype =   length =
SEQUENCE: 157
000

SEQ ID NO: 158         moltype =   length =
SEQUENCE: 158
000

SEQ ID NO: 159         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 159
caccagtctg attatctccc attcact                                      27

SEQ ID NO: 160         moltype = AA  length = 9
FEATURE                Location/Qualifiers
REGION                 1..9
                       note = Synthetic
source                 1..9
                       mol_type = protein
                       organism = synthetic construct
SEQUENCE: 160
HQSDYLPFT                                                        9

SEQ ID NO: 161         moltype = DNA  length = 363
FEATURE                Location/Qualifiers
```

```
misc_feature           1..363
                       note = Synthetic
source                 1..363
                       mol_type = other DNA
                       organism = synthetic construct
SEQUENCE: 161
cagctgcagc tgcaggagtc gggcccagga ctggtgaagc cttcggagac cctgtccctc  60
acctgcactg tctctggtgg ctccatcagc cgtattagtt actactgggg ctggatccgc  120
cagcccccag ggaaggggct ggagtggatt gggagtatct atgatagtgg gagtacctac  180
tacaacccgt ccctcaagag tcgagtcacc atatccatag acacgtccaa gaaccagttc  240
tccctgaagc tgagctctgt gaccgccgca gacacggctg tgtattactg tgtgagatat  300
agcagttcgt ccgccttcgc ttttgactac tggggccagg gaaccctggt caccgtctcc  360
tca                                                                363

SEQ ID NO: 162         moltype = AA  length = 121
FEATURE                Location/Qualifiers
REGION                 1..121
                       note = Synthetic
source                 1..121
                       mol_type = protein
                       organism = synthetic construct
SEQUENCE: 162
QLQLQESGPG LVKPSETLSL TCTVSGGSIS RISYYWGWIR QPPGKGLEWI GSIYDSGSTY  60
YNPSLKSRVT ISIDTSKNQF SLKLSSVTAA DTAVYYCVRY SSSSAFAFDY WGQGTLVTVS  120
S                                                                  121

SEQ ID NO: 163         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 163
ggtggctcca tcagccgtat tagttactac                                   30

SEQ ID NO: 164         moltype = AA  length = 10
FEATURE                Location/Qualifiers
REGION                 1..10
                       note = Synthetic
source                 1..10
                       mol_type = protein
                       organism = synthetic construct
SEQUENCE: 164
GGSISRISYY                                                         10

SEQ ID NO: 165         moltype = DNA  length = 21
FEATURE                Location/Qualifiers
misc_feature           1..21
                       note = Synthetic
source                 1..21
                       mol_type = other DNA
                       organism = synthetic construct
SEQUENCE: 165
atctatgata gtgggagtac c                                            21

SEQ ID NO: 166         moltype = AA  length = 7
FEATURE                Location/Qualifiers
REGION                 1..7
                       note = Synthetic
source                 1..7
                       mol_type = protein
                       organism = synthetic construct
SEQUENCE: 166
IYDSGST                                                            7

SEQ ID NO: 167         moltype = DNA  length = 39
FEATURE                Location/Qualifiers
misc_feature           1..39
                       note = Synthetic
source                 1..39
                       mol_type = other DNA
                       organism = synthetic construct
SEQUENCE: 167
gtgagatata gcagttcgtc cgccttcgct tttgactac                         39

SEQ ID NO: 168         moltype = AA  length = 13
FEATURE                Location/Qualifiers
REGION                 1..13
```

```
                        note = Synthetic
source                  1..13
                        mol_type = protein
                        organism = synthetic construct
SEQUENCE: 168
VRYSSSSAFA FDY                                                    13

SEQ ID NO: 169          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 169
gacatccaga tgacccagtc tccatcttcc gtgtctgcat ctgtaggaga cagagtcacc  60
atcacttgtc gggcgagtca gggtattagc agttggttag cctggtatca gcagaaacca  120
gggaaagccc ctaagctcct gatctatgct gcatccagtt tgcaaagtgg ggtcccatca  180
aggttcagcg gcagtggatc tgggacagat ttcactctca ccatcagcag cctgcagcct  240
gaagattttg caacttacta ttgtcaacag gctaacagtt tcccattcac tttcggccct  300
gggaccaaag tggatatcaa acga                                        324

SEQ ID NO: 170          moltype = AA  length = 108
FEATURE                 Location/Qualifiers
REGION                  1..108
                        note = Synthetic
source                  1..108
                        mol_type = protein
                        organism = synthetic construct
SEQUENCE: 170
DIQMTQSPSS VSASVGDRVT ITCRASQGIS SWLAWYQQKP GKAPKLLIYA ASSLQSGVPS  60
RFSGSGSGTD FTLTISSLQP EDFATYYCQQ ANSFPFTFGP GTKVDIKR              108

SEQ ID NO: 171          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 171
cagggtatta gcagttgg                                               18

SEQ ID NO: 172          moltype = AA  length = 6
FEATURE                 Location/Qualifiers
REGION                  1..6
                        note = Synthetic
source                  1..6
                        mol_type = protein
                        organism = synthetic construct
SEQUENCE: 172
QGISSW                                                            6

SEQ ID NO: 173          moltype =   length =
SEQUENCE: 173
000

SEQ ID NO: 174          moltype =   length =
SEQUENCE: 174
000

SEQ ID NO: 175          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 175
caacaggcta acagtttccc attcact                                     27

SEQ ID NO: 176          moltype = AA  length = 9
FEATURE                 Location/Qualifiers
REGION                  1..9
                        note = Synthetic
source                  1..9
                        mol_type = protein
                        organism = synthetic construct
SEQUENCE: 176
```

```
QQANSFPFT                                                      9

SEQ ID NO: 177          moltype = DNA  length = 360
FEATURE                 Location/Qualifiers
misc_feature            1..360
                        note = Synthetic
source                  1..360
                        mol_type = other DNA
                        organism = synthetic construct
SEQUENCE: 177
cagctgcagc tgcaggagtc gggcccagga ctggtgaagc cttcggagac cctgtccctc  60
acctgcactg tctctggtgg ctccatcagc agtagtactt actactgggg ctggatccgc  120
cagcccccag ggaaggggct ggagtggatt gggagtttct attatagtgg gagcacctac  180
tacaacccgt ccctcaagag tcgagtcacc atatccgtag gcacgtccaa gaaccagttc  240
tccctgaagc tgagctctgt gaccgccgca gacacggctg tttatttctg tgcgagaggg  300
gggctcctgg ggagaccttt tgttatctgg ggccaaggga caatggtcac cgtctcttca  360

SEQ ID NO: 178          moltype = AA  length = 120
FEATURE                 Location/Qualifiers
REGION                  1..120
                        note = Synthetic
source                  1..120
                        mol_type = protein
                        organism = synthetic construct
SEQUENCE: 178
QLQLQESGPG LVKPSETLSL TCTVSGGSIS SSTYYWGWIR QPPGKGLEWI GSFYYSGSTY  60
YNPSLKSRVT ISVGTSKNQF SLKLSSVTAA DTAVYFCARG GLLGRPFVIW GQGTMVTVSS  120

SEQ ID NO: 179          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 179
ggtggctcca tcagcagtag tacttactac                               30

SEQ ID NO: 180          moltype = AA  length = 10
FEATURE                 Location/Qualifiers
REGION                  1..10
                        note = Synthetic
source                  1..10
                        mol_type = protein
                        organism = synthetic construct
SEQUENCE: 180
GGSISSSTYY                                                     10

SEQ ID NO: 181          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 181
ttctattata gtgggagcac c                                        21

SEQ ID NO: 182          moltype = AA  length = 7
FEATURE                 Location/Qualifiers
REGION                  1..7
                        note = Synthetic
source                  1..7
                        mol_type = protein
                        organism = synthetic construct
SEQUENCE: 182
FYYSGST                                                        7

SEQ ID NO: 183          moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 183
gcgagagggg ggctcctggg gagacctttt gttatc                        36

SEQ ID NO: 184          moltype = AA  length = 12
```

-continued

```
FEATURE                Location/Qualifiers
REGION                 1..12
                       note = Synthetic
source                 1..12
                       mol_type = protein
                       organism = synthetic construct
SEQUENCE: 184
ARGGLLGRPF VI                                                  12

SEQ ID NO: 185         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 185
gacatccaga tgacccagtc tccatcctcc ctgtctgcat ctgtaggaga cagagtcacc  60
atcacttgcc gggcaagtca gggcattaga aatgatttag gctggtatca gcagaaacca  120
gggaaagccc ctaagcgcct gatctatgct gcatccagtt tgcaaagtgg ggtcccatca  180
aggttcagcg gcagtggatc tgggacagaa ttcactctca caatcagcag cctgcagcct  240
gaagattttg caacttatta ctgtctacag cataatagtt acccgctcac tttcggcgga  300
gggaccaagg tggagatcaa acga                                     324

SEQ ID NO: 186         moltype = AA  length = 108
FEATURE                Location/Qualifiers
REGION                 1..108
                       note = Synthetic
source                 1..108
                       mol_type = protein
                       organism = synthetic construct
SEQUENCE: 186
DIQMTQSPSS LSASVGDRVT ITCRASQGIR NDLGWYQQKP GKAPKRLIYA ASSLQSGVPS  60
RFSGSGSGTE FTLTISSLQP EDFATYYCLQ HNSYPLTFGG GTKVEIKR            108

SEQ ID NO: 187         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 187
cagggcatta gaaatgat                                            18

SEQ ID NO: 188         moltype = AA  length = 6
FEATURE                Location/Qualifiers
REGION                 1..6
                       note = Synthetic
source                 1..6
                       mol_type = protein
                       organism = synthetic construct
SEQUENCE: 188
QGIRND                                                         6

SEQ ID NO: 189         moltype =   length =
SEQUENCE: 189
000

SEQ ID NO: 190         moltype =   length =
SEQUENCE: 190
000

SEQ ID NO: 191         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 191
ctacagcata atagttaccc gctcact                                  27

SEQ ID NO: 192         moltype = AA  length = 9
FEATURE                Location/Qualifiers
REGION                 1..9
                       note = Synthetic
source                 1..9
                       mol_type = protein
```

```
                       organism = synthetic construct
SEQUENCE: 192
LQHNSYPLT                                                          9

SEQ ID NO: 193         moltype = DNA  length = 366
FEATURE                Location/Qualifiers
misc_feature           1..366
                       note = Synthetic
source                 1..366
                       mol_type = other DNA
                       organism = synthetic construct
SEQUENCE: 193
gaggtgcagc tggtggagtc taggggaggc ttggtacagc ctggggggtc cctgagactc  60
tcctgtgcag cctctggatt cacttttagc agctatgcca tgagctgggt ccgccaggct  120
ccagggaagg ggctggagtg ggtctcagct attagtggta gtggtggtag cacattctac  180
gcagactccg tgaagggccg gttcaccatc tccagagaca attccaagaa cacggtatat  240
ctgcaaatga acagcctgag agccgaggac acggccgtat attactgtgc gaaagccctc  300
gtattgcgat tttggagtgg gttaggggac tactggggcc agggaaccct ggtcaccgtc  360
tcctca                                                             366

SEQ ID NO: 194         moltype = AA  length = 122
FEATURE                Location/Qualifiers
REGION                 1..122
                       note = Synthetic
source                 1..122
                       mol_type = protein
                       organism = synthetic construct
SEQUENCE: 194
EVQLVESRGG LVQPGGSLRL SCAASGFTFS SYAMSWVRQA PGKGLEWVSA ISGSGGSTFY  60
ADSVKGRFTI SRDNSKNTVY LQMNSLRAED TAVYYCAKAL VLRFLEWLGD YWGQGTLVTV  120
SS                                                                 122

SEQ ID NO: 195         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 195
ggattcactt ttagcagcta tgcc                                         24

SEQ ID NO: 196         moltype = AA  length = 8
FEATURE                Location/Qualifiers
REGION                 1..8
                       note = Synthetic
source                 1..8
                       mol_type = protein
                       organism = synthetic construct
SEQUENCE: 196
GFTFSSYA                                                           8

SEQ ID NO: 197         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 197
attagtggta gtggtggtag caca                                         24

SEQ ID NO: 198         moltype = AA  length = 8
FEATURE                Location/Qualifiers
REGION                 1..8
                       note = Synthetic
source                 1..8
                       mol_type = protein
                       organism = synthetic construct
SEQUENCE: 198
ISGSGGST                                                           8

SEQ ID NO: 199         moltype = DNA  length = 45
FEATURE                Location/Qualifiers
misc_feature           1..45
                       note = Synthetic
source                 1..45
                       mol_type = other DNA
                       organism = synthetic construct
```

-continued

```
SEQUENCE: 199
gcgaaagccc tcgtattgcg atttttggag tggttagggg actac                45

SEQ ID NO: 200         moltype = AA  length = 15
FEATURE                Location/Qualifiers
REGION                 1..15
                       note = Synthetic
source                 1..15
                       mol_type = protein
                       organism = synthetic construct
SEQUENCE: 200
AKALVLRFLE WLGDY                                                 15

SEQ ID NO: 201         moltype = DNA  length = 321
FEATURE                Location/Qualifiers
misc_feature           1..321
                       note = Synthetic
source                 1..321
                       mol_type = other DNA
                       organism = synthetic construct
SEQUENCE: 201
gacatccaga tgacccagtc tccttccacc ctgtctgcat ctgtaggaga cagagtcacc  60
atcacttgtc gggccagtca gagtattagt agctggttgg cctggtttca gcagaaacca  120
gggaaagccc ctaagctcct gatctataag gcgtctagtt tagaaagtgg ggtcccatca  180
aggttcagcg gcagtggatc tgggacagaa ttcactctca ccatcagcag cctgcagcct  240
gatgattttg caacttatta ctgtcaacag tataaaagtt attggacgtt cggccaaggg  300
accaaggtgg aaatcaaacg a                                          321

SEQ ID NO: 202         moltype = AA  length = 107
FEATURE                Location/Qualifiers
REGION                 1..107
                       note = Synthetic
source                 1..107
                       mol_type = protein
                       organism = synthetic construct
SEQUENCE: 202
DIQMTQSPST LSASVGDRVT ITCRASQSIS SWLAWFQQKP GKAPKLLIYK ASSLESGVPS  60
RFSGSGSGTE FTLTISSLQP DDFATYYCQQ YKSYWTFGQG TKVEIKR              107

SEQ ID NO: 203         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 203
cagagtatta gtagctgg                                              18

SEQ ID NO: 204         moltype = AA  length = 6
FEATURE                Location/Qualifiers
REGION                 1..6
                       note = Synthetic
source                 1..6
                       mol_type = protein
                       organism = synthetic construct
SEQUENCE: 204
QSISSW                                                           6

SEQ ID NO: 205         moltype =   length =
SEQUENCE: 205
000

SEQ ID NO: 206         moltype =   length =
SEQUENCE: 206
000

SEQ ID NO: 207         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 207
caacagtata aaagttattg gacg                                       24

SEQ ID NO: 208         moltype = AA  length = 8
FEATURE                Location/Qualifiers
```

```
REGION                  1..8
                        note = Synthetic
source                  1..8
                        mol_type = protein
                        organism = synthetic construct
SEQUENCE: 208
QQYKSYWT                                                            8

SEQ ID NO: 209          moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 209
gaggtgcagc tggtggagtc tgggggaggc ctggtacagc ctggggggtc cctgagactc  60
tcctgtgcag cctctggatt cacctttagc agctatgcca tgagctgggt ccgccaggct  120
ccagggaagg ggctggagtg ggtctcaagt attagtggta gtggtgatag cacattctac  180
acagactccg tgaagggccg gttcaccatc tccagagaca tttccaagaa cacgctgtat  240
ctgcaaatga acagcctgag agccgaggac acggccgtat attactgtgc gaaagatcgt  300
cttctatggt tcggggactt aatatccccc tttcactact ggggccaggg aaccctggtc  360
accgtctcct ca                                                       372

SEQ ID NO: 210          moltype = AA  length = 124
FEATURE                 Location/Qualifiers
REGION                  1..124
                        note = Synthetic
source                  1..124
                        mol_type = protein
                        organism = synthetic construct
SEQUENCE: 210
EVQLVESGGG LVQPGGSLRL SCAASGFTFS SYAMSWVRQA PGKGLEWVSS ISGSGDSTFY  60
TDSVKGRFTI SRDISKNTLY LQMNSLRAED TAVYYCAKDR LLWFGDLISP FHYWGQGTLV  120
TVSS                                                                124

SEQ ID NO: 211          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 211
ggattcacct ttagcagcta tgcc                                          24

SEQ ID NO: 212          moltype = AA  length = 8
FEATURE                 Location/Qualifiers
REGION                  1..8
                        note = Synthetic
source                  1..8
                        mol_type = protein
                        organism = synthetic construct
SEQUENCE: 212
GFTFSSYA                                                            8

SEQ ID NO: 213          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 213
attagtggta gtggtgatag caca                                          24

SEQ ID NO: 214          moltype = AA  length = 8
FEATURE                 Location/Qualifiers
REGION                  1..8
                        note = Synthetic
source                  1..8
                        mol_type = protein
                        organism = synthetic construct
SEQUENCE: 214
ISGSGDST                                                            8

SEQ ID NO: 215          moltype = DNA  length = 51
FEATURE                 Location/Qualifiers
misc_feature            1..51
```

```
                        note = Synthetic
source                  1..51
                        mol_type = other DNA
                        organism = synthetic construct
SEQUENCE: 215
gcgaaagatc gtcttctatg gttcggggac ttaatatccc cctttcacta c           51

SEQ ID NO: 216          moltype = AA  length = 17
FEATURE                 Location/Qualifiers
REGION                  1..17
                        note = Synthetic
source                  1..17
                        mol_type = protein
                        organism = synthetic construct
SEQUENCE: 216
AKDRLLWFGD LISPFHY                                                 17

SEQ ID NO: 217          moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 217
gaaattgtgt tgacgcagtc tccaggcacc ctgtctttgt ctccagggga aagagccacc  60
ctctcctgca gggccagtca gagtgttagc aacatctact tagcctggta ccagcagaaa  120
cctgcccagg ctcccaggct cctcatctat ggtgcatcca gcagggccac tggcatccca  180
gacaggttta gtgtcagtgg gtctgggaca gacttcactc tcaccatcag cagactggag  240
cctgaagatt ttgcagtgta ttactgtcag cagtatggta gctcacctcg gacgttcggc  300
caagggacca aggtggaaat caaacga                                      327

SEQ ID NO: 218          moltype = AA  length = 109
FEATURE                 Location/Qualifiers
REGION                  1..109
                        note = Synthetic
source                  1..109
                        mol_type = protein
                        organism = synthetic construct
SEQUENCE: 218
EIVLTQSPGT LSLSPGERAT LSCRASQSVS NIYLAWYQQK PAQAPRLLIY GASSRATGIP  60
DRFSVSGSGT DFTLTISRLE PEDFAVYYCQ QYGSSPRTFG QGTKVEIKR               109

SEQ ID NO: 219          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 219
cagagtgtta gcaacatcta c                                            21

SEQ ID NO: 220          moltype = AA  length = 7
FEATURE                 Location/Qualifiers
REGION                  1..7
                        note = Synthetic
source                  1..7
                        mol_type = protein
                        organism = synthetic construct
SEQUENCE: 220
QSVSNIY                                                            7

SEQ ID NO: 221          moltype =   length =
SEQUENCE: 221
000

SEQ ID NO: 222          moltype =   length =
SEQUENCE: 222
000

SEQ ID NO: 223          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 223
```

-continued

```
cagcagtatg gtagctcacc tcggacg                                       27

SEQ ID NO: 224         moltype = AA  length = 9
FEATURE                Location/Qualifiers
REGION                 1..9
                       note = Synthetic
source                 1..9
                       mol_type = protein
                       organism = synthetic construct
SEQUENCE: 224
QQYGSSPRT                                                           9

SEQ ID NO: 225         moltype = DNA  length = 366
FEATURE                Location/Qualifiers
misc_feature           1..366
                       note = Synthetic
source                 1..366
                       mol_type = other DNA
                       organism = synthetic construct
SEQUENCE: 225
gaggtgcagc tggtggagtc tgggggaggc ttggtacagc ctgggggggtc cctgagactc  60
tcctgtacag cctctggatt cacctttagc agctatgcca tgagttgggt ccgccaggct  120
ccagggaagg ggctggaatg ggtctcagct attagtggga ctggtagtag tacatacttc  180
acagactccg tgaagggccg gttcgccatc tccagagaca attccaagaa cacgctgtat  240
ctgcaaatga acagcctgag agccgaggac acggccgtat attactgtgc gaaagatgga  300
gagtggctct ctacggtgac cctttttgac tactggggcc agggaaccct ggtcaccgtc  360
tcctca                                                              366

SEQ ID NO: 226         moltype = AA  length = 122
FEATURE                Location/Qualifiers
REGION                 1..122
                       note = Synthetic
source                 1..122
                       mol_type = protein
                       organism = synthetic construct
SEQUENCE: 226
EVQLVESGGG LVQPGGSLRL SCTASGFTFS SYAMSWVRQA PGKGLEWVSA ISGTGSSTYF  60
TDSVKGRFAI SRDNSKNTLY LQMNSLRAED TAVYYCAKDG EWLSTVTLFD YWGQGTLVTV  120
SS                                                                  122

SEQ ID NO: 227         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 227
ggattcacct ttagcagcta tgcc                                          24

SEQ ID NO: 228         moltype = AA  length = 8
FEATURE                Location/Qualifiers
REGION                 1..8
                       note = Synthetic
source                 1..8
                       mol_type = protein
                       organism = synthetic construct
SEQUENCE: 228
GFTFSSYA                                                            8

SEQ ID NO: 229         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 229
attagtggga ctggtagtag taca                                          24

SEQ ID NO: 230         moltype = AA  length = 8
FEATURE                Location/Qualifiers
REGION                 1..8
                       note = Synthetic
source                 1..8
                       mol_type = protein
                       organism = synthetic construct
SEQUENCE: 230
ISGTGSST                                                            8
```

```
SEQ ID NO: 231          moltype = DNA  length = 45
FEATURE                 Location/Qualifiers
misc_feature            1..45
                        note = Synthetic
source                  1..45
                        mol_type = other DNA
                        organism = synthetic construct
SEQUENCE: 231
gcgaaagatg gagagtggct ctctacggtg accctttttg actac                    45

SEQ ID NO: 232          moltype = AA  length = 15
FEATURE                 Location/Qualifiers
REGION                  1..15
                        note = Synthetic
source                  1..15
                        mol_type = protein
                        organism = synthetic construct
SEQUENCE: 232
AKDGEWLSTV TLFDY                                                     15

SEQ ID NO: 233          moltype = DNA  length = 330
FEATURE                 Location/Qualifiers
misc_feature            1..330
                        note = Synthetic
source                  1..330
                        mol_type = other DNA
                        organism = synthetic construct
SEQUENCE: 233
gaaattgtga tgacgcagtc tccagccacc ctgtctgtgt ctccagggga aagagccacc  60
ctctcctgca gggccagtca gagtgttagc agcaacttag cctggtacca gcagaaacct  120
ggccaggctc ccaggctcct catctatggt gcatccacca gggccactgg tatcccagcc  180
aggttcagtg gcagtgggtc tgggacagat ttcactctca ccatcagcag cctgcagtct  240
gaagattttg cactttatta ctgtcagcag tattttatct ggcctccgca tcccactttc  300
ggccctggga ccaaagtgga tatcaaacga                                     330

SEQ ID NO: 234          moltype = AA  length = 110
FEATURE                 Location/Qualifiers
REGION                  1..110
                        note = Synthetic
source                  1..110
                        mol_type = protein
                        organism = synthetic construct
SEQUENCE: 234
EIVMTQSPAT LSVSPGERAT LSCRASQSVS SNLAWYQQKP GQAPRLLIYG ASTRATGIPA  60
RFSGSGSGTD FTLTISSLQS EDFALYYCQQ YFIWPPHPTF GPGTKVDIKR              110

SEQ ID NO: 235          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 235
cagagtgtta gcagcaac                                                  18

SEQ ID NO: 236          moltype = AA  length = 6
FEATURE                 Location/Qualifiers
REGION                  1..6
                        note = Synthetic
source                  1..6
                        mol_type = protein
                        organism = synthetic construct
SEQUENCE: 236
QSVSSN                                                               6

SEQ ID NO: 237          moltype =   length =
SEQUENCE: 237
000

SEQ ID NO: 238          moltype =   length =
SEQUENCE: 238
000

SEQ ID NO: 239          moltype = DNA  length = 33
FEATURE                 Location/Qualifiers
misc_feature            1..33
                        note = Synthetic
```

```
source                  1..33
                        mol_type = other DNA
                        organism = synthetic construct
SEQUENCE: 239
cagcagtatt ttatctggcc tccgcatccc act                                   33

SEQ ID NO: 240          moltype = AA  length = 11
FEATURE                 Location/Qualifiers
REGION                  1..11
                        note = Synthetic
source                  1..11
                        mol_type = protein
                        organism = synthetic construct
SEQUENCE: 240
QQYFIWPPHP T                                                           11

SEQ ID NO: 241          moltype = DNA  length = 363
FEATURE                 Location/Qualifiers
misc_feature            1..363
                        note = Synthetic
source                  1..363
                        mol_type = other DNA
                        organism = synthetic construct
SEQUENCE: 241
caggtgcagc tggtggagtc tgggggagcc gtggtccagc ctgggaggtc cctgagactc  60
tcctgtgcag cctctggatt caccttcagt tactatggca tgcactgggt ccgccaggct  120
ccaggcaagg ggctggagtg ggtggcagtt atatcatatg atggaagtaa aaaatactat  180
gcagactccg tgaagggccg attcaccatc tccagagaca attccaagaa cacgctgtat  240
ctgcaaatga acagcctgag agctgaggac acggctgtgt attactgtgc gaaagatctg  300
acagtagact tctactacgg tatggacgtc tggggccaag ggaccacggt caccgtctcc  360
tca                                                                    363

SEQ ID NO: 242          moltype = AA  length = 121
FEATURE                 Location/Qualifiers
REGION                  1..121
                        note = Synthetic
source                  1..121
                        mol_type = protein
                        organism = synthetic construct
SEQUENCE: 242
QVQLVESGGA VVQPGRSLRL SCAASGFTFS YYGMHWVRQA PGKGLEWVAV ISYDGSKKYY  60
ADSVKGRFTI SRDNSKNTLY LQMNSLRAED TAVYYCAKDL TVDFYYGMDV WGQGTTVTVS  120
S                                                                      121

SEQ ID NO: 243          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 243
ggattcacct tcagttacta tggc                                             24

SEQ ID NO: 244          moltype = AA  length = 8
FEATURE                 Location/Qualifiers
REGION                  1..8
                        note = Synthetic
source                  1..8
                        mol_type = protein
                        organism = synthetic construct
SEQUENCE: 244
GFTFSYYG                                                               8

SEQ ID NO: 245          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 245
atatcatatg atggaagtaa aaaa                                             24

SEQ ID NO: 246          moltype = AA  length = 8
FEATURE                 Location/Qualifiers
REGION                  1..8
                        note = Synthetic
source                  1..8
```

```
                         mol_type = protein
                         organism = synthetic construct
SEQUENCE: 246
ISYDGSKK                                                          8

SEQ ID NO: 247           moltype = DNA  length = 42
FEATURE                  Location/Qualifiers
misc_feature             1..42
                         note = Synthetic
source                   1..42
                         mol_type = other DNA
                         organism = synthetic construct
SEQUENCE: 247
gcgaaagatc tgacagtaga cttctactac ggtatggacg tc                    42

SEQ ID NO: 248           moltype = AA  length = 14
FEATURE                  Location/Qualifiers
REGION                   1..14
                         note = Synthetic
source                   1..14
                         mol_type = protein
                         organism = synthetic construct
SEQUENCE: 248
AKDLTVDFYY GMDV                                                   14

SEQ ID NO: 249           moltype = DNA  length = 324
FEATURE                  Location/Qualifiers
misc_feature             1..324
                         note = Synthetic
source                   1..324
                         mol_type = other DNA
                         organism = synthetic construct
SEQUENCE: 249
gacatccaga tgacccagtc tccatcttcc gtgtctgcat ctgtaggaga cagagtcacc  60
atcacttgtc gggcgagtca gggtattagc agctggttag cctggtatca gcagaaacca  120
gggaaagccc ctaagctcct gatctatgct acatccagtt tgcaaagtgg ggccccatca  180
aggttcagcg gcagtggatc tgggacagat ttcactctca ccatcagcag cctgcagcct  240
gaagattttg caacttactt ttgtcaacag gctaacagtt tcccatacac ttttggccag  300
gggaccaagc tggagatcaa acga                                        324

SEQ ID NO: 250           moltype = AA  length = 108
FEATURE                  Location/Qualifiers
REGION                   1..108
                         note = Synthetic
source                   1..108
                         mol_type = protein
                         organism = synthetic construct
SEQUENCE: 250
DIQMTQSPSS VSASVGDRVT ITCRASQGIS SWLAWYQQKP GKAPKLLIYA TSSLQSGAPS  60
RFSGSGSGTD FTLTISSLQP EDFATYFCQQ ANSFPYTFGQ GTKLEIKR              108

SEQ ID NO: 251           moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 251
cagggtatta gcagctgg                                               18

SEQ ID NO: 252           moltype = AA  length = 6
FEATURE                  Location/Qualifiers
REGION                   1..6
                         note = Synthetic
source                   1..6
                         mol_type = protein
                         organism = synthetic construct
SEQUENCE: 252
QGISSW                                                            6

SEQ ID NO: 253           moltype =   length =
SEQUENCE: 253
000

SEQ ID NO: 254           moltype =   length =
SEQUENCE: 254
000
```

-continued

```
SEQ ID NO: 255          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 255
caacaggcta acagtttccc atacact                                      27

SEQ ID NO: 256          moltype = AA  length = 9
FEATURE                 Location/Qualifiers
REGION                  1..9
                        note = Synthetic
source                  1..9
                        mol_type = protein
                        organism = synthetic construct
SEQUENCE: 256
QQANSFPYT                                                          9

SEQ ID NO: 257          moltype = DNA  length = 342
FEATURE                 Location/Qualifiers
misc_feature            1..342
                        note = Synthetic
source                  1..342
                        mol_type = other DNA
                        organism = synthetic construct
SEQUENCE: 257
caggtgcagc tgcaggagtc gggcccagga ctggtgaagc cttcggagac cctgtccctc  60
acctgcactg tctctgatgg ctccatcagt agttactact ggagctggat ccggcagccc  120
ccagggaggg gactggagtg gattgggttt atctattaca gtgggagcac cagctacaac  180
ccctccctca agagtcgagt caccatttca gtagacacgt ccatgagcca gttctccctg  240
aagctgaggt ctgtgaccgc cgcagacacg gccgtgtatt actgtgcgcg tgggagcccc  300
tttgactact ggggcccggg aaccctggtc accgtctcct ca                     342

SEQ ID NO: 258          moltype = AA  length = 114
FEATURE                 Location/Qualifiers
REGION                  1..114
                        note = Synthetic
source                  1..114
                        mol_type = protein
                        organism = synthetic construct
SEQUENCE: 258
QVQLQESGPG LVKPSETLSL TCTVSDGSIS SYYWSWIRQP PGRGLEWIGF IYYSGSTSYN  60
PSLKSRVTIS VDTSMSQFSL KLRSVTAADT AVYYCARGSP FDYWGPGTLV TVSS        114

SEQ ID NO: 259          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 259
gatggctcca tcagtagtta ctac                                         24

SEQ ID NO: 260          moltype = AA  length = 8
FEATURE                 Location/Qualifiers
REGION                  1..8
                        note = Synthetic
source                  1..8
                        mol_type = protein
                        organism = synthetic construct
SEQUENCE: 260
DGSISSYY                                                           8

SEQ ID NO: 261          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 261
atctattaca gtgggagcac c                                            21

SEQ ID NO: 262          moltype = AA  length = 7
FEATURE                 Location/Qualifiers
REGION                  1..7
```

```
                        note = Synthetic
source                  1..7
                        mol_type = protein
                        organism = synthetic construct
SEQUENCE: 262
IYYSGST                                                     7

SEQ ID NO: 263          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 263
gcgcgtggga gcccctttga ctac                                  24

SEQ ID NO: 264          moltype = AA  length = 8
FEATURE                 Location/Qualifiers
REGION                  1..8
                        note = Synthetic
source                  1..8
                        mol_type = protein
                        organism = synthetic construct
SEQUENCE: 264
ARGSPFDY                                                    8

SEQ ID NO: 265          moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 265
gaaattgtgt tgacgcagtc tccaggcacc ctgtctttgt ctccagggga aagagccacc  60
ctctcctgca gggccagtca gagtgttagc agcagctact tagcctggta ccagcaaaga  120
cctggccagg ctcccagcct cctcatctct ggtgcatcca ggagggccac tggcatccca  180
gacaggttca gtggcagtgg gtctgggaca gacttcactc tcaccatcag aagactggag  240
cctgaagatt ttgcaatgta ttactgtcag cagtatggta gttcacctcc cactttcggc  300
ggagggacca aggtggagat caaacga                                327

SEQ ID NO: 266          moltype = AA  length = 109
FEATURE                 Location/Qualifiers
REGION                  1..109
                        note = Synthetic
source                  1..109
                        mol_type = protein
                        organism = synthetic construct
SEQUENCE: 266
EIVLTQSPGT LSLSPGERAT LSCRASQSVS SSYLAWYQQR PGQAPSLLIS GASRRATGIP  60
DRFSGSGSGT DFTLTIRRLE PEDFAMYYCQ QYGSSPPTFG GGTKVEIKR          109

SEQ ID NO: 267          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 267
cagagtgtta gcagcagcta c                                     21

SEQ ID NO: 268          moltype = AA  length = 7
FEATURE                 Location/Qualifiers
REGION                  1..7
                        note = Synthetic
source                  1..7
                        mol_type = protein
                        organism = synthetic construct
SEQUENCE: 268
QSVSSSY                                                     7

SEQ ID NO: 269          moltype =   length =
SEQUENCE: 269
000

SEQ ID NO: 270          moltype =   length =
SEQUENCE: 270
```

```
000

SEQ ID NO: 271         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 271
cagcagtatg gtagttcacc tcccact                                     27

SEQ ID NO: 272         moltype = AA  length = 9
FEATURE                Location/Qualifiers
REGION                 1..9
                       note = Synthetic
source                 1..9
                       mol_type = protein
                       organism = synthetic construct
SEQUENCE: 272
QQYGSSPPT                                                         9

SEQ ID NO: 273         moltype = DNA  length = 363
FEATURE                Location/Qualifiers
misc_feature           1..363
                       note = Synthetic
source                 1..363
                       mol_type = other DNA
                       organism = synthetic construct
SEQUENCE: 273
gaggtgcagc tggtggagtc tgggggaggc ttggtccagc ctggggggtc cctgagactc  60
tcctgtgcag cctctggatt cacgttcagt aactatgcta tgcactgggt ccgccaggct  120
ccagggaagg gactggaata tgtttcagct attagtagta atgggggtag tacatattat  180
gcagactctg tgaagggcag aatcaccatc tccagagaca attccaagaa cacgctgtat  240
cttcaaatgg gcagcctgag agctgaggat atggctgtgt attactgtgc gagagggcga  300
ccgtactact actacttcgg tatggacgtc tggggccaag ggaccacggt caccgtctcc  360
tca                                                               363

SEQ ID NO: 274         moltype = AA  length = 121
FEATURE                Location/Qualifiers
REGION                 1..121
                       note = Synthetic
source                 1..121
                       mol_type = protein
                       organism = synthetic construct
SEQUENCE: 274
EVQLVESGGG LVQPGGSLRL SCAASGFTFS NYAMHWVRQA PGKGLEYVSA ISSNGGSTYY  60
ADSVKGRITI SRDNSKNTLY LQMGSLRAED MAVYYCARGR PYYYYFGMDV WGQGTTVTVS  120
S                                                                 121

SEQ ID NO: 275         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 275
ggattcacgt tcagtaacta tgct                                        24

SEQ ID NO: 276         moltype = AA  length = 8
FEATURE                Location/Qualifiers
REGION                 1..8
                       note = Synthetic
source                 1..8
                       mol_type = protein
                       organism = synthetic construct
SEQUENCE: 276
GFTFSNYA                                                          8

SEQ ID NO: 277         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 277
attagtagta atgggggtag taca                                        24
```

```
SEQ ID NO: 278         moltype = AA  length = 8
FEATURE                Location/Qualifiers
REGION                 1..8
                       note = Synthetic
source                 1..8
                       mol_type = protein
                       organism = synthetic construct
SEQUENCE: 278
ISSNGGST                                                           8

SEQ ID NO: 279         moltype = DNA  length = 42
FEATURE                Location/Qualifiers
misc_feature           1..42
                       note = Synthetic
source                 1..42
                       mol_type = other DNA
                       organism = synthetic construct
SEQUENCE: 279
gcgagagggc gaccgtacta ctactacttc ggtatggacg tc                     42

SEQ ID NO: 280         moltype = AA  length = 14
FEATURE                Location/Qualifiers
REGION                 1..14
                       note = Synthetic
source                 1..14
                       mol_type = protein
                       organism = synthetic construct
SEQUENCE: 280
ARGRPYYYYF GMDV                                                    14

SEQ ID NO: 281         moltype = DNA  length = 339
FEATURE                Location/Qualifiers
misc_feature           1..339
                       note = Synthetic
source                 1..339
                       mol_type = other DNA
                       organism = synthetic construct
SEQUENCE: 281
gatattgtga tgactcagac tccagtctcc tcacctgtca cccttggaca gccggcctcc  60
atctcctgca ggtctagtca aagcctcgta cacagtgatg gaaacaccta cttgagttgg  120
tttcagcaga ggccgggcca gcctccaaga ctcctaattt ataagatttc taaccggttc  180
tctggggtcc cagacagatt cagtggcagt ggggcaggga cagatttcac actgaaaatc  240
agcagggtgg aagctgagga tgtcggggtt tattactgca tgcaagctac acaatttcct  300
ctcaatttcg gcggagggac caaggtggag atcaaacga                         339

SEQ ID NO: 282         moltype = AA  length = 113
FEATURE                Location/Qualifiers
REGION                 1..113
                       note = Synthetic
source                 1..113
                       mol_type = protein
                       organism = synthetic construct
SEQUENCE: 282
DIVMTQTPVS SPVTLGQPAS ISCRSSQSLV HSDGNTYLSW FQQRPGQPPR LLIYKISNRF  60
SGVPDRFSGS GAGTDFTLKI SRVEAEDVGV YYCMQATQFP LNFGGGTKVE IKR         113

SEQ ID NO: 283         moltype = DNA  length = 33
FEATURE                Location/Qualifiers
misc_feature           1..33
                       note = Synthetic
source                 1..33
                       mol_type = other DNA
                       organism = synthetic construct
SEQUENCE: 283
caaagcctcg tacacagtga tggaaacacc tac                               33

SEQ ID NO: 284         moltype = AA  length = 11
FEATURE                Location/Qualifiers
REGION                 1..11
                       note = Synthetic
source                 1..11
                       mol_type = protein
                       organism = synthetic construct
SEQUENCE: 284
QSLVHSDGNT Y                                                       11

SEQ ID NO: 285         moltype =   length =
SEQUENCE: 285
```

```
000

SEQ ID NO: 286         moltype =   length =
SEQUENCE: 286
000

SEQ ID NO: 287         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 287
atgcaagcta cacaatttcc tctcaat                                          27

SEQ ID NO: 288         moltype = AA  length = 9
FEATURE                Location/Qualifiers
REGION                 1..9
                       note = Synthetic
source                 1..9
                       mol_type = protein
                       organism = synthetic construct
SEQUENCE: 288
MQATQFPLN                                                              9

SEQ ID NO: 289         moltype = DNA  length = 366
FEATURE                Location/Qualifiers
misc_feature           1..366
                       note = Synthetic
source                 1..366
                       mol_type = other DNA
                       organism = synthetic construct
SEQUENCE: 289
gaggtgcagc tggtggagtc tgggggaggc ttggtacagc ctggggggtc cctgagactc  60
tcctgtgcag cctctggatt cacctttagg acctatgcca tgacctgggt ccgccaggct  120
ccagggaagg ggctagactg ggtctcagct attactggtg atggtggtaa tacatactac  180
gcagactccg tgaagggccg gttcaccatt tccagagaca attccaagaa cacgctgtat  240
ctgcaaatga acagcctgag agccgaggac acggccatct attactgtgc gaaagatcag  300
agattcagct ttgctctata ctactttgac tactggggcc agggaaccct ggtcactgtc  360
tcctca                                                                 366

SEQ ID NO: 290         moltype = AA  length = 122
FEATURE                Location/Qualifiers
REGION                 1..122
                       note = Synthetic
source                 1..122
                       mol_type = protein
                       organism = synthetic construct
SEQUENCE: 290
EVQLVESGGG LVQPGGSLRL SCAASGFTFR TYAMTWVRQA PGKGLDWVSA ITGDGGNTYY  60
ADSVKGRFTI SRDNSKNTLY LQMNSLRAED TAIYYCAKDQ RFSFALYYFD YWGQGTLVTV  120
SS                                                                     122

SEQ ID NO: 291         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 291
ggattcacct ttaggaccta tgcc                                             24

SEQ ID NO: 292         moltype = AA  length = 8
FEATURE                Location/Qualifiers
REGION                 1..8
                       note = Synthetic
source                 1..8
                       mol_type = protein
                       organism = synthetic construct
SEQUENCE: 292
GFTFRTYA                                                               8

SEQ ID NO: 293         moltype = DNA  length = 24
FEATURE                Location/Qualifiers
misc_feature           1..24
                       note = Synthetic
source                 1..24
```

```
                         mol_type = other DNA
                         organism = synthetic construct
SEQUENCE: 293
attactggtg atggtggtaa taca                                            24

SEQ ID NO: 294           moltype = AA  length = 8
FEATURE                  Location/Qualifiers
REGION                   1..8
                         note = Synthetic
source                   1..8
                         mol_type = protein
                         organism = synthetic construct
SEQUENCE: 294
ITGDGGNT                                                              8

SEQ ID NO: 295           moltype = DNA  length = 45
FEATURE                  Location/Qualifiers
misc_feature             1..45
                         note = Synthetic
source                   1..45
                         mol_type = other DNA
                         organism = synthetic construct
SEQUENCE: 295
gcgaaagatc agagattcag ctttgctcta tactactttg actac                     45

SEQ ID NO: 296           moltype = AA  length = 15
FEATURE                  Location/Qualifiers
REGION                   1..15
                         note = Synthetic
source                   1..15
                         mol_type = protein
                         organism = synthetic construct
SEQUENCE: 296
AKDQRFSFAL YYFDY                                                      15

SEQ ID NO: 297           moltype = DNA  length = 324
FEATURE                  Location/Qualifiers
misc_feature             1..324
                         note = Synthetic
source                   1..324
                         mol_type = other DNA
                         organism = synthetic construct
SEQUENCE: 297
gacatccaga tgacccagtc tccatcttcc gtgtctgcat ctgtaggaga cagagtcacc  60
atcacttgtc gggcgagtca gggtattagc agctggttag cctggtatca gcagaaacca  120
gggaacgccc ctaagctcct gatctatgct gcattcagtt tgcaaagtgg ggtcccgtca  180
aggttcagcg gcagtggatc tgggacagat ttcactctca ccatcagcag cctgcagcct  240
gaagattttg caacttacta ttgtcaacag gctaacaatt tcccgtggac gttcggccaa  300
gggaccaagg tggaaatcaa acga                                            324

SEQ ID NO: 298           moltype = AA  length = 108
FEATURE                  Location/Qualifiers
REGION                   1..108
                         note = Synthetic
source                   1..108
                         mol_type = protein
                         organism = synthetic construct
SEQUENCE: 298
DIQMTQSPSS VSASVGDRVT ITCRASQGIS SWLAWYQQKP GNAPKLLIYA AFSLQSGVPS  60
RFSGSGSGTD FTLTISSLQP EDFATYYCQQ ANNFPWTFGQ GTKVEIKR                 108

SEQ ID NO: 299           moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 299
cagggtatta gcagctgg                                                   18

SEQ ID NO: 300           moltype = AA  length = 6
FEATURE                  Location/Qualifiers
REGION                   1..6
                         note = Synthetic
source                   1..6
                         mol_type = protein
                         organism = synthetic construct
SEQUENCE: 300
```

```
QGISSW                                                          6

SEQ ID NO: 301         moltype =   length =
SEQUENCE: 301
000

SEQ ID NO: 302         moltype =   length =
SEQUENCE: 302
000

SEQ ID NO: 303         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 303
caacaggcta acaatttccc gtggacg                                   27

SEQ ID NO: 304         moltype = AA  length = 9
FEATURE                Location/Qualifiers
REGION                 1..9
                       note = Synthetic
source                 1..9
                       mol_type = protein
                       organism = synthetic construct
SEQUENCE: 304
QQANNFPWT                                                       9

SEQ ID NO: 305         moltype = DNA  length = 354
FEATURE                Location/Qualifiers
misc_feature           1..354
                       note = Synthetic
source                 1..354
                       mol_type = other DNA
                       organism = synthetic construct
SEQUENCE: 305
caggtgcagc tggtggagtc tgggggaggc gtggtccagc ctgggaggtc cctgagactc  60
tcctgtgcag cctctggatt caccttcagt aactatgaca tgcactgggt ccgccaggct  120
ccaggcaagg ggctggagtg gatggcagtt atatcatatg atggaattaa taaatattat  180
gcagactccg tgaagggccg attcaccatc tccagagaca attccaagaa cacgctgtat  240
ctgcaaatga acagcctgag agctgaggac acggctgtgt attactgtgc gaaaggtact  300
tactcctggt acttcgatct ctggggccgt ggcaccctgg tcactgtctc ctca        354

SEQ ID NO: 306         moltype = AA  length = 118
FEATURE                Location/Qualifiers
REGION                 1..118
                       note = Synthetic
source                 1..118
                       mol_type = protein
                       organism = synthetic construct
SEQUENCE: 306
QVQLVESGGG VVQPGRSLRL SCAASGFTFS NYDMHWVRQA PGKGLEWMAV ISYDGINKYY  60
ADSVKGRFTI SRDNSKNTLY LQMNSLRAED TAVYYCAKGT YSWYFDLWGR GTLVTVSS    118

SEQ ID NO: 307         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 307
ggattcacct tcagtaacta tgac                                      24

SEQ ID NO: 308         moltype = AA  length = 8
FEATURE                Location/Qualifiers
REGION                 1..8
                       note = Synthetic
source                 1..8
                       mol_type = protein
                       organism = synthetic construct
SEQUENCE: 308
GFTFSNYD                                                        8

SEQ ID NO: 309         moltype = DNA  length = 24
FEATURE                Location/Qualifiers
misc_feature           1..24
```

```
                        note = Synthetic
source                  1..24
                        mol_type = other DNA
                        organism = synthetic construct
SEQUENCE: 309
atatcatatg atggaattaa taaa                                          24

SEQ ID NO: 310          moltype = AA  length = 8
FEATURE                 Location/Qualifiers
REGION                  1..8
                        note = Synthetic
source                  1..8
                        mol_type = protein
                        organism = synthetic construct
SEQUENCE: 310
ISYDGINK                                                            8

SEQ ID NO: 311          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 311
gcgaaaggta cttactcctg gtacttcgat ctc                                33

SEQ ID NO: 312          moltype = AA  length = 11
FEATURE                 Location/Qualifiers
REGION                  1..11
                        note = Synthetic
source                  1..11
                        mol_type = protein
                        organism = synthetic construct
SEQUENCE: 312
AKGTYSWYFD L                                                        11

SEQ ID NO: 313          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 313
gacatccaga tgacccagtc tccttccacc ctgtctacat ctgtaggaga cagagtcacc  60
atcacttgcc gggccagtca gactattagt agctggttgg cctggtatca gcagaaacca  120
gggaaagccc ctaagctcct gatctataag gcgtctcgtt tagaaagtgg ggtcccatca  180
aggttcagcg gcagtggatc tgggacagaa ttcactctca ccatcagcag cctgcagcct  240
gatgattttg caacttatta ctgccaacag tataatagtt attcgtggac gttcggccaa  300
gggaccaagg tggaaatcaa acga                                          324

SEQ ID NO: 314          moltype = AA  length = 108
FEATURE                 Location/Qualifiers
REGION                  1..108
                        note = Synthetic
source                  1..108
                        mol_type = protein
                        organism = synthetic construct
SEQUENCE: 314
DIQMTQSPST LSTSVGDRVT ITCRASQTIS SWLAWYQQKP GKAPKLLIYK ASRLESGVPS  60
RFSGSGSGTE FTLTISSLQP DDFATYYCQQ YNSYSWTFGQ GTKVEIKR                108

SEQ ID NO: 315          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 315
cagactatta gtagctgg                                                 18

SEQ ID NO: 316          moltype = AA  length = 6
FEATURE                 Location/Qualifiers
REGION                  1..6
                        note = Synthetic
source                  1..6
                        mol_type = protein
```

```
                         organism = synthetic construct
SEQUENCE: 316
QTISSW                                                              6

SEQ ID NO: 317           moltype =   length =
SEQUENCE: 317
000

SEQ ID NO: 318           moltype =   length =
SEQUENCE: 318
000

SEQ ID NO: 319           moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 319
caacagtata atagttattc gtggacg                                       27

SEQ ID NO: 320           moltype = AA  length = 9
FEATURE                  Location/Qualifiers
REGION                   1..9
                         note = Synthetic
source                   1..9
                         mol_type = protein
                         organism = synthetic construct
SEQUENCE: 320
QQYNSYSWT                                                           9

SEQ ID NO: 321           moltype = DNA  length = 366
FEATURE                  Location/Qualifiers
misc_feature             1..366
                         note = Synthetic
source                   1..366
                         mol_type = other DNA
                         organism = synthetic construct
SEQUENCE: 321
gaagtgcagc tggtggagtc tgggggaggc ttggtacagc ctggcaggtc cctgagactc  60
tcctgtgcag cctctggatt cacctttgat gcttatgcca tgcactgggt ccggcaagct  120
ccagggaagg gcctggagtg ggtctcaggt attagttgga atagtggtag cataggctat  180
gcggactctg tgaagggccg attcaccatt tccagagaca acgccaagaa ctccctgtat  240
ctgcaaatga acagtctgag agaagaggac acggccttgt attactgtgc aaaagataaa  300
attttggaac tttactacta cggtatggac gtctggggcc aagggaccac ggtcaccgtc  360
tcctca                                                              366

SEQ ID NO: 322           moltype = AA  length = 122
FEATURE                  Location/Qualifiers
REGION                   1..122
                         note = Synthetic
source                   1..122
                         mol_type = protein
                         organism = synthetic construct
SEQUENCE: 322
EVQLVESGGG LVQPGRSLRL SCAASGFTFD AYAMHWVRQA PGKGLEWVSG ISWNSGSIGY  60
ADSVKGRFTI SRDNAKNSLY LQMNSLREED TALYYCAKDK ILELYYYGMD VWGQGTTVTV  120
SS                                                                  122

SEQ ID NO: 323           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 323
ggattcacct ttgatgctta tgcc                                          24

SEQ ID NO: 324           moltype = AA  length = 8
FEATURE                  Location/Qualifiers
REGION                   1..8
                         note = Synthetic
source                   1..8
                         mol_type = protein
                         organism = synthetic construct
SEQUENCE: 324
GFTFDAYA                                                            8
```

```
SEQ ID NO: 325          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 325
attagttgga atagtggtag cata                                        24

SEQ ID NO: 326          moltype = AA  length = 8
FEATURE                 Location/Qualifiers
REGION                  1..8
                        note = Synthetic
source                  1..8
                        mol_type = protein
                        organism = synthetic construct
SEQUENCE: 326
ISWNSGSI                                                          8

SEQ ID NO: 327          moltype = DNA  length = 45
FEATURE                 Location/Qualifiers
misc_feature            1..45
                        note = Synthetic
source                  1..45
                        mol_type = other DNA
                        organism = synthetic construct
SEQUENCE: 327
gcaaaagata aaattttgga actttactac tacggtatgg acgtc                 45

SEQ ID NO: 328          moltype = AA  length = 15
FEATURE                 Location/Qualifiers
REGION                  1..15
                        note = Synthetic
source                  1..15
                        mol_type = protein
                        organism = synthetic construct
SEQUENCE: 328
AKDKILELYY YGMDV                                                  15

SEQ ID NO: 329          moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 329
gaggtgcagc tggtggagtc tgggggagac ttggtacagc ctggggggtc cctgagactc  60
tcctgttcag cctctggatt cacctttaac atctatgcca tgagctgggt ccgccaggct  120
ccagggaagg ggctggagtg ggtctcaggt attagtggta gtggtggtag cacatactac  180
gcagactccg tgaagggccg gttcaccatc tccagagaca attcaaagaa cacgctgtat  240
ttccaaatga atagcctgag agtcgaggac acggccgtat attactgtgc gaaaaaaata  300
agcagctcgt cctactacta ctacgctatg gacgtctggg gccaagggac cacggtcacc  360
gtctcctca                                                         369

SEQ ID NO: 330          moltype = AA  length = 123
FEATURE                 Location/Qualifiers
REGION                  1..123
                        note = Synthetic
source                  1..123
                        mol_type = protein
                        organism = synthetic construct
SEQUENCE: 330
EVQLVESGGD LVQPGGSLRL SCSASGFTFN IYAMSWVRQA PGKGLEWVSG ISGSGGSTYY  60
ADSVKGRFTI SRDNSKNTLY FQMNSLRVED TAVYYCAKKI SSSSYYYYAM DVWGQGTTVT  120
VSS                                                               123

SEQ ID NO: 331          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 331
ggattcacct ttaacatcta tgcc                                        24
```

```
SEQ ID NO: 332         moltype = AA  length = 8
FEATURE                Location/Qualifiers
REGION                 1..8
                       note = Synthetic
source                 1..8
                       mol_type = protein
                       organism = synthetic construct
SEQUENCE: 332
GFTFNIYA                                                          8

SEQ ID NO: 333         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 333
attagtggta gtggtggtag caca                                        24

SEQ ID NO: 334         moltype = AA  length = 8
FEATURE                Location/Qualifiers
REGION                 1..8
                       note = Synthetic
source                 1..8
                       mol_type = protein
                       organism = synthetic construct
SEQUENCE: 334
ISGSGGST                                                          8

SEQ ID NO: 335         moltype = DNA  length = 48
FEATURE                Location/Qualifiers
misc_feature           1..48
                       note = Synthetic
source                 1..48
                       mol_type = other DNA
                       organism = synthetic construct
SEQUENCE: 335
gcgaaaaaaa taagcagctc gtcctactac tactacgcta tggacgtc              48

SEQ ID NO: 336         moltype = AA  length = 16
FEATURE                Location/Qualifiers
REGION                 1..16
                       note = Synthetic
source                 1..16
                       mol_type = protein
                       organism = synthetic construct
SEQUENCE: 336
AKKISSSSYY YYAMDV                                                 16

SEQ ID NO: 337         moltype = DNA  length = 355
FEATURE                Location/Qualifiers
misc_feature           1..355
                       note = Synthetic
source                 1..355
                       mol_type = other DNA
                       organism = synthetic construct
SEQUENCE: 337
caggtgcagc tggtgcagtc tggggctgag gtgaagaagc ctgggtcctc ggtgaaggtc  60
tcctgcaagg cttctggagg caccttcagc agatatgata tcagctgggt gcgacaggcc  120
cctggacaag gacttgagtg gatgggaggg atcatcccta tctttggtac atcaaactac  180
gcacagaagt tccagggcag agtcacgatt accacggacg aatccacgag tacagtctac  240
atggagctga gcagtctgag atctgaagac acggccgtgt attattgtgc gagaggaggt  300
cgatatggct ggttcgaccc ctggggccag ggaaccctgg tcaccgtctc ctcag      355

SEQ ID NO: 338         moltype = AA  length = 118
FEATURE                Location/Qualifiers
REGION                 1..118
                       note = Synthetic
source                 1..118
                       mol_type = protein
                       organism = synthetic construct
SEQUENCE: 338
QVQLVQSGAE VKKPGSSVKV SCKASGGTFS RYDISWVRQA PGQGLEWMGG IIPIFGTSNY  60
AQKFQGRVTI TTDESTSTVY MELSSLRSED TAVYYCARGG RYGWFDPWGQ GTLVTVSS    118

SEQ ID NO: 339         moltype = DNA  length = 24
FEATURE                Location/Qualifiers
misc_feature           1..24
```

```
                        note = Synthetic
source                  1..24
                        mol_type = other DNA
                        organism = synthetic construct
SEQUENCE: 339
ggaggcacct tcagcagata tgat                                        24

SEQ ID NO: 340          moltype = AA  length = 8
FEATURE                 Location/Qualifiers
REGION                  1..8
                        note = Synthetic
source                  1..8
                        mol_type = protein
                        organism = synthetic construct
SEQUENCE: 340
GGTFSRYD                                                          8

SEQ ID NO: 341          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 341
atcatcccta tctttggtac atca                                        24

SEQ ID NO: 342          moltype = AA  length = 8
FEATURE                 Location/Qualifiers
REGION                  1..8
                        note = Synthetic
source                  1..8
                        mol_type = protein
                        organism = synthetic construct
SEQUENCE: 342
IIPIFGTS                                                          8

SEQ ID NO: 343          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 343
gcgagaggag gtcgatatgg ctggttcgac ccc                              33

SEQ ID NO: 344          moltype = AA  length = 11
FEATURE                 Location/Qualifiers
REGION                  1..11
                        note = Synthetic
source                  1..11
                        mol_type = protein
                        organism = synthetic construct
SEQUENCE: 344
ARGGRYGWFD P                                                      11

SEQ ID NO: 345          moltype = DNA  length = 375
FEATURE                 Location/Qualifiers
misc_feature            1..375
                        note = Synthetic
source                  1..375
                        mol_type = other DNA
                        organism = synthetic construct
SEQUENCE: 345
gaggtgcagc tggtggagtc tgggggaggc ttggtacagc ctggggggtc cctgagactc  60
tcctgtgcag cctctggatt cacctttagc agctttgcca tgagctgggt ccgccaggct  120
ccagggaagg aactggagtg ggtctcatct attagtggtc gtggtggtag cacatactac  180
gcagactccg tgaggggccg gttcaccatc tccagagaca attccaagat cacgctgtat  240
ctgcaaatga acagcctgag agccgaggac acggccgtat attactgtgc gaaagatatt  300
gtcttccggt ataccagctc ggcctactgg tacttcgatc tctggggccg tggcaccctg  360
gtcaccgtct cctca                                                  375

SEQ ID NO: 346          moltype = AA  length = 125
FEATURE                 Location/Qualifiers
REGION                  1..125
                        note = Synthetic
source                  1..125
                        mol_type = protein
```

```
                         organism = synthetic construct
SEQUENCE: 346
EVQLVESGGG LVQPGGSLRL SCAASGFTFS SFAMSWVRQA PGKELEWVSS ISGRGGSTYY  60
ADSVRGRFTI SRDNSKITLY LQMNSLRAED TAVYYCAKDI VFRYTSSAYW YFDLWGRGTL  120
VTVSS                                                              125

SEQ ID NO: 347           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 347
ggattcacct ttagcagctt tgcc                                         24

SEQ ID NO: 348           moltype = AA  length = 8
FEATURE                  Location/Qualifiers
REGION                   1..8
                         note = Synthetic
source                   1..8
                         mol_type = protein
                         organism = synthetic construct
SEQUENCE: 348
GFTFSSFA                                                           8

SEQ ID NO: 349           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 349
attagtggtc gtggtggtag caca                                         24

SEQ ID NO: 350           moltype = AA  length = 8
FEATURE                  Location/Qualifiers
REGION                   1..8
                         note = Synthetic
source                   1..8
                         mol_type = protein
                         organism = synthetic construct
SEQUENCE: 350
ISGRGGST                                                           8

SEQ ID NO: 351           moltype = DNA  length = 54
FEATURE                  Location/Qualifiers
misc_feature             1..54
                         note = Synthetic
source                   1..54
                         mol_type = other DNA
                         organism = synthetic construct
SEQUENCE: 351
gcgaaagata ttgtcttccg gtataccagc tcggcctact ggtacttcga tctc        54

SEQ ID NO: 352           moltype = AA  length = 18
FEATURE                  Location/Qualifiers
REGION                   1..18
                         note = Synthetic
source                   1..18
                         mol_type = protein
                         organism = synthetic construct
SEQUENCE: 352
AKDIVFRYTS SAYWYFDL                                                18

SEQ ID NO: 353           moltype = DNA  length = 375
FEATURE                  Location/Qualifiers
misc_feature             1..375
                         note = Synthetic
source                   1..375
                         mol_type = other DNA
                         organism = synthetic construct
SEQUENCE: 353
gaggtgcagc tggtggagtc tgggggaggc ttggtacagc ctggggggtc cctgagactc  60
tcctgtgcag cctctggatt cacctttagc agctatggca tgaactgggt ccgccaggct  120
ccagggaagg ggctggagtg ggtctcagtt attagtggta gtggtggtag cacatactac  180
gcagactccg tgaagggccg gttcaccatc tccagagaca attccaagaa cacgctgtat  240
ctgcaaatga acagcctgag agccgaggac acggccgtat attactgtgc gaaagatcgt  300
```

```
tggacgtatt actatgatag tagtggttcc ccctttgact actggggcca gggaaccctg  360
gtcaccgtct cctca                                                  375

SEQ ID NO: 354          moltype = AA  length = 125
FEATURE                 Location/Qualifiers
REGION                  1..125
                        note = Synthetic
source                  1..125
                        mol_type = protein
                        organism = synthetic construct
SEQUENCE: 354
EVQLVESGGG LVQPGGSLRL SCAASGFTFS SYGMNWVRQA PGKGLEWVSV ISGSGGSTYY  60
ADSVKGRFTI SRDNSKNTLY LQMNSLRAED TAVYYCAKDR WTYYYDSSGS PFDYWGQGTL  120
VTVSS                                                             125

SEQ ID NO: 355          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 355
ggattcacct ttagcagcta tggc                                        24

SEQ ID NO: 356          moltype = AA  length = 8
FEATURE                 Location/Qualifiers
REGION                  1..8
                        note = Synthetic
source                  1..8
                        mol_type = protein
                        organism = synthetic construct
SEQUENCE: 356
GFTFSSYG                                                          8

SEQ ID NO: 357          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 357
attagtggta gtggtggtag caca                                        24

SEQ ID NO: 358          moltype = AA  length = 8
FEATURE                 Location/Qualifiers
REGION                  1..8
                        note = Synthetic
source                  1..8
                        mol_type = protein
                        organism = synthetic construct
SEQUENCE: 358
ISGSGGST                                                          8

SEQ ID NO: 359          moltype = DNA  length = 54
FEATURE                 Location/Qualifiers
misc_feature            1..54
                        note = Synthetic
source                  1..54
                        mol_type = other DNA
                        organism = synthetic construct
SEQUENCE: 359
gcgaaagatc gttggacgta ttactatgat agtagtggtt ccccctttga ctac       54

SEQ ID NO: 360          moltype = AA  length = 18
FEATURE                 Location/Qualifiers
REGION                  1..18
                        note = Synthetic
source                  1..18
                        mol_type = protein
                        organism = synthetic construct
SEQUENCE: 360
AKDRWTYYYD SSGSPFDY                                               18

SEQ ID NO: 361          moltype = DNA  length = 324
FEATURE                 Location/Qualifiers
misc_feature            1..324
                        note = Synthetic
```

```
source                  1..324
                        mol_type = other DNA
                        organism = synthetic construct
SEQUENCE: 361
gaaattgtgt tgacgcagtc tccaggcacc ctgtctttgt ctccagggga aagagccacc  60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcaccttg gacgttcggc  300
caagggacca aggtggaaat caaa                                         324

SEQ ID NO: 362          moltype = AA  length = 108
FEATURE                 Location/Qualifiers
REGION                  1..108
                        note = Synthetic
source                  1..108
                        mol_type = protein
                        organism = synthetic construct
SEQUENCE: 362
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPWTFG QGTKVEIK               108

SEQ ID NO: 363          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 363
cagagtgtta gcagcagcta c                                            21

SEQ ID NO: 364          moltype = AA  length = 7
FEATURE                 Location/Qualifiers
REGION                  1..7
                        note = Synthetic
source                  1..7
                        mol_type = protein
                        organism = synthetic construct
SEQUENCE: 364
QSVSSSY                                                            7

SEQ ID NO: 365          moltype =   length =
SEQUENCE: 365
000

SEQ ID NO: 366          moltype =   length =
SEQUENCE: 366
000

SEQ ID NO: 367          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 367
cagcagtatg gtagctcacc ttggacg                                      27

SEQ ID NO: 368          moltype = AA  length = 9
FEATURE                 Location/Qualifiers
REGION                  1..9
                        note = Synthetic
source                  1..9
                        mol_type = protein
                        organism = synthetic construct
SEQUENCE: 368
QQYGSSPWT                                                          9

SEQ ID NO: 369          moltype = DNA  length = 363
FEATURE                 Location/Qualifiers
misc_feature            1..363
                        note = Synthetic
source                  1..363
                        mol_type = other DNA
                        organism = synthetic construct
SEQUENCE: 369
gaggtgcagc tggtggagtc tgggggaggc tttgtacagc ctgggggtc cctgagactc  60
```

-continued

```
tcctgtgcag cctctggatt cacttttagc agttatgcca tgagttgggt ccgccaggct  120
ccaggtaagg ggctggagtg ggtctcagct attagtggta ctggtagtaa cacatactac  180
gcagactccg tgaagggccg gttcaccatc tccagagaca attccaagaa cacgctgtat  240
ctgcaaatga acagcctgag agccgaggac acggccgttt actactgtgc gaaagatcgc  300
gtgactacag taacctacta ctttgactac tggggccagg gaaccctggt caccgtctcc  360
tca                                                               363

SEQ ID NO: 370          moltype = AA  length = 121
FEATURE                 Location/Qualifiers
REGION                  1..121
                        note = Synthetic
source                  1..121
                        mol_type = protein
                        organism = synthetic construct
SEQUENCE: 370
EVQLVESGGG FVQPGGSLRL SCAASGFTFS SYAMSWVRQA PGKGLEWVSA ISGTGSNTYY  60
ADSVKGRFTI SRDNSKNTLY LQMNSLRAED TAVYYCAKDR VTTVTYYFDY WGQGTLVTVS  120
S                                                                 121

SEQ ID NO: 371          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 371
ggattcactt ttagcagtta tgcc                                        24

SEQ ID NO: 372          moltype = AA  length = 8
FEATURE                 Location/Qualifiers
REGION                  1..8
                        note = Synthetic
source                  1..8
                        mol_type = protein
                        organism = synthetic construct
SEQUENCE: 372
GFTFSSYA                                                          8

SEQ ID NO: 373          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 373
attagtggta ctggtagtaa caca                                        24

SEQ ID NO: 374          moltype = AA  length = 8
FEATURE                 Location/Qualifiers
REGION                  1..8
                        note = Synthetic
source                  1..8
                        mol_type = protein
                        organism = synthetic construct
SEQUENCE: 374
ISGTGSNT                                                          8

SEQ ID NO: 375          moltype = DNA  length = 42
FEATURE                 Location/Qualifiers
misc_feature            1..42
                        note = Synthetic
source                  1..42
                        mol_type = other DNA
                        organism = synthetic construct
SEQUENCE: 375
gcgaaagatc gcgtgactac agtaacctac tactttgact ac                    42

SEQ ID NO: 376          moltype = AA  length = 14
FEATURE                 Location/Qualifiers
REGION                  1..14
                        note = Synthetic
source                  1..14
                        mol_type = protein
                        organism = synthetic construct
SEQUENCE: 376
AKDRVTTVTY YFDY                                                   14
```

```
SEQ ID NO: 377          moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 377
gaggtgcagc tggtggagtc tgggggaggc ttggtacagc ctggggggtc cctgagactc  60
tcctgtgcag cctctggttt cacctttagc agctatgcca tgaactgggt ccgccaggct  120
ccagggaagg gactggagtg ggtctcagct attagtggta gtggtgatag cacatactac  180
gcagactccg tgaagggccg gttcaccatc tccagagaca attccaggac cacgctgtct  240
ctgcaattga acagcctgag agccgaggac acggccgtat attactgtgc gaaagatcga  300
ctactatggt tcggggaatt aggatcccca tttcactact ggggccaggg aaccctggtc  360
accgtctcct ca                                                      372

SEQ ID NO: 378          moltype = AA  length = 124
FEATURE                 Location/Qualifiers
REGION                  1..124
                        note = Synthetic
source                  1..124
                        mol_type = protein
                        organism = synthetic construct
SEQUENCE: 378
EVQLVESGGG LVQPGGSLRL SCAASGFTFS SYAMNWVRQA PGKGLEWVSA ISGSGDSTYY  60
ADSVKGRFTI SRDNSRTTLS LQLNSLRAED TAVYYCAKDR LLWFGELGSP FHYWGQGTLV  120
TVSS                                                               124

SEQ ID NO: 379          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 379
ggtttcacct ttagcagcta tgcc                                         24

SEQ ID NO: 380          moltype = AA  length = 8
FEATURE                 Location/Qualifiers
REGION                  1..8
                        note = Synthetic
source                  1..8
                        mol_type = protein
                        organism = synthetic construct
SEQUENCE: 380
GFTFSSYA                                                           8

SEQ ID NO: 381          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 381
attagtggta gtggtgatag caca                                         24

SEQ ID NO: 382          moltype = AA  length = 8
FEATURE                 Location/Qualifiers
REGION                  1..8
                        note = Synthetic
source                  1..8
                        mol_type = protein
                        organism = synthetic construct
SEQUENCE: 382
ISGSGDST                                                           8

SEQ ID NO: 383          moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 383
gcgaaagatc gactactatg gttcggggaa ttaggatccc catttcacta c           51

SEQ ID NO: 384          moltype = AA  length = 17
```

```
FEATURE                Location/Qualifiers
REGION                 1..17
                       note = Synthetic
source                 1..17
                       mol_type = protein
                       organism = synthetic construct
SEQUENCE: 384
AKDRLLWFGE LGSPFHY                                                17

SEQ ID NO: 385         moltype = DNA  length = 363
FEATURE                Location/Qualifiers
misc_feature           1..363
                       note = Synthetic
source                 1..363
                       mol_type = other DNA
                       organism = synthetic construct
SEQUENCE: 385
gaggtgcagc tggtggagtc tgggggaggc ttggaacagc ctgggggggtc cctgagactc  60
tcctgtgcag cctctggatt cacctttagc agctatgcca tgagctgggt ccgccaggct  120
ccagggaagg ggctggagtg ggtctcagtc attagtggta gtggtggtta cacaaactac  180
gcagactccg tgaagggccg gttcaccatc tccagagaca attccaagaa cacgctgtat  240
ctgcaaatga accgcctgag agccgaggac tcggccgttt attactgtgc gaggcataat  300
tggaactacg actattacgg tatggacgtc tggggccagg ggaccacggt caccgtctcc  360
tca                                                               363

SEQ ID NO: 386         moltype = AA  length = 121
FEATURE                Location/Qualifiers
REGION                 1..121
                       note = Synthetic
source                 1..121
                       mol_type = protein
                       organism = synthetic construct
SEQUENCE: 386
EVQLVESGGG LEQPGGSLRL SCAASGFTFS SYAMSWVRQA PGKGLEWVSV ISGSGGYTNY  60
ADSVKGRFTI SRDNSKNTLY LQMNRLRAED SAVYYCARHN WNYDYYGMDV WGQGTTVTVS  120
S                                                                 121

SEQ ID NO: 387         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 387
ggattcacct ttagcagcta tgcc                                        24

SEQ ID NO: 388         moltype = AA  length = 8
FEATURE                Location/Qualifiers
REGION                 1..8
                       note = Synthetic
source                 1..8
                       mol_type = protein
                       organism = synthetic construct
SEQUENCE: 388
GFTFSSYA                                                          8

SEQ ID NO: 389         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 389
attagtggta gtggtggtta caca                                        24

SEQ ID NO: 390         moltype = AA  length = 8
FEATURE                Location/Qualifiers
REGION                 1..8
                       note = Synthetic
source                 1..8
                       mol_type = protein
                       organism = synthetic construct
SEQUENCE: 390
ISGSGGYT                                                          8

SEQ ID NO: 391         moltype = DNA  length = 42
FEATURE                Location/Qualifiers
```

```
misc_feature          1..42
                      note = Synthetic
source                1..42
                      mol_type = other DNA
                      organism = synthetic construct
SEQUENCE: 391
gcgaggcata attggaacta cgactattac ggtatggacg tc                        42

SEQ ID NO: 392        moltype = AA  length = 14
FEATURE               Location/Qualifiers
REGION                1..14
                      note = Synthetic
source                1..14
                      mol_type = protein
                      organism = synthetic construct
SEQUENCE: 392
ARHNWNYDYY GMDV                                                       14

SEQ ID NO: 393        moltype = DNA  length = 360
FEATURE               Location/Qualifiers
misc_feature          1..360
                      note = Synthetic
source                1..360
                      mol_type = other DNA
                      organism = synthetic construct
SEQUENCE: 393
caggtgcagc tggtggagtc tgggggaggc gtggtccagt ctgggaggtc cctgagactc  60
tcctgtgcag ccgctggatt caccttcagt aattatggca tgcactgggt ccgccaggct  120
ccaggcaagg ggctggagtg ggtggcactt atgtcatttg atggaagtga taaatactat  180
gcagactccg tgaagggccg attcaccatc tccagagaca attccaagaa cacgttgtat  240
ctgcaaatga acagcctgag agctgaggac acggctctgt attactgtgc gaaaggatac  300
gatttttgga gtggttattg ggactactgg ggccagggaa ccctggtcac cgtctcctca  360

SEQ ID NO: 394        moltype = AA  length = 120
FEATURE               Location/Qualifiers
REGION                1..120
                      note = Synthetic
source                1..120
                      mol_type = protein
                      organism = synthetic construct
SEQUENCE: 394
QVQLVESGGG VVQSGRSLRL SCAAAGFTFS NYGMHWVRQA PGKGLEWVAL MSFDGSDKYY  60
ADSVKGRFTI SRDNSKNTLY LQMNSLRAED TALYYCAKGY DFWSGYWDYW GQGTLVTVSS  120

SEQ ID NO: 395        moltype = DNA  length = 24
FEATURE               Location/Qualifiers
misc_feature          1..24
                      note = Synthetic
source                1..24
                      mol_type = other DNA
                      organism = synthetic construct
SEQUENCE: 395
ggattcacct tcagtaatta tggc                                            24

SEQ ID NO: 396        moltype = AA  length = 8
FEATURE               Location/Qualifiers
REGION                1..8
                      note = Synthetic
source                1..8
                      mol_type = protein
                      organism = synthetic construct
SEQUENCE: 396
GFTFSNYG                                                              8

SEQ ID NO: 397        moltype = DNA  length = 24
FEATURE               Location/Qualifiers
misc_feature          1..24
                      note = Synthetic
source                1..24
                      mol_type = other DNA
                      organism = synthetic construct
SEQUENCE: 397
atgtcatttg atggaagtga taaa                                            24

SEQ ID NO: 398        moltype = AA  length = 8
FEATURE               Location/Qualifiers
REGION                1..8
                      note = Synthetic
source                1..8
```

```
                        mol_type = protein
                        organism = synthetic construct
SEQUENCE: 398
MSFDGSDK                                                        8

SEQ ID NO: 399          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 399
gcgaaaggat acgatttttg gagtggttat tgggactac                      39

SEQ ID NO: 400          moltype = AA  length = 13
FEATURE                 Location/Qualifiers
REGION                  1..13
                        note = Synthetic
source                  1..13
                        mol_type = protein
                        organism = synthetic construct
SEQUENCE: 400
AKGYDFWSGY WDY                                                  13

SEQ ID NO: 401          moltype = DNA  length = 351
FEATURE                 Location/Qualifiers
misc_feature            1..351
                        note = Synthetic
source                  1..351
                        mol_type = other DNA
                        organism = synthetic construct
SEQUENCE: 401
gaggtgcagc tggtggagtc tgggggaggc ttggtacaac ctggggggtc cctgagactc  60
tcctgtgcag cctctggatt cacctttagc acctatgcca tgagctgggt ccgccaggct  120
ccagggaagg ggcttgagtg ggtctcaact attagtggtc gttctgatat tacatacttc  180
gcagactccg tgaagggccg gtttaccgtc tccagagaca attccaagac cacgctatat  240
ctccaaatga acagtctgag agccgaggac acggccgtat attactgtgc gacagatgac  300
gacctgcccc ttgactactg gggccaggga accctggtca ccgtctcctc a        351

SEQ ID NO: 402          moltype = AA  length = 117
FEATURE                 Location/Qualifiers
REGION                  1..117
                        note = Synthetic
source                  1..117
                        mol_type = protein
                        organism = synthetic construct
SEQUENCE: 402
EVQLVESGGG LVQPGGSLRL SCAASGFTFS TYAMSWVRQA PGKGLEWVST ISGRSDITYF  60
ADSVKGRFTV SRDNSKTTLY LQMNSLRAED TAVYYCATDD DLPLDYWGQG TLVTVSS     117

SEQ ID NO: 403          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 403
ggattcacct ttagcaccta tgcc                                      24

SEQ ID NO: 404          moltype = AA  length = 8
FEATURE                 Location/Qualifiers
REGION                  1..8
                        note = Synthetic
source                  1..8
                        mol_type = protein
                        organism = synthetic construct
SEQUENCE: 404
GFTFSTYA                                                        8

SEQ ID NO: 405          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 405
```

```
attagtggtc gttctgatat taca                                   24

SEQ ID NO: 406         moltype = AA  length = 8
FEATURE                Location/Qualifiers
REGION                 1..8
                       note = Synthetic
source                 1..8
                       mol_type = protein
                       organism = synthetic construct
SEQUENCE: 406
ISGRSDIT                                                     8

SEQ ID NO: 407         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 407
gcgacagatg acgacctgcc ccttgactac                             30

SEQ ID NO: 408         moltype = AA  length = 10
FEATURE                Location/Qualifiers
REGION                 1..10
                       note = Synthetic
source                 1..10
                       mol_type = protein
                       organism = synthetic construct
SEQUENCE: 408
ATDDDLPLDY                                                   10

SEQ ID NO: 409         moltype = DNA  length = 354
FEATURE                Location/Qualifiers
misc_feature           1..354
                       note = Synthetic
source                 1..354
                       mol_type = other DNA
                       organism = synthetic construct
SEQUENCE: 409
caggtgcagc tggtgcagtc tgggactgag gtgaagaagc ctgggtcctc ggtgaaggtc  60
tcctgcaagg cttctggagg caccttcagc agatatactt tcagctgggt gcgacaggcc  120
cctggacaag ggcttgagtg gatgggaggg atcatcccta tctttggtac aacaaactac  180
gcacagaagt tccagggcag agtcacgatt accacggacg aatccacgag cacagtctac  240
atggagctga gcagcctgag atctgaggac acggccgtgt attattgtac cagaggaggt  300
cgatatggct ggttcgaccc ctggggccag ggaaccctgg tcaccgtctc ctca        354

SEQ ID NO: 410         moltype = AA  length = 118
FEATURE                Location/Qualifiers
REGION                 1..118
                       note = Synthetic
source                 1..118
                       mol_type = protein
                       organism = synthetic construct
SEQUENCE: 410
QVQLVQSGTE VKKPGSSVKV SCKASGGTFS RYTFSWVRQA PGQGLEWMGG IIPIFGTTNY  60
AQKFQGRVTI TTDESTSTVY MELSSLRSED TAVYYCTRGG RYGWFDPWGQ GTLVTVSS    118

SEQ ID NO: 411         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 411
ggaggcacct tcagcagata tact                                   24

SEQ ID NO: 412         moltype = AA  length = 8
FEATURE                Location/Qualifiers
REGION                 1..8
                       note = Synthetic
source                 1..8
                       mol_type = protein
                       organism = synthetic construct
SEQUENCE: 412
GGTFSRYT                                                     8

SEQ ID NO: 413         moltype = DNA  length = 24
```

```
FEATURE                 Location/Qualifiers
misc_feature            1..24
                        note = Synthetic
source                  1..24
                        mol_type = other DNA
                        organism = synthetic construct
SEQUENCE: 413
atcatcccta tctttggtac aaca                                        24

SEQ ID NO: 414          moltype = AA  length = 8
FEATURE                 Location/Qualifiers
REGION                  1..8
                        note = Synthetic
source                  1..8
                        mol_type = protein
                        organism = synthetic construct
SEQUENCE: 414
IIPIFGTT                                                          8

SEQ ID NO: 415          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 415
accagaggag gtcgatatgg ctggttcgac ccc                              33

SEQ ID NO: 416          moltype = AA  length = 11
FEATURE                 Location/Qualifiers
REGION                  1..11
                        note = Synthetic
source                  1..11
                        mol_type = protein
                        organism = synthetic construct
SEQUENCE: 416
TRGGRYGWFD P                                                      11

SEQ ID NO: 417          moltype = AA  length = 403
FEATURE                 Location/Qualifiers
REGION                  1..403
                        note = His-myc tagged human MSR1 antibody (extracellular
                         domain)
source                  1..403
                        mol_type = protein
                        organism = Homo sapiens
SEQUENCE: 417
HHHHHHEQKL ISEEDLGGEQ KLISEEDLKW ETKNCSVSST NANDITQSLT GKGNDSEEEM  60
RFQEVFMEHM SNMEKRIQHI LDMEANLMDT EHFQNFSMTT DQRFNDILLQ LSTLFSSVQG  120
HGNAIDEISK SLISLNTTLL DLQLNIENLN GKIQENTFKQ QEEISKLEER VYNVSAEIMA  180
MKEEQVHLEQ EIKGEVKVLN NITNDLRLKD WEHSQTLRNI TLIQGPPGPP GEKGDRGPTG  240
ESGPRGFPGP IGPPGLKGDR GAIGFPGSRG LPGYAGRPGN SGPKGQKGEK GSGNTLTPFT  300
KVRLVGGSGP HEGRVEILHS GQWGTICDDR WEVRVGQVVC RSLGYPGVQA VHKAAHFGQG  360
TGPIWLNEVF CFGRESSIEE CKIRQWGTRA CSHSEDAGVT CTL                   403

SEQ ID NO: 418          moltype = AA  length = 403
FEATURE                 Location/Qualifiers
REGION                  1..403
                        note = His-myc tagged monkey MSR1 antibody (extracellular
                         domain)
source                  1..403
                        mol_type = protein
                        organism = Macaca fascicularis
SEQUENCE: 418
HHHHHHEQKL ISEEDLGGEQ KLISEEDLKW ETKNCSIGST NADDITQSLT GKGNDSEAET  60
RFQEVFMEHM SNMEKRIQHI SDMEANLIDA EHFQNFSMTT DQRFNDILLQ LSTLFSSVQG  120
HGNTIDEISK SLISLNTTLL DLQLNIEKLN GKIQEKTFKQ QEEISKLEEH VYNVSAEIMA  180
MKEEQVHLEQ EIKGEVKVLN NITNDLRLKD WEHSQTLRNI TLIQGPPGPP GEKGDRGPTG  240
ESGPRGFPGP VGPPGLKGDR GAIGFPGSRG LPGYAGRPGN SGPKGQKGEK GSGNTLTSFK  300
KVRLVGGSGP HEGRVEILHS GQWGTICDDR WEVRVGQVIC RSLGYPGVQA VHKAAHFGQG  360
TGPIWLNEVY CFGRESSIEE CKIRQWGTRT CSHSEDAGVT CTL                   403

SEQ ID NO: 419          moltype = DNA  length = 360
FEATURE                 Location/Qualifiers
misc_feature            1..360
                        note = Synthetic
source                  1..360
                        mol_type = other DNA
```

```
                        organism = synthetic construct
SEQUENCE: 419
gaggtgcagc tggtggagtc tgggggaggc ctggtcaagc cggggggtc cctgagactc  60
tcctgtgcag cctctggatt cactttcagt agatatagta tgaactgggt ccgccaggct  120
ccagggaagg ggctggagtg ggtctcatcc attagcagta gcagtagtta catatactac  180
ggagacacag tgaagggccg attcaccatc tccagagaca acgccaagaa gtcactgtat  240
ctgcaaatga acagcctgag agccgaggac acggctgtct attactgtgt gagagatcga  300
ggacagctcg tcctctactt tgactactgg ggccagggaa ccctggtcac cgtctcctca  360

SEQ ID NO: 420          moltype = AA  length = 120
FEATURE                 Location/Qualifiers
REGION                  1..120
                        note = Synthetic
source                  1..120
                        mol_type = protein
                        organism = synthetic construct
SEQUENCE: 420
EVQLVESGGG LVKPGGSLRL SCAASGFTFS RYSMNWVRQA PGKGLEWVSS ISSSSSYIYY  60
GDTVKGRFTI SRDNAKKSLY LQMNSLRAED TAVYYCVRDR GQLVLYFDYW GQGTLVTVSS  120

SEQ ID NO: 421          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 421
ggattcactt tcagtagata tagt                                        24

SEQ ID NO: 422          moltype = AA  length = 8
FEATURE                 Location/Qualifiers
REGION                  1..8
                        note = Synthetic
source                  1..8
                        mol_type = protein
                        organism = synthetic construct
SEQUENCE: 422
GFTFSRYS                                                          8

SEQ ID NO: 423          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 423
attagcagta gcagtagtta cata                                        24

SEQ ID NO: 424          moltype = AA  length = 8
FEATURE                 Location/Qualifiers
REGION                  1..8
                        note = Synthetic
source                  1..8
                        mol_type = protein
                        organism = synthetic construct
SEQUENCE: 424
ISSSSSYI                                                          8

SEQ ID NO: 425          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 425
gtgagagatc gaggacagct cgtcctctac tttgactac                        39

SEQ ID NO: 426          moltype = AA  length = 13
FEATURE                 Location/Qualifiers
REGION                  1..13
                        note = Synthetic
source                  1..13
                        mol_type = protein
                        organism = synthetic construct
SEQUENCE: 426
VRDRGQLVLY FDY                                                    13
```

```
SEQ ID NO: 427         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 427
gacatccaga tgacccagtc tccagcctcc ctgtctacat ctataagaga cagagtcacc  60
atcacttgcc gggcaagtct gagcattagc agctttttaa attggtttca gcagagacca  120
gggaaagccc ctaaactcct gatctatgtt gcatccaatt tgcaaagtgg ggtcccatca  180
agattcagtg acagtggatc tgggacagat ttcactctca ccatcagcag tctgcaacct  240
gaagattttg caacttacta ctgtcaacag aattacagta cccctccgat caccttcggc  300
caagggacac gactggagat taaa                                         324

SEQ ID NO: 428         moltype = AA  length = 108
FEATURE                Location/Qualifiers
REGION                 1..108
                       note = Synthetic
source                 1..108
                       mol_type = protein
                       organism = synthetic construct
SEQUENCE: 428
DIQMTQSPAS LSTSIRDRVT ITCRASLSIS SFLNWFQQRP GKAPKLLIYV ASNLQSGVPS  60
RFSDSGSGTD FTLTISSLQP EDFATYYCQQ NYSTPPITFG QGTRLEIK                108

SEQ ID NO: 429         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 429
ctgagcatta gcagcttt                                                18

SEQ ID NO: 430         moltype = AA  length = 6
FEATURE                Location/Qualifiers
REGION                 1..6
                       note = Synthetic
source                 1..6
                       mol_type = protein
                       organism = synthetic construct
SEQUENCE: 430
LSISSF                                                             6

SEQ ID NO: 431         moltype =   length =
SEQUENCE: 431
000

SEQ ID NO: 432         moltype =   length =
SEQUENCE: 432
000

SEQ ID NO: 433         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 433
caacagaatt acagtacccc tccgatcacc                                   30

SEQ ID NO: 434         moltype = AA  length = 10
FEATURE                Location/Qualifiers
REGION                 1..10
                       note = Synthetic
source                 1..10
                       mol_type = protein
                       organism = synthetic construct
SEQUENCE: 434
QQNYSTPPIT                                                         10

SEQ ID NO: 435         moltype = DNA  length = 369
FEATURE                Location/Qualifiers
misc_feature           1..369
                       note = Synthetic
```

```
source                  1..369
                        mol_type = other DNA
                        organism = synthetic construct
SEQUENCE: 435
caggtgcagc tggtggagtc tgggggaggc gtggtccagc ctgggaggtc cctgagactc  60
tcctgtgcgg gctctggatt caccttcagt agctatggct tgcactgggt ccgccaggct  120
ccaggcaagg ggctggagtg ggtggcagtt atatcatatg atggaagtaa taaatattat  180
gcagactccg tgaagggccg attcaccatc tccagagaca attccaagaa cacgctgtat  240
ctgcaaatga gcagcctgag agctgaggac acggctgtgt attactgtgc gaaagatcga  300
cttgtacgat attctgactg gccattcttt gactattggg gccagggaac cctggtcacc  360
gtctcctca                                                          369

SEQ ID NO: 436          moltype = AA  length = 123
FEATURE                 Location/Qualifiers
REGION                  1..123
                        note = Synthetic
source                  1..123
                        mol_type = protein
                        organism = synthetic construct
SEQUENCE: 436
QVQLVESGGG VVQPGRSLRL SCAGSGFTFS SYGLHWVRQA PGKGLEWVAV ISYDGSNKYY  60
ADSVKGRFTI SRDNSKNTLY LQMSSLRAED TAVYYCAKDR LVRYSDWPFF DYWGQGTLVT  120
VSS                                                                123

SEQ ID NO: 437          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 437
ggattcacct tcagtagcta tggc                                         24

SEQ ID NO: 438          moltype = AA  length = 8
FEATURE                 Location/Qualifiers
REGION                  1..8
                        note = Synthetic
source                  1..8
                        mol_type = protein
                        organism = synthetic construct
SEQUENCE: 438
GFTFSSYG                                                           8

SEQ ID NO: 439          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 439
atatcatatg atggaagtaa taaa                                         24

SEQ ID NO: 440          moltype = AA  length = 8
FEATURE                 Location/Qualifiers
REGION                  1..8
                        note = Synthetic
source                  1..8
                        mol_type = protein
                        organism = synthetic construct
SEQUENCE: 440
ISYDGSNK                                                           8

SEQ ID NO: 441          moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 441
gcgaaagatc gacttgtacg atattctgac tggccattct ttgactat               48

SEQ ID NO: 442          moltype = AA  length = 16
FEATURE                 Location/Qualifiers
REGION                  1..16
                        note = Synthetic
source                  1..16
```

```
                        mol_type = protein
                        organism = synthetic construct
SEQUENCE: 442
AKDRLVRYSD WPFFDY                                                    16

SEQ ID NO: 443          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 443
gacatccaga tgacccagtc tccatcctcc ctgtctgcat ctgtaggaga cagagtcacc  60
atcacttgcc gggcaagtca aaacattacc agctatttga attgctatca gcagaaacca  120
gggaaagccc ctaaactcct gatctatgct gcatccagtt tgyaaagtgg ggtcccatca  180
aggttcagtg gcagtggatc tgggacagat ttcactctca ccatcagcag tctgcaacct  240
gaagattttg caacttacta ctgtcaacag agtttcagta gtcctccgat caccttcggc  300
caagggacac gactggagat taca                                           324

SEQ ID NO: 444          moltype = AA  length = 108
FEATURE                 Location/Qualifiers
REGION                  1..108
                        note = Synthetic
VARIANT                 55
                        note = MOD_RES - Any amino acid
source                  1..108
                        mol_type = protein
                        organism = synthetic construct
SEQUENCE: 444
DIQMTQSPSS LSASVGDRVT ITCRASQNIT SYLNCYQQKP GKAPKLLIYA ASSLXSGVPS  60
RFSGSGSGTD FTLTISSLQP EDFATYYCQQ SFSSPPITFG QGTRLEIT                 108

SEQ ID NO: 445          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 445
caaaacatta ccagctat                                                  18

SEQ ID NO: 446          moltype = AA  length = 6
FEATURE                 Location/Qualifiers
REGION                  1..6
                        note = Synthetic
source                  1..6
                        mol_type = protein
                        organism = synthetic construct
SEQUENCE: 446
QNITSY                                                               6

SEQ ID NO: 447          moltype =   length =
SEQUENCE: 447
000

SEQ ID NO: 448          moltype =   length =
SEQUENCE: 448
000

SEQ ID NO: 449          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 449
caacagagtt tcagtagtcc tccgatcacc                                     30

SEQ ID NO: 450          moltype = AA  length = 10
FEATURE                 Location/Qualifiers
REGION                  1..10
                        note = Synthetic
source                  1..10
                        mol_type = protein
                        organism = synthetic construct
SEQUENCE: 450
```

```
QQSFSSPPIT                                                        10

SEQ ID NO: 451         moltype = DNA  length = 348
FEATURE                Location/Qualifiers
misc_feature           1..348
                       note = Synthetic
source                 1..348
                       mol_type = other DNA
                       organism = synthetic construct
SEQUENCE: 451
caggtgcagc tgcaggagtc gggcccagga ctggtgaagc cttcggagac cctgtccctc  60
acctgcactg tctctggtgg ctccatcagt agttactact ggagctggat ccggcagccc  120
ccagggaagg gactggaatg gattgggtac atctattaca gtgggagcgc caactacaac  180
ccctccctca agagtcgagt caccatatca gtagacacgt ccaagaacca gttctccctg  240
aagctaagct ctgtgaccgc tgcggacacg gccgtgtatt actgtgtgag agaccgggac  300
ctactccttg accactgggg ccagggaacc ctggtcaccg tctcctca              348

SEQ ID NO: 452         moltype = AA  length = 116
FEATURE                Location/Qualifiers
REGION                 1..116
                       note = Synthetic
source                 1..116
                       mol_type = protein
                       organism = synthetic construct
SEQUENCE: 452
QVQLQESGPG LVKPSETLSL TCTVSGGSIS SYYWSWIRQP PGKGLEWIGY IYYSGSANYN  60
PSLKSRVTIS VDTSKNQFSL KLSSVTAADT AVYYCVRDRD LLLDHWGQGT LVTVSS      116

SEQ ID NO: 453         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 453
ggtggctcca tcagtagtta ctac                                        24

SEQ ID NO: 454         moltype = AA  length = 8
FEATURE                Location/Qualifiers
REGION                 1..8
                       note = Synthetic
source                 1..8
                       mol_type = protein
                       organism = synthetic construct
SEQUENCE: 454
GGSISSYY                                                          8

SEQ ID NO: 455         moltype = DNA  length = 21
FEATURE                Location/Qualifiers
misc_feature           1..21
                       note = Synthetic
source                 1..21
                       mol_type = other DNA
                       organism = synthetic construct
SEQUENCE: 455
atctattaca gtgggagcgc c                                           21

SEQ ID NO: 456         moltype = AA  length = 7
FEATURE                Location/Qualifiers
REGION                 1..7
                       note = Synthetic
source                 1..7
                       mol_type = protein
                       organism = synthetic construct
SEQUENCE: 456
IYYSGSA                                                           7

SEQ ID NO: 457         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 457
gtgagagacc gggacctact ccttgaccac                                  30

SEQ ID NO: 458         moltype = AA  length = 10
```

```
FEATURE                Location/Qualifiers
REGION                 1..10
                       note = Synthetic
source                 1..10
                       mol_type = protein
                       organism = synthetic construct
SEQUENCE: 458
VRDRDLLLDH                                                      10

SEQ ID NO: 459         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 459
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                      324

SEQ ID NO: 460         moltype = AA  length = 108
FEATURE                Location/Qualifiers
REGION                 1..108
                       note = Synthetic
source                 1..108
                       mol_type = protein
                       organism = synthetic construct
SEQUENCE: 460
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK            108

SEQ ID NO: 461         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 461
cagagcatta gcagctat                                             18

SEQ ID NO: 462         moltype = AA  length = 6
FEATURE                Location/Qualifiers
REGION                 1..6
                       note = Synthetic
source                 1..6
                       mol_type = protein
                       organism = synthetic construct
SEQUENCE: 462
QSISSY                                                          6

SEQ ID NO: 463         moltype =   length =
SEQUENCE: 463
000

SEQ ID NO: 464         moltype =   length =
SEQUENCE: 464
000

SEQ ID NO: 465         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 465
caacagagtt acagtacccc tccgatcacc                                30

SEQ ID NO: 466         moltype = AA  length = 10
FEATURE                Location/Qualifiers
REGION                 1..10
                       note = Synthetic
source                 1..10
                       mol_type = protein
```

```
                         organism = synthetic construct
SEQUENCE: 466
QQSYSTPPIT                                                                10

SEQ ID NO: 467           moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 467
KSSQSVLSRA NNNYYVA                                                        17

SEQ ID NO: 468           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 468
WASTREF                                                                   7

SEQ ID NO: 469           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 469
QQYYTSRRT                                                                 9

SEQ ID NO: 470           moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 470
DYYMH                                                                     5

SEQ ID NO: 471           moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 471
WINPKSGGTN YAQRFQG                                                        17

SEQ ID NO: 472           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 472
DCGSGGLRDF                                                                10

SEQ ID NO: 473           moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 473
RSNQNLLSSS NNNYLA                                                         16

SEQ ID NO: 474           moltype = AA  length = 7
FEATURE                  Location/Qualifiers
REGION                   1..7
                         note = Description of Artificial Sequence: Synthetic peptide
source                   1..7
```

```
                        mol_type = protein
                        organism = synthetic construct
SEQUENCE: 474
WASTRES                                                     7

SEQ ID NO: 475          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 475
QQYYANPRT                                                   9

SEQ ID NO: 476          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 476
DYYIH                                                       5

SEQ ID NO: 477          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 477
WINPNTGGTY YAQKFRD                                          17

SEQ ID NO: 478          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 478
DCGRGGLRDI                                                  10

SEQ ID NO: 479          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 479
KSNQNVLASS NDKNYLA                                          17

SEQ ID NO: 480          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 480
WASIRES                                                     7

SEQ ID NO: 481          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 481
QQYYTNPRT                                                   9

SEQ ID NO: 482          moltype = AA  length = 5
FEATURE                 Location/Qualifiers
REGION                  1..5
                        note = Description of Artificial Sequence: Synthetic peptide
```

```
source                  1..5
                        mol_type = protein
                        organism = synthetic construct
SEQUENCE: 482
DYYIH                                                                     5

SEQ ID NO: 483          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 483
WINPNTGGTN YAQKFQG                                                        17

SEQ ID NO: 484          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 484
DCGNAGLRDI                                                                10

SEQ ID NO: 485          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 485
KSSQNVLYSS NNKNYLA                                                        17

SEQ ID NO: 486          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 486
WASTRES                                                                   7

SEQ ID NO: 487          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 487
QQYYTSPPYT                                                                10

SEQ ID NO: 488          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 488
SYWIG                                                                     5

SEQ ID NO: 489          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 489
IIHPGDSKTR YSPSFQG                                                        17

SEQ ID NO: 490          moltype = AA  length = 29
FEATURE                 Location/Qualifiers
REGION                  1..29
```

```
                        note = Description of Artificial Sequence: Synthetic peptide
source                  1..29
                        mol_type = protein
                        organism = synthetic construct
SEQUENCE: 490
LYCSGGSCYS DRAFSSLGAG GYYYYGMGV                                     29

SEQ ID NO: 491          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 491
DIQMTQSPDS LAVSLGERAT INCKSSQSVL SRANNNYYVA WYQHKPGQPP KLLIYWASTR  60
EFGVPDRFSG SGSGTDFTLT INSLQAEDVA VYYCQQYYTS RRTFGQGTKV EIK         113

SEQ ID NO: 492          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 492
QVQLVQSGAE VRKPGASVKV SCKASGYSFT DYYMHWVRQA PGQGLEWMGW INPKSGGTNY  60
AQRFQGRVTM TGDTSISAAY MDLASLTSDD TAVYYCVKDC GSGGLRDFWG QGTTVTVSS   119

SEQ ID NO: 493          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 493
DIQMTQSPDS LSVSLGERAT INCRSNQNLL SSSNNNYLAW YQQKPGQPLK LLIYWASTRE  60
SGVPDRFSGS GSGTDFTLTI SSLQAEDVAV YYCQQYYANP RTFGQGTKVE IK          112

SEQ ID NO: 494          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 494
QVQLQQSRVE VKRPGTSVKV SCKTSGYTFS DYYIHWVRLA PGQGLELMGW INPNTGGTYY  60
AQKFRDRVTM TRDTSIATAY LEMSSLTSDD TAVYYCAKDC GRGGLRDIWG PGTMVTVSS   119

SEQ ID NO: 495          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 495
EIVLTQSPDS LAVSLGERAT INCKSNQNVL ASSNDKNYLA WFQHKPGQPL KLLIYWASIR  60
ESGVPDRFSG SGSGTDFTLT ISSLRAEDVA VYYCQQYYTN PRTFGQGTKV EFN         113

SEQ ID NO: 496          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 496
EVQLVQSGAE VKKPGTSVKV SCKASGYTFT DYYIHWVRLA PGQGLELMGW INPNTGGTNY  60
AQKFQGRVTM TRDTSIATAY MELSSLTSDD TAVYYCAKDC GNAGLRDIWG QGTTVTVSS   119
```

```
SEQ ID NO: 497          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 497
DIQLTQSPDS LAVSLGERAT INCKSSQNVL YSSNNKNYLA WYQQKPGQPP KLLIYWASTR  60
ESGVPDRFSG SGSGTDFTLT ISSLQAEDVA VYYCQQYYTS PPYTFGQGTK LEIE        114

SEQ ID NO: 498          moltype = AA  length = 138
FEATURE                 Location/Qualifiers
REGION                  1..138
                        note = Description of Artificial Sequence: Synthetic
                         polypeptide
source                  1..138
                        mol_type = protein
                        organism = synthetic construct
SEQUENCE: 498
EVQLVQSGAE VKKPGESLKI SCKGSGYSFT SYWIGWVRQM PGKGLEWMGI IHPGDSKTRY  60
SPSFQGQVTI SADKSISTAY LQWNSLKASD TAMYYCARLY CSGGSCYSDR AFSSLGAGGY  120
YYYGMGVWGQ GTTVTVSS                                                138

SEQ ID NO: 499          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 499
RASQTISGWL A                                                       11

SEQ ID NO: 500          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 500
KASTLES                                                            7

SEQ ID NO: 501          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 501
QQYKSYSFN                                                          9

SEQ ID NO: 502          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 502
SYDIN                                                              5

SEQ ID NO: 503          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 503
WMNANSGNTG YAQKFQG                                                 17

SEQ ID NO: 504          moltype = AA  length = 15
FEATURE                 Location/Qualifiers
REGION                  1..15
                        note = Description of Artificial Sequence: Synthetic peptide
```

-continued

```
source                  1..15
                        mol_type = protein
                        organism = synthetic construct
SEQUENCE: 504
SSILVRGALG RYFDL                                                15

SEQ ID NO: 505          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 505
RASQTISGWL A                                                    11

SEQ ID NO: 506          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 506
KASTLES                                                         7

SEQ ID NO: 507          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 507
QQYKSYSFN                                                       9

SEQ ID NO: 508          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 508
SYDIN                                                           5

SEQ ID NO: 509          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 509
WMNANSGNTG YAQKFQG                                              17

SEQ ID NO: 510          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 510
SSILVRGALG RYFDL                                                15

SEQ ID NO: 511          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 511
RASQFVSRTS LA                                                   12

SEQ ID NO: 512          moltype = AA  length = 7
FEATURE                 Location/Qualifiers
REGION                  1..7
```

```
                        note = Description of Artificial Sequence: Synthetic peptide
source                  1..7
                        mol_type = protein
                        organism = synthetic construct
SEQUENCE: 512
ETSSRAT                                                                   7

SEQ ID NO: 513          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 513
HKYGSGPRT                                                                 9

SEQ ID NO: 514          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 514
NYDFI                                                                     5

SEQ ID NO: 515          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 515
WMNPNSYNTG YGQKFQG                                                        17

SEQ ID NO: 516          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 516
AVRGQLLSEY                                                                10

SEQ ID NO: 517          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 517
RASQSVSSSY LA                                                             12

SEQ ID NO: 518          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 518
DASSRAT                                                                   7

SEQ ID NO: 519          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 519
QKYGSTPRP                                                                 9

SEQ ID NO: 520          moltype = AA  length = 5
FEATURE                 Location/Qualifiers
```

-continued

```
REGION               1..5
                     note = Description of Artificial Sequence: Synthetic peptide
source               1..5
                     mol_type = protein
                     organism = synthetic construct
SEQUENCE: 520
SYDIN                                                                5

SEQ ID NO: 521       moltype = AA  length = 17
FEATURE              Location/Qualifiers
REGION               1..17
                     note = Description of Artificial Sequence: Synthetic peptide
source               1..17
                     mol_type = protein
                     organism = synthetic construct
SEQUENCE: 521
WMNPNSGNTN YAQRFQG                                                   17

SEQ ID NO: 522       moltype = AA  length = 17
FEATURE              Location/Qualifiers
REGION               1..17
                     note = Description of Artificial Sequence: Synthetic peptide
source               1..17
                     mol_type = protein
                     organism = synthetic construct
SEQUENCE: 522
ERWSKDTGHY YYYGMDV                                                   17

SEQ ID NO: 523       moltype = AA  length = 11
FEATURE              Location/Qualifiers
REGION               1..11
                     note = Description of Artificial Sequence: Synthetic peptide
source               1..11
                     mol_type = protein
                     organism = synthetic construct
SEQUENCE: 523
RASLDITNHL A                                                         11

SEQ ID NO: 524       moltype = AA  length = 7
FEATURE              Location/Qualifiers
REGION               1..7
                     note = Description of Artificial Sequence: Synthetic peptide
source               1..7
                     mol_type = protein
                     organism = synthetic construct
SEQUENCE: 524
EASILQS                                                              7

SEQ ID NO: 525       moltype = AA  length = 9
FEATURE              Location/Qualifiers
REGION               1..9
                     note = Description of Artificial Sequence: Synthetic peptide
source               1..9
                     mol_type = protein
                     organism = synthetic construct
SEQUENCE: 525
EKCNSTPRT                                                            9

SEQ ID NO: 526       moltype = AA  length = 5
FEATURE              Location/Qualifiers
REGION               1..5
                     note = Description of Artificial Sequence: Synthetic peptide
source               1..5
                     mol_type = protein
                     organism = synthetic construct
SEQUENCE: 526
NYDIN                                                                5

SEQ ID NO: 527       moltype = AA  length = 17
FEATURE              Location/Qualifiers
REGION               1..17
                     note = Description of Artificial Sequence: Synthetic peptide
source               1..17
                     mol_type = protein
                     organism = synthetic construct
SEQUENCE: 527
WMNPSSGRTG YAPKFRG                                                   17

SEQ ID NO: 528       moltype = AA  length = 18
```

```
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 528
GGGYYDSSGN YHISGLDV                                                     18

SEQ ID NO: 529          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 529
RASQSVGAIY LA                                                           12

SEQ ID NO: 530          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 530
GVSNRAT                                                                 7

SEQ ID NO: 531          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 531
QLYTSSRALT                                                              10

SEQ ID NO: 532          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 532
AYAMN                                                                   5

SEQ ID NO: 533          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 533
SITKNSDSLY YADSVKG                                                      17

SEQ ID NO: 534          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 534
LAARIMATDY                                                              10

SEQ ID NO: 535          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 535
RASQGIRNGL G                                                            11
```

-continued

```
SEQ ID NO: 536          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 536
PASTLES                                                                    7

SEQ ID NO: 537          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 537
LQDHNYPPT                                                                  9

SEQ ID NO: 538          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 538
YYSMI                                                                      5

SEQ ID NO: 539          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 539
SIDSSSRYLY YADSVKG                                                         17

SEQ ID NO: 540          moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 540
DGDDILSVYR GSGRPFDY                                                        18

SEQ ID NO: 541          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 541
RASQGIRNGL G                                                               11

SEQ ID NO: 542          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 542
PASTLES                                                                    7

SEQ ID NO: 543          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 543
LQDHNYPPS                                                                  9
```

```
SEQ ID NO: 544          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 544
YYSMI                                                                5

SEQ ID NO: 545          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 545
SIDSSSRYRY YTDSVKG                                                   17

SEQ ID NO: 546          moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 546
DGDDILSVYQ GSGRPFDY                                                  18

SEQ ID NO: 547          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 547
RASQSVRTNV A                                                         11

SEQ ID NO: 548          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 548
GASTRAS                                                              7

SEQ ID NO: 549          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 549
LQYNTWPRT                                                            9

SEQ ID NO: 550          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 550
TNDMS                                                                5

SEQ ID NO: 551          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 551
```

-continued

```
TIIGIDDTTH YADSVRG                                  17

SEQ ID NO: 552         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 552
NSGIYSF                                             7

SEQ ID NO: 553         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 553
RASQDIGSSL A                                        11

SEQ ID NO: 554         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 554
ATSTLQS                                             7

SEQ ID NO: 555         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 555
QQLNNYVHS                                           9

SEQ ID NO: 556         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 556
DYAMG                                               5

SEQ ID NO: 557         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 557
VVTGHSYRTH YADSVKG                                  17

SEQ ID NO: 558         moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 558
RIWSYGDDSF DV                                       12

SEQ ID NO: 559         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
```

```
SEQUENCE: 559
RASQSIGDRL A                                                      11

SEQ ID NO: 560          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 560
WASNLEG                                                           7

SEQ ID NO: 561          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 561
QQYKSQWS                                                          8

SEQ ID NO: 562          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 562
SYAMN                                                             5

SEQ ID NO: 563          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 563
YISSIETIYY ADSVKG                                                 16

SEQ ID NO: 564          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 564
DRLVDVPLSS PNS                                                    13

SEQ ID NO: 565          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 565
KSSQSIFRTS RNKNLLN                                                17

SEQ ID NO: 566          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 566
WASTRKS                                                           7

SEQ ID NO: 567          moltype = AA  length = 9
FEATURE                 Location/Qualifiers
REGION                  1..9
                        note = Description of Artificial Sequence: Synthetic peptide
source                  1..9
                        mol_type = protein
```

```
                        organism = synthetic construct
SEQUENCE: 567
QQYFSPPYT                                                                      9

SEQ ID NO: 568          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 568
SFWMH                                                                          5

SEQ ID NO: 569          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 569
FTNNEGTTTA YADSVRG                                                             17

SEQ ID NO: 570          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 570
GDGGLDD                                                                        7

SEQ ID NO: 571          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 571
RASQFTNHYL N                                                                   11

SEQ ID NO: 572          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 572
VASNLQS                                                                        7

SEQ ID NO: 573          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 573
QQSYRTPYT                                                                      9

SEQ ID NO: 574          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 574
SGYYN                                                                          5

SEQ ID NO: 575          moltype = AA  length = 16
FEATURE                 Location/Qualifiers
REGION                  1..16
                        note = Description of Artificial Sequence: Synthetic peptide
source                  1..16
```

```
                         mol_type = protein
                         organism = synthetic construct
SEQUENCE: 575
YILSGAHTDI KASLGS                                                    16

SEQ ID NO: 576           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 576
SGVYSKYSLD V                                                         11

SEQ ID NO: 577           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 577
DIVMTQSPSI LSASVGDRVT ITCRASQTIS GWLAWYQQKP AEAPKLLIYK ASTLESGVPS  60
RFSGSGSGTE FTLTISSLQP DDFGIYYCQQ YKSYSFNFGQ GTKVEIK                107

SEQ ID NO: 578           moltype = AA  length = 124
FEATURE                  Location/Qualifiers
REGION                   1..124
                         note = Description of Artificial Sequence: Synthetic
                          polypeptide
VARIANT                  1
                         note = MOD_RES - Gln or Glu
VARIANT                  2
                         note = MOD_RES - Met, Ile or Val
source                   1..124
                         mol_type = protein
                         organism = synthetic construct
SEQUENCE: 578
XXQLVQSGAE VKKPGASVKV SCEASGYTLT SYDINWVRQA TGQGPEWMGW MNANSGNTGY  60
AQKFQGRVTL TGDTSISTAY MELSSLRSED TAVYYCARSS ILVRGALGRY FDLWGRGTLV  120
TVSS                                                                124

SEQ ID NO: 579           moltype = AA  length = 214
FEATURE                  Location/Qualifiers
REGION                   1..214
                         note = Description of Artificial Sequence: Synthetic
                          polypeptide
source                   1..214
                         mol_type = protein
                         organism = synthetic construct
SEQUENCE: 579
DIVMTQSPSI LSASVGDRVT ITCRASQTIS GWLAWYQQKP AEAPKLLIYK ASTLESGVPS  60
RFSGSGSGTE FTLTISSLQP DDFGIYYCQQ YKSYSFNFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                                214

SEQ ID NO: 580           moltype = AA  length = 453
FEATURE                  Location/Qualifiers
REGION                   1..453
                         note = Description of Artificial Sequence: Synthetic
                          polypeptide
source                   1..453
                         mol_type = protein
                         organism = synthetic construct
SEQUENCE: 580
QMQLVQSGAE VKKPGASVKV SCEASGYTLT SYDINWVRQA TGQGPEWMGW MNANSGNTGY  60
AQKFQGRVTL TGDTSISTAY MELSSLRSED TAVYYCARSS ILVRGALGRY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                                 453

SEQ ID NO: 581           moltype = AA  length = 214
FEATURE                  Location/Qualifiers
REGION                   1..214
```

```
                         note = Description of Artificial Sequence: Synthetic
                          polypeptide
source                   1..214
                         mol_type = protein
                         organism = synthetic construct
SEQUENCE: 581
DIVMTQSPSI LSASVGDRVT ITCRASQTIS GWLAWYQQKP AEAPKLLIYK ASTLESGVPS  60
RFSGSGSGTE FTLTISSLQP DDFGIYYCQQ YKSYSFNFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPCTKSFN RGEC                             214

SEQ ID NO: 582           moltype = AA  length = 453
FEATURE                  Location/Qualifiers
REGION                   1..453
                         note = Description of Artificial Sequence: Synthetic
                          polypeptide
VARIANT                  2
                         note = MOD_RES - Met, Ile or Val
source                   1..453
                         mol_type = protein
                         organism = synthetic construct
SEQUENCE: 582
EXQLVQSGAE VKKPGASVKV SCEASGYTLT SYDINWVRQA TGQGPEWMGW MNANSGNTGY  60
AQKFQGRVTL TGDTSISTAY MELSSLRSED TAVYYCARSS ILVRGALGRY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                              453

SEQ ID NO: 583           moltype = AA  length = 453
FEATURE                  Location/Qualifiers
REGION                   1..453
                         note = Description of Artificial Sequence: Synthetic
                          polypeptide
VARIANT                  2
                         note = MOD_RES - Met, Ile or Val
source                   1..453
                         mol_type = protein
                         organism = synthetic construct
SEQUENCE: 583
EXQLVQSGAE VKKPGASVKV SCEASGYTLT SYDINWVRQA TGQGPEWMGW MNANSGNTGY  60
AQKFQGRVTL TGDTSISTAY MELSSLRSED TAVYYCARSS ILVRGALGRY FDLWGRGTLV  120
TVSSCSTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                              453

SEQ ID NO: 584           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 584
GEGGLDD                                                           7

SEQ ID NO: 585           moltype = AA  length = 113
FEATURE                  Location/Qualifiers
REGION                   1..113
                         note = Description of Artificial Sequence: Synthetic
                          polypeptide
source                   1..113
                         mol_type = protein
                         organism = synthetic construct
SEQUENCE: 585
DIQLTQSPDS LAVSLGERAT INCKSSQSIF RTSRNKNLLN WYQQRPGQPP RLLIHWASTR  60
KSGVPDRFSG SGFGTDFTLT ITSLQAEDVA IYYCQQYFSP PYTFGQGTKL EIK         113

SEQ ID NO: 586           moltype = AA  length = 116
FEATURE                  Location/Qualifiers
REGION                   1..116
                         note = Description of Artificial Sequence: Synthetic
                          polypeptide
source                   1..116
```

```
                        mol_type = protein
                        organism = synthetic construct
SEQUENCE: 586
EVQLVESGGG LVQPGGSLRL SCSASGFSFN SFWMHWVRQV PGKGLVWISF TNNEGTTTAY  60
ADSVRGRFII SRDNAKNTLY LEMNNLRGED TAVYYCARGD GGLDDWGQGT LVTVSS      116

SEQ ID NO: 587          moltype = AA  length = 220
FEATURE                 Location/Qualifiers
REGION                  1..220
                        note = Description of Artificial Sequence: Synthetic
                         polypeptide
source                  1..220
                        mol_type = protein
                        organism = synthetic construct
SEQUENCE: 587
DIQLTQSPDS LAVSLGERAT INCKSSQSIF RTSRNKNLLN WYQQRPGQPP RLLIHWASTR  60
KSGVPDRFSG SGFGTDFTLT ITSLQAEDVA IYYCQQYFSP PYTFGQGTKL EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 588          moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 588
EVQLVESGGG LVQPGGSLRL SCSASGFSFN SFWMHWVRQV PGKGLVWISF TNNEGTTTAY  60
ADSVRGRFII SRDNAKNTLY LEMNNLRGED TAVYYCARGE GGLDDWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 589          moltype = AA  length = 220
FEATURE                 Location/Qualifiers
REGION                  1..220
                        note = Description of Artificial Sequence: Synthetic
                         polypeptide
source                  1..220
                        mol_type = protein
                        organism = synthetic construct
SEQUENCE: 589
DIQLTQSPDS LAVSLGERAT INCKSSQSIF RTSRNKNLLN WYQQRPGQPP RLLIHWASTR  60
KSGVPDRFSG SGFGTDFTLT ITSLQAEDVA IYYCQQYFSP PYTFGQGTKL EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 590          moltype = AA  length = 444
FEATURE                 Location/Qualifiers
REGION                  1..444
                        note = Description of Artificial Sequence: Synthetic
                         polypeptide
source                  1..444
                        mol_type = protein
                        organism = synthetic construct
SEQUENCE: 590
EVQLVESGGG LVQPGGSLRL SCSASGFSFN SFWMHWVRQV PGKGLVWISF TNNEGTTTAY  60
ADSVRGRFII SRDNAKNTLY LEMNNLRGED TAVYYCARGE GGLDDWGQGT LVTVSSCSTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLGKEYKCK VSNKALPAPI EKTISKAKGQ PREPQVYTLP PSREEMTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 591          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 591
```

-continued

```
QMQLQESGPG LVKPSETLSL SCSVSGASAS SGYYNWVRQT PGGGLEWIAY ILSGAHTDIK  60
ASLGSRVAVS VDTSKNQVTL RLSSVTAADT ATYYCARSGV YSKYSLDVWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                   448

SEQ ID NO: 592          moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 592
EVQLVQSGGD LVQPGGSLRL SCAASGFTFS DYAMGWVRQA PGKGLEWLSV VTGHSYRTHY  60
ADSVKGRFII SRDNSKNTLF LQMNSLRAED TAVYYCAKRI WSYGDDSFDV WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                   450

SEQ ID NO: 593          moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 593
EVQLVQSGGG VVQPGGSLRL SCAASGFTFS SYAMNWVRQA PGKGLEWVSY ISSIETIYYA  60
DSVKGRFTIS RDNAKNSLYL QMNSLRDEDT AVYYCARDRL VDVPLSSPNS WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                   450

SEQ ID NO: 594          moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 594
EVQLVESGGG LVQPGGSLRL SCSASGFSFN SFWMHWVRQV PGKGLVWISF TNNEGTTTAY  60
ADSVRGRFII SRDNAKNTLY LEMNNLRGED TAVYYCARGD GGLDDWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 595          moltype = AA  length = 453
FEATURE                 Location/Qualifiers
REGION                  1..453
                        note = Description of Artificial Sequence: Synthetic
                         polypeptide
source                  1..453
                        mol_type = protein
                        organism = synthetic construct
SEQUENCE: 595
EMQLVQSGAE VKKPGASVKV SCEASGYTLT SYDINWVRQA TGQGPEWMGW MNANSGNTGY  60
AQKFQGRVTL TGDTSISTAY MELSSLRSED TAVYYCARSS ILVRGALGRY FDLWGRGTLV  120
TVSSCSTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
```

```
KSRWQQGNVF SCSVMHEALH NHYTQKSLSL SPG                           453

SEQ ID NO: 596         moltype = AA  length = 453
FEATURE                Location/Qualifiers
REGION                 1..453
                       note = Description of Artificial Sequence: Synthetic
                        polypeptide
source                 1..453
                       mol_type = protein
                       organism = synthetic construct
SEQUENCE: 596
EMQLVQSGAE VKKPGASVKV SCEASGYTLT SYDINWVRQA TGQGPEWMGW MNANSGNTGY  60
AQKFQGRVTL TGDTSISTAY MELSSLRSED TAVYYCARSS ILVRGALGRY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                           453

SEQ ID NO: 597         moltype = AA  length = 453
FEATURE                Location/Qualifiers
REGION                 1..453
                       note = Description of Artificial Sequence: Synthetic
                        polypeptide
source                 1..453
                       mol_type = protein
                       organism = synthetic construct
SEQUENCE: 597
EIQLVQSGAE VKKPGASVKV SCEASGYTLT SYDINWVRQA TGQGPEWMGW MNANSGNTGY  60
AQKFQGRVTL TGDTSISTAY MELSSLRSED TAVYYCARSS ILVRGALGRY FDLWGRGTLV  120
TVSSCSTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                           453

SEQ ID NO: 598         moltype = AA  length = 453
FEATURE                Location/Qualifiers
REGION                 1..453
                       note = Description of Artificial Sequence: Synthetic
                        polypeptide
source                 1..453
                       mol_type = protein
                       organism = synthetic construct
SEQUENCE: 598
EIQLVQSGAE VKKPGASVKV SCEASGYTLT SYDINWVRQA TGQGPEWMGW MNANSGNTGY  60
AQKFQGRVTL TGDTSISTAY MELSSLRSED TAVYYCARSS ILVRGALGRY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                           453

SEQ ID NO: 599         moltype = AA  length = 453
FEATURE                Location/Qualifiers
REGION                 1..453
                       note = Description of Artificial Sequence: Synthetic
                        polypeptide
source                 1..453
                       mol_type = protein
                       organism = synthetic construct
SEQUENCE: 599
EVQLVQSGAE VKKPGASVKV SCEASGYTLT SYDINWVRQA TGQGPEWMGW MNANSGNTGY  60
AQKFQGRVTL TGDTSISTAY MELSSLRSED TAVYYCARSS ILVRGALGRY FDLWGRGTLV  120
TVSSCSTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                           453

SEQ ID NO: 600         moltype = AA  length = 453
FEATURE                Location/Qualifiers
REGION                 1..453
                       note = Description of Artificial Sequence: Synthetic
                        polypeptide
```

```
source                  1..453
                        mol_type = protein
                        organism = synthetic construct
SEQUENCE: 600
EVQLVQSGAE VKKPGASVKV SCEASGYTLT SYDINWVRQA TGQGPEWMGW MNANSGNTGY  60
AQKFQGRVTL TGDTSISTAY MELSSLRSED TAVYYCARSS ILVRGALGRY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                               453

SEQ ID NO: 601          moltype = AA  length = 220
FEATURE                 Location/Qualifiers
REGION                  1..220
                        note = Description of Artificial Sequence: Synthetic
                         polypeptide
source                  1..220
                        mol_type = protein
                        organism = synthetic construct
SEQUENCE: 601
DIQLTQSPDS LAVSLGERAT INCKSSQSIF RTSRNKNLLN WYQQRPGQPP RLLIHWASTR  60
KSGVPDRFSG SGFGTDFTLT ITSLQAEDVA IYYCQQYFSP PYTFGQGTKL EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP CTKSFNRGEC                        220

SEQ ID NO: 602          moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 602
EVQLVESGGG LVQPGGSLRL SCSASGFSFN SFWMHWVRQV PGKGLVWISF TNNEGTTTAY  60
ADSVRGRFII SRDNAKNTLY LEMNNLRGED TAVYYCARGD GGLDDWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 603          moltype = AA  length = 445
FEATURE                 Location/Qualifiers
REGION                  1..445
                        note = Description of Artificial Sequence: Synthetic
                         polypeptide
source                  1..445
                        mol_type = protein
                        organism = synthetic construct
SEQUENCE: 603
EVQLVESGGG LVQPGGSLRL SCSASGFSFN SFWMHWVRQV PGKGLVWISF TNNEGTTTAY  60
ADSVRGRFII SRDNAKNTLY LEMNNLRGED TAVYYCARGE GGLDDWGQGT LVTVSSCSTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                        445

SEQ ID NO: 604          moltype = AA  length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 604
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330
```

-continued

```
SEQ ID NO: 605         moltype = AA  length = 330
FEATURE                Location/Qualifiers
REGION                 1..330
                       note = Description of Artificial Sequence: Synthetic
                        polypeptide
source                 1..330
                       mol_type = protein
                       organism = synthetic construct
SEQUENCE: 605
CSTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                 330

SEQ ID NO: 606         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 606
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107

SEQ ID NO: 607         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 607
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPCTK SFNRGEC               107

SEQ ID NO: 608         moltype = AA  length = 116
FEATURE                Location/Qualifiers
REGION                 1..116
                       note = Description of Artificial Sequence: Synthetic
                        polypeptide
source                 1..116
                       mol_type = protein
                       organism = synthetic construct
SEQUENCE: 608
EVQLVESGGG LVQPGGSLRL SCSASGFSFN SFWMHWVRQV PGKGLVWISF TNNEGTTTAY  60
ADSVRGRFII SRDNAKNTLY LEMNNLRGED TAVYYCARGE GGLDDWGQGT LVTVSS     116

SEQ ID NO: 609         moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 609
EVQLVESGGG LVQPGGSLRL SCSASGFSFN SFWMHWVRQV PGKGLVWISF TNNEGTTTAY  60
ADSVRGRFII SRDNAKNTLY LEMNNLRGED TAVYYCARGE GGLDDWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 610         moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 610
```

```
DIQLTQSPSI LSASVGDRVT ITCRASQTIS GWLAWYQQKP AEAPKLLIYK ASTLESGVPS  60
RFSGSGSGTE FTLTISSLQP DDFGIYYCQQ YKSYSFNFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 611         moltype = AA  length = 215
FEATURE                Location/Qualifiers
REGION                 1..215
                       note = Description of Artificial Sequence: Synthetic
                        polypeptide
source                 1..215
                       mol_type = protein
                       organism = synthetic construct
SEQUENCE: 611
EIVLTQSPGT LSLSPGERAT LSCRASQFVS RTSLAWFQQK PGQPPRLLIY ETSSRATGIP  60
DRFSGSGSGT DFTLTISRLE PEDFAMYYCH KYGSGPRTFG QGTKVEVKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 612         moltype = AA  length = 215
FEATURE                Location/Qualifiers
REGION                 1..215
                       note = Description of Artificial Sequence: Synthetic
                        polypeptide
source                 1..215
                       mol_type = protein
                       organism = synthetic construct
SEQUENCE: 612
ETTLTQSPGT LSLSPGERAT LSCRASQSVS SSYLAWYQQK PGQAPKVLIY DASSRATGIP  60
DRFSGSGSGT DFTLTISRLE PEDFAVYYCQ KYGSTPRPFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 613         moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 613
DVVMTQSSSS LSASVGDRVT ITCRASLDIT NHLAWYQQKP GELPKLLIYE ASILQSGVPS  60
RFSGSGSGTD FTLTISSLQP EDVATYYCEK CNSTPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 614         moltype = AA  length = 216
FEATURE                Location/Qualifiers
REGION                 1..216
                       note = Description of Artificial Sequence: Synthetic
                        polypeptide
source                 1..216
                       mol_type = protein
                       organism = synthetic construct
SEQUENCE: 614
EIVMTQSPGT LSLSPGERAT LSCRASQSVG AIYLAWYQQE PGRAPTLLFY GVSNRATGIP  60
DRFSCSGSGT DFTLTISRLE PEDFAVYYCQ LYTSSRALTF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 615         moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 615
EIVLTQSPSS LSASVGDRVT ITCRASQGIR NGLGWYQQTP GKAPKLLIYP ASTLESGVPS  60
RFSGSGSDRD FTLTITSLQP EDFATYYCLQ DHNYPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 616         moltype = AA  length = 214
FEATURE                Location/Qualifiers
REGION                 1..214
                       note = Description of Artificial Sequence: Synthetic
```

-continued

```
                        polypeptide
source                  1..214
                        mol_type = protein
                        organism = synthetic construct
SEQUENCE: 616
DIQMTQSPSS LSASVGDRVT ITCRASQGIR NGLGWYQQIP GKAPKLLIYP ASTLESGVPS  60
RFSGSGSDRD FTLTITSLQP EDFATYYCLQ DHNYPPSFSQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 617          moltype = AA  length = 214
FEATURE                 Location/Qualifiers
REGION                  1..214
                        note = Description of Artificial Sequence: Synthetic
                        polypeptide
source                  1..214
                        mol_type = protein
                        organism = synthetic construct
SEQUENCE: 617
DIQMTQSPAT LSVSPGETVT LSCRASQSVR TNVAWYRHKA GQAPMILVSG ASTRASGAPA  60
RFSGSGYGTE FTLTITSLQS EDFAVYYCLQ YNTWPRTFGQ GTKVEVKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 618          moltype = AA  length = 214
FEATURE                 Location/Qualifiers
REGION                  1..214
                        note = Description of Artificial Sequence: Synthetic
                        polypeptide
source                  1..214
                        mol_type = protein
                        organism = synthetic construct
SEQUENCE: 618
DVVMTQSPSF LSASVGDRVT LTCRASQDIG SSLAWYQQRP GKAPNLLIYA TSTLQSGVPS  60
RFSGSGFGTE FTLTISTLQP EDFATYYCQQ LNNYVHSFGP GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 619          moltype = AA  length = 213
FEATURE                 Location/Qualifiers
REGION                  1..213
                        note = Description of Artificial Sequence: Synthetic
                        polypeptide
source                  1..213
                        mol_type = protein
                        organism = synthetic construct
SEQUENCE: 619
ETTLTQSPST LSASVGDRVT ITCRASQSIG DRLAWYQQKP GKAPKVLIYW ASNLEGGVPS  60
RFSGTGSGTE FALTISGLQP DDLATYYCQQ YKSQWSFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 620          moltype = AA  length = 214
FEATURE                 Location/Qualifiers
REGION                  1..214
                        note = Description of Artificial Sequence: Synthetic
                        polypeptide
source                  1..214
                        mol_type = protein
                        organism = synthetic construct
SEQUENCE: 620
DIQLTQSPSS LSASVGDRVT ITCRASQFTN HYLNWYQHKP GRAPKLMISV ASNLQSGVPS  60
RFTGSESGTD FTLTISGLQP EDFATYYCQQ SYRTPYTFGQ GSRLEMKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 621          moltype = AA  length = 453
FEATURE                 Location/Qualifiers
REGION                  1..453
                        note = Description of Artificial Sequence: Synthetic
                        polypeptide
source                  1..453
                        mol_type = protein
                        organism = synthetic construct
SEQUENCE: 621
QVQLQQSGAE VKKPGASVKV SCEASGYTLT SYDINWVRQA TGQGPEWMGW MNANSGNTGY  60
AQKFQGRVTL TGDTSISTAY MELSSLRSED TAVYYCAGSS ILVRGALGRY FDLWGRGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
```

```
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPG                                453

SEQ ID NO: 622          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 622
EVQLVQSGAE VVKPGASLKV SCKASGYIII NYDFIWVRQA TGQGPEWMGW MNPNSYNTGY  60
GQKFQGRVTM TWDSSMSTAY MELSSLTSAD TAVYYCARAV RGQLLSEYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                     448

SEQ ID NO: 623          moltype = AA  length = 455
FEATURE                 Location/Qualifiers
REGION                  1..455
                        note = Description of Artificial Sequence: Synthetic
                         polypeptide
source                  1..455
                        mol_type = protein
                        organism = synthetic construct
SEQUENCE: 623
QVQLQQSGAE VKKPGASVKV SCRASGYTFT SYDINWVRQA PGQGLEWMGW MNPNSGNTNY  60
AQRFQGRLTM TKNTSINTAY MELSSLRSED TAVYYCATER WSKDTGHYYY YGMDVWGQGT  120
TVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PELLGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYTL  360
PPSREEMTKN QVSLTCLVKG FYPSDIAVEW ESNGQPENNY KTTPPVLDSD GSFFLYSKLT  420
VDKSRWQQGN VFSCSVMHEA LHNHYTQKSL SLSPG                              455

SEQ ID NO: 624          moltype = AA  length = 456
FEATURE                 Location/Qualifiers
REGION                  1..456
                        note = Description of Artificial Sequence: Synthetic
                         polypeptide
source                  1..456
                        mol_type = protein
                        organism = synthetic construct
SEQUENCE: 624
QVQLQQSGAE VKRPGASVKV SCEASGYTVS NYDINWVRQA TGQGLEWMGW MNPSSGRTGY  60
APKFRGRVTM TRSTSISTAY MELSSLTSED TAVYYCARGG GYYDSSGNYH ISGLDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSREEMTK NQVSLTCLVK GFYPSDIAVE WESNGQPENN YKTTPPVLDS DGSFFLYSKL  420
TVDKSRWQQG NVFSCSVMHE ALHNHYTQKS LSLSPG                             456

SEQ ID NO: 625          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 625
QITLKESGGG LIKPGGSLRL SCATSGFPFS AYAMNWVRQA PGRGLEWVSS ITKNSDSLYY  60
ADSVKGRFTI SRDNAGNSLY LQMNSLRVED TAVYYCATLA ARIMATDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                     448

SEQ ID NO: 626          moltype = AA  length = 456
FEATURE                 Location/Qualifiers
```

-continued

```
REGION                 1..456
                       note = Description of Artificial Sequence: Synthetic
                        polypeptide
source                 1..456
                       mol_type = protein
                       organism = synthetic construct
SEQUENCE: 626
EVQLVQSGGG LVKPGESLRL SCAASGFSFD YYSMIWVRQA PGKGLEWVSS IDSSSRYLYY  60
ADSVKGRFTI SRDNAQNSLY LQMSGLRVED TAVYYCARDG DDILSVYRGS GRPFDYWGQG  120
TLVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSREEMTK NQVSLTCLVK GFYPSDIAVE WESNGQPENN YKTTPPVLDS DGSFFLYSKL  420
TVDKSRWQQG NVFSCSVMHE ALHNHYTQKS LSLSPG                          456

SEQ ID NO: 627         moltype = AA  length = 456
FEATURE                Location/Qualifiers
REGION                 1..456
                       note = Description of Artificial Sequence: Synthetic
                        polypeptide
source                 1..456
                       mol_type = protein
                       organism = synthetic construct
SEQUENCE: 627
QVQLQQSGGG LVNPGESLRL SCAASGFSFN YYSMIWVRQA PGKGLEWVSS IDSSSRYRYY  60
TDSVKGRFTI SRDNAQNSLY LQMSALRVED TAVYYCARDG DDILSVYQGS GRPFDYWGQG  120
TLVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSREEMTK NQVSLTCLVK GFYPSDIAVE WESNGQPENN YKTTPPVLDS DGSFFLYSKL  420
TVDKSRWQQG NVFSCSVMHE ALHNHYTQKS LSLSPG                          456

SEQ ID NO: 628         moltype = AA  length = 445
FEATURE                Location/Qualifiers
REGION                 1..445
                       note = Description of Artificial Sequence: Synthetic
                        polypeptide
source                 1..445
                       mol_type = protein
                       organism = synthetic construct
SEQUENCE: 628
QVQLQQSGGG LEQPGGSLRI SCAASGFTFN TNDMSWVRQA PGKGLQWVST IIGIDDTTHY  60
ADSVRGRFTV SRDTSKNMVY LQMNSLRVED TALYYCVKNS GIYSFWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                      445

SEQ ID NO: 629         moltype = DNA  length = 351
FEATURE                Location/Qualifiers
misc_feature           1..351
                       note = synthetic
source                 1..351
                       mol_type = other DNA
                       organism = synthetic construct
SEQUENCE: 629
gaggtgcagc tggtggagtc tgggggaggc ttggtacagc ctggggggtc cctgacactc  60
tcctgtacag cctctggatt ctcctttagc agctatgtca tgagctgggt ccgccagtct  120
cctgggaagg ggctggagtg ggtctcagct attggtggta gtggtactag tacatactac  180
agagactccg tgaagggccg gttcaccatc tccagagaca attccaagaa cacactgaat  240
ctgcaaatga gcagcctgag agccgaggac acggccgtat attactgtgc gagagatggg  300
ctggggcacc gggactactg gggccaggga accctggtca ccgtctcctc a         351

SEQ ID NO: 630         moltype = AA  length = 117
FEATURE                Location/Qualifiers
REGION                 1..117
                       note = synthetic
source                 1..117
                       mol_type = protein
                       organism = synthetic construct
SEQUENCE: 630
EVQLVESGGG LVQPGGSLTL SCTASGFSFS SYVMSWVRQS PGKGLEWVSA IGGSGTSTYY  60
RDSVKGRFTI SRDNSKNTLN LQMSSLRAED TAVYYCARDG LGHRDYWGQG TLVTVSS     117

SEQ ID NO: 631         moltype = DNA  length = 24
```

```
FEATURE                 Location/Qualifiers
misc_feature            1..24
                        note = synthetic
source                  1..24
                        mol_type = other DNA
                        organism = synthetic construct
SEQUENCE: 631
ggattctcct ttagcagcta tgtc                                        24

SEQ ID NO: 632          moltype = AA  length = 8
FEATURE                 Location/Qualifiers
REGION                  1..8
                        note = synthetic
source                  1..8
                        mol_type = protein
                        organism = synthetic construct
SEQUENCE: 632
GFSFSSYV                                                          8

SEQ ID NO: 633          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 633
attggtggta gtggtactag taca                                        24

SEQ ID NO: 634          moltype = AA  length = 8
FEATURE                 Location/Qualifiers
REGION                  1..8
                        note = synthetic
source                  1..8
                        mol_type = protein
                        organism = synthetic construct
SEQUENCE: 634
IGGSGTST                                                          8

SEQ ID NO: 635          moltype = DNA  length = 30
FEATURE                 Location/Qualifiers
misc_feature            1..30
                        note = synthetic
source                  1..30
                        mol_type = other DNA
                        organism = synthetic construct
SEQUENCE: 635
gcgagagatg ggctggggca ccgggactac                                  30

SEQ ID NO: 636          moltype = AA  length = 10
FEATURE                 Location/Qualifiers
REGION                  1..10
                        note = synthetic
source                  1..10
                        mol_type = protein
                        organism = synthetic construct
SEQUENCE: 636
ARDGLGHRDY                                                        10

SEQ ID NO: 637          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 637
gacatccaga tgacccagtc tccatcttcc gtgtctgcat ctgtaggaga cagagtcacc  60
atcacttgtc gggcgagtca gggtattaac agctggttag cctggtatca gcagaaacca  120
gggaaagccc ctaaactcct gatctatgct gcatccagtt tacaaagtgg ggtcccatca  180
aggttcagcg gcagtggttc tgggacagat ttcactctca ccatcagcag cctccagcct  240
gaagattttg caacttacta ttgtcaacag gctaacagtt tcccattcac tttcggccct  300
gggaccaaag tggatatcaa a                                           321

SEQ ID NO: 638          moltype = AA  length = 107
FEATURE                 Location/Qualifiers
REGION                  1..107
                        note = synthetic
source                  1..107
```

```
                         mol_type = protein
                         organism = synthetic construct
SEQUENCE: 638
DIQMTQSPSS VSASVGDRVT ITCRASQGIN SWLAWYQQKP GKAPKLLIYA ASSLQSGVPS  60
RFSGSGSGTD FTLTISSLQP EDFATYYCQQ ANSFPFTFGP GTKVDIK                107

SEQ ID NO: 639           moltype = DNA  length = 18
FEATURE                  Location/Qualifiers
misc_feature             1..18
                         note = synthetic
source                   1..18
                         mol_type = other DNA
                         organism = synthetic construct
SEQUENCE: 639
cagggtatta acagctgg                                                18

SEQ ID NO: 640           moltype = AA  length = 6
FEATURE                  Location/Qualifiers
REGION                   1..6
                         note = synthetic
source                   1..6
                         mol_type = protein
                         organism = synthetic construct
SEQUENCE: 640
QGINSW                                                             6

SEQ ID NO: 641           moltype =   length =
SEQUENCE: 641
000

SEQ ID NO: 642           moltype =   length =
SEQUENCE: 642
000

SEQ ID NO: 643           moltype = DNA  length = 27
FEATURE                  Location/Qualifiers
misc_feature             1..27
                         note = synthetic
source                   1..27
                         mol_type = other DNA
                         organism = synthetic construct
SEQUENCE: 643
caacaggcta acagtttccc attcact                                      27

SEQ ID NO: 644           moltype = AA  length = 9
FEATURE                  Location/Qualifiers
REGION                   1..9
                         note = synthetic
source                   1..9
                         mol_type = protein
                         organism = synthetic construct
SEQUENCE: 644
QQANSFPFT                                                          9

SEQ ID NO: 645           moltype = DNA  length = 990
FEATURE                  Location/Qualifiers
misc_feature             1..990
                         note = hIgG1 Heavy Chain (WT) NA
source                   1..990
                         mol_type = other DNA
                         organism = synthetic construct
SEQUENCE: 645
gcctccacca agggcccatc ggtcttcccc ctggcaccct cctccaagag cacctctggg  60
ggcacagcgg ccctgggctg cctggtcaag gactacttcc ccgaaccggt gacggtgtcg  120
tggaactcag gcgccctgac cagcggcgtg cacaccttcc cggctgtcct acagtcctca  180
ggactctact ccctcagcag cgtggtgacc gtgccctcca gcagcttggg cacccagacc  240
tacatctgca acgtgaatca caagcccagc aacaccaagg tggacaagaa agttgagccc  300
aaatcttgtg acaaaactca cacatgccca ccgtgcccag cacctgaact cctgggggga  360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg  480
tacgtggacg gcgtggaggt gcataatgcc aagacaaagc cgcgggagga gcagtacaac  540
agcacgtacc gtgtggtcag cgtcctcacc gtcctgcacc aggactggct gaatggcaag  600
gagtacaagt gcaaggtctc caacaaagcc ctcccagccc ccatcgagaa aaccatctcc  660
aaagccaaag ggcagccccg agaaccacag gtgtacaccc tgcccccatc ccgggatgag  720
ctgaccaaga accaggtcag cctgacctgc ctggtcaaag gcttctatcc cagcgacatc  780
gccgtggagt gggagagcaa tgggcagccg gagaacaact acaagaccac gcctcccgtg  840
ctggactccg acggctcctt cttcctctac agcaagctca ccgtggacaa gagcaggtgg  900
cagcagggga acgtcttctc atgctccgtg atgcatgagg ctctgcacaa ccactacacg  960
cagaagtccc tctccctgtc tccgggtaaa                                   990
```

```
SEQ ID NO: 646          moltype = AA  length = 330
FEATURE                 Location/Qualifiers
REGION                  1..330
                        note = hIgG1 Heavy Chain (WT)
source                  1..330
                        mol_type = protein
                        organism = synthetic construct
SEQUENCE: 646
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 647          moltype = DNA  length = 990
FEATURE                 Location/Qualifiers
misc_feature            1..990
                        note = hIgG1 Heavy Chain */* Mutation NA
source                  1..990
                        mol_type = other DNA
                        organism = synthetic construct
SEQUENCE: 647
gcctcaacta agggcccaag cgtctttcca ttggctccat ccagtaaatc aacttcaggg  60
gggaccgcag ctctggggtg cctcgtgaag gactacttcc ctgaacctgt cacagtctcc  120
tggaactccg gggctctgac cagcggagtt cacacctttc ctgccgtgct tcagtcttcc  180
gggctgtact cattgagcag tgtcgttact gtaccatcct cctccctggg tactcaaacc  240
tacatctgta atgtgaacca caagccctcc aacaccaagg ttgacaaaaa ggtggaacca  300
aagagttgtg ataagactca tacctgcccc ccatgtcctg cccccgagct gctgggagga  360
ccttcagtgt tcttgttccc tcccaaacca aaagacactt tgatgatttc acgaacccct  420
gaagtgacct gtgtggtggt cgatgtcagc cacgaagacc ctgaagttaa gtttaactgg  480
tatgtggatg gcgtagaggt tcacaacgct aagactaaac ccagagagga gcaatataat  540
agtacctata gggtcgtgtc tgtgctgaca gtcttgcatc aggactggct taacggtaag  600
gagtacaagt gtaaggtgtc aaacaaggca ctgcctgcac ctatcgagaa gaccatctct  660
aaggccaaag gtcaaccaag ggagccccag gtatatactt tgccaccctc tcgggacgag  720
ctgacaaaaa atcaggtgag tctgacctgt ctcgtgaaag gattttaccc tagcgacatc  780
gccgtggagt gggagagtaa tggccagccc gagaataact acaagaccac cccaccagtt  840
ctggactctg acgggtcttt cttcctttat agtaagctga ccgtagataa gtctcgctgg  900
cagcaaggca atgtattctc ttgcagtgtc atgcacgagg ccctccataa ccgattcacc  960
caaaaatctc tgtctctgtc tcctggaaag                                  990

SEQ ID NO: 648          moltype = AA  length = 330
FEATURE                 Location/Qualifiers
REGION                  1..330
                        note = hIgG1 Heavy Chain */* Mutation (H435R,Y436F)
source                  1..330
                        mol_type = protein
                        organism = synthetic construct
SEQUENCE: 648
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNRFT QKSLSLSPGK                                  330

SEQ ID NO: 649          moltype = DNA  length = 378
FEATURE                 Location/Qualifiers
misc_feature            1..378
                        note = synthetic
source                  1..378
                        mol_type = other DNA
                        organism = synthetic construct
SEQUENCE: 649
caggtgcagc tggtggagtc tgggggaggc gtggtccagc ctgggaggtc cctgagactc  60
tcctgtgcag tgtctggact catcttcagt aactatggca tgcactgggt ccgccaggct  120
ccaggcaagg ggctggagtg ggtggcagtt atatggtatg atggaagtaa taaatactat  180
gtagactccg tgaagggccg cttcaccatc tccagagaca attccaagaa cacgctgtat  240
ctgcaaatga acagcctgag aggcgaggac acggctatat attactgtgc gagagatcgg  300
agagggctgg aactatttaa ctactactac cacggtttgg acgtctgggg ccaagggacc  360
acggtcaccg tctcctca                                               378

SEQ ID NO: 650          moltype = AA  length = 126
FEATURE                 Location/Qualifiers
REGION                  1..126
                        note = synthetic
source                  1..126
                        mol_type = protein
```

```
                          organism = synthetic construct
SEQUENCE: 650
QVQLVESGGG VVQPGRSLRL SCAVSGLIFS NYGMHWVRQA PGKGLEWVAV IWYDGSNKYY  60
VDSVKGRFTI SRDNSKNTLY LQMNSLRGED TAIYYCARDR RGLELFNYYY HGLDVWGQGT  120
TVTVSS                                                            126

SEQ ID NO: 651            moltype = DNA  length = 24
FEATURE                   Location/Qualifiers
misc_feature              1..24
                          note = synthetic
source                    1..24
                          mol_type = other DNA
                          organism = synthetic construct
SEQUENCE: 651
ggactcatct tcagtaacta tggc                                        24

SEQ ID NO: 652            moltype = AA  length = 8
FEATURE                   Location/Qualifiers
REGION                    1..8
                          note = synthetic
source                    1..8
                          mol_type = protein
                          organism = synthetic construct
SEQUENCE: 652
GLIFSNYG                                                          8

SEQ ID NO: 653            moltype = DNA  length = 24
FEATURE                   Location/Qualifiers
misc_feature              1..24
                          note = synthetic
source                    1..24
                          mol_type = other DNA
                          organism = synthetic construct
SEQUENCE: 653
atatggtatg atggaagtaa taaa                                        24

SEQ ID NO: 654            moltype = AA  length = 8
FEATURE                   Location/Qualifiers
REGION                    1..8
                          note = synthetic
source                    1..8
                          mol_type = protein
                          organism = synthetic construct
SEQUENCE: 654
IWYDGSNK                                                          8

SEQ ID NO: 655            moltype = DNA  length = 57
FEATURE                   Location/Qualifiers
misc_feature              1..57
                          note = synthetic
source                    1..57
                          mol_type = other DNA
                          organism = synthetic construct
SEQUENCE: 655
gcgagagatc ggagagggct ggaactattt aactactact accacggttt ggacgtc     57

SEQ ID NO: 656            moltype = AA  length = 19
FEATURE                   Location/Qualifiers
REGION                    1..19
                          note = synthetic
source                    1..19
                          mol_type = protein
                          organism = synthetic construct
SEQUENCE: 656
ARDRRGLELF NYYYHGLDV                                              19

SEQ ID NO: 657            moltype = DNA  length = 321
FEATURE                   Location/Qualifiers
misc_feature              1..321
                          note = synthetic
source                    1..321
                          mol_type = other DNA
                          organism = synthetic construct
SEQUENCE: 657
gacatccaga tgacccagtc tccatcctca ctgtctgcat ctgtaggaga cagagtcacc  60
atcacttgtc gggcgagtca gggcattagc aatttttag cctggtttca gcagaaacca   120
gggaaagccc ctaagtccct gatctatgct gcatccagtt tgcaaagtgg ggtcccatca  180
aagttcagcg gcagtggatc tgggacagat ttcactctca ccatcagcag cctgcagcct  240
gaagattttg caacttatta ctgccaacag tataatagtt acccattcac tttcggccct  300
```

```
gggaccaaag tggatatcaa a                                          321

SEQ ID NO: 658         moltype = AA  length = 107
FEATURE                Location/Qualifiers
REGION                 1..107
                       note = synthetic
source                 1..107
                       mol_type = protein
                       organism = synthetic construct
SEQUENCE: 658
DIQMTQSPSS LSASVGDRVT ITCRASQGIS NFLAWFQQKP GKAPKSLIYA ASSLQSGVPS  60
KFSGSGSGTD FTLTISSLQP EDFATYYCQQ YNSYPFTFGP GTKVDIK              107

SEQ ID NO: 659         moltype = DNA  length = 18
FEATURE                Location/Qualifiers
misc_feature           1..18
                       note = synthetic
source                 1..18
                       mol_type = other DNA
                       organism = synthetic construct
SEQUENCE: 659
cagggcatta gcaatttt                                              18

SEQ ID NO: 660         moltype = AA  length = 6
FEATURE                Location/Qualifiers
REGION                 1..6
                       note = synthetic
source                 1..6
                       mol_type = protein
                       organism = synthetic construct
SEQUENCE: 660
QGISNF                                                           6

SEQ ID NO: 661         moltype =   length =
SEQUENCE: 661
000

SEQ ID NO: 662         moltype =   length =
SEQUENCE: 662
000

SEQ ID NO: 663         moltype = DNA  length = 27
FEATURE                Location/Qualifiers
misc_feature           1..27
                       note = synthetic
source                 1..27
                       mol_type = other DNA
                       organism = synthetic construct
SEQUENCE: 663
caacagtata atagttaccc attcact                                    27

SEQ ID NO: 664         moltype = AA  length = 9
FEATURE                Location/Qualifiers
REGION                 1..9
                       note = synthetic
source                 1..9
                       mol_type = protein
                       organism = synthetic construct
SEQUENCE: 664
QQYNSYPFT                                                        9

SEQ ID NO: 665         moltype = DNA  length = 1371
FEATURE                Location/Qualifiers
misc_feature           1..1371
                       note = synthetic
source                 1..1371
                       mol_type = other DNA
                       organism = synthetic construct
SEQUENCE: 665
caggtgcagc tggtggagtc tgggggaggc gtggtccagc ctgggaggtc cctgagactc  60
tcctgtgcag tgtctggact catcttcagt aactatggca tgcactgggt ccgccaggct  120
ccaggcaagg ggctggagtg ggtggcagtt atatggtatg atggaagtaa taaatactat  180
gtagactccg tgaagggccg cttcaccatc tccagagaca attccaagaa cacgctgtat  240
ctgcaaatga acagcctgag aggcgaggac acggctatat attactgtgc gagagatcgg  300
agagggctgg aactatttaa ctactactac cacggtttgg acgtctgggg ccaagggacc  360
acggtcaccg tctcctcagc ctcaacaaaa ggtccctcag tctttcctct tgctccatcc  420
tccaaaagta catcaggagg taccgcagcc cttggatgcc tcgtcaagga ttattttccc  480
gaaccagtta ccgtttcctg gaactcaggc gctctcacct ctggagtaca tacttttcct  540
gcagtcctcc aatcctctgg cctttactcc ctttctagcg tagtaaccgt accatcatca  600
```

```
tccctcggaa cccaaactta tatctgtaat gttaatcaca aacccagcaa caccaaagta  660
gacaaaaaag ttgaacctaa atcatgcgat aaaacccaca cttgcccccc ctgtccagca  720
ccagaactcc ttggcggccc ctcagttttc ctttttccac caaagcccaa agacaccctt  780
atgatctcca gaacccccga agttacatgc gtagtcgttg acgtttctca cgaagatcca  840
gaagtcaaat tcaattggta cgttgatggc gttgaagtcc ataatgcaaa aacaaaaccc  900
cgagaagaac agtacaattc aacatatcga gtagttagcg tacttacagt tctgcaccaa  960
gattggctga acggaaaaga atataaatgt aaagtctcta acaaagcact ccctgcccca  1020
attgaaaaaa caatctcaaa agccaaaggc caacctcgcg aacctcaggt ttacacactt  1080
ccccccctccc gcgacgaact gactaaaaac caggtttcct tgacatgcct tgtaaaaggt  1140
ttttacccct ccgatatcgc cgtagaatgg gaatctaatg gacaaccaga aaacaattac  1200
aaaactaccc ctcctgtgct cgattccgat ggctcttttt tcctctattc taagctcacc  1260
gttgacaagt ctcgttggca gcagggaaac gtattcagtt gcagcgtcat gcacgaagcc  1320
cttcataata gattcaccca aaagtctctt tctctctctc ctggtaagta g           1371
```

```
SEQ ID NO: 666          moltype = AA  length = 456
FEATURE                 Location/Qualifiers
REGION                  1..456
                        note = synthetic
source                  1..456
                        mol_type = protein
                        organism = synthetic construct
SEQUENCE: 666
QVQLVESGGG VVQPGRSLRL SCAVSGLIFS NYGMHWVRQA PGKGLEWVAV IWYDGSNKYY  60
VDSVKGRFTI SRDNSKNTLY LQMNSLRGED TAIYYCARDR RGLELFNYYY HGLDVWGQGT  120
TVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PELLGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYTL  360
PPSRDELTKN QVSLTCLVKG FYPSDIAVEW ESNGQPENNY KTTPPVLDSD GSFFLYSKLT  420
VDKSRWQQGN VFSCSVMHEA LHNRFTQKSL SLSPGK                            456
```

```
SEQ ID NO: 667          moltype = DNA  length = 645
FEATURE                 Location/Qualifiers
misc_feature            1..645
                        note = synthetic
source                  1..645
                        mol_type = other DNA
                        organism = synthetic construct
SEQUENCE: 667
gacatccaga tgacccagtc tccatcctca ctgtctgcat ctgtaggaga cagagtcacc  60
atcacttgtc gggcgagtca gggcattagc aattttttag cctggtttca gcagaaacca  120
gggaaagccc ctaagtccct gatctatgct gcatccagtt tgcaaagtgg ggtcccatca  180
aagttcagcg gcagtggatc tgggacagat ttcactctca ccatcagcag cctgcagcct  240
gaagattttg caacttatta ctgccaacag tataatagtt acccattcac tttcggccct  300
gggaccaaag tggatatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645
```

```
SEQ ID NO: 668          moltype = AA  length = 214
FEATURE                 Location/Qualifiers
REGION                  1..214
                        note = synthetic
source                  1..214
                        mol_type = protein
                        organism = synthetic construct
SEQUENCE: 668
DIQMTQSPSS LSASVGDRVT ITCRASQGIS NFLAWFQQKP GKAPKSLIYA ASSLQSGVPS  60
KFSGSGSGTD FTLTISSLQP EDFATYYCQQ YNSYPFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

```
SEQ ID NO: 669          moltype = DNA  length = 354
FEATURE                 Location/Qualifiers
misc_feature            1..354
                        note = synthetic
source                  1..354
                        mol_type = other DNA
                        organism = synthetic construct
SEQUENCE: 669
gaggtgcagc tggtggagtc tgggggaggc ctggtacagc ctggggggtc cctgagactc  60
tcctgtgcag cctctggatt cacctttaac agctatgcca tgagctggtt ccgccagact  120
ccagggaagg ggctggagtg gctctcagct atgactggta gtggtggtaa cacatactac  180
gcagactccg tgaagggccg gttcaccatc tccagagaca attccaagaa cacgctgtat  240
ctgcaaatga acaacctgag agccgaggac acggccgtat attactgtgc ggtggataca  300
accatggccc actttgacta ctggggccag ggaaccctgg tcaccgtctc ctca        354
```

```
SEQ ID NO: 670          moltype = AA  length = 118
FEATURE                 Location/Qualifiers
REGION                  1..118
                        note = synthetic
source                  1..118
                        mol_type = protein
                        organism = synthetic construct
SEQUENCE: 670
EVQLVESGGG LVQPGGSLRL SCAASGFTFN SYAMSWFRQT PGKGLEWLSA MTGSGGNTYY  60
ADSVKGRFTI SRDNSKNTLY LQMNNLRAED TAVYYCAVDT TMAHFDYWGQ GTLVTVSS    118

SEQ ID NO: 671          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 671
ggattcacct ttaacagcta tgcc                                          24

SEQ ID NO: 672          moltype = AA  length = 8
FEATURE                 Location/Qualifiers
REGION                  1..8
                        note = synthetic
source                  1..8
                        mol_type = protein
                        organism = synthetic construct
SEQUENCE: 672
GFTFNSYA                                                            8

SEQ ID NO: 673          moltype = DNA  length = 24
FEATURE                 Location/Qualifiers
misc_feature            1..24
                        note = synthetic
source                  1..24
                        mol_type = other DNA
                        organism = synthetic construct
SEQUENCE: 673
atgactggta gtggtggtaa caca                                          24

SEQ ID NO: 674          moltype = AA  length = 8
FEATURE                 Location/Qualifiers
REGION                  1..8
                        note = synthetic
source                  1..8
                        mol_type = protein
                        organism = synthetic construct
SEQUENCE: 674
MTGSGGNT                                                            8

SEQ ID NO: 675          moltype = DNA  length = 33
FEATURE                 Location/Qualifiers
misc_feature            1..33
                        note = synthetic
source                  1..33
                        mol_type = other DNA
                        organism = synthetic construct
SEQUENCE: 675
gcggtggata caaccatggc ccactttgac tac                                33

SEQ ID NO: 676          moltype = AA  length = 11
FEATURE                 Location/Qualifiers
REGION                  1..11
                        note = synthetic
source                  1..11
                        mol_type = protein
                        organism = synthetic construct
SEQUENCE: 676
AVDTTMAHFD Y                                                        11

SEQ ID NO: 677          moltype = DNA  length = 321
FEATURE                 Location/Qualifiers
misc_feature            1..321
                        note = synthetic
source                  1..321
                        mol_type = other DNA
                        organism = synthetic construct
SEQUENCE: 677
```

-continued

```
gacatccaga tgacccagtc tccatcttcc gtgtctgcat ctgtaggaga cagagtcacc  60
atcacttgtc gggcgagtca gggtattagc agctggttag cctggtatca gcagaaacca  120
gggaaagccc ctaagctcct gatctatgct gcttccactt tacaaagtgg ggtcccatca  180
aggttcagtg gcagtggatc tgggacagat ttcactctca ccatcagcag cctgcagcct  240
gaagattttg caacttacta ttgtcaacgg attaacagtt tcccattcac tttcggccct  300
gggaccaaag tggatatcaa a                                             321

SEQ ID NO: 678          moltype = AA  length = 107
FEATURE                 Location/Qualifiers
REGION                  1..107
                        note = synthetic
source                  1..107
                        mol_type = protein
                        organism = synthetic construct
SEQUENCE: 678
DIQMTQSPSS VSASVGDRVT ITCRASQGIS SWLAWYQQKP GKAPKLLIYA ASTLQSGVPS  60
RFSGSGSGTD FTLTISSLQP EDFATYYCQR INSFPFTFGP GTKVDIK               107

SEQ ID NO: 679          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 679
cagggtatta gcagctgg                                                 18

SEQ ID NO: 680          moltype = AA  length = 6
FEATURE                 Location/Qualifiers
REGION                  1..6
                        note = synthetic
source                  1..6
                        mol_type = protein
                        organism = synthetic construct
SEQUENCE: 680
QGISSW                                                              6

SEQ ID NO: 681          moltype =   length =
SEQUENCE: 681
000

SEQ ID NO: 682          moltype = DNA  length = 27
FEATURE                 Location/Qualifiers
misc_feature            1..27
                        note = synthetic
source                  1..27
                        mol_type = other DNA
                        organism = synthetic construct
SEQUENCE: 682
caacggatta acagtttccc attcact                                       27

SEQ ID NO: 683          moltype = AA  length = 9
FEATURE                 Location/Qualifiers
REGION                  1..9
                        note = synthetic
source                  1..9
                        mol_type = protein
                        organism = synthetic construct
SEQUENCE: 683
QRINSFPFT                                                           9

SEQ ID NO: 684          moltype = DNA  length = 1347
FEATURE                 Location/Qualifiers
misc_feature            1..1347
                        note = synthetic
source                  1..1347
                        mol_type = other DNA
                        organism = synthetic construct
SEQUENCE: 684
gaggtgcagc tggtggagtc tgggggaggc ctggtacagc ctggggggtc cctgagactc  60
tcctgtgcag cctctggatt cacctttaac agctatgcca tgagctggtt ccgccagact  120
ccagggaagg ggctggagtg gctctcagct atgactggta gtggtggtaa cacatactac  180
gcagactccg tgaagggccg gttcaccatc tccagagaca attccaagaa cacgctgtat  240
ctgcaaatga acaacctgag agccgaggac acggccgtat attactgtgc ggtggataca  300
accatggccc actttgacta ctggggccag ggaaccctgg tcaccgtctc ctcagcctca  360
acaaaaggtc cctcagtctt tcctcttgct ccatcctcca aaagtacatc aggaggtacc  420
gcagcccttg gatgcctcgt caaggattat tttcccgaac cagttaccgt ttcctggaac  480
tcaggcgctc tcacctctgg agtacatact tttcctgcag tcctccaatc ctctggcctt  540
```

```
tactcccttt ctagcgtagt aaccgtacca tcatcatccc tcggaaccca aacttatatc  600
tgtaatgtta atcacaaacc cagcaacacc aaagtagaca aaaaagttga acctaaatca  660
tgcgataaaa cccacacttg cccccccctgt ccagcaccag aactccttgg cggcccctca  720
gttttccttt ttccaccaaa gcccaaagac acccttatga tctccagaac ccccgaagtt  780
acatgcgtag tcgttgacgt ttctcacgaa gatccagaag tcaaattcaa ttggtacgtt  840
gatggcgttg aagtccataa tgcaaaaaca aaaccccgag aagaacagta caattcaaca  900
tatcgagtag ttagcgtact tacagttctg caccaagatt ggctgaacgg aaaagaatat  960
aaatgtaaag tctctaacaa agcactccct gccccaattg aaaaaacaat ctcaaaagcc  1020
aaaggccaac ctcgcgaacc tcaggtttac acacttcccc cctcccgcga cgaactgact  1080
aaaaaccagg tttccttgac atgccttgta aaaggttttt acccctccga tatcgccgta  1140
gaatgggaat ctaatggaca accagaaaac aattacaaaa ctacccctcc tgtgctcgat  1200
tccgatggct cttttttcct ctattctaag ctcaccgttg acaagtctcg ttggcagcag  1260
ggaaacgtat tcagttgcag cgtcatgcac gaagcccttc ataatagatt cacccaaaag  1320
tctctttctc tctctcctgg taagtag                                    1347

SEQ ID NO: 685         moltype = AA  length = 448
FEATURE                Location/Qualifiers
REGION                 1..448
                       note = synthetic
source                 1..448
                       mol_type = protein
                       organism = synthetic construct
SEQUENCE: 685
EVQLVESGGG LVQPGGSLRL SCAASGFTFN SYAMSWFRQT PGKGLEWLSA MTGSGGNTYY  60
ADSVKGRFTI SRDNSKNTLY LQMNNLRAED TAVYYCAVDT TMAHFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNRFTQK SLSLSPGK                                   448

SEQ ID NO: 686         moltype = DNA  length = 645
FEATURE                Location/Qualifiers
misc_feature           1..645
                       note = synthetic
source                 1..645
                       mol_type = other DNA
                       organism = synthetic construct
SEQUENCE: 686
gacatccaga tgacccagtc tccatcttcc gtgtctgcat ctgtaggaga cagagtcacc  60
atcacttgtc gggcgagtca gggtattagc agctggttag cctggtatca gcagaaacca  120
gggaaagccc ctaagctcct gatctatgct gcttccactt tacaaagtgg ggtcccatca  180
aggttcagtg gcagtggatc tgggacagat ttcactctca ccatcagcag cctgcagcct  240
gaagattttg caacttacta ttgtcaacgg attaacagtt tcccattcac tttcggccct  300
gggaccaaag tggatatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                645

SEQ ID NO: 687         moltype = AA  length = 214
FEATURE                Location/Qualifiers
REGION                 1..214
                       note = synthetic
source                 1..214
                       mol_type = protein
                       organism = synthetic construct
SEQUENCE: 687
DIQMTQSPSS VSASVGDRVT ITCRASQGIS SWLAWYQQKP GKAPKLLIYA ASTLQSGVPS  60
RFSGSGSGTD FTLTISSLQP EDFATYYCQR INSFPFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 688         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 688
HHHHHHHHH                                                        9

SEQ ID NO: 689         moltype = AA  length = 6
FEATURE                Location/Qualifiers
REGION                 1..6
                       note = Description of Artificial Sequence: Synthetic peptide
```

-continued

```
source                  1..6
                        mol_type = protein
                        organism = synthetic construct
SEQUENCE: 689
HHHHHH                                                      6

SEQ ID NO: 690          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 690
HHHHH                                                       5
```

What is claimed is:

1. A compound having a structure according to formula (V):

(V)

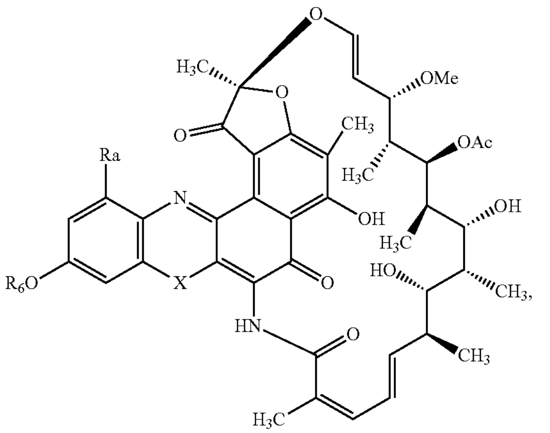

or a pharmaceutically acceptable salt thereof wherein:

X is selected from —O— and —NR*—;

$R_a$ is selected from hydrogen and —OR*;

$R_6$ is selected from $R_N$, an aliphatic $C_6$-$C_{20}$ hydrocarbon, an aromatic $C_5$-$C_{20}$ hydrocarbon, a heteroaromatic $C_1$-$C_{20}$ hydrocarbon, a cyclic aliphatic $C_3$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_6$ is optionally substituted with one or more of -OH, —OR*, —$NH_2$, —NHR*, —$N(R^*)_2$, —$N(R^*)_3^+$, —N(R*)-(C═O)-R*, —(C═O)-R*, —CHO, —$CO_2H$, —$CO_2R^*$ and combinations thereof;

$R_N$ is selected from:

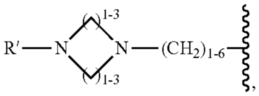

,

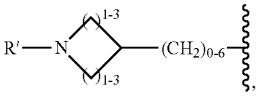

,

-continued

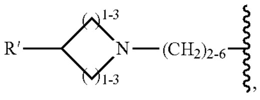

,

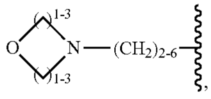

,

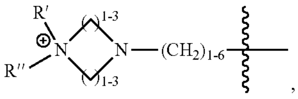

,

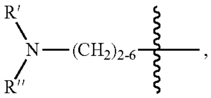

,

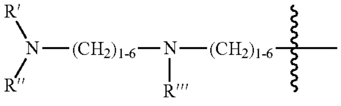

,

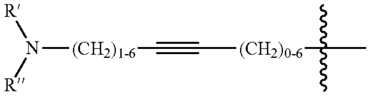

and

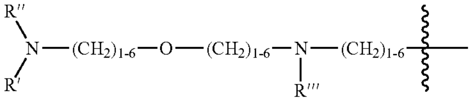

wherein the ~ symbol represents the point of attachment; and R', R" and R'" are selected from a hydrogen, a $C_1$-$C_6$ aliphatic hydrocarbon, and a protecting group selected from FMOC and Boc, or wherein R' and R" together form an aliphatic monocyclic, an aliphatic bicyclic, or an aliphatic polycyclic structure; and R* is independently at each occurrence selected from hydrogen, an aliphatic $C_1$-$C_6$ hydrocarbon, an aromatic $C_6$-$C_7$ hydrocarbon, and combinations thereof, which optionally comprise 1-3 heteroatoms selected from O, N and combinations thereof.

2. A compound having a structure according to formula (V):

(V)

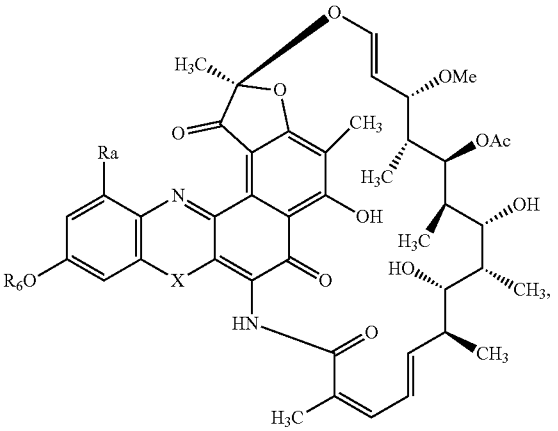

or a pharmaceutically acceptable salt thereof wherein:

X is selected from —O— and —NR*—;

$R_a$ is selected from hydrogen and —OR*;

$R_6$ is selected from $R_N$, an aliphatic $C_6$-$C_{20}$ hydrocarbon, an aromatic $C_5$-$C_{20}$ hydrocarbon, a heteroaromatic $C_1$-$C_{20}$ hydrocarbon, a cyclic aliphatic $C_3$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_6$ is optionally substituted with one or more of -OH, —OR*, -$NH_2$, —NHR*, —$N(R^*)_2$, —$N(R^*)_3^+$, —N(R*)-(C═O)-R*, —(C═O)-R*, —CHO, —$CO_2H$, —$CO_2R^*$ and combinations thereof;

$R_N$ is selected from:

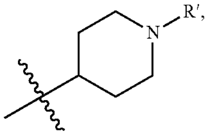 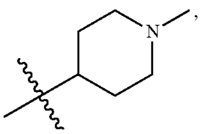

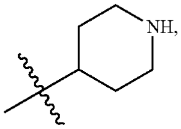 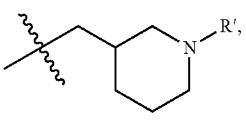

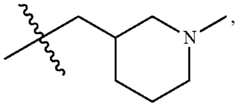 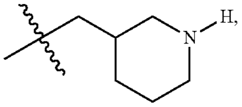

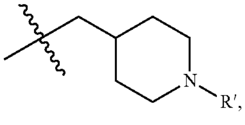 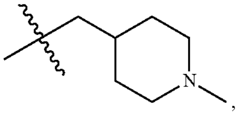

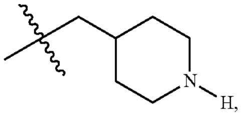

-continued

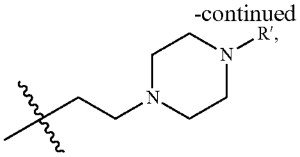

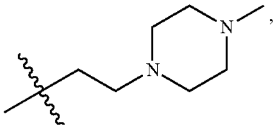

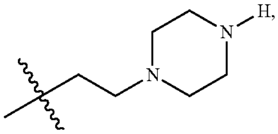 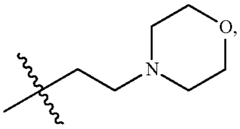

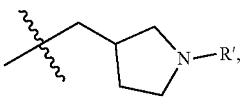 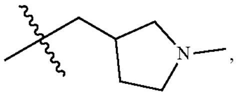

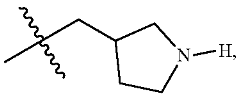 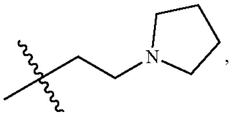

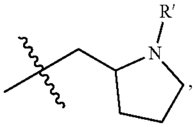 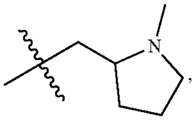

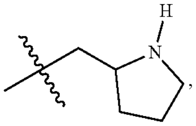 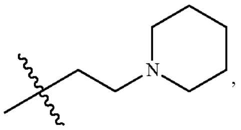

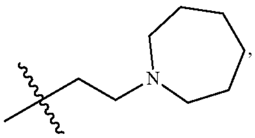 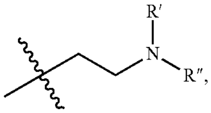

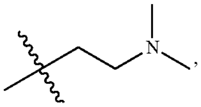 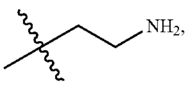

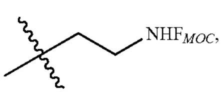 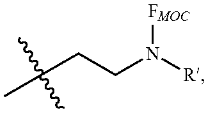

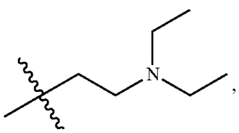 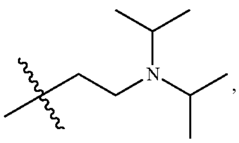

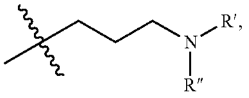 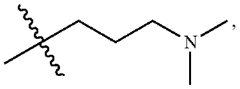

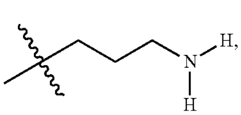 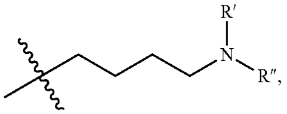

-continued

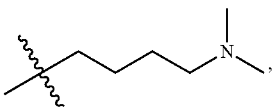,

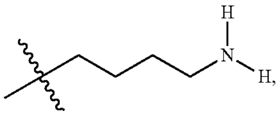,

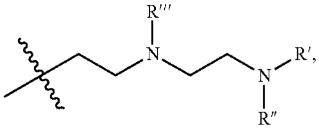,

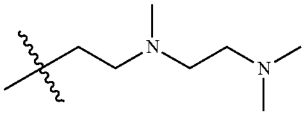,

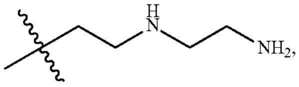,

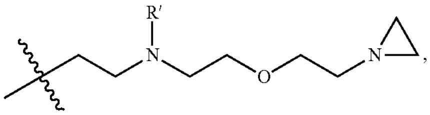,

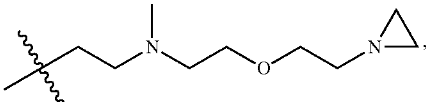,

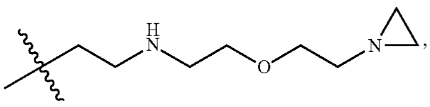,

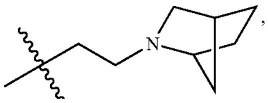, 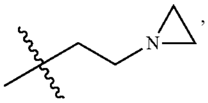, and

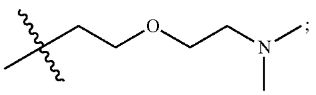;

wherein R', R" and R"' are independently at each occurrence selected from hydrogen and an aliphatic hydrocarbon, and wherein the ~~~ symbol represents the point of attachment, and R* is independently at each occurrence selected from hydrogen, an aliphatic $C_1$-$C_{20}$ hydrocarbon, an aromatic $C_5$-$C_{20}$ hydrocarbon, a heteroaromatic $C_1$-$C_{20}$ hydrocarbon, a cyclic aliphatic $C_3$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

3. A compound having the structure selected from the group consisting of:

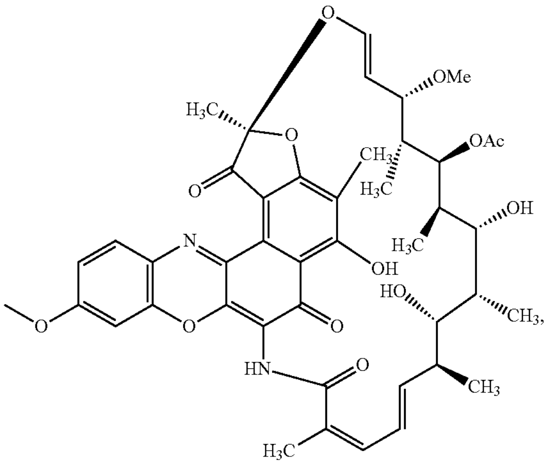,

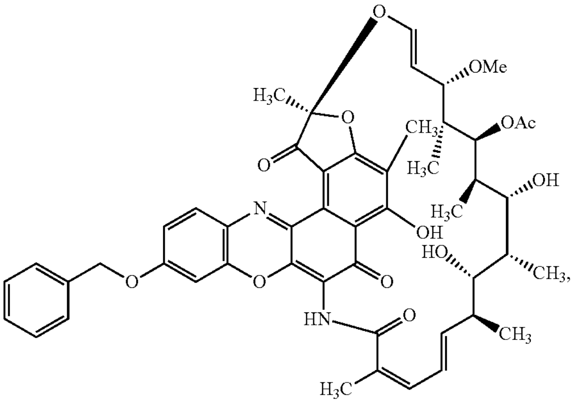,

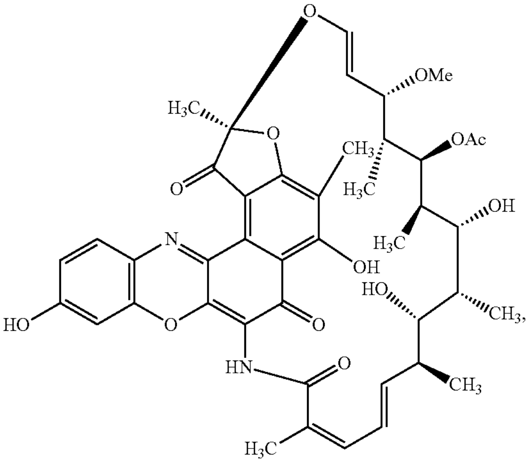,

-continued
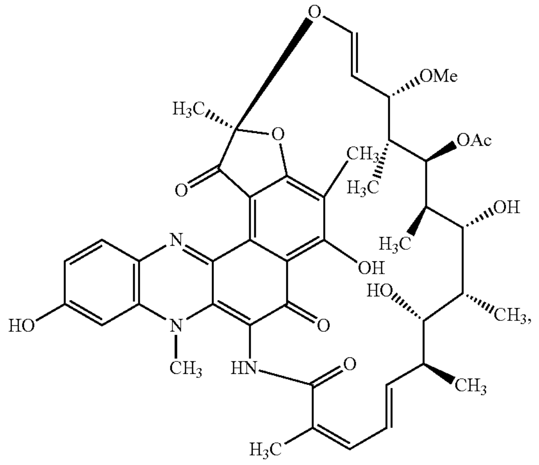
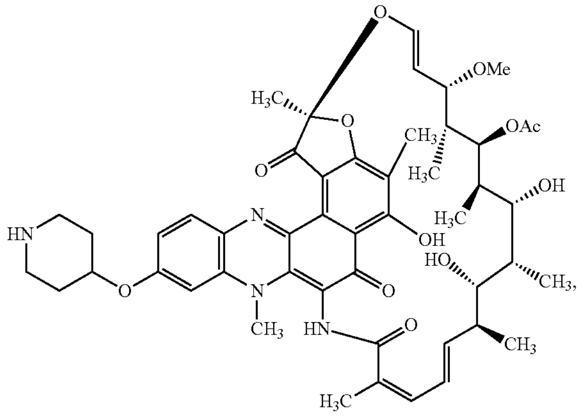
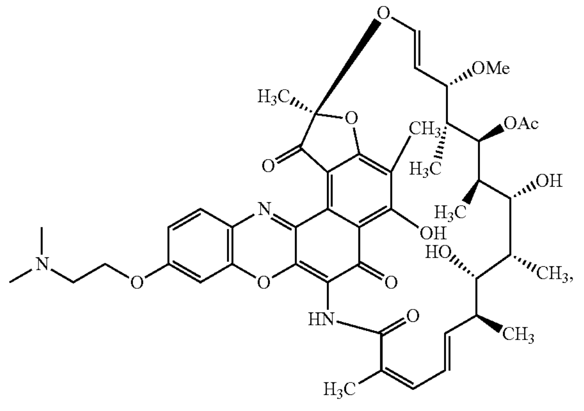
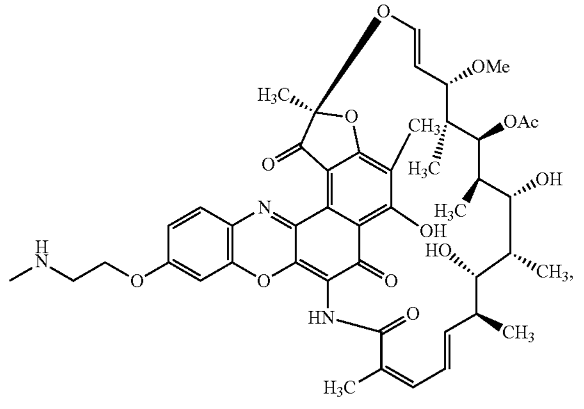
-continued
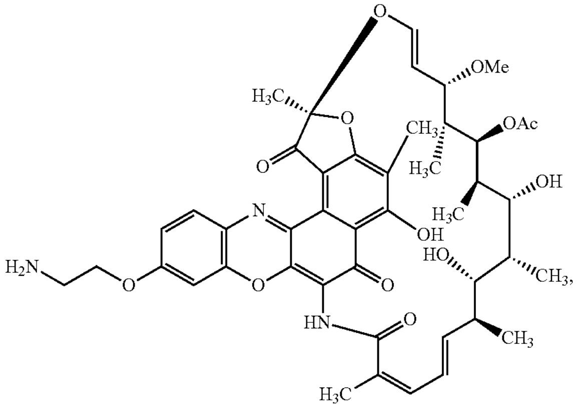
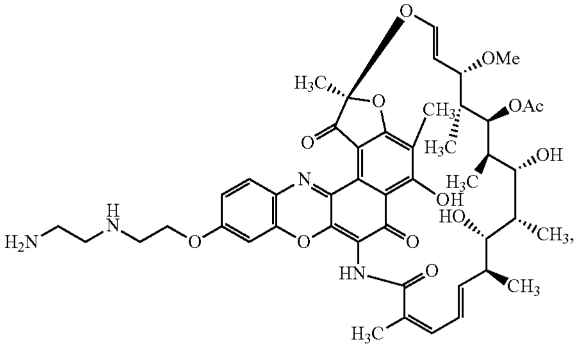
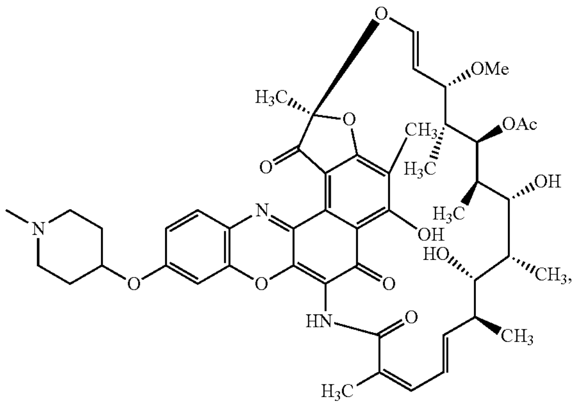
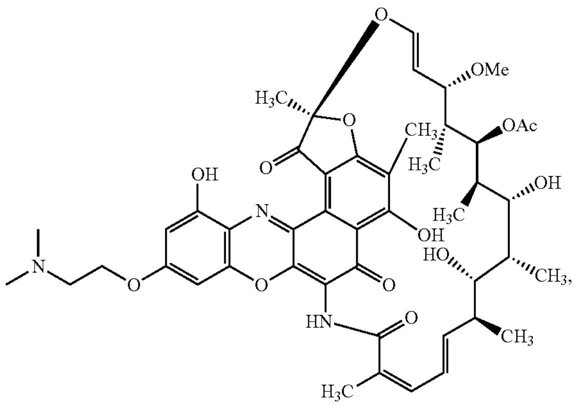

-continued
-continued
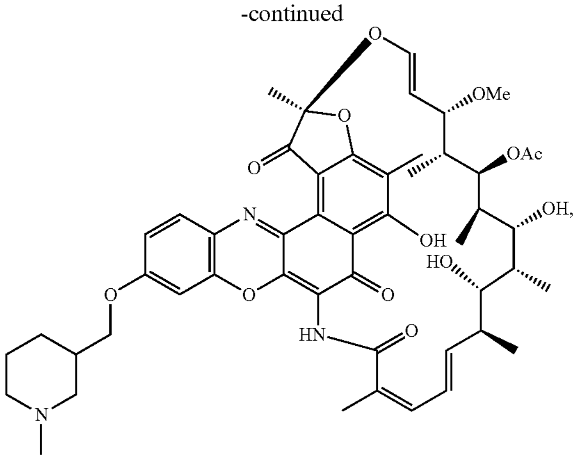
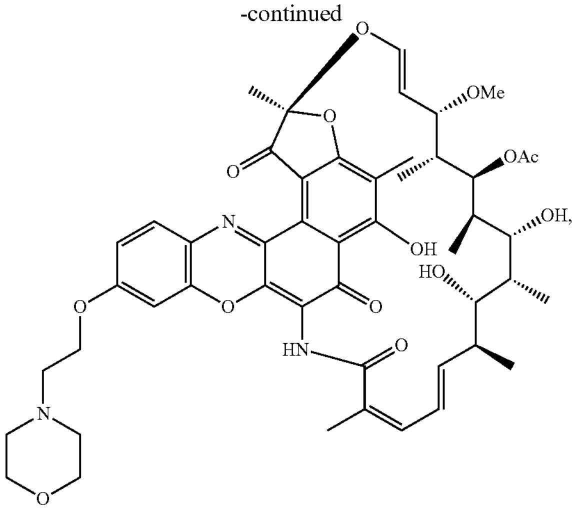
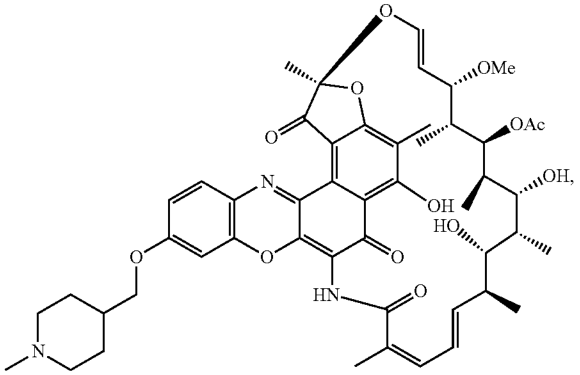
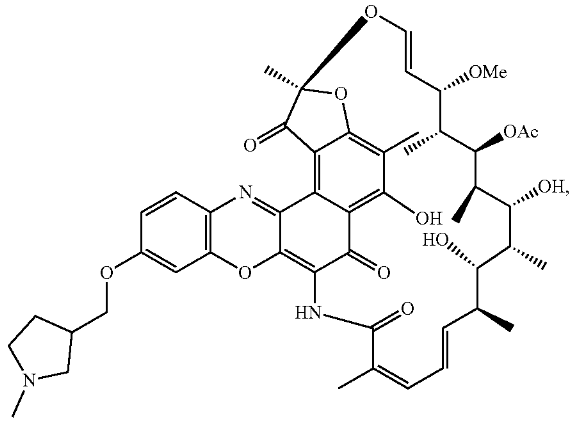
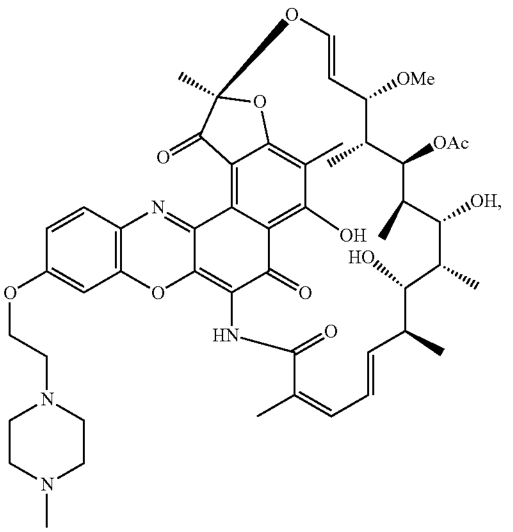
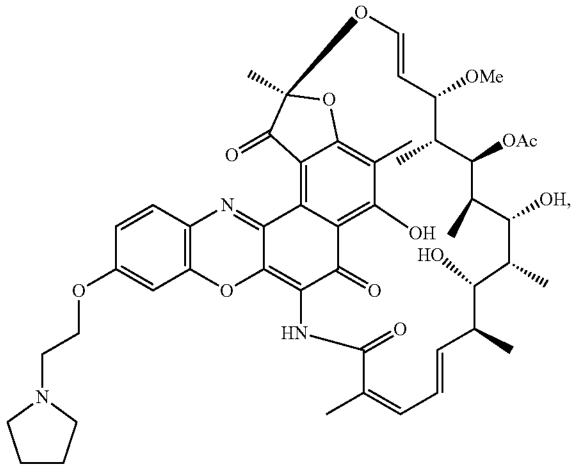

-continued
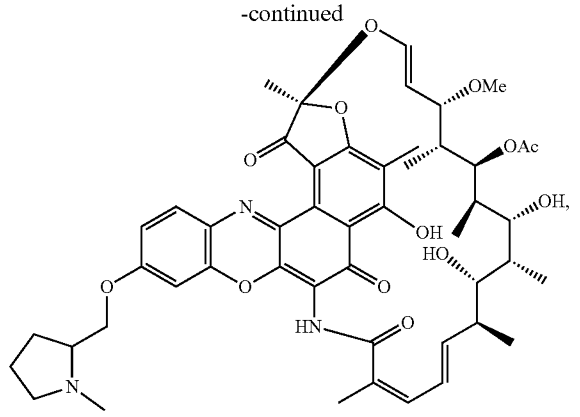
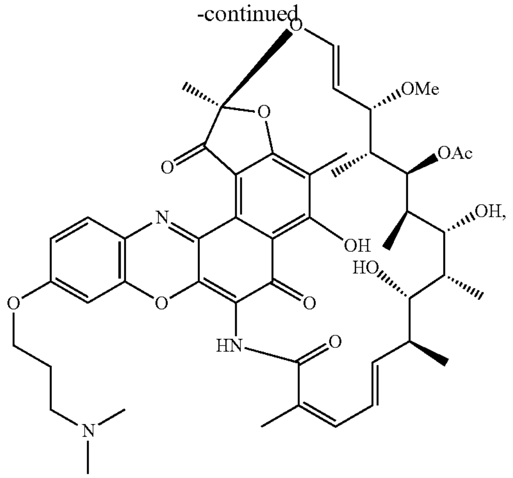
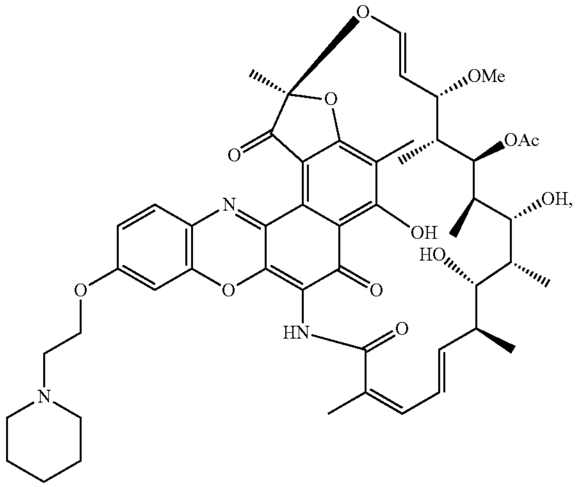
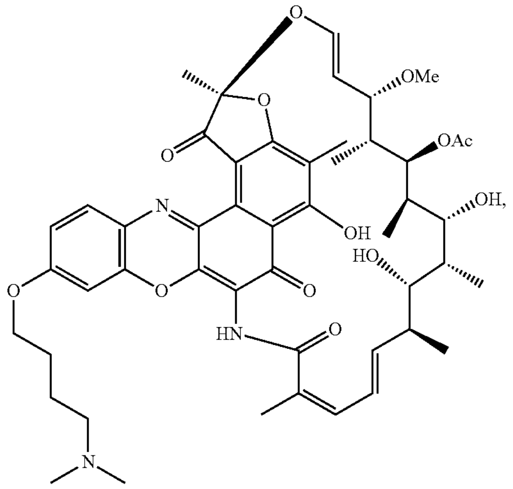
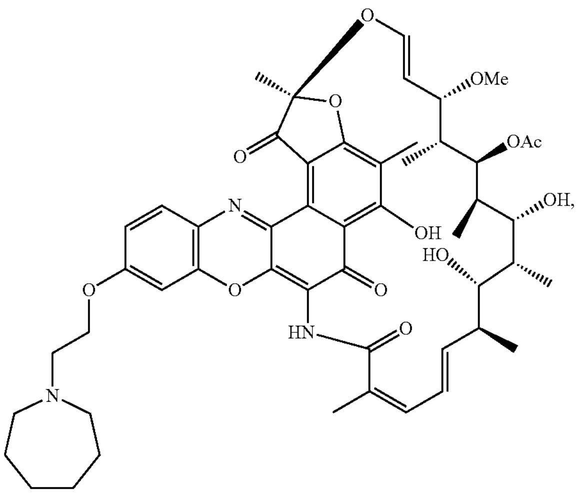
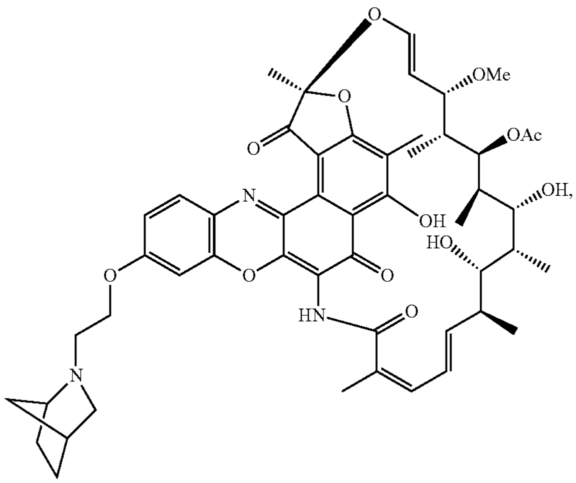

-continued
-continued
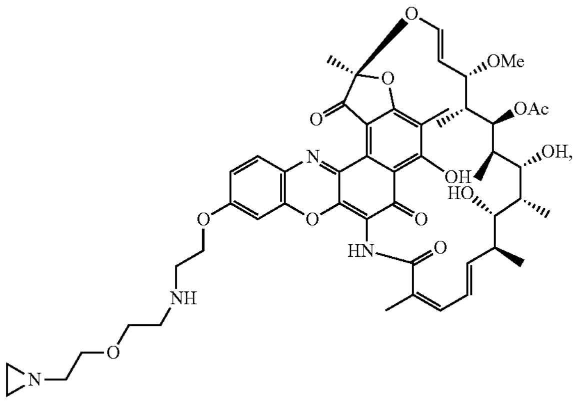
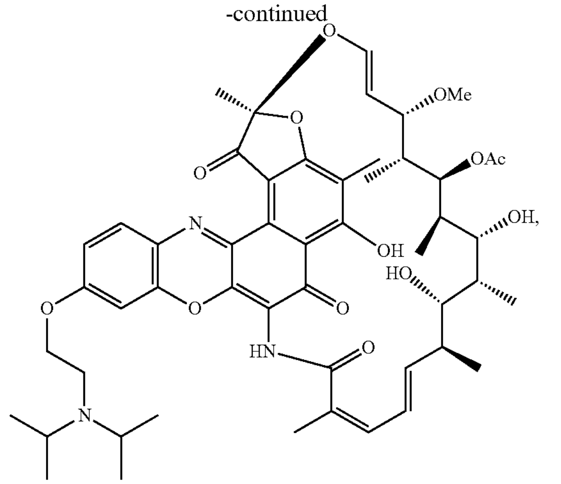
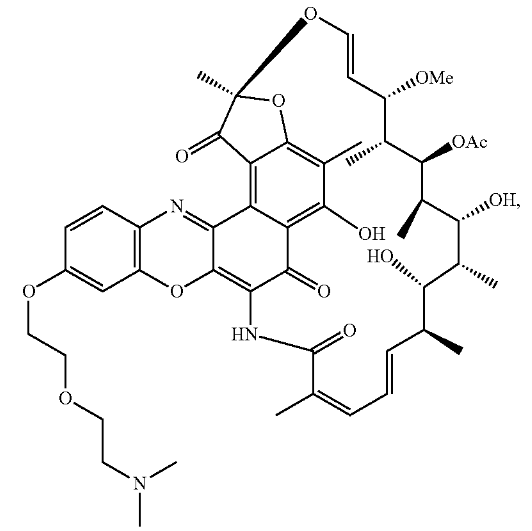
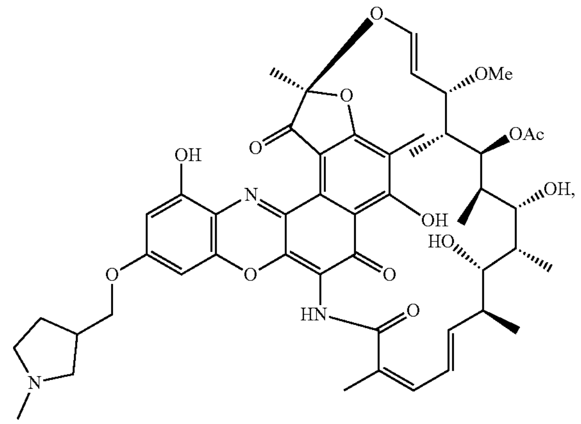
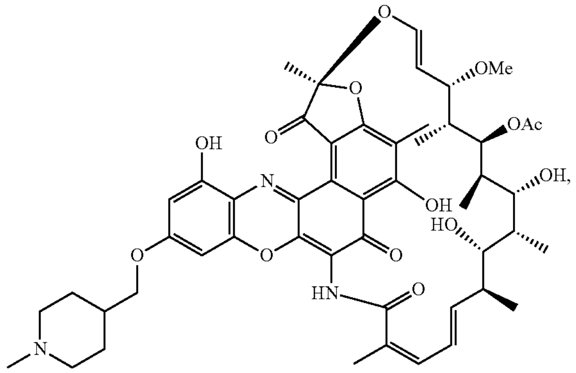
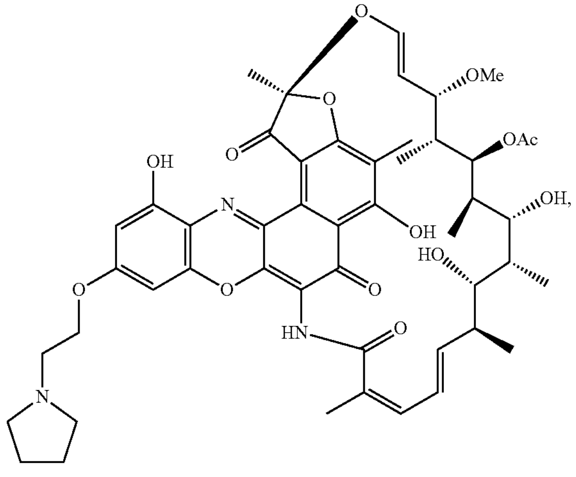

-continued
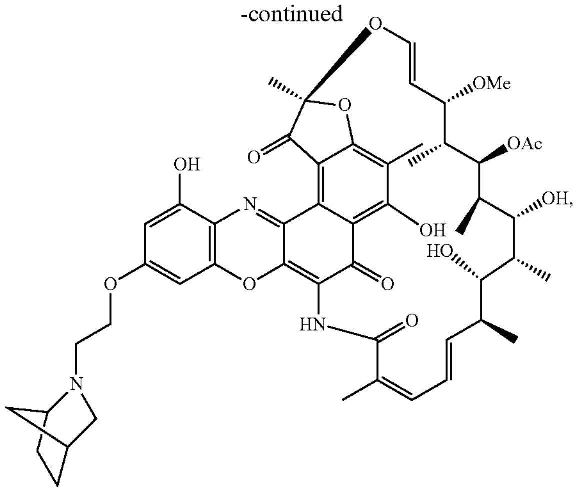
-continued
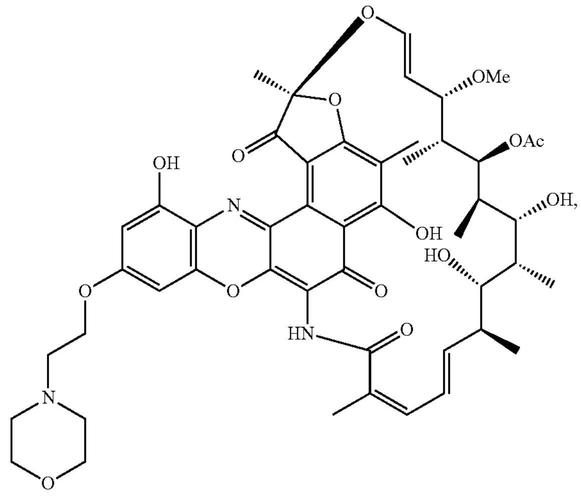
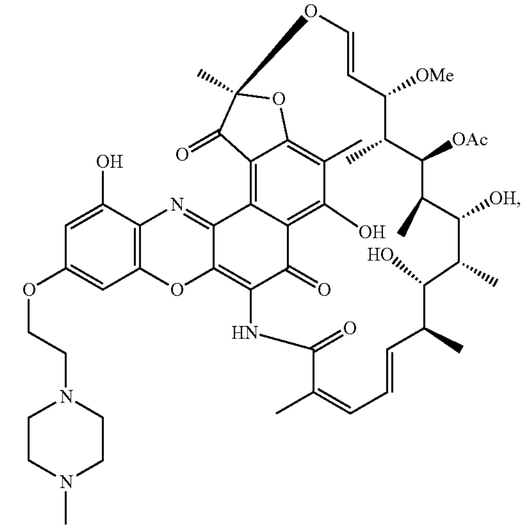
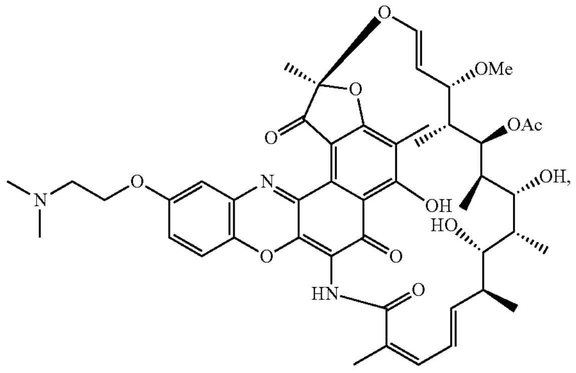
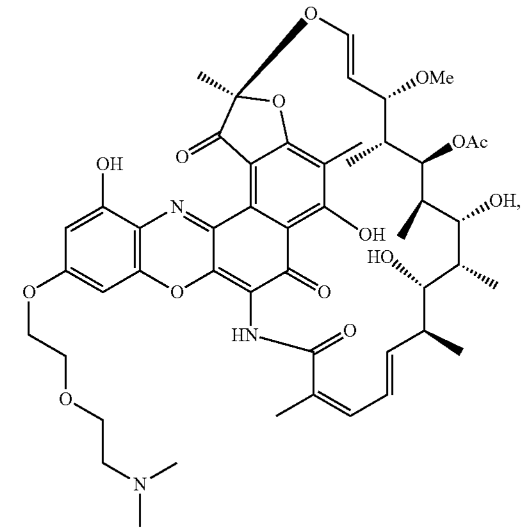
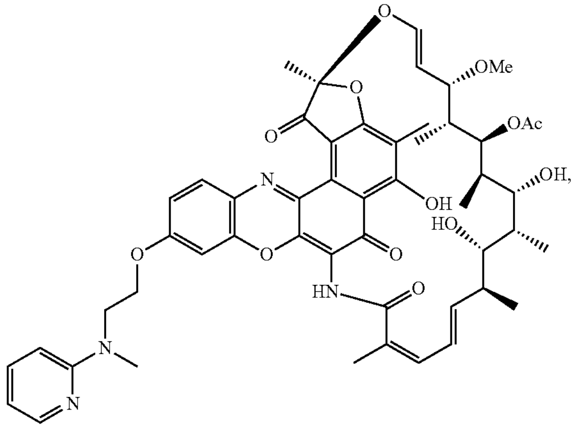

-continued
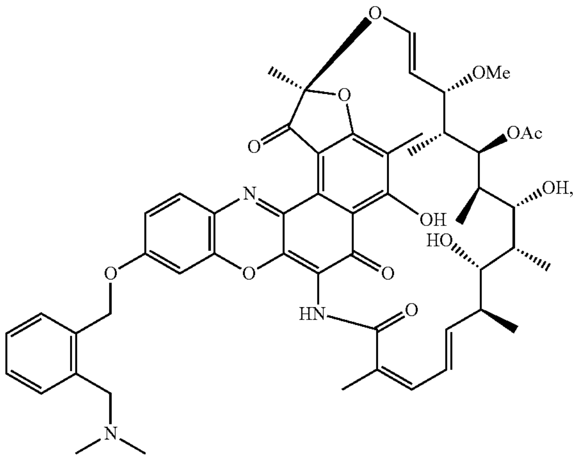
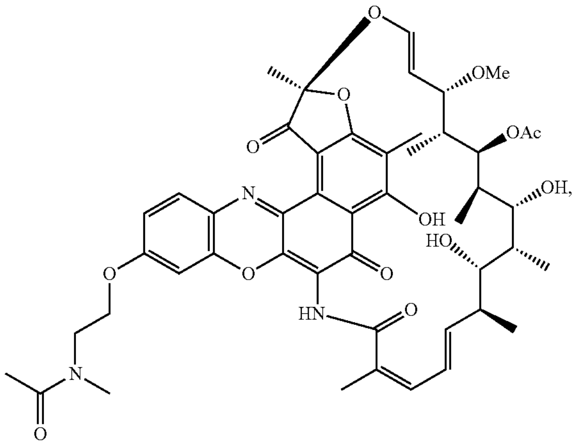
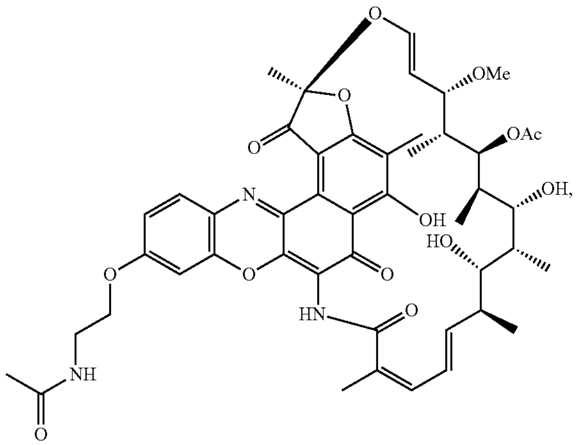
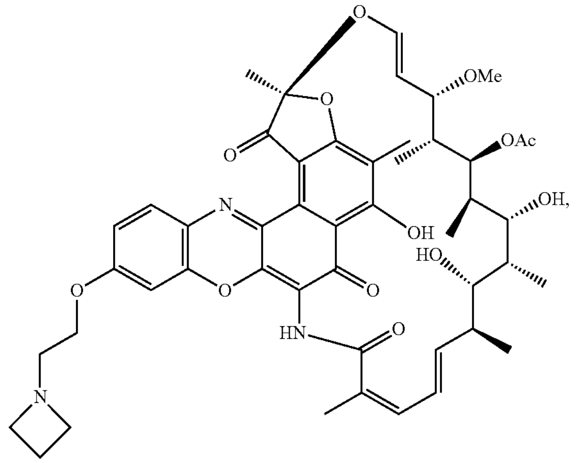
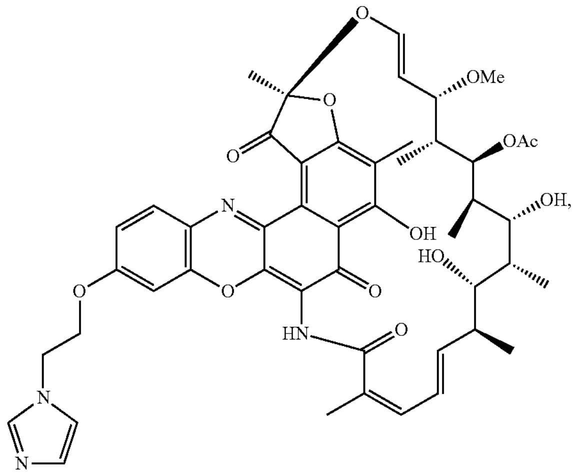
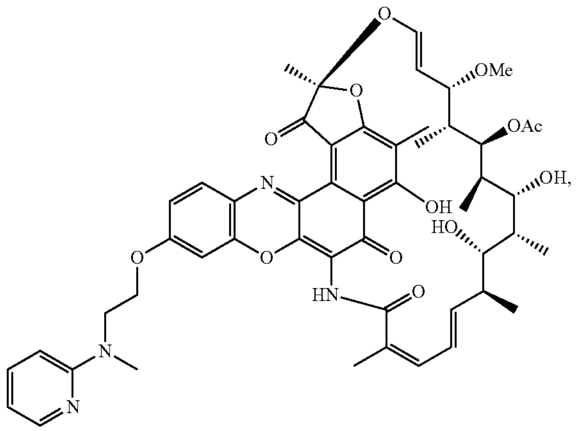

-continued
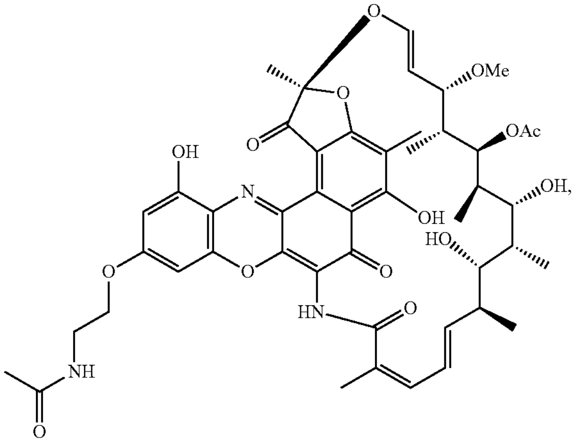
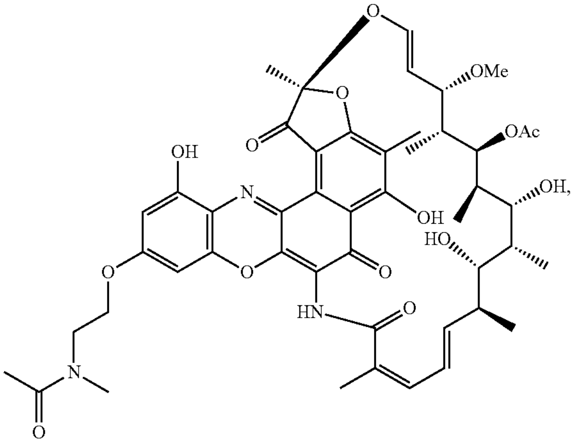
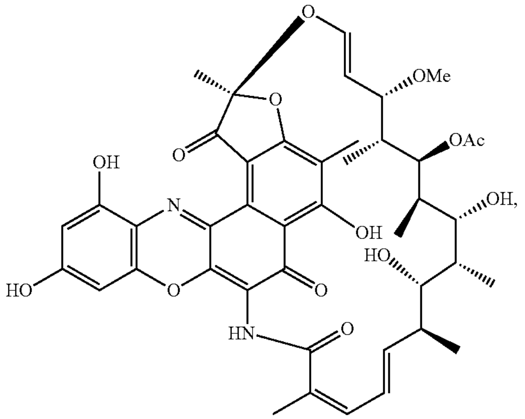
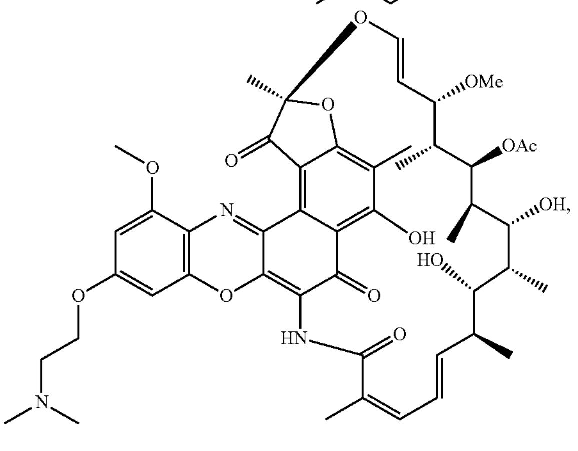
-continued
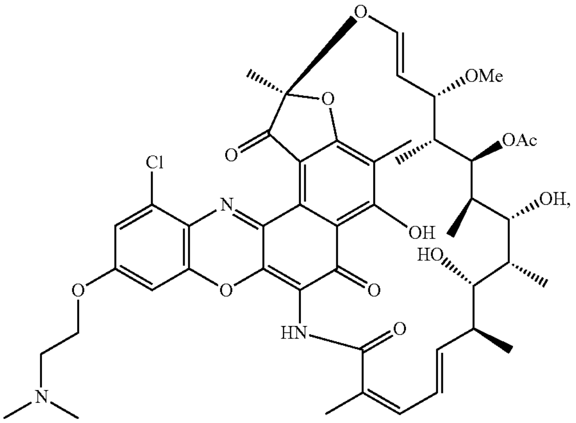
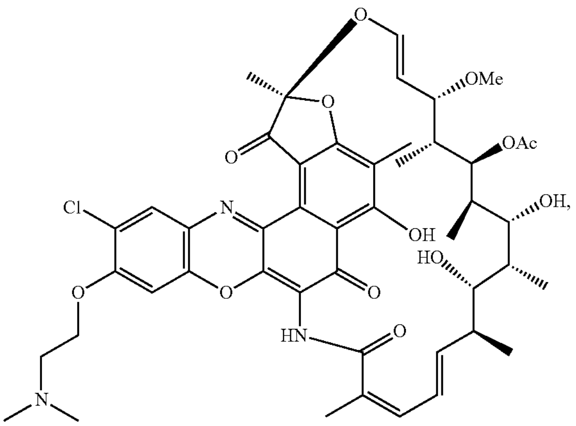
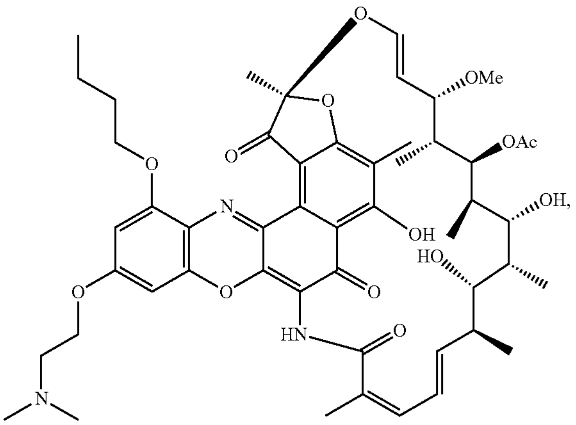
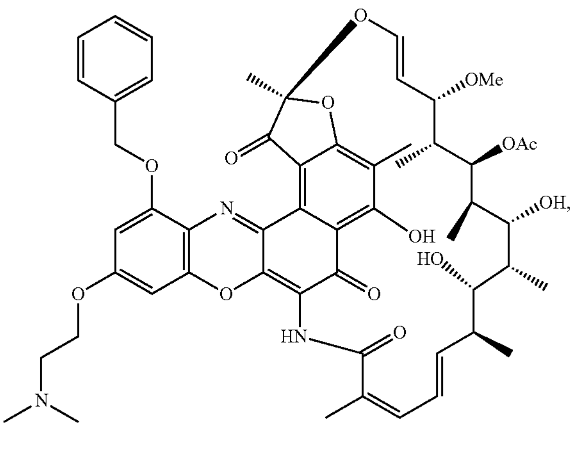

-continued

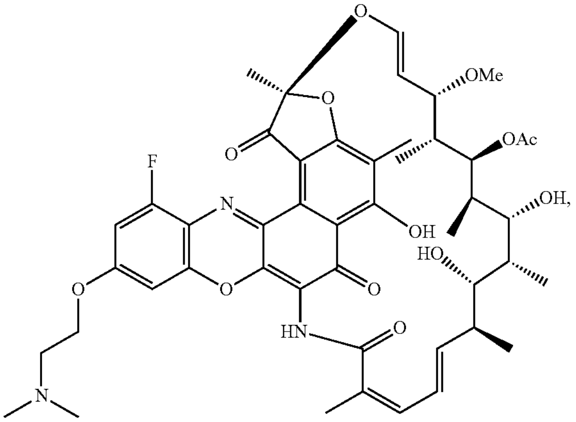

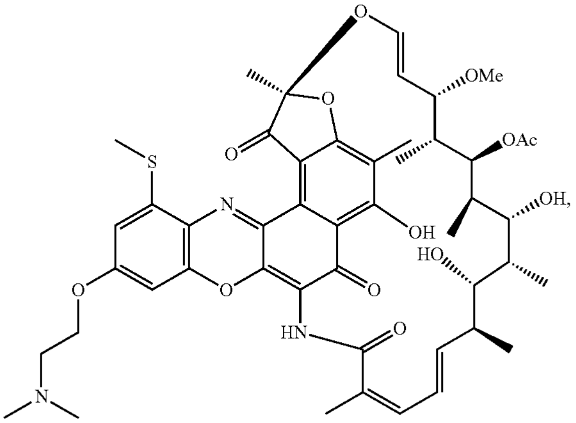

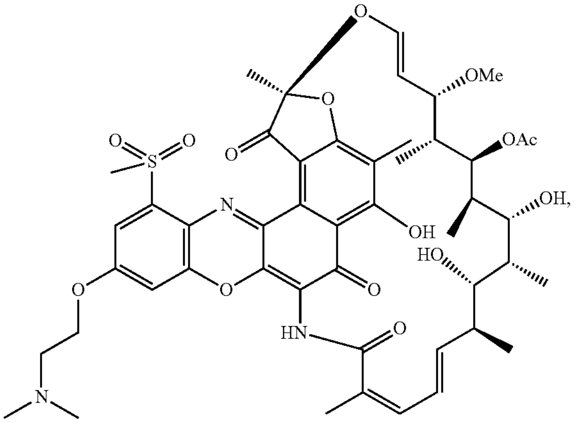

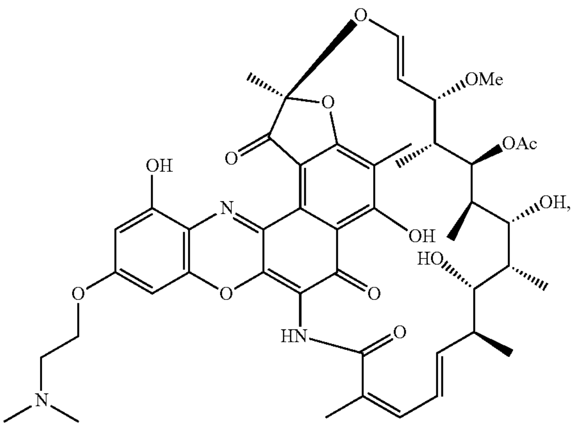

-continued

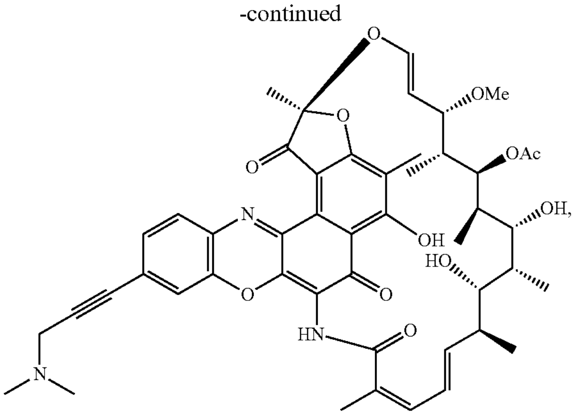

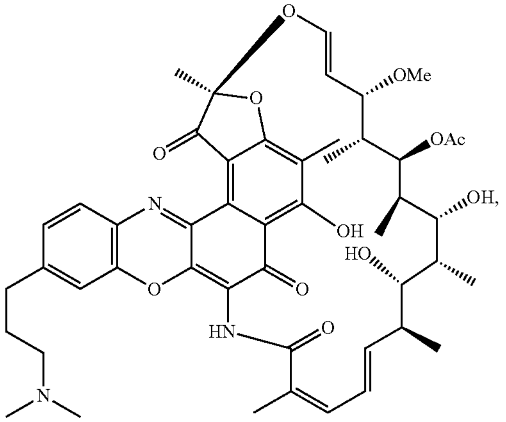

and

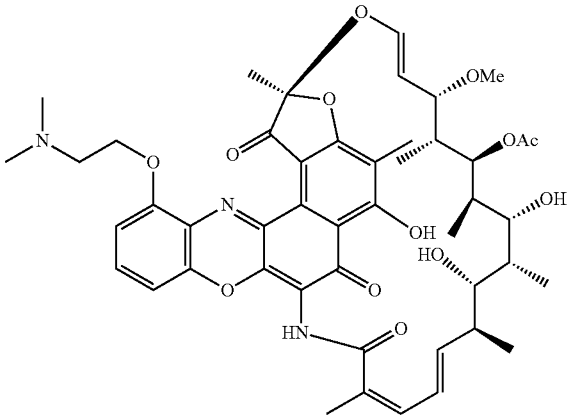

or a pharmaceutically acceptable salt thereof.

4. A pharmaceutical composition consisting of the compound of claim 1 or a pharmaceutically acceptable salt thereof and a pharmaceutically acceptable carrier.

5. A pharmaceutical dosage form consisting of the compound of claim 1 or a pharmaceutically acceptable salt thereof.

6. A method of preventing or inhibiting growth of a bacterium consisting of administering an effective amount of the compound of claim 1.

7. The method of claim 6, wherein the bacterium is a Gram-positive bacterium.

8. The method of claim 6, wherein the bacterium is *Staphylococcus aureus*.

9. The method of claim 6, wherein the bacterium is selected from the group consisting of methicillin-resistant *Staphylococcus aureus* (MRSA), vancomycin-resistant *Staphylococcus aureus* (VRSA), and methicillin-susceptible *Staphylococcus aureus* (MSSA).

10. A method of treating a bacterial infection in a subject in need of such treatment consisting of administering to the subject an effective amount of the compound of claim 1.

11. The method of claim 10, wherein the bacterial infection is a Gram-positive bacterial infection.

12. The method of claim 10, wherein the bacterial infection is a *Staphylococcus aureus* infection.

13. The method of claim 10, wherein the bacterial infection is selected from the group consisting of a methicillin-resistant *Staphylococcus aureus* (MRSA) infection, a vancomycin-resistant *Staphylococcus aureus* (VRSA) infection, and a methicillin-susceptible *Staphylococcus aureus* (MSSA) infection.

14. The method of claim 10, wherein the subject is human.

15. The method of claim 10, further comprising administering a second therapeutic agent, wherein the second therapeutic agent is a second antibiotic selected from an aminoglycoside, a beta-lactam, a macrolide, a cyclic peptide, a tetracycline, a fluoroquinoline, a fluoroquinolone, and an oxazolidinone.

* * * * *